United States Patent [19]

Biller et al.

[11] Patent Number: 5,760,246

[45] Date of Patent: Jun. 2, 1998

[54] CONFORMATIONALLY RESTRICTED AROMATIC INHIBITORS OF MICROSOMAL TRIGLYCERIDE TRANSFER PROTEIN AND METHOD

[76] Inventors: Scott A. Biller, 31 Second St., Hopewell, N.J. 08525; John K. Dickson, 14 Shelter Rock Rd., Eastampton, N.J. 08060; R. Michael Lawrence, 48 W. Crown Ter., Yardley, Pa. 19067; David R. Magnin, 40 Cottage Ct., Hamilton, N.J. 08690; Michael A. Poss, 15 Valerie La., Lawrenceville, N.J. 08468; Jeffrey A. Robl, 7 Tulip Dr., Newtown, Pa. 18940; William A. Slusarchyk, 19 Richmond Dr., Skillman, N.J. 08558; Richard B. Sulsky, 71 Gregory La., Franklin Park, N.J. 08823; Joseph A. Tino, 11 Chopin La., Lawrenceville, N.J. 08648

[21] Appl. No.: 767,923

[22] Filed: Dec. 17, 1996

[51] Int. Cl.$^6$ ............................................. C07D 235/16
[52] U.S. Cl. .................... 548/309.7; 544/139; 544/182; 544/256; 544/311; 544/316; 546/270; 546/277; 546/297; 546/265; 546/308; 546/337; 548/132; 548/136; 548/110; 548/171; 548/187; 548/144; 548/221; 548/264.4; 548/307.1; 548/324.1; 548/507; 549/14; 549/218; 549/371; 549/388; 549/441; 558/83; 564/153; 564/155; 564/172
[58] Field of Search .................... 548/309.7, 132, 548/136, 144, 160, 171, 187, 221, 264.4, 307.1, 324.1, 507; 514/395; 544/139, 182, 256, 311, 316; 546/265, 270, 277, 297, 308, 337; 549/14, 218, 341, 388, 441; 558/83; 564/153, 155, 172

[56] References Cited

U.S. PATENT DOCUMENTS

| | | |
|---|---|---|
| 2,776,299 | 1/1957 | Cusic et al. |
| 3,095,425 | 6/1963 | Zirkle |
| 3,128,279 | 4/1964 | Temple et al. |
| 3,153,050 | 10/1964 | Davis |
| 3,304,307 | 2/1967 | Mizzoni |
| 3,484,457 | 12/1969 | Mushowski et al. |
| 3,532,722 | 10/1970 | Belleau et al. |
| 3,660,485 | 5/1972 | Cusic et al. |
| 3,726,897 | 4/1973 | Schindler |
| 3,772,348 | 11/1973 | Blattner et al. |
| 3,843,657 | 10/1974 | Lowrie |
| 3,914,255 | 10/1975 | Sheehan |
| 3,917,603 | 11/1975 | Gosteli |
| 3,957,757 | 5/1976 | Allais et al. |
| 4,072,583 | 2/1978 | Hallcher et al. |
| 4,197,313 | 4/1980 | Lacefield et al. |
| 4,277,495 | 7/1981 | Lacefield et al. |
| 4,282,170 | 8/1981 | Lavagnino et al. |
| 4,436,745 | 3/1984 | York, Jr. |
| 4,486,592 | 12/1984 | Lacefield et al. |
| 4,508,735 | 4/1985 | Lacefield et al. |
| 4,537,892 | 8/1985 | York, Jr. |
| 4,552,982 | 11/1985 | Lacefield et al. |
| 4,717,725 | 1/1988 | York, Jr. |
| 4,864,028 | 9/1989 | York, Jr. |
| 5,070,100 | 12/1991 | York, Jr. |
| 5,087,628 | 2/1992 | Earl et al. |
| 5,153,211 | 10/1992 | York, Jr. |
| 5,173,489 | 12/1992 | Earl et al. |
| 5,272,269 | 12/1993 | Jensen |
| 5,595,872 | 1/1997 | Wetterau ........................ 435/6 |

FOREIGN PATENT DOCUMENTS

| | | |
|---|---|---|
| 743963 | 7/1965 | Canada |
| 795330 | 9/1968 | Canada |
| 065392 | 5/1981 | European Pat. Off. |
| 187509A | 12/1984 | European Pat. Off. |
| 364123 | 10/1988 | European Pat. Off. |
| 456183 | 5/1990 | European Pat. Off. |
| 773756 | 8/1954 | United Kingdom |
| 830825 | 1/1957 | United Kingdom |
| 1174419 | 7/1968 | United Kingdom |
| 1137821 | 4/1969 | United Kingdom |
| WO93/11764 | 12/1991 | WIPO |
| WO93/14092 | 1/1992 | WIPO |
| WO96/40640 | 12/1996 | WIPO |

*Primary Examiner*—Robert Gerstl
*Attorney, Agent, or Firm*—Burton Rodney

[57] ABSTRACT

Novel compounds are provided which are inhibitors of MTP and thus are useful for lowering serum lipids and treating atherosclerosis and related diseases, and have the structure

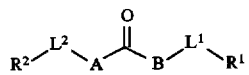

I or

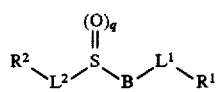

IA or

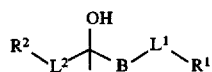

IB including pharmaceutically acceptable salts thereof or prodrug esters thereof, wherein q is 0, 1 or 2;

$R^x$ is H, alkyl, aryl or halogen;

A is (1) a bond;
(2) —O—; or
(3)

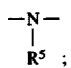

;

B is:
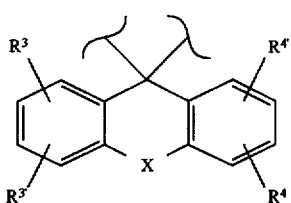
or
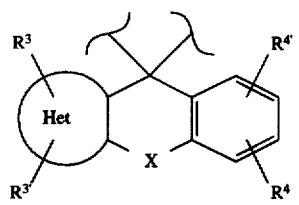
or
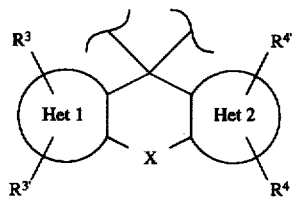
or
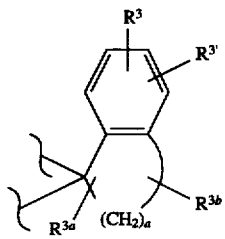
(a = 2, 3 or 4)
or
-continued
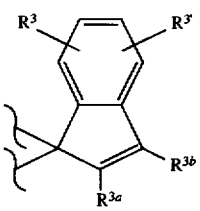
or
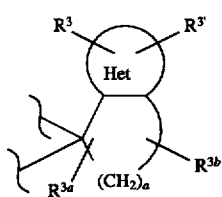
or
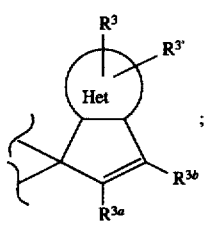
;
and wherein $L^2$, $L^1$, $R^1$, $R^2$, $R^3$, $R^{3'}$, $R^{3a}$, $R^{3b}$, $R^4$, $R^{4'}$, $R^5$, X,
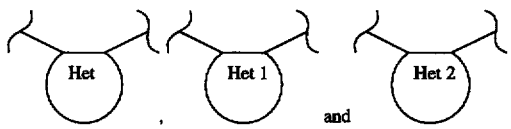
are as defined herein.
10 Claims, No Drawings

CONFORMATIONALLY RESTRICTED AROMATIC INHIBITORS OF MICROSOMAL TRIGLYCERIDE TRANSFER PROTEIN AND METHOD

FIELD OF THE INVENTION

This invention relates to novel conformationally restricted aromatic compounds which inhibit microsomal triglyceride transfer protein, and to methods for decreasing serum lipids and treating atherosclerosis employing such compounds.

BACKGROUND OF THE INVENTION

The microsomal triglyceride transfer protein (MTP) catalyzes the transport of triglyceride (TG), cholesteryl ester (CE), and phosphatidylcholine (PC) between small unilamellar vesicles (SUV). Wetterau & Zilversmit, Chem. Phys. Lipids 38, 205–22 (1985). When transfer rates are expressed as the percent of the donor lipid transferred per time, MTP expresses a distinct preference for neutral lipid transport (TG and CE), relative to phospholipid transport. The protein from bovine liver has been isolated and characterized. Wetterau & Zilversmit, Chem. Phys. Lipids 38, 205–22 (1985). Polyacrylamide gel electrophoresis (PAGE) analysis of the purified protein suggests that the transfer protein is a complex of two subunits of apparent molecular weights 58,000 and 88,000, since a single band was present when purified MTP was electrophoresed under nondenaturing condition, while two bands of apparent molecular weights 58,000 and 88,000 were identified when electrophoresis was performed in the presence of sodium dodecyl sulfate (SDS). These two polypeptides are hereinafter referred to as 58 kDa and 88 kDa, respectively, or the 58 kDa and the 88 kDa component of MTP, respectively, or the low molecular weight subunit and the high molecular weight subunit of MTP, respectively.

Characterization of the 58,000 molecular weight component of bovine MTP indicates that it is the previously characterized multifunctional protein, protein disulfide isomerase (PDI). Wetterau et al., J. Biol. Chem. 265, 9800–7 (1990). The presence of PDI in the transfer protein is supported by evidence showing that (1) the amino terminal 25 amino acids of the bovine 58,000 kDa component of MTP is identical to that of bovine PDI, and (2) disulfide isomerase activity was expressed by bovine MTP following the dissociation of the 58 kDa–88 kDa protein complex. In addition, antibodies raised against bovine PDI, a protein which by itself has no TG transfer activity, were able to immunoprecipitate bovine TG transfer activity from a solution containing purified bovine MTP.

PDI normally plays a role in the folding and assembly of newly synthesized disulfide bonded proteins within the lumen of the endoplasmic reticulum. Bulleid & Freedman, Nature 335, 649–51 (1988). It catalyzes the proper pairing of cysteine residues into disulfide bonds, thus catalyzing the proper folding of disulfide bonded proteins. In addition, PDI has been reported to be identical to the beta subunit of human prolyl 4-hydroxylase. Koivu et al., J. Biol. Chem. 262, 6447–9 (1987). The role of PDI in the bovine transfer protein is not clear. It does appear to be an essential component of the transfer protein as dissociation of PDI from the 88 kDa component of bovine MTP by either low concentrations of a denaturant (guanidine HCl), a chaotropic agent (sodium perchlorate), or a nondenaturing detergent (octyl glucoside) results in a loss of transfer activity. Wetterau et al., Biochemistry 30, 9728–35 (1991). Isolated bovine PDI has no apparent lipid transfer activity, suggesting that either the 88 kDa polypeptide is the transfer protein or that it confers transfer activity to the protein complex.

The tissue and subcellular distribution of MTP activity in rats has been investigated. Wetterau & Zilversmit, Biochem. Biophys. Acta 875, 610–7 (1986). Lipid transfer activity was found in liver and intestine. Little or no transfer activity was found in plasma, brain, heart, or kidney. Within the liver, MTP was a soluble protein located within the lumen of the microsomal fraction. Approximately equal concentrations were found in the smooth and rough microsomes.

Abetalipoproteinemia is an autosomal recessive disease characterized by a virtual absence of plasma lipoproteins which contain apolipoprotein B (apoB). Kane & Havel in The Metabolic Basis of Inherited Disease, Sixth edition, 1139–64 (1989). Plasma TG levels may be as low as a few mg/dL, and they fail to rise after fat ingestion. Plasma cholesterol levels are often only 20–45 mg/dL. These abnormalities are the result of a genetic defect in the assembly and/or secretion of very low density lipoproteins (VLDL) in the liver and chylomicrons in the intestine. The molecular basis for this defect has not been previously determined. In subjects examined, triglyceride, phospholipid, and cholesterol synthesis appear normal. At autopsy, subjects are free of atherosclerosis. Schaefer et al., Clin. Chem. 34, B9–12 (1988). A link between the apoB gene and abetalipoproteinemia has been excluded in several families. Talmud et al., J. Clin. Invest. 82, 1803–6 (1988) and Huang et al., Am. J. Hum. Genet. 46, 1141–8 (1990).

Subjects with abetalipoproteinemia are afflicted with numerous maladies. Kane & Havel, supra. Subjects have fat malabsorption and TG accumulation in their enterocytes and hepatocytes. Due to the absence of TG-rich plasma lipoproteins, there is a defect in the transport of fat-soluble vitamins such as vitamin E. This results in acanthocytosis of erythrocytes, spinocerebellar ataxia with degeneration of the fasciculus cuneatus and gracilis, peripheral neuropathy, degenerative pigmentary retinopathy, and ceroid myopathy. Treatment of abetalipoproteinemic subjects includes dietary restriction of fat intake and dietary supplementation with vitamins A, E and K.

In vitro, MTP catalyzes the transport of lipid molecules between phospholipid membranes. Presumably, it plays a similar role in vivo, and thus plays some role in lipid metabolism. The subcellular (lumen of the microsomal fraction) and tissue distribution (liver and intestine) of MTP have led to speculation that it plays a role in the assembly of plasma lipoproteins, as these are the sites of plasma lipoprotein assembly. Wetterau & Zilversmit, Biochem. Biophys. Acta 875, 610–7 (1986). The ability of MTP to catalyze the transport of TG between membranes is consistent with this hypothesis, and suggests that MTP may catalyze the transport of TG from its site of synthesis in the endoplasmic reticulum (ER) membrane to nascent lipoprotein particles within the lumen of the ER.

Olofsson and colleagues have studied lipoprotein assembly in HepG2 cells. Bostrom et al., J. Biol. Chem. 263, 4434–42 (1988). Their results suggest small precursor lipoproteins become larger with time. This would be consistent with the addition or transfer of lipid molecules to nascent lipoproteins as they are assembled. MTP may play a role in this process. In support of this hypothesis, Howell and Palade, J. Cell Biol. 92, 833–45 (1982), isolated nascent lipoproteins from the hepatic Golgi fraction of rat liver. There was a spectrum of sizes of particles present with varying lipid and protein compositions. Particles of high density lipoprotein (HDL) density, yet containing apoB, were found. Higgins and Hutson, *J. Lipid Res.* 25, 1295–1305 (1984), reported lipoproteins isolated from Golgi were consistently larger than those from the endoplasmic reticulum, again suggesting the assembly of lipoproteins is a progressive event. However, there is no direct evidence in the prior art demonstrating that MTP plays a role in lipid metabolism or the assembly of plasma lipoprotein.

Recent reports (Science, Vol. 258, page 999, 1992; D. Sharp et al, Nature, Vol. 365, page 65, 1993) demonstrate that the defect causing abetalipoproteinemia is in the MTP gene, and as a result, the MTP protein. Individuals with abetalipoproteinemia have no MTP activity, as a result of mutations in the MTP gene, some of which have been characterized. These results indicate that MTP is required for the synthesis of apoB containing lipoproteins, such as VLDL, the precursor to LDL. It therefore follows that inhibitors of MTP would inhibit the synthesis of VLDL and LDL, thereby lowering VLDL levels, LDL levels, cholesterol levels, and triglyceride levels in animals and man.

Canadian Patent Application No. 2,091,102 published Mar. 2, 1994 (corresponding to U.S. application Ser. No. 117,362, filed Sep. 3, 1993 (file DC21b)) which is incorporated herein by reference), reports MTP inhibitors which also block the production of apoB containing lipoproteins in a human hepatic cell line (HepG2 cells). This provides further support for the proposal that an MTP inhibitor would lower apoB containing lipoprotein and lipid levels in vivo. This Canadian patent application discloses a method for identifying the MTP inhibitors

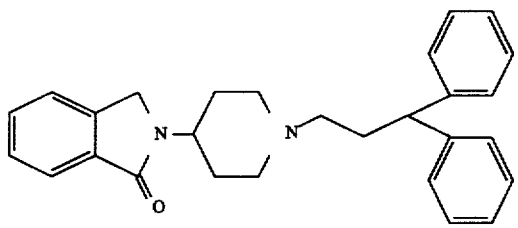

which has the name 2-[1-(3,3-diphenylpropyl)-4-piperidinyl]-2,3-dihydro-3-oxo-1H-isoindole hydrochloride and

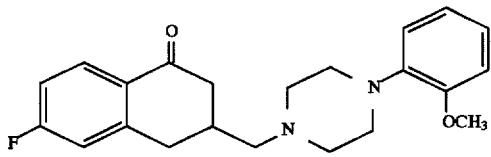

which has the name 1-[3-(6-fluoro-1-tetralanyl)methyl]-4-O-methoxyphenyl piperazine.

EP 0643057A1 published Mar. 15, 1995, discloses MTP inhibitors of the structure

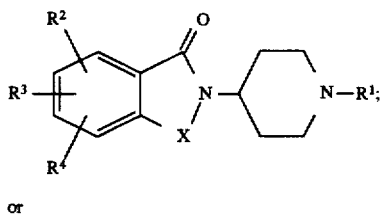

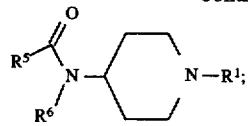

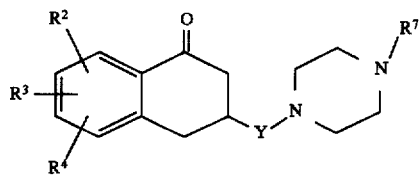

where X is: $CHR^8$,

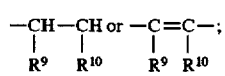

$R^8$, $R^9$ and $R^{10}$ are independently hydrogen, alkyl, alkenyl, alkynyl, aryl, arylalkyl, heteroaryl, heteroarylalkyl, cycloalkyl, or cycloalkylalkyl;

Y is $-(CH_2)_m-$ or

where m is 2 or 3;

$R^1$ is alkyl, alkenyl, alkynyl, aryl, heteroaryl, arylalkyl (wherein alkyl has at least 2 carbons), diarylalkyl, arylalkenyl, diarylalkenyl, arylalkynyl, diarylalkynyl, diarylalkylaryl, heteroarylalkyl (wherein alkyl has at least 2 carbons), cycloalkyl, or cycloalkylalkyl (wherein alkyl has at least 2 carbons); all of the aforementioned $R^1$ groups being optionally substituted through available carbon atoms with 1, 2, or 3 groups selected from halo, haloalkyl, alkyl, alkenyl, alkoxy, aryloxy, aryl, arylalkyl, alkylmercapto, arylmercapto, cycloalkyl, cycloalkylalkyl, heteroaryl, fluorenyl, heteroarylalkyl, hydroxy or oxo; or $R^1$ is a group of the structure

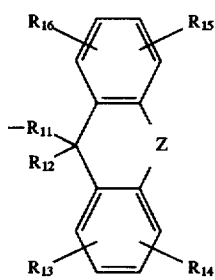

$R^{11}$ is a bond, alkylene, alkenylene or alkynylene of up to 6 carbon atoms, arylene (for example

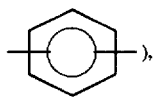), or mixed arylene-alkylene (for example

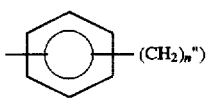

where n is 1 to 6;

$R^{12}$ is hydrogen, alkyl, alkenyl, aryl, heteroaryl, haloalkyl, arylalkyl, arylalkenyl, cycloalkyl, aryloxy, alkoxy, arylalkoxy, heteroarylalkyl or cycloalkylalkyl;

Z is a bond, O, S, N-alkyl, N-aryl, or alkylene or alkenylene of from 1 to 5 carbon atoms;

$R^{13}$, $R^{14}$, $R^{15}$, and $R^{16}$ are independently hydrogen, alkyl, halo, haloalkyl, aryl, cycloalkyl, cycloheteroalkyl, alkenyl, alkynyl, hydroxy, alkoxy, nitro, amino, thio, alkylsulfonyl, arylsulfonyl, alkylthio, arylthio, carboxy, aminocarbonyl, alkylcarbonyloxy, alkylcarbonylamino, arylalkyl, heteroaryl, heteroarylalkyl, or aryloxy;

or $R^1$ is

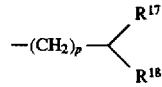

wherein p is 1 to 8 and $R^{17}$ and $R^{18}$ are each independently H, alkyl, alkenyl, aryl, arylalkyl, heteroaryl, heteroarylalkyl, cycloalkyl or cycloalkylalkyl, at least one of $R^{17}$ and $R^{18}$ being other than H;

or $R^1$ is

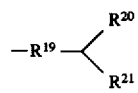

wherein $R^{19}$ is aryl or heteroaryl;

$R^{20}$ is aryl or heteroaryl;

$R^{21}$ is H, alkyl, aryl, alkylaryl, arylalkyl, aryloxy, arylalkoxy, heteroaryl, heteroarylalkyl, heteroarylalkoxy, cycloalkyl, cycloalkylalkyl or cycloalkylalkoxy;

$R^2$, $R^3$, $R^4$ are independently hydrogen, halo, alkyl, haloalkyl, alkenyl, alkoxy, aryloxy, aryl, arylalkyl, alkylmercapto, arylmercapto, cycloalkyl, cycloalkylalkyl, heteroaryl, heteroarylalkyl, hydroxy or haloalkyl;

$R^5$ is alkyl of at least 2 carbons, alkenyl, alkynyl, aryl, heteroaryl, arylalkyl, heteroarylalkyl, cycloalkyl, cycloalkylalkyl, polycycloalkyl, polycycloalkylalkyl, cycloalkenyl, cycloalkenylalkyl, polycycloalkenyl, polycycloalkenylalkyl, heteroarylcarbonyl, all of the $R^5$ and $R^6$ substituents being optionally substituted through available carbon atoms with 1, 2, or 3 groups selected from hydrogen, halo, alkyl, haloalkyl, alkoxy, haloalkoxy, alkenyl, alkynyl, cycloalkyl, cycloalkylalkyl, cycloheteroalkyl, cycloheteroalkylalkyl, aryl, heteroaryl, arylalkyl, arylcycloalkyl, arylalkynyl, aryloxy, aryloxyalkyl, arylalkoxy, arylazo, heteroaryloxo, heteroarylalkyl, heteroarylalkenyl, heteroaryloxy, hydroxy, nitro, cyano, amino, substituted amino (wherein the amino includes 1 or 2 substituents which are alkyl, or aryl or any of the other aryl compounds mentioned in the definitions), thiol, alkylthio, arylthio, heteroarylthio, arylthioalkyl, alkylcarbonyl, arylcarbonyl, arylaminocarbonyl, alkoxycarbonyl, aminocarbonyl, alkynylaminocarbonyl, alkylaminocarbonyl, alkenylaminocarbonyl, alkylcarbonyloxy, arylcarbonyloxy, alkylcarbonylamino, arylcarbonylamino, arylsulfinyl, arylsulfinylalkyl, arylsulfonyl, alkylsulfonyl, arylsulfonylamino; with the proviso that when $R^5$ is $CH_3$, $R^6$ is not H; and where $R^5$ is phenyl, the phenyl preferably includes an ortho hydrophobic substituent such as alkyl, haloalkyl, aryl, aryloxy or arylalkyl;

$R^6$ is hydrogen or $C_1$-$C_4$ alkyl or $C_1$-$C_4$ alkenyl;

$R^7$ is alkyl, aryl or arylalkyl wherein alkyl or the alkyl portion is optionally substituted with oxo; and including pharmaceutically acceptable salts and anions thereof.

In the formula I compounds, where X is $CH_2$ and $R^2$, $R^3$ and $R^4$ are each H, $R^1$ will be other than 3,3-diphenylpropyl.

In the formula III compounds, where one of $R^2$, $R^3$ and $R^4$ is 6-fluoro, and the others are H, $R^7$ will be other than 4-O-methoxyphenyl.

U.S. application Ser. No. 472,067, filed Jun. 6, 1995 (file DC21e) discloses compounds of the structure

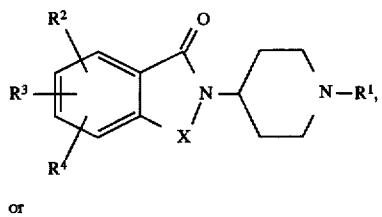

or

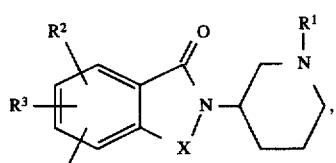

or

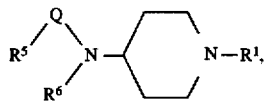

or

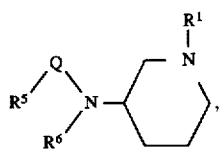

or

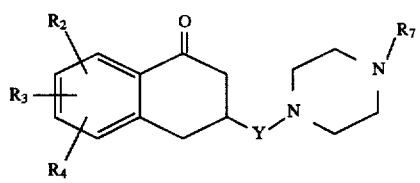

where Q is

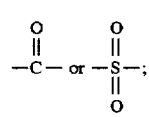

X is: CHR⁸.

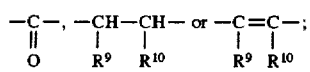

R⁸, R⁹ and R¹⁰ are independently hydrogen, alkyl, alkenyl, alkynyl, aryl, arylalkyl, heteroaryl, heteroarylalkyl, cycloalkyl, or cycloalkylalkyl;

Y is —(CH$_2$)$_m$— or

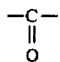

wherein m is 2 or 3;

R¹ is alkyl, alkenyl, alkynyl, aryl, heteroaryl, arylalkyl wherein alkyl has at least 2 carbons, diarylalkyl, arylalkenyl, diarylalkenyl, arylalkynyl, diarylalkynyl, diarylalkylaryl, heteroarylalkyl wherein alkyl has at least 2 carbons, cycloalkyl, or cycloalkylalkyl wherein alkyl has at least 2 carbons, all optionally substituted through available carbon atoms with 1, 2, 3 or 4 groups selected from halo, haloalkyl, alkyl, alkenyl, alkoxy, aryloxy, aryl, arylalkyl, alkylmercapto, arylmercapto, cycloalkyl, cyclo-alkylalkyl, heteroaryl, fluorenyl, heteroarylalkyl, hydroxy or oxo;

or R¹ is a fluorenyl-type group of the structure

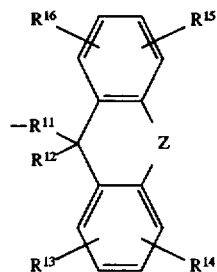

A or

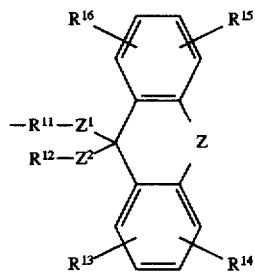

B or

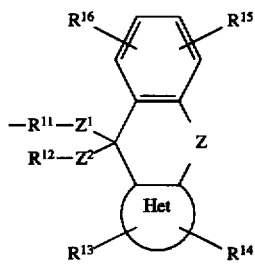

C or

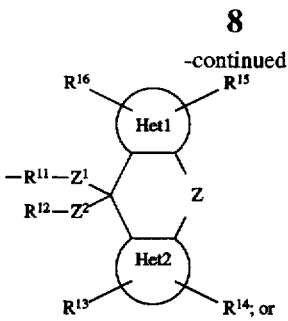

D

R¹ is an indenyl-type group of the structure

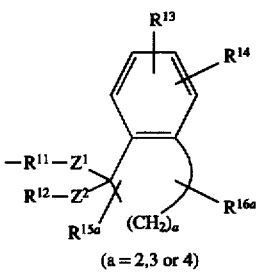

E (a = 2, 3 or 4)

or

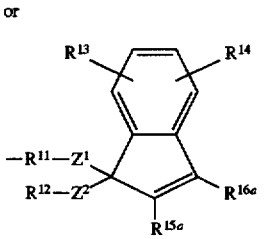

F or

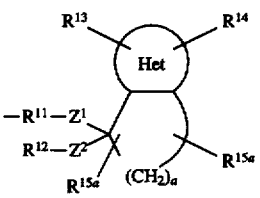

G or

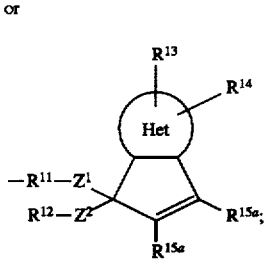

H

Z¹ and Z² are the same or different and are independently a bond, O, S, $$\overset{S}{\underset{O}{\overset{\|}{\|}}}, \left(\overset{S}{\underset{O}{\overset{\|}{\|}}}\right)_2, -NH-\overset{O}{\overset{\|}{C}}-, -\underset{alkyl}{N}-\overset{O}{\overset{\|}{C}}-,$$

$$-\overset{O}{\overset{\|}{C}}- \text{ or } -\overset{H}{\underset{OH}{\overset{|}{C}}}-,$$

with the proviso that with respect to B, at least one of $Z^1$ and $Z^2$ will be other than a bond; $R^{11}$ is a bond, alkylene, alkenylene or alkynylene of up to 10 carbon atoms; arylene or mixed arylene-alkylene; $R^{12}$ is hydrogen, alkyl, alkenyl, aryl, haloalkyl, trihaloalkyl, trihaloalkylalkyl, heteroaryl, heteroarylalkyl, arylalkyl, arylalkenyl, cyclo-alkyl, aryloxy, alkoxy, arylalkoxy or cycloalkyl-alkyl, with the provisos that (1) when $R^{12}$ is H, aryloxy, alkoxy or arylalkoxy, then $Z^2$ is

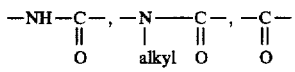

or a bond and (2) when $Z^2$ is a bond, $R^{12}$ cannot be heteroaryl or heteroarylalkyl;

Z is bond, O, S, N-alkyl, N-aryl, or alkylene or alkenylene from 1 to 5 carbon atoms; $R^{13}$, $R^{14}$, $R^{15}$, and $R^{16}$ are independently hydrogen, alkyl, halo, haloalkyl, aryl, cycloalkyl, cyclo-heteroalkyl, alkenyl, alkynyl, hydroxy, alkoxy, nitro, amino, thio, alkylsulfonyl, arylsulfonyl, alkylthio, arylthio, aminocarbonyl, alkylcarbon-yloxy, arylcarbonylamino, alkylcarbonylamino, arylalkyl, heteroaryl, heteroarylalkyl or aryloxy;

$R^{15a}$ and $R^{16a}$ are independently hydrogen, alkyl, halo, haloalkyl, aryl, cycloalkyl, cycloheteroalkyl, alkenyl, alkynyl, alkoxy, alkylsulfonyl, arylsulfonyl, alkylthio, arylthio, aminocarbonyl, alkylcarbonyloxy, arylcarbonylamino, alkylcarbonylamino, arylalkyl, heteroaryl, heteroarylalkyl, or aryloxy;

or $R^1$ is a group of the structure

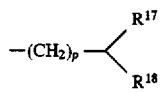

wherein p is 1 to 8 and $R^{17}$ and $R^{18}$ are each independently H, alkyl, alkenyl, aryl, arylalkyl, heteroaryl, heteroarylalkyl, cycloalkyl or cycloalkylalkyl at least one of $R^{17}$ and $R^{18}$ being other than H;

or $R^1$ is a group of the structure

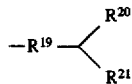

wherein $R^{19}$ is aryl or heteroaryl;

$R^{20}$ is aryl or heteroaryl;

$R^{21}$ is H, alkyl, aryl, alkylaryl, arylalkyl, aryloxy, arylalkoxy, heteroaryl, heteroarylalkyl, heteroarylalkoxy, cycloalkyl, cycloalkylalkyl or cycloalkylalkoxy;

$R^2$, $R^3$, $R^4$ are independently hydrogen, halo, alkyl, alkenyl, alkoxy, aryloxy, aryl, arylalkyl, alkylmercapto, arylmercapto, cycloalkyl, cycloalkylalkyl, heteroaryl, heteroarylalkyl, hydroxy or haloalkyl;

$R^5$ is independently alkyl, alkenyl, alkynyl, aryl, alkoxy, aryloxy, arylalkoxy, heteroaryl, arylalkyl, heteroarylalkyl, cycloalkyl, cycloalkylalkyl, polycycloalkyl, polycycloalkylalkyl, cycloalkenyl, cycloheteroalkyl, heteroaryloxy, cycloalkenylalkyl, polycycloalkenyl, polycycloalkenylalkyl, heteroarylcarbonyl, amino, alkylamino, arylamino, heteroarylamino, cycloalkyloxy, cycloalkylamino, all optionally substituted through available carbon atoms with 1, 2, 3 or 4 groups selected from hydrogen, halo, alkyl, haloalkyl, alkoxy, haloalkoxy, alkenyl, alkynyl, cycloalkyl, cycloalkylalkyl, cycloheteroalkyl, cycloheteroalkylalkyl, aryl, heteroaryl, arylalkyl, arylcycloalkyl, arylalkenyl, arylalkynyl, aryloxy, aryloxyalkyl, arylalkoxy, arylazo, heteroaryloxo, heteroarylalkyl, heteroarylalkenyl, heteroaryloxy, hydroxy, nitro, cyano, amino, substituted amino, thiol, alkylthio, arylthio, heteroarylthio, arylthioalkyl, alkylcarbonyl, arylcarbonyl, arylaminocarbonyl, alkoxycarbonyl, aminocarbonyl, alkynylaminocarbonyl, alkylaminocarbonyl, alkenyl-aminocarbonyl, alkylcarbonyloxy, arylcarbonyloxy, alkylcarbonylamino, arylcarbonylamino, arylsul-finyl, arylsulfinylalkyl, arylsulfonyl, alkylsul-fonyl, arylsulfonylamino, heteroarylcarbonylamino, heteroarylsulfinyl, heteroarylthio, heteroarylsulfonyl, alkylsulfinyl;

$R^6$ is hydrogen or $C_1$-$C_4$ alkyl or $C_1$-$C_4$ alkenyl; all optionally substituted with 1, 2, 3 or 4 groups which may independently be any of the substituents listed in the definition of $R^5$ set out above;

$R^7$ is alkyl, aryl or arylalkyl wherein alkyl by itself or as part of arylalkyl is optionally substituted with oxo

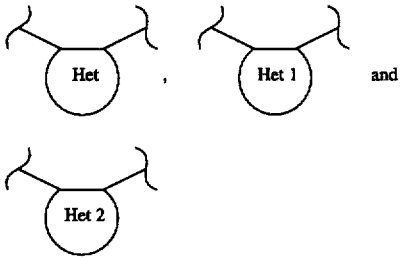

are the same or different and are independently selected from heteroaryl containing 5- or 6-ring members; and
N-oxides

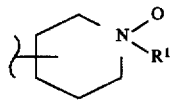

thereof; and pharmaceutically acceptable salts thereof;

with the provisos that where in the first formula X is $CH_2$, and $R^2$, $R^3$ and $R^4$ are each H, then $R^1$ will be other than 3,3-diphenylpropyl, and in the fifth formula, where one of $R^2$, $R^3$ and $R^4$ is 6-fluoro, and the others are H, $R^7$ will be other than 4-(2-methoxyphenyl).

SUMMARY OF THE INVENTION

In accordance with the present invention, novel compounds are provided which are inhibitors of MTP and have the structure

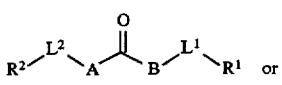

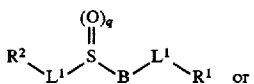

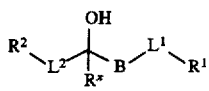
IB including pharmaceutically acceptable salts thereof, wherein q is 0, 1 or 2;

A is (1) a bond;
(2) —O—; or
(3)

where $R^5$ is H or lower alkyl.

B is a fluorenyl-type group of the structure:


or


or

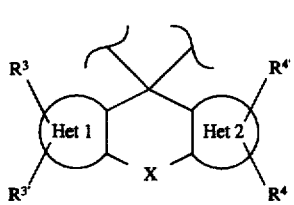

(the above B is also referred to as a fluorenyl-type ring or moiety); or

B is an indenyl-type group of the structure

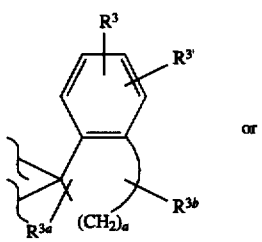

(a = 2, 3 or 4)

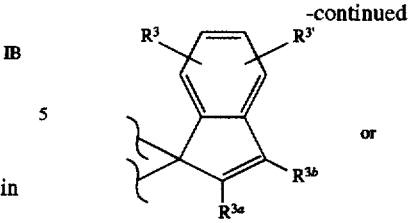

or

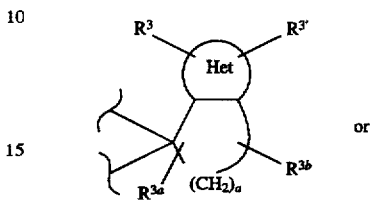

or

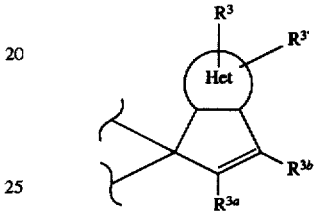

(the above B is also referred to as an indenyl-type ring or moiety);

$R^x$ is H, alkyl or aryl;

$R^1$ is H, alkyl, alkenyl, alkynyl, alkoxyl, (alkyl or aryl)$_3$Si (where each alkyl or aryl group is independent), cycloalkyl, cycloalkenyl, substituted alkylamino, substituted arylalkylamino, aryl, arylalkyl, arylamino, aryloxy, heteroaryl, heteroarylamino, heteroaryloxy, arylsulfonylamino, heteroarylsulfonylamino, arylthio, arylsulfinyl, arylsulfonyl, alkylthio, alkylsulfinyl, alkylsulfonyl, heteroarylthio, heteroarylsulfinyl, heteroarylsulfonyl, —PO($R^{13}$)($R^{14}$), (where $R^{13}$ and $R^{14}$ are independently alkyl, aryl, alkoxy, aryloxy, heteroaryl, heteroarylalkyl, heteroaryloxy, heteroarylalkoxy, cycloheteroalkyl, cycloheteroalkylalkyl, cycloheteroalkoxy, or cycloheteroalkylalkoxy); $R^1$ can also be aminocarbonyl (where the amino may optionally be substituted with one or two aryl, alkyl or heteroaryl groups); cyano, 1,1-(alkoxyl or aryloxy)$_2$alkyl (where the two aryl or alkyl substituents can be independently defined, or linked to one another to form a ring, such as 1,3-dioxane or 1,3-dioxolane, connected to $L^1$ (or $L^2$ in the case of $R^2$) at the 2-position); 1,3-dioxane or 1,3-dioxolane connected to $L^1$ (or $L^2$ in the case of $R^2$) at the 4-position.

The $R^1$ group may have from one to four substituents, which can be any of the $R^3$ groups or $R^1$ groups, and any of the preferred $R^1$ substituents set out below.

$R^1$ may be substituted with the following preferred substituents: alkylcarbonylamino, cycloalkylcarbonylamino, arylcarbonylamino, heteroarylcarbonylamino, alkoxycarbonylamino, aryloxycarbonylamino, heteroaryloxylcarbonylamino, uriedo (where the uriedo nitrogens may be substituted with alkyl, aryl or heteroaryl), heterocyclylcarbonylamino (where the heterocycle is connected to the carbonyl group via a nitrogen or carbon atom), alkylsulfonylamino, arylsulfonylamino, heteroarylsulfonylamino,

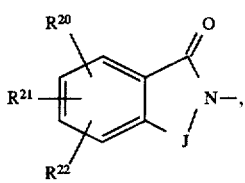

where J is: CHR²³,

—C—, —CH—CH— or —C=C—;
‖     |   |        |  |
O    R²⁴ R²⁵     R²⁴ R²⁵

$R^{23}$, $R^{24}$ and $R^{25}$ are independently hydrogen, alkyl, alkenyl, alkynyl, aryl, arylalkyl, heteroaryl, heteroarylalkyl, cycloalkyl, or cycloalkylalkyl;

$R^{20}$, $R^{21}$, $R^{22}$ are independently hydrogen, halo, alkyl, alkenyl, alkoxy, aryloxy, aryl, arylalkyl, alkylmercapto, arylmercapto, cycloalkyl, cycloalkylalkyl, heteroaryl, heteroarylalkyl, hydroxy or haloalkyl; and these preferred substituents may either be directly attached to $R^1$, or attached via an alkylene chain at an open position.

$R^2$ is the same or different from $R^1$ and is independently any of the groups set out for $R^1$, H or polyhaloalkyl (such as $CF_3CH_2$, $CF_3CF_2CH_2$ or $CF_3$), and may be substituted with one to four of any of the groups defined for $R^3$, or any of the substituents preferred for $R^1$.

$L^1$ is a linking group containing from 1 to 10 carbons in a linear chain (including alkylene, alkenylene or alkynylene), which may contain, within the linking chain any of the following: one or two alkenes, one or two alkynes, an oxygen, an amino group optionally substituted with alkyl or aryl, an oxo group; and may be substituted with one to five alkyl or halo groups (preferably F).

$L^2$ may be the same or different from $L^1$ and may independently be any of the $L^1$ groups set out above or a singe bond.

$R^3$, $R^{3'}$, $R^4$ and $R^{4'}$ may be the same or different and are independently selected from H, halogen, $CF_3$, haloalkyl, hydroxy, alkoxy, alkyl, aryl, alkenyl, alkenyloxy, alkynyl, alkynyloxy, alkanoyl, nitro, amino, thiol, alkylthio, alkylsulfinyl, alkylsulfonyl, carboxy, alkoxycarbonyl, aminocarbonyl, alkylcarbonyloxy, alkylcarbonylamino, cycloheteroalkyl, cyano, Ar, Ar-alkyl, ArO, Ar-amino, Ar-thio, Ar-sulfinyl, Ar-sulfonyl, Ar-carbonyl, Ar-carbonyloxy or Ar-carbonylamino, wherein Ar is aryl or heteroaryl and Ar may optionally include 1, 2 or 3 additional rings fused to Ar;

$R^{3a}$ and $R^{3b}$ are the same or different and are independently any of the $R^3$ groups except hydroxy, nitro, amino or thio;

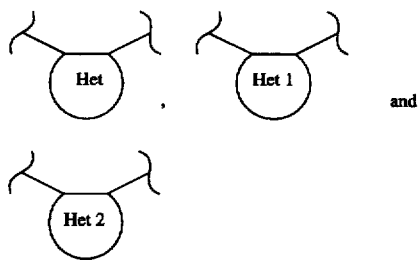

are the same or different and independently represent a 5 or 6 membered heteroaryl ring which may contain 1, 2, 3 or 4 heteroatoms in the ring which are independently N, S or O; and including N-oxides.

X (in the fluorenyl type ring) is a bond, or is one of the following groups:

 (1)

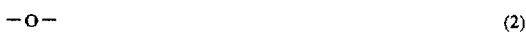 (2)

 (3)

 (4)

 (5)

 (6)

 (7)

wherein
Y is O, N—$R^6$ or S;
n' is 0, 1 or 2;
$R^6$ is H, lower alkyl, aryl, —C(O)—$R^{11}$ or —C(O)—O—$R^{11}$;
$R^7$ and $R^8$ are the same or different and are independently H, alkyl, aryl, halogen, —O—$R^{12}$, or
$R^7$ and $R^8$ together can be oxygen to form a ketone;
$R^9$, $R^{10}$, $R^{9'}$ and $R^{10'}$ are the same or different and are independently H, lower alkyl, aryl or —O—$R^{11}$;
$R^{9''}$ and $R^{10''}$ are the same or different and are independently H, lower alkyl, aryl, halogen or —O—$R^{11}$;
$R^{11}$ is alky or aryl;
$R^{12}$ is H, alkyl or aryl.

The following provisos apply to formula I compounds:

(a) when $R^1$ is unsubstituted alkyl or unsubstituted arylalkyl, $L^1$ cannot contain amino;

(b) when $R^1$ is alkyl, $L^1$ cannot contain amino and oxo in adjacent positions (to form an amido group);

(c) when $R^2L^2A$- is $H_2N$—, $R^1L^1$ cannot contain amino;

(d) when $R^1$ is cyano, $L^1$ must have more than 2 carbons;

(e) $R^1L^1$ must contain at least 3 carbons.

With respect to compounds of the invention IA and IB, $R^2L^2$ cannot have an O or N atom directly attached to $S=(O)_q$ or $CR^x(OH)$, and for IA, $R^2L^2$ cannot be H.

With respect to compounds of the invention I, IA and IB, where $R^1$ or $R^2$ is cycloheteroalkyl, $R^1$ or $R^2$ is exclusive of 1-piperidinyl, 1-pyrrolidinyl, 1-azetidinyl or 1-(2-oxopyrrolidinyl).

The pharmaceutically acceptable salts of the compounds of formulae I, IA and IB include alkali metal salts such as lithium, sodium or potassium, alkaline earth metal salts such as calcium or magnesium, as well as zinc or aluminum and other cations such as ammonium, choline, diethanolamine, ethylenediamine, t-butylamine, t-octylamine, dehydroabietylamine, as well as pharmaceutically acceptable anions such as chloride, bromide, iodide, tartrate, acetate, methanesulfonate, maleate, succinate, glutarate, and salts of naturally occurring amino acids such as arginine, lysine, alanine and the like, and prodrug esters thereof.

In addition, in accordance with the present invention, a method for preventing, inhibiting or treating atherosclerosis, pancreatitis or obesity is provided, wherein a compound of formula I, IA or IB as defined hereinbefore (and including compounds excluded by provisos (a), (b), (c), (d) and (e) set out hereinbefore) is administered in an amount which decreases the activity of microsomal triglyceride transfer protein.

Furthermore, in accordance with the present invention, a method is provided for lowering serum lipid levels, cholesterol and/or triglycerides, or inhibiting and/or treating hyperlipemia, hyperlipidemia, hyperlipoproteinemia, hypercholesterolemia hypertriglyceridemia and/or hyperglycemia, non-insulin dependent diabetes (Type II diabetes), wherein a compound of formula I, IA or IB as defined hereinbefore (and including compounds excluded by provisos (a), (b), (c), (d) and (e) set out hereinbefore) is administered in an amount which decreases the activity of microsomal triglyceride transfer protein.

DETAILED DESCRIPTION OF THE INVENTION

The following definitions apply to the terms as used throughout this specification, unless otherwise limited in specific instances.

The term "MTP" refers to a polypeptide or protein complex that (1) if obtained from an organism (e. g., cows, humans, etc.), can be isolated from the microsomal fraction of homogenized tissue; and (2) stimulates the transport of triglycerides, cholesterol esters, or phospholipids from synthetic phospholipid vesicles, membranes or lipoproteins to synthetic vesicles, membranes, or lipoproteins and which is distinct from the cholesterol ester transfer protein [Drayna et al., Nature 327, 632–634 (1987)] which may have similar catalytic properties.

The phrase "stabilizing" atherosclerosis as used in the present application refers to slowing down the development of and/or inhibiting the formation of new atherosclerotic lesions.

The phrase "causing the regression of" atherosclerosis as used in the present application refers to reducing and/or eliminating atherosclerotic lesions.

Unless otherwise indicated, the term "lower alkyl", "alkyl" or "alk" as employed herein alone or as part of another group includes both straight and branched chain hydrocarbons, containing 1 to 40 carbons, preferably 1 to 20 carbons, more preferably 1 to 12 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1 to 4 substituents which may be any of the $R^3$ groups, or the $R^1$ substituents set out herein.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclicalkyl, bicyclicalkyl and tricyclicalkyl, containing a total of 3 to 20 carbons forming the rings, preferably 4 to 12 carbons, forming the ring and which may be fused to 1 aromatic ring as described for aryl, which include cyclopropyl, cyclobutyl, cyclopentyl, cyclohexyl, cycloheptyl, cyclooctyl, cyclodecyl and cyclododecyl, cyclohexenyl,

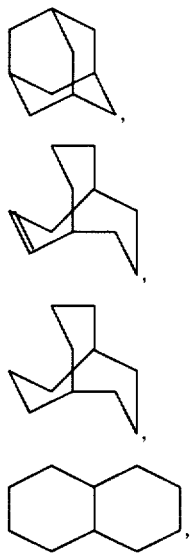

any of which groups may be optionally substituted with 1 to 4 substituents which may be any of the $R^3$ groups, or the $R^1$ substituents set out herein.

The term "cycloalkenyl" as employed herein alone or as part of another group refers to cyclic hydrocarbons containing 5 to 20 carbons, preferably 6 to 12 carbons and 1 or 2 double bonds. Exemplary cycloalkenyl groups include cyclopentenyl, cyclohexenyl, cycloheptenyl, cyclooctenyl, cyclohexadienyl, and cycloheptadienyl, which may be optionally substituted as defined for cycloalkyl.

The term "polycycloalkyl" as employed herein alone or as part of another group refers to a bridged multicyclic group containing 5 to 20 carbons and containing 0 to 3 bridges, preferably 6 to 12 carbons and 1 or 2 bridges. Exemplary polycycloalkyl groups include [3.3.0]-bicyclooctanyl, adamantanyl, [2.2.1]-bicycloheptanyl, [2.2.2]-bicyclooctanyl and the like and may be optionally substituted as defined for cycloalkyl.

The term "polycycloalkenyl" as employed herein alone or as part of another group refers to a bridged multicyclic group containing 5 to 20 carbons and containing 0 to 3 bridges and containing 1 or 2 double bonds, preferably 6 to 12 carbons and 1 or 2 bridges. Exemplary polycycloalkyl groups include [3.3.0]-bicyclooctenyl, [2.2.1]-bicycloheptenyl, [2.2.2]-bicyclooctenyl and the like and may be optionally substituted as defined for cycloalkyl.

The term "aryl" as employed herein alone or as part of another group refers to monocyclic and bicyclic aromatic groups containing 6 to 10 carbons in the ring portion (such as phenyl or naphthyl) and may optionally include one to three additional rings fused to aryl (such as aryl, cycloalkyl or heteroaryl rings) and may be optionally substituted through available carbon atoms with 1, 2, or 3 groups selected from hydrogen, halo, haloalkyl, alkyl, haloalkyl, alkoxy, haloal-koxy, alkenyl, trifluoromethyl, trifluoromethoxy, alkynyl, cycloalkylalkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl or any of the other aryl compounds mentioned in the definitions), thiol, alkylthio, arylthio, hetero-arylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl or any of the $R^3$ groups, or the $R^1$ substituents set out herein.

The term "aralkyl", "aryl-alkyl" or "aryllower alkyl" as used herein alone or as part of another group refers to alkyl groups as discussed above having an aryl substituent, such as benzyl or phenethyl, or naphthylpropyl, or an aryl as defined above.

The term "lower alkoxy", "alkoxy", "aryloxy" or "aralkoxy" as employed herein alone or as part of another group includes any of the above alkyl, aralkyl or aryl groups linked to an oxygen atom.

The term "amino" as employed herein alone or as part of another group may optionally be substituted with one or two substituents such as alkyl, aryl, arylalkyl, heteroaryl, heteroarylalkyl, cycloheteroalkyl, cycloheteroalkylalkyl and/or cycloalkyl.

The term "lower alkylthio", alkylthio", "arylthio" or "aralkylthio" as employed herein alone or as part of another group includes any of the above alkyl, aralkyl or aryl groups linked to a sulfur atom.

The term "lower alkylamino", "alkylamino", "arylamino", or "arylalkylamino" as employed herein alone or as part of another group includes any of the above alkyl, aryl or arylalkyl groups linked to a nitrogen atom.

The term "acyl" as employed herein by itself or part of another group, as defined herein, refers to an organic radical linked to a carbonyl

group; examples of acyl groups include alkanoyl, alkenoyl, aroyl, aralkanoyl, heteroaroyl, cycloalkanoyl, and the like.

The term "alkanoyl" as used herein alone or as part of another group refers to alkyl linked to a carbonyl group.

Unless otherwise indicated, the term "lower alkenyl" or "alkenyl" as used herein by itself or as part of another group refers to straight or branched chain radicals of 2 to 20 carbons, preferably 3 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonylamino, nitro, cyano, thiol, alkylthio or any of the $R^3$ groups, or the $R^1$ substituents set out herein.

Unless otherwise indicated, the term "lower alkynyl" or "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, or any of the $R^3$ groups, or the $R^1$ substituents set out herein.

The term "alkylene" as employed herein alone or as part of another group refers to alkyl groups as defined above having single bonds for attachment to other groups at two different carbon atoms and may optionally be substituted as defined above for "alkyl".

The terms "alkenylene" and "alkynylene" as employed herein alone or as part of another group refer to alkenyl groups as defined above and alkynyl groups as defined above, respectively, having single bonds for attachment at two different carbon atoms.

Suitable alkylene, alkenylene or alkynylene groups or $(CH_2)_m$, $(CH_2)_n$ or $(CH_2)_p$ (which may include alkylene, alkenylene or alkynylene groups) as defined herein, may optionally include 1, 2, or 3 substituents which include any of the $R^3$ groups, or the $R^1$ substituents set out herein.

Examples of alkylene, alkenylene and alkynylene include

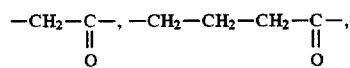

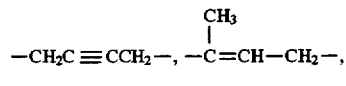

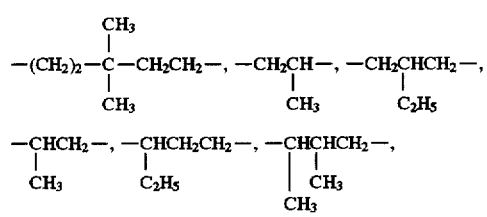

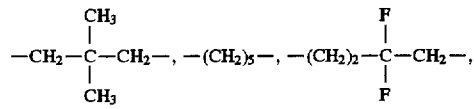

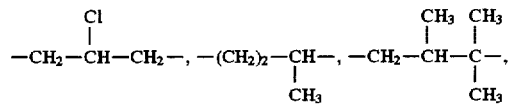

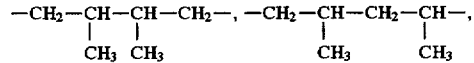

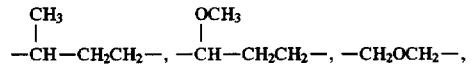

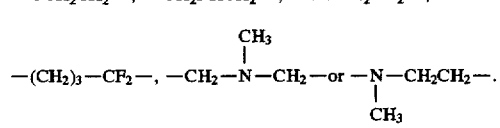

The term "halogen" or "halo" as used herein alone or as part of another group refers to chlorine, bromine, fluorine, and iodine as well as $CF_3$, with chlorine or fluorine being preferred.

The term "metal ion" refers to alkali metal ions such as sodium, potassium or lithium and alkaline earth metal ions such as magnesium and calcium, as well as zinc and aluminum.

The term "cycloheteroalkyl" as used herein alone or as part of another group refers to a 5-, 6- or 7-membered saturated or partially unsaturated ring which includes 1 to 2 hetero atoms such as nitrogen, oxygen and/or sulfur, linked through a carbon atom or a heteroatom, where possible, optionally via the linker $(CH_2)_p$ (which is defined above), such as

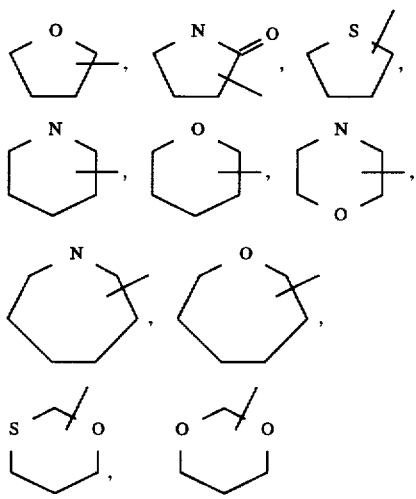

and the like. The above groups may include 1 to 4 substituents such as alkyl, halo, oxo and/or any of of the $R^3$ groups, or the $R^1$ substituents set out herein. In addition, any of the above rings can be fused to a cycloalkyl, aryl, heteroaryl or cycloheteroalkyl ring.

The term "heteroaryl" as used herein alone or as part of another group refers to a 5- or 6-membered aromatic ring which includes 1, 2, 3 or 4 hetero atoms such as nitrogen, oxygen or sulfur, and such rings fused to an aryl, cycloalkyl, heteroaryl or cycloheteroalkyl ring (e.g. benzothiophenyl, indolyl), and includes possible N-oxides, such as

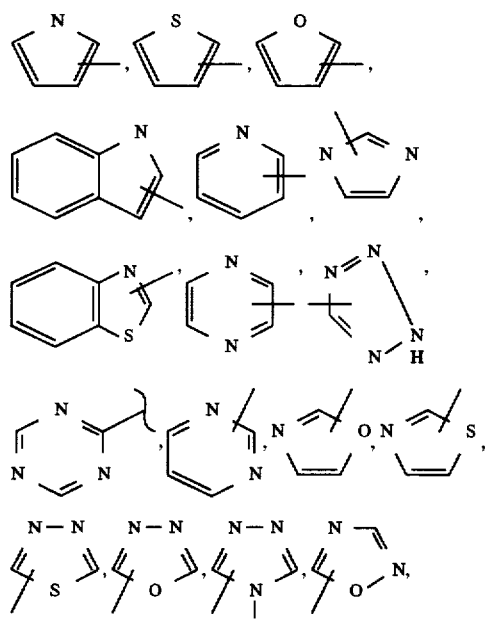

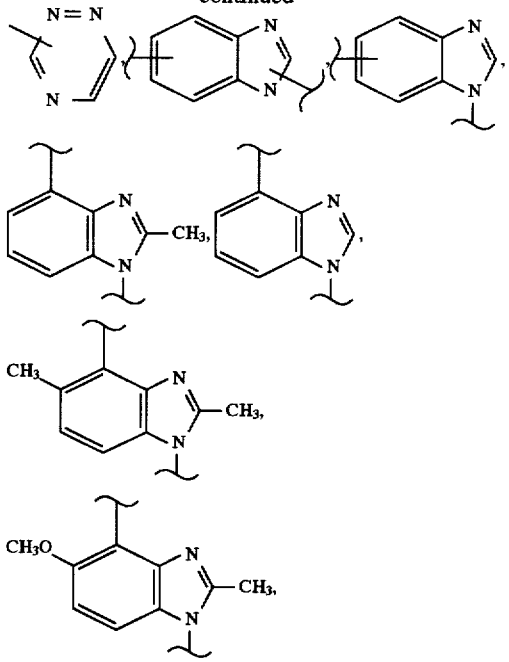

and the like.

Ar may be either aryl or heteroaryl as defined above.

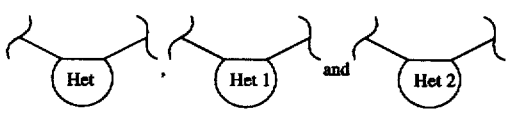

are the same or different, as defined hereinbefore, and are attached to the central ring of the indenyl or fluorenyl type group at adjacent positions (that is, ortho or 1,2-positions). Examples of such groups include

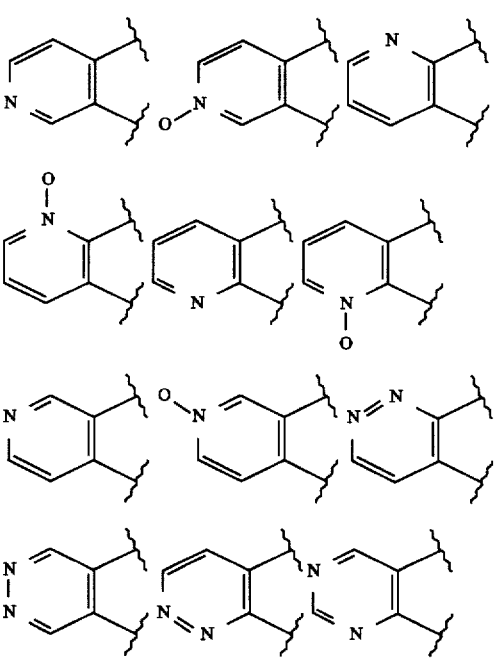

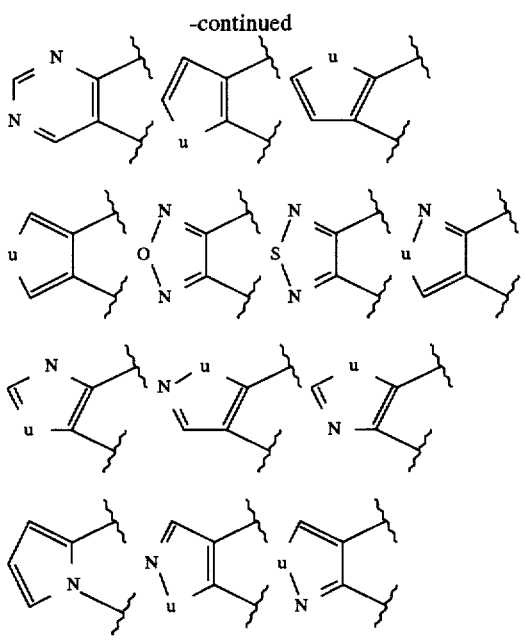

wherein u is selected from O, S, and $NR^{7a}$; $R^{7a}$ is H, lower alkyl, aryl, —C(O)$R^{7b}$, —C(O)O$R^{7b}$; $R^{7b}$ is alkyl or aryl.

The heteroaryl groups including the above groups may optionally include 1 to 4 substituents such as any of the $R^3$ groups, or the $R^1$ substituents set out herein. In addition, any of the above rings can be fused to a cycloalkyl, aryl, heteroaryl or cycloheteroalkyl ring.

The term cycloheteroalkylalkyl" as used herein alone or as part of another group refers to cycloheteroalkyl groups as defined above linked through a C atom or heteroatom to a $(CH_2)_p$ chain.

The term "heteroarylalkyl", or "heteroarylalkenyl" as used herein alone or as part of another group refers to a heteroaryl group as defined above linked through a C atom or heteroatom to a —$(CH_2)_p$-chain, alkylene or alkenylene as defined above.

The term "polyhaloalkyl" as used herein refers to an "alkyl" group as defined above which includes from 2 to 9, preferably from 2 to 5, halo substituents, such as F or Cl, preferably F, such as $CF_3CH_2$, $CF_3$ or $CF_3CF_2CH_2$.

Preferred are compounds of formula I wherein A is NH, B is

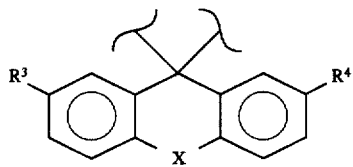

X is a bond, oxygen or sulfur; $R^3$ and $R^4$ are independently H or F.

Preferred $R^1$ groups are aryl, preferably phenyl, heteroaryl, preferably imidazoyl, benzimidazolyl, indolyl, or pyridyl (preferably substituted with one of the preferred $R^1$ substituents: arylcarbonylamino, heteroarylcarbonylamino, cycloalkylcarbonylamino, alkoxycarbonylamino, alkylsulfonylamino, arylsulfonylamino, heteroarylsulfonylamino), PO(OAlkyl)$_2$, heteroarylthio, benzthiazole-2-thio, imidazole-2-thio, alkyl, or alkenyl, cycloalkyl such as cyclohexyl, or 1,3-dioxan-2-yl.

Preferred $R^2$ groups are alkyl, polyfluoroalkyl (such as 1,1,1-trifluoroethyl), alkenyl, aryl or heteroaryl (preferably substituted with one of the preferred $R^1$ substituents above), or PO(OAlkyl)$_2$.

If $R^2$ is alkyl, 1,1,1-trifluoroethyl, or alkenyl, it is preferred that $R^1$ is other than alkyl or alkenyl.

It is preferred that $L^1$ contains 1 to 5 atoms in the linear chain and $L^2$ is a bond or lower alkylene.

Preferred embodiments of formula IA and formula IB compounds of the invention include those where B, $L^1$, $L^2$, $R^1$ and $R^2$ are as set out with respect to the preferred embodiments of the formula I compounds, q is 0 or 2 and $R^x$ is H.

Also preferred are compounds of the structure

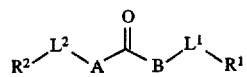

where B is

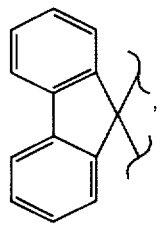

A is NH, $L^2$ is a bond, $R^2$ is $CF_3CH_2$, $L^1$ is —$CH_2CH_2CH_2$— or —$CH_2CH_2CH_2CH_2$—, and $R^1$ is heteroaryl which is a 5-membered aromatic ring which includes 2 nitrogens, which ring is fused to an aryl ring and is substituted on the aryl moiety. Examples of preferred $R^1$ groups include substituted benzimidazole groups including

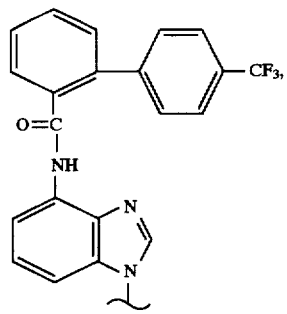

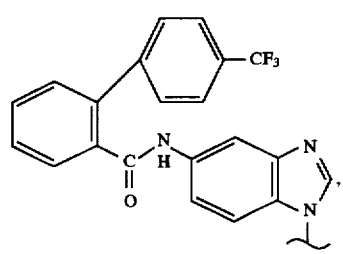

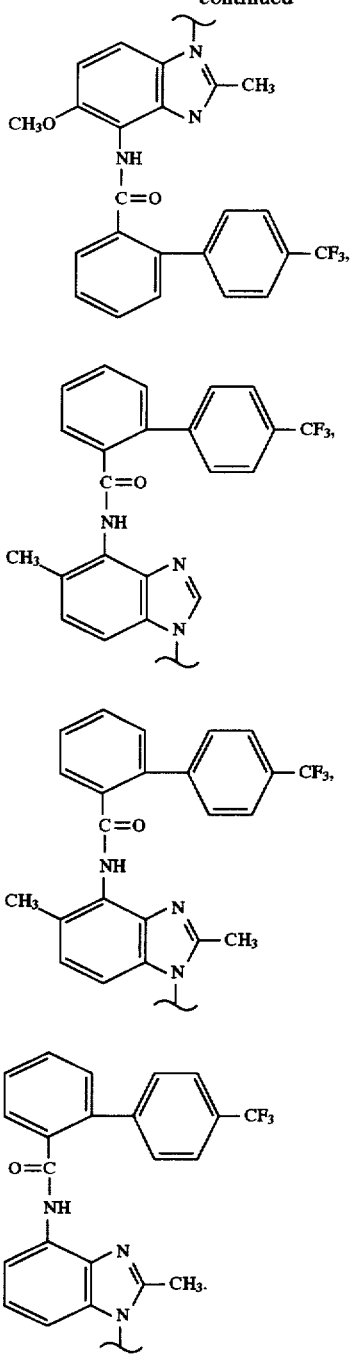

The compounds of formulae I, IA and IB may be prepared by the exemplary processes described in the following reaction schemes. Exemplary reagents and procedures for these reactions appear hereinafter and in the working Examples.

Reaction Scheme 1 (Amides)

Preparations of Compounds of Formula I where A is —N—
                                                          |
                                                          R⁵

-continued
Reaction Scheme 1 (Amides)

Scheme 1A

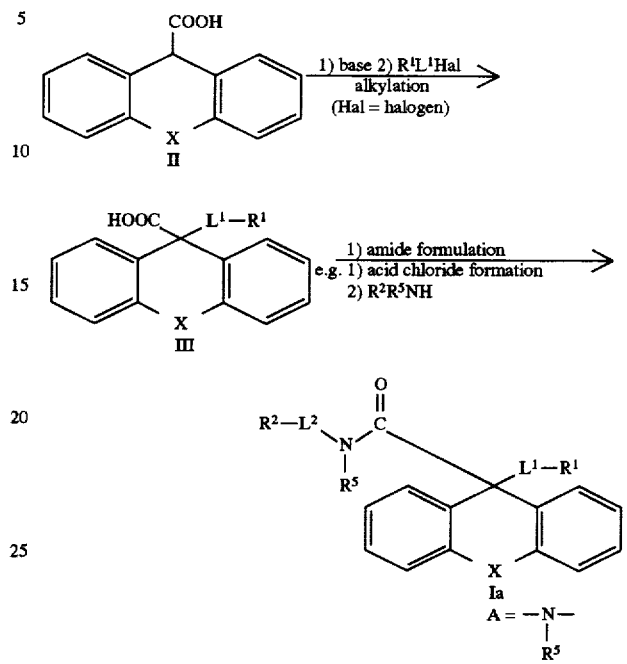

Scheme 1B

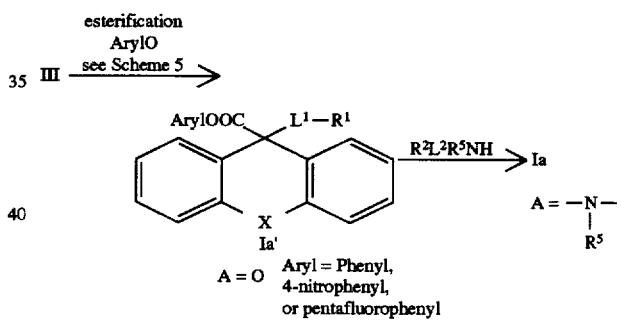

It will be appreciated that in the above reactions and the reactions to follow, unless otherwise indicated, the moiety "B" in the starting materials, intermediates and final products is set out as

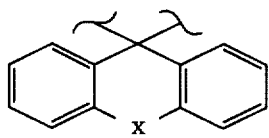

for purposes of illustration only.

It will be appreciated that the "B" moiety in the starting materials, intermediates and final products in all reactions set forth herein, unless indicated to the contrary may be any of the fluorenyl-type groups

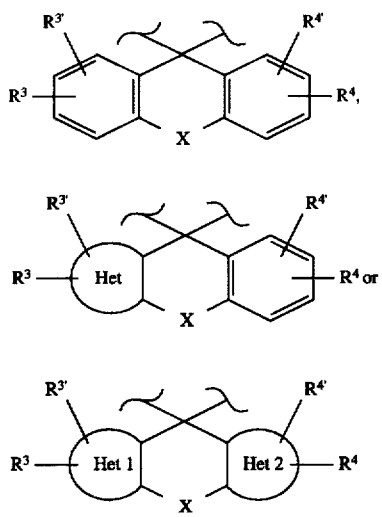

as well as any of indenyl-type groups

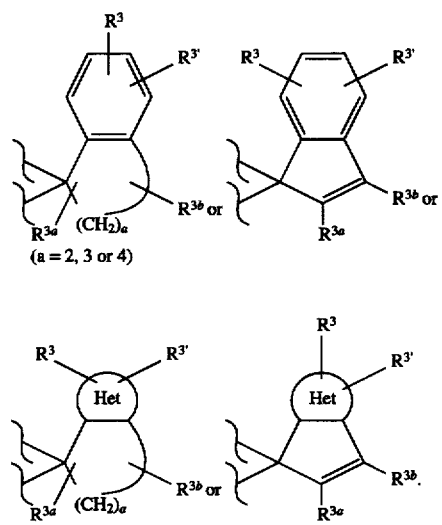

The above B moieties (including all fluorenyl-type groups and all indenyl-type groups) are collectively referred to as "fluorenyl-type" moieties. The use of the first fluorenyl-type group (as set out in the previous paragraph) in the Reaction Schemes is for purposes of illustration only; any of the 3 fluorenyl groups or 4 indenyl groups as set out above may be employed in any of the Reaction Schemes set out herein in place of

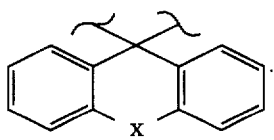

Scheme 1C
Preparation of Starting Acids II and Dianion III

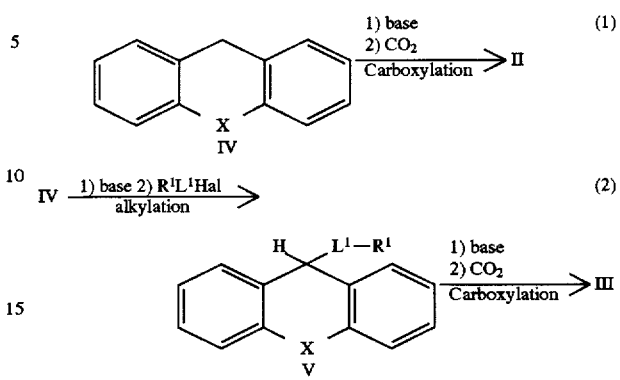

As indicated above, the starting Compound IV may also be

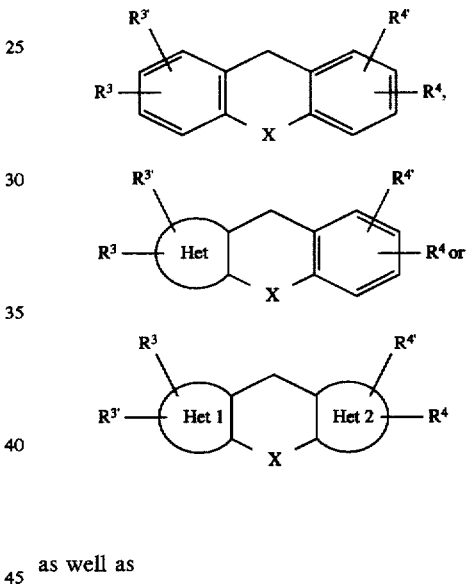

as well as

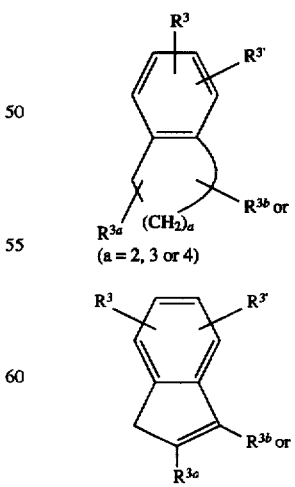

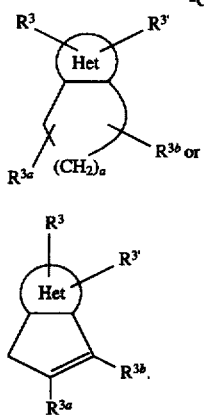

The above are collectively referred to "fluorenyl-type compounds".

As seen in Scheme 1A, in accordance with another aspect of the present invention, the solution of acid II in an inert organic solvent, such as tetrahydrofuran, dioxane or diethyl ether, at a reduced temperature of within the range of from about −40° C. to about room temperature, is treated with base such as potassium hydroxide, potassium tert-butoxide, lithium or potassium bis(trimethylsilylamide), or n-butyllithium in an inert organic solvent such as hexane, tetrahydrofuran or diethyl ether, while maintaining temperature of the reaction mixture below from about −40° C. to about room temperature. The reaction mixture is treated with $R^1$ halide such as an alkylhalide, for example, 3-phenylpropylbromide to form the alkylated product III.

The above dianion formation reaction is carried out employing a molar ratio of $R^1$halide:acid II of within the range from about 10:1 to about 0.5:1, preferably from about 2:1 to about 0.8:1.

Alternatively, the compound III may be prepared as shown in Scheme 1C(2) wherein fluorenyl-type compound IV is treated with base, such as described above, for example n-butyllithium, and then reacted with $R^1$halide, such as alkylhalide, as described above, to give compound V. Treatment of V with base, such as described hereinbefore such as n-butyl-lithium, followed by treatment of the reaction mixture with $CO_2$ (carboxylation) gives III.

As seen in Scheme 1C(1), acid II may be formed by treating fluorenyl-type compound IV with base (as described above with respect to Scheme 1C(2), followed by treatment with $CO_2$ (carboxylation), to form II.

The amide Ia of the invention is formed by treating III with thionyl chloride or oxalyl chloride in an inert organic solvent such as dichloromethane (optionally in the presence of dimethylformamide (DMF)) to form the acid chloride IIIA

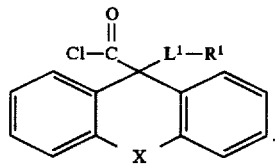  IIIA

Acid chloride IIIA, without separation from the reaction mixture, is treated with amine $(R^2L^2)R^5NH$ at a reduced temperature within the range from about −40° C. to about room temperature, to form the amide Ia.

In carrying out the above reaction to form amide Ia, the amine will be employed in a molar ratio to acid chloride IIIA within the range from about 4:1, to about 1:1, optionally in the presence of a tertiary amine base or other acid scavenger.

Alternatively, as seen in Scheme 1B, amide I may be prepared by esterifying III (as shown in Scheme 6) by reacting III with a phenol such as phenol, 4-nitrophenol, or pentafluorophenol and DCC (dicyclo-hexylcarbodiimide) or EDCI (1-(3-dimethylamino-propyl)-3-ethylcarbodiimide), optionally in the presence of HOBT (1-hydroxybenzotriazole) through the intermediary of an aryl ester such as phenyl, p-$NO_2$-phenyl or pentafluorophenyl, followed by treatment with a primary or secondary amine to give Ia.

In carrying out the above reaction, the amine will be employed in a molar ratio to ester within the range form about 10:1, to about 1:1.

Alternative formation of amide Ia from acid III and $R^2R^5NH$ can be carried out via standard literature procedures.

Reaction Scheme 2 (Amides)

Alternative Preparation of Compounds of Formula Ia where A is —N—$R^5$

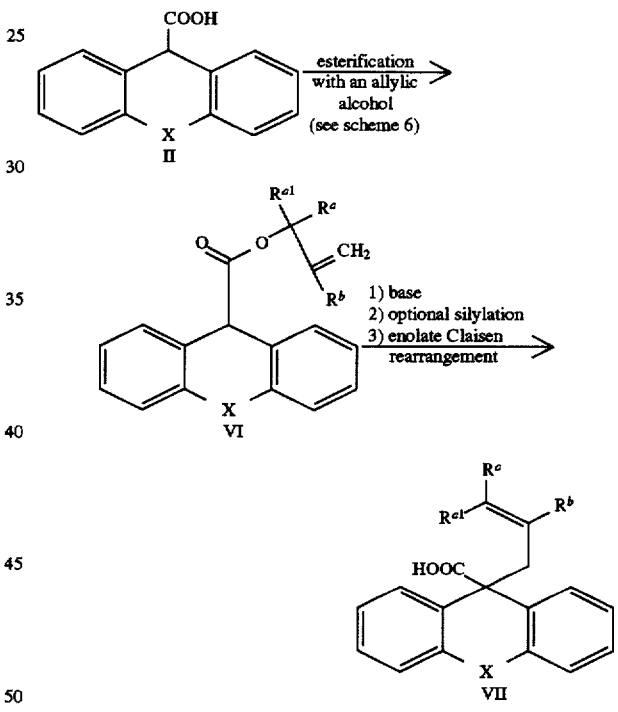

where $R^a$, $R^{a1}$, $R^b$ independently are H, alkyl, aryl, cycloalkyl or heteroaryl

As seen in Reaction Scheme 2, amides of the invention of structure I can also be prepared by esterifying acid II with an allylic alcohol (as described in Scheme 5), to form ester VI which is treated with base, such as lithium diisopropyl amide or potassium bis(trimethylsilylamide) (optionally in the presence of a triorganosilylchloride, such as trimethylsilylchloride), to give the enolate-Claisen rearrangement acid product VII. Acid VII is then converted to amide Ia of the invention employing conditions as described with respect to Scheme 1.

In carrying out the above reaction, the base treatment and enolate-Claisen rearrangement were performed at a temperature within the range of from about −20° to about 100° C., preferably from about 25° to about 80° C., to form Ia where $R^1L^1$ is as defined above in Scheme 2.

Reaction Scheme 3 (Amides)

Alternative Preparation of Compounds of Formula Ic where A = —N—
$\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad$|
$\quad\quad\quad\quad\quad\quad\quad\quad\quad\quad\quad\quad\quad\quad\quad\quad\quad\quad\quad\quad\quad\quad\quad\quad\quad\quad\quad\quad\quad\quad$R$^5$

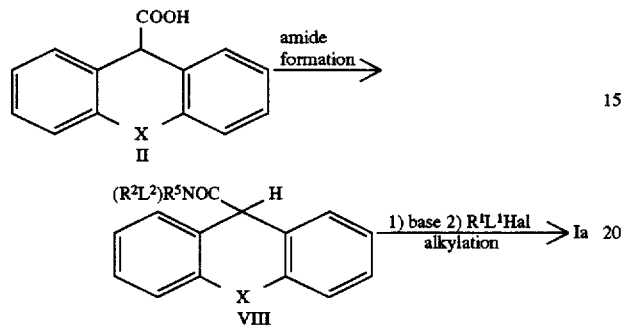

As seen in Reaction Scheme 3, compounds of structure I of the invention can be prepared optionally through amide formation (as described in Reaction Scheme 1 or via other known coupling procedures) from acid II to give compounds of formula VIII. Treatment of VIII with base, such as lithium diisopropylamide or n-BuLi, or potassium bis(trimethylsilyl)amide, followed by quenching the anion with an alkyl halide gives compounds of the formula I. In the specific case where $R^5$ is H, a dianion can be prepared requiring ≧ two equivalents of base; the dianion can be trapped with an alkyl halide to give I.

Reaction Scheme 4

Preparation of Ketones I (A is a bond)
Scheme 4A

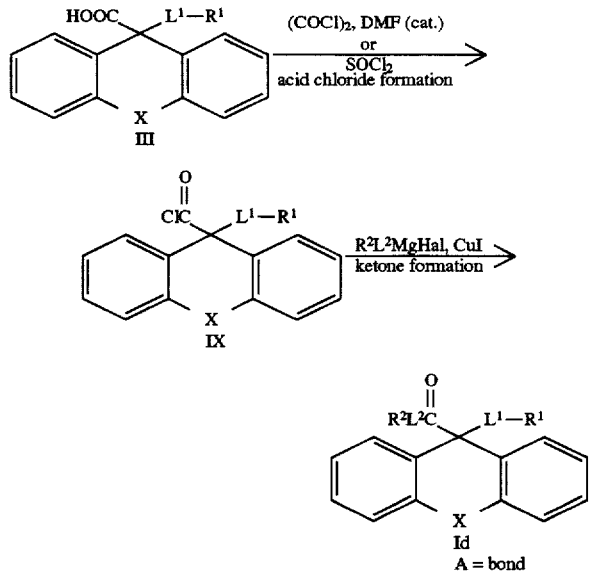

-continued
Reaction Scheme 4

Scheme 4B

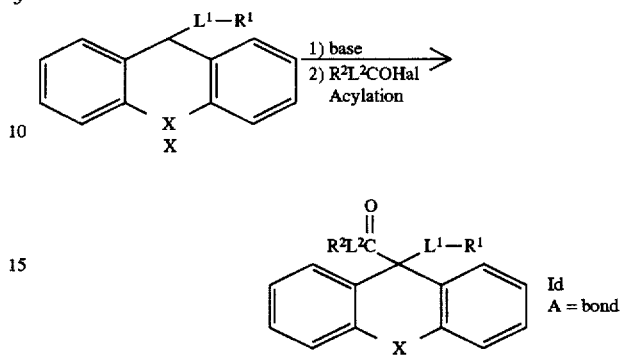

Compounds of the formula I of the invention wherein A=bond can be prepared as shown in Reaction Schemes 4A and 4B.

As seen in Scheme 4A, acid chloride formation under standard methods gives compound IX, which can be reacted with Grignard reagents and copper (I) iodide to give the compound of the invention I.

As seen in Scheme 4B, optionally, ketones can be formed by treatment of X with base, followed by acylation with an acid halide ($R^2L^2COHal$), preferably chloride or fluoride, to give compounds of the invention I.

Reaction Scheme 5 (Class Esters)

Preparations of Esters I (A — — O —)

Scheme 5A:

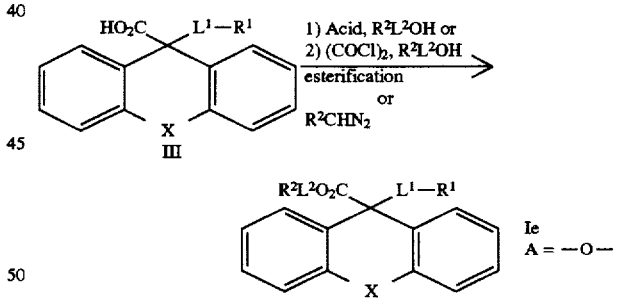

Scheme 5B:

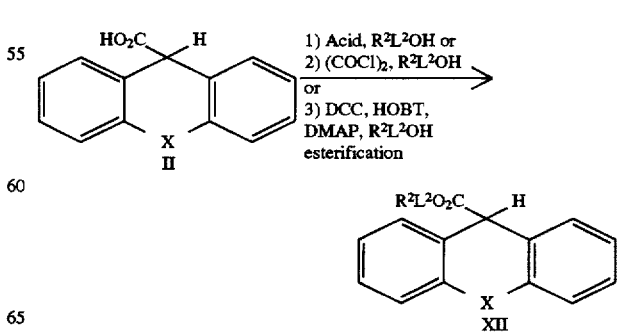

-continued
Reaction Scheme 5 (Class Esters)

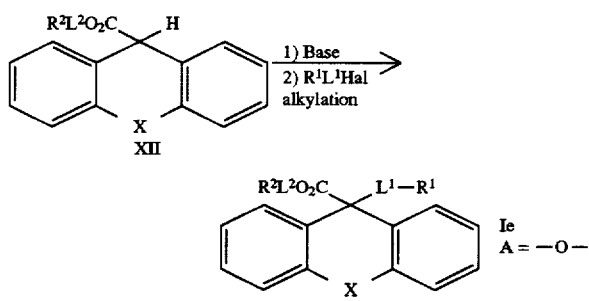

XII

Ie
A = —O—

As seen in Reaction Scheme 5A, compounds of formula I of the invention wherein A=oxygen can be prepared by an acid catalyzed esterification of acid III employing an acid such as $H_2SO_4$ or p-toluene-sulfonic acid in the presence of an alcohol such as allyl alcohol, ethanol or methanol. Alternatively, activation of the acid III to the acid chloride (with oxaly chloride or thionyl chloride) followed by treatment with an alcohol optionally in the presence of a tertiary amine base or other acid scavenger, gives compounds of formula I.

Various additional methods of activation include mixed anhydride formation (($CF_3COO)_2$ or i-BuOCOCl) or formation of the acylimidazole (carbonyldiimidazole) or with DCC and HOBT in the presence of DMAP (4-dimethylaminopyridine). These activated intermediates readily form esters upon treatment with alcohols.

Scheme 5B involves esterification of acids II to compound XII which is subjected to alkylation to give Ie.

Reaction Scheme 6 (Class Alcohols IB)

Preparation of Alcohols (IB)

Scheme 6a:

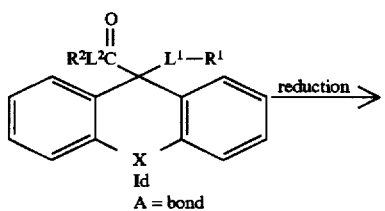

Id
A = bond

IBa

Scheme 6B:

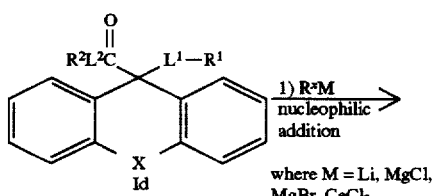

Id
A = bond
where M = Li, MgCl, MgBr, $CeCl_2$,

-continued
Reaction Scheme 6 (Class Alcohols IB)

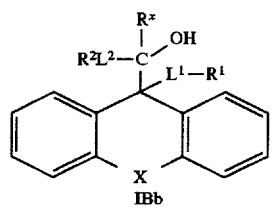

IBb

Compounds of formula Id, with A=bond, can be reduced by methods known in the art, such as sodium borohydride, to give alcohols of the invention IBa (Scheme 5A).

Ketones of formula Id can also be reacted with alkyl metals, such as alkyl lithium or Grignard reagents, to give the tertiary alcohols of the invention of structure IBb (Scheme 6B).

Reaction Scheme 7 (Amides from Isocyanates)

Preparation of Amides If (A is NH)
Scheme 8A

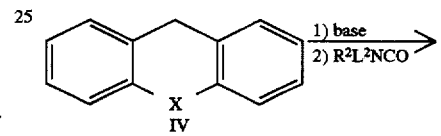

IV

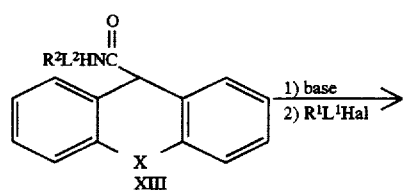

XIII

If
A = NH

Scheme 8B

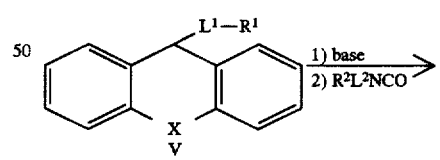

V

If
A = NH

Compounds of formula I where A is —NH— (amides) can be prepared by the methods shown in Reaction Scheme 7A from known compound IV. Treatment of compound IV with base, such as n-BuLi, followed by reacting the anion with an isocyanate gives compound XIII. Compound XIII can be further transformed to compounds of the formula If as shown above.
In a similar manner, as seen in Scheme 7B, compound V can be transformed to compounds of the formula If.
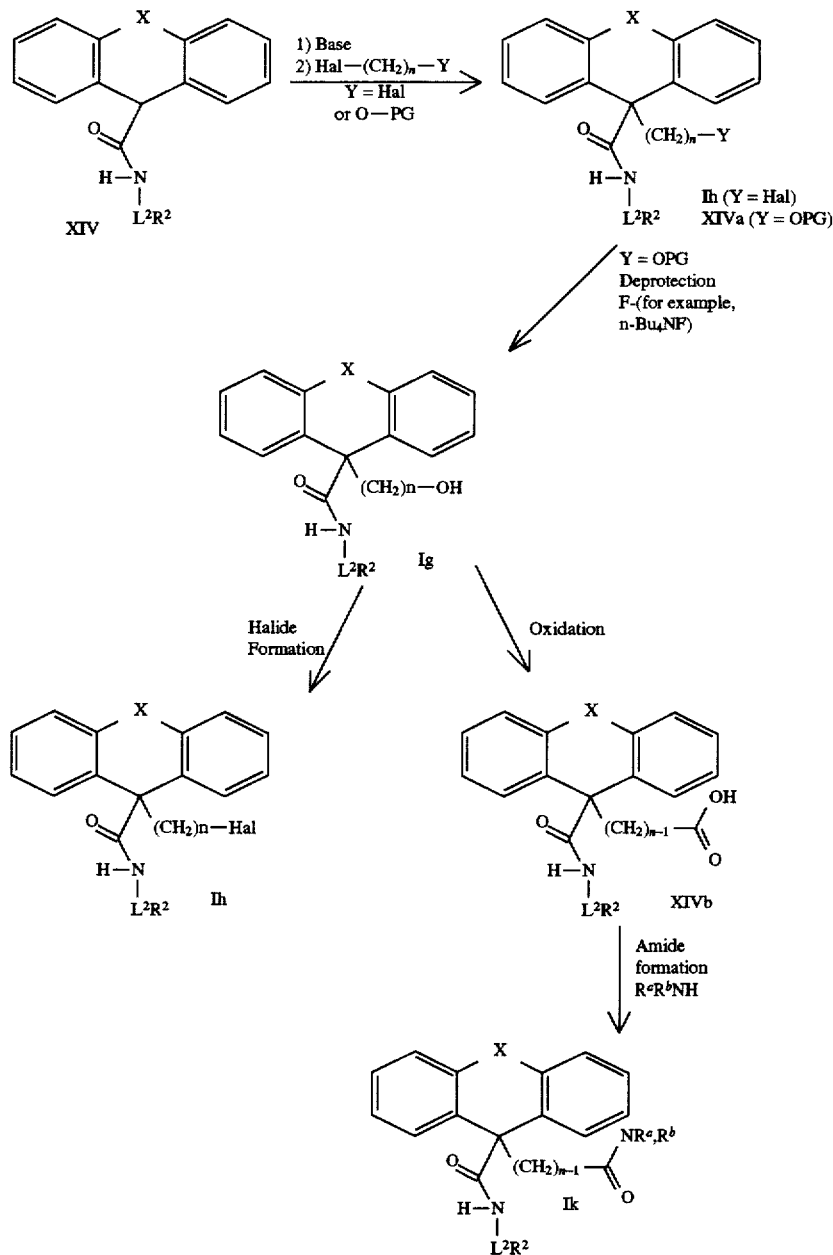
Reaction Scheme 8
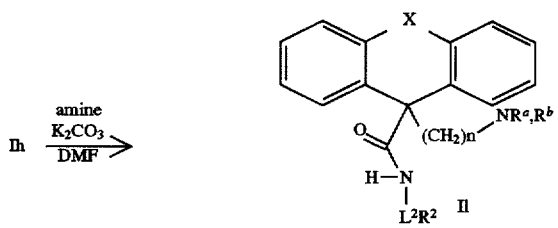

-continued
Reaction Scheme 8

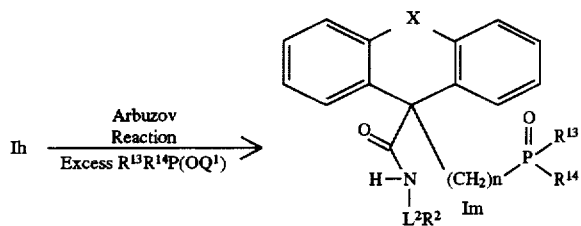

Ih $\xrightarrow[\text{Excess } R^{13}R^{14}P(OQ^1)]{\text{Arbuzov Reaction}}$

−20° C. to 180° C.
and $Q^1$ is alkyl, triorganosilyl (such as trimethylsilyl
or t-butyldimethylsilyl), H, the latter in the
presence of base such as butyllithium, sodium
hydride, or sodium bis-(trimethylsilylamide)

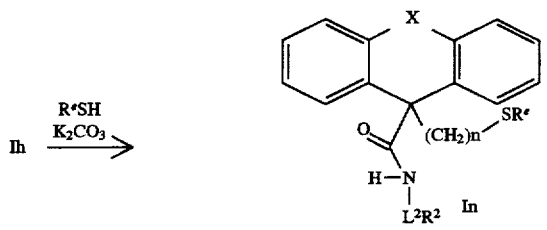

Ih $\xrightarrow[\text{K}_2\text{CO}_3]{\text{R}^e\text{SH}}$ ($R^e$ is alkyl, aryl, arylalkyl, heteroaryl,
2-benzthiazolyl), 2-imidazolyl)

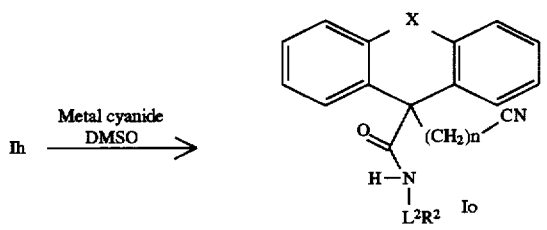

Ih $\xrightarrow[\text{DMSO}]{\text{Metal cyanide}}$

Scheme 8A
Alternate Scheme for Compound Im

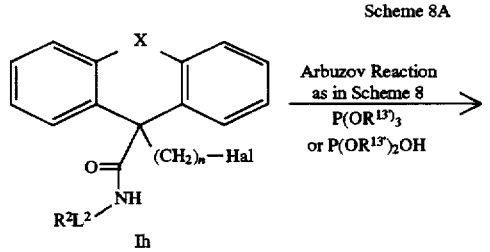

$\xrightarrow[\text{P(OR}^{13'})_3 \text{ or P(OR}^{13'})_2\text{OH}]{\text{Arbuzov Reaction as in Scheme 8}}$

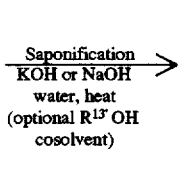

-continued
Scheme 8A
Alternate Scheme for Compound Im

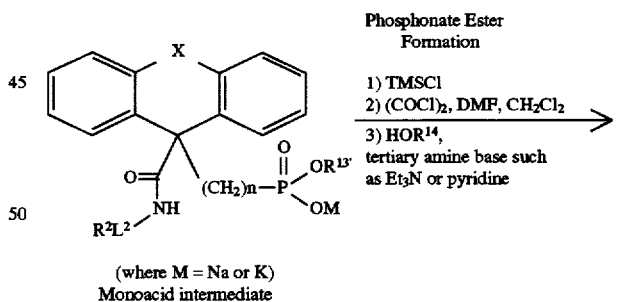

Phosphonate Ester Formation
1) TMSCl
2) (COCl)$_2$, DMF, CH$_2$Cl$_2$
3) HOR$^{14'}$, tertiary amine base such as Et$_3$N or pyridine (where M = Na or K)
Monoacid intermediate $\xrightarrow[\text{water, heat (optional R}^{13'}\text{OH cosolvent)}]{\text{Saponification KOH or NaOH}}$

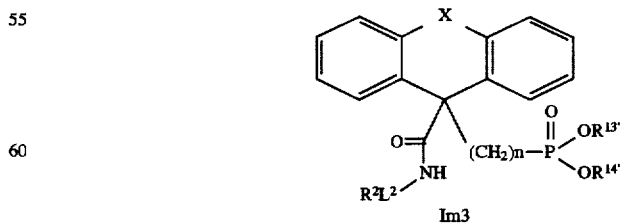

Scheme 8B

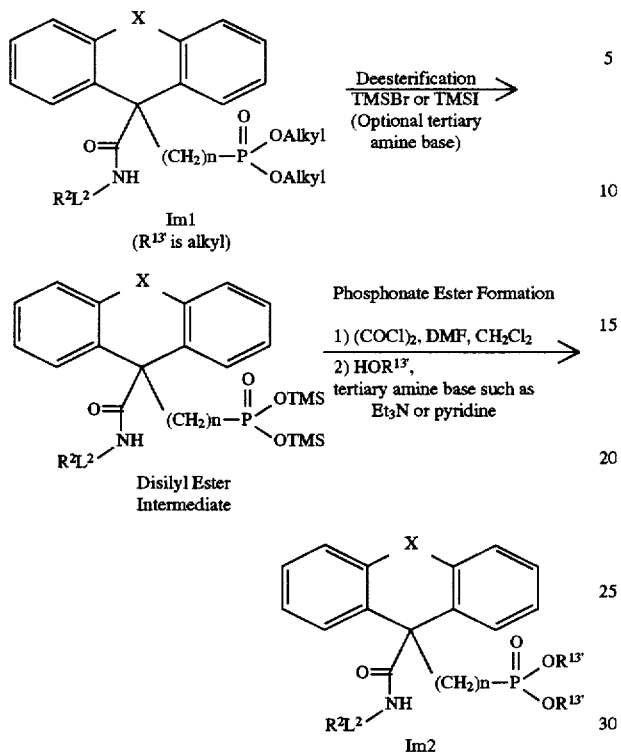

For example, the alcohol Iq can be converted to the halide Ih of the invention by either activation through the sulfonate ester (tosyl chloride, or mesyl chloride) and iodide displacement (NaI or KI in acetone or 2-butanone), or by reaction with triphenylphosphine, $I_2$ and imidazole. The iodide Ih can undergo an Arbuzov reaction to form phosphonates, phosphinates and phosphine oxides of the invention Im. The Arbuzov reaction can be accomplished with phosphites, phosphinites, and phosphonites (for example, $R^{13}R^{14}$POalkyl or $R^{13}R^{14}$POSi(alkyl)$_3$ or $R^{13}R^{14}$POH, the latter being in the presence of a base such as butyllithium, sodium hydride or sodium bis(trimethylsilylamide)) at temperatures within the range from about $-20°$ C. to about $180°$ C. Alternately, displacement reactions to form amines Il, thioethers In or nitriles Io can be easily accomplished. To form amines Il, iodide Ih, can be treated with amines in DMF with or without $K_2CO_3$. Thioethers In can also be formed under similar conditions. The nitrites If are prepared from either KCN or NaCN in hot DMSO. The alcohol can also be oxidized to a carboxylic acid. The acids can also be used as intermediates to form amides of the invention Ik by methods previously described. The sulfur atom of In can be oxidized under standard conditions to sulfoxide Ip or sulfone Iq.

Scheme 9
Sulfur Oxidation

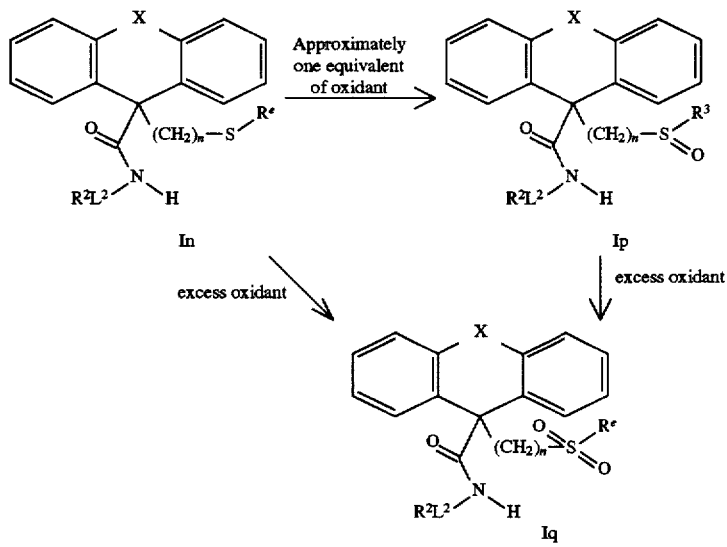

The above sulfur oxidations to the sulfoxide or sulfone are carried out by employing standard sulfur oxidation procedures in the art. Suitable oxidants include peracids (such as m-chloroperbenzoic acid) and sodium periodate.

Compounds I of the invention may be modified by the various transformations set out in Reaction Scheme 8. Protected alcohol XIVa can be converted into a wide variety of functional groups through the intermediacy of a halide Ih.

Reaction Scheme 10 (Preparation of Acetals)

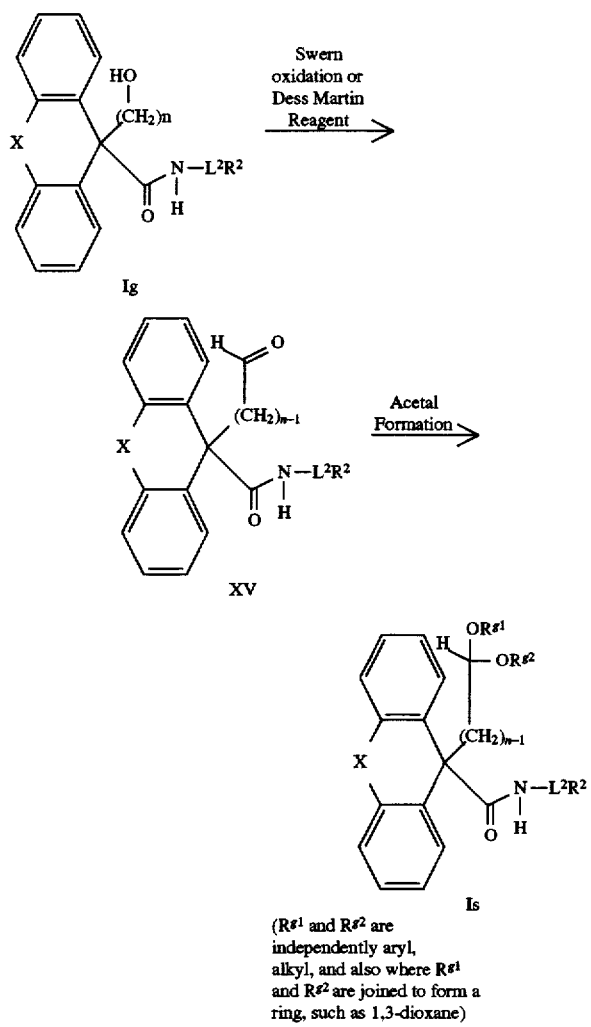

(R$^{s1}$ and R$^{s2}$ are independently aryl, alkyl, and also where R$^{s1}$ and R$^{s2}$ are joined to form a ring, such as 1,3-dioxane)

Acetals of the invention Is can be prepared from alcohol Ig by oxidation of the alcohol to the aldehyde XV. Prefered reagents to accomplish the transformation are either the Swern oxidation ((COCl)$_2$, DMSO, triethylamine) or Dess-Martin Periodinane. The aldehyde XV can be converted to the acetal Is with excess alcohol such as 1,3-propanediol or ethylene glycol in the presence of a catalytic amount of acid such as H$_2$SO$_4$ or p-toluenesulfonic acid, optionally in the presence of a dehydrating agent such as 4A sieves or trimethyl orthoformate.

Reaction Scheme 11
Preparation of Phosphonates in R$^2$

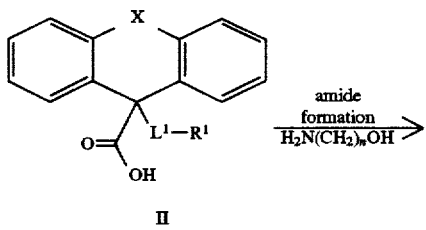

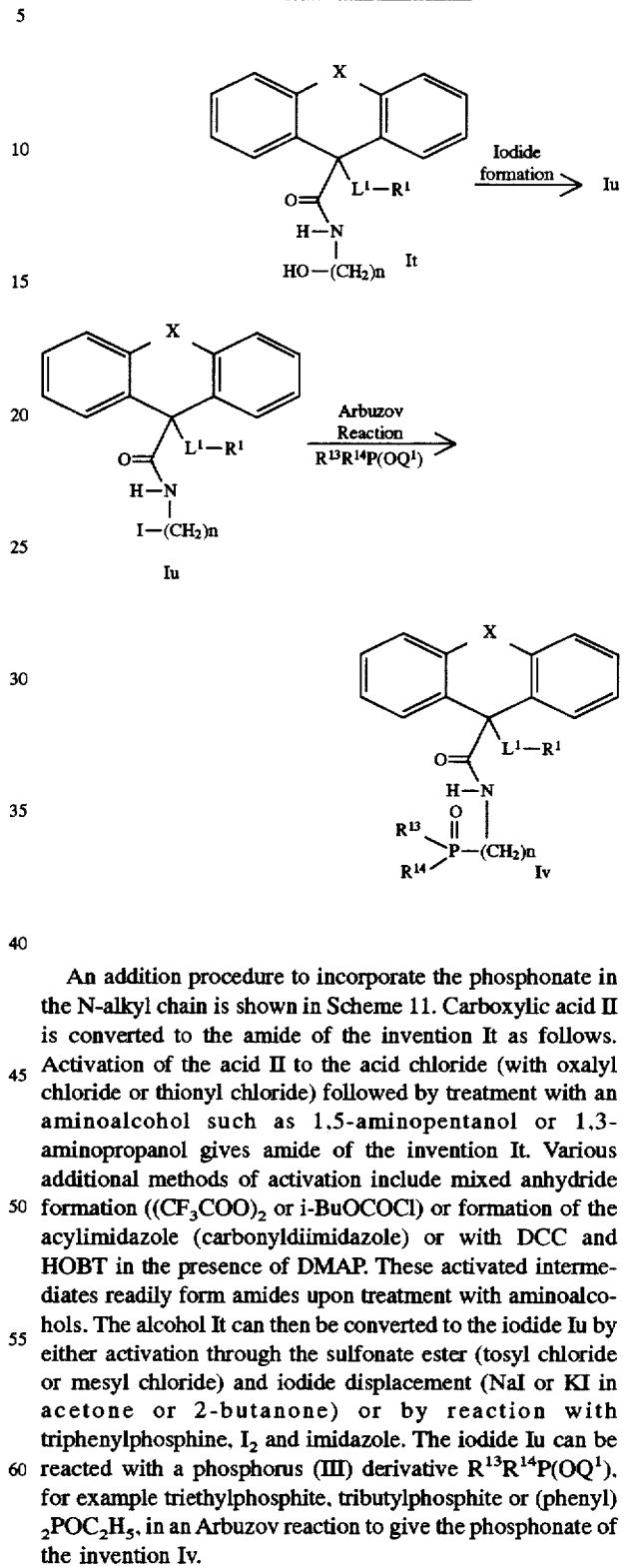

An addition procedure to incorporate the phosphonate in the N-alkyl chain is shown in Scheme 11. Carboxylic acid II is converted to the amide of the invention It as follows. Activation of the acid II to the acid chloride (with oxalyl chloride or thionyl chloride) followed by treatment with an aminoalcohol such as 1,5-aminopentanol or 1,3-aminopropanol gives amide of the invention It. Various additional methods of activation include mixed anhydride formation ((CF$_3$COO)$_2$ or i-BuOCOCl) or formation of the acylimidazole (carbonyldiimidazole) or with DCC and HOBT in the presence of DMAP. These activated intermediates readily form amides upon treatment with aminoalcohols. The alcohol It can then be converted to the iodide Iu by either activation through the sulfonate ester (tosyl chloride or mesyl chloride) and iodide displacement (NaI or KI in acetone or 2-butanone) or by reaction with triphenylphosphine, I$_2$ and imidazole. The iodide Iu can be reacted with a phosphorus (III) derivative R$^{13}$R$^{14}$P(OQ$^1$), for example triethylphosphite, tributylphosphite or (phenyl)$_2$POC$_2$H$_5$, in an Arbuzov reaction to give the phosphonate of the invention Iv.

Reaction Scheme 12
Preparation of Thioderivatives IA

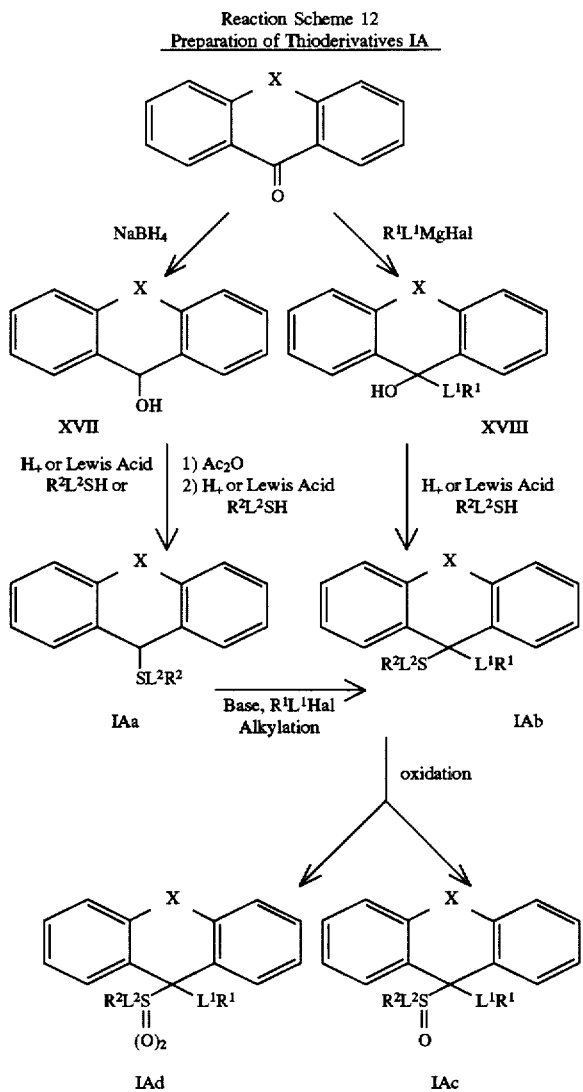

Reaction Scheme 13

Preparation of Compounds of Formula I where A is $-\underset{\underset{R^5}{|}}{N}-$
where $R^5$ is preferably H and $L^1$ is a linking group as defined above.

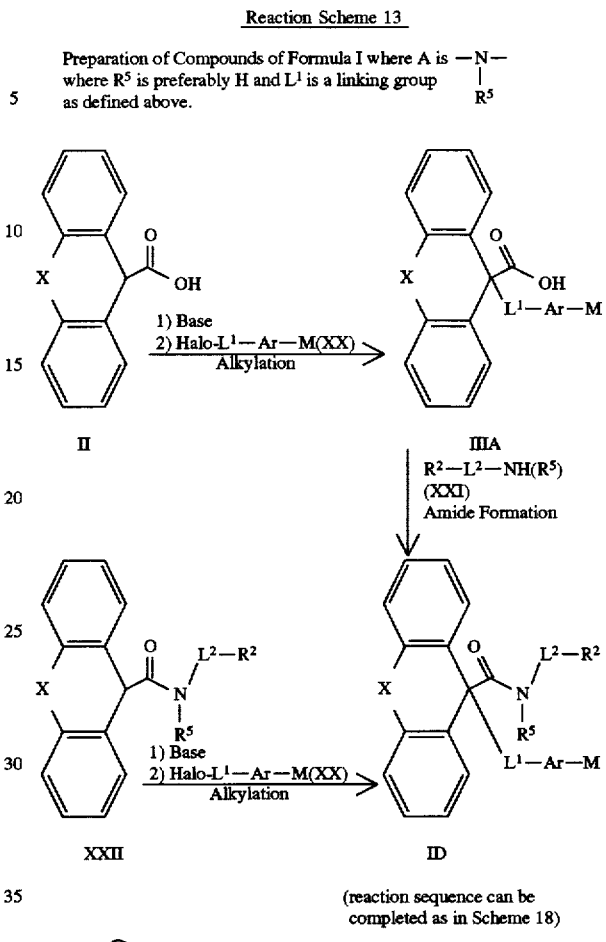

(reaction sequence can be completed as in Scheme 18)

1) Ar or (Ar) is aryl or heteroaryl
2) M is $NO_2$, N-$PG^1$, $NHCOR^q$, $NHSO_2R^r$, $N(PG^2)COR^q$, $N(PG^2)SO_2R^r$
Examples of protecting groups for nitrogen ($PG^1$) are Stabase
$(-Si(CH_3)_2-CH_2CH_2-(CH_3)_2Si-)$, $BOC(t\text{-}BuylO-CO-)$, bis-BOC or phthalimido.
3) Examples of $PG^2$ are BOC, $(CH_3)_3Si-$ or $t\text{-}Bu(CH_3)_2Si-$ Reaction Scheme 12 outlines the general procedure for the preparation of the sulfides, sulfones and sulfoxides IA of the invention. Ketone XVI can be reduced with $NaBH_4$ to give alcohol XVII. The alcohol XVII can undergo solvolysis by treatment with acid ($H_2SO_4$, or $BF_3$-etherate, $TiCl_4$) in the presence of a thiol ($R^2L^2SH$) such as butanethiol to give thio compound of the invention IAa. An alternate method to give IAa proceeds via acetate formation ($Ac_2O$), followed by the solvolysis reaction. Thioether IAa can be alkylated (n-BuLi, $R^1L^1Hal$) by treatment with base and trapping with an alkyl halide to give sulfide of the invention IAb. The thioether in IAb can be oxidized to the sulfoxide IAc by mCPBA (m-chloroperbenzoic acid), or $NaIO_4$. Sulfone IAd can be obtained from IAb by oxidation with, for example, mCPBA by employing 2 or more equivalents of oxidizing agent.

Alternately, ketone XVI can be reacted with a Grignard to give XVII which can undergo solvolyis reactions ($H_2SO_4$, $R^2L^2SH$, or $BF_3$-etherate, $R^2SH$) to give sulfide IAb. The sulfones and sulfoxides can be obtained as described above.

Compounds of the invention of formula I where A is $-\underset{\underset{R^5}{|}}{N}-$ and $R^5$ is preferably H, and $L^1$ is a linking group as defined above can be prepared as shown in Reaction Scheme 13.

As seen in Scheme 13, acid II is treated with base and alkylated by reaction with halide XX, as described with respect to Scheme 1, to form alkylated intermediate IIIA. IIIA is reacted with amine XXI (using the amide formation procedure as described in Scheme 1) to form amide of the invention ID.

Where M in ID is $NO_2$, $NHCOR^q$ or $NHSO_2R^r$, ID represents a final product.

Where M includes a protecting group, the protecting group may be removed as shown in Scheme 18.

Where desired, acid II may undergo amide formation by reaction with amine XXI to form amide XXII via various known procedures, which is then alkylated to form ID.

Reaction Scheme 14

Preparation of Compounds I, IA or IB where $R^1$ is aryl or heteroaryl.

Scheme 14(A) where linking heteroatom T is a substituent on Ar

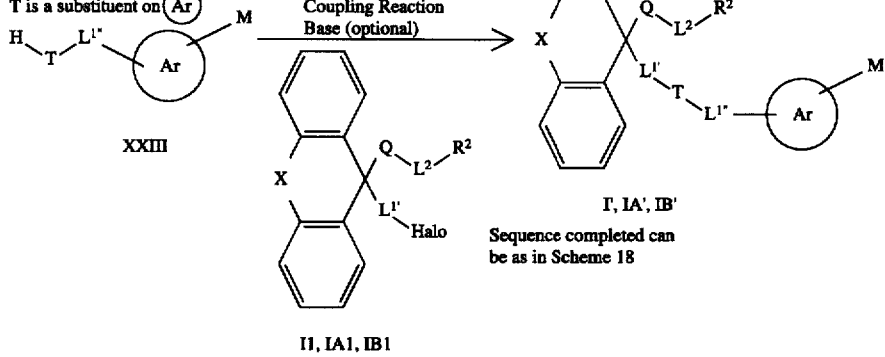

Sequence completed can be as in Scheme 18

M and (Ar) are defined as in Scheme 13.

T is either
(1) a heteroatom (O, NH, N(alkyl) or S), as a substituent on (Ar) linked to (Ar) via the linker $L^{1"}$, where $L^{1"}$ can either be a bond, or is defined as is $L^1$, or (as depicted below)
(2) a nitrogen atom, as a ring member of Ar, in which case $L^{1"}$ does not exist
$L^{1'}$ is a linker such as defined for $L^1$, or a bond.

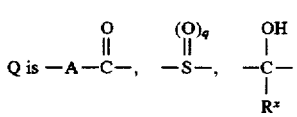

Note that the group $-L^{1'}-T-L^{1"}-$ defines $L^1$.
Scheme 14(B) where the linking nitrogen is a ring member of (Ar)

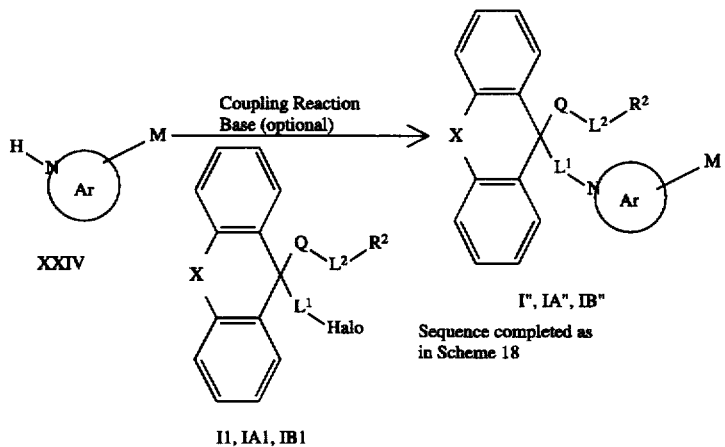

Sequence completed as in Scheme 18

Compounds of the invention of formula I, IA or IB where $R^1$ is aryl or heteroaryl may be prepared as shown in Reaction Schemes 14(A) and 14(B).

In Scheme 14(A) compounds of formula I', IA' or IB' (where $R^1$ is aryl or heteroaryl) may be prepared by coupling compound XXIII with compound I1, IA1 or IB1, respectively, optionally in the presence of a base as described with respect to Scheme 1.

Compounds I', IA', IB', I", IIA" and IB" may be subjected to deprotection and/or further converted, where necessary as shown in Scheme 18.

In Scheme 14(B) compounds of formula I", IA" or IB" (where $R^1$ is heteroaryl and (Ar) is linked to $L^1$ via a ring nitrogen)) may be prepared by coupling XXIV with I1, IA1 or IB1, optionally in the presence of a base.

XXV in the presence of a catalyst, such as palladium, $Pd(Ph_3P)_4$ or $Pd(Ph_3P)_2Cl_2$ in the presence of an amine (e.g. $BuNH_2$, $Et_3N$) and a Copper (I) salt (e.g. CuI) to form compound of the invention I3, IA3 or IB3, respectively, and subjecting I3, IA3 or IB3 to hydrogenation to form compound of the invention I4, IA4 or IB4.

Compound I3, IA3, IB3, I4, IA4 or IB4 may be subjected to deprotection and further conversion if necessary, as described in Reaction Scheme 18.

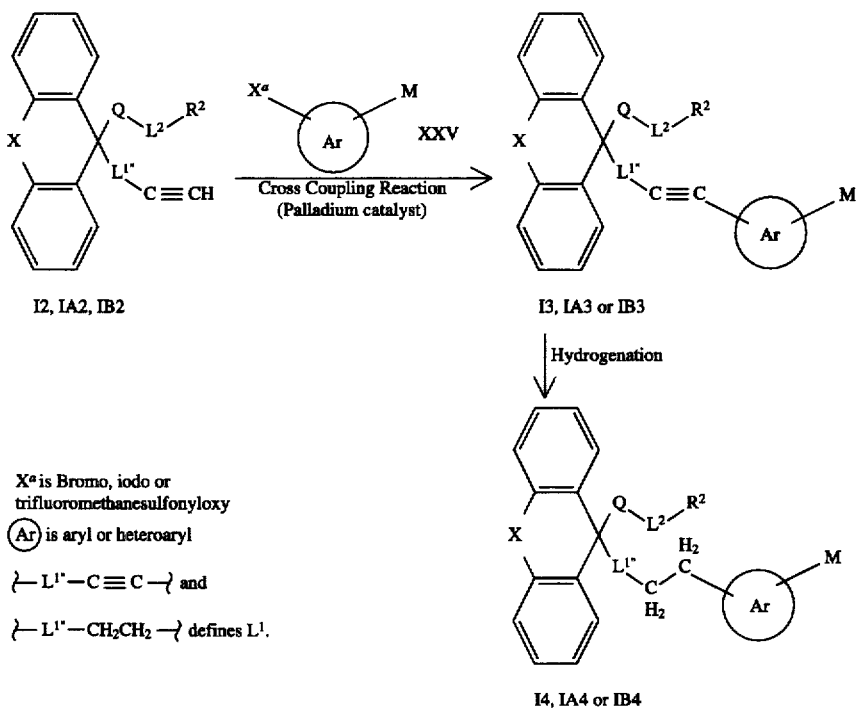

Compounds of the invention of formula I, IA or IB where $R^1$ is (Ar) may be prepared as shown in Reaction Scheme 15.

In Scheme 15, acetylenic starting compound I2, IA2 or IB2 is made to undergo a Castro-Stevens cross coupling with

Reaction Scheme 16

Alternate Preparation of Compounds I, IA or IB where R¹ is (Ar)

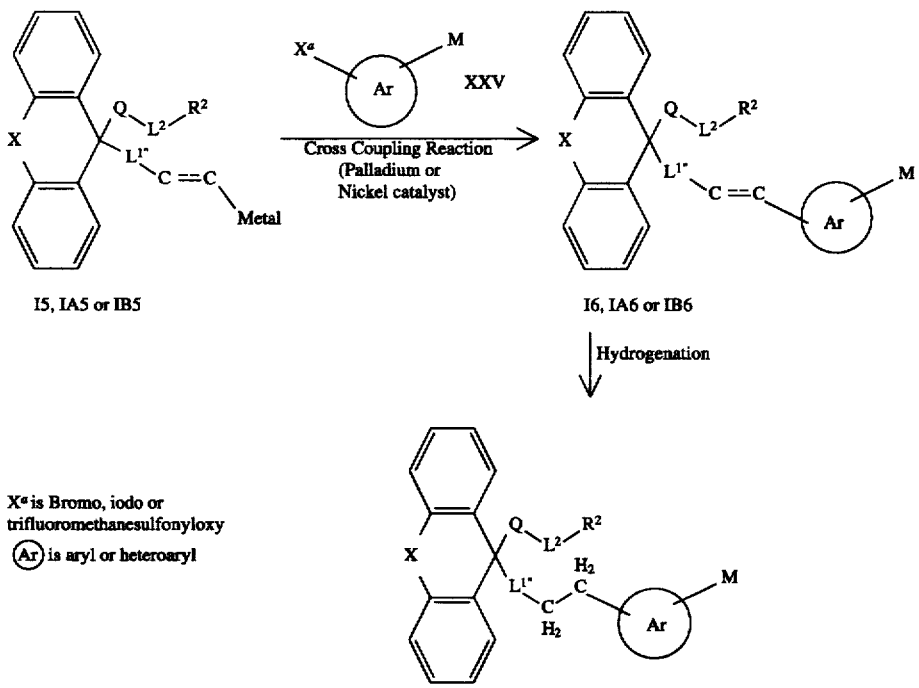

X$^a$ is Bromo, iodo or trifluoromethanesulfonyloxy (Ar) is aryl or heteroaryl

I4, IA4 or IB4
Sequence can be completed as in Scheme 18

C ═ C represents a single or double C—C bond, and if a double bond can have either cis or trans stereochemistry.

Metal can be ZnHalo, MgHalo, SnBu$_3$, B(alkyl)$_2$, B(OH)$_2$

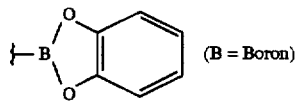 (B = Boron)

╞—L$^{1''}$—CH$_2$—CH$_2$—╡ and ╞—L$^{1''}$—C ═ C—╡ define the linker L$^1$

In an alternative procedure as shown in Reaction Scheme 16 compound I4, IA4 or IB4 may be prepared starting with compound I5, IA5 or IB5, respectively, which is made to undergo a cross coupling reaction with XXV in the presence of a palladium or nickel catalyst, to form I6, IA6 or IB6, respectively, which is hydrogenated to form I4, IA4 or IB4, respectively.

Reaction Scheme 17

Preparation of Compounds I, IA or IB where $L^1$ is an N-containing moiety

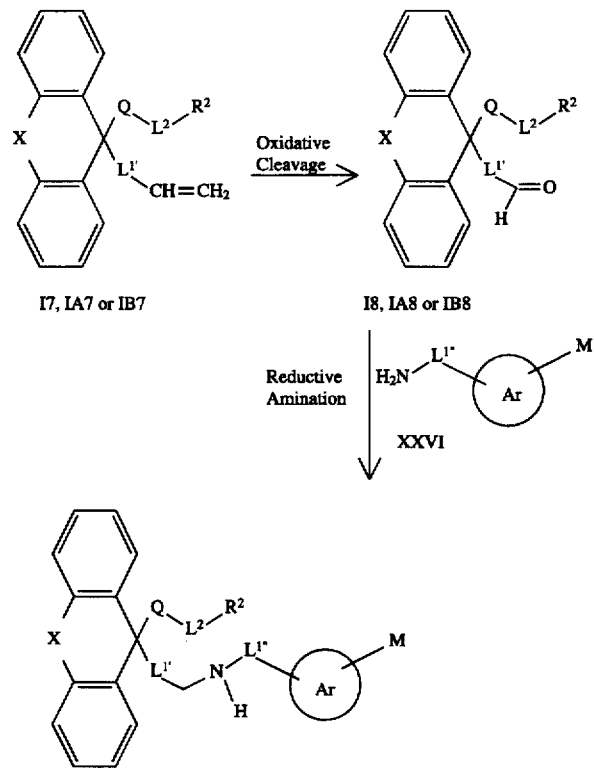

I7, IA7 or IB7 → I8, IA8 or IB8

Oxidative Cleavage

Reductive Amination with $H_2N-L^{1''}-Ar-M$ (XXVI)

I9, IA9 or IB9
Sequence can be completed as in Scheme 18

Oxidative Cleavage:
Ozone in $CH_2Cl_2$ or $CH_3OH$,
at low temperature (−78° C. to 25° C.)
followed by reductive workup
$Ph_3P$, $(CH_3)_2S$ or Zn, acetic acid;
alternatively, use $NaIO_4/OsO_4$ in
t-BuOH or THF, or mixtures
with optional water added
(Lemieux-Johnson reaction).

Reductive amination: $NaBH_4$, $NaBH_3CN$
or $NaB(OAc)_3H$, in $CH_2Cl_2$, MeOH, i-PrOH,
t-BuOH, THF, DMF or mixtures thereof,
optionally in the presence of an acid catalyst
such as HCl or $Ti(OCH(CH_3)_2)_4$.

Note that $-L^{1'}CH_2NHL^{1''}$ defines $L^1$

Compounds of the invention of formula I, IA or IB where $L^1$ is an N-containing moiety may be prepared as shown in Reaction Scheme 17 wherein starting compound I7, IA7 or IB7 is made to undergo oxidative cleavage, as described above, to form aldehyde I8, IA8 or IB8, respectively, which is subjected to reductive amination by reaction with amine XXVI, as described above, to form compound of the invention I9, IA9 or IB9, respectively.

Compound I9, Ia9 or IB9 may undergo deprotection, if necessary, as shown in Scheme 18.

Reaction Scheme 18

Preparation of final products from M containing intermediates in Schemes 13 to 17

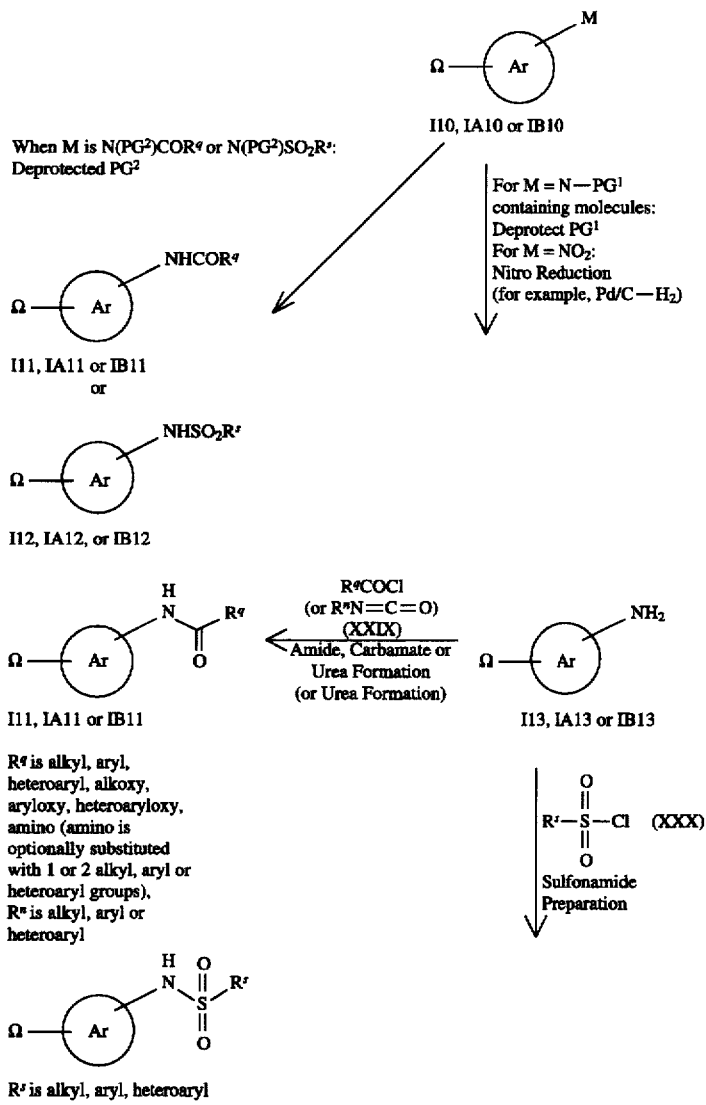

In a preferred method, superior yields of final products (I11, IA11, IB11, I12, IA12, IB12) are obtained when the intermediate I13, IA13, IB13 is reacted with R$^q$COCl, R$^n$N=C=O or R$^s$SO$_2$Cl immediately after formation of I13, IA13 or IB13, preferably in situ.

1) Ω represents

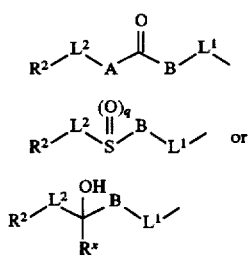

-continued 2) (Ar) is aryl or heteroaryl

3) M is NO$_2$, N—PG, NHCOR$^q$, NHSO$_2$R$^s$, N(PG$^2$)COR$^q$, N(PG$^2$)SO$_2$R$^s$
   Examples of protecting groups for nitrogen (PG$^1$) are Stabase (—Si(CH$_3$)$_2$—CH$_2$CH$_2$—(CH$_3$)$_2$Si—), BOC (t-ButylO-CO—) and bis-BOC.
4) Examples of PG$^2$ are BOC, (CH$_3$)$_3$Si— or t-Bu(CH$_3$)$_2$Si—
5) Deprotection according to the prior art.

The compounds of the invention may be employed in preventing, stabilizing or causing regression of atherosclerosis in a mammalian species by administering a therapeutically effective amount of a compound to decrease the activity of MTP.

The compounds of the invention can be tested for MTP inhibitory activity employing the procedures set out in U.S. application Ser. No. 117,362 filed Sep. 3, 1993, employing MTP isolated from one of the following sources:

(1) bovine liver microsomes, (2) HepG$_2$ cells (human hepatoma cells) or (3) recombinant human MTP expressed in baculovirus.

The compounds of the invention may also be employed in lowering serum lipid levels, such as cholesterol or triglyceride (TG) levels, in a mammalian species, by administering a therapeutically effective amount of a compound to decrease the activity of MTP.

The compounds of the invention may be employed in the treatment of various other conditions or diseases using agents which decrease activity of MTP. For example, compounds of the invention decrease the amount or activity of MTP and therefore decrease serum cholesterol and TG levels, and TG, fatty acid and cholesterol absorption and thus are useful in treating hypercholesterolemia, hypertriglyceridemia, hyperlipidemia, pancreatitis, hyperglycemia and obesity.

The compounds of the present invention are agents that decrease the activity of MTP and can be administered to various mammalian species, such as monkeys, dogs, cats, rats, humans, etc., in need of such treatment. These agents can be administered systemically, such as orally or parenterally.

The agents that decrease the activity or amount of MTP can be incorporated in a conventional systemic dosage form, such as a tablet, capsule, elixir or injectable formulation. The above dosage forms will also include the necessary physiologically acceptable carrier material, excipient, lubricant, buffer, antibacterial, bulking agent (such as mannitol), antioxidants (ascorbic acid or sodium bisulfite) or the like. Oral dosage forms are preferred, although parenteral forms are quite satisfactory as well.

The dose administered must be carefully adjusted according to the age, weight, and condition of the patient, as well as the route of administration, dosage form and regimen, and the desired result. In general, the dosage forms described above may be administered in amounts of from about 5 to about 500 mg per day in single or divided doses of one to four times daily.

The following Examples represent preferred embodiments of the invention. All temperatures are in °C. unless indicated otherwise.

Where structures are set in the following Examples which include hetero atoms with unfilled valency, it will be understood that hydrogen is attached to such hetero atoms to fulfill valency requirements.

EXAMPLE 1

N-(Phenylmethyl)-9-(3-phenylpropyl)-9H-fluorene-9-carboxamide

A. N-(Phenylmethyl)-9H-fluorene-9-carboxamide

A solution of 9-fluorene carboxylic acid (2.10 g, 10.0 mmol) in 50 mL of CH$_2$Cl$_2$ was treated with oxalyl chloride in dichloromethane (6.0 mL, 12.0 mmol) and two drops of DMF. After 0.75 h, the mixture was concentrated under reduced pressure to give a white solid. The solid was diluted with 50 mL of CH$_2$Cl$_2$, cooled to 0° C., treated with benzylamine (1.17 g, 11.0 mmol) and pyridine (0.87 g, 11 mmol). The transparent yellow solution was stirred for 3 h at room temperature and diluted with ethyl acetate and water. The organic fraction was dried over Na$_2$SO$_4$ and concentrated to a white solid. The solid purified by trituration with hexanes and recrystalization from hot methanol to give 2.60 g (86%) of title compound as white flakes. mp 195°–200° C.

TLC Silica gel (3:7 ethyl acetate/hexane) R$_f$=0.30.

Mass Spec. (CI—NH$_3$, + ions) m/z 300 (M+H), 317 (M+NH$_4$).

Anal. Calc'd for C$_{21}$H$_{17}$NO: C, 84.25; H, 5.72; N, 4.68
Found: C, 83.96; H, 5.68; N, 4.54.

B. N-(Phenylmethyl)-9-(3-phenylpropyl)-9H-fluorene-9-carboxamide

To a suspension of Part A compound (0.35 g, 1.17 mmol) in THF (10 mL) at 0° C. was added n-butyllithium in hexanes (1.0 mL, 2.4 mmol) dropwise at such at rate to maintain the internal temperature near 0° C. The resulting bright orange solution was stirred at 0° C. for 0.5 h and treated with 1-bromo-3-phenylpropane (0.26 g, 1.30 mmol). The mixture was slowly warmed to room temperature and stirred for 3 h and diluted with NH$_4$Cl (20 mL) and ethyl acetate (50 mL). The layers were separated, the organic fraction dried (Na$_2$SO$_4$) and concentrated. The remainder was purified by column chromatography on silica gel (30 g) with 2:8 ethyl acetate/hexane to give 0.33 g (67%) of title compound as a white solid. The solid was recrystalized from hot hexane to give 0.25 g (51%) of title compound as white flakes. mp 94° C.

TLC Silica gel (3:7 ethyl acetate/hexane) R$_f$=0.70.

Mass Spec. (CI—NH$_3$, + ions) m/z 418 (M+H), 435 (M+NH$_4$).

Anal. Calc'd for C$_{30}$H$_{27}$NO: C, 86.30; H, 6.52; N, 3.35
Found: C, 85.99; H, 6.47; N, 3.21.

Examples 2–4 were prepared from Example 1 Part A by the method described in Example 1, Part B.

EXAMPLE 2

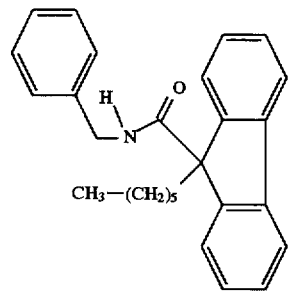

MS (Cl—NH$_3$, + ions) m/e 384 (M+H).

mp: 79°–82°

Anal. Cald'd for C$_{27}$H$_{29}$NO: C, 84.56; H, 7.62; N, 3.65
Found: C, 84.22; H, 7.72; N, 3.65.

EXAMPLE 3

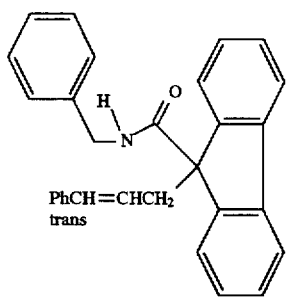

MS (Cl—NH$_3$, + ions) m/e 416 (M+H).

mp: 134°

Anal. Cald'd for C$_{30}$H$_{25}$NO: C, 86.72; H, 6.06; N, 3.37 Found: C, 86.61; H, 6.23; N, 3.31.

EXAMPLE 4

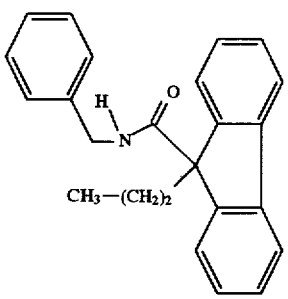

MS (Cl—NH$_3$, + ions) m/e 342 (M+H), 359 (M+NH$_4$).

mp: 96°

Anal. Cald'd for C$_{24}$H$_{23}$NO: C, 84.42; H, 6.79; N, 4.10 Found: C, 84.29; H, 6.72; N, 3.96.

EXAMPLE 5

(E)-N-Ethyl-9-(3-phenyl-2-propenyl)-9H-fluorene-9-carboxamide

A

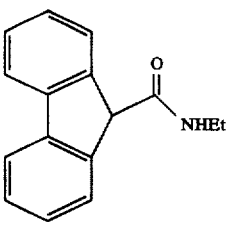

A solution of 9-fluorene carboxylic acid (2.10 g, 10.0 mmol) in 50 mL of CH$_2$Cl$_2$ was treated with oxalyl chloride in dichloromethane (6.0 mL, 12.0 mmol) and two drops of DMF. After 0.75 h, the mixture was concentrated under reduced pressure to give a white solid. The solid was diluted with 50 mL of CH$_2$Cl$_2$, cooled to 0° C., treated with ethylamine (1.0 g, 22 mmol). The transparent yellow solution was stirred for 3 h at room temperature and diluted with ethyl acetate and water. The organic fraction was dried over Na$_2$SO$_4$ and concentrated to a white solid. The solid purified by trituration with hexanes and recrystalization from hot methanol to give 2.60 g (86%) of title compound as white flakes. mp 233°–234° C.

B. (E)-N-Ethyl-9-(3-phenyl-2-propenyl)-9H-fluorene-9-carboxamide

To a suspension of Part A compound (1.00 g, 4.21 mmol) in THF (25 mL) at 0°÷C. was added n-butyllithium in hexanes (3.53 mL, 8.84 mmol) dropwise at such at rate to maintain the internal temperature near 0° C. The resulting bright yellow solution was stirred at 0° C. for 0.5 h and treated with cinnamyl chloride (0.79 g, 4.63 mmol). The mixture was slowly warmed to room temperature and stirred for 2 h when it was diluted with water (40 mL) and ethyl acetate (40 mL). The layers were separated, the organic fraction dried (Na$_2$SO$_4$) and concentrated. The remainder was triturated with hexanes and the resulting solid recrystalized from hot methanol to give 1.20 g (79%) of title compound as white needles.

mp 144° C.

TLC Silica gel (3:7 ethyl acetate/hexane) R$_f$=0.6.

Anal. Calc'd for C$_{25}$H$_{23}$NO: C, 84.95; H, 6.56; N, 3.96 Found: C, 84.53; H, 6.74; N, 3.95.

Example 6–10 can be prepared from Example 5 Part A compound by the method described in Example 5 Part B.

EXAMPLE 6

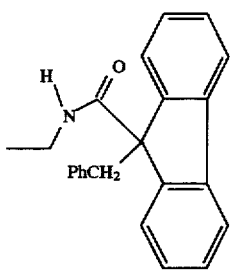

MS (Cl—NH$_3$, + ions) m/e 328 (M+H).

mp: 126°–128°

Anal. Cald'd for C$_{23}$H$_{21}$NO: C, 84.37; H, 6.46; N, 4.29 Found: C, 84.22; H, 6.42; N, 4.58.

EXAMPLE 7

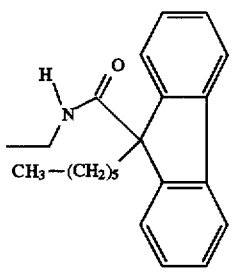

MS (Cl—NH$_3$, + ions) m/e 322 (M+H).

mp: 70°

Anal. Cald'd for C$_{22}$H$_{27}$NO: C, 82.20; H, 8.47; N, 4.36 Found: C, 82.07; H, 8.55; N, 4.74.

EXAMPLE 8

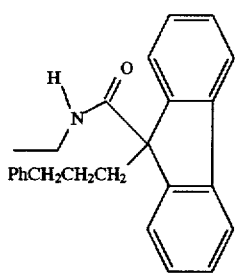

MS (CI, + ions) m/z 356 (M+H).
mp: 72°–73°
Anal. Cald'd for $C_{25}H_{25}NO+0.3\ H_2O$: C, 83.08; H, 7.16; N, 3.88 Found: C, 82.84; H, 7.89; N, 3.78.

EXAMPLE 9

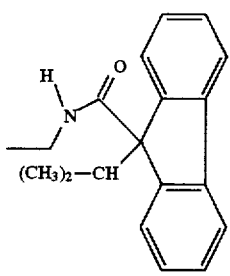

MS (Cl—$NH_3$, + ions) m/e 280 (M+H).
mp: 66°–67°
Anal. Cald'd for $C_{19}H_{21}NO$: C, 81.68; H, 7.58; N, 5.01 Found: C, 81.60; H, 7.87; N, 5.08.

EXAMPLE 10

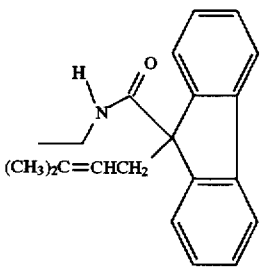

MS (Cl—$NH_3$, + ions) m/e 306 (M+H).
mp: 78°
Anal. Cald'd for $C_{21}H_{23}NO$: C, 82.59; H, 7.59; N, 4.59 Found: C, 82.37; H, 7.74; N, 4.57.

EXAMPLE 11

9-[4-(Dibutoxyphosphinyl)butyl]-N-propyl-9H-fluorene-9-carboxamide

A. N-Propyl-9-fluorene-carboxamide

A solution of 9-fluorene carboxylic acid (20.0 g, 95 mmol) in 200 mL of $CH_2Cl_2$ was treated with oxalyl chloride (12.5 g, 105 mmol) and 0.2 mL of DMF. After 0.75 h, the mixture was concentrated under reduced pressure to give a white solid. The solid was diluted with 100 mL of THF cooled to –40° C., treated with propylamine (11.8 g, 200 mmol). The suspension was stirred for 3 h at room temperature and diluted with ethyl acetate and water. The organic fraction was dried over $Na_2SO_4$ and concentrated to a white solid. The solid purified by trituration with hot hexanes and recrystalization from hot methanol to give 17.5 g (87%) of title compound as white flakes. mp 197°–199° C.

TLC Silica gel (3:7 ethyl acetate/hexane) $R_f$=0.30.
MS (CI—$NH_3$, + ions) m/e 252 (M+H).

B. Dibutyl (4-bromobutyl)phosphonate

A mixture of 1,4-dibromobutane (129 g, 600 mmol) and tributyl phosphite (15.0 g, 60 mmol) was heated to 118° C. (bath temperature) for 6 h. The volatiles were removed by short path distillation (0.4 mm Hg, 40° C.) to leave 20 g (100%) of part b compound as an amber colored oil. The oil can be purified by flash column chromatography on silica gel with 1:9 acetone/dichloromethane.

TLC: (1:9 acetone/dichloromethane) $R_f$=0.55.
$^{13}$C NMR ($d_6$-acetone) δ 64.4 (d, J=6 Hz), 33.1, 33.0 (d, J=22 Hz), 32.4 (d, J=6 Hz), 24.0 (J=140 Hz), 21.1 (J=5 Hz), 18.5, 13.0 ppm.

C. Dibutyl (4-Iodobutyl)phosphonate

A mixture of Part B compound (4.8 g, 14.58 mmol), potassium iodide (20.0 g, 120 mmol) and acetone (200 mL) was heated to reflux for 2.5 h and cooled to room temperature. The solids were filtered and the filtrate concentrated. The remainder was diluted with ether and filtered. The ether fraction was concentrated to give 5.32 g (97%) of title compound as a pale yellow oil.

TLC: (1:9 acetone/dichloromethane) $R_f$=0.55.
$^{13}$C NMR ($CDCl_3$) δ 65.2 (d, J=7 Hz), 33.7 (d, J=17 Hz), 32.4 (d, J=6 Hz), 24.2 (J=140 Hz), 18.6, 13.5, 5.5 ppm.

D. 9-[4-(Dibutoxyphosphinyl)butyl]-N-propyl-9H-fluorene-9-carboxamide

A solution of Part A compound (3.00 g, 11.95 mmol) in 30 mL of THF at –40° was treated with n-BuLi (5.20 mL, 13 mmol) in hexanes at such a rate to maintain the internal temperature below –35°. The orange yellow solution was stirred for 0.5 h and treated with Part C compound (4.30 g, 11.50 mmol). The mixture was warmed to room temperature over 0.5 h and after 2 h at room temperature was quenched with 100 mL of $NH_4Cl$ solution and 100 mL of ethyl acetate. The organic fraction was dried ($MgSO_4$) and concentrated. The remainder was purified by column chromatography on silica gel (400 g) with 1:9 acetone/dichloromethane to give 4.30 g (75%) of title compound as a colorless oil.

TLC Silica gel (7:3 ethyl acetate/hexane) $R_f$=0.5.
Mass Spec. (ES, + ions) m/e 500 (M+H).
Anal. Calc'd for $C_{29}H_{42}NO_4P+0.6\ H_2O$: C, 68.29; H, 8.53; N, 2.75; P, 6.07 Found: C, 68.34; H, 8.45; N, 2.70; P, 6.03.

EXAMPLE 12

(E)-9-(3-Phenyl-2-propenyl)-N-propyl-9H-fluorene-9-carboxamide

To a suspension of 500 mg (1.99 mmol) of Example 11 Part A compound in 10 mL of THF, at 0° C. under argon, was added dropwise 2.5 mL (3.98 mmol) of n-BuLi (1.6M in hexanes). The resulting orange solution was stirred at 0° C. for 0.5 h at which time 305 μL (2.19 mmol) of cinnamyl chloride was added. The reaction was warmed to RT and allowed to stir for 1 h at which time it was diluted with 1:1 ethyl acetate/water (30 mL). The organics were dried (NaSO$_4$) and evaporated to dryness. Purification by crystallization from hot methanol provided 350 mg (48%) of title compound as a white solid.

mp 95°–97° C.

TLC Silica gel (1:1 hexanes/ethyl acetate) R$_f$=0.59.

MS (Cl—NH$_3$, + ions) m/e 368 (M+H).

Anal. calcd. for C$_{26}$H$_{25}$NO+0.62 mol H$_2$O: C, 82.47; H, 6.98; N, 3.70 Found: C, 82.67; H, 6.92; N, 3.50.

Examples 13–21 can be prepared from Example 11 Part A by the method in Example 11 Part D or Example 12 Part A.

EXAMPLE 13

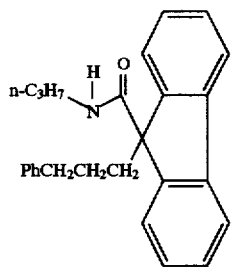

MS (Cl—NH$_3$, + ions) m/e 370 (M+H).

mp: 57°–59°

Anal. Cald'd for C$_{26}$H$_{27}$NO: C, 84.51; H, 7.36; N, 3.79 Found: C, 84.53; H, 7.41; N, 3.70.

EXAMPLE 14

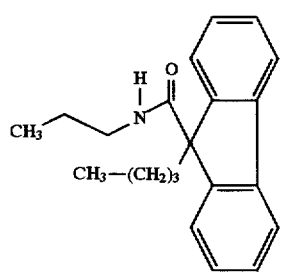

MS (Cl—NH$_3$, + ions) m/e 308 (M+H).

mp: 60°–62°

Anal. Cald'd for C$_{21}$H$_{25}$NO+0.05 mol C$_6$H$_{14}$: C, 82.07; H, 8.32; N, 4.49 Found: C, 82.12; H, 8.76; N, 4.65.

EXAMPLE 15

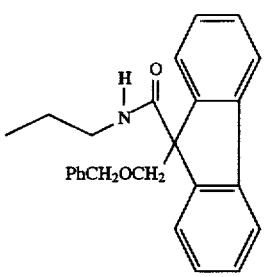

MS (Cl—NH$_3$, + ions) m/e 372 (M+H).

Anal. Cald'd for C$_{25}$H$_{25}$NO$_2$: C, 80.83; H, 6.78; N, 3.77 Found: C, 80.48; H, 6.90; N, 3.71.

EXAMPLE 16

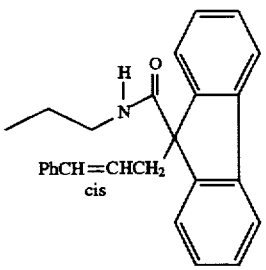

MS (Cl—NH$_3$, + ions) m/e 368 (M+H).

Anal. Cald'd for C$_{26}$H$_{25}$NO+0.31 mol H$_2$O: C, 83.71; H, 6.92; N, 3.75 Found: C, 83.84; H, 6.95; N, 3.62.

EXAMPLE 17

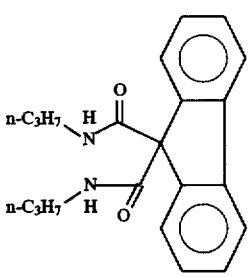

MS (Cl—NH$_3$, + ions) m/e 337 (M+H).

Anal. Cald'd for C$_{21}$H$_{24}$N$_2$O$_2$: C, 74.97; H, 7.19; N, 8.33 Found: C, 74.94; H, 7.17; N, 7.80.

EXAMPLE 18

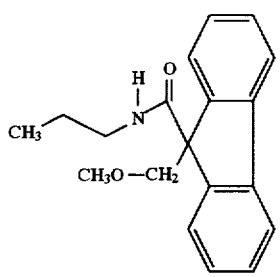

MS (Cl—NH₃, + ions) m/e 296 (M+H).

mp: 69°–73°

Anal. Cald'd for $C_{19}H_{21}NO_2+0.09$ mol $C_{21}H_{25}NO_3$: C, 76.98; H, 7.19; N, 4.68 Found: C, 76.71; H, 7.42; N, 4.65.

EXAMPLE 19

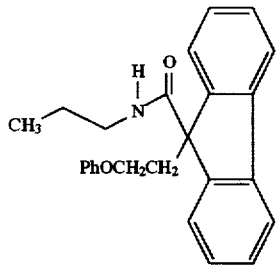

MS (Cl—NH₃, + ions) m/e 372 (M+H).

Anal. Cald'd for $C_{25}H_{25}NO_2+0.86$ mol $H_2O$: C, 77.60; H, 6.96; N, 3.62 Found: C, 77.92; H, 6.54; N, 3.88.

EXAMPLE 20

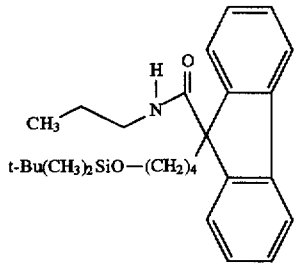

MS (Cl—NH₃, + ions) m/e 438 (M+H).

mp: 45°–47°

Anal. Cald'd for $C_{27}H_{39}NSiO_2$: C, 74.09; H, 8.98; N, 3.20 Found: C, 73.83; H, 9.34; N, 3.25.

EXAMPLE 21

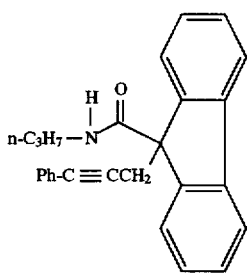

MS (ES, + ions) m/z 366 (M+H).

mp: 120°–123°

Anal. Cald'd for $C_{26}H_{23}NO+0.15$ mol $H_2O$: C, 84.76; H, 6.38; N, 3.80 Found: C, 84.81; H, 6.29; N, 3.75.

EXAMPLE 22

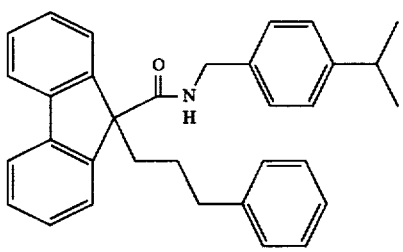

A. 9-(3-Phenylpropyl)-9H-fluorene-9-carboxylic acid

To a solution of 10 g (48 mmol, 1 eq) of (9H)-flourene-9-carboxylic acid in 200 mL of THF at 0° C. was added 40 mL (100 mmol, 2.1 eq) of a 2.5M solution of n-butyllithium in hexanes dropwise over 15 min. (First equivalent resulted in precipitation of Li salt of the carboxylate; solution became homogeneous as dianion formed.) The resulting green solution of dianion was stirred at 0° C. for 10 min and 10.1 mL (66 mmol, 1.4 eq) of 1-bromo-3-phenylpropane was added quickly over 3 min. The reaction was stirred at 0° C. and allowed to warm to RT as the ice bath melted. After 16 h, the basic reaction mixture (pH ~14) was extracted with water (1×200 mL, 2×50 mL). The combined aqueous layers were acidified (to pH ~1) with 5N HCl and extracted with ether (3×100 mL). The combined ether solutions were dried (MgSO₄), filtered and concentrated to afford 16.4 g of a viscous golden oil. Flash chromatography of the oil on silica gel (250 g) eluted with 20% acetone in toluene containing 0.1% acetic acid afforded 12.6 g of a yellow oil. The product was crystallized by slow evaporation of an ether/hexanes solution and then recrystallized from ether/hexanes to afford 10.5 g (67%) of title compound as a white crystalline solid. m.p. 123°–125° C.

TLC (silica gel, 10% MeOH in $CH_2Cl_2$, UV and $I_2$) $R_f=0.67$.

B. 9-(3-Phenylpropyl)-9H-fluorene-9-carboxylic acid, 4-nitrophenyl ester

To a solution of 10 g (30.4 mmol, 1 eq) of Part A compound in 100 mL of $CH_2Cl_2$ was added 100 μL of DMF. The solution was cooled to 0° C. and 22.8 mL (45.7 mmol, 1.5 eq) of a 2.0M oxalyl chloride solution in $CH_2Cl_2$ was added over 5 min. The resulting bubbling solution was stirred at 0° C. for 1.5 h (until bubbling had ceased). The solution was concentrated and the residual oil was taken up in 50 mL of CH$_2$Cl$_2$ and reconcentrated. The resulting oil was dissolved in 150 mL of CH$_2$Cl$_2$ and 188 mg (1.5 mmol, 0.05 eq) of 4-dimethylaminopyridine was added. The solution was cooled to 0° C. and 5.1 mL (36.5 mmol, 1.2 eq) of triethylamine was added. To the resulting dark brown cloudy solution was added 12.7 g (91.3 mmol, 3 eq) of p-nitrophenol as a solid. Upon addition the reaction quickly became clear and the resulting clear reaction mixture was allowed to warm to RT as the ice bath melted. (TLC indicated the reaction was essentially complete after 40 min.) After 15 h, the reaction was washed with 100 mL of ice-cold 1N HCl. The organic solution was filtered through cotton and concentrated to afford 24.84 g of a viscous golden-brown oil which was adsorbed onto silica gel (25 g) and chromatographed on silica gel (200 g) eluted with 10% ethyl acetate in hexanes to afford 13.54 g of a yellow solid. The solid was further purified by recrystallization from ether/hexanes to provide 13.2 g (97%) of title compound as a pale yellow crystalline solid. m.p. 110°–112° C.

TLC (silica gel, 25% EtOAc in hexanes, UV and I$_2$) R$_f$=0.39.

MS (CI, pos. ions): m/z 467 (M+NH$_4$), 450 (M+H).

Anal. Calcd. for C$_{29}$H$_{23}$NO$_4$: C, 77.49; H, 5.16;N, 3.12 Found: C, 77.27; H, 4.90; N, 2.99.

C.

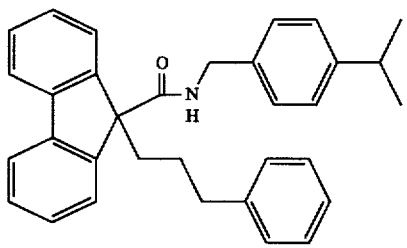

The title compound was prepared via an automated procedure carried out on a Zymark Benchmate® Workstation using the following procedure.

The Benchmate® delivered 1 mL (80 mg, 0.18 mmol, 1 eq) of a stock solution of Part B compound in THF (80 mg/mL) to a 16 mm×100 mm culture tube. The tube was removed and placed on a balance where 40 mg (0.27 mmol, 1.5 eq) of 4-isopropylbenzylamine was added manually by a Pipetman. The reaction was allowed to proceed until all reactions in the run were complete as indicated by disappearance of Part B compound by TLC (silica gel, 2% MeOH in CH$_2$Cl$_2$, R$_f$ 0.88, visualized by UV and I$_2$).

The product was purified via solid phase extraction using a Varian SAX anion exchange column (1 g of sorbent, chloride form) on the Benchmate® by the procedure outlined below:

1) Syringe washed with 5 mL 300 mM KOH in MeOH.
2) Syringe washed with 5 mL 300 mM KOH in MeOH.
3) Column conditioned with 10 mL of 300 mM KOH(aq) in MeOH (0.25 mL/sec).
4) Column conditioned with 10 mL of MeOH (0.25 mL/sec).
5) Column conditioned with 10 mL of CH$_2$Cl$_2$ (0.25 mL/sec).
6) THF (1 mL) added to reaction mixture.
7) Reaction mixture loaded onto SAX column (0.05 mL/sec) and effluent collected into a second tube.
8) Column rinsed with 1 mL of THF and effluent collected into second tube.
9) Column rinsed with 2 mL of CH$_2$Cl$_2$ and effluent collected into second tube.
10) Syringe washed with 10 mL of CH$_2$Cl$_2$.
11) Syringe washed with 5 mL of MeOH.
12) Syringe washed with 4 mL of 300 mM KOH(aq) in MeOH.
13) Syringe washed with 4 mL of 300 mM KOH(aq) in MeOH.

This procedure was followed by a second solid phase extraction using a Varian SCX cation exchange column (500 mg of sorbent) on the Benchmate® by the procedure outlined below:

1) Column conditioned with 10 mL of CH$_2$Cl$_2$ (0.25 mL/sec).
2) Reaction mixture loaded onto SCX column (0.05 mL/sec) and effluent collected into product tube (tared).
3) Column rinsed with 2 mL of CH$_2$Cl$_2$ and effluent collected into product tube.
4) Syringe washed with 5 mL of CH$_2$Cl$_2$.
5) Syringe washed with 5 mL of CH$_2$Cl$_2$.

The product solution (approx. 5 mL) was concentrated using a speed vacuum for 14 h to afford 78 mg (94%) of title compound as a pale yellow oil.

HPLC Purity=94%; retention time=9.5 minutes. Column: YMC-Pack ODS 6.0×150 mm C18 with a 4×23 mm OSDA S-5 µm guard column. Buffer: 10 mM KH$_2$PO$_4$ (pH 5.4, unadjusted). Elution: Isocratic at 85:15 buffer:actetonitrile for 5 minutes; linear gradient from 85:15 to 5:95 buffer:acetonitrile over 9 minutes followed by isocratic 5:95 buffer::acetonitrile for 2 minutes with return to 85:15 buffer:acetonitrile over 2 minutes.

MS (CI, + ions): m/z 460 (M+H).

EXAMPLE 23 TO 58

Examples 23–58 can be prepared from Example 22 Part B compound by the method in Example 22, Part C.

EXAMPLE 23

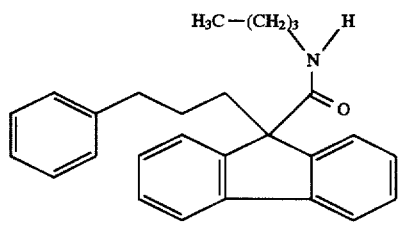

mp 73°–75° C.

MS (CI, pos. ions) 384 (M+H).

Anal. Cald'd for C$_{27}$H$_{29}$NO+0.04 H$_2$O: C, 84.40; H, 7.63;N, 3.65 Found: C, 84.02; H, 7.73; N, 3.66.

65
EXAMPLE 24–25
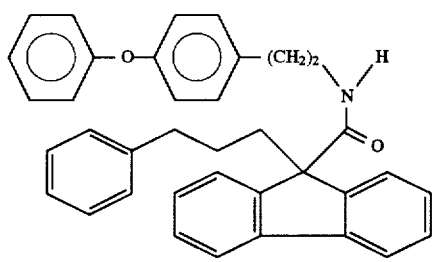
MS (CI, pos. ions) 524 (M+H).
EXAMPLE 26
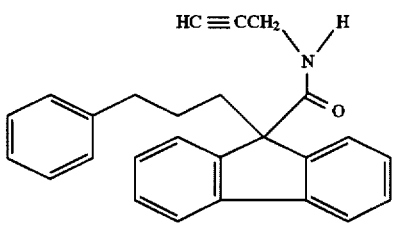
MS (CI, pos. ions) 366 (M+H).
EXAMPLE 27
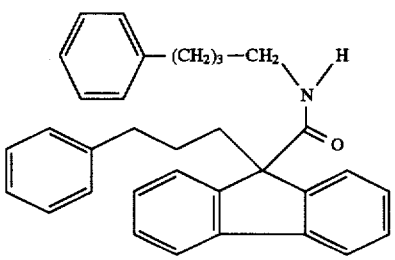
MS (CI, pos. ions) 460 (M+H).
EXAMPLE 28
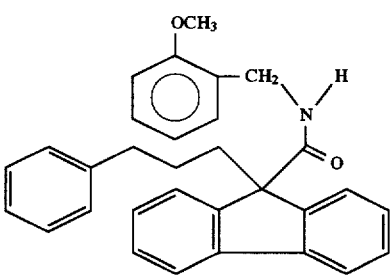
MS (CI, pos. ions) 448 (M+H).
66
EXAMPLE 29–30
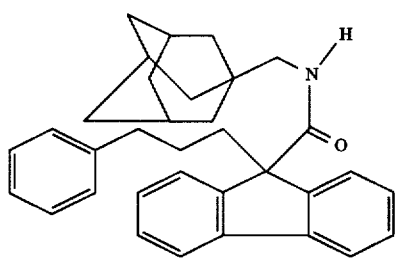
MS (electrospray, pos. ions) 476 (M+H).
EXAMPLE 31
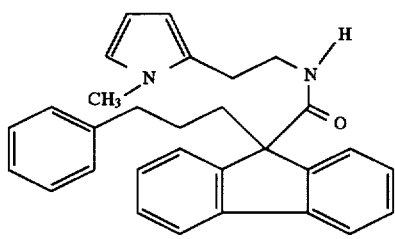
MS (electrospray, pos. ions) 435 (M+H).
EXAMPLE 32
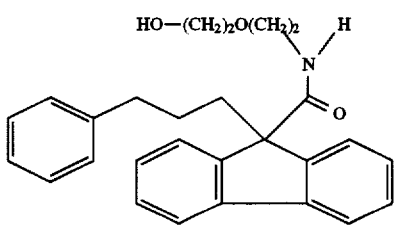
MS (electrospray, pos. ions) 416 (M+H).
EXAMPLE 33
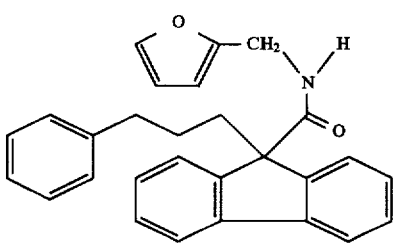
MS (electrospray, pos. ions) 408 (M+H).

EXAMPLE 34
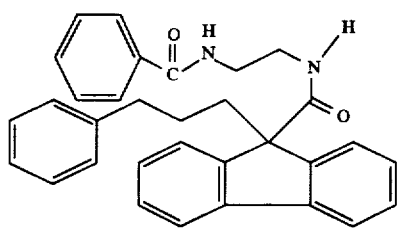
MS (electrospray, pos. ions) 475 (M+H).
EXAMPLE 35-36
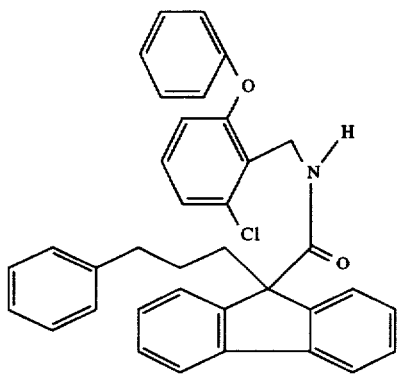
MS (electrospray, pos. ions) 544 (M+H).
EXAMPLE 37
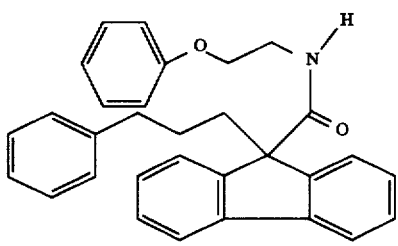
MS (electrospray, pos. ions) 448 (M+H).
EXAMPLE 38
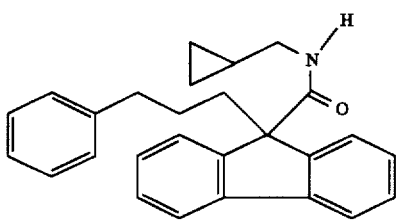
MS (electrospray, pos. ions) 382 (M+H).
EXAMPLE 39
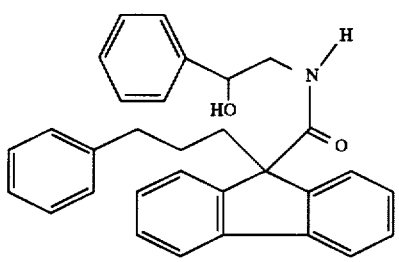
MS (electrospray, pos. ions) 448 (M+H).
EXAMPLE 40
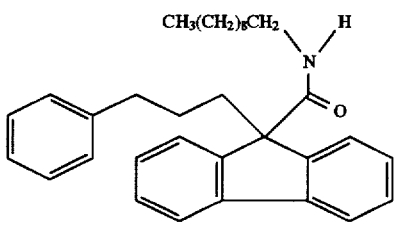
MS (electrospray, pos. ions) 468 (M+H).
EXAMPLE 41
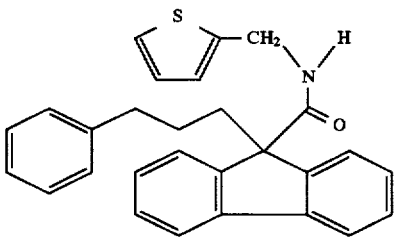
MS (electrospray, pos. ions) 424 (M+H).
EXAMPLE 42
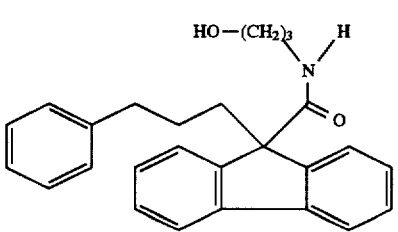
MS (electrospray, pos. ions) 386 (M+H).

EXAMPLE 43-44

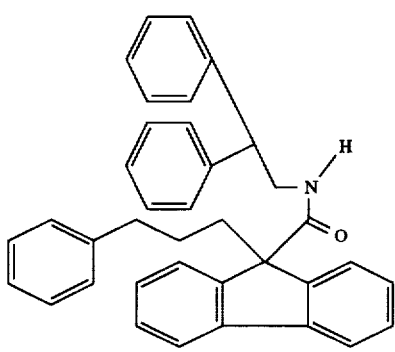

MS (electrospray, pos. ions) 508 (M+H).

EXAMPLE 45

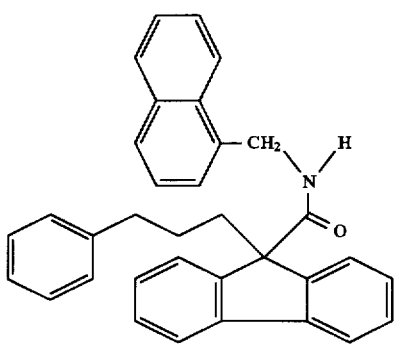

MS (electrospray, pos. ions) 468 (M+H).

EXAMPLE 46

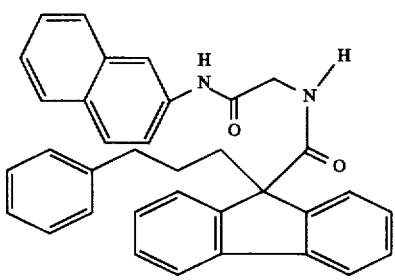

MS (electrospray, pos. ions) 511 (M+H).

EXAMPLE 47

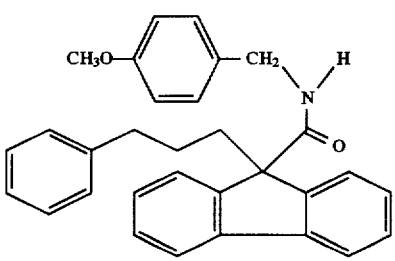

M.P. 105°–107° C.
MS (CI, + ions) m/z 448

Anal. Cald'd for $C_{31}H_{29}NO_2+0.15$ $H_2O$: C, 82.69; H, 6.56; N, 3.11 Found: C, 82.36; H, 6.37; N, 2.99.

EXAMPLE 48

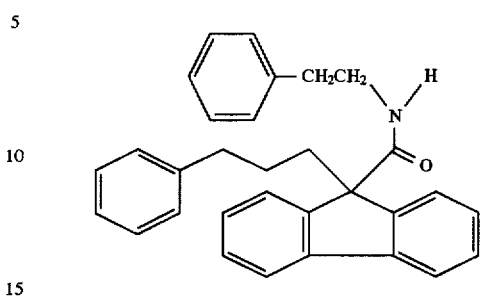

M.P. 104°–105° C.
MS (CI, + ions) m/z 432
Anal. Cald'd for $C_{31}H_{29}NO$: C, 86.27; H, 6.77; N, 3.25 Found: C, 85.87; H, 6.60; N, 3.14.

EXAMPLE 49

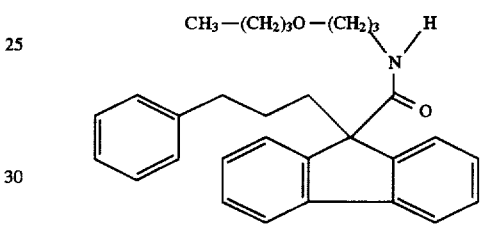

MS (CI, + ions) m/z 442
Anal. Cald'd for $C_{30}H_{35}NO_2$: C, 81.59; H, 7.99; N, 3.17 Found: C, 81.93; H, 8.11; N, 3.04.

EXAMPLE 50

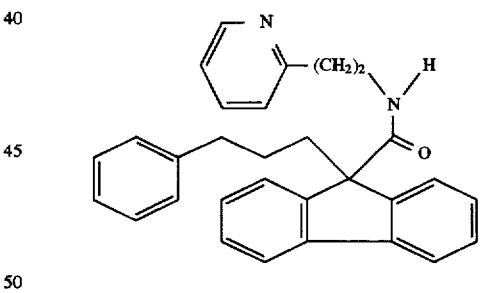

MS (electrospray, pos. ions) 433 (M+H)

EXAMPLE 51

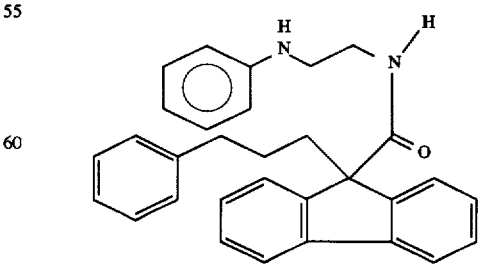

MS (electrospray, pos. ions) 447 (M+H)

EXAMPLE 52

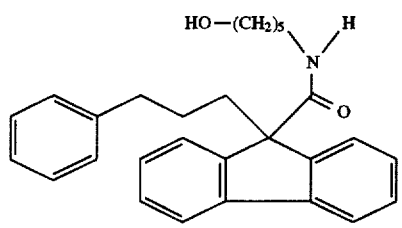

MS (Cl. + ions) m/z 414 (M+H)

Anal. Cald'd for $C_{28}H_{31}NO_2 + 0.1$ $CH_2Cl_2$: C. 79.97; H. 7.45; N. 3.32 Found: C. 80.29; H. 7.57; N. 3.27.

EXAMPLE 53

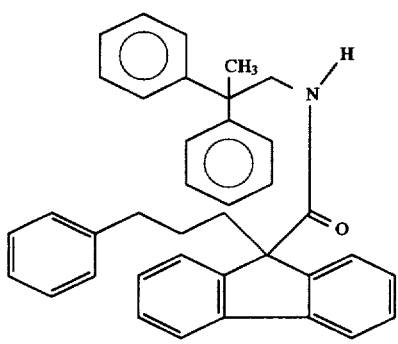

MS (electrospray, pos. ions) 458 (M+H)

EXAMPLE 54

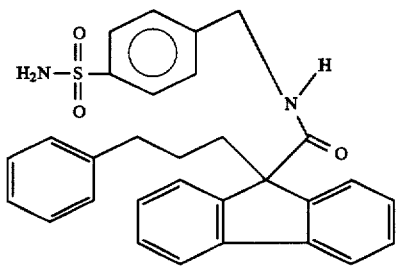

MS (electrospray, pos. ions) 497

EXAMPLE 55

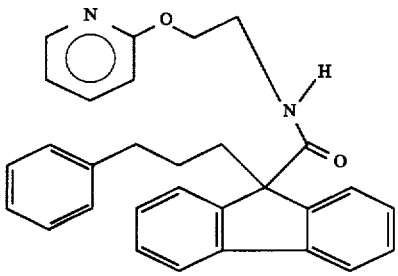

MS (electrospray, pos. ions) 449 (M+H)

EXAMPLE 56

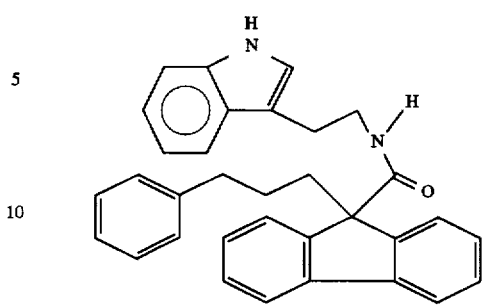

MS (electrospray, pos. ions) 471 (M+H)

EXAMPLE 57

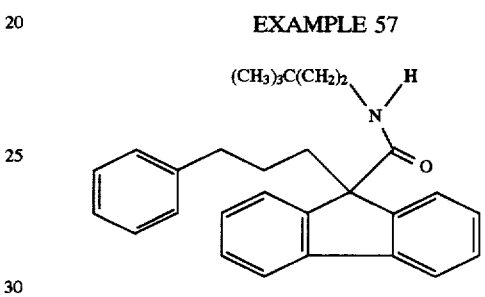

MS (electrospray, pos. ions) 412 (M+H)

EXAMPLE 58

9-(3-Phenylpropyl)-N-(2,2,2-trifluoroethyl)-9H-fluorene-9-carboxamide

A solution of oxalyl chloride in dichloromethane (1 mL, 2.0 mmol) was added to a stirred suspension of Example 22 Part A compound (0.30 g 0.90 mmol) in 5 mL of dichloromethane. The reaction mass was treated with 1 drop of DMF, allowed to stir for 2 h and concentrated. The remainder was diluted with 10 mL of THF, cooled to $-40°$ and treated with 2,2,2-trifluoroethylamine (0.44 g, 7.5 mmol) and warmed to RT over 3 h. The reaction mixture was diluted with 20 mL of water and 50 mL of ethyl acetate. The organic fraction was extracted with 15 mL of 1M KOH, dried ($MgSO_4$) and concentrated. The remainder was purified by column chromatography on silica gel (50 g) with hexanes (100 mL) followed by 2:8 ethyl acetate/hexane (300 mL) to give 0.28 g (88%) of title compound as a white solid. The resulting solid was recrystalized from 1.5 mL of a 10:1 ethanol/water solution to give 0.19 g (52%) of title compound as needles. mp 86°–88° C.

TLC Silica gel (3:7 ethyl acetate/hexane) $R_f=0.7$.

Mass Spec. (ES, + ions) m/z 410 (M+H).

Anal. Calc'd for $C_{25}H_{22}NOF_3$ C, 73.34; H, 5.42; N, 3.42 Found: C, 72.98; H, 4.94; N, 3.35.

EXAMPLE 59

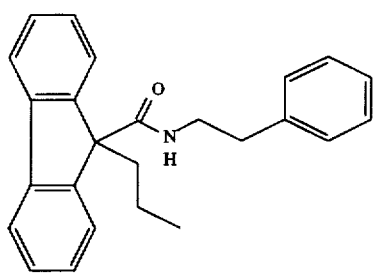

A.

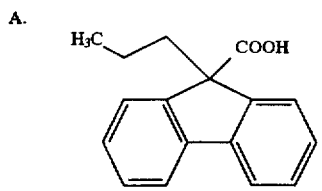

A solution of (9H)-9-fluorenecarboxylic acid (12 g, 57 mmol) in 250 ml of THF was cooled to 0° C. under an argon atmosphere and 2 equiv. (71.25 ml) of a 1.6M n-butyl lithium solution in hexane was added followed by the addition of n-propyl iodide (7.5 ml, 13.1 g, 77 mmol). The reaction mixture was stirred at 0° C. for 6 hrs. TLC, silica, MeOH:CH$_2$Cl$_2$ (1:9) showed starting acid still present, therefore, an additional 1 ml of n-propyl iodide was added and the reaction stirred for 4 hrs at 0° C. The reaction was quenched by adding 75 ml of water and the pH was adjusted to pH 1 with 3N HCl. The reaction mixture was extracted with hexane (3×200 ml) and the hexane extract washed with water, brine and dried over anhy. sodium sulfate. The solvents were evaporated yielding the crude product as a yellow oil which was dissolved in ~250 ml of ethanol and heated at reflux with Darco G-60, filtered through Celite and concentrated to approximately one half of the original volume. Water was slowly added until the mixture became cloudy. The mixture was reheated and slowly allowed to cool to room temperature yielding 10.5 grams (73%) of title compound as colorless crystals. m.p. 120°–122° C.

Anal Calc'd for C$_{17}$H$_{16}$O$_2$ (MW 252.3): C, 80.93; H, 6.39 Found: C, 81.01; H, 6.22.

B.

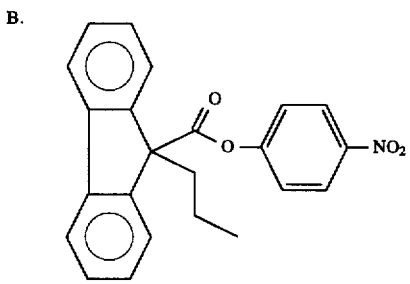

Example 59 Part B was prepared analogously to Example 22 Part B starting with Example 59 Part A (1.5 g, 5.95 mmol), 4.5 mL (8.92 mmol) of oxalyl chloride, 6 drops (catalytic) of dimethylformamide, 2.5 g (17.8 mmol) of 4-nitrophenol, and 1 mL (7.14 mmol) of triethylamine.

C.

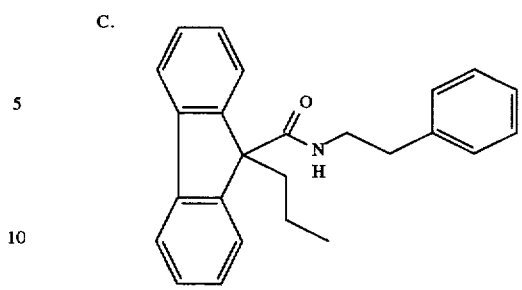

Example 59 compound was prepared via an automated procedure carried out on a Zymark Benchmate® Workstation using the following procedure.

The Benchmate® delivered 1 mL (44 mg, 0.11 mmol, 1 eq) of a stock solution of Example 59 Part B in THF (44 mg/mL) to a 16 mm×100 mm culture tube. The tube was removed and placed on a balance where phenethyl amine (24 mg, 0.17 mmol) was added manually. The reaction was allowed to proceed until all reactions in the run were complete as indicated by disappearance of Example 59 Part B compound by TLC (silica gel, 2% MeOH in CH$_2$Cl$_2$, visualized by UV and I$_2$).

The product was purified in an analogous manner to Example 22, Part C, to give title compound as a colorless solid in 81% yield. MS (electrospray, + ions) m/z 356 (M+H).

EXAMPLES 60 TO 84

Examples 60–84 can be prepared from Example 59 Part B compound by the method in Example 59 Part C.

EXAMPLE 60

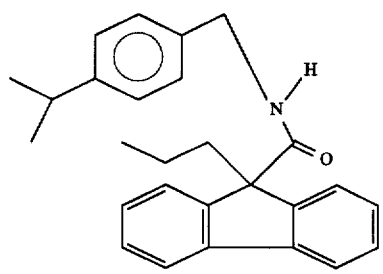

MS (electrospray, pos. ions) 384 (M+H)

EXAMPLE 61–62

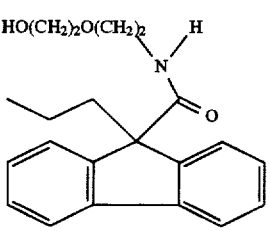

MS (electrospray, pos. ions) 340 (M+H)

EXAMPLE 63
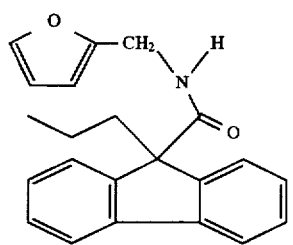
MS (electrospray, pos. ions) 399 (M+H)
EXAMPLE 64
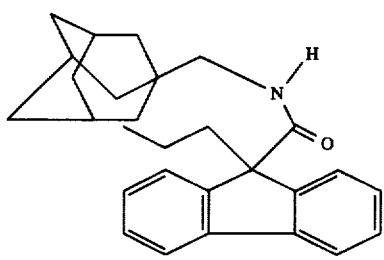
MS (electrospray, pos. ions) 400 (M+H)
EXAMPLE 65
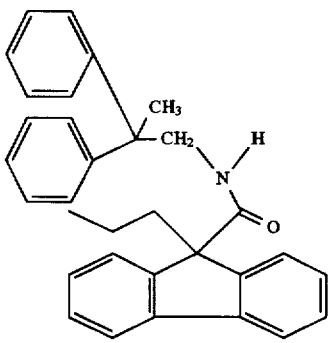
MS (electrospray, pos. ions) 446 (M+H)
EXAMPLE 66
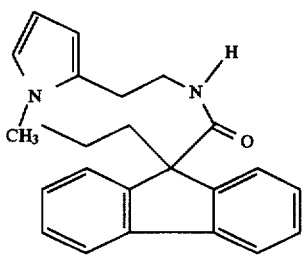
MS (electrospray, pos. ions) 359 (M+H)
EXAMPLE 67
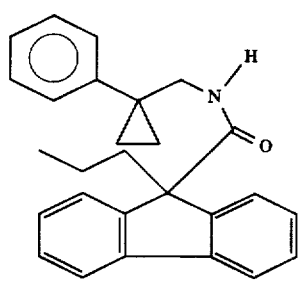
MS (electrospray, pos. ions) 382 (M+H)
EXAMPLE 68
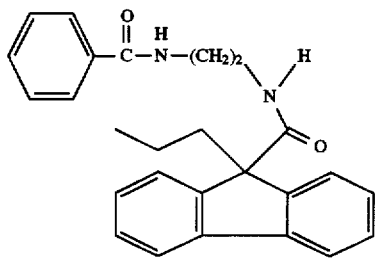
MS (electrospray, pos. ions) 399 (M+H)
EXAMPLE 69
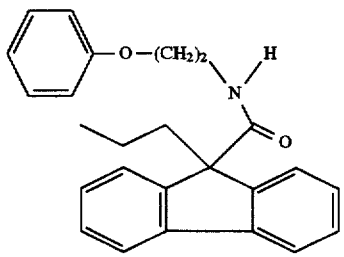
MS (electrospray, pos. ions) 372 (M+H)
EXAMPLE 70
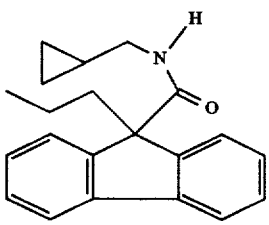
MS (electrospray, pos. ions) 306 (M+H)

EXAMPLE 71
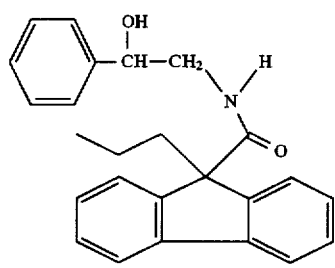
MS (electrospray, pos. ions) 372 (M+H)
EXAMPLE 72
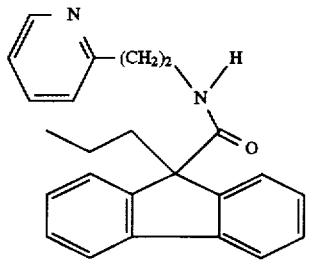
MS (electrospray, pos. ions) 357 (M+H)
EXAMPLE 73
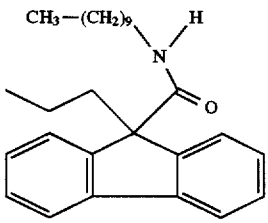
MS (electrospray, pos. ions) 392 (M+H)
EXAMPLE 74
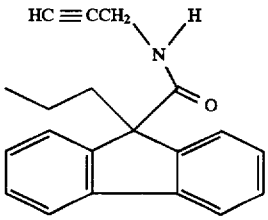
MS (electrospray, pos. ions) 291 (M+H)
EXAMPLE 75
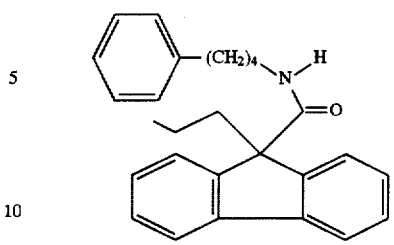
MS (electrospray, pos. ions) 384 (M+H)
EXAMPLE 76
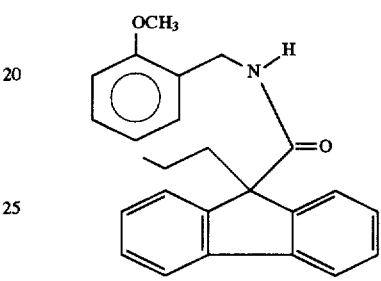
MS (electrospray, pos. ions) 372 (M+H)
EXAMPLE 77
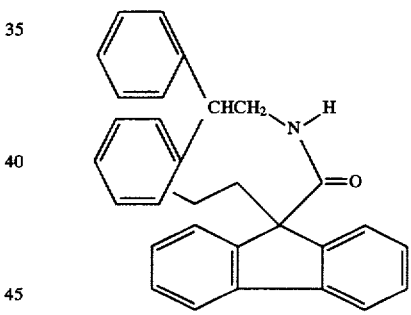
MS (electrospray, pos. ions) 432 (M+H)
EXAMPLE 78
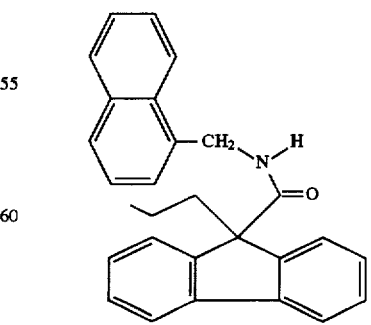
MS (electrospray, pos. ions) 392 (M+H)

EXAMPLE 79

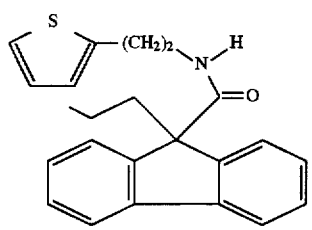

MS (electrospray, pos. ions) 362 (M+H)

EXAMPLE 80

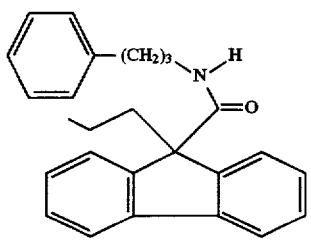

MS (electrospray, pos. ions) 370 (M+H)

EXAMPLE 81

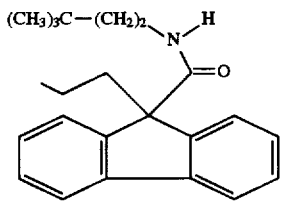

MS (electrospray, pos. ions) 336 (M+H)

EXAMPLE 82

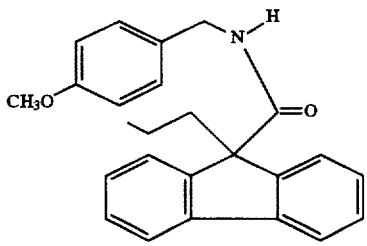

MS (electrospray, pos. ions) 372 (M+H)

EXAMPLE 83

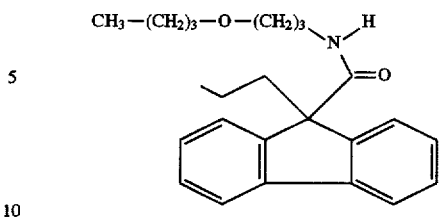

MS (electrospray, pos. ions) 366 (M+H)

EXAMPLE 84

N-Methyl-N-(phenylmethyl)-9-propyl-9H-fluorene-9-carboxamide

A. 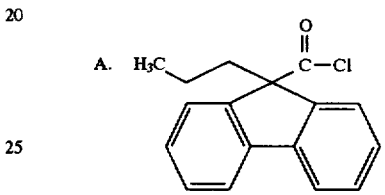

A solution of Example 59 Part A compound (2.02 g, 8 mmol) in 15 ml of dry dichloromethane was cooled to 0° C. under an argon atmosphere. N,N-Dimethylformamide (50 μl) was added to the reaction mixture followed by the addition of oxalyl chloride (0.77 ml, 1.12 g, 8.8 mmol) over a 10 minute period. After stirring for 15 min at 0° C. the reaction was allowed to warm to room temperature and stir for 1 hr. The volatiles were removed under vacuum and the oily residue was redissolved several times in dichloromethane and evaporated yielding the title acid chloride as a colorless solid which was used without any further purification.

B. N-Methyl-N-(phenylmethyl)-9-propyl-9H-fluorene-9-carboxamide

A solution of Example 84 Part A compound (1 mmol) in 8 ml of dry THF was cooled to 0° C. under an argon atmosphere and 2.1 equiv. of N-methyl-N-benzylamine (255 mg, 2.1 mmol) was added. After stirring at ambient temperature for 2 hrs. the reaction was diluted with 25 ml of ethyl acetate and washed with sat. sodium bicarbonate solution. The ethyl acetate extract was washed with sodium bicarbonate, water, brine and dried over anhy. sodium sulfate. The crude product was purified by flash chromatography on Merck EM silica gel eluting with 5% EtOAc/hexane yielding 186 mg (53%) of pure title product as a colorless solid. m.p. 73°–74° C.

Anal Calc'd for $C_{25}H_{25}NO$ (FW 355.48): C, 84.47; H, 7.09; N, 3.94. Found: C, 84.57; H, 7.16; N, 3.90.

EXAMPLES 85 to 92

Examples 85 to 92 can be prepared from Example 84 Part A compound by the method in Example 84, Part B.

EXAMPLE 85

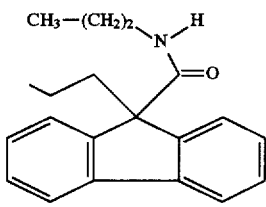

M.P. 96°–98° C. Mass Spec. (CI) (M+H)⁺=308⁺. Anal. Cald'd for $C_{21}H_{25}NO$: C, 82.04; H, 8.20; N, 4.56. Found: C, 82.06; H, 8.46; N, 4.48.

EXAMPLE 86

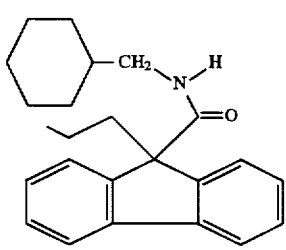

M.P. 106°–107° C. Mass Spec. (CI) (M+H)⁺=348. Anal. Cald'd for $C_{24}H_{29}NO$: C, 82.95; H, 8.41; N, 4.03. Found: C, 82.71; H, 8.22; N, 3.82.

EXAMPLE 87

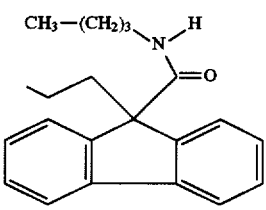

M.P. 60°–62° C. Mass Spec. (CI) (M+H)=308. Anal. Cald'd for $C_{21}H_{25}NO$: C, 82.04; H, 8.20; N, 4.56. Found: C, 82.09; H, 8.35; N, 4.42.

EXAMPLE 88

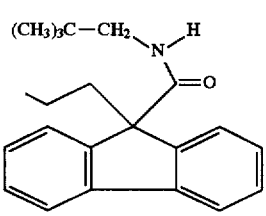

M.P. 62°–64° C. Mass Spec. (CI) (M+H)=322. Anal. Cald'd for $C_{22}H_{27}NO$: C, 82.20; H, 8.47; N, 4.36. Found: C, 81.86; H, 8.19; N, 4.41.

EXAMPLE 89

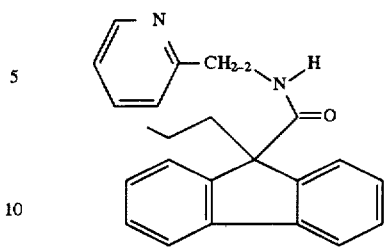

M.P. 102°–103° C. Mass Spec. (CI) (M+H)=343. Anal. Cald'd for $C_{23}H_{22}N_2O$: C, 80.67; H, 6.48; N, 8.18. Found: C, 80.51; H, 6.46; N, 8.04.

EXAMPLE 90

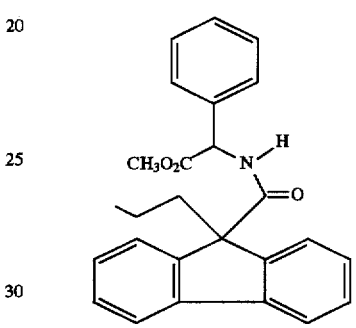

Mass Spec. (CI) (M+H)=400. Anal. Cald'd for $C_{26}H_{25}NO_3+0.1H_2O$: C, 77.87; H, 6.33; N, 3.49. Found: C, 77.87; H, 6.35; N, 3.53.

EXAMPLE 91

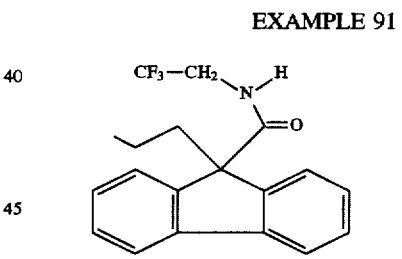

M.P. 113°–115° C. MS (CI, +ions) m/z 334 (M+H). Anal. Cald'd for $C_{19}H_{18}NOF_3$: C, 68.46; H, 5.44; N, 4.20; F, 17.10. Found: C, 68.24; H, 5.70; N, 4.18; F, 17.22.

EXAMPLE 92

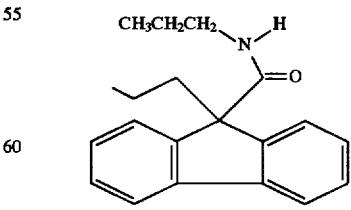

M.P. 75°–77° C. MS (CI, +ions) m/z 294 (M+H). Anal. Cald'd for $C_{20}H_{23}NO$: C, 81.87; H, 7.90; N, 4.77. Found: C, 81.88; H, 8.18; N, 4.70.

EXAMPLE 93

9-(2-Propenyl)-N-(2-pyridinylmethyl)-9H-fluorene-9-carboxamide

A.

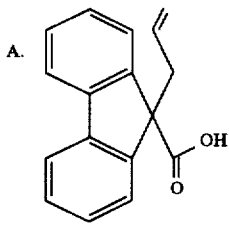

To a methoxyethanol solution (100 ml) of 9H-fluorene-9-carboxylic acid (10.83 g, 0.0515 mol) under argon was added solid KOH (6.8 g, 0.103 mol). After about 15 min the KOH had dissolved resulting in a blue-green colored solution. Allyl bromide (8.9 ml, 0.526 mol) was then added and stirred at room temperature for 2 h. The reaction mixture was partitioned between EtOAc/H$_2$O and the aqueous layer extracted twice with EtOAc. The aqueous layer was brought to pH 2 with 1N HCl, extracted twice with EtOAc, and the combined organics were dried over Na$_2$SO$_4$. Evaporation in vacuo gave 11.63 g of a brown colored oily-solid. The residue was co-evaporated with CH$_2$Cl$_2$, Et$_2$O, EtOAc, and hexanes to give an orange colored solid 9.19 g (70% recovery). A portion of the material (400 mg) was purified by flash chromatography (twice, 3×13 cm), eluting with 3%MeOH:CH$_2$Cl$_2$ to give title compound as a colorless solid (160 mg). m.p. 128°–130° C.

MS: (CI, M+NH$_4^+$): m/z 268. Anal. Calc. for C$_{17}$H$_{14}$O$_2$.0.13H$_2$O: C, 80.80; H, 5.69. Found: C, 80.80; H, 5.61.

Alternative Preparation of Part A Compound

To a THF (15 ml) supension of 9-fluorene carboxylic acid (5.28 g, 0.025 mol) at 0° C. under argon was added sodium hexamethyldisilizane (50 mL, 0.05 mol, 1M in THF), initial solid formation, and the final greenish-brown solution stirred for 5 min. Allyl bromide (2.3 mL, 0.0265 mol) was added and after 1 h the mixture was poured into cold water. The aqueous layer was extracted with EtOAc and the organic layer washed with water. The combined aqueous layers were brought to pH 1 with 3N HCl and extracted with EtOAc. The organics were washed with brine, dried over Na$_2$SO$_4$, and the volatiles removed in vacuo to give an oily-solid residue (6.96 g). The residue was crystallized from EtOH/water to give 2.81 g colorless solid. After concentrating the mother liquor, a second crop (1.04 g) and third crop (0.5 g) were obtained of Part A compound (4.35 g, 69% yield). mp 128°–130° C.

B.

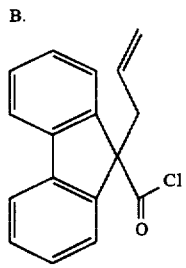

To a CH$_2$Cl$_2$ (40 ml) solution of Part A compound (3.83 g, 0.015 mol) at 0° C. under argon was added oxalyl chloride (2 ml, 0.023 mol) then DMF (90 μL). After 15 min. at 0° C. and 1.5 h at room temperature, the volatiles were removed in vacuo and the residue co-evaporated with CH$_2$Cl$_2$ to give title compound, which was used directly.

C. 9-(2-Propenyl)-N-(2-pyridinylmethyl)-9H-fluorene-9-carboxamide

To a THF (35 ml) solution of Part B acid chloride (0.015 mol) at −5° C. under argon was added 2-(aminomethyl)pyridine (3.4 mL, 0.033 mol), with extra THF (10 mL) added to improve stirring. After 15 min, the mixture was brought to room temperature for 4 h. At 0° C., the reaction mixture was quenched with saturated NaHCO$_3$, the aqueous layer extracted 3 times with EtOAc, the combined organic layers were washed with H$_2$O, brine and dried over Na$_2$SO$_4$. The volatiles were removed in vacuo to give a colored solid (5.1 g). The residue was purified by flash column chromatography (SiO$_2$, 10 by 20 cm), eluting with 2.5% MeOH:CH$_2$Cl$_2$, to give title compound (2.67 g, 51% yield) as a colorless solid. m.p. 110°–111° C.

MS:(CI, (M+H)$^+$): 341 m/z. Anal. Calc. for C$_{23}$H$_{20}$N$_2$O: C, 81.15; H, 5.92; N, 8.23. Found: C, 80.95; H, 5.99; N, 8.21.

EXAMPLES 94 to 102

EXAMPLE 94 to 102 can be prepared from Example 93 Part B compound by the method in Example 93 Part C.

EXAMPLE 94

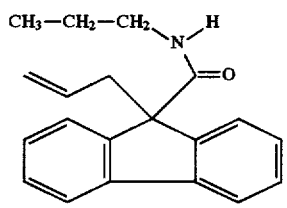

mp 85.5°–86.5° C. MS (CI, (M+H)$^+$) m/z 292. Anal. Cald'd for C$_{20}$H$_{21}$NO: C, 82.44; H, 7.26; N, 4.81. Found: C, 82.31; H, 7.44; N, 4.77.

EXAMPLE 95

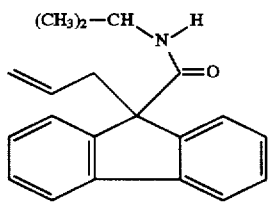

mp 74°–75.5° C. MS (CI, (M+H)$^+$) m/z 292. Anal. Cald'd for C$_{20}$H$_{21}$NO.0.09H$_2$O: C, 81.98; H, 7.29; N, 4.78. Found: C, 82.02; H, 7.33; N, 4.74.

EXAMPLE 96

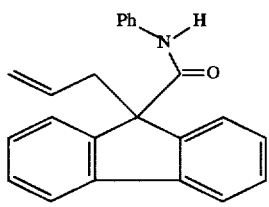

mp 112.5°–114° C. MS (CI, (M+H)⁺) m/z 326. Anal. Cald'd for $C_{23}H_{19}NO.0.12H_2O$: C, 84.32; H, 5.92; N, 4.27. Found: C, 84.35; H, 5.76; N, 4.24.

EXAMPLE 97

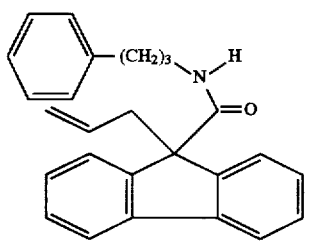

mp 74.5°–75.5° C. MS (CI, (M+H)⁺) m/z 368. Anal. Cald'd for $C_{26}H_{25}NO.0.13 H_2O$: C, 84.42; H, 6.88; N, 3.79. Found: C, 84.48; H, 6.84; N, 3.73.

EXAMPLE 98

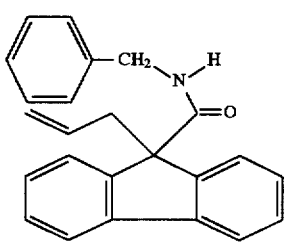

mp 80.5°–81.5° C. MS (CI, (M+H)⁺) m/z 340. Anal. Cald'd for $C_{24}H_{21}NO$: C, 84.92; H, 6.24; N, 4.13. Found: C, 84.58; H, 6.15; N, 4.10.

EXAMPLE 99

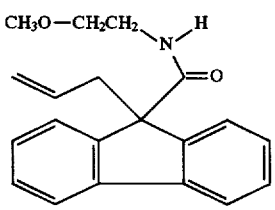

mp 87°–88.5° C. MS (CI, (M+H)⁺) m/z 308. Anal. Cald'd for $C_{20}H_{21}NO_2$: C, 78.15; H, 6.89; N, 4.56. Found: C, 78.05; H, 6.83; N, 4.47.

EXAMPLE 100

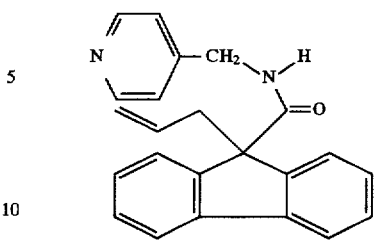

Mp 127°–128° C. MS (CI, (M+H)⁺) m/z 341. Anal. Cald'd for $C_{23}H_{20}N_2O$: C, 81.15; H, 5.92; N, 8.23. Found: C, 81.27; H, 5.88; N, 8.11.

EXAMPLE 101

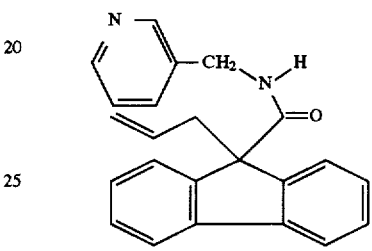

mp 68°–71° C. MS (CI, (M+H)⁺) m/z 341. Anal. Cald'd for $C_{23}H_{20}N_2O$: C, 81.15; H, 5.92; N, 8.23. Found: C, 81.11; H, 5.86; N, 8.12.

EXAMPLE 102

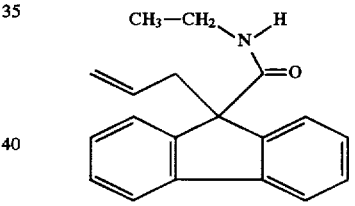

mp 87.5°–88.5° C. Anal. Cald'd for $C_{19}H_{19}NO.0.13 H_2O$: C, 81.57; H, 6.94; N, 5.01. Found: C, 81.58; H, 6.79; N, 5.00.

EXAMPLE 103

9-(1-Piperidinylcarbonyl)-9-(2-propenyl)-9H-fluorene

To a 0° C. suspension under argon of Example 93 Part A compound (0.495 g, 1.98 mmol), piperidine (0.39 ml, 3.94 mmol), hydroxybenzotriazole hydrate (0.40 g, 2.96 mmol), and N-methylmorpholine (0.22 ml, 2.00 mmol) in DMF (6 ml) was added EDCI (0.44 g, 2.27 mmol) and the reaction was allowed to come to room temperature overnight. After 24 h, the reaction was quenched with saturated $NaHCO_3$, the aqueous layer extracted twice with EtOAc, and the combined organics dried over $Na_2SO_4$ overnight. The volatiles were removed in vacuo to give an oil (600 mg). The residue was purified by flash column chromatography ($SiO_2$, 3 by 17 cm), eluting with $CH_2Cl_2$ to give title compound (0.265 g, 42% yield) as a colorless solid. m.p. 64°–66° C.

MS: (CI, +ions): m/z 318 (M+H). Anal. Calc. for $C_{22}H_{23}NO$: C, 83.24; H, 7.30; N, 4.41. Found: C, 83.25; H, 7.32; N, 4.36.

EXAMPLE 104

N-Butyl-9-(2-propenyl)-9H-fluorene-9-carboxamide

To a CH₂Cl₂ (8 ml) and pyridine (0.28 ml) solution of Example 93 Part A compound (400 mg, 1.60 mmol) under argon was added cyanuric fluoride (0.27 mL, 3.20 mmol). After 1.5 h, the cloudy reaction mixture was partitioned between ice-water and CH₂Cl₂. The organics were dried over Na₂SO₄, and the volatiles removed in vacuo to give an oily-solid residue (420 mg). The crude residue was used directly in the subsequent reaction.

To a THF (7 ml) solution of the above crude residue (1.5 mmol) at 0° C. under argon was added n-butylamine (0.3 mL, 3.04 mmol) and the reaction brought to room temperature. After 16 h, the mixture was quenched with saturated NaHCO₃, the aqueous layer extracted 2 times with EtOAc, and the combined organic layers were washed with brine and dried over Na₂SO₄. The volatiles were removed in vacuo to give an oily-solid (470 mg). The residue was purified by flash column chromatography (SiO₂, 5 by 6 cm), eluting with 12.5% EtOAc:hexanes, to give title compound (362 mg, 79% yield) as a colorless solid, m.p. 62.5°–64° C.

MS: (CI, M+H+): m/z 306. Anal. Calc. for $C_{21}H_{23}NO$: C, 82.59; H, 7.59; N, 4.59. Found: C, 82.72; H, 7.45; N, 4.46.

EXAMPLES 105–106

9-(2,3-Dihydroxypropyl)-N-ethyl-9H-fluorene-9-carboxamide

To an acetone:H₂O (4 ml, 9:1) suspension of Example 102 compound (191 mg, 0.689 mmol) and N-methylmorpholine-N-oxide (215 mg, 1.59 mmol) under argon was added OsO₄ (several small crystals). After stirring at room temperature overnight, the reaction was cooled and then quenched with aq. sodium metabisulfite. The reaction mixture was stirred 15 min. and the aqueous layer extracted twice with EtOAc. The organics were washed with brine, dried over Na₂SO₄, and concentrated to an oil (220 mg). The residue was purified by flash column chromatography (SiO₂, 3 by 9 cm), eluting with 4:1 EtOAc:CH₂Cl₂, to give title compound (106 mg, 49% yield) as a colorless, hygroscopic foam.

MS: (CI, M+H+): m/z 312. Anal. Calc. for $C_{19}H_{21}NO_3 \cdot 0.4\ H_2O$: C, 71.64; H, 6.90; N, 4.40. Found: C, 71.68; H, 6.84; N, 4.36.

EXAMPLE 107

9-(3-Phenylpropyl)-N-(3-hydroxy)propyl-9H-xanthene-9-carboxamide

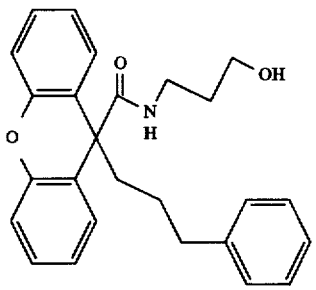

A. 9-(3-Phenylpropyl)-9H-xanthene-9-carboxylic acid

To a solution of 10 g (44 mmol, 1 eq) of 9-xanthenylcarboxylic acid in 200 mL of THF at 0° C. was added 37.2 mL (93 mmol, 2.1 eq) of a 2.5M solution of n-butyllithium in hexanes dropwise over 15 min. (First equivalent resulted in precipitation of Li salt of the carboxylate; solution became homogeneous as dianion formed.) The resulting orange solution of dianion was stirred at 0° C. for 10 min and 9.4 mL (62 mmol, 1.4 eq) of 1-bromo-3-phenylpropane was added quickly over 3 min. The reaction was stirred at 0° C. and allowed to warm to RT as the ice bath melted. After 16 h, the basic reaction mixture (pH ~14) was extracted with water (3×100 mL). The combined aqueous layers were acidified (to pH ~1) with 6N HCl and extracted with ether (3×100 mL). The combined ether solutions were dried (MgSO₄), filtered and concentrated to afford 17.04 g of a viscous golden oil. The oil was dissolved in hot hexanes using a small amount of CH₂Cl₂ to effect complete dissolution. Concentration of this solution resulted in a yellow solid which was recrystallized from ether/hexanes to afford 13.3 g (88%) of title compound as a white crystalline solid, m.p. 137°–138° C.

TLC (silica gel, 10% MeOH in CH₂Cl₂, UV and I₂). $R_f=0.52$.

B. 9-(3-Phenylpropyl)-9H-xanthene-9-carboxylic acid, 4-nitrophenyl ester

To a solution of 10 g (29.0 mmol, 1 eq) of Part A compound in 100 mL of CH₂Cl₂ was added 100 μL of DMF. The solution was cooled to 0° C. and 22.0 mL (43.6 mmol, 1.5 eq) of a 2.0M oxalyl chloride solution in CH₂Cl₂ was added over 5 min. The resulting bubbling solution was stirred at 0° C. for 1.5 h (until bubbling had ceased). The solution was concentrated and the residual oil was taken up in 50 mL of CH₂Cl₂ and reconcentrated. The resulting oil was dissolved in 150 mL of CH₂Cl₂ and 188 mg (1.52 mmol, 0.05 eq) of 4-dimethylaminopyridine was added. The solution was cooled to 0° C. and 4.9 mL (34.8 mmol, 1.2 eq) of triethylamine was added. To the resulting dark brown cloudy solution was added 12.1 g (87.1 mmol, 3 eq) of p-nitrophenol as a solid. Upon addition the reaction quickly became clear and the resulting clear reaction mixture was allowed to warm to RT as the ice bath melted. (TLC indicated the reaction was essentially complete after 40 min.) After 15 h, the reaction was washed with 100 mL of ice-cold 1N HCl. The organic solution was filtered through cotton and concentrated to afford 24.22 g of a viscous golden-brown oil which was chromatographed on silica gel (200 g) eluted with 25% hexanes in CH₂Cl₂ to afford 13.45 g of a viscous golden oil. The product was cystallized by concentrating down a ether/hexane solution and the crude solid was then recrystallized from ether/hexanes to afford 11.8 g (87%) of title compound as an off-white crystalline solid, m.p. 93°–94° C.

TLC (silica gel, 25% EtOAc in hexanes, UV and I₂) $R_f=0.39$. MS(CI, pos. ions): m/z 483 (M+NH₄), 466 (M+H). Anal. Calcd. for $C_{29}H_{23}NO_5$: C, 74.83; H, 4.98; N, 3.01. Found: C, 74.61; H, 4.71; N, 2.88.

C. 9-(3-Phenylpropyl)-N-(3-hydroxy)propyl-9H-xanthene-9-carboxamide

The title compound was prepared via an automated procedure carried out on a Zymark Benchmate® Workstation using the following procedure.

The Benchmate® delivered 1 mL (80 mg, 0.18 mmol, 1 eq) of a stock solution of title compound in THF (80 mg/mL) to a 16 mm×100 mm culture tube. The tube was removed and placed on a balance where 3-amino-1-propanol (24 mg, 0.27 mmol) was added manually. The reaction was allowed to proceed until all reactions in the run were complete as indicated by disappearance of title compound by TLC (silica gel, 2% MeOH in CH$_2$Cl$_2$, visualized by UV and I$_2$).

The product was purified in an analogous manner to Example 22, Part C, to give title compound as a pale oil (55 mg) in 69% yield. MS (electrospray, pos. ions)=402 (M+H).

EXAMPLES 108–140

Examples 108 to 140 can be prepared from Example 107 Part B compound by the method in Example 107, Part C.

EXAMPLE 108

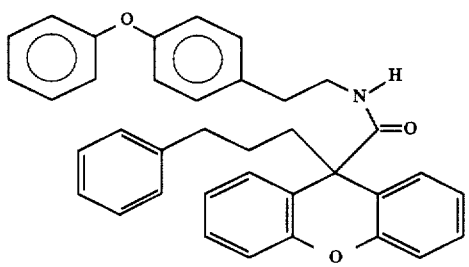

MS (CI, pos. ions) 540 (M+H).

EXAMPLES 109–110

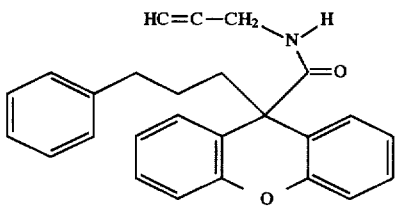

MS (CI, pos. ions) 382 (M+H).

EXAMPLE 111

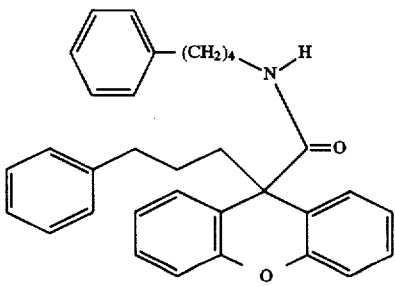

MS (CI, pos. ions) 476 (M+H).

EXAMPLE 112

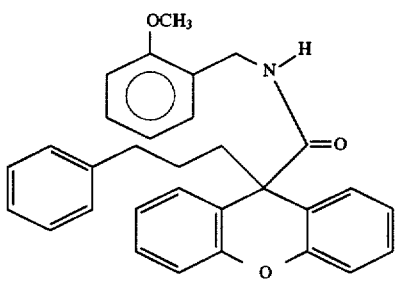

MS (CI, pos. ions) 464 (M+H).

EXAMPLE 113

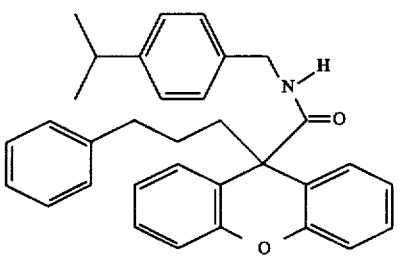

MS (CI, pos. ions) 476 (M+H).

EXAMPLES 114–115

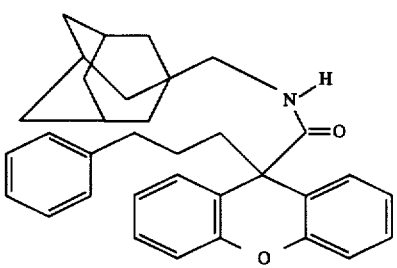

MS (electrospray, pos. ions) 492 (M+H).

EXAMPLE 116

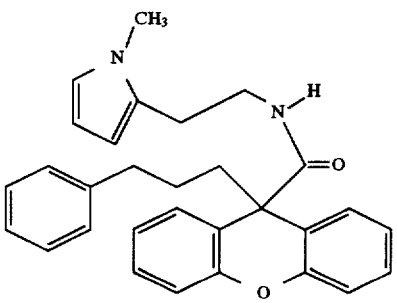

MS (electrospray, pos. ions) 451 (M+H).

EXAMPLE 117
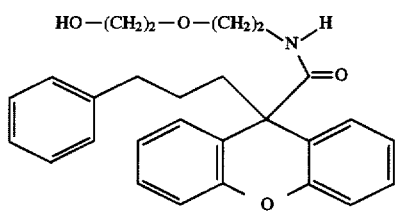
MS (electrospray, pos. ions) 432 (M+H).
EXAMPLE 118
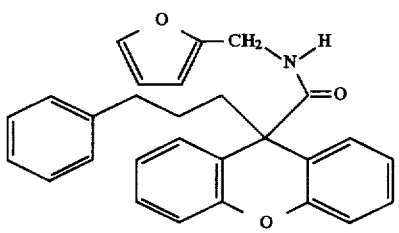
MS (electrospray, pos. ions) 424 (M+H).
EXAMPLE 119
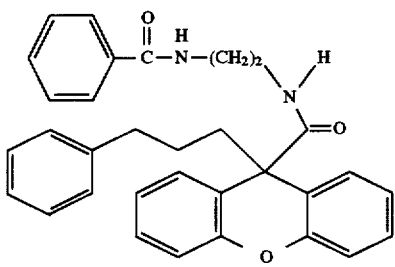
MS (electrospray, pos. ions) 491 (M+H).
EXAMPLES 120–121
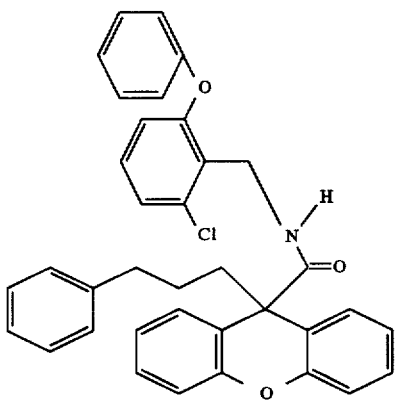
MS (electrospray, pos. ions) 560 (M+H).
EXAMPLE 122
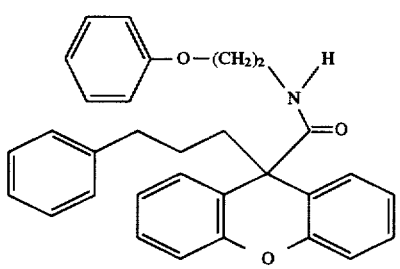
MS (electrospray, pos. ions) 464 (M+H).
EXAMPLE 123
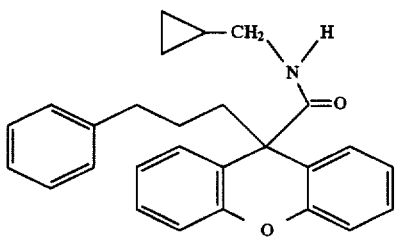
MS (electrospray, pos. ions) 398 (M+H).
EXAMPLE 124
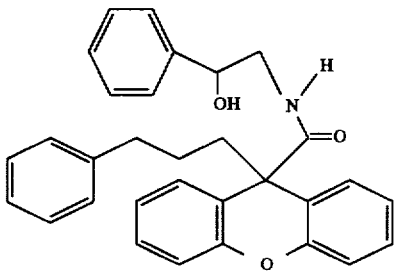
MS (electrospray, pos. ions) 464 (M+H).
EXAMPLE 125
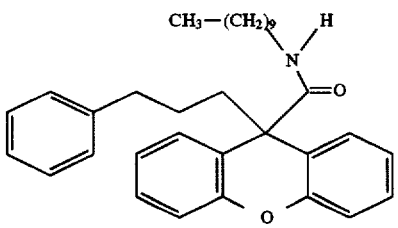
MS (electrospray, pos. ions) 484 (M+H).

EXAMPLE 126
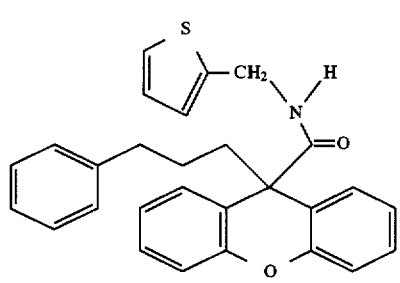
MS (electrospray, pos. ions) 440 (M+H).
EXAMPLE 127–128
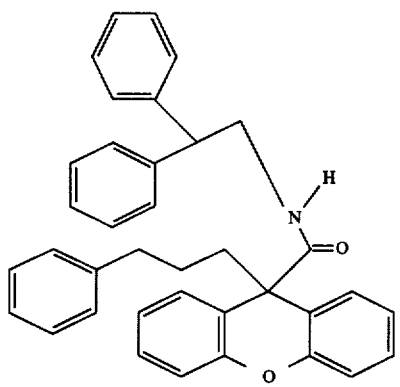
MS (electrospray, pos. ions) 524 (M+H).
EXAMPLE 129
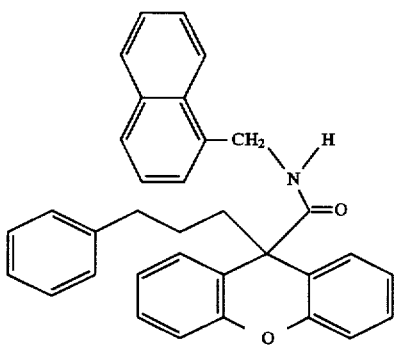
MS (electrospray, pos. ions) 484 (M+H).
EXAMPLE 130
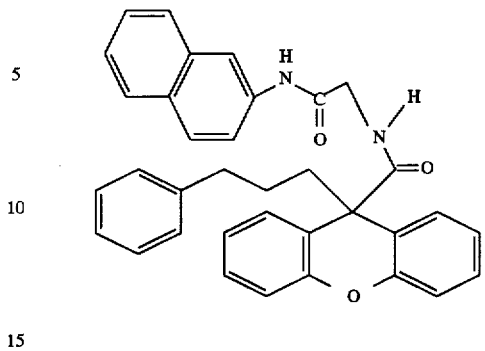
MS (electrospray, pos. ions) 527 (M+H).
EXAMPLE 131
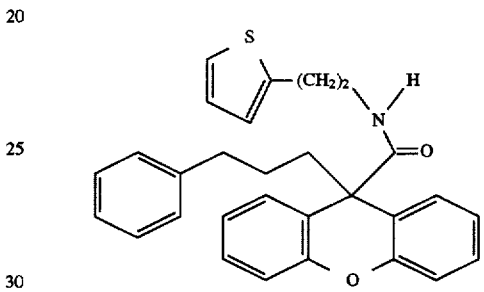
MS (electrospray, pos. ions) 454 (M+H).
EXAMPLE 132
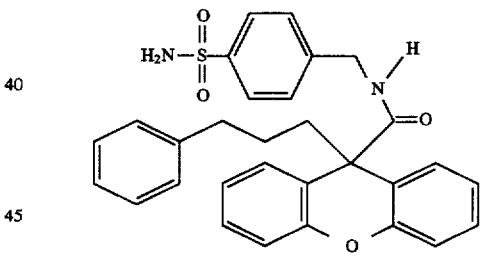
MS (electrospray, pos. ions) 513 (M+H).
EXAMPLE 133
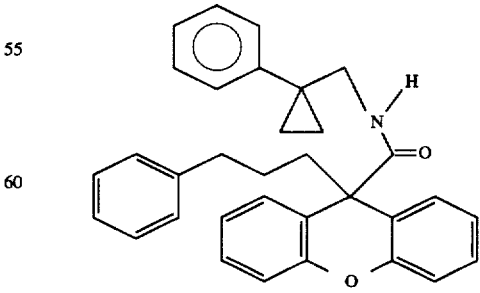
MS (electrospray, pos. ions) 474 (M+H).

EXAMPLE 134
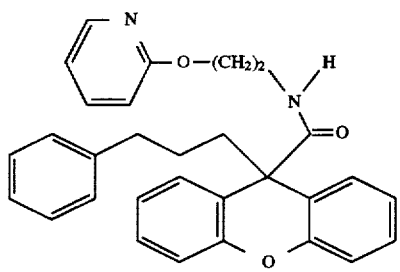
MS (electrospray, pos. ions) 465 (M+H).
EXAMPLE 135
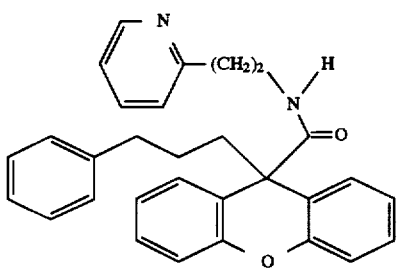
MS (electrospray, pos. ions) 449 (M+H).
EXAMPLE 136
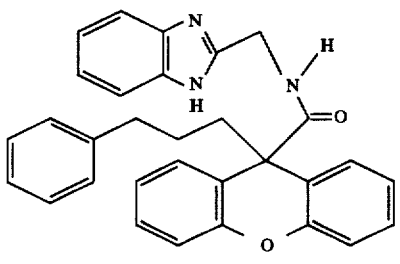
MS (electrospray, pos. ions) 474 (M+H).
EXAMPLE 137
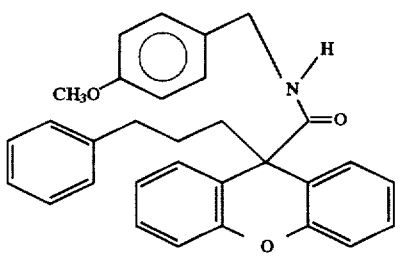
MS (electrospray, pos. ions) 464 (M+H).
EXAMPLE 138
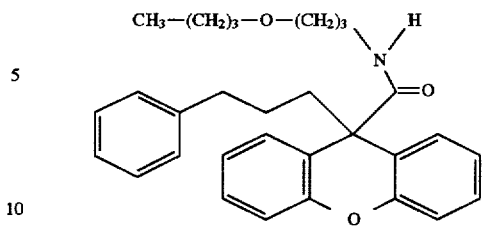
MS (electrospray, pos. ions) 458 (M+H).
EXAMPLE 139
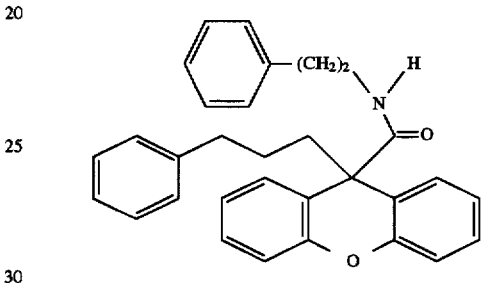
MS (electrospray, pos. ions) 448 (M+H).
EXAMPLE 140
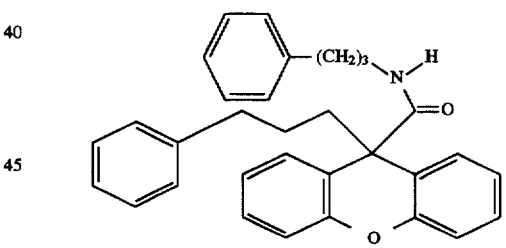
MS (electrospray, pos. ions) 462 (M+H).
EXAMPLE 141
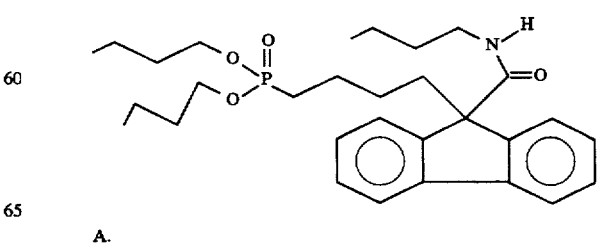
A.

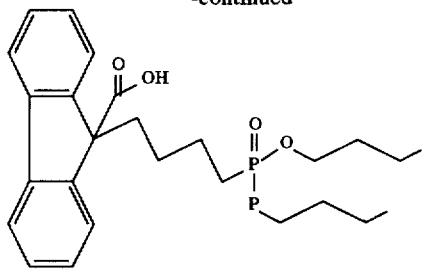

To a suspension of fluorene-(9H)-9-carboxylic acid (0.45 g, 2.18 mmol) in THF (5 mL) at −78° C. was added n-butyllithium in hexanes (1.70 mL, 4.20 mmol) dropwise at such a rate to maintain the internal temperature below −40° C. The resulting bright yellow solution was stirred at −40° C. for 0.5 h and treated with compound Example 11, Part B (0.60 g, 1.82 mmol). The mixture was slowly warmed to room temperature and stirred for 6 h when the mixture was treated with 0.1 g (10 mol%) of tetrabutylammonium iodide and allowed to stir overnight. The mixture was diluted with 0.1N HCl (25 mL, 2.50 mmol) and ethyl acetate (50 mL). The layers were separated, the organic fraction dried ($Na_2SO_4$) and concentrated to give 1 g of crude oil. This material could be purified by flash chromatography (silica gel, eluting with 5% MeOH:ethyl acetate) and crystallization from hexane/ethyl acetate/methylene chloride to gave title compound as a colorless solid. mp 123°–125° C.

TLC Silica gel (3:7:1 acetone/dichloromethane/acetic acid) $R_f$=0.45.

B.

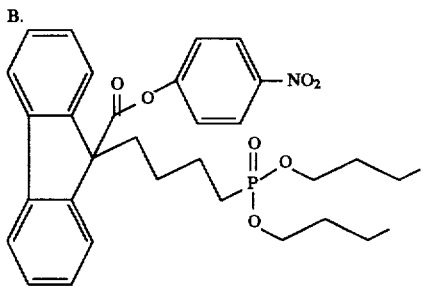

Part B compound was prepared as described for Example 22 Part B compound, using 7.59 g (16.5 mmol) of Example 144 Part A compound, 12.4 mL (24.9 mmol) of oxalyl chloride, 100 μL (catalytic) of dimethylformamide, 101 mg (0.8 mmol) of 4-dimethylaminopyridine, 2.01 g (19.8 mmol) of triethylamine, and 6.91 g (49.6 mmol) of 4-nitrophenol in $CH_2Cl_2$ (ml). The crude product was purified by flash chromatography on silica gel (400 g) eluted with methylene chloride (3 L), followed by 2% methanol in methylene chloride. The product was further purified flash chromatography on silica gel (150 g) eluted with 7:3 hexanes:ethyl acetate (3 L) followed by 6:4 hexanes:ethyl acetate (3 L), to provide 6.29 g (73%) of title compound, as a pale yellow oil.

TLC Silica gel (9:1 toluene:acetone, visualization by UV, $I_2$) $R_f$=0.27.

C.

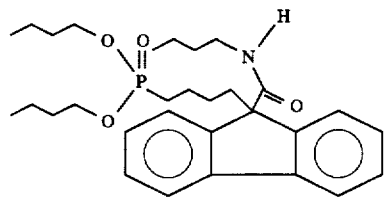

A solution of 104 mg (0.18 mmol) of Part B compound in 1 mL of THF was treated with 20 mg (0.36 mmol) of n-butylamine for 16 hours. The product was purified via solid phase extraction using a Varian SAX anion exchange column (1 g of sorbent, chloride form) by the procedure outlined below:

1) Column conditioned with 10 mL of 300 mM KOH(aq) in MeOH.
2) Column conditioned with 10 mL of MeOH.
3) Column conditioned with 10 ML of $CH_2Cl_2$.
4) Reaction mixture loaded onto SAX column and effluent collected into a product tube.
5) Column rinsed with 1 mL of THF and effluent collected into product tube.
6) Column rinsed with 2 mL of $CH_2Cl_2$ and effluent collected into product tube.

This procedure was followed by a second solid phase extraction using a Varian SCX cation exchange column (1 mg of sorbent) by the procedure outlined below:

1) Column conditioned with 10 mL of $CH_2Cl_2$.
2) Reaction mixture loaded onto SCX column and effluent collected into product tube (tared).
3) Column rinsed with 2 mL of $CH_2Cl_2$ and effluent collected into product tube.

The product solution (approx. 5 mL) was concentrated using a speed vac for 14 h to afford 59 mg (63%) of title compound as a clear oil.

HPLC Purity=90%; retention time=13.0 minutes. Column: EM Lichropshere C8 Select-B 250 mm. Solvent A: 10% methanol:90% water:0.2% $H_3PO_4$. Solvent B: 90% methanol:10% water:0.2% $H_3PO_4$. Elution: Linear gradient from 30:70 A:B over 10 minutes followed by isocratic 100%B for 10 minutes.

MS (Electrospray, +ions): m/z 598 (M+H).

EXAMPLES 142 to 185

Examples 142 to 175 can be prepared from Example 141 Part B compound by the method in Example 141 Part C. For examples where the starting amine is a salt, the amine was free based by partitioning between THF and aqueous saturated sodium bicarbonate or by adding an equimolar amount of triethylamine. Note, Bu stands for n-butyl.

EXAMPLE 142
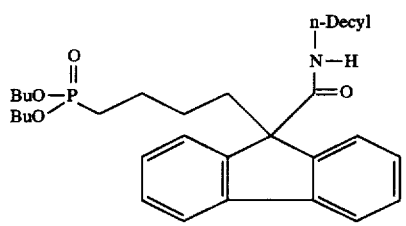
MS (ES, +ions) m/z 598 (M+H).
EXAMPLE 143
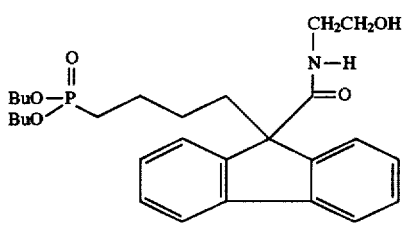
MS (ES, +ions) 501 (M+H).
EXAMPLE 144
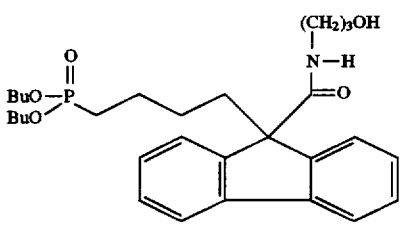
MS (ES, +ions) 516 (M+H).
EXAMPLE 145
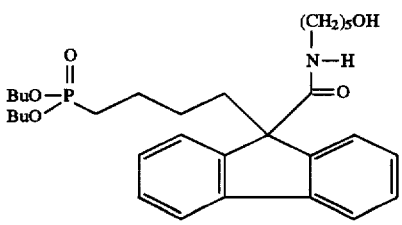
MS (ES, +ions) 544 (M+H).
EXAMPLE 146
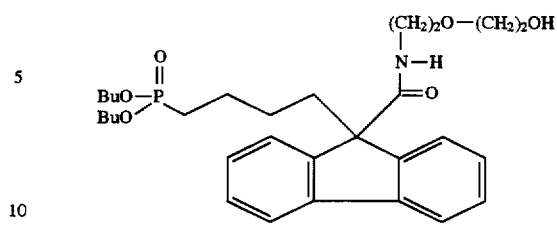
MS (ES, +ions) 546 (M+H).
EXAMPLES 147–148
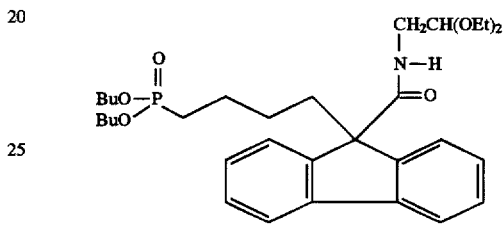
MS (ES, +ions) 596 (M+Na).
EXAMPLE 149
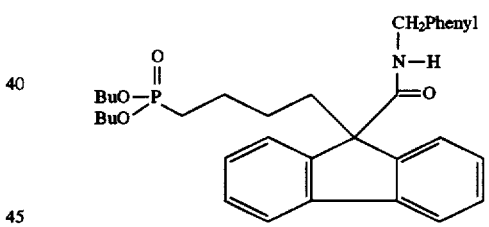
MS (ES, +ions) 548 (M+H).
EXAMPLE 150
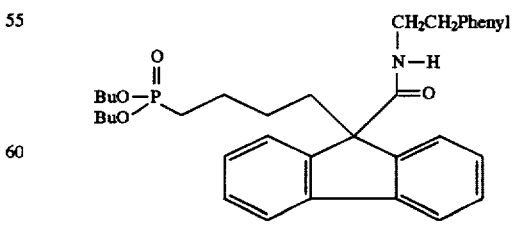
MS (ES, +ions) 562 (M+H).

EXAMPLE 151
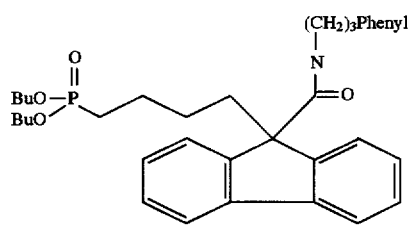
MS (ES, +ions) 576 (M+H).
EXAMPLE 152
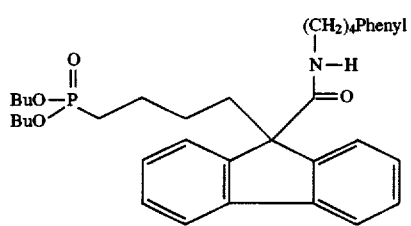
MS (ES, +ions) 590 (M+H).
EXAMPLE 153
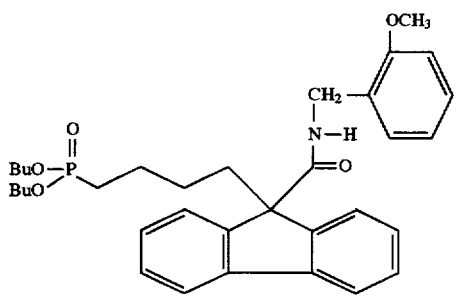
MS (ES, +ions) 578 (M+H).
EXAMPLE 154
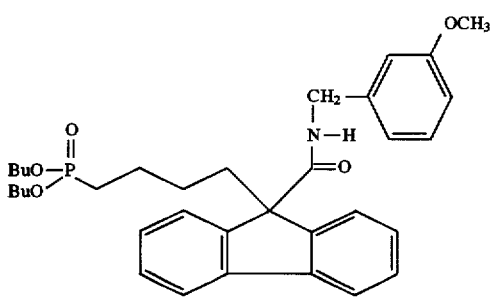
MS (ES, +ions) 578 (M+H).
EXAMPLE 155
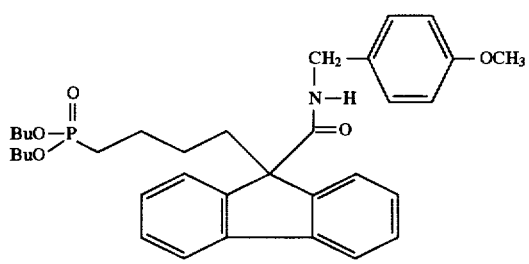
MS (ES, +ions) 578 (M+H).
EXAMPLES 156–157
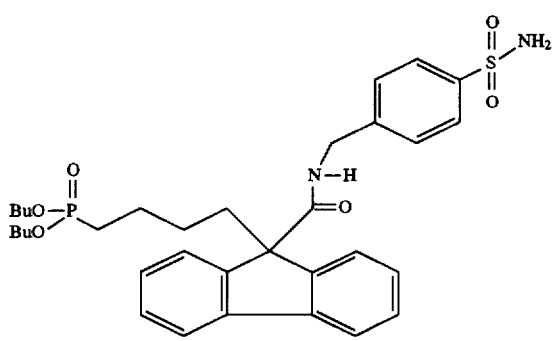
MS (ES, +ions) 627 (M+H).
EXAMPLE 158
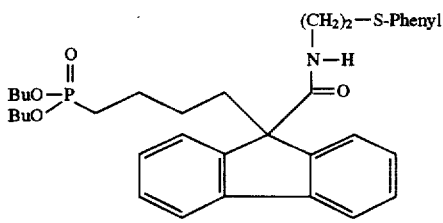
MS (ES, +ions) 594 (M+H).
EXAMPLE 159
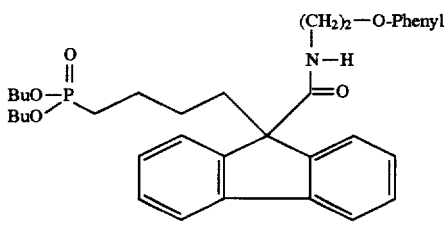
MS (ES, +ions) 578 (M+H).

EXAMPLE 160
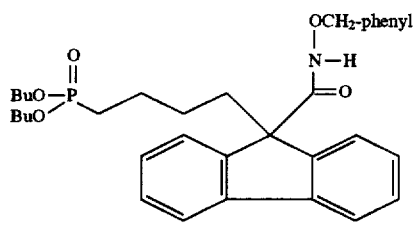
MS (ES, +ions) 564 (M+H).
EXAMPLES 161-162
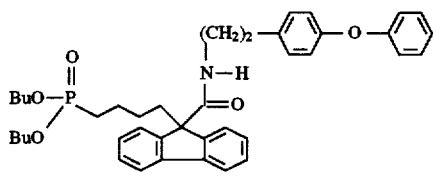
MS (ES, +ions) 654 (M+H).
EXAMPLE 163
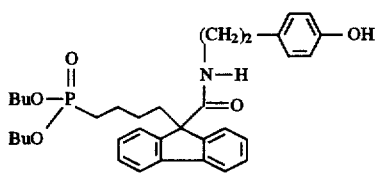
MS (ES, +ions) 578 (M+H).
EXAMPLE 164
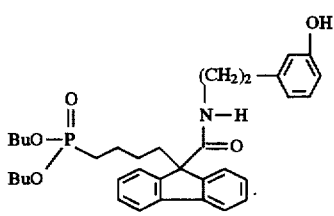
MS (ES, +ions) 578 (M+H).
EXAMPLE 165
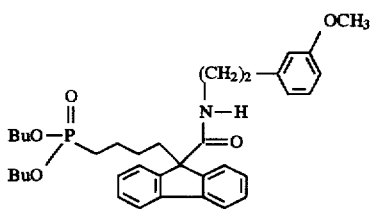
MS (ES, +ions) 592 (M+H).
EXAMPLE 166
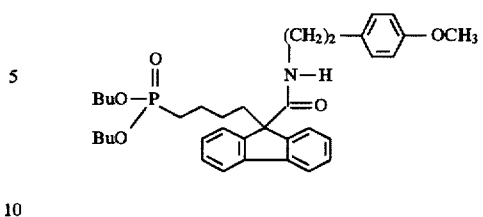
MS (ES, +ions) 592 (M+H).
EXAMPLE 167
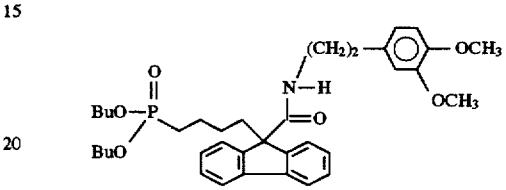
MS (ES, +ions) 622 (M+H).
EXAMPLE 168
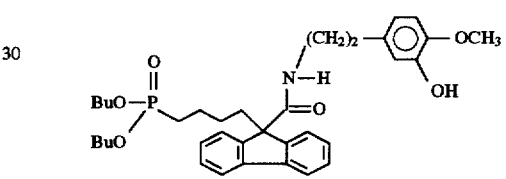
MS (ES, +ions) 608 (M+H).
EXAMPLE 169
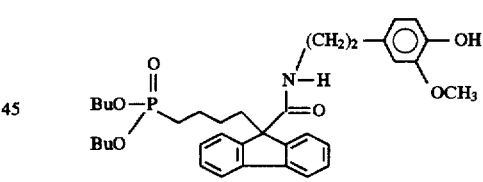
MS (ES, +ions) 608 (M+H).
EXAMPLE 170
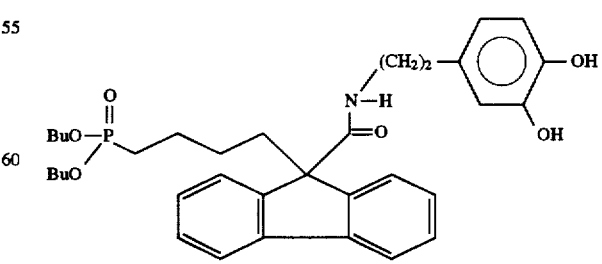
MS (ES, +ions) 594 (M+H).

EXAMPLE 171

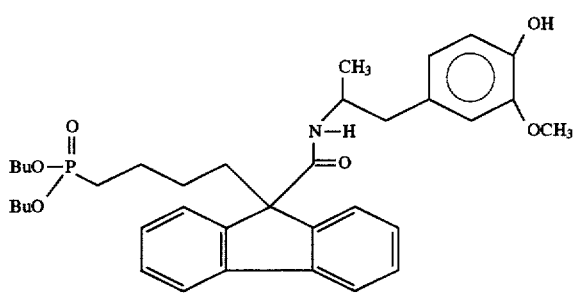

MS (ES, +ions) 622 (M+H).

EXAMPLE 172

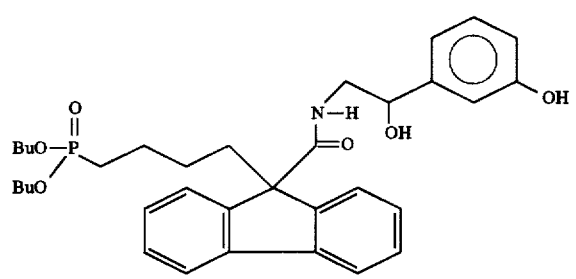

MS (ES, +ions) 594 (M+H).

EXAMPLE 173

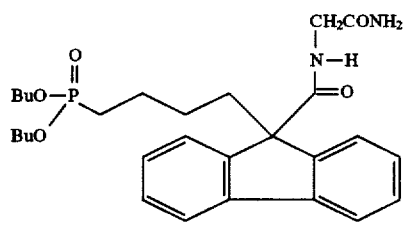

MS (ES, +ions) 515 (M+H).

EXAMPLES 174–175

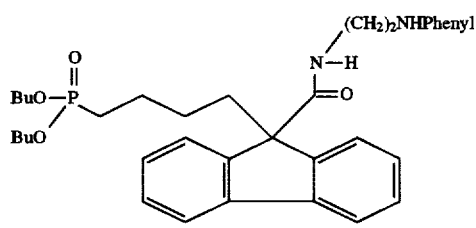

A solution of 104 mg (0.18 mmol) of Example 141 Part B compound in 1 mL of THF was treated with 22 mg (0.16 mmol, 0.9 eq) of N-phenethylaminediamine 20 for 48 hours. The product was purified via solid phase extraction using a Varian SCX anion exchange column (1 g of sorbent, 0.6 meq/g) by the procedure outlined below:

1) Column conditioned with 10 mL of CH$_2$Cl$_2$ (0.25 mL/sec).
2) Reaction mixture loaded onto SCX column (0.05 mL/sec).
3) Column rinsed with 10 mL of methanol.
4) Column rinsed with 4 mL of 1M NH$_3$/methanol and effluent collected into product tube.
5) Syringe washed with 2 mL of methanol.

This procedure was followed by a second solid phase extraction using a Varian SAX cation exchange column (1 g of sorbent, 0.7 meq/g) on the Benchmate® by the procedure outlined below:

1) Syringe washed with 4 mL of methanol.
2) Column conditioned with 10 mL of CH$_2$Cl$_2$ (0.25 mL/sec).
3) Product solution from SCX column loaded onto SAX column (0.05 mL/sec) and effluent collected into product tube (tared).
4) Column rinsed with 2 mL of CH$_2$Cl$_2$ and effluent collected into product tube.
5) Syringe washed with 4 mL of methanol.

The product solution (approx. 5 mL) was concentrated using a speed vac for 14 h to afford 66 mg (72%) of the title compound as a yellow semisolid.

MS (Electrospray, +ions): m/z 577 (M+H).

Examples 176 to 185 can be prepared from Example 141 Part B compound by the method in Example 175.

EXAMPLE 176

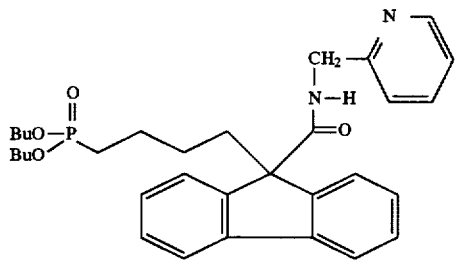

MS (ES, +ions) 549 (M+H).

EXAMPLE 177

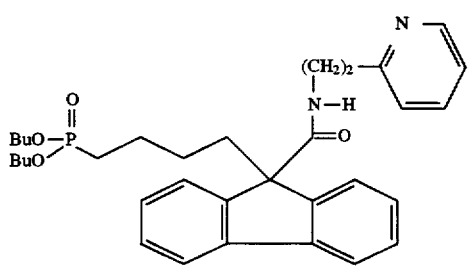

MS (ES, +ions) 563 (M+H).

EXAMPLE 178

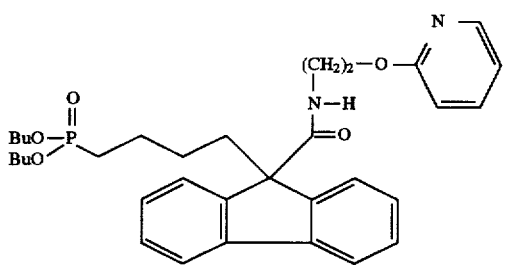

MS (ES, +ions) 579 (M+H).

EXAMPLE 179

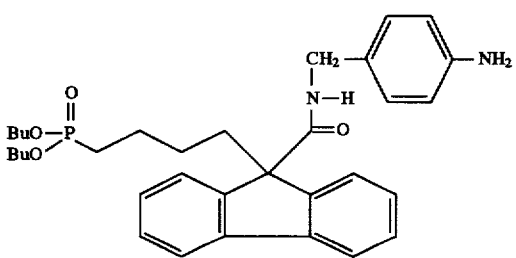

MS (ES, +ions) 563 (M+H).

EXAMPLE 180

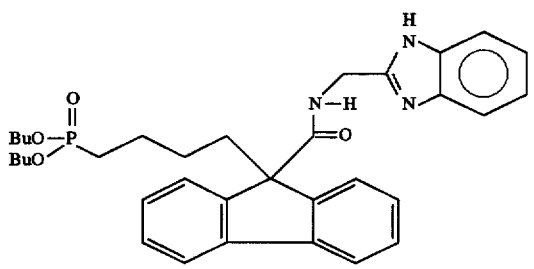

MS (ES, +ions) 588 (M+H).

EXAMPLE 181

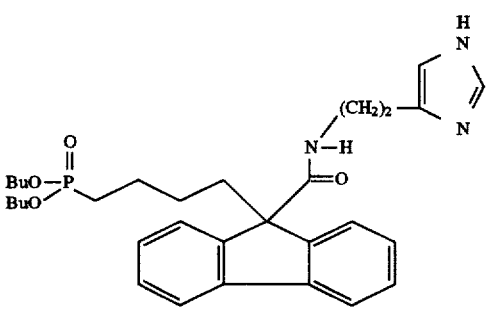

MS (ES, +ions) 552 (M+H).

EXAMPLES 182–185

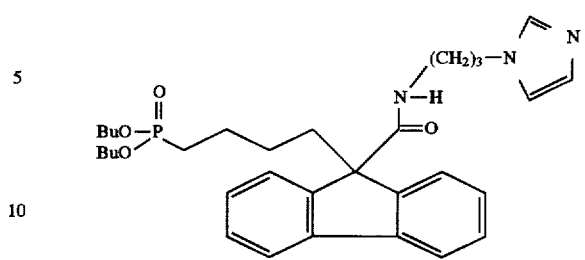

MS (ES, +ions) 566 (M+H).

EXAMPLE 186

9-[4-(Dibutoxyphosphinyl)butyl]-N-(2,2,2-trifluoroethyl)-9H-fluorene-9-carboxamide A solution of Example 141 Part A compound (0.90 g, 2 mmol) in 5 mL of $CH_2Cl_2$ was treated with oxalyl chloride in dichloromethane (1.5 mL, 3.00 mmol) and two drops of DMF. After 0.5 h, the mixture was concentrated under reduced pressure to give a yelow oil. The oil was diluted with 10 mL of tetrahydro-furan, cooled to 0° C. and treated with 2,2,2-trifluo-roethylamine (0.39 g, 4.00 mmol) and triethylamine (0.2 g, 2.0 mmol). The mixture was stirred for 3 h at room temperature and diluted with ethyl acetate (50 mL) and water (50 mL). The organic fraction was washed with 1N HCl (5 mL) dried over $Na_2SO_4$ and concentrated to a yellow oil. The oil was purified by flash column chromatography on silica gel (100 g) with 1:9 acetone/dichloromethane to give 0.69 g (59% overall yield) of title compound as a clear oil.

TLC Silica gel (1:9 acetone/dichloromethane) $R_f$=0.3. Mass Spec. ($CI-NH_3$, +ions) m/e 540 (M+H). Anal. Calc'd for $C_{28}H_{37}F_3NO_4P$+0.3 $H_2O$: C, 61.76; H, 6.95; N, 2.57; F, 10.47; P, 5.69. Found: C, 61.71; H, 6.78; N, 2.62; F, 10.66; P, 5.47.

ALTERNATE EXAMPLE 186

9-[4-(Dibutoxyphosphinyl)butyl]-N-(2,2,2-trifluoroethyl)-9H-fluorene-9-carboxamide

A.

Butyllithium (8.4 mL, 2.5M in hexane, 21 mmol) was added dropwise over 10 min to a solution of 9-fluorenecarboxylic acid (2.10 g, 10 mmol) in THF (50 mL) at 0° C. under argon. During addition of the first equivalent of BuLi, the reaction became thick with a white precipitate which became yellow and cleared after addition of the second equivalent. The reaction was stirred at 0° C. for 20 min, then cis-1,4-dichloro-2-butene (1.2 mL, 11 mmol) was added dropwise over 5 min. The reaction lightened in color during addition and was stirred at 0° C. for 3 h, then poured into 1N HCl (50 mL) and extracted with $CH_2Cl_2$ (3×50 mL).

The combined organic layers were washed with brine (30 mL) then dried over MgSO$_4$. Evaporation provided 3.5 g of a yellow oil containing crystalline solid. The crude residue was triturated with hexane (20 mL). The supernatant was decanted, and the residue pumped under high vacuum to give 2.93 g of title compound as a tan solid.

B.

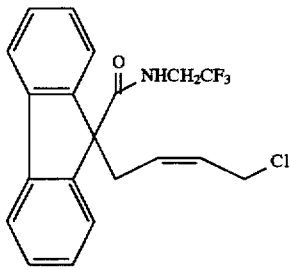

To a stirred solution of 10.0 g (33.5 mmol) of Part A compound in 100 mL of dichloromethane at RT was added 20.0 mL (40 mmol) of 2M oxalyl chloride in dichloromethane followed by 30 μL of DMF. The reaction was allowed to stir at RT for 2 h when the solvent was evaporated and the semisolid residue pumped (≈1 mm pressure) for 0.5 h. The residue was dissolved by adding 300 mL of ether and cooled to 0° C. The mixture was treated with 7.30 g (67 mmol) of 2,2,2-trifluoroethylamine and warmed to room temperature. The mixture was diluted with 150 mL of ethyl acetate and 100 mL of 0.5M HCL. The layers were separated, the organics dried (Na$_2$SO$_4$) and concentrated. The remainder was purified by flash column chromatography on silica gel (250 g) eluting with 1:9 ethyl acetate/hexanes (800 mL) followed by 1:5 ethyl acetate/hexanes (1L). Pure fractions were pooled and concentrated to give 9.25 g (73%) of title compound as a white solid. mp: 87°–89° C.

C.

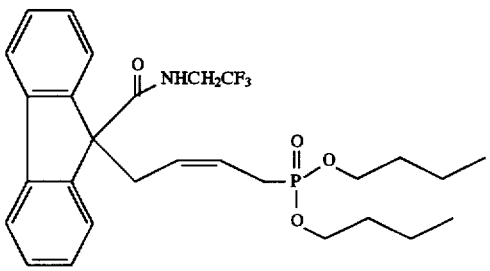

A mixture of Part B compound (7.60 g, 20 mmol) and tributylphosphite (25 g, 100 mmol) was warmed to 120° C. for 24 h. The volitals were removed by short path distillation (0.2 mm Hg, 118° C.) to leave 11.5 g of a colorless oil. The oil was purified by flash column chromatography on silica gel (500 g) eluting with 5:95 acetone/dichloromethane (1 L) followed by 1:5 acetone/dichloromethane (1L). Pure fractions were pooled to give 8.80 g (82%) of title compound as a colorless oil which gradually turned to a waxy solid.

TLC Silica gel (1:5 acetone/dichloromethane) R$_f$=0.5.

D. 9-[4-(Dibutoxyphosphinyl)butyl]-N-(2,2,2-trifluoroethyl)-9H-fluorene-9-carboxamide A suspension of 8.50 g (15.8 mmol) of Part C compound in 200 mL of ethanol was warmed to 40° C. for a few minutes to completely dissolve the crystalline solids. The resulting colorless solution was treated with 0.5 g of 10% Pd/carbon and the reaction vessel placed under an atmosphere of H$_2$ (balloon pressure). The reaction mixture was stirred for 25 h when it was filtered through a pad of celite. The colorless filtrate was filtered through a pad of celite and concentrated to give 8.3 g (95%) of title compound as a colorless oil. The oil gradually turned to white solid on standing. mp: 71°–74° C.

TLC Silica gel (1:5 acetone/dichloromethane) R$_f$=0.5.

MS (ES, +ions) m/z 540 (M+H). Anal. Calc'd for C$_{28}$H$_{37}$F$_3$NO$_4$P: C, 62.33; H, 6.91; F, 10.56; N, 2.60; P, 5.74. Found: C, 62.36; H, 7.00; F, 10.63; N, 2.56; P, 5.86.

EXAMPLE 187

9-(2-Propenyl)-9H-fluorene-9-carboxylic acid, ethyl ester

An ethanol (7 ml) solution of Example 93 Part B (275 mg, 1.04 mmol) was stirred at room temperature for 1 h, then stored at –20° C. overnight. After warming, the volatiles were removed in vacuo to give an oil (300 mg). The residue was purified by flash column chromatography (SiO$_2$, 3 by 9 cm), eluting with 5%EtOAc:hexanes to give title compound (211 mg, 73% yield) as a colorless oil.

MS: (CI): m/z 296 (M+NH$_4$)$^+$.

EXAMPLE 188

9-(4-Cyanobutyl)-N-propyl-9H-fluorene-9-carboxamide

To a solution of 400 mg (0.92 mmol) of Example 11 Part C compound in 1 mL of DMSO, under argon at RT, was added 180 mg (2.77 mmol) of potassium cyanide (KCN). The mixture was stirred at RT for 18 h, at which time the reaction was diluted with ether and washed with sodium bisulfite, NaHCO$_3$, water, brine, dried (Na$_2$SO$_4$) and evaporated. Recrystallization was attained from hot hexanes to provide 225 mg (74%) of title compound as a white solid. mp 102°–104° C. TLC Silica gel (95:5 dichloromethane/isopropanol). R$_f$=0.43. MS (CI-NH$_3$, +ions) m/e 333 (M+H). Anal. Calcd. for C$_{22}$H$_{24}$N$_2$O$_1$: C, 79.48; H, 7.28; N, 8.43. Found: C, 79.17; H, 7.40; N, 8.34.

EXAMPLE 189

1-[9-(3-Phenylpropyl)-9H-fluorene-9-yl]-1-butanone (4 mmol) in 15 ml of tetrahydrofuran was cooled to –20° C. under an argon atmosphere and anhy. copper iodide (50 mg) was added. A 2M solution of n-propyl magnesium chloride in ether (2 ml, 4 mmol) was added over a 5 minute period. The reacton was stirred at –20° C. for 2.5 hrs. and then at 0° C. for 30 min. The reaction was quenched with a saturated solution of ammonium chloride and extracted with ethyl acetate (3×20ml). The ethyl acetate extract was washed with water, brine and dried over anhy. sodium sulfate. The crude ketone was purified on a Merck EM silica column eluting with 5% ethyl acetate/hexane yielding 850 mg (64%) of title compound as a colorless oil.

MS (CI, +ions) 355 (M+H). Anal Calc'd for C$_{26}$H$_{26}$O: C, 87.74; H, 7.41. Found: C, 87.70; H, 7.45.

EXAMPLE 190

9-(3-Phenylpropyl)-α-propyl-9H-fluorene-9-methanol

A solution of Example 189 compound (400 mg, 1.13 mmol) in 25 ml of methanol was cooled to 0° C. under an argon atmosphere. Sodium borohydride (93 mg, 2.45 mmol) was added portion wise over 10 minutes and the mixture was then stirred for 30 min. longer at 0° C. The reaction was diluted with 0.1N hydrochloric acid to pH 4. The reaction mixture was diluted with 30 ml of water and extracted with ethyl acetate (3×20 ml). The ethyl acetate extract was washed with water, brine and dried over sodium sulfate. The crude product was purified on a Merck EM silica column eluting with 10% ethyl acetate/hexane yielding 345 mg (86%) of title compound as a colorless oil.

MS (CI, +ions) 374 (M+NH$_4$). Anal Calc'd for C$_{26}$H$_{28}$O+ 0.65H$_2$O (FW 368.21): C, 84.79; H, 8.02. Found: C, 84.83; H, 7.94.

EXAMPLE 191

4-Hydroxy-1-(9-propyl-9H-fluoren-9-yl)butanone

A solution of Example 59 Part B compound (1.07 g, 3.97 mmol) in THF (10 mL) under argon was cooled to 0° C. Copper (I) iodide (38 mg, 0.20 mmol) was added followed by dropwise addition of

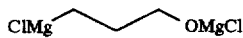

(prepared analogously to Umio, et al, J. Med. Chem. 1972, 15, 855) (14.5 mL, 0.3M in THF, 4.37 mmol) over 10 min. Upon addition, a deep red color appeared but quickly dissipated with stirring. The opaque yellow reaction was stirred at 0° C. for 45 min, then quenched by addition of saturated NH$_4$Cl (10 ML). The reaction was diluted with water (10 mL) and extracted with EtOAc (3×30 mL). The combined organic layers were washed with saturated NH$_4$Cl, water, and brine (10 mL each), then dried over MgSO$_4$. Evaporation gave 1.3 g of a yellow oil, which was purified by flash chromatography on silica gel (150 g), loading in 50% EtOAc/hexane, and eluting with 25% EtOAc/hexane to provide title compound (885 mg, 76%) as a colorless oil.

Anal. Calcd. for C$_{20}$H$_{22}$O$_2$.0.5H$_2$O: C, 79.19; H, 7.64. Found: C, 79.07; H, 7.32.

EXAMPLE 192

N-[3-(Dibutoxyphosphinyl)propyl]-9-propyl-9H-fluorene-9-carboxamide

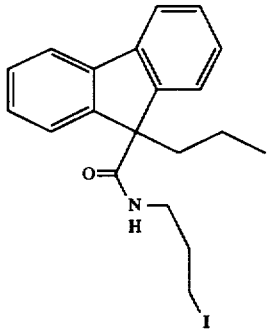

A solution of oxalyl chloride in dichloromethane (1 mL, 2.0 mmol) was added to a stirred suspension of Example 59 Part A compound (0.44 g 1.74 mmol) in 10 mL of dichloromethane. The reaction mass was treated with 1 drop of DMF, allowed to stir for 0.5 h and concentrated. The remainder was diluted with 10 mL of THF, cooled to –40° and treated with 1,3-propanolamine (0.26 g, 3.50 mmol) and warmed to RT over 3 h. The reaction mixture was diluted with 20 mL of water and 50 mL of ethyl acetate. The organic fraction was extracted with water (3X), dried (MgSO$_4$) and concentrated. The crude alcohol was carried on to the next step without further characterization.

To a stirred solution of 0.50 g (1.58 mmol) of the crude alcohol, 0.46 g (1.74 mmol) of triphenylphosphine, and 0.21 g (3.15 mmol) of imidazole in 10 mL of THF under argon at room temperature was added a solution of 0.44 g (1.74 mmol) of iodine in 10 mL of THF, dropwise over 15 min. After the addition was complete, the reaction was stirred at RT for 2 h and diluted with 100 mL of ethyl acetate and washed with a saturated solution of Na$_2$SO$_3$. The organic phase was dried (MgSO$_4$) and concentrated. The residue was purified by flash chromatography on silica gel (100 g) eluted with 15:85 ethyl acetate/hexanes to give 0.42 g (64%) of title compound as a white solid.

TLC Silica gel (1:3 ethyl acetate/hexanes) R$_f$=0.6. Mass Spec (CI-NH$_3$, +ions) m/e 420 (M+H).

B. N-[3-(Dibutoxyphosphinyl)propyl]-9-propyl-9H-fluorene-9-carboxamide

A mixture of Part A compound (0.35 g, 0.83 mmol) and tributylphosphite (1.2 mL, 1.9 mmol) was warmed to 120° C. for 18 h. The mixture was purified by short path distillation (0.2 mm Hg. 110° C.) to leave 0.34 g of title compound as a colorless oil. The oil was purified by flash chromatography on silica gel (50 g) eluting with 1:9 isopropanol/dichloromethane to give 0.30 g (78%) of title compound as a colorless oil.

TLC Silica gel (5:95 2-propanol/dichloromethane). R$_f$=0.3. Mass Spec. (ES, +ions) m/z 486 (M+H). Anal. Calc'd for C$_{28}$H$_{40}$NO$_4$P+0.90H$_2$O: C, 67.04; H, 8.39; N, 2.79. Found: C, 67.09; H, 8.54; N, 2.72.

EXAMPLE 193

N-[5-(Dibutoxyphosphinyl)pentyl-9-propyl-9H-fluorene-9-carboxamide

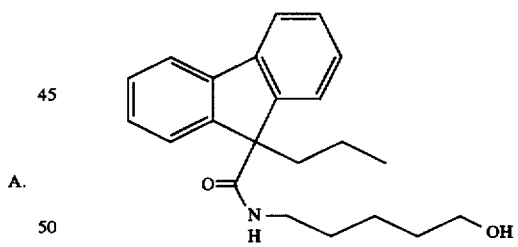

N-(5-Hydroxypentyl)-9-propyl-9H-fluorene-9-carboxamide

A solution of oxalyl chloride in dichloromethane (1 mL, 2.0 mmol) was added to a stirred suspension of Example 59 Part A compound (0.40 g 1.58 mmol) in 10 mL of dichloromethane. The reaction mass was treated with 1 drop of DMF, allowed to stir for 0.5 h and concentrated. The remainder was diluted with 10 mL of THF, cooled to –78° and treated with 1,5-pentanolamine (0.41 g, 4 mmol) and warmed to RT over 3 h. The reaction mixture was diluted with 20 mL of water and 50 mL of ethyl acetate. The organic fraction was extracted with water (3X), dried (MgSO$_4$) and concentrated. The remainder was purified by column chromatography on silica gel (100 g) with 1:1 ethyl acetate/hexanes (500 mL) followed by 7:3 ethyl acetate/hexane (400 mL) to give 0.53 g (98%) of title compound as an oil. The resulting oil gradually solidified (4 days standing) to a white solid.

mp 48°–51°. TLC Silica gel (1:1 ethyl acetate/hexane) $R_f$=0.3. Mass Spec. (CI, +ions) m/z 338 (M+H). Anal. Calc'd for $C_{22}H_{27}NO_2+0.3H_2O$: C, 77.13; H, 8.11; N, 4.09. Found: C, 77.10; H, 8.23; N, 4.00.

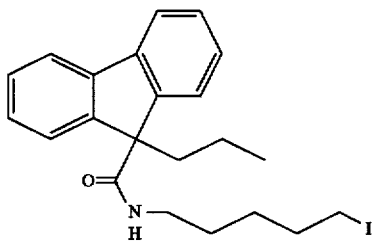

B.

To a stirred solution of 0.50 g (1.50 mmol) of Part A compound, 0.47 g (1.80 mmol) of triphenylphosphine, and 0.20 g (3.00 mmol) of imidazole in 10 mL of THF under argon at room temperature was added a solution of 0.46 g (1.8 mmol) of iodine in 10 mL of THF, dropwise over 15 min. After the addition was complete, the reaction was stirred at RT for 2 h and diluted with 100 mL of ethyl acetate and washed with a saturated solution of $Na_2SO_3$. The organic phase was dried ($MgSO_4$) and concentrated. The residue was purified by flash chromatography on silica gel (100 g) eluted with 15:85 ethyl acetate/hexanes to give 0.58 g (87%) of title compound as a colorless oil. TLC Silica gel (1:9 ethyl acetate/hexanes) $R_f$=0.3. Mass Spec (CI-NH$_3$, +ions) m/e 448 (M+H).

C. N-[5-(Dibutoxyphosphinyl)pentyl]-9-propyl-9H-fluorene-9-carboxamide

A mixture of Part B compound (0.28 g, 0.63 mmol) and tributylphosphite (2 mL, 8 mmol) was warmed to 120° C. for 18 h. The volitals were removed by short path distillation (0.2 mm Hg, 110° C.) to leave 0.30 g (88%) of title compound as a colorless oil.

TLC Silica gel (5:95 2-propanol/dichloromethane) $R_f$=0.3. Mass Spec. (ES, +ions) m/z 536 (M+Na), 514 (M+H). Anal. Calc'd for $C_{30}H_{44}NO_4P+1.0H_2O$: C, 67.62; H, 8.73; N, 2.63; P, 5.81. Found: C, 67.31; H, 8.33; N, 2.94; P, 6.05.

EXAMPLES 194–195

(E)-9-[4-(Dibutoxyphosphinyl)-2-butenyl]-2,7-difluoro-N-propyl-9H-fluorene-9-carboxamide

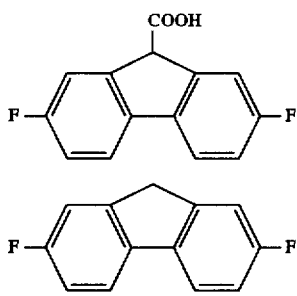

A.

A(1).

To a THF (25 ml) supension of 2,7-diaminofluorene (7.17 g, 0.036 mol) at −10° C. under argon was added aqueous HBF$_4$ (71 mL, 1.13 mol, 48–50%). Near the end of addition stirring became difficult due to solid formation, although most of the solid went into solution upon complete addition of acid. A saturated aqueous solution of sodium nitrite (7.1 g in 11 mL, 0.103 mol) was added and after 1.5 h the mixture was filtered, washing with 5% aq. HBF$_4$, MeOH, then ether, and the collected solid dried briefly on the fliter flask. The resulting brown solid (9.7 g) was used in the subsequent reaction.

The above solid was suspended in xylenes (100 ml) and heated to 110° C. for 2 h, with gas evolution observed, then brought to reflux for an additional 2 h. The solution was decanted from a black tar in the reaction flask and the volatiles removed under high vacuum to give a dark tan solid (7.5 g). The solid was crystallized from hot EtOH to give title compound (1.4 g) as a colorless solid. An ether wash of the black tar was combined with the mother liquor and concentrated in vacuo. The oily-solid residue (4.3 g) was purified by flash column chromatography ($SiO_2$, 9 by 16 cm), eluting with hexanes then 2.5% EtOAc:hexanes, to give title compound (2.44 g, total 3.84 g, 52% yield) as a colorless solid.

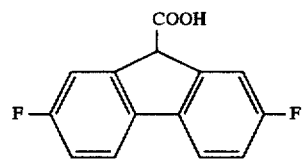

A(2).

To a THF (15 ml) solution of Part A(1) compound (1.38 g, 6.82 mmol) at −5° C. (ice/brine bath) under argon was added dropwise n-BuLi (3.4 ml, 8.50 mmol, 2.5M in hexanes). After 1.15 h, crushed solid C0$_2$ (excess) was added, followed by $Et_2O$ (~5 ml), and the reaction allowed to stir at room temperature for 19 h. The brown colored reaction mixture was cooled to 0° C., quenched with 2N HCl, and the aqueous layer extracted twice with EtOAc. The combined organics were dried over $Na_2SO_4$ and evaporated in vacuo to give crude title compound (1.64 g, 98% recovery, contaminated with A(1), seen by $^1$H NMR), as a colorless solid suitable for the next reaction. Trituration with hexanes can remove unreacted starting material Compound A(1).

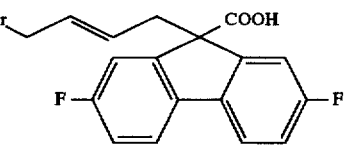

B.

A solution of Part A 2,7-difluorofluorene-9-carboxylic acid (500mg, 2.05 mmol) in 5 ml of THF was cooled to −30° C. under an argon atmosphere and 2 equiv. of a 2.5M solution of n-butyl lithium in hexane (1.64 ml, 4.1 mmol) was added. The mixture was stirred for 5 min. at −30° C. and was then added to a cold (−30° C.) solution of 1,4-dibromo-2-butene (2.14 g, 10 mmol) in 4 ml of THF. The reaction mixture was stirred at −30° C. for 30 min and was then quenched with 1N HCl and extracted with ethyl acetate (3×10 ml). The ethyl acetate extract was washed with water, brine and dried over anhy. sodium sulfate. The crude title material was purified on a Merck EM silica column eluting with 5% isopropanol/dichloromethane yielding 480 mg (62%) as a colorless solid, m.p. 142°–146° C. (Mass Spec. M+H=380).

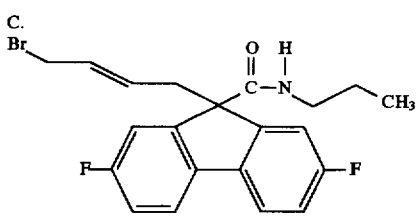

The Part B carboxylic acid (476 mg, 1 mmol) was dissolved in 12 ml of dichloromethane and DMF (50 μl) was added. The mixture was cooled to 0° C. under an argon atmosphere and oxalyl chloride (178 mg, 1.4 mmol) was added and the mixture allowed to warm to ambient temperature and stir for 2.5 hrs. The mixture was evaporated several times from dichlormethane yielding the crude acid chloride as a pale yellow solid.

The acid chloride was dissolved in 8 ml of THF and cooled to 0° C. under an argon atmosphere. Triethylamine (152 mg, 1.5 mmol) was added followed by the addition of n-propyl amine (77 mg, 1.3 mmol). The reaction was allowed to warm to ambient temperature and stir overnight. The reaction was quenched by adding sat. sodium bicarbonate and extracted with dichloromethane (4×20 ml). The crude product was purified on a Merck EM silica column eluting with 5% ethyl acetate/hexane yielding 420 mg (80%) of title compound as a pale yellow oil. (Mass Spec, M+H= 421).

D. (E)-9-[4-(Dibutoxyphosphinyl)-2-butenyl]-2,7-difluoro-N-propyl-9H-fluorene-9-carboxamide A solution of Part C compound (400 mg, 0.95 mmol) in tributyl phosphite (1.8 ml) was heated at 90° C. overnight. Excess tributyl phosphite was removed under vacuum at 100° C. and the oily residue was purified on a Merck EM silica column eluting with 3% isopropanol/dichloromethane yielding 353 mg (70%) of title compound as a colorless oil.

MS (CI, +ions) 534 (M+H). Anal Calc'd for $C_{29}H_{38}NF_2PO_4+0.3H_2O$: C, 64.61; H, 7.22; N, 2.60. Found: C, 64.69; H, 7.50; N, 2.52.

EXAMPLE 196

9-[4-(Dibutoxyphosphinyl)butyl]-2,7-difluoro-N-propyl-9H-fluorene-9-carboxamide

An ethanol solution of Example 195 compound (260 mg, 0.49 mmol) containing 50 mg of 10% palladium on carbon was stirred under a hydrogen atmosphere (balloon) for 14 hrs. The reaction was filtered through a 0.2 μm nylon filter to remove the catalyst and the solvent evaporated yielding 235 mg (90%) of title compound as a colorless oil.

MS (CI, +ions) 536 (M+H). Anal Calc'd for $C_{29}H_{40}NF_2PO_4+0.5H_2O$: C, 64.73; H, 7.54; N, 2.60. Found: C, 64.78; H, 7.50; N, 2.55.

EXAMPLE 197

9-[4-(Diethoxyphosphinyl)butyl]-N-propyl-9H-fluorene-9-carboxamide

To 400 mg (0.92 mmol) of Example 11 Part C compound was added 475 μL (2.77 mmol) of triethylphosphite (neat). The mixture was heated to 120° C. for 18 h and bulb to bulb distilled (5 mm, 100° C.) to remove lower boiling impurities and provide a yellow oil. Flash chromatography was performed on 50 g of silica gel eluting with 97:3 dichloromethane/isopropanol to provide 300 mg (75%) of title compound as a pale yellow oil.

TLC Silica gel (95:5 dichloromethane/isopropanol) $R_f$=0.38. MS (CI-NH$_3$, +ions) m/e 444 (M+H). Anal. Calcd. for $C_{25}H_{34}NO_4P+0.75$ mol $H_2O$: C, 65.20; H, 7.85; N, 3.04; P, 6.73. Found: C, 65.30; H, 7.57; N, 2.94; P, 6.53.

EXAMPLE 198

9-[4-(Diphenylphosphinyl)butyl]-N-propyl-9H-fluorene-9-carboxamide

To 400 mg (0.92 mmol) of Example 11 Part C compound was added 600 μL (2.77 mmol) of ethyldiphenyl phosphinite (neat, Aldrich). The mixture was heated to 120° C. for 18 h. Flash chromatography was performed on 100 g of silica gel eluting with 97:3 dichloromethane/isopropanol to provide a white solid, which was further purified by crystalization from hot methanol triturated with water to provide 100 mg (22%) of title compound as a white solid. mp 163°–165° C.

TLC Silica gel (95:5 dichloromethane/isopropanol) $R_f$=0.34. MS (CI-NH$_3$, +ions) m/e 508 (M+H). Anal. Calcd. for $C_{33}H_{34}NO_2P$: C, 78.08; H, 6.75; N, 2.76; P, 6.10. Found: C, 77.75; H, 6.76; N, 2.73; P, 5.97. $^{13}C$ NMR (75 MHz, CDCl$_3$) is consistent with the indicated compound.

EXAMPLE 199

[4-[9-(Butylthio)-9H-fluoren-9-yl]butyl]phosphonic acid, dibutyl ester

A.

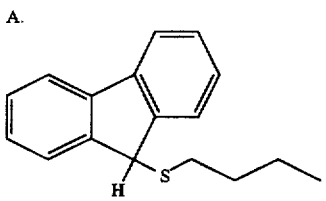

A solution of 9-acetoxy-(9H)-fluorene (1.00 g, 4.46 mmol) and butanethiol (0.34 g, 3.79 mmol) in 10 mL of dichloromethane at −20° C. was treated with borontrifluoride etherate (0.59 g, 4.17 mmol). The reaction was stirred for 1 h at −20° C. and warmed to room temperature. After stirring for 18 h the contents of the flask were purified by column chromatography on silica gel (100 g) with hexanes followed by 1:9 dichloromethane/hexanes to give 0.76 g (98%) of title compound as a colorless oil.

TLC Silica gel (1:9 dichloromethane/hexanes) $R_f$=0.5. $^{13}C$ NMR (CDCl$_3$, 75 MHz) δ145.1, 140.6, 127.8, 127.4, 125.4, 119.7, 48.8, 31.1, 27.4, 21.8, 13.5 ppm.

B. [4-[9-(Butylthio)-9H-fluoren-9-yl]butyl]phosphonic acid, dibutyl ester

A solution of Part A compound (0.76 g, 2.99 mmol) in 10 mL of THF at −78° C. was treated with n-butyllithium in hexanes (1.64 mL, 4.09 mmol) followed by Example 11 Part B bromide (1.15 g, 3.50 mmol). The reaction was stirred for 0.5 h and warmed to room temperature for 18 h. The contents of the flask were diluted with 30 mL of aqueous NH$_4$Cl solution and 30 mL of ethyl acetate. The organic fraction was dried (Na$_2$SO$_4$) and concentrated. The remainder was purified by column chromatography on silica gel (50 g) with 2:98 acetone/dichloromethane (500 mL) followed by 5:95 acetone/dichloromethane to give 0.90 (66%) of title compound as a colorless oil.

TLC Silica gel (5:95 acetone/dichloromethane) $R_f$=0.6. Mass Spec. (ES, +ions) m/e 520 (M+NH$_4$), 503 (M+H). Anal. Calc'd for C$_{29}$H$_{43}$O$_3$PS+1.35H$_2$O: C, 66.10; H, 8.74; P, 5.88; S, 6.08. Found: C, 65.72; H, 8.29; P, 5.99; S, 5.71.

EXAMPLE 200

[4-[9-(Butylsulfonyl)-9H-fluoren-9-yl]butyl] phosphinic acid, dibutyl ester

To a suspension of Example 199 Part B compound (0.35 g, 0.69 mmol) in dichloromethane (5 mL) at 0° C. was added 3-chloroperoxybenzoic acid (m-CPBA) (0.52 g, 50% by weight≈0.1.52 mmol) in one portion. The mixture was stirred for 1 h when it was diluted with 0.1M KOH (20 mL) and ether (30 mL). The organic fraction was dried (Na$_2$SO$_4$) and concentrated. The remainder was purified by column chromatography on silica gel (50 g) with 1:9 acetone/dichloromethane to give 0.32 g (86%) of title compound as a colorless oil.

TLC Silica gel (1:9 acetone/dichloromethane) $R_f$=0.5. Mass Spec. (CI-NH$_3$, +ions) m/e 535 (M+H), 413 (M+H-C$_4$H$_9$SO$_2$).

Anal. Calc'd for C$_{29}$H$_{43}$O$_5$SP+0.3H$_2$O: C, 64.40; H, 8.14; P, 5.73; S, 5.93. Found: C, 64.38; H, 7.94; P, 5.63; S, 5.52.

EXAMPLE 201

[4-[9-(Butylsulfinyl)-9H-fluoren-9-yl]butyl] phosphonic acid, dibutyl ester

To a suspension of Example 199 Part B sulfide (0.40 g, 0.80 mmol) in dichloromethane (5 mL) at 0° C. was added 3-chloroperoxybenzoic acid (0.34 g, 50% by weight≈0.80 mmol) in one portion. The mixture was stirred for 1 h when it was diluted with 0.1M KOH (10 mL) and ether (30 mL). The organic fraction was dried (Na$_2$SO$_4$) and concentrated. The remainder was purified by column chromatography on silica gel (50 g) with 2:8 acetone/dichloromethane to give 0.25 g (60%) of title compound as a colorles oil.

TLC Silica gel (1:4 acetone/dichloromethane) $R_f$=0.3. Mass Spec. (ES, +ions) m/e 1054 (2M+H), 519 (M+H). Anal. Calc'd for C$_{29}$H$_{43}$O$_4$SP+0.85H$_2$O: C, 65.23; H, 8.44; P, 5.80; S, 6.00. Found: C, 65.23; H, 8.30; P, 5.99; S, 5.71.

EXAMPLE 202

5-[4-(Dibutoxyphosphinyl)butyl]-N-propyl-5H-indeno-[1,2-b]pyridine-5-carboxamide

A.

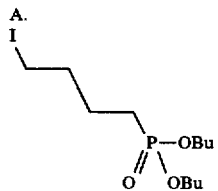

To a THF (10 ml) solution of dibutyl phosphite (4 g, 0.021 mol) at 0° C. under argon was added dropwise sodium hexamethyldisilazane (21 ml, 1M in THF), with the reaction mixture turning a yellow color. After 20 min, 1,4-diiodobutane (6.58 g, 0.021 mol) was added and the reaction kept at 0° C. for 1.15 h, and 5° C. overnight. The reaction was quenched with sat. NH$_4$Cl and the aqueous layer was extracted with EtOAc. The organics were dried over Na$_2$SO$_4$ and concentrated to an oil (8 g). The residue was purified by flash column chromatography (SiO$_2$, 5 by 15 cm), eluting with CH$_2$Cl$_2$, then 10% EtOAc:CH$_2$Cl$_2$, to give title compound (1.9 g, 24% yield) as a colorless oil. MS: (CI, M+H$^+$): m/z 377.

B.

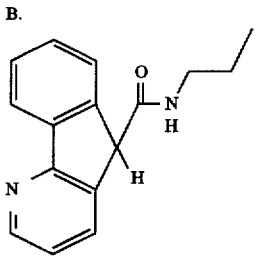

B(1).

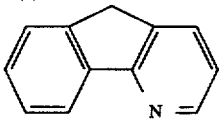

A suspension of 4-aza-9-fluorenone (4 g, 0.022 mol) in hydrazine hydrate (4 ml) and diethylene glycol (40 ml) under argon was heated to 105°–110° C. for 1 h, then the resulting orange colored suspension was heated to 200° C. for 1.5 h. The reaction was cooled and then poured into H$_2$O. The aqueous layer was extracted twice with EtOAc, the combined organics washed with brine, dried over Na$_2$SO$_4$, and concentrated to a colorless solid (3.8 g). The residue was crystallized from hot hexanes, with seeding, to give title compound (2.91 g, 76% yield, contaminated with 4% diethylene glycol) as a colorless solid. mp 91°–93° C. MS: (CI, M+H$^+$): m/z 168.

Anal. Calc. for C$_{12}$H$_9$N.0.07H$_2$O: C, 85.56; H, 5.47; N, 8.31. Found: C, 85.56; H, 5.39; N, 8.31.

B(2).

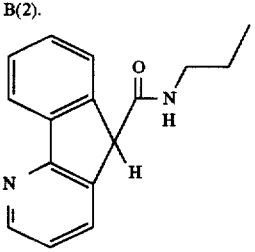

To a THF (7 ml) solution of Part B(1) compound (405 mg, 2.42 mmol) and propyl isocyanate (227 mg, 2.67 mmol) at −10° C. under argon was added dropwise sodium hexamethyldisilazane (3 ml, 1M in THF), with the reaction mixture turning a red color. After 15 min and 35 min, more propyl isocyanate (200 then 136 mg, 3.95 mmol) was added. The reaction solution turned to a green color upon the third addition of isocyanate and the reaction was quenched with sat. NH$_4$Cl. The aqueous layer was extracted twice with EtOAc, the combined organics dried over Na$_2$SO$_4$, and concentrated to an oily-solid (1 g). The residue was combined with a similar reaction (from 0.55 mmol of Part B(1) compound) and was purified by flash column chromatography (SiO$_2$, 5 by 9.5 cm), eluting with 30, 35, 40, then 50% EtOAc:CH$_2$Cl$_2$, to give title compound (287 mg, 39% yield) as a colorless solid. mp 171°–172° C.; MS: (electrospray, M+H$^+$): m/z 253.

C. 5-[4-(Dibutoxyphosphinyl)butyl]-N-propyl-5H-indeno[1,2-b]pyridine-5-carboxamide To a THF (3 ml, degassed) suspension of Part B compound (200 mg, 0.793 mmol), at 0° C. under argon was added dropwise n-BuLi (0.7 ml, 2.5M in hexanes), with a red colored solid falling from solution after all the base was added. After 10 min, Part A compound (325 mg, 0.864 mmol) was added and the reaction stirred an additional 2 h. The brown reaction mixture was quenched with sat. NH₄Cl and the aqueous layer was extracted twice with EtOAc, the combined organics dried over Na₂SO₄, and concentrated to a brown colored oil (400 mg). The residue was purified by flash column chromatography (SiO₂, 5 by 9.5 cm), eluting with 27 and 35% CH₃CN:CH₂Cl₂, then 4 and 10% iPrOH:CH₂Cl₂, to give title compound (184.5 mg, 46% yield) as a colorless solid. mp 93.5°–96° C.

MS: (CI, M+H⁺) : m/z 501. Anal. Calc. for $C_{26}H_{41}N_2O_4P$: C, 67.18; H, 8.25; N, 5.60; P 6.19. Found: C, 67.24; H, 8.28; N, 5.61; P 5.83.

EXAMPLE 203

(E)-9-[4-(Dibutoxyphosphinyl)-2-butenyl]-2,7-difluoro-N-(2,2,2-trifluoroethyl)-9H-fluorene-9-carboxamide

A.

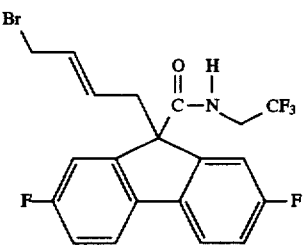

The Example 195 Part B carboxylic acid (465 mg, 1.23 mmol) was dissolved in 10 ml of dichloromethane and DMF (50 μl) was added. The mixture was cooled to 0° C. under an argon atmosphere and oxalyl chloride (165 mg, 1.3 mmol) was added and the mixture allowed to warm to ambient temperature and stir for 2.5 hrs. The mixture was evaporated several times from dichlormethane yielding the crude acid chloride as a pale yellow solid.

The acid chloride was dissolved in 5 ml of THF and cooled to 0° C. under an argon atmosphere. Triethylamine (142 mg, 1.4 mmol) was added followed by the addition of 2,2,2-trifluoroethylamine (139 mg, 1.4 mmol). The reaction was allowed to warm to ambient temperature and stir overnight. The reaction was quenched by adding sat. sodium bicarbonate and extracted with ethyl acetate (3×20 ml). The crude product was purified on a Merck EM silica column eluting with 10% ethyl acetate/hexane yielding 230 mg (38%) of title compound as a pale yellow solid, (Mass Spec, M+H=461).

B. (E)-9-[4-(Dibutoxyphosphinyl)-2-butenyl]-2,7-difluoro-N-(2,2,2-trifluoroethyl)-9H-fluorene-9-carboxamide A solution of Part A compound (230 mg, 0.5 mmol) in tributyl phosphite (3 ml) was heated at 110° C. overnight. Excess tributyl phosphite was removed under vacuum at 100° C. and the oily residue was purified on a Merck EM silica column eluting with 3% isopropanol/dichloromethane yielding 186 mg (68%) of title compound as a colorless solid, m.p. 142°–144° C.

MS (CI, +ions) 574 (M+H). Anal Calc'd for $C_{28}H_{33}NF_5PO_4$+0.3H₂O: C, 58.63; H, 5.80; N, 2.44; F, 16.56; P, 5.40. Found: C, 58.91; H, 5.88; N, 2.47; F, 16.24; P, 5.50.

EXAMPLES 204–205

9-[4-[4-[[(2-Phenoxyphenyl)carbonyl]amino]phenyl]butyl]-N-propyl-9H-fluorene-9-carboxamide To a solution of 2-phenoxybenzoic acid (Aldrich Chemical Co.) (111 mg, 0.518 mmol) and DMF (2 drops) in CH₂Cl₂ (1.5 mL) was added oxalyl chloride (389 μL, 2.0M in CH₂Cl₂, 0.777 mmol). The reaction bubbled for 10 min, then was stirred at RT under argon for 1.5 h. The reaction was concentrated in vacuo, and the resulting residue was dissolved in CH₂Cl₂ (1.5 mL) and added dropwise to a solution of Example 204 Part A compound (172 mg, 0.432 mmol) and triethylamine (90 μL, 0.648 mmol) in CH₂Cl₂ (1.5 mL) at 0° C. under argon. The reaction was stirred at 0° C. for 10 min, diluted with CH₂Cl₂ (20 mL), washed with saturated NaHCO₃ (5 mL) and brine (5 mL), then dried over Na₂SO₄. Evaporation gave a yellow oil, which was dissolved in a minimum amount of CH₂Cl₂ and purified by flash chromatography on silica gel (50 g) eluting with 30% EtOAc/hexane to provide title compound (211 mg, 82%) as a yellow gum.

MS (CI, +ions) m/z 595 (M+H). Anal. Calcd. for $C_{40}H_{38}N_2O_3$·0.4 CH₂Cl₂: C, 77.18; H, 6.22; N, 4.46. Found: C, 77.18; H, 6.20; N, 4.87.

EXAMPLES 206–208

9-[3-[4-(Benzoylamino)]phenyl]-N-propyl-9H-fluorene-9-carboxamide

To a solution of Example 207 Part A compound (100 mg, 0.26 mmol) and triethylamine (0.04 mL, 0.39 mmol) in dichloromethane at 0° C. was added dropwise a solution of benzoyl chloride (0.04 mL, 0.31 mmol) in dichloromethane (1 mL). The reaction was stirred at 0° C. for 20 min. Ethyl acetate (50 mL) was added and the solution was washed with saturated sodium bicarbonate solution (2×30 mL), water (2×30 mL), brine (2×30 mL) and dried over MgSO₄. Purification was performed by flash chromatography on silica gel (50 g), loaded and eluted with 30% ethyl acetate in hexane. Pure fractions were combined and evaporated to give a solid. The resulting solid was recrystallized from ethyl acetate/hexane to give title compound (52 mg, 41%) as a white solid.

m.p. 187°–190° C. MS (CI, +ions) m/z 489 (M+H). Anal. Calc. for $C_{33}H_{32}N_2O_2$·1.0H₂O: C, 78.23; H, 6.76; N, 5.53. Found: C, 78.44; H, 6.54; N, 5.43.

EXAMPLES 209–210

9-[5-[(6-Ethoxy-2-benzothiazolyl)thio]pentyl]-N-propyl-9H-fluorene-9-carboxamide

A.

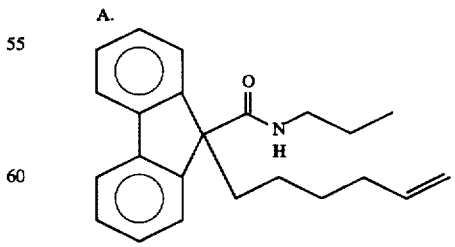

To a mixture of 3.0 g (11.95 mmol) of Example 11 Part C compound in 30 mL of THF, under argon at 0° C., was added 9.4 mL (23.90 mmol) of n-BuLi (2.5 M in hexanes)

dropwise. The dianion was stirred for 0.5 h at which time 1.9 mL (14.34 mmol) of 6-bromo-1-hexene (Aldrich) was added dropwise. The reaction gradually warmed to RT and was stirred for 6 days. The reaction was diluted with a 1:1 mixture of ethyl acetate/water and separated. The organics were washed with brine, dried ($Na_2SO_4$) and evaporated. Flash chromatography was performed on 200 g of silica gel eluting with 4:1 hexanes/ethyl acetate to provide 3.0 g (77%) of title compound as a pale yellow solid.

mp 54°–56° C. TLC Silica gel (4:1 hexanes/ethyl acetate) $R_f$=0.27. MS (CI-$NH_3$, +ions) m/e 334 (M+H). Anal. Calc. for $C_{23}H_{27}NO$: C, 82.84; H, 8.16; N, 4.20. Found: C, 82.90; H, 8.18; N, 4.59.

B.

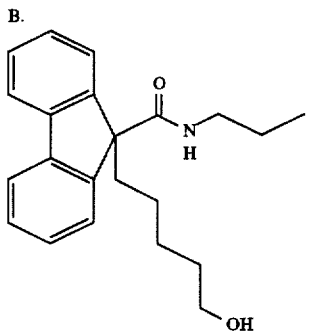

To a solution of 2.0 g (6.00 mmol) of Part A compound in 20 mL of methanol, under nitrogen at –78° C., was bubbled $O_3$ for 0.5 h. The solution was purged with nitrogen and treated with 718 mg (18.89 mmol) of sodium borohydride (~5 pellets). The mixture was gradually warmed to room temperature and was stirred for 18 h, at which time the reaction was diluted with ether and quenched with $NH_4Cl$. The organics were washed with water, brine, dried ($Na_2SO_4$) and evaporated. Flash chromatography was performed on 200 g of silica gel eluting with 1:1 hexanes/ethyl acetate to provide 1.6 g (80%) of title compound as a colorless oil.

TLC Silica gel (1:1 hexanes/ethyl acetate) $R_f$=0.13. Anal. Calcd. for $C_{22}H_{27}NO_2$+0.40 mol $H_2O$+0.15 mol $CH_2Cl_2$. C, 74.44; H, 7.92; N, 3.92. Found: C, 74.50; H, 7.62; N, 3.73.

C.

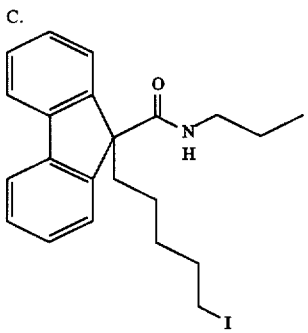

To a solution of 1.4 g (4.15 mmol) of Part B compound in 20 mL of THF, under argon at 0° C., was added 620 mg (9.13 mmol) of imidazole and 1.4 g (5.40 mmol) of triphenylphosphine. This mixture was stirred at 0° C. for 0.5 h, at which time 1.4 g (5.40 mmol) of iodine in 10 mL of THF was added dropwise. The reaction was stirred for 1.5 h, at 0° C., at which time it was diluted with hexanes and washed with sodium bisulfite, $NaHCO_3$, brine, dried ($Na_2SO_4$) and evaporated. Flash chromatography was performed on 50 g of silica gel eluting with 1:1 hexanes/ethyl acetate to provide 1.57 g (84%) of title compound as a white solid.

TLC: Silica gel (1:1 hexanes/ethyl acetate). $R_f$=0.63. MS (ES, +ions) m/e 448 (M+H).

D. 9-[5-[(6-Ethoxy-2-benzothiazolyl)thio]pentyl]-N-propyl-9H-fluorene-9-carboxamide To a solution of 200 mg (0.45 mmol) of Part C compound in 5 mL of DMF, under argon at RT, was added 125 mg (0.90 mmol) of $K_2CO_3$ followed by 114 mg (0.54 mmol) of 6-ethoxy-2-mercaptobenzothiazole. The reaction was stirred for 18 h at which time it was diluted with ether and the organics were washed with water, brine, dried ($Na_2SO_4$) and evaporated. Flash chromatography was performed on 50 g of silica gel eluting with 95:5 dichloromethane/isopropanol to provide 120 mg (50%) of title compound as a biege solid.

mp 67°–70° C. TLC Silica gel (95:5 dichloromethane/isopropanol). $R_f$=0.35. MS (CI-$NH_3$, +ions) m/e 531 (M+H). Anal. Calcd. for $C_{31}H_{34}N_2O_2S_2$: C, 70.15; H, 6.46; N, 5.28; S, 12.08. Found: C, 69.95; H, 6.20; N, 5.22; S, 12.11.

EXAMPLE 211

9-[4-[4-(Benzoylamino)phenyl]butyl]-N-propyl-9H-fluorene-9-carboxamide

Benzoyl chloride (156 μL, 1.35 mmol) was added dropwise to a solution of Example 207 Part A compound (490 mg, 1.23 mmol) and triethylamine (257 μL, 1.85 mmol) in $CH_2Cl_2$ (4 mL) at 0° C. under argon. The reaction was stirred at 0° C. for 30 min, diluted with $CH_2Cl_2$ (20 mL) and $CHCl_3$ (20 mL), washed with 1N KOH (2×10 mL) and water (10 mL), then dried over $MgSO_4$. Evaporation gave a yellow solid, which was adsorbed onto silica gel (10 g), then purified by flash chromatography on silica gel (150 g) eluting with 5% EtOAc/$CH_2Cl_2$ to give a solid. The product was dried under high vacuum at 50° C. overnight to provide title compound (412 mg, 67%) as a white solid.

mp 171°–173° C. Anal. Calcd. for $C_{34}H_{34}N_2O_2 \cdot 0.4H_2O$: C, 81.24; H, 6.82; N, 5.57. Found: C, 80.88; H, 6.83; N, 5.33.

EXAMPLE 212

9-[5-(Dibutoxyphosphinyl)pentyl]-N-propyl-9H-fluorene-9-carboxamide

To 400 mg (0.89 mmol) of Example 209 Part A compound, under argon, was added 1.2 mL (4.45 mmol) of tributylphosphite (neat). The mixture was heated to 120° C. for 18 h and bulb to bulb distilled (5 mm, 100° C.) to remove lower boiling impurities and provide a pale yellow oil. Flash chromatography was performed on 75 g of silica gel eluting with 95:5 dichloromethane/isopropanol to provide 440 mg (96%) of title compound as a pale yellow oil.

TLC Silica gel (95:5 dichloromethane/isopropanol) $R_f$=0.29. IR 3434, 2959, 2934, 2872, 1665, 1508, 1449, 1244, 1024, 978, 743 $cm^{-1}$. $^1H$ NMR (300 MHz, $CDCl_3$) is consistent with the indicated compound. MS (CI-$NH_3$, +ions) m/e 514 (M+H). Anal. Calcd. for $C_{30}H_{44}NO_4P$: C, 70.15; H, 8.63; P, 6.03. Found: C, 70.60; H, 8.80; P, 5.86. $^{13}C$ NMR (75 MHz, $CDCl_3$) is consistent with the indicated compound.

The following compounds were prepared employing procedures as described hereinbefore.

EXAMPLE 213

N,N-Diethyl-9-(2-propenyl)-9H-fluorene-9-carboxamide

MS (CI, M+H)$^+$ m/z 306 Anal. Calcd for $C_{21}H_{23}NO \cdot 0.14H_2O$: C, 81.90; H, 7.62; N, 4.55. Found: C, 82.11; H, 7.52; N, 4.34. mp 84°–86° C.

EXAMPLE 214

N-Ethyl-9-propyl-9H-fluorene-9-carboxamide

MS (CI, M+H)+ m/z 280. Anal. Calcd for $C_{19}H_{21}NO$: C, 81.68; H, 7.58; N, 5.01. Found: C, 81.45; H, 7.77; N, 5.06. mp 96°–97.5° C.

EXAMPLE 215

N-Ethyl-9-(2-propenyl)-9H-xanthene-9-carboxamide

MS (CI-NH$_3$, +ions) m/e 311 (M+NH$_4$), 294 (M+H). Anal. Calcd for $C_{19}H_{19}O_2N$: C, 77.79; H, 6.53; N, 4.77. Found: C, 77.87; H, 6.57; N, 4.77. mp 111°–112° C.

EXAMPLE 216

N-Ethyl-9-(3-phenylpropyl)-9H-xanthene-9-carboxamide

MS (CI-NH$_3$, +ions) m/e 372 (M+H). Anal. Calcd for $C_{25}H_{25}NO_2$: C, 80.83; H, 6.78; N, 3.77. Found: C, 80.77; H, 6.88; N, 3.83. mp 130° C.

EXAMPLES 217–218

9-Hexyl-N-propyl-9H-xanthene-9-carboxamide

MS (CI-NH$_3$, +ions) m/e 352 (M+H). Anal. Calcd for $C_{23}H_{29}NO_2$: C, 78.60; H, 8.32; N, 3.98. Found: C, 78.64; H, 8.46; N, 3.96. mp 76°–77.5° C.

EXAMPLE 219

N-Methoxy-N-methyl-9-propyl-9H-fluorene-9-carboxamide

CI-Mass Spec. (M+H)=296. Anal. Calcd for $C_{19}H_{21}NO_2$: C, 77.26; H, 7.17; N, 4.74. Found: C, 77.12; H, 7.04; N, 4.68. mp 73.75° C.

EXAMPLE 220

10,11-Dihydro-5-(3-phenyl-2-propenyl)-N-propyl-5H-dibenzo[a,d]cycloheptene-5-carboxamide MS (CI-NH$_3$, +ions) m/e 396 (M+H). Anal. Calcd for $C_{28}H_{29}NO$: C, 85.02; H, 7.39; N, 3.54. Found: C, 84.66; H, 7.46; N, 3.46. mp 159° C.

EXAMPLE 221

N-Methyl-9-propyl-9H-fluorene-9-carboxamide

CI-Mass Spec. (M+H)=266. Anal. Calcd for $C_{18}H_{19}NO + 0.12H_2O$: C, 80.82; H, 7.25; N, 5.24. Found: C, 80.90; H, 7.26; N, 5.16. mp 145°–146° C.

EXAMPLE 222

1-(9-Propyl-9H-fluoren-9-yl)-1-pentanone

CI-Mass Spec. (M+H)=293. Anal. Calcd for $C_{21}H_{24}O$: C, 86.20; H, 8.24. Found: C, 85.86; H, 8.14. mp 56°–58° C.

EXAMPLE 223

α-Butyl-9-propyl-9H-fluorene-9-methanol

CI-Mass Spec. (M+NH$_4$)=312+. Anal. Calcd for $C_{21}H_{26}O + 0.12H_2O$: C, 85.05; H, 8.92. Found: C, 85.05; H, 8.87. mp 88°–90° C.

EXAMPLE 224

1-(9-Propyl-9H-fluoren-9-yl)-1-butanone

CI-Mass Spec. (M+H)=279. Anal. Calcd for $C_{20}H_{22}O + 0.1H_2O$: C, 85.79; H, 7.98. Found: C, 85.79; H, 8.15. mp 65°–67° C.

EXAMPLE 225

α,9-Dipropyl-9H-fluorene-9-methanol

CI-Mass Spec. (M+NH$_3$)=298. Anal. Calcd for $C_{20}H_{24}O + 0.1H_2O$: C, 85.15; H, 8.64. Found: C, 85.15; H, 8.72. mp 83°–85° C.

EXAMPLE 226

10,11-Dihydro-5-(2-propenyl)-N-propyl-5H-dibenzo-[a,d]cycloheptene-5-carboxamide MS (CI-NH$_3$, +ions) m/e 320 (M+H). Anal. Calcd for $C_{22}H_{25}NO$: C, 81.98; H, 7.92; N, 4.35. Found: C, 82.01; H, 7.91; N, 4.32. mp 76°–79° C.

EXAMPLE 227

9-(3-Phenylpropyl)-N-propyl-9H-thioxanthene-9-carboxamide

MS (CI-NH$_3$, +ions) m/e 402 (M+H). Anal. Calcd for $C_{26}H_{27}NOS$: C, 77.77; H, 6.78; N, 3.49. Found: C, 77.60; H, 6.83; N, 3.42. mp 130°–131° C.

EXAMPLE 228

N,9-Dipropyl-9H-thioxanthene-9-carboxamide

MS (CI-NH$_3$, +ions) m/e 326 (M+H). Anal. Calcd for $C_{20}H_{23}NOS$: C, 73.81; H, 7.12; N, 4.30. Found: C, 73.84; H, 7.36; N, 4.24. mp 132°–133° C.

EXAMPLE 229

10,11-Dihydro-5-(3-phenylpropyl)-N-propyl-5H-dibenzo-[a,d]cycloheptane-5-carboxamide MS (CI, NH$_3$, +ions) m/z 398 (M+H). Anal. Calcd for $C_{28}H_{31}NO + 0.4H_2O$: C, 82.90; H, 7.93; N, 3.45. Found: C, 82.99; H, 7.95; N, 3.36. mp 109°–112° C.

EXAMPLE 230

(E)-2,7-Difluoro-9-(3-phenyl-2-propenyl)-N-propyl-9H-fluorene-9-carboxamide

MS (CI, M+H)+ m/z 404. Anal. Calcd for $C_{26}H_{23}NF_2O$: C, 77.40; H, 5.75; N, 3.47. Found: C, 77.32; H, 5.70; N, 3.33. mp 124°–126° C.

EXAMPLE 231

9-(3-Phenylpropyl)-N-(2-pyridinylmethyl)-9H-fluorene-9-carboxamide

CI-Mass Spec. (M+H)=419. Anal. Calcd for $C_{29}H_{26}N_2O$: C, 83.22; H, 6.26; N, 6.70. Found: C, 83.42; H, 6.31; N, 6.62. mp 115°–116° C.

EXAMPLE 232

2,7-Difluoro-9-(3-phenylpropyl)-N-propyl-9H-fluorene-9-carboxamide

MS (CI, M+H)+ m/z 406. Anal. Calcd for $C_{26}H_{25}F_2NO \cdot 0.12H_2O$: C, 76.62; H, 6.24; N, 3.44; F, 9.32. Found: C, 76.64; H, 6.33; N, 3.42; F, 9.12. Mp 99°–100.5° C.

EXAMPLE 233

2,7-Difluoro-9-(3-phenylpropyl)-N-(4-pyridinylmethyl)-9H-fluorene-9-carboxamide

MS (electrospray, M+H)⁺ m/z 455⁺. Anal. Calcd for $C_{29}H_{24}N_2F_2O.0.25H_2O$: C, 75.88; H, 5.38; N, 6.10. Found: C, 75.93; H, 5.15; N, 6.04. mp 60°–62° C.

EXAMPLE 234

9-(Butylthio)-9-propyl-9H-fluorene

MS (CI-NH₃, +ions) m/e 297 (M+H), 207 (M+H—$C_4H_{10}S$). Anal. Calcd for $C_{20}H_{24}S$: C, 81.03; H, 8.16; N, 10.81. Found: C, 81.40; H, 8.47; N, 10.85.

EXAMPLE 235

9-(Butylsulfinyl)-9-propyl-9H-fluorene

MS (ES, +ions) m/e 625 (2M+H), 313 (M+H). Anal. Calcd for $C_{20}H_{24}SO$: C, 76.88; H, 7.74; N, 10.26. Found: C, 77.12; H, 7.78; N, 9.93. mp 57°–59° C.

EXAMPLE 236

9-(4-Hydroxybutyl)-N-propyl-9H-fluorene-9-carboxamide

MS (CI-NH₃, +ions) m/e 324 (M+H). Anal. Calcd for $C_{21}H_{25}NO_2$: C, 77.99; H, 7.79; N, 4.33. Found: C, 77.89; H, 7.92; N, 4.35. mp 73°–75° C.

EXAMPLE 237

9-[4-(Phenylthio)butyl]-N-propyl-9H-fluorene-9-carboxamide

MS (CI-NH₃, +ions) m/e 416 (M+H). Anal. Calcd for $C_{27}H_{29}NOS$: C, 78.03; H, 7.03; N, 3.37; S, 7.71. Found: C, 77.70; H, 7.26; N, 3.35; S, 7.51. mp 50°–53° C.

EXAMPLE 238–240 cis-N,9-Dipropyl-1H-thioxanthene-9-carboxamide, 10-oxide

MS (CI-NH₃, +ions) m/e 342 (M+H). Anal. Calcd for $C_{20}H_{23}NO_2S$: C, 70.35; H, 6.79; N, 4.10. Found: C, 70.25; H, 6.86; N, 4.10. mp 201°–204° C.

EXAMPLE 241

5-(2-Propenyl)-N-propyl-5H-indeno[1,2-b]pyridine-5-carboxamide

MS (CI, M+H)⁺ m/z 293⁺. Anal. Calcd for $C_{19}H_{20}N_2O.0.1H_2O$: C, 77.58; H, 6.92; N, 9.52. Found: C, 77.50; H, 6.84; N, 9.57. mp 131°–133.5° C.

EXAMPLE 242

(E)-5-(3-Phenyl-2-propenyl)-N-propyl-5H-indeno[1,2-b]pyridine-5-carboxamide mp 153–154.5. MS (CI, M+H)⁺ m/z 369⁺. Anal. Calcd for $C_{25}H_{24}N_2O$: C, 80.32; H, 6.63; N, 7.49. Found: C, 80.26; H, 6.51; N, 7.55.

EXAMPLE 243

N-Ethyl-N-methyl-9-(2-propenyl)-9H-fluorene-9-carboxamide

MS (CI, M+H)⁺ m/z 292. Anal. Calcd for $C_{20}H_{21}NO.0.06$ dioxane: C, 81.94; H, 7.30; N, 4.72. Found: C, 81.76; H, 7.39; N, 4.68.

EXAMPLE 244

N,9-Dipropyl-9H-thioxanthene-9-carboxamide, 10,10-dioxide

MS (CI-NH₃, +ions) m/z 380 (M+Na) 375 (M+NH₄), 358 (M+H). Anal. Calcd for $C_{20}H_{23}NO_3S+0.6CH_2Cl_2$: C, 60.58; H, 5.97; N, 3.43. Found: C, 60.58; H, 5.79; N, 3.39. mp 264°–266° C.

EXAMPLE 245 trans-N,9-Dipropyl-9H-thioxanthene-9-carboxamide, 10-oxide

MS (CI-NH₃, +ions) m/z 342 (M+H). Anal. Calcd for $C_{20}H_{23}NO_2S+0.4H_2O$: C, 68.92; H, 6.88; N, 4.02. Found: C, 68.96; H, 7.18; N, 3.98. mp 147°–150° C.

EXAMPLE 246

9-[3-(Dibutoxyphosphinyl)propyl]-N-(2-pyridinylmethyl)-9H-fluorene-9-carboxamide CI-Mass Spec. (M+H)=535. Anal. Calcd for $C_{31}H_{39}N_2PO_4.0.5H_2O$: C, 68.48; H, 7.42; N, 5.15; P, 5.70. Found: C, 68.28; H, 7.23; N, 5.28; P, 5.50.

EXAMPLE 247

1-(9-Propyl-9H-fluorene-9-yl)-2-(1-piperidinyl)ethanone, monohydrochloride

MS (ES) 334 (M+H). Anal. Calcd for $C_{23}H_{28}ClNO.H_2O$: C, 71.21; H, 7.79; N, 3.61. Found: C, 71.01; H, 7.75; N, 3.93.

EXAMPLE 248

N-(5-Hydroxypentyl)-9-propyl-9H-fluorene-9-carboxamide

MS (CI, +ions) m/z 338 (M+H). Anal. Calcd for $C_{22}H_{27}NO_2+0.3H_2O$: C, 77.13; H, 8.11; N, 4.09/ Found: C, 77.10; H, 8.23; N, 4.00. mp 48.51° C.

EXAMPLE 249

9-(3-Cyanopropyl)-N-propyl-9H-fluorene-9-carboxamide

MS (ES, +ions) m/z 319 (M+H) Anal. Calcd for $C_{21}H_{22}N_2O$: C, 79.21; H, 6.96; N, 8.80. Found: C, 78.98; H, 6.89; N, 8.68. mp 80°–83° C.

EXAMPLE 250

N-[[4-[[(9-Propyl-9H-fluoren-9-yl)carbonyl]amino]phenyl]methyl]-9-propyl-9H-fluorene-9-carboxamide MS (CI, +ions) 591 (M+H). Anal. Calcd for $C_{41}H_{38}N_2O_2.0.3H_2O$: C, 82.60; H, 6.53; N, 4.70. Found: C, 82.62; H, 6.44; N, 4.64. mp 188°–190° C.

EXAMPLE 251

N-[4-(4-Aminophenyl)methyl]-9-propyl-9H-fluorene-9-carboxamide

MS (ES, +ions) 357 (M+H). Anal. Calcd for $C_{24}H_{24}N_2O.0.7H_2O$: C, 78.10; H, 6.94; N, 7.59. Found: C, 78.26; H, 6.70; N, 7.48. mp 96°–99° C.

EXAMPLE 252

9-[3-(Dibutoxyphosphinyl)propyl]-N-propyl-9H-fluorene-9-carboxamide

MS (CI-NH$_3$, +ions) m/e 486 (M+H). Anal. Calcd for C$_{28}$H$_{40}$NO$_4$P+0.75 mol H$_2$O: C, 67.37; H, 8.38; N, 2.81; P, 6.21. Found: C, 67.49; H, 8.28; N, 2.69; P, 6.45.

EXAMPLES 253–254

N-Methyl-9-(3-phenylpropyl)-9H-fluorene-9-carboxamide

MS (CI, +ions) m/z 342 (M+H). Anal. Calcd for C$_{24}$H$_{23}$NO+0.2H$_2$O: C, 83.51; H, 6.84; N, 4.06. Found: C, 83.55; H, 6.69; N, 4.02. mp 101°–102° C.

EXAMPLE 255

2-(Dimethylamino)-9-(3-phenylpropyl)-N-propyl-9H-fluorene-9-carboxamide

MS (CI, M+H)$^+$ m/z 413$^+$. Anal. Calcd for C$_{28}$H$_{32}$N$_2$O.0.34H$_2$O: C, 80.32; H, 7.87; N, 6.69. Found: C, 80.30; H, 7.74; N, 6.71.

EXAMPLE 256

9-[4-(Dibutoxyphosphinyl)-2-butenyl]-N-propyl-9H-fluorene-9-carboxamide

MS (ES) 498 (M+H). Anal. Calcd for C$_{29}$H$_{40}$NO$_4$P: C, 70.00; H, 8.10; N, 2.81; P, 6.22. Found: C, 69.85; H, 8.15; N, 3.13; P, 6.19.

EXAMPLE 257

9-[4-(4-Nitrophenyl)butyl]-N-propyl-9H-fluorene-9-carboxamide

MS (ES) 429 (M+H). Anal. Calcd for C$_{27}$H$_{28}$N$_2$O$_3$: C, 75.68; H, 6.59; N, 6.54. Found: C, 75.70; H, 6.58; N, 6.57. mp 109°–110° C.

EXAMPLE 258

9-[3-(4-Nitrophenyl)-2-propenyl]-N-propyl-9H-fluorene-9-carboxamide

MS (CI, +ions) 413 (M+H). Anal. Calcd for C$_{26}$H$_{24}$N$_2$O$_3$.0.3H$_2$O: C, 74.73; H, 5.93; N, 6.70. Found: C, 74.54; H, 5.75; N, 6.67. mp 143°–146° C.

EXAMPLE 259

5-(3-Phenylpropyl)-N-propyl-5H-indeno[1,2-b]pyridine-5-carboxamide

MS (CI, M+H)$^+$ m/z 371$^+$. Anal. Calcd for C$_{25}$H$_{26}$N$_2$O: C, 81.05; H, 7.07; N, 7.56. Found: C, 80.97; H, 7.12; N, 7.51. mp 124.5°–126° C.

EXAMPLE 260

9-[4-(4-Aminophenyl)butyl]-N-propyl-9H-fluorene-9-carboxamide

MS (CI) 399 (M+H). Anal. Calcd for C$_{27}$H$_{30}$N$_2$O.0.3H$_2$O: C, 80.28; H, 7.64; N, 6.93. Found: C, 80.37; H, 7.53; N, 7.34.

EXAMPLE 261

9-[3-(4-Aminophenyl)propyl]-N-propyl-9H-fluorene-9-carboxamide

MS (CI, +ions) 385 (M+H). Anal. Calcd for C$_{26}$H$_{28}$N$_2$O.0.3H$_2$O: C, 80.09; H, 7.39; N, 7.18. Found: C, 80.01; H, 7.31; N, 7.17. mp 138°–140° C.

EXAMPLE 262

9-[4-(Dibutoxyphosphinyl)butyl]-9H-fluorene-9-carboxylic acid, methyl ester

MS (CI, +ions) m/z 473 (M+H). Anal. Calcd for C$_{27}$H$_{37}$O$_5$P: C, 68.63; H, 7.89; N, 6.55. Found: C, 68.37; H, 7.96; N, 6.21.

EXAMPLE 263

N,N-Dibutyl-9-[(propylamino)carbonyl]-9H-fluorene-9-butanamide

MS (CI-NH$_3$, +ions) m/e 449 (M+H). Anal. Calcd for C$_{29}$H$_{40}$N$_2$O$_2$+0.29 mol H$_2$O: C, 76.75; H, 9.01; N, 6.17. Found: C, 76.71; H, 8.92; N, 6.21. mp 109°–111° C.

EXAMPLE 264

9-(5-Cyanopentyl)-N-propyl-9H-fluorene-9-carboxamide

MS (ES, +ions) m/e 347 (M+H). Anal. Calcd for C$_{23}$H$_{26}$N$_2$O: C, 79.73; H, 7.56; N, 8.09. Found: C, 79.25; H, 7.55; N, 7.76. mp 92°–94° C.

EXAMPLES 265–266

(Z)-9-[4-[(6-Ethoxy-2-benzothiazolyl)thio]-2-butenyl]-N-propyl-9H-fluorene-9-carboxamide

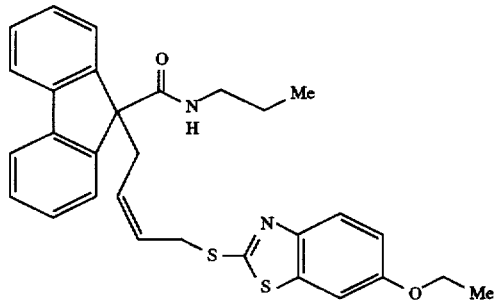

A.

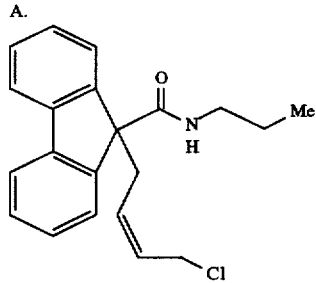

Butyllithium (8.4 mL, 2.5M in hexane, 21 mmol) was added dropwise over 10 min to a solution of 9-fluorenecarboxylic acid (2.10 g, 10 mmol) in THF (50 mL) at 0° C. under argon. During addition of the first equivalent of BuLi, the reaction became thick with a white precipitate which became yellow and cleared after addition of the second equivalent. The reaction was stirred at 0° C. for 20 min, then cis-1,4-dichloro-2-butene (1.2 mL, 11 mmol) was added dropwise over 5 min. The reaction lightened in color during addition and was stirred at 0° C. for 3 h, then poured into 1N HCl (50 mL) and extracted with CH$_2$Cl$_2$ (3×50 mL). The combined organic layers were washed with brine (30 mL) then dried over MgSO$_4$. Evaporation provided 3.5 g of a yellow oil containing crystalline solid. The crude residue was triturated with hexane (20 mL). The supernatant was decanted, and the residue pumped under high vacuum to give 2.93 g of a tan solid.

To a suspension of the crude acid prepared above (1.42 g, 4.77 mmol) and N,N-dimethylformamide (5 drops) in CH$_2$Cl$_2$ (15 mL) at room temperature under argon was added oxalyl chloride (3.6 mL, 2.0 M in CH$_2$Cl$_2$, 7.16 mmol). The reaction bubbled for 10 min, then the reaction was stirred at room temperature for 1.5 h, at which time all solids had dissolved. The reaction was concentrated in vacuo to give an orange oil. The crude acid chloride was dissolved in CH$_2$Cl$_2$ (15 mL) and cooled to 0° C. Propylamine (1.2 mL, 14.3 mmol) was added dropwise over 1 min, and the reaction was stirred at 0° C. for 10 min. The reaction was partitioned between EtOAc (50 mL) and water (20 mL). The organic layer was washed with 1N HCl (2×20 mL) and brine (20 mL), then dried over MgSO$_4$. Evaporation gave 1.7 g of an orange oil, which was purified by flash chromatography on silica gel (150 g) eluting with CH$_2$Cl$_2$ to give title compound (1.38 g, 84%) as a pale yellow oil.

B. (Z)-9-[4-[(6-Ethoxy-2-benzothiazolyl)thio]-2-butenyl]-N-propyl-9H-fluorene-9-carboxamide To a solution of 500 mg (1.47 mmol) of Part A compound in 5 mL of DMF, under argon at RT, was added 400 mg (2.94 mmol) of K$_2$CO$_3$ followed by 466 mg (2.20 mmol) of 6-ethoxy-2-mercaptobenzothiazole. The reaction was stirred for 5 h at RT, at which time it was heated to 50° C. for 16 h. The reaction was diluted with ether and the organics were washed with water (2x), brine, dried (Na$_2$SO$_4$) and evaporated. Flash chromatography was performed on 100 g of silica gel eluting with 3:2 hexanes/ethyl acetate to provide 450 mg (60%) of title compound as a biege solid.

mp 135°–137° C. Anal. Calcd. for C$_{30}$H$_{30}$N$_2$O$_2$S$_2$+0.55 mol H$_2$O: C, 68.68; H, 5.98; N, 5.34; S, 12.22. Found: C, 68.88; H, 5.77; N, 5.14; S, 12.26.

EXAMPLE 267

9-[4-(Dibutoxyphosphinyl)butyl]-N-(2,2,2-trifluoropropyl)-9H-xanthene-9-carboxamide

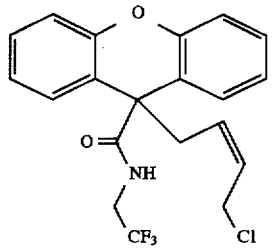

A.

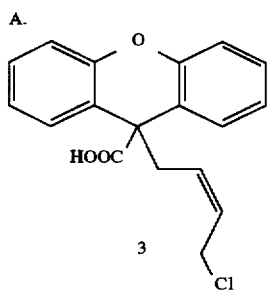

To a stirred solution of 5.00 g (22.1 mmol) of xanthene carboxylic acid in 100 mL of THF at 0° C. was added 19.5 mL (48.7 mmol) of 2.5M butyllithium in hexanes followed by 3.05 g (24.32 mmol) of cis-1,4-dichloro-2-butene. The reaction was allowed to stir at 0° C. for 24 h when the mixture was diluted with 250 mL of ethyl acetate and 100 mL of 0.5M HCl. The layers were separated, the organics dried (Na$_2$SO$_4$) and concentrated. The remainder was purified by flash column chromatography on silica gel (250 g) eluting with 30:70:0.5 ethyl acetate/hexanes/acetic acid to give 4.6 g (66%) of title compound as a white solid. mp 134°–135° C.

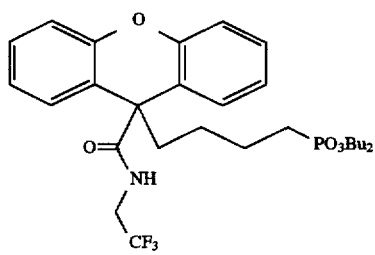

To a stirred solution of 2.00 g (6.35 mmol) of Part A compound in 100 mL of dichloromethane at RT was added 3.6 mL (7.2 mmol) of 2M oxalyl chloride in dichloromethane followed by 2 drops of DMF. The reaction was allowed to stir at RT for 2.5 h when the solvent was evaporated and the semisolid residue pumped ($\approx$1 mm pressure) for 0.5 h. The residue was dissolved by adding 300 mL of THF and cooled to 0° C. The mixture was treated with 0.9 g (7 mmol) of trifluoroethylamine hydrochloride and 1.41 g (14 mmol) of triethylamine and warmed to room temperature. The mixture was stirred overnight and diluted with 150 mL of ethyl acetate and 50 mL of 0.5M HCl. The layers were separated, the organics dried (Na$_2$SO$_4$) and concentrated. The remainder was purified by trituration with hot methanol to give 1.30 g (52%) of title compound as a white solid. mp 153°–159° C.

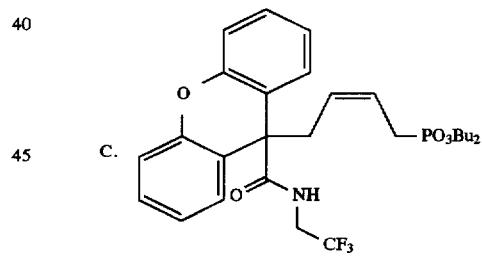

A mixture of Part B compound (0.53 g, 1.34 mmol) and tributylphosphite (3.00 g, 12 mmol) was heated to 115°–120° C. for 24 h. The mixture was concentrated by bulb-to-bulb distillation to leave an amber colored oil. The remainder was purified by flash column chromatography on silica gel (60 g) eluting with 9:1 dichloromethane/acetone to give 0.65 g (86%) of title compound as a colorless oil.

TLC Silica gel (9:1 dichloromethane/acetone) R$_f$=0.4.

D. 9-[4-(Dibutoxyphosphinyl)butyl]-N-(2,2,2-trifluoropropyl)-9H-xanthene-9-carboxamide A solution of Part C compound (0.60 g, 1.06 mmol) in ethanol (10 mL) was treated ith 40 mg of 10% Pd/Carbon and placed under an atm of H$_2$ for 18 h. The mixture was diluted with 25 mL of ethanol and filtered through a pad of Celite. The filtrate was concentrated to an oil which gradually solidified to give 0.32 g (91%) of title compound as a colorless oil which gradually turned to a white solid on standing. mp 102°–105° C.

Mass Spec. (ES. +ions) m/z 573 (M+NH$_4$), 556 (M+H). Anal. Calc'd for C$_{28}$H$_{37}$NO$_5$PF$_3$+0.65H$_2$O: C, 59.25; H, 6.81; N, 2.47; P, 5.46. Found: C, 59.59; H, 6.53; N, 2.14; P, 5.03.

EXAMPLES 268–269

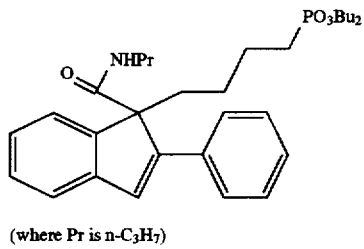

(where Pr is n-C$_3$H$_7$)

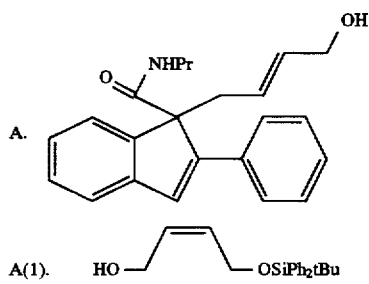

To a slurry of sodium hydride (6.975 g, 60% mineral oil dispersion, 0.174 mol) in 200 mL of THF at room temperature under argon was added cis-2-butene-1,4-diol (15.36 g, 0.174 mol) over 20 minutes. Gas evolved and a thick precipitate formed. The slurry was stirred for 16 h and then was rapidly treated with t-butyl diphenylchlorosilane (47.82 g, 0.174 mol). The reactions warmed to 40° C. autogenously and a clear solution formed. After 15 min, the reaction was quenched with water and extracted twice with hexanes. The organic layers were combined, dried (Na$_2$SO$_4$) and evaporated. Purification by flash chromatography (12×30 cm column, dichloromethane) gave title compound as a colorless oil, 46.6 g, 82%.

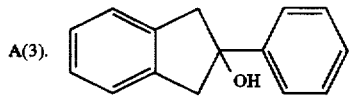

To a stirred solution of Part A(1) compound (6.53 g, 20.0 mmol) and triethylamine (3.53 mL, 25.3 mmol) in 50 mL of dichloromethane at room temperature under argon was added acetic anhydride (2.4 mL, 22.5 mmol) and DMAP (20 mg, 0.16 mmol). After 2 h, TLC indicated that no alcohol remained. The reaction was evaporated at less than 30° C. and the residue partitioned between 10% citric acid and hexanes. The organic layer was washed with water and saturated sodium bicarbonate solution, dried (Na$_2$SO$_4$) and evaporated. The isolated colorless oil, title compound (7.02 g, 95%), was used without further purification.

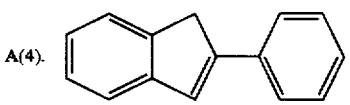

Anhydrous cerium chloride (16.00 g, 64.9 mmol) was stirred in an evacuated flask heated in an oil bath to 145° C. for 2 h. The flask was flooded with argon, cooled to room temperature and then to 0° C. in an ice bath. To this powder was added 150 mL of THF. The stirred slurry was warmed to room temperature. After 14 h, the flask was again cooled to 0° C. and phenylmagnesium chloride solution (21.2 mL, 63.6 mmol, 3M in ether) was added. The resulting yellow slurry was stirred for 1.5 h and then a solution of 2-indanone (Aldrich, purified by flash chromatography) (5.45 g, 41.2 mmol, freshly chromatographed) was added. After 30 min, the reaction mixture was quenched with 10% citric acid and extracted twice with ether. The organic extracts were dried (MgSO$_4$) and evaporated. Purification by flash chromatography (5×20 cm column, 17:3 dichloromethane/hexanes) gave title compound as a colorless oil, 6.66 g, 77%.

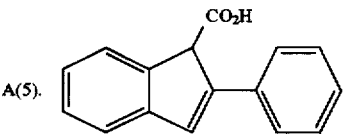

To Part A(3) compound (neat) (6.40 g, 30.4 mmol) was added potassium bisulfate (6.4 g, 47 mmol). The mixture was stirred under argon and placed in an oil bath heated to 160° C. for 20 min. The resulting solid mass was cooled, partitioned between dichloromethane and water. The organic layer was dried (MgSO$_4$) and evaporated to provide title compound (5.84 g, 100%) as a white solid, mp 163°–164° C. The compound was used in subsequent reactions without further purification.

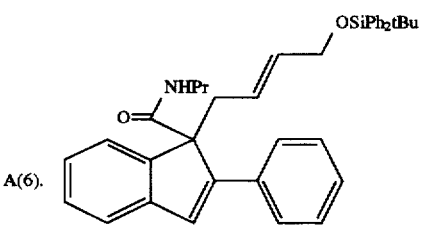

To a solution of Part A(4) compound (1.481 g, 7.70 mmol) in 20 mL of THF at 0° C. under argon was added n-butyllithium (3.0 mL, 7.50 mmol, 2.5M in hexanes) over 10 min. The resulting deep orange solution was stirred for 1 h. The reaction was quenched with several small pieces of THF-washed dry ice. The resulting thick yellow slurry was stirred for 1 h and then treated with 20 mL of 2M potassium hydroxide solution. This solution was extracted twice with ether and the aqueous residue was brought to pH 2 with 3N sulfuric acid. The mixture was extracted three times with ethyl acetate, the extracts combined, dried (MgSO$_4$) and evaporated to give title compound as a light yellow powder (1.50 g, 82%), mp 212°–215° C. The compound was used in subsequent reactions without further purification.

A mixture of Part A(5) compound (890 mg, 3.77 mmol), Part A(2) compound (2.55 g, 3.77 mmol) and triphenylphosphine (190 mg, 0.724 mmol) was evaporated twice from toluene. The mixture was dissolved in 20 mL of THF, stirred under argon and treated with bis(trimethylsilyl)acetamide (BSA) (3.7 mL, 15 mmol). After 30 min, tetrakis (triphenylphosphine)palladium(O) (430 mg, 0.39 mmol) was added and the reaction set to reflux. After 16 h, the orange solution was cooled, evaporated and re-evaporated twice from methanol. The gummy residue was dissolved in ether and washed once with 10% citric acid. The organic extract was dried (MgSO$_4$), evaporated and re-evaporated once from toluene.

To a stirred solution of this product in 10 mL of dichloromethane under argon at room temperature was added oxalyl chloride (0.9 mL, 7.0 mmol) and then DMF (0.05 mL). After 1 h, the reaction was evaporated to give an orange oil which was dissolved in 10 mL of THF.

This solution was added to a stirred solution of n-propylamine (1.4 mmol, 16 mmol) in 10 mL of THF at 0° C. over 10 min. After 1 h, the reaction mixture was diluted with ether and washed once with 10% citric acid. The organic extract was dried (MgSO$_4$) and evaporated. Purification by flash chromatography (5×20 cm column, dichloromethane) gave title compound as an orange oil, 1.50 g, 77%.

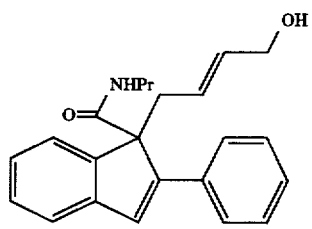

A(7).

To a stirred solution of Part A(6) compound (2.15 g, 4.18 mmol) in 15 mL of THF at room temperature under argon was added tetrabutylammonium fluoride (10 mL, 10 mmol, 1M in THF). After 1 h, the reaction was quenched with brine and extracted three times with ethyl acetate. The organic extract was dried (MgSO$_4$) and evaporated. Purification by flash chromatography (5×15 cm column, 3:2 hexanes/ethyl acetate) gave title compound as a colorless glass, 1.09 g, 75%.

B.

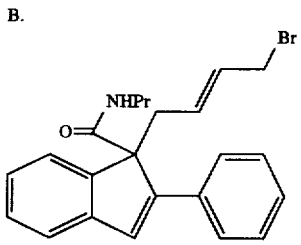

To a solution of 400 mg (1.15 mmol) of Part A compound and 600 mg (2.3 mmol) of triphenylphosphine in 4 mL of THF at room temperature under argon was added 763 mg (2.3 mmol) of tetrabromomethane. After two hours, the reaction mixture was evaporated at less than 25° C. Purification by flash chromatography on silica gel (2.5×15 cm column, dichloromethane) gave title compound as a white solid, mp 82°–84° C., 440 mg, 95%.

C.

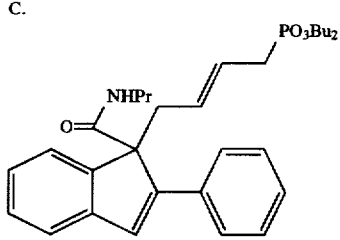

A stirred solution of Part B compound (350 mg, 0.853 mmol) in 2 mL of tributyl phosphite was heated to 110° C. under argon for two hours. The reaction mixture was subjected to bulb-to-bulb distillation at 0.5 mm Hg and 100° C. to remove excess tributylphosphite. The residue was purified by flash chromatography on silica gel (2.5×15 cm column, 2:1 ethylacetate/hexanes) to give title compound as a colorless oil, 425 mg, 95%.

MS (electrospray, +ions) m/e 524 (M+H), 541 (M+NH$_4$). Anal. Calc'd for C$_{31}$H$_{42}$NO$_4$P.0.19H$_2$O: C, 70.64; H, 8.10; N 2.66; P, 5.88. Found: C, 70.64; H, 8.11; N 2.56; P, 6.18.

EXAMPLE 270

9-[4-(Dibutoxyphosphinyl)butyl]-2,7-difluoro-N-(2, 2,2-trifluoroethyl)-9H-fluorene-9-carboxamide

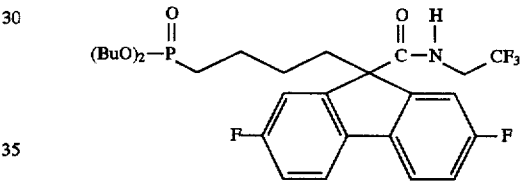

A solution of Example 203 compound (574 mg, 1 mmol) in 25 ml of absolute ethanol containing 250 mg of 10% Pd on carbon as catalyst was stirred under a hydrogen atmosphere (balloon) for 48 hours. The reaction was filtered after stirring 24 hrs and fresh catalyst added. The reaction was filtered through a 0.45 μm nylon filter and the solvent evaporated yielding 538 mg (94%) of title compound as a colorless oil.

Mass Spec (CI).m/z 576 (M+H). Anal Calc'd for C$_{28}$H$_{35}$NF$_5$PO$_4$: C, 58.43; H, 6.13; N, 2.43; F, 16.50; P, 5.38. Found: C, 58.54; H, 5.86; N, 2.39; F, 16.41; P, 5.39.

EXAMPLE 271

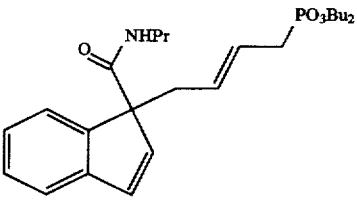

A.

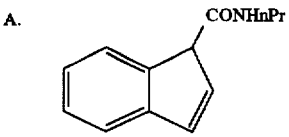

To a stirred slurry of

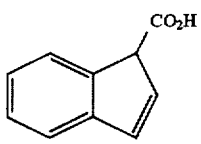

(3.20 g, 20.0 mmol) in 20 mL of dichloromethane at room temperature under argon was added 15.0 mL of oxalyl chloride (2M in dichloromethane, 30.0 mmol) and 0.1 mL of DMF. The resulting yellow solution was stirred one hour and then evaporated at 25° C. The semi-solid residue was redissolved in 15 mL of THF and added drop-wise to a solution of n-propylamine (3.5 mL, 43 mmol) in 25 mL of THF at −10° C. under argon. After one hour, the reaction mixture was partitioned between ethyl acetate and 10% citric acid solution. The organic extract was separated, dried (MgSO₄) and evaporated. Purification by flash chromatography on silica gel (5×20 cm column, 1:2 ethyl acetate/hexanes) gave title compound as a yellow solid, 2.36 g, 59%, mp 83°–86° C.

B.

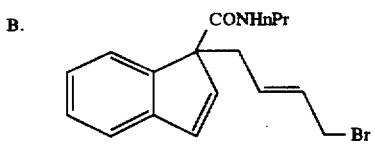

To a stirred solution of Part A compound (1.28 g, 6.36 mmol) in 25 mL of THF under argon at 0° C. was added 26.0 mL of potassium bis(trimethylsilyl)amide (0.5M in toluene, 13.0 mmol) over 20 min. A deep purple solution formed. After 30 min, a solution of (E)-1,4-dibromobutene (4.0 g, 18.7 mmol, Aldrich) in 10 mL of THF was added over 10 min. After 30 min, the reaction mixture was partitioned between ethyl acetate and 1M hydro-chloric acid. The organic extract was separated, dried (MgSO₄) and evaporated. Purification by flash chromatography on silica gel (5×15 cm column, 19:81 ethyl acetate/hexanes) gave title compound as a colorless oil, 547 mg, 26%.

C.

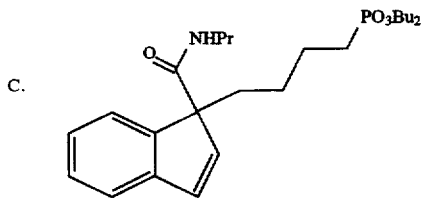

A stirred solution of Part B compound (530 mg, 1.59 mmol) in 3.5 mL of tributyl phosphite was heated to 110° C. under argon for 3 hours. The reaction mixture was subjected to bulb-to-bulb distillation at 0.5 mm Hg and 100° C. to remove excess tributylphosphite. The residue was purified by flash chromatography on silica gel (2.5×15 cm column, 3:1 ethylacetate/hexanes) to give title compound, as a colorless oil, 565 mg, 79%.

Anal. Calc'd for $C_{25}H_{38}NO_4P \cdot 0.25H_2O$: C, 66.42; H, 8.58; N 3.10; P, 6.85. Found: C, 66.43; H, 8.57; N 3.05; P, 6.90. MS (electrospray, +ions) m/e 448.2 (M+H), 465.3 (M+NH₄).

EXAMPLE 272

(E)-9-[4-(Dibutoxyphosphinyl)-2-butenyl]-N-propyl-9H-fluorene-9-carboxamide

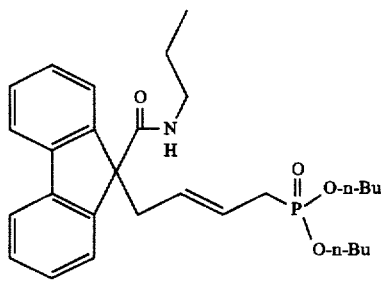

A.

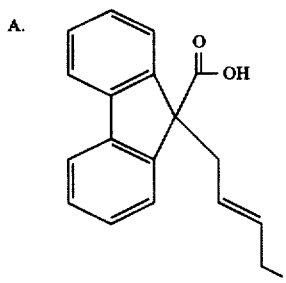

To a THF (150 ml) suspension of 9-fluorenecarboxylic acid (10 g, 0.048 mol) at 0° C. under argon was added dropwise sodium bis(trimethylsilyl)amide (100 ml, 1M in THF). After 30 min, 1,4-trans-2-butene (10.2 g, 0.048 mol) was added and the reaction allowed to stir for 1 h. The reaction mixture was quenched with 1N HCl and the aqueous layer extracted 3 times with EtOAc. The combined organics were dried over Na₂SO₄ and evaporated in vacuo to give an oily-solid residue (18 g). The residue was purified by flash column chromatography (SiO₂, 10 by 25 cm), eluting with 6.5% MeOH:CH₂Cl₂ to give title compound (2.48 g, 15% yield) as an oily solid. MS: (CI, M+NH₄⁺): m/z 360⁺.

B.

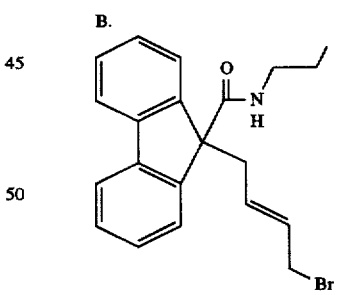

To a CH₂Cl₂ (30 ml) solution at 0° C. of Part A compound (2.48 g, 7.22 mmol) under argon was added oxalyl chloride (1.46 g, 11.4 mmol) and DMF (0.1 ml). The reaction mixture was stirred at room temperature for 2.5 h and the volatiles were removed in vacuo. The crude residue containing acid chloride was co-evaporated with CH₂Cl₂ and used directly in the following reaction.

To a THF (26 ml) solution of the acid chloride (7.22 mmol) at 0° C. under argon was added n-propylamine (0.899 g, 15.2 mmol) and the reaction was stirred for 1.45 h. After warming to room temperature for 15 min, the mixture was stored at −80° C. overnight. The reaction mixture was partitioned between EtOAc and water, the aqueous layer extracted twice with EtOAc, the combined organics washed with brine, dried over $Na_2SO_4$, and evaporated to give title compound (2.79 g, >100% crude recovery, containing EtOAc) as a slightly orange colored oil. MS: (CI, M+H$^+$): m/z 384$^+$.

C. (E)-9-[4-(Dibutoxyphosphinyl)-2-butenyl)]-N-propyl-9H-fluorene-9-carboxamide

A solution of Part B compound (977 mg, 2.54 mmol) and tri-n-butyl phosphite (2.75 ml) under argon was heated at 120° C. for 17 h. The volatiles were removed in vacuo to give an oil (1.26 g). The residue was purified by flash column chromatography (SiO$_2$, 5 by 10 cm), eluting with 2.5% MeOH:CH$_2$Cl$_2$, to give after heating at 70° C. in vacuo overnight title compound (120 mg, 10% yield from Part A compound) as a colorless oil. The bulk of title compound was isolated as colorless oil containing residual tri-n-butyl phosphite (1.07 g).

MS: (CI, M+H$^+$): m/z 498. Anal. Calc. for $C_{29}H_{40}NO_4P$ . 0.90 H$_2$O: C, 67.78; H, 8.20; N, 2.73 Found: C, 67.75; H, 7.91; N, 2.76.

EXAMPLE 273

9-[4-[4-(Benzoylamino)-1H-imidazol-1-yl]butyl]-N-(2,2,2-trifluoroethyl)-9H-fluorene-9-carboxamide

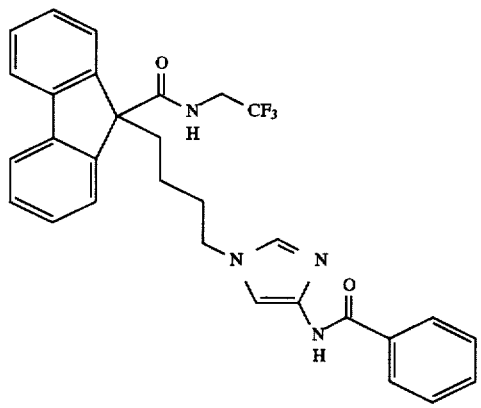

A.

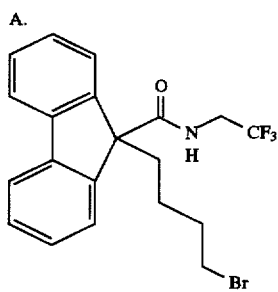

A(1).

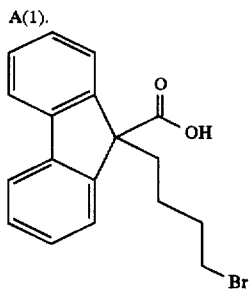

To a solution of 9-fluorenecarboxylic acid (50 g, 240 mmol) in THF (1200 mL) at 0° C. was added dropwise a solution of n-butyllithium (2.5M, 211 mL, 530 mmol) in THF. The yellow reaction was stirred at 0° C. for 1 h, then 1,4-dibromobutane (31.3 mL, 260 mmol) was added dropwise over 30 min. The reaction was stirred at 0° C. for 30 min, then the reaction was warmed to RT for 30 h. The reaction was extracted with water (3×750 mL). The combined aqueous layers were extracted with ethyl ether (800 mL). The aqueous layer was made acidic with HCl solution (1N, 500 mL), then extracted with dichloromethane (3×750 mL). The combined organic layers were dried over MgSO$_4$. Evaporation gave title compound (71 g, 85%) as a white solid.

A(2).

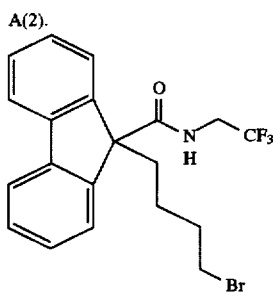

To a solution of Part A(1) acid (60 g, 173 mmol) and DMF (100 μL) in CH$_2$Cl$_2$ (600 mL) under argon at 0° C. was added oxalyl chloride (104 mL, 2.0M in CH$_2$Cl$_2$, 208 mmol) dropwise. The reaction was stirred at 0° C. for 10 min, then warmed to room temperature and stirred for 1.5 h. The reaction was concentrated in vacuo to give the crude acid chloride as a yellow oil. To a suspension of 2,2,2-trifluoroethylamine hydrochloride (25.9 g, 191 mmol) in CH$_2$Cl$_2$ (500 mL) at 0° C. under argon was added triethylamine (73 mL, 521 mmol) followed by dropwise addition of a solution of the crude acid chloride in CH$_2$Cl$_2$ (15 mL). The reaction was stirred at 0° C. for 1 h, diluted with CH$_2$Cl$_2$ (500 mL), and washed with water (2×300 mL), 1N HCl (2×300 mL), saturated NaHCO$_3$ (2×300 mL), and brine (2×300 mL), then dried over MgSO$_4$. Evaporation gave 80 g of a oil which was purified by flash chromatography on silica gel (2.5 kg). The crude product was loaded in a mixture of CH$_2$Cl$_2$ and hexane, and eluted with a step gradient of 10% EtOAc/hexane (4 L) to 15% EtOAc/hexane (2 L) to 20% EtOAc/hexane (4 L). Pure fractions were combined and evaporated to give title compound (52.5 g, 71%) as a white solid (mp 88°–92° C.)

B.

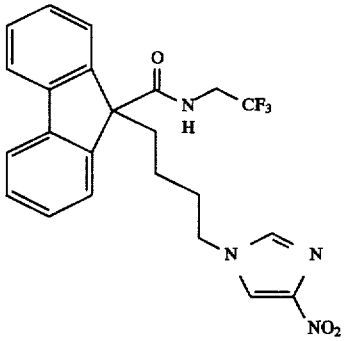

A mixture of Part A (1.55 g, 3.64 mmol), 4-nitroimidazole (452 mg, 4.00 mmol), and anhydrous potassium carbonate (552 mg, 4.00 mmol) in DMF (5 mL) was heated at 50° C.

under argon for 6 h, cooled to RT, and the solvent was removed in vacuo. The yellow residue was partitioned between EtOAc (50 mL) and water (10 mL). The aqueous layer was extracted with EtOAc (3 mL). The combined organic extracts were washed with water (3×10 mL) and brine (20 mL), then dried over $Na_2SO_4$. Evaporation gave 1.77 g of a foamy gum, which was purified by flash chromatography on silica gel (120 g) eluting with 15% EtOAc/$CH_2CH_2$ to provide title compound (1.51 g, 91%) as a white foam.

C. 9-[4-[4-(Benzoylamino)-1H-imidazol-1-yl]butyl]-N-(2,2,2-trifluoroethyl)-9H-fluorene-9-carboxamide Palladium on carbon (10%) (35 mg, 0.033 mmol) was added to a solution of Part B compound (300 mg, 0.655 mmol) in dry EtOAc (2 mL), and the mixture was hydrogenated (balloon) at RT overnight. The reaction was degassed with argon, cooled to 0° C., and benzoyl chloride (83 μL, 0.72 mmol) was added dropwise. The reaction was stirred at 0° C. for 20 min, filtered through Celite, and washed with EtOAc (5 mL). The brown filtrate was washed with saturated $NaHCO_3$ (2×2 mL) and brine (1 mL), then dried over $Na_2SO_4$. Evaporation gave 282 mg of a dark brown oil, which was purified by flash chromatography on silica gel (50 g) eluting with 2% MeOH/$CH_2CH_2$ to provide title compound (253 mg, 73%) as a brown foam.

MS (ES): 533 [M+H]Anal. Calcd. for $C_{30}H_{27}F_3N_4O_2$ · 0.5 $H_2O$: C, 66.53; H, 5.21; N, 10.35; F, 10.52 Found: C, 66.60; H, 5.13; N, 10.19; F, 10.86.

EXAMPLE 274

9-[4-[5-(Benzoylamino)-2-pyridinyl]butyl]-N-(2,2,2-trifluoroethyl)-9H-fluorene-9-carboxamide

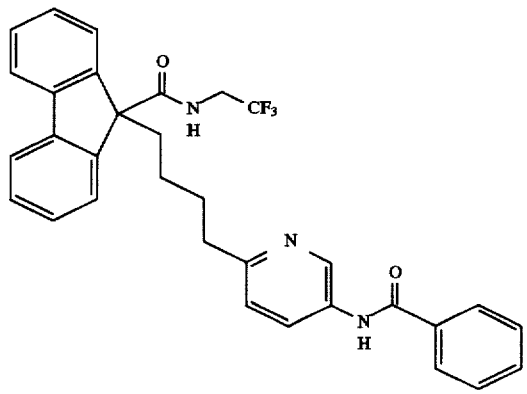

A.

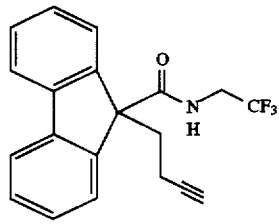

Butyllithium (12.6 mL, 31.5 mmmol) was added dropwise over 5 min to a solution of 9-fluorenecarboxylic acid (3.0 g, 14.3 mmol) in THF (150 mL) at 0° C. under argon. The reaction went cloudy during addition, then cleared upon completion. The reaction was stirred at 0° C. for 30 min, then 3-butynyl p-toluenesulfonate (9.6 g, 42.9 mmol) was added dropwise. The amber reaction was warmed to RT, then stirred for 24 h. The reaction solution was extracted with water (2×75 mL). The combined aqueous layers were washed with $Et_2O$ (50 mL), then acidified with 1N HCl (30 mL). The cloudy mixture was extracted with $CH_2Cl_2$ (2×50 mL), and the combined organic layers were dried over $MgSO_4$. Evaporation gave 1.85 g of a crude orange gummy solid.

A portion (1.75 g) of crude acid product was dissolved in $CH_2Cl_2$ (20 mL) under argon. A catalytic amount of DMF (26 μL, 0.33 mmol) was added, followed by oxalyl chloride (5.0 mL, 2.0M in $CH_2Cl_2$, 10 mmol) slowly. After bubbling for a few minutes, the reaction was stirred at RT for 1.5 h, then concentrated in vacuo. The crude acid chloride was dissolved in $CH_2Cl_2$ (20 mL) and added dropwise to a suspension of 2,2,2-trifluoroethylamine hydrochloride (1.08 g, 8.02 mmol) and triethylamine (2.8 mL, 20 mmol) in $CH_2Cl_2$ (30 mL) at 0° C. under argon. The reaction was stirred at 0° C. for 10 min, diluted with $CH_2Cl_2$ (50 mL), washed with 1N HCl (2×20 mL) and saturated $NaHCO_3$ (20 mL), then dried over $Na_2SO_4$. Evaporation gave 2.24 g of a dark orange semi-solid, which was dissolved in 2:1 $CH_2Cl_2$:10% EtOAc/hexane and purified by flash chromatography on silica gel (175 g) eluting with 10% EtOAc/hexane to provide title compound (1.16 g, 22%) as a yellow solid (mp 109°–113° C.).

B.

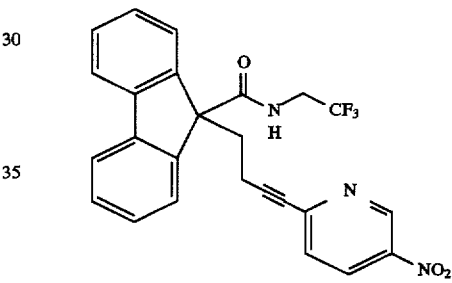

Copper (I) iodide (4 mg, 0.02 mmol) was added to a solution of Part A compound (343 mg, 1 mmol) and 2-bromo-5-nitropyridine (203 mg, 1 mmol) in a mixture of triethylamine (3 mL) and DMF (2 mL). The yellow solution was degassed with argon then cooled to 0° C. Bis(triphenylphosphine)palladium (II) chloride (14 mg, 0.02 mmol) was added and the reaction was stirred at 0° C. for 10 min then at RT for 6 h. The reaction was diluted with water (20 mL) and extracted with EtOAc (2×20 mL). The combined organic layers were washed with water (3×10 mL) then dried over $K_2CO_3$. Evaporation gave 520 mg of a brown foamy gum, which was purified by flash chromatography on silica gel (65 g) eluting with 20% EtOAc/hexane to provide title compound (342 mg, 74%) as a yellow foam.

C. 9-[4-[5-(Benzoylamino)-2-pyridinyl]butyl]-N-(2,2,2-trifluoroethyl)-9H-fluorene-9-carboxamide A mixture of Part B compound (334 mg, 0.718 mmol) and 10% palladium on carbon (38 mg, 0.036 mmol) in EtOAc (2 mL) was hydrogenated (balloon) at RT for 6 h, filtered through Celite with the aid of EtOAc (30 mL), then concentrated in vacuo to give 292 mg of the aminopyridine as a brown gum.

A portion of amine (262 mg, 0.597 mmol) was dissolved in $CH_2Cl_2$ (3 mL), cooled to 0° C. under argon, then treated sequentially with triethylamine (125 μL, 0.896 mmol) and benzoyl chloride (77 μL, 0.658 mmol) dropwise. The reaction was stirred at 0° C. for 1 h, diluted with $CH_2Cl_2$ (5 mL), washed with saturated NaHCO₃ (2×1 mL) and brine (1 mL), then dried over Na₂SO₄. Evaporation gave 360 mg of a green foam, which was purified by flash chromatography on silica gel (50 g) eluting with 50% EtOAc/hexane to give 192 mg of impure product as a yellow glassy foam. The product was further purified by recrystallization from EtOAc/hexane. The first two crops were combined and dried in a vacuum oven at 50° C. overnight to afford title compound (90 mg, 21%) as an off-white solid.

mp 166°–169° C. MS (ES): 544 [M+H]. Anal. Calcd. for C₃₂H₂₈F₃N₃O₂ . 0.3 H₂O: C, 70.01; H, 5.25; N, 7.65 Found: C, 70.06; H, 4.98; N, 7.33.

EXAMPLE 275

9-[4-[4-[(2-Phenoxybenzoyl)amino]-1H-imidazol-1-yl]-butyl]-N-(2,2,2-trifluoroethyl)-9H-fluorene-9-carboxamide

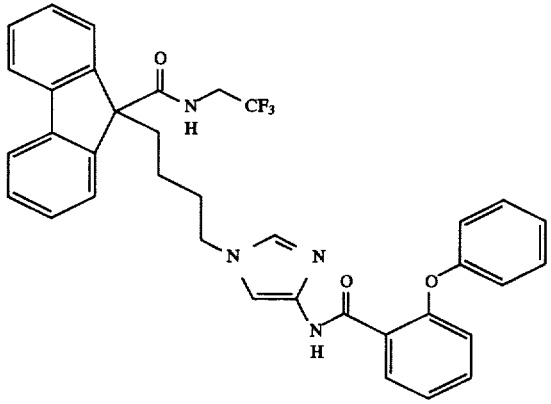

A. 2-Phenoxybenzoic Acid Chloride

To a solution of 2-phenoxybenzoic acid (500 mg, 2.33 mmol) and DMF (1 drop) in CH₂Cl₂ (10 mL) under argon was added oxalyl chloride (1.3 mL, 2.0M in CH₂Cl₂, 2.6 mmol) dropwise. Bubbling of escaping gasses continued for 5 min after addition. The reaction was stirred at room temperature for 1 h, then concentrated in vacuo to give the title compound as a crude pale yellow oil.

B. 9-[4-[4-[(2-Phenoxybenzoyl)amino]-1H-imidazol-1-yl]butyl]-N-(2,2,2-trifluoroethyl)-9H-fluorene-9-carboxamide Palladium on carbon (10%) (74 mg, 0.07 mmol) was added to a solution of Example 273 Part B compound (640 mg, 1.4 mmol) in dry EtOAc (5 mL), and the mixture was hydrogenated (balloon) at RT overnight. The reaction was degassed with argon, cooled to 0° C., and triethylamine (290 µL, 2.10 mmol) was added. A solution of Part A acid chloride in CH₂Cl₂ (2 mL) was added dropwise over 5 min. The resulting thick reaction was stirred at 0° C. for 30 min and filtered through Celite. The filter cake was rinsed with CH₂Cl₂ (3×20 mL). The filtrate was washed with saturated NaHCO₃ (10 mL) and brine (10 mL), then dried over MgSO₄. Evaporation gave 1.0 g of a dark brown foam, which was purified by flash chromatography on silica gel (75 g) eluting with 2% MeOH/CH₂Cl₂ to provide title compound (670 mg, 77%) as a yellow foam.

MS (ES): 625 [M+H]. Anal. Calcd. for C₃₆H₃₁F₃N₄O₃: C, 69.22; H, 5.00; N, 8.97; F, 9.12 Found: C, 68.84; H, 4.90; N, 8.80; F, 8.80.

EXAMPLE 276

9-[4-[(2-Bromo-5-pyridinyl)amino]butyl]-N-propyl-9H-fluorene-9-carboxamide

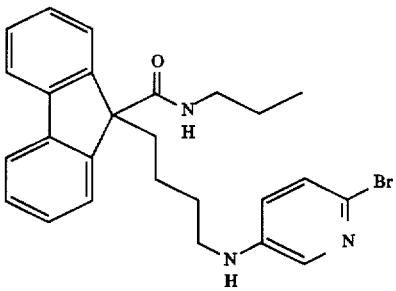

A.

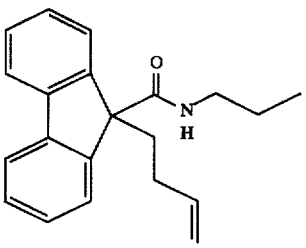

The title compound was prepared from 9-fluorenecarboxylic acid (4.2 g, 20 mmol) and 4-bromo-1-butene (2.2 mL, 22 mmol) according to the procedure for Part A compound in Example 274 to give title compound (5.1 g, 84%) as a white solid (mp 67°–69° C.).

B. 9-[4-[(2-Bromo-5-pyridinyl)amino]butyl]-N-propyl-9H-fluorene-9-carboxamide

A solution of Part A compound (500 mg, 1.64 mmol) in THF (2 mL) was added to a solution of 9-borabicyclo[3.3.1]nonane (3.3 mL, 0.5M in THF, 1.64 mmol) at 0° C. under argon. The clear, colorless reaction was stirred at RT for 5 h, then diluted further with dioxane (10 mL). Anhydrous potassium phosphate anhydrous (316 mg, 1.49 mmol) was added, followed by tetrakis(triphenylphosphine)palladium (52 mg, 0.045 mmol). 2-Bromo-5-nitropyridine (302 mg, 1.49 mmol) was added and the reaction was stirred at 60° C. overnight, then cooled to RT. Water (30 mL) was added and the reaction was stirred vigorously in the air for 2 h. The reaction mixture was extracted with EtOAc (100 mL, then 20 mL), and the combined organic layers were washed with brine (2×20 mL), then dried over MgSO₄. Evaporation gave 1.2 g of a brown oil, which was dissolved in a minimum amount of CH₂Cl₂ and purified by flash chromatography on silica gel (75 g) eluting with 40% EtOAc/hexane to provide 200 mg of impure product as a yellow foam. Additional chromatography eluting with 50% EtOAc/hexane gave title compound (147 mg, 19%) as a yellow solid.

mp 139°–141° C. MS (ES): 478/480 [M+H]. Anal. Calcd. for C₂₆H₂₈BrN₃O . 0.3 H₂O: C, 64.54; H, 5.96; N, 8.68 Found: C, 64.61; H, 5.88; N, 8.66.

EXAMPLES 277 to 286

The following additional compounds were prepared following procedures set out hereinbefore.

EXAMPLE 277

9-[2-[[[4-(Benzoylamino)phenyl]sulfonyl]amino]ethyl]-N-(2,2,2-trifluoroethyl)-9H-fluorene-9-carboxamide mp 235°–236° C. MS (ES) 594 (M+H); 1187 (2M+H) Anal. Calc'd for C₃₁H₂₆F₃N₃O₄S: C, 62.72; H, 4.41; N, 7.08; F, 9.60; S, 5.40 Found: C, 62.56; H, 4.45; N, 7.00; F, 9.54; S, 5.21.

EXAMPLE 278

9-(4-Phenylbutyl)-N-propyl-9H-fluorene-9-carboxamide mp 88°–90° C. MS (CI) 384 (M+H) Anal. Calc'd for $C_{27}H_{29}NO$: C, 84.56; H, 7.62; N, 3.65 Found: C, 84.62; H, 7.66; N, 3.72.

EXAMPLE 279

3-[(9-Propyl-9H-fluoren-9-yl)sulfonyl]propanoic acid, methyl ester mp 74°–77° C. MS (FAB, + ions) m/z 376 (M+NH$_4$) m/z 359 (M+H) Anal. Calc'd for $C_{20}H_{22}O_4S.0.29\ H_2O$: C, 66.04; H, 6.26; N, 8.81 Found: C, 66.04; H, 6.11; N, 8.45.

EXAMPLE 280

9-[4-[(6-Ethoxy-2-benzothiazolyl)thio]butyl]-N-propyl-9H-fluorene-9-carboxamide

Mp 109°–111° C. MS (ES, + ions) m/z 517 (M+H) Anal. Calc'd for $C_{30}H_{32}N_2O_2S_2+0.40$ mol $H_2O$: C, 68.78; H, 6.31; N, 5.35; S, 12.24 Found: C, 68.56; H, 6.07; N, 5.57; S, 12.23.

EXAMPLE 281

9-[3-[(6-Ethoxy-2-benzothiazolyl)thio]propyl]-N-propyl-9H-fluorene-9-carboxamide mp 82°–85° C. MS (ES, + ions) m/z 503 (M+H) Anal. Calc'd for $C_{29}H_{30}N_2O_2S_2+0.56$ mol $H_2O$: C, 67.93; H, 6.12; N, 5.46; S, 12.50 Found: C, 68.03; H, 5.83; N, 5.36; S, 12.51.

EXAMPLE 282

(Z)-9-[4-(Diethoxyphosphinyl)-2-butenyl]-N-(2,2,2-trifluoroethyl)-9H-fluorene-9-carboxamide Mp 88°–91° C. MS (CI-NH$_3$, + ions) m/z 482 (M+H) Anal. Calc'd for $C_{24}H_{27}NO_4PF_3$: C, 59.87; H, 5.65; N, 2.91; P, 6.43; F, 11.84 Found: C, 59.52; H, 5.61; N, 2.89; P, 6.92; F, 11.94.

EXAMPLE 283

9-[4-(Diethoxyphosphinyl)butyl]-N-(2,2,2-trifluoroethyl)-9H-fluorene-9-carboxamide mp 87°–89° C. MS (FAB) m/z 484 (M+H) Anal. Calc'd for $C_{24}H_{29}NO_4PF_3+0.13$ mol $H_2O$: C, 59.33; H, 6.07; N, 2.88; P, 6.37; F, 11.73 Found: C, 59.09; H, 5.98; N, 2.95; P, 6.51; F, 11.92.

EXAMPLE 284

9-[4-(Dibutoxyphosphinyl)butyl]-N-(2,2,3,3,3-pentafluoropropyl)-9H-fluorene-9-carboxamide mp 56°–57° C. MS (ES, + ions) m/z 590 (M+H) Anal. Calc'd for $C_{29}H_{37}NO_4F_5P$: C, 59.08; H, 6.33; N, 2.38; P, 5.25; F, 16.11 Found: C, 58.80; H, 6.34; N, 2.26; P, 5.05; F, 15.90.

EXAMPLE 285

9-[4-(Dibutoxyphosphinyl)butyl]-N-propyl-9H-xanthene-9-carboxamide mp 64°–67° C. MS (ES, + ions) m/z 516 (M+H) Anal. Calc'd for $C_{29}H_{42}O_5NP$: C, 67.55; H, 8.21; N, 2.72; P, 6.01 Found: C, 67.25; H, 8.17; N, 2.68; P, 5.99.

EXAMPLE 286

9-[4-(Dibutoxyphosphinyl)butyl]-N-(2,2,3,3,4,4,4-heptafluorobutyl)-9H-fluorene-9-carboxamide MS (ES, + ions) m/z 657 (M+NH$_4$), 640 (M+H) Anal. Calc'd for $C_{30}H_{37}NF_7PO_4$: C, 56.34; H, 5.83; N, 2.19; F, 20.79; P, 4.84 Found: C, 56.03; H, 5.91; N, 2.15; F, 20.74; P, 4.77.

The following compounds of the invention may be prepared following the procedures described hereinbefore and in the working Examples.

TABLE

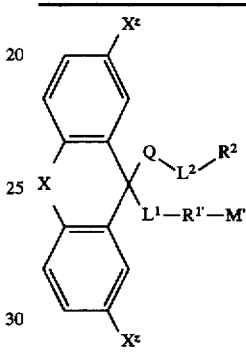

X is bond or O
X$^z$ is H or F
Q is CONH, CO or SO$_2$
L$^2$—R$^2$ CH$_2$CF$_3$, CH$_2$CF$_2$CF$_3$, propyl, butyl, —(CH$_2$)$_5$PO(Obutyl)$_2$
M' is benzamido, 2-phenoxybenzamido, 2-phenylbenzamido, cyclohexanecarboxamido, 2-methoxy-3-pyridinecarboxamido, benzenesulfonamido, phenylureido, t-butoxycarbonylamino, 2,3-dihydro-1-oxo-1H-isoindol-2-yl, 2,3-dihydro-1,3-dioxo-1H-isoindol-2-yl-(2-phthalimido)
INCLUDES: N-OXIDES OF ALL PYRIDINES Examples of —L$^1$—R$^1'$—

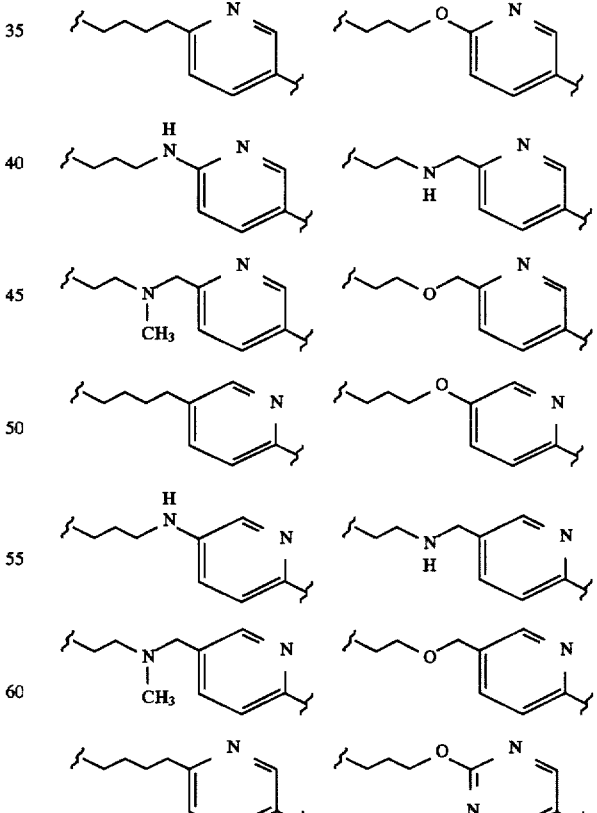

TABLE-continued
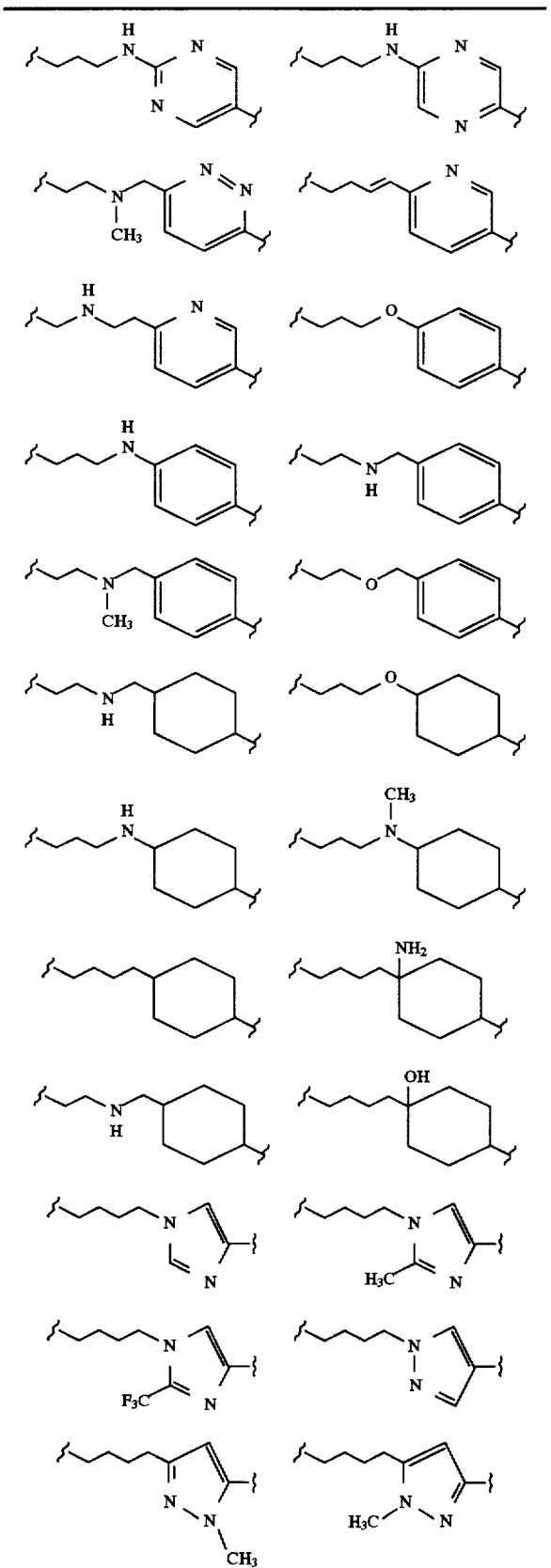
TABLE-continued
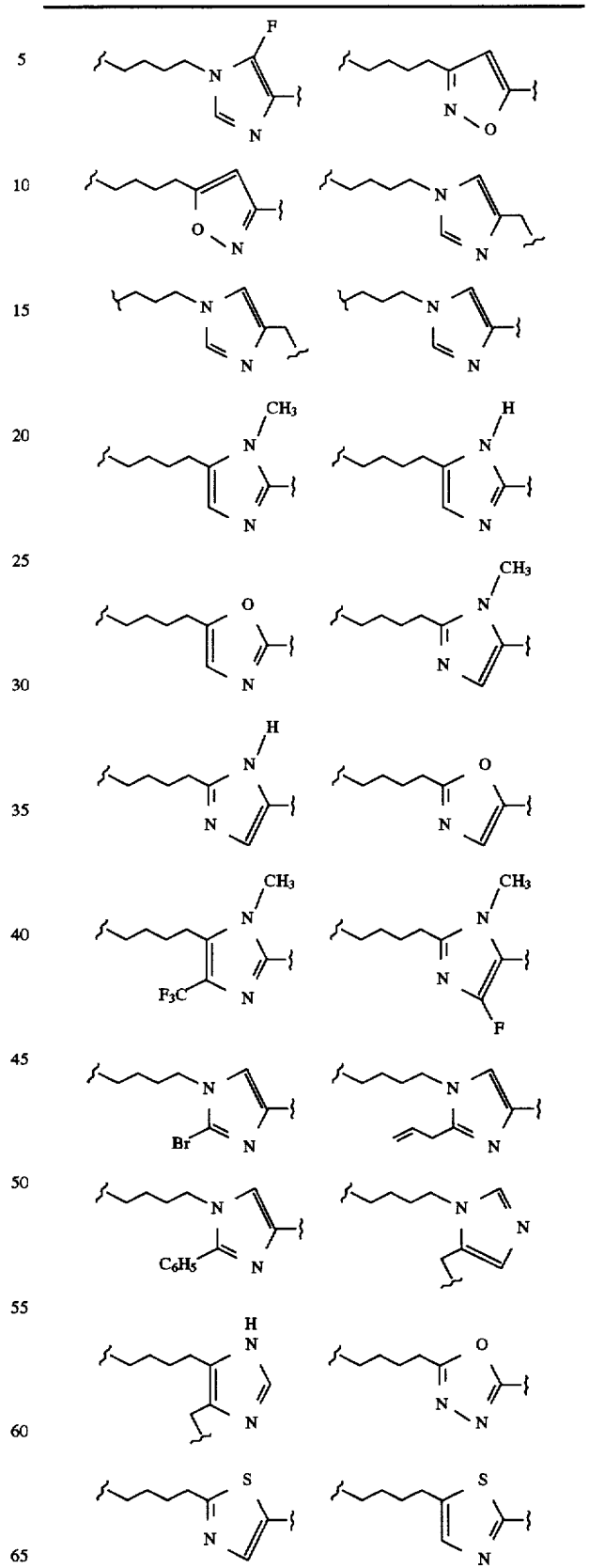

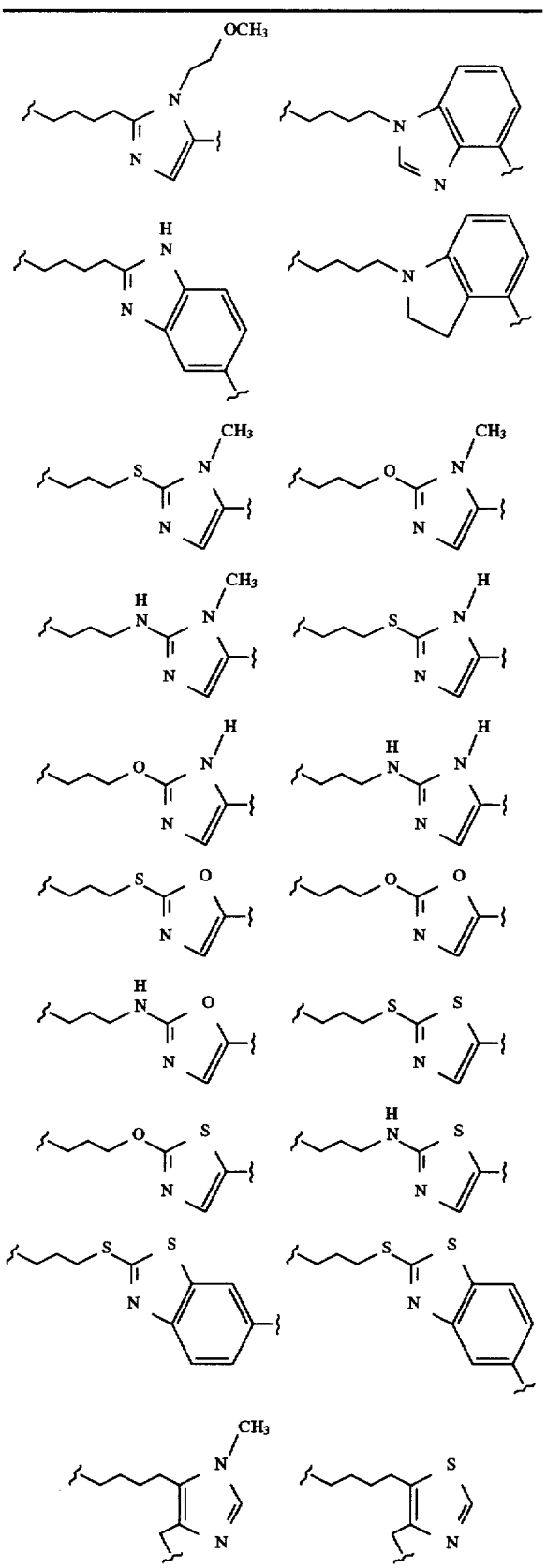
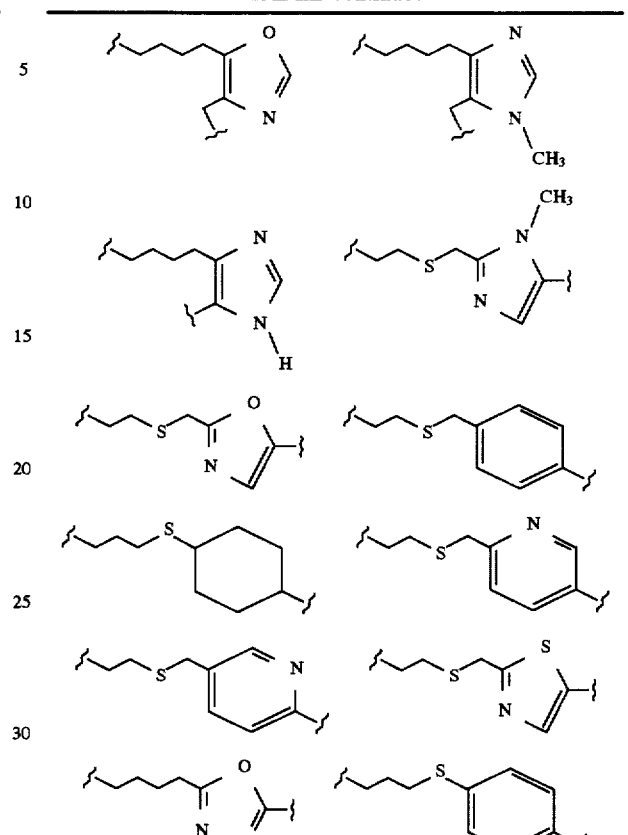
EXAMPLE 287
9-[4-(Dibutoxyphosphinyl)butyl]-N-propyl-9H-indeno-[2,1-b]pyridine-9-carboxamide
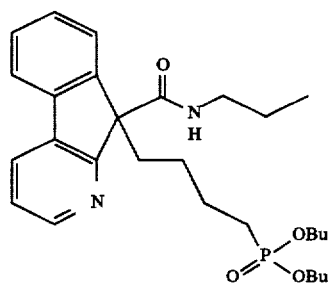
A.
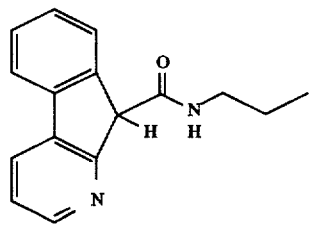
A THF (5 ml) solution of 1-aza-fluorene (233 mg, 1.39 mmol; prepared from benzo(f)quinoline by known procedures, Kloc, K. Journal f. prakt. Chemie, 319, 959–967

(1977) and Kloc. K. Heterocycles, 9, 849–852 (1978)) and n-propylisocyanate (0.13 ml, 1.39 mmol) was degassed three times by cooling to −78° C., evacuating, and allowing to warm to room temperature, and finally purging with argon. To the degassed solution at −10° C. was added dropwise sodium bis(trimethylsilyl)amide (1.4 ml, 1M in THF). After 5 min, a second portion of n-propylisocyanate (0.13 ml, 1.39 mmol) was added to the red solution. The now green colored reaction mixture was quenched after a further 15 min with saturated NH₄Cl. The aqueous layer was extracted with EtOAc, the organics washed with brine, dried over Na₂SO₄ and evaporated in vacuo to give a red colored oily-solid residue (535 mg). The residue was purified by flash column chromatography (SilicAR® buffered silica gel, 5 by 7 cm), eluting with 20% EtOAc:CH₂Cl₂, and flushing with 5% MeOH:CH₂Cl₂ to give title compound (202 mg, 58% yield) as an orange colored solid, mp 131°–133° C. MS: (FAB, M+H⁺): m/z 253⁺.

B. 9-[4-(Dibutoxyphosphinyl)butyl]-N-propyl-9H-indeno[2,1-b]pyridine-9-carboxamide To a THF (5 ml, degassed) suspension of Part A compound (250 mg, 0.990 mmol) at 0° C. under argon was added dropwise n-BuLi (0.8 ml, 2.5M in hexanes), with a red colored solid falling from solution after all the base was added. After 10 min, Example 202 Part A iodide (403 mg, 1.07 mmol) was added and the reaction stirred 1 h. Little reaction had occurred by TLC analysis, so a second portion of Example 202 Part A iodide (110 mg, 0.294 mmol) was added and the reaction mixture was stirred at room temperature for 3 h. The brown reaction mixture was quenched with sat. NH₄Cl and the aqueous layer was extracted twice with EtOAc. The combined organics were washed with brine, dried over Na₂SO₄, and concentrated to a brown colored oil (740 mg). The residue was purified by flash column chromatography (SilicAr CC-7, 74 g), eluting with 3.75% MeOH:CH₂Cl₂:0.2% NH₄OH to give impure title compound (386 mg) The residue was purified further by flash column chromatography (SilicAr CC-7, 60 g), eluting with 2.5% MeOH:EtOAc to give title compound (260 mg, 52% yield) as a colored oil. MS (electrospray, + ions) m/z 501 (M+H).

EXAMPLE 288

9-[4-[4-[(Phenylsulfonyl)amino]phenyl]butyl]-N-(2,2,2-trifluoroethyl)-9H-fluorene-9-carboxamide

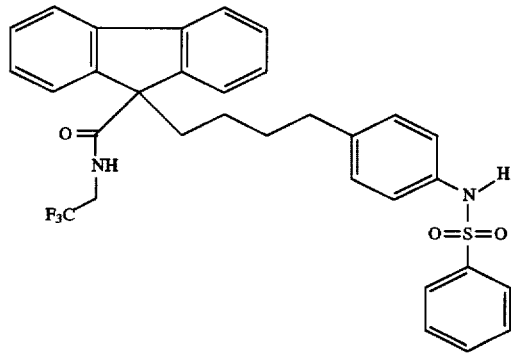

A.

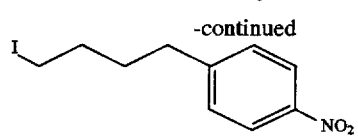

A solution of iodine (1.40 g, 5.5 mmol) in THF (5 mL) was added dropwise over 5 min to a solution of 4-(4-nitrophenyl)-1-butanol (975 mg, 5 mmol), triphenylphosphine (1.44 g, 5.5 mmol), and imidazole (749 mg, 11 mmol) in THF (10 mL) under argon at room temperature. The dark orange solution was stirred at room temperature for 15 min, diluted with hexane (50 mL), then washed with 10% sodium bisulfite, saturated NaHCO₃, and brine (20 mL each). The organic layer was dried over MgSO₄ and filtered. To the filtrate was added silica gel (4 g) and the mixture was concentrated in vacuo to give a yellow powder, which was purified by flash chromatography on silica gel (120 g) eluting with 25% CH₂Cl₂/hexane to give title iodide (1.33 g, 87%) as a pale yellow crystalline solid (mp 44°–45° C.).

B.

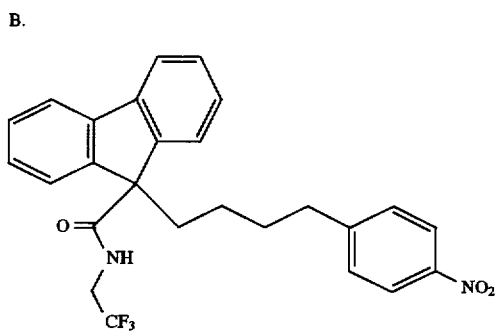

Butyllithium (2.0 mL, 2.5M in hexane, 5.0 mmol) was added to a solution of 9-fluorenecarboxylic acid (480 mg, 2.3 mmol) in THF (10 mL) at 0° C. under argon over 5 min. The reaction went from a clear solution to a white suspension then to a yellow solution during addition. The reaction was stirred at 0° C. for 20 min, whereupon a solution of Part A iodide (671 mg, 2.2 mmol) in THF (4 mL) was added dropwise over 5 min. The reaction was stirred at 0° C. for 1.5 h, warmed to room temperature, then stirred at room temperature for 3.5 h. The reaction was quenched with 1N HCl to pH≈3, diluted with water (10 mL), then extracted with EtOAc (2×20 mL). The combined organic layers were washed with water and brine (10 mL each), then dried over MgSO₄. Evaporation gave a residue, which was azeotroped with toluene (10 mL) to give crude acid in the form of a dark foam

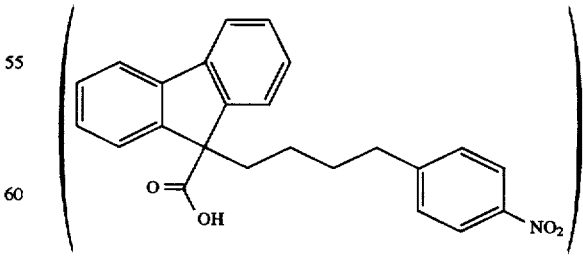

To a solution of the crude acid prepared above containing 3 drops of DMF in CH₂Cl₂ (6 mL) at room temperature under argon was added oxalyl chloride (3 mL, 2.0M in CH₂Cl₂, 6.0 mmol). The reaction was allowed to stir at room temperature for 1.5 h. The reaction was concentrated in vacuo to provide a dark oil, which was diluted with THF (5 mL) and cooled to 0° C. under argon. Trifluoroethylamine (0.63 g, 8 mmol) was added dropwise over 2 min, and the reaction was stirred at 0° C. for 3 h. The reaction was partitioned between EtOAc (30 mL) and water (10 mL). The organic layer was washed with 1N HCl (7 mL) and brine (5 mL), then dried over MgSO$_4$. Evaporation gave 974 mg of a brown oil, which was dissolved in CH$_2$Cl$_2$ and purified by flash chromatography on silica gel (75 g) eluting with 15:85 EtOAc/hexane to afford title compound (0.75 g, 69%) as a thick oil.

C. 9-[4-[4-[(Phenylsulfonyl)amino]phenyl]-butyl]-N-(2,2,2-trifluoroethyl)-9H-fluorene-9-carboxamide A mixture of Part B compound (220 mg, 0.47 mmol) and 10% palladium on carbon (20 mg) in EtOAc (15 mL) was hydrogenated (balloon pressure) at room temperature for 18 h, filtered through Celite with the aid of EtOAc, then concentrated in vacuo to give a residue, which was pumped under high vacuum to provide a thick oil.

Phenylsulfonyl chloride (80 mg, 0.46 mmol) was added to a solution of the crude amine (≈0.45 mmol) and pyridine (35 mg, 0.46 mmol) in CH$_2$Cl$_2$ (4 mL) at room temperature under argon. The reaction was stirred for 2 h, diluted with ethyl acetate (50 mL), washed with 1N HCl (10 mL) and water (10 mL), then dried over MgSO$_4$. Evaporation gave an oil, which was adsorbed onto silica gel (10 g), then purified by flash chromatography on silica gel (50 g) eluting with 30% EtOAc/hexane to give 0.23 g (88%) of title compound as a pink solid.

mp: 130°–132° C. Anal Calc'd for C$_{32}$H$_{29}$N$_2$SO$_3$F$_3$+0.2 CH$_2$Cl$_2$: C, 64.93; H, 4.98; N, 4.70; S, 5.38; F, 9.57 Found: C, 65.16; H, 5.08; N, 4.55; S, 5.52; F, 9.17.

EXAMPLE 289

[4-[9-(1-Oxopentyl)-9H-fluorene-9-yl]butyl] phosphonic acid, dibutyl ester

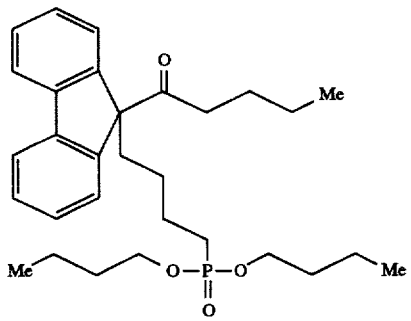

A.

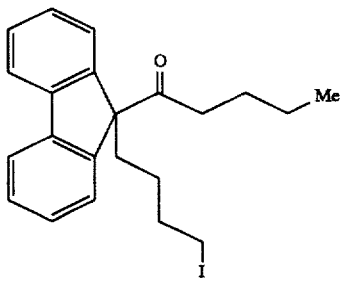

A(1).

-continued

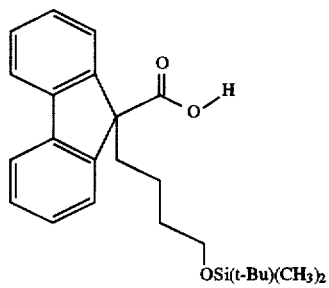

To a solution of 5 g (23.78 mmol) of 9-fluorenecarboxylic acid in 20 mL of THF, under argon at 0° C., was added 20.6 mL (52.32 mmol) of n-butyllithium (2.5M in hexanes) dropwise. The orange-red anion was stirred for 0.5 h, at which time 7.5 g (23.78 mmol) of

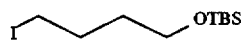

(where TBS is t-Bu(CH$_3$)$_2$.Si—)was added dropwise. The reaction gradually warmed to room temperature and was stirred for 36 h, at which time it was diluted with a 1:1 mixture of ethyl acetate/H$_2$O (250 mL). The organics were washed with NaHCO$_3$, brine, dried (Na$_2$SO$_4$) and evaporated. Flash chromatography was performed on 250 g of silica gel eluting with 9:1 dichloromethane/isopropanol to provide 4.9 g (52%) of title compound as a yellow oil.

TLC: Silica gel (9:1 dichloromethane/isopropanol) R$_f$=0.50.

A(2).

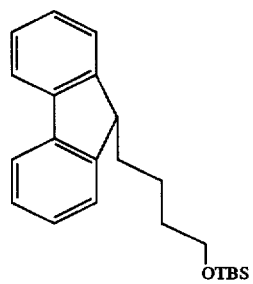

To 550 mg (1.38 mmol) of Part A(1) compound was added 5 mL of DMSO. The reaction was stirred for 18 h, under argon at room temperature, at which time it was diluted with ether and washed with water (3×). Flash chromatography was performed on 100 g of silica gel eluting with 95:5 hexanes/ethyl acetate to provide 340 mg (70%) of title compound as a pale yellow oil.

TLC: Silica gel (95:5 hexanes/ethylacetate) R$_f$=0.31.

A(3).

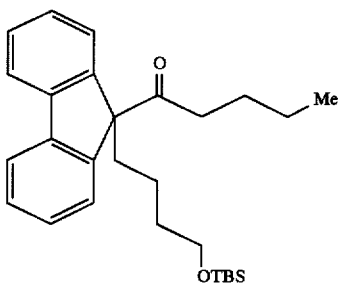

To a solution of 340 mg (0.96 mmol) of Part A(2) compound in 3 mL of THF, under argon at 0° C., was added dropwise 462 µL (1.16 mmol) of n-butyllithium (2.5M in hexanes). The resulting anion was stirred for 0.5 h, at which time 140 µL (1.16 mmol) of freshly distilled valeryl chloride (Aldrich) was added dropwise. The reaction was stirred for 2 h, at which time it was diluted with ether and quenched with NaHCO$_3$. The organics were washed with water, brine, dried (NaSO$_4$) and evaporated. Flash chromatography was performed on 100 g of silica gel eluting with 95:5 hexanes/dichloromethane to provide 290 mg (69%) of title compound as a pale yellow oil.

TLC: Silica gel (95:5 hexanes/ethyl acetate) R$_f$=0.36. MS (CI-NH$_3$, + ions) m/e 397 (M+H). Anal. Calcd. for C$_{24}$H$_{32}$O$_3$Si+0.15 mol H$_2$O. C, 72.20; H, 8.15 Found: C, 72.20; H, 7.88.

A(4).

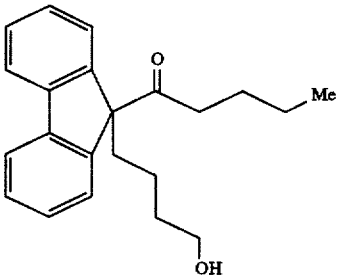

To 200 mg (0.46 mmol) of Part A(3) compound was added 1 mL of 5:95 aqueous HF/acetonitrile. The reaction was stirred, under argon at room temperature, for 3 h, at which time it was diluted with ether and washed with NaHCO$_3$, water (3×), brine, dried (MgSO$_4$) and evaporated. Flash chromatography was performed on 50 g of silica gel eluting with 7:3 hexanes/ethyl acetate to provide 120 mg (81%) of title compound as a pale yellow oil.

TLC: Silica gel (8:2 hexanes/ethyl acetate) R$_f$=0.15.

A(5).

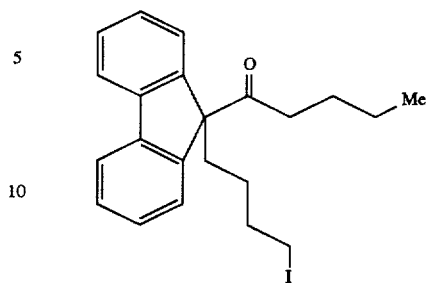

To a solution of 120 mg (0.37 mmol) of Part A(4) compound in 1.5 mL of THF, under argon at 0° C., was added 55 mg (0.81 mmol) of imidazole followed by 126 mg (0.48 mmol) of triphenylphosphine. The mixture was stirred for 0.5 h, at which time 122 mg (0.48 mmol) of iodine in 1 mL of THF was added dropwise. The reaction was stirred for 1 h at 0° C., 1 h at room temperature, then diluted with hexanes and washed with fresh sodium bisulfite solution, NaHCO$_3$, water, brine, dried (MgSO$_4$) and evaporated. Flash chromatography was performed on 25 g of silica gel eluting with 9:1 hexanes/ethyl acetate to provide 130 mg (81%) of title compound as a colorless oil.

TLC: Silica gel (9:1 hexanes/ethyl acetate) R$_f$=0.40.

B. [4-[9-(1-Oxopentyl)-9H-fluorene-9-yl]butyl] phosphonic acid, dibutyl ester

To 220 mg (0.51 mmol) of Part A iodide was added 688 µL (2.55 mmol) of tributylphosphite (neat). The mixture was heated to 120° C. for 32 h and bulb to bulb distilled (5 mm, 100° C.) to remove lower boiling impurities and provide 260 mg (87%) of title compound as a pale yellow oil.

MS (ES NH$_3$, + ions) m/e 516 (M+NH$_4$), 499 (M+H). Anal. Calcd for C$_{30}$H$_{43}$O$_4$P+0.24 mol CH$_2$Cl$_2$. C, 69.98; H, 8.44; P, 5.97 Found: C, 69.97; H, 8.41; P, 6.26.

EXAMPLE 290

9-[5-(Dibutoxyphosphinyl)pentyl]-N-(2,2,2-trifluoroethyl)-9H-fluorene-9-carboxamide

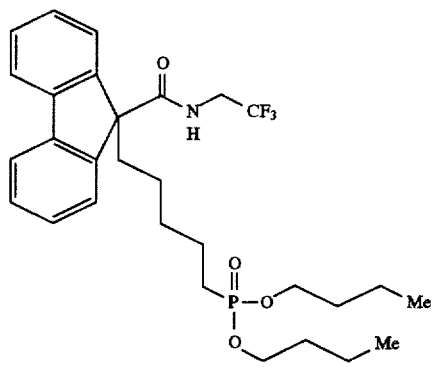

A.

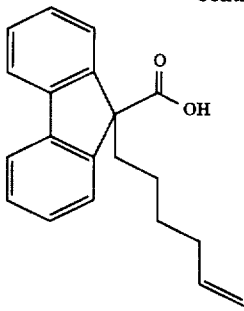

To a solution of 3.0 g (14.30 mmol) of 9-fluorenecarboxylic acid in 50 mL of THF, under argon at 0° C., was added dropwise 11.4 mL (28.60 mmol) of n-BuLi (2.5M in hexanes). The anion was stirred for 0.5 h at which time 2.3 mL (17.16 mmol) of 6-bromo-1-hexene was added dropwise. The reaction gradually warmed to room temperature and was stirred for 18 h, at which time it was diluted with a 1:1 mixture of ethyl acetate/water (200 mL). The organics were washed with NaHCO$_3$, water, brine, dried (Na$_2$SO$_4$) and evaporated. Flash chromatography was performed on 200 g of silica gel eluting with 95:5 dichloromethane/isopropanol to provide 900 mg (22%) of title compound as a pale yellow solid.

MS (CI-NH$_3$, + ions) m/z 310 (M+NH$_4$), 293 (M+H).

B.

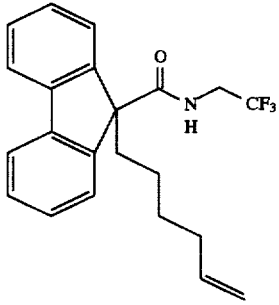

To a solution of 800 mg (2.74 mmol) of Part A compound in 10 mL of CH$_2$Cl$_2$, under argon at room temperature, was added dropwise two drops of DMF and 2.0 mL (4.11 mmol) of oxalyl chloride (2.0M in CH$_2$Cl$_2$). The reaction was stirred for 45 min. when it was evaporated to dryness.

In another flask, 446 mg (3.29 mmol) of 2,2,2-trifluoroethylamine in 10 mL of CH$_2$Cl$_2$, under argon at 0° C., was added 1.1 mL (8.22 mmol) of triethylamine. This slurry was stirred for 15 min at which time the above acid chloride, in 5 mL of CH$_2$Cl$_2$, was added dropwse. The reaction gradually warmed to room temperature and was stirred for 18 h, at which time it was diluted with ether and washed with water, 1N HCl, NaHCO$_3$, water, brine, dried (Na$_2$SO$_4$) and evaporated. Flash chromatography was performed on 100 g of silica gel eluting with 6:4 hexanes/ethyl acetate to provide 740 mg (74%) of title compound as a pale yellow solid.

MS (ES NH$_3$, − ions) m/z 372 (M−H).

C.

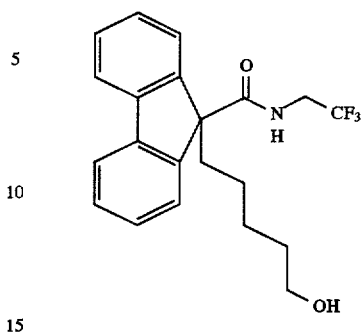

250 mg (0.67 mmol) of Part B compound in 2 mL of methanol, at −78° C., was treated with a stream of O$_2$/O$_3$ for 0.5 h, at which time the reaction was purged with N$_2$ and treated with 76 mg (2.0 mmol) of sodium borohydride pellets. The reaction gradually warmed to room temperature and was stirred for 18 h, at which time it was diluted with ether and washed with NH$_4$Cl, water, brine, dried (Na$_2$SO$_4$) and evaporated. Flash chromatography was performed on 100 g of silica gel eluting with 3:2 hexanes/ethyl acetate to provide 200 mg (79%) of title compound as a white solid.

MS (ES NH$_3$, −.ions) m/z 376 (M−H).

D.

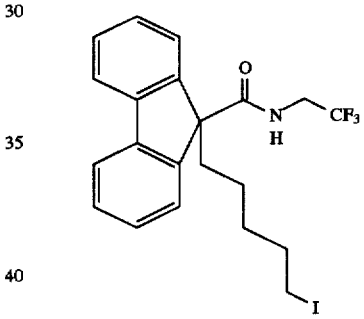

To a solution of 200 mg (0.53 mmol) of Part C compound in 3 mL of THF, under argon at 0° C., was added 76 mg (1.12 mmol) of imidazole followed by 180 mg (0.69 mmol) of triphenylphosphine. This mixture was stirred for 0.5 h at which time 175 mg (0.69 mmol) of iodine in 3 mL of THF was added dropwise. The reaction was stirred at 0° C. for 1 h, at room temperature for 1 h, then diluted with hexanes and washed with fresh sodium bisulfite solution. The organics were washed with NaHCO$_3$, water, brine, dried (Na$_2$SO$_4$) and evaporated. Flash chromatography was performed on 50 g of silica gel eluting with 9:1 hexanes/ethyl acetate to provide 200 mg (78%) of title compound as a white solid.

E. 9-[5-(Dibutoxyphosphinyl)pentyl]-N-(2,2,2-trifluoroethyl)-9H-fluorene-9-carboxamide To 200 mg (0.41 mmol) of Part D compound was added 555 μL (2.05 mmol) of tributylphosphite (neat). The mixture was heated to 120° C. for 18 h and bulb to bulb distilled (5 mm, 100° C.) to remove lower boiling impurities and provide 234 mg (98%) of title compound as a white solid.

mp 88°–91° C. MS (ES NH$_3$, + ions) m/z 571 (M+NH$_4$), 554 (M+H). Anal. Calcd. for C$_{29}$H$_{39}$NO$_4$PF$_3$+0.3 H$_2$O: C, 62.31; H, 7.14; N, 2.51; P, 5.54 Found: C, 62.35; H, 7.21; N, 2.38; P, 5.76.

EXAMPLE 291

9-[3-[[5-[(2-Phenoxybenzoyl)amino]-2-pyridinyl]oxy]-propyl]-N-(2,2,2-trifluoroethyl)-9H-fluorene-9-carboxamide, monohydrochloride

A.

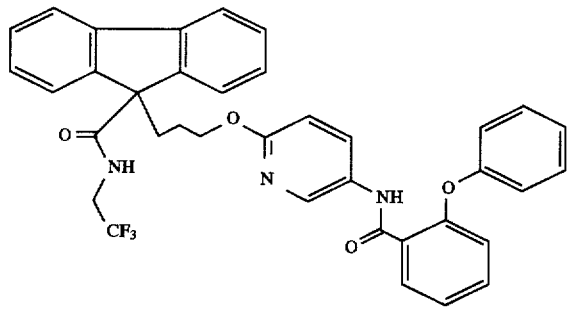

To a stirred solution of 12.6 g (60 mmol) of 9-fluorenecarboxylic acid in 600 mL of dry THF at 0° under argon was added, over 20 min, 53 mL of 2.5M n-butyllithium in hexane (132.5 mmol). The mixture was stirred for 30 min and then 7.3 mL (72 mmol) of 4-bromo-1-butene were added. The reaction was sirred at 0° C. for 10 min and then at room temperature for 2 days. Additional 4-bromo-1-butene (3.0 mL, 30 mmol) was added and stirring was continued for 2 days longer. Water (100 mL) was added and the mixture was concentrated to remove THF. Additional water was added and the mixture was extracted with ether (2×200 mL). The aqueous layer was layered with CH₂Cl₂ and acidified with 1N HCl (pH <2). After three extractions with CH₂Cl₂, the combined CH₂Cl₂ fraction was washed with water (2×), dried (MgSO₄), and concentrated to give 14.5 g (92%) of title compound as an amorphous pale yellow solid.

B.

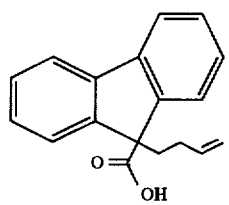

Part A compound (9.1 g, 34.5 mmol) was dried by concentration in vacuo from dry THF and dry toluene (2×) and then in vacuo overnight. To a solution of this acid in 100 mL of dry CH₂Cl₂ and 133 μL of DMF under nitrogen was slowly added 26 mL of 2.0M oxalyl chloride in CH₂Cl₂ (52 mmol). The reaction was stirred at room temperature for 1.5 h and then concentrated in vacuo and dried for 1 h at 0.5 mm to give the crude acid chloride of Part A compound. Triethylamine (14.5 mL, 104 mmol) was added to a stirred suspension of 2,2,2-trifluoroethylamine hydrochloride in 70 mL of dry CH₂Cl₂ at 0° C. under argon and the slurry was stirred at 0° C. for 10 min. A solution of the crude acid chloride of Part A compound in 35 mL of CH₂Cl₂ was added over 15 min keeping the internal temperature <12° C. The reaction was stirred at 0° C. for 1 h and then it was diluted with 175 mL of CH₂Cl₂. The CH₂Cl₂ was washed with 1N HCl (2×70 mL), water (175 mL), 5% NaHCO₃ (110 mL) and water (2×175 mL), dried (Na₂SO₄), and concentrated to give crude title compound as a solid (11.4 g). This solid was combined with an additional 6.54 g of crude title compound, and the combined crude title compound was chromatographed over 700 g of silica gel using CH₂Cl₂ to provide 15.5 g (82%) of title compound as a solid having mp 105°–107° C.

C.

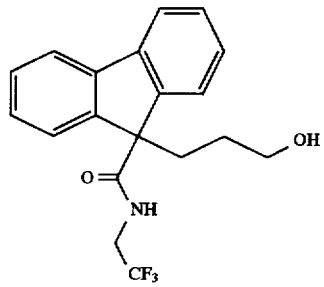

A solution of Part B compound (0.50 g, 1.44 mmol) in 20 mL of 1:1 dichloromethane/methanol at −78° C. was treated with a stream of O₂/O₃ until the solution turned light blue. The mixture was treated with NaBH₄ (1 pellet, 0.2 g, 5.26 mmol) and stirred for 18 h. The resulting colorless solution was diluted with 1:1 NH₄Cl solution/ethyl acetate (150 mL) and the layers separated. The organic fraction was dried (MgSO₄), filtered, and concentrated to give 0.44 g (89%) of title compound as a white solid.

mp 111°–114° C.

D.

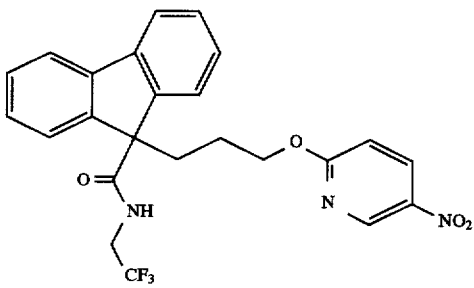

A solution of Part C compound (0.50 g, 1.43 mmol) in THF (7 mL) was treated with NaH (38 mg, 1.57 mmol) and stirred for 0.5 h. After all of the gray solid was consumed, 2-bromo-5-nitropyridine (0.32 g, 1.57 mmol) was added to the reaction mixture. The resulting dark orange solution was stirred at room temperature for 18 h, diluted with 1:1 water/ethyl acetate (150 mL) and the layers separated. The organic fraction was dried (MgSO₄), filtered, and concentrated. The remainder was purified by flash chromatography on silica gel (50 g) eluting with 1:4 ethyl acetate/hexane to give title compound (0.81 g, 99%) as a pale yellow yellow oil.

E. 9-[3-[[5-[(2-Phenoxybenzoyl)amino]-2-pyridinyl]oxy]propyl]-N-(2,2,2-trifluoroethyl)-9H-fluorene-9-carboxamide, monohydrochloride A mixture of Part D compound (0.78 g, 1.65 mmol) and 10% palladium on carbon (80 mg) in EtOAc (20 mL) was hydrogenated (balloon pressure) at room temperature for 18 h. 2-Phenoxybenzoyl chloride (0.46 g, 2.00 mmol) was added to the solution of the crude amine (≈1.65 mmol) and pyridine (0.14 g, 1.78 mmol). The reaction was stirred for 2 h, diluted with ethyl acetate (50 mL), washed with NaHCO₃ solution (20 mL), and dried over MgSO₄. Evaporation gave an oil, which was purified by flash chromatography on silica gel (75 g) eluting with 40% EtOAc/hexane to give 0.78 g (75%) of a white foam. The foam was diluted with ether and treated with 4N HCl in dioxane. A white solid formed which was collected by filtration. The solid was dried under vacuum (20 mm Hg) at room temperature for 18 h to give (0.70 g, 63%) of title compound (HCl salt) as a white solid.

mp 110°–115° C. MS (FAB, + ions) m/z 638 (M+H). Anal Calc'd for $C_{38}H_{30}N_3O_4+1.0\ H_2O+1.0\ HCl$: C, 64.21; H, 4.81; N, 6.07; F, 8.23 Found: C, 64.46; H, 4.88; N, 5.86; F, 8.13.

EXAMPLE 292

[6-[9-[[(2,2,2-Trifluoroethyl)amino]carbonyl]-9H-fluoren-9-yl]hexyl]phosphonic acid, dibutyl ester

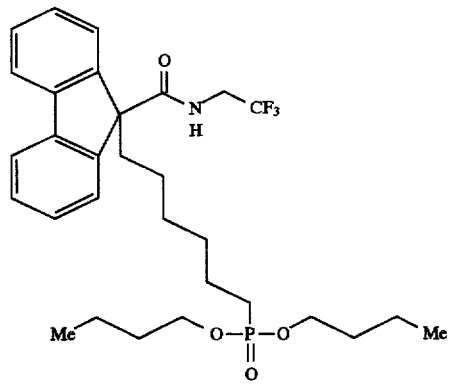

A.

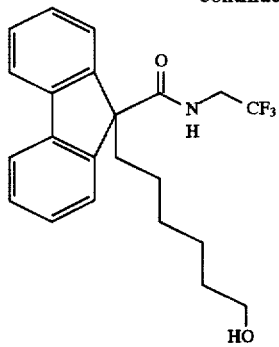

To 400 mg (1.07 mmol) of Example 290 Part B compound was added 3.7 mL (1.87 mmol) of 9-BBN (9-borabicyclo[3.3.1]nonane, 0.5M in THF). The reaction was stirred for 18 h, at which time it was cooled to 0° C. and treated dropwise with 1.25 mL (3.74 mmol) of 3N NaOH and 432 µL (3.74 mmol) of 30% H₂O₂ simultaneously. The biphasic mixture was stirred vigorously for 18 h, at which time it was extracted with ethyl acetate and the organic layer was washed with H₂O, brine, dried (Na₂SO₄) and evaporated. Flash chromatography was performed on 100 g of silica gel eluting with 1:1 hexanes/ethyl acetate to provide 320 mg (77%) of title compound as a white solid.

MS (ES NH₃, + ions) m/z 409 (M+NH₄).

B.

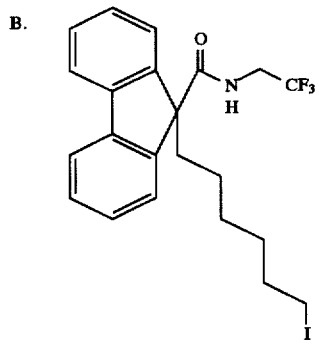

To a solution of 310 mg (0.793 mmol) of Part A compound in 5 mL of THF, under argon at 0° C., was added 118 mg (1.74 mmol) of imidazole followed by 270 mg (1.03 mmol) of triphenylphosphine. The mixture was stirred for 0.5 h at which time 262 mg (1.03 mmol) of iodine in 3 mL of THF was added dropwise. The reaction was stirred at 0° C. for 1 h, room temperature for 1 h then diluted with hexanes. The organics were washed with fresh sodium bisulfite solution, NaHCO₃, water, brine, dried (Na₂SO₄) and evaporated. Flash chromatography was performed on 25 g of silica gel eluting with 9:1 hexanes/ethyl acetate to provide 310 mg (78%) of title compound as a white solid.

C. [6-[9-[[(2,2,2-Trifluoroethyl)amino]-carbonyl]-9H-fluoren-9-yl]hexyl]phosphonic acid, dibutyl ester To 150 mg (0.30 mmol) of Part B compound was added 405 µL (1.50 mmol) of tributylphosphite (neat). The mixture was heated to 120° C. for 18 h and bulb to bulb distilled (5 mm, 100° C.) to remove lower boiling impurities and provide 165 mg (98%) of title compound as a pale yellow oil.

161

MS (ES NH₃, + ions) m/z 568 (M+H). Anal. Calcd. for C₃₀H₄₁NO₄PF₃+0.24 CH₂Cl₂: C, 61.77; H, 7.11; N, 2.38; P, 5.27; F, 9.69 Found: C, 61.80; H, 7.20; N, 2.36; P, 5.15; F, 9.60.

EXAMPLE 293

9-[4-[5-[(2-Phenoxybenzoyl)amino]-2-pyridinyl] butyl]-N-(2,2,2-trifluoroethyl)-9H-fluorene-9-carboxamide, monohydrochloride

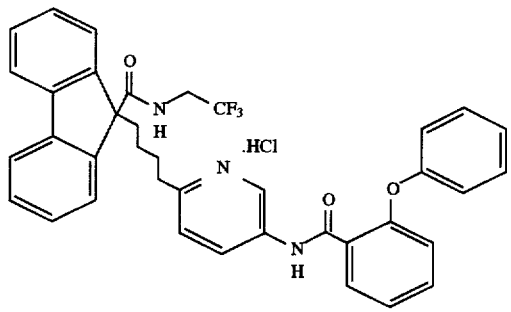

Following the procedure in Example 274 Part C, Example 274 Part B compound (1.02 g, 2.19 mmol) was reacted with Example 275 Part A compound (prepared from 563 mg (2.63 mmol) of 2-phenoxybenzoic acid) to provide 712 mg of product as the free amine.

A portion of the desired product (317 mg) was dissolved in MeOH (2 mL) and a solution of 1.1N HCl/Et₂O (0.9 mL, 1.0 mmol) was added. The solution was concentrated in vacuo and the residue was triturated with Et₂O to give a foamy solid, which was pumped under high vacuum overnight to afford title compound (302 mg, 47%) as a foamy beige solid.

MS (ES, + ions) m/z 636 (M+H) Anal. Calcd for C₃₈H₃₃Cl₃N₃O₃+0.5H₂O: C, 67.01; H, 5.03; N, 6.17; Cl, 5.20; F, 8.37 Found: C, 67.04; H, 5.02; N, 6.03; Cl, 5.55; F, 8.20.

162

EXAMPLE 294

9-[4-[4-(Benzoylamino)-2-methyl-1H-imidazol-1-yl]-butyl]-N-(2,2,2-trifluoroethyl)-9H-fluorene-9-carboxamide

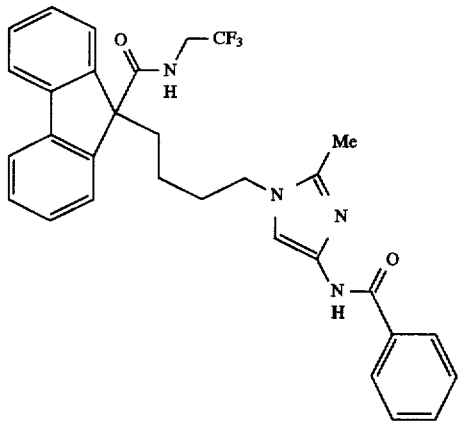

A.

To a solid mixture of Example 273 Part A(2) compound (1.00 g, 2.35 mmoL), 2-methyl-5-nitroimidazole (400 mg, 3.15 mmol), and K₂CO₃ (2.82 mmol) was added DMF (5 mL) and the mixture was stirred at room temperature for 3 days. The reaction was partitioned between EtOAc and saturated NaHCO₃ and the organic layer was washed successively with H₂O and brine. The solution was dried (Na₂SO₄), filtered, and stripped. The residue was triturated with Et₂O/EtOAc/hexane to give title compound (973 mg, 88%) as a white solid. mp 145°–147° C.

B. 9-[4-[4-(Benzoylamino)-2-methyl-1H-imidazol-1-yl]-butyl]-N-(2,2,2-trifluoroethyl)-9H-fluorene-9-carboxamide A solution of compound Part A (171 mg, 0.36 mmol) in dry 1,4-dioxane (3.9 mL) was hydrogenated (balloon) over 10% Pd/C (35 mg) at room temperature for 5 hours. Additional 10% Pd/C (40 mg) was added and stirring over H₂ was continued for an additional 16 hours. The reaction flask was evacuated and the atmosphere was replaced with air. To this slurry was added triethylamine (TEA) (200 μL, 145 mg, 1.4 mmol) followed by benzoyl chloride (100 μL). After one hour at room temperature, the mixture was filtered through Celite, diluted with EtOAc and subsequently washed with saturated NaHCO₃, H₂O, and brine, then dried (Na₂SO₄), filtered, and stripped to give a brown oil. The residue was partially purified by flash chromatography on silica gel (2/98-MeOH/CH₂Cl₂ as eluant). Further flash chromatographic separation (EtOAc as eluant) afforded title compound which was isolated as a light yellow solid foam by trituration and stripping from EtOAc/hexanes (88 mg, 45%).

Anal. Calc'd for $C_{31}H_{29}F_3N_4O_2 \cdot 0.2H_2O + 0.2C_6H_{14}$: C, 68.16; H, 5.72; N, 9.87; F, 10.04 Found: C, 68.02; H, 5.76; N, 9.61; F, 9.65.

EXAMPLE 295

9-[4-[4-[(2-Phenoxybenzoyl)amino]-2-methyl-1H-imidazol-1-yl]butyl]-N-(2,2,2-trifluoroethyl)-9H-fluorene-9-carboxamide, monohydrochloride

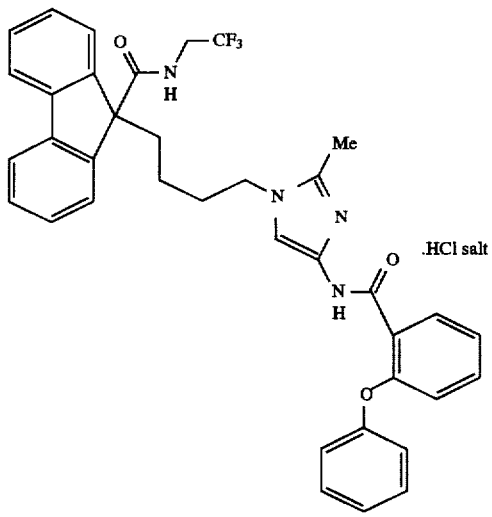

A. and B.

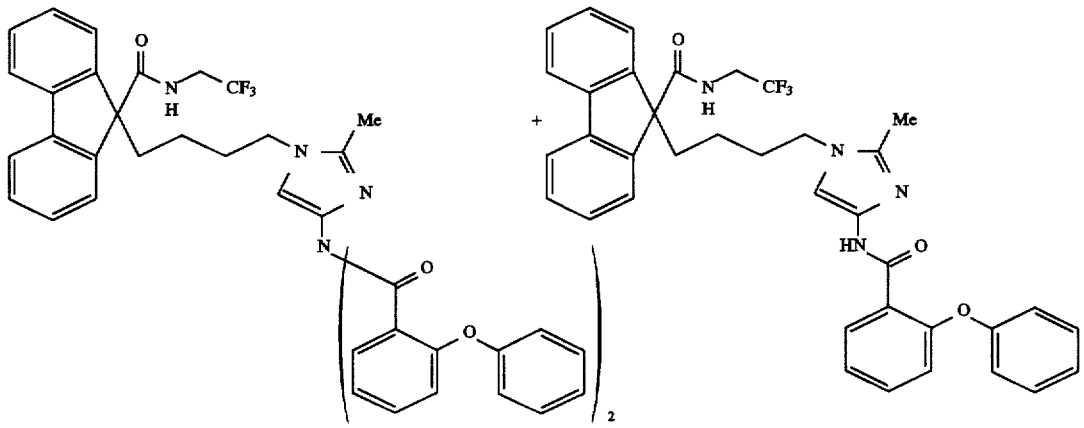

A solution of Example 294 Part A compound (350 mg, 0.65 mmol) in dry 1,4-dioxane (7 mL) was hydrogenated (balloon) over 10% Pd/C (126 mg) at room temperature for 28 hours. The reaction flask was evacuated and the atmosphere was replaced with air. To this slurry was added triethylamine (TEA) (300 μL, 218 mg, 2.15 mmol) followed by 2-phenoxybenzoic acid chloride (320 mg, 1.37 mmol) in dry THF (2 mL). After 1.5 hours at room temperature, the mixture was filtered through Celite, diluted with EtOAc and subsequently washed with saturated NaHCO₃, H₂O, and brine, then dried (Na₂SO₄), filtered, and stripped to give a brown oil. The residue was purified by flash chromatography on Merck SiO₂ (1:1-acetone:hexanes as eluant) to give a R_f 0.36 (1:1-acetone:hexanes) as a light brown foam (≈400 mg).

The mixture was separated by preparative HPLC (YMC-Pack ODS-A, 250×30 mm column, eluted with B:A solvent mixture, 50 to 100% B over a 20 minute linear gradient followed by 100% B (solvent A: 90% H₂O—10% MeOH—0.1% trifluoroacetic acid (TFA); solvent B: 10% H₂O—90% MeOH—0.1% TFA); flow rate 25 mL/min detecting at 254 nm). The desired fractions were stripped and the residues were partitioned between EtOAc and saturated NaHCO₃. The organic extracts were washed with brine, dried (Na₂SO₄), filtered and stripped to afford Part A compound (182 mg) and Part B compound (87 mg) as foams.

C. 9-[4-[4-[(2-Phenoxybenzoyl)amino]-2-methyl-1H-imidazol-1-yl]butyl]-N-(2,2,2-trifluoroethyl)-9H-fluorene-9-carboxamide, monohydrochloride Part A compound (≈180 mg) was dissolved in MeOH (6 mL) and treated with K₂CO₃ (62 mg). HPLC analysis after 5 hours indicated that all of Part A compound was converted to Part B compound and 2-phenoxybenzoic acid methyl ester. The mixture was partitioned between EtOAc and H₂O. The organic layer was washed with H₂O and brine, then dried (Na₂SO₄), filtered and stripped. The residue was combined with Part B compound from above and flash chromatographed (SiO₂, 7/3-EtOAc/hexanes as eluant) to afford pure Part B compound as a pale yellow foam (210 mg, 51% from Example 294 Part A compound).

The foam was dissolved in THF (400 μL), diluted with Et₂O (5 mL) and treated with 140 μL of 4N HCl in 1,4-dioxane. The resulting precipitate was collected by filtration and dried in vacuo to afford title compound as a white solid (212 mg, 48% from Example 294 Part A compound).

mp 200°–202° C. MS (ESI, + ions) m/z 639 (M+H)⁺; (ESI, − ions) m/z 637 (M−H)⁻.

EXAMPLE 296

9-[3-[[2-(Benzoylamino)-5-pyridinyl]amino]propyl]-N-(2,2,2-trifluoroethyl)-9H-fluorene-9-carboxamide, monohydrochloride

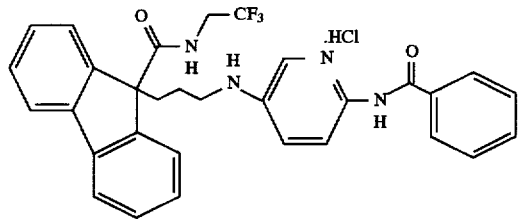

contains 0.3 mole water, 0.1 mole ethyl acetate, and 0.3 mole ethyl ether

A. 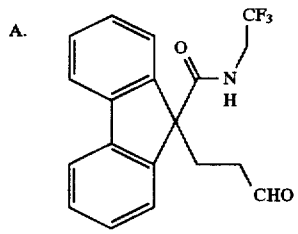

Ozone (Welsbach generator) was bubbled through a stirred solution of 2.07 g (6 mmol) of Example 291 Part B compound in 25 mL of dry MeOH at −65° C. for 45 min. Nitrogen was bubbled through the solution for 10 min, 5 mL of dimethyl sulfide was added, and the reaction was warmed to room temperature. The solvent was removed and the residue was taken up in EtOAc. The EtOAc was washed with water (3×), dried (Na₂SO₄) and concentrated to an oil (2.21 g). Chromatography of the oil over 150 g of silica gel packed in 1% EtOAc in CH₂Cl₂, by elution with 2% EtOAc in CH₂Cl₂, afforded 1.11 g (53%) of title compound as an oily residue.

B. 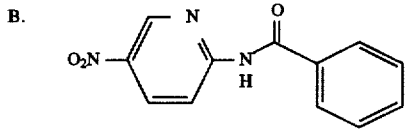

Benzoyl chloride (8.2 mL, 70 mmol) was added to a stirred suspension of 7.5 g (54 mmol) of

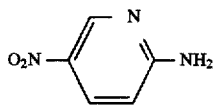

and 13 mL (160 mmol) of dry pyridine in 50 mL of dry THF and the mixture was stirred for 20 h at room temperature. The reaction was filtered and the filtrate was concentrated to a gummy residue, which was slurried with CH₂Cl₂, water, and 10% aq. NaHCO₃ to give crystals. The crystals were collected by filtration, washed with CH₂Cl₂, and dried to give 7.44 g pale yellow crystals, which were recrystallized from hot 95% EtOH to give 7.18 g of pale yellow crystalline title compound (55%) having mp 169°–170° C.

C. 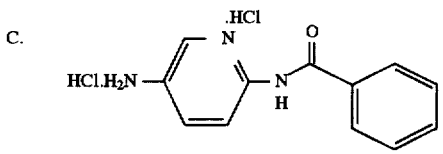

Part B compound (2.92 g, 12 mmol) was hydrogenated with 360 mg of 10% Pd/C in 50 mL of AcOH at 1 atmosphere for 1.5 h. Concentrated HCl (2.1 mL, 24.5 mmol) was added and the solids were collected by filtration. Trituration of the wet moist solid with EtOH and then filtration through a 45μ nylon filter gave a filtrate, which was concentrated to a 25 mL yellow slurry. Et₂O (150 mL) was added and the solids were collected, washed with Et₂O, and dried for 2 h to give 2.77 g (81%) of title compound as a solid.

D. 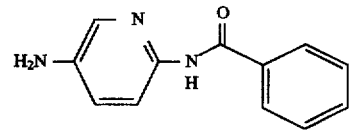

Part C compound (286 mg, 1 mmol) was dissolved in water and layered with CH₂Cl₂. Aqueous 5% NaHCO₃ was added and after extracting, the CH₂Cl₂ layer was washed with 5% NaHCO₃ and then water (2×), dried (Na₂SO₄), and concentrated to give 189 mg (89%) of title compound as an amorphous pale yellow solid.

E.

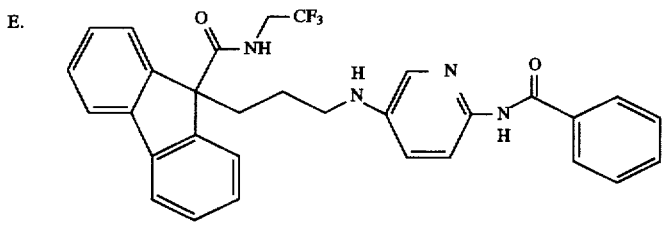

Acetic acid (0.29 mL, 5.1 mmol) was added to a stirred suspension of 180 mg (0.85 mmol) of Part D compound and 297 mg (0.85 mmol) of Part A compound in 5 mL of 1,2-dichloroethane. After 5 min, NaBH(OAc)₃ (540 mg, 2.55 mmol) was added to the clear solution and the reaction was stirred for 16 h at room temperature. The reaction was diluted with CH₂Cl₂ and 5% NaHCO₃ and the layers were separated. The CH₂Cl₂ was washed with 5% NaHCO₃ and water (2×), dried (Na₂SO₄), and concentrated to a foam (479 mg). Chromatography of this foam over a column of silica gel (40 g) packed in CH₂Cl₂, by eluting with CH₂Cl₂-MeOH (97:3), gave 429 mg of impure title compound. Chromatography of the 429 mg sample over 40 g of silica gel using CH₂Cl₂-EtOAc (8:2) gave 246 mg (53%) of title compound as a gummy residue.

F. 9-[3-[[2-(Benzoylamino)-5-pyridinyl]-amino]propyl]-N-(2,2,2-trifluoroethyl)-9H-fluorene-9-carboxamide, monohydrochloride To a solution of Part E compound (243 mg, 0.446 mmol) in 3 mL of dry THF was added 0.4 mL of 4N HCl in dioxane (1.6 mmol). Ether was added to the clear solution and the precipitate was collected, washed with Et₂O, and dried at 40° C./0.5 mm for 4 h to give 225 mg (82%) title compound as a pale yellow solid having mp 120°–126° C.

MS (ESI-NH₃, + ions) 545 (M+H); (− ions) 543 (M−H). Anal. Calcd for C₃₁H₂₇F₃N₄O₂+HCl+0.3 H₂O+0.1 EtOAc+ 0.3 Et₂O: C, 63.41; H, 5.29; N, 9.07; Cl, 5.74; F, 9.23 Found: C, 63.40; H, 5.25; N, 8.88; Cl, 5.60; F, 9.10.

EXAMPLE 297

[[4-(Benzoylamino)phenyl]methyl][2-[9-[[(2,2,2-trifluoroethyl)amino]carbonyl]-9H-fluoren-9-yl]ethyl]-carbamic acid, 1,1-dimethylethyl ester

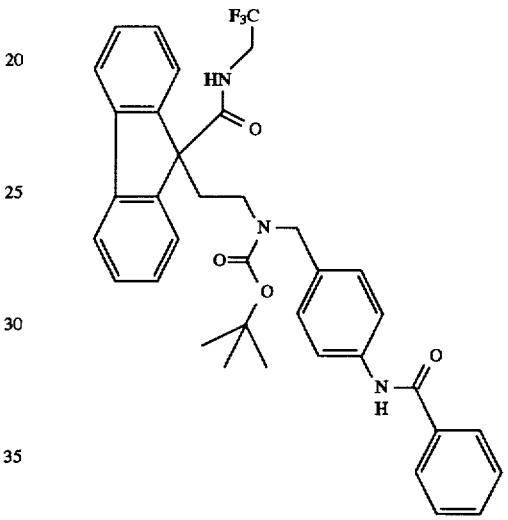

A.

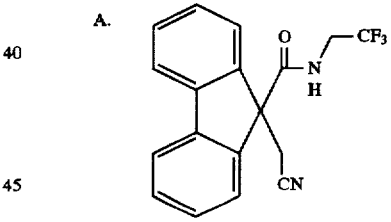

Butyllithium (18 mL, 2.5M in hexanes, 44 mmol) was added dropwise over 10 min to a solution of 9-fluorenecarboxylic acid (4.2 g, 20 mmol) in THF (200 mL) at 0° C. under argon. The slightly heterogeneous dark yellow reaction was stirred at 0° C. for 30 min, then chloroacetonitrile (1.5 mL, 24 mmol) was added dropwise over 3 min. The orange reaction was stirred at 0° C. for 30 min, warmed to room temperature and stirred for 3 h. The reaction was extracted with water (2×100 mL) and the combined aqueous extracts were washed with Et₂O (100 mL). The aqueous layer was acidified to pH<2 with 1N HCl and extracted with CH₂Cl₂ (3×50 mL). The combined organic extracts were dried over MgSO₄, filtered, and concentrated in vacuo to give 4.7 g of a light yellow solid (mp 138°–145° C.).

A portion (2.63 g) of the crude carboxylic acid was dissolved in CH₂Cl₂ (30 mL) under argon. N,N-Dimethylformamide (40 μL, 0.53 mmol) was added followed by oxalyl chloride (8.0 mL, 2.0M in CH₂Cl₂, 15.9 mmol). The reaction bubbled for a few minutes and was allowed to stir at room temperature for 1.5 h. The reaction was concentrated in vacuo then pumped under high vacuum to give the crude acid chloride. Triethylamine (4.4 mL, 31.8 mmol) was added to a suspension of 2,2,2-trifluoroethylamine hydrochloride (1.71 g, 12.7 mmol) in CH$_2$Cl$_2$ (20 mL) at 0° C. under argon. The resulting thick slurry was stirred at 0° C. for 5 min, then a solution of the crude acid chloride in CH$_2$Cl$_2$ (10 mL) was added dropwise over 5 min. The reaction was stirred at 0° C. for 10 min, diluted with CH$_2$Cl$_2$ (50 mL), washed with 1N HCl (2×20 mL) and saturated NaHCO$_3$ (30 mL), then dried over Na$_2$SO$_4$. Evaporation gave 3.5 g of a yellow foam which was purified by flash chromatography on silica (150 g) eluting with CH$_2$Cl$_2$ to give title compound (2.74 g, 76%) as a white solid (mp 159–159.5).

B.

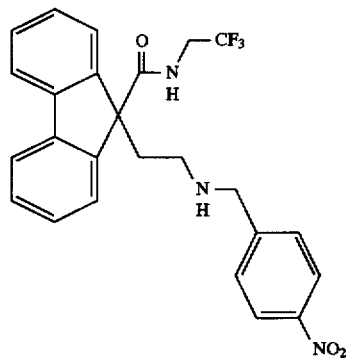

To a solution of Part A compound (2.7 g, 8.2 mmol) in methanol (30 ml) and chloroform (1.3 ml, 16 mmol) was added platinum oxide (186 mg, 0.82 mmol). The reaction mixture was hydrogenated (balloon) for 3.5 days, filtered through Celite and concentrated in vacuo to give 3.13 g of the crude amine hydrochloride.

4-Nitrobenzyl bromide (1.57 g, 7.3 mmol) was added to a stirred solution of the crude amine hydrochloride (2.7 g, 7.3 mmol) and triethylamine (1.0 ml, 7.3 mmol) in THF (15 ml) at 0° C. The reaction stirred under argon in a melting ice bath overnight. Reaction mixture partitioned between ethyl acetate and saturated sodium bicarbonate solution. Aqueous layer extracted one time with ethyl acetate. The combined organic layers were dried (Na$_2$SO$_4$), and the solvent removed in vacuo to give a yellow oil which was purified by flash chromatography (SiO$_2$, 400 g) packed and run with 30% EtOAc in methylene chloride to give title compound as a clear oil (940 mg, 27.5% yield).

C.

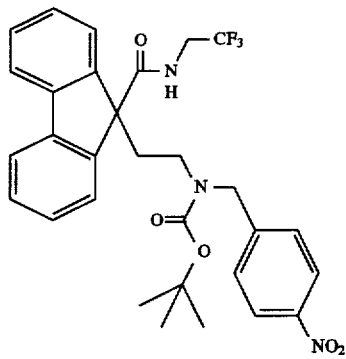

To the yellow solution of Part B compound (900 mg, 1.9 mmol) and 4-dimethylaminopyridine (280 mg, 2.3 mmol) in methylene chloride (10 ml) was added di-tert-butyldicarbonate (500 mg, 2.3 mmol) and the reaction stirred under argon at room temperature 1.5 h. More di-tert-butyldicarbonate (85 mg, 0.46 mmol) was added and the reaction stirred 1 h. The reaction was partitioned between methylene chloride and brine.

The organic layer was dried (Na$_2$SO$_4$) and the solvent removed in vacuo to give a yellow oil which was purified by flash chromatography (SiO$_2$, 100 g) packed and run with 5% EtOAc in methylene chloride to give title compound as a solid white foam (944 mg, 86.6% yield).

D. [[4-(Benzoylamino)phenyl]methyl][2-[9-[[(2,2,2-trifluoroethyl)amino]carbonyl]-9H-fluoren-9-yl]ethyl]carbamic acid, 1,1-dimethylethyl ester 10% Palladium on carbon (200 mg, catalyst) was added to a solution of Part C compound (860 mg, 1.5 mmol) in EtOAc (10 ml) and the mixture hydrogenated (balloon) for 2 h. The reaction was filtered through Celite and the Celite rinsed with EtOAc. A portion of the resulting amine solution (32 ml) was used in the next reaction.

To the amine solution (15 ml, ~0.71 mmol) cooled to −5° C. was added triethylamine (99 μl, 0.71 mmol) followed by benzoyl chloride (82 μl, 0.71 mmol). The reaction was stirred at −5° C. under argon for 2 h. The reaction mixture was partitioned between ethyl acetate and water. The organic layer was dried (Na$_2$SO$_4$) and the solvent removed in vacuo to give a clear oil which was purified by flash chromatography (SiO$_2$, 50 g) packed and run with 30% EtOAc in hexanes to give title compound as a solid white foam (369 mg, 80.9% yield).

mp 96°–98° C. MS (ESI, + ions) m/z 644 (M+H). Anal. calc'd for C$_{37}$H$_{36}$F$_3$N$_3$O$_4$: C, 69.04; H, 5.64; N, 6.53 Found: C, 68.94; H, 5.65; N, 6.27.

EXAMPLE 298

9-[2-[[[4-(Benzoylamino)phenyl]methyl]amino]ethyl]-N-(2,2,2-trifluoroethyl)-9H-fluorene-9-carboxamide, monohydrochloride

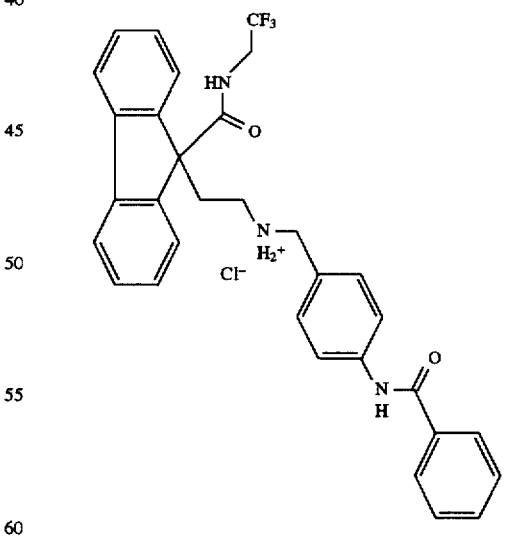

A solution of Example 297 compound (264 mg, 0.41 mmol) in 1.1 ml 4.0M HCl in dioxane was stirred under argon at room temperature for 2 h. The solvent was removed in vacuo at 30° C. The residue was mixed with toluene, and the toluene removed in vacuo to give title compound as a white solid (193 mg, 81.1% yield).

mp 135°–38° C. MS (ESI, + ions) m/z 544 (M+H); 1087 (2M+H). Anal. calc'd for $C_{32}H_{28}F_3N_3O_2$+1 HCl+0.1 dioxane+0.1 toluene: C, 65.49; H, 5.25; N,6.92 Found: C, 65.54; H, 5.50; N,6.66.

EXAMPLE 299

9-[4-[Butoxy(tetrahydrofuran-2-ylmethoxy) phosphinyl]-butyl]-N-(2,2,2-trifluoroethyl)-9H-fluorene-9-carboxamide

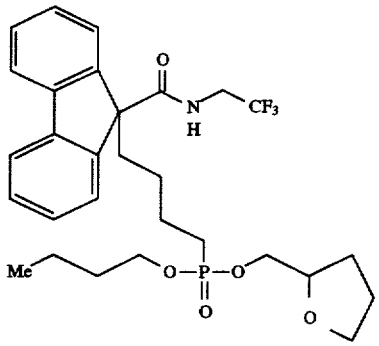

A.

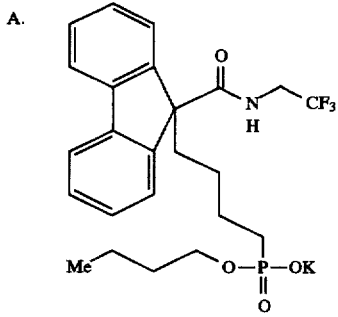

To a solution of 1 g (1.85 mmol) of Example 186 compound in 10 mL of a 3:7 water/n-butanol solution was added 1 g (18.50 mmol) of KOH pellets. The mixture was heated to 100° C. for 5 days, at which time it was evaporated to remove n-butanol and freeze dried. The residue was purified by MPLC on a column of CHP20P gel (2.5 cm diam.×20 cm height) eluting with water (1 L) followed by a gradient created by the gradual addition of 500 mL of acetonitrile to a reservoir of 700 mL of water. Fractions #34 to 40 were pooled. The acetonitrile was removed under reduced pressure and the aqueous solution was freeze dried to provide 695 mg (72%) of title compound as a white lyophilate.

TLC: silica gel (8:1:1 n-propanol/water/aqueous $NH_3$) $R_f$=0.63. MS((ES-$NH_4OH$, + ions) m/z 525 (M+H+$CH_3CN$), 501 (M+$NH_4$), 484 (M+H) Anal. Calcd for $C_{24}H_{28}NO_4PF_3K$+0.93 $H_2O$. C, 53.56; H, 5.59; N, 2.60; P, 5.75 Found: C, 53.60; H, 5.56; N, 2.56; P, 5.78.

B. 9-[4-[Butoxy(tetrahydrofuran-2-ylmethoxy) phosphinyl]-butyl]-N-(2,2,2-trifluoroethyl)-9H-fluorene-9-carboxamide To a solution of 200 mg (0.38 mmol) of Part A compound in 3 mL of toluene, under argon at room temperature, was added dropwise 53 μL (0.73 mmol) of triethylamine followed by 146 μL (1.15 mmol) of chlorotrimethylsilane. The reaction was stirred for 1 h at which time it was evaporated to dryness to provide a pale yellow solid. The solid was dissolved in 3 mL of dichloromethane, under argon at room temperature, and treated with two drops of DMF followed by the dropwise addition of 283 μL (0.57 mmol) of oxalyl chloride (2.0M in dichloromethane). The reaction was stirred for 0.5 h at which time it was evaporated to dryness to provide a yellow solid. The solid was dissolved in 3 mL of THF, under argon at room temperature, and treated dropwise with 58 μL (0.57 mmol) of tetrahydrofurfuryl alcohol and 31 μL (0.38 mmol) of pyridine. The reaction was stirred for 18 h at which time it was diluted with ether and washed with $NaHCO_3$, brine, dried ($Na_2SO_4$) and evaporated. Flash chromatography was performed on 75 g of silica gel eluting with 97:3 dichloromethane/isopropanol to provide 75 mg (35%) of title compound as a pale yellow oil.

MS (FAB, ± ions) m/z 568 (M+H), (FAB, − ion) 566 (M−H). HRMS molecular ion calcd for $C_{29}H_{38}NO_5PF_3$ (M+H) 568.24398, found 568.2440.

EXAMPLE 300

9-[4-[Butoxy(2-pyridinylmethoxy)phosphinyl]-butyl]-N-(2,2,2-trifluoroethyl)-9H-fluorene-9-carboxamide

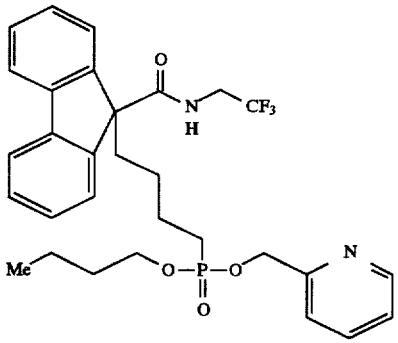

To a solution of 200 mg (0.38 mmol) of Example 299 Part A compound in 3 mL of toluene, under argon at room temperature, was added dropwise 53 μL (0.73 mmol) of triehtylamine followed by 146 μL (1.15 mmol) of chlorotrimethylsilane. The reaction was stirred for 1 h at which time it was evaporated to dryness to provide a pale yellow solid. The solid was dissolved in 3 mL of dichloromethane, under argon at room temperature, and treated with two drops of DMF followed by the dropwise addition of 290 μL (0.58 mmol) of oxalyl chloride (2.0M in dichloromethane). The reaction was stirred for 0.5 h at which time it was evaporated to dryness to provide a yellow solid. The solid was dissolved in 3 mL of THF, under argon at RT, and treated dropwise with 73 μL (0.77 mmol) of 2-pyridylcarbinol. The reaction was stirred for 18 h at which time it was diluted with ether and washed with $NaHCO_3$, brine, dried ($Na_2SO_4$) and evaporated. Flash chromatography was performed on 65 g of silica gel eluting with 97:3 dichloromethane/isopropanol to provide 160 mg (73%) of title compound as a pale yellow oil.

MS (ES-$NH_4OH$, ± ions) m/z 575 (M+H). Anal. Calcd. for $C_{30}H_{34}N_2O_4PF_3$+0.65 $H_2O$: C, 61.46; H, 6.07; N, 4.78; F, 9.72; P, 5.28. Found: C, 61.07; H, 5.88; N, 5.00; F, 9.55; P, 5.26.

The following additional compounds of the invention were prepared following the procedures set out herein.

EXAMPLE 301

9-[4-(Dipropoxyphosphinyl)butyl]-N-(2,2,2-trifluoroethyl)-9H-fluorene-9-carboxamide MS (ES-$NH_4OH$, + ions) m/z 529 (M+$NH_4$), 512 (M+H). Anal. Calc'd for $C_{26}H_{33}N_4PF_3$+0.23 $CH_2Cl_2$: C, 59.32; H, 6.35; N, 2.64; P, 5.83 Found: C, 59.31; H, 6.46; N, 2.88; P, 5.68.

EXAMPLE 302

9-[4-[4-[[(4-Nitrophenyl)sulfonyl]amino]phenyl]-butyl]-N-(2,2,2-trifluoroethyl)-9H-fluorene-9-carboxamide mp 136°–138° C. MS (ES, – ions) m/z 622 (M–H). Anal. Calc'd for $C_{32}H_{28}N_3SO_5F_3+2.00$ $CH_2Cl_2$: C, 51.60; H, 4.06; N, 5.30; S, 4.04 Found: C, 51.70; H, 4.00; N, 5.20; S, 4.17.

EXAMPLE 303

9-[4-[4-[[(2-Nitrophenyl)sulfonyl]amino]phenyl]-butyl]-N-(2,2,2-trifluoroethyl)-9H-fluorene-9-carboxamide mp 60°–64° C. MS (ES, – ions) m/z 622 (M–H). Anal. Calc'd for $C_{32}H_{28}N_3SO_5F_3+0.5$ $CH_2Cl_2$: C, 58.60; H, 4.39; N, 6.31; S, 4.81 Found: C, 58.61; H, 4.41; N, 6.14; S, 4.88.

EXAMPLE 304

9-[4-(Dibutoxyphosphinyl)butyl]-3,6-difluoro-N-(2,2,2-trifluoroethyl)-9H-fluorene-9-carboxamide MS (ESI, M+H)$^+$=576 m/z$^+$. Anal. Calc'd for $C_{28}H_{35}F_5NO_4P$ . 0.25 $H_2O$: C, 57.98; H, 6.17; N, 2.41 Found: C, 57.95; H, 6.22; N, 2.23.

EXAMPLE 305

9-[3-[[5-[(2-Phenoxybenzoyl)amino]-2-pyridinyl]oxy]propyl]-N-propyl-9H-fluorene-9-carboxamide mp 104°–108° C. MS (FAB, + ions) m/z 598 (M+H). Anal. Calc'd for $C_{38}H_{35}N_3O_4$: C, 76.36; H, 5.90; N, 7.03 Found: C, 75.86; H, 5.80; N, 6.96.

EXAMPLE 306

9-[6-[(6-Ethoxy-2-benzothiazolyl)thio]hexyl]-N-(2,2,2-trifluoroethyl)-9H-fluorene-9-carboxamide MS (FAB, + ions) m/z 585 (M+H). Anal. Calc'd for $C_{31}H_{31}N_2O_2S_2F_3$: C, 63.68; H, 5.34; N, 4.79; F, 9.75 Found: C, 63.43; H, 5.37; N, 4.61; F, 9.78.

EXAMPLE 307

[4-[9-[[(2,2,2-Trifluoroethyl)amino]carbonyl]-9H-fluoren-9-yl]-butyl]phosphonic acid, di(1-methylethyl) ester mp 91°–94° C. MS (ES-NH$_4$OH, + ions) m/z 512 (M+H). Anal. Calc'd for $C_{26}H_{33}NO_4PF_3+0.13$ $CH_2Cl_2$: C, 60.06; H, 6.42; N, 2.68; P, 5.93; F, 10.91 Found: C, 60.21; H, 6.70; N, 2.68; P, 6.00; F, 10.64.

EXAMPLE 308

[[4-[(2-Phenoxybenzoyl)amino]phenyl]methyl][2-[9-[[(2,2,2-trifluoroethyl)amino]carbonyl]-9H-fluoren-9-yl]ethyl]carbamic acid, 1,1-dimethylethyl ester mp 83°–85° C. MS (ESI, + ions) m/z 753 (M+NH$_4$). Anal. Calc'd for $C_{43}H_{40}F_3N_3O_5+1.4$ $H_2O$: C, 67.87; H, 5.67; N, 5.52 Found: C, 67.85; H, 5.34; N, 5.42.

EXAMPLE 309

9-[2-[[[4-[(2-Phenoxybenzoyl)amino]phenyl]methyl]amino]ethyl]-N-(2,2,2-trifluoroethyl)-9H-fluorene-9-carboxamide, monohydrochloride mp 260°–62° C. MS (ESI, + ions) m/z 636 (M+H). Anal. Calc'd for $C_{38}H_{32}F_3N_3O_3$ . HCl: C, 67.90; H, 4.95; N, 6.25 Found: C, 56.06; H, 4.07; N, 4.93.

EXAMPLE 310

[1-[4-[9-[[(2,2,2-Trifluoroethyl)amino]carbonyl]-9H-fluoren-9-yl]butyl]-1H-imidazol-4-yl]carbamic acid, 1,1-dimethylethyl ester MS (ESI, + ions) m/z 543 (M+H)$^+$; (ESI, – ions) m/z 541 (M–H)$^-$. Anal. Calc'd for $C_{29}H_{33}F_3N_4O_3+0.1$ $C_6H_{14}$: C, 64.50; H, 6.29; N, 10.16; F, 10.34 Found: C, 64.18; H, 6.39; N, 9.86; F, 9.54.

The following Examples 311 to 313 describe preparation of compounds of the invention employing solid phase synthesis techniques as described hereinafter.

EXAMPLE 311

9-[4-[(6-Ethoxy-2-benzothiazolyl)thio]butyl]-N-propyl-9H-fluorene-9-carboxamide

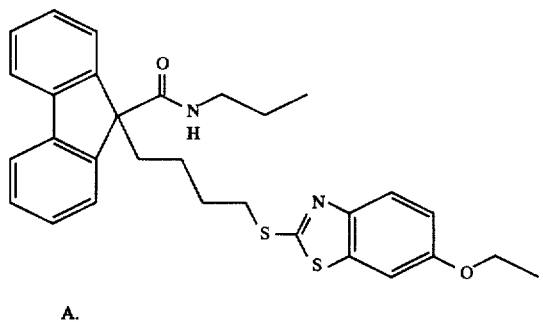

A.

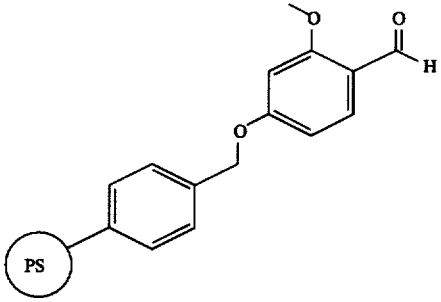

PS = 1% Divinylbenzene cross-linked polystyrene resin, 100–200 mesh

To a magnetically stirred suspension of 4.8 g (120 mmol, 10 eq) of sodium hydride (60% mineral oil dispersion) in 30 mL of dimethylformamide (DMF) at 0° C. was added a solution of 18.2 g (120 mmol, 10 eq) of 4-hydroxy-2-methoxybenzaldehyde in 50 mL of DMF dropwise over 75 min. The reaction was allowed to warm to room temperature (RT) and stirred for an additional 75 min. The stirbar was removed and 10 g (12 mmol, 1 eq) of Merrifield resin (loading of 1.2 mmol/g, Advanced Chemtech) was added. The flask was placed in a heating mantel mounted on a vortex mixer and heated at 70° C. (internal temperature) while vortexing for 26 h. The contents of the reaction vessel were transferred to a large filter funnel with a scintered-glass frit (porosity C) and rinsed sequentially with DMF (3×100 mL), 1:1 DMF:water (3×100 mL), water (2×100 mL) and MeOH (5×100 mL). The resin was dried under high vacuum (0.1 mm Hg) for 72 h to afford 11.16 g (98% of expected weight) of title product as a tacky non-freeflowing tan resin. The resin was characterized by gel-phase $^{13}$C-NMR and elemental analysis (chlorine and oxygen).

Elemental Analysis: Chlorine: Expected 0% Cl for 100% loading; found 0.21%. Starting Cl content of resin was 4.26%. Residual Cl consistent with 95% resin loading. Oxygen: Expected 5.76% for 100% loading; found 6.21%.

B.

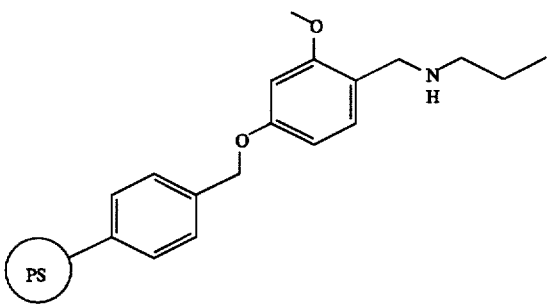

To a 25 mL Varian polypropylene tube fitted with a polyethylene frit and a luer stopcock was added 500 mg of Part A resin. The tube was sealed with a 19 mm Aldrich Suba septa and the resin was swollen in 5 mL of dry DMF, mixed by vortexing for 1 min and the DMF was removed using vacuum and $N_2$ pressure in order to maintain the vessel under inert atmosphere. Trimethyl orthoformate (1 mL) was added followed by 3.2 mL of DMF and 0.8 mL (10.0 mmol, 18 eq) of n-propylamine. The reaction mixture was vortexed for 18 h at room temperature. After removal of the reaction solution by nitrogen pressure and vacuum, 5 mL of a 200 mg/mL solution of sodium triacetoxyboro-hydride in DMF (1 g, 4.7 mmol, 8 eq) and 100 μL of acetic acid were added. The reaction mixture was vortexed for 8 h at room temperature. The reaction solution was removed and the resin was rinsed with DMF (4×5 mL), 1:1 DMF:water (2×5 mL), water (1×5 mL), DMF (3×5 mL) and dichloromethane ($CH_2Cl_2$) (4×5 mL). The last $CH_2Cl_2$ rinse was done with dry $CH_2Cl_2$ in the tube with the septa in place using nitrogen gas and vacuum to filter away the solvent and keep the reaction vessel under inert atmosphere. The title resin was used in the next step without characterization.

C.

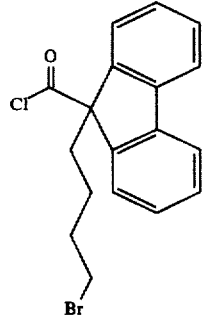

To 3.45 g (10 mmol, 1 eq) of Example 273 Part A(1) compound in 15 mL of $CH_2Cl_2$ was added 100 μL of DMF. The resulting solution was cooled to 0° C. and 7.5 mL (15 mmol, 1.5 eq) of a 2.0M oxalyl chloride solution in $CH_2Cl_2$ was added. The bubbling reaction mixture was stirred at 0° C. for 15 min and then allowed to warm to room temperature. After 2 h, the reaction mixture was concentrated to afford the crude acid title chloride as a yellowish orange solid/oil mixture which was dissolved in $CH_2Cl_2$ and used without purification.

D.

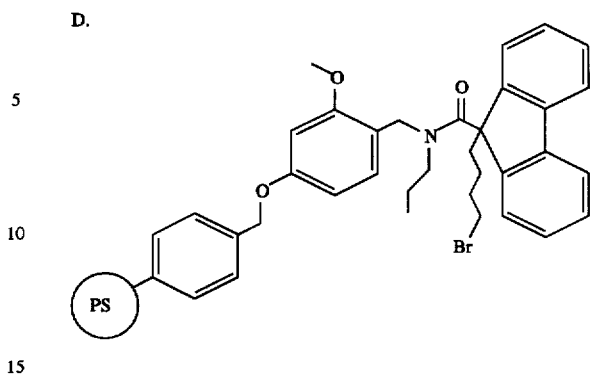

To the Part B resin in the polypropylene tube were added 1 mL of diisopropylethyl amine (5.7 mmol, 10 eq) and 1 mL of $CH_2Cl_2$ and the resulting mixture was mixed for 2 min. The tube was cooled to 0° C. in an ice bath and 4 mL (2.2 mmol, 4 eq) of a solution of Part C acid chloride in $CH_2Cl_2$ was added. The resulting orange reaction mixture was mixed by vortexing at room temperature for 19 h. and then rinsed with $CH_2Cl_2$ (4×5 mL) to afford title resin which was used in the next step without characterization.

E.

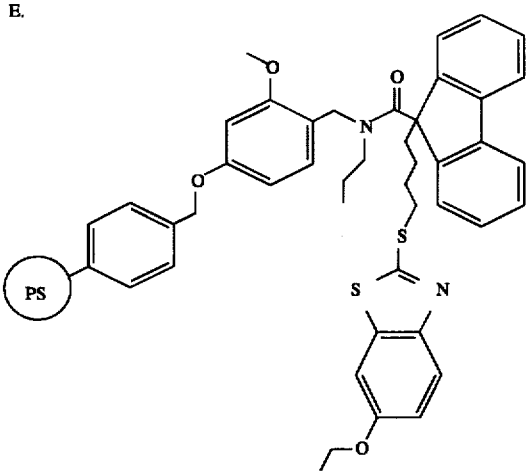

The Part D resin in the sealed polypropylene tube was swollen in 5 mL of dry DMF and vortexed for 2 min. The solvent was removed with $N_2$ and vacuum and a solution of 1.16 g (5.5 mmol, 10 eq) of 6-ethoxy-2-mercaptobenzothiazole in 4 mL of DMF was added to the resin followed by 5 mL (5 mmol, 9 eq) of a 1.0M solution of sodium bistrimethylsilylamide in THF. Vortexing was initiated and the reaction mixture was mixed for 17 h at room temperature. The reaction solution was filtered away and the title resin was rinsed with DMF (4×5 mL), 1:1 DMF:water (2×5 mL), water (1×5 mL), DMF (3×5 mL) and dichloromethane ($CH_2Cl_2$) (4×5 mL).

F. 9-[4-[(6-Ethoxy-2-benzothiazolyl)thio]-butyl]-N-propyl-9H-fluorene-9-carboxamide The Part E resin was treated with 5 mL of 100% trifluoroacetic acid and vortexed for 90 min. The reaction solution was collected, the resin was rinsed with $CH_2Cl_2$ (3×1 mL) and the combined reaction solution and rinses were concentrated. The products from 3 parallel reactions were each redissolved in 15 mL of $CH_2Cl_2$, pooled and reconcentrated to afford 393 mg (46% crude) of an off-white solid. Recrystallization from MeOH afforded 339 mg (40%) of title compound as a white solid.

mp 112°–113.5° C. MS (electrospray, pos. ions): m/z 517 (M+H). Anal. Calcd for $C_{30}H_{32}N_2O_2S_2$: C, 69.73; H, 6.24; N, 5.42; S, 12.41 Found: C, 69.48; H, 6.22; N, 5.39; S, 12.25.

EXAMPLE 312

9-[4-[(4,5-Diphenyl-1H-imidazol-2-yl)thio]butyl]-N-[2-(4-methoxyphenyl)ethyl]-9H-fluorene-9-carboxamide

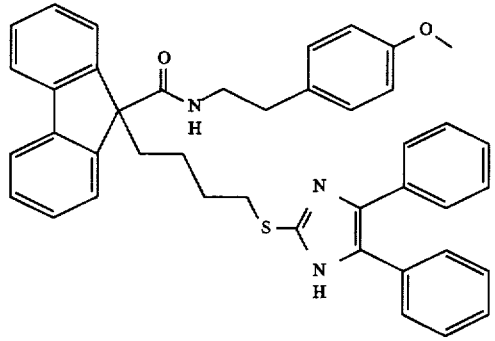

A.

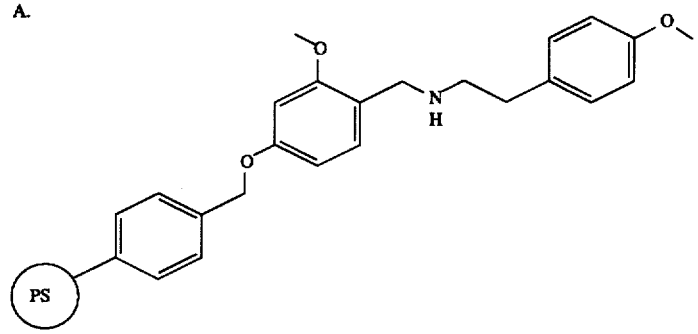

To a 25 mL Varian polypropylene tube fitted with a polyethylene frit and a luer stopcock was added 500 mg of Example 311 Part A resin. The tube was sealed with a 19 mm Aldrich Suba septa and the resin was swollen in 5 mL of dry DMF, mixed by vortexing for 1 min and the DMF was removed using vacuum and $N_2$ pressure in order to maintain the vessel under inert atmosphere. Trimethyl orthoformate (1 mL) was added followed by 2.6 mL of DMF and 1.46 mL (1.51 g, 10.0 mmol, 18 eq) of p-methoxyphenethylamine. The reaction mixture was vortexed for 18 h at RT. After removal of the reaction solution by nitrogen pressure and vacuum, 5 mL of a 200 mg/mL solution of sodium triacetoxyborohydride in DMF (1 g, 4.7 mmol, 8 eq) and 100 μL of acetic acid were added. The reaction mixture was vortexed for 8 h at room temperature. The reaction solution was removed and the resin was rinsed with DMF (4×5 mL), 1:1 DMF:water (2×5 mL), water (1×5 mL), DMF (3×5 mL) and dichloromethane ($CH_2Cl_2$) (4×5 mL). The last $CH_2Cl_2$ rinse was done with dry $CH_2Cl_2$ in the tube with the septa in place using nitrogen gas and vacuum to filter away the solvent and keep the reaction vessel under inert atmosphere. The title resin was used in the next step without characterization.

B.

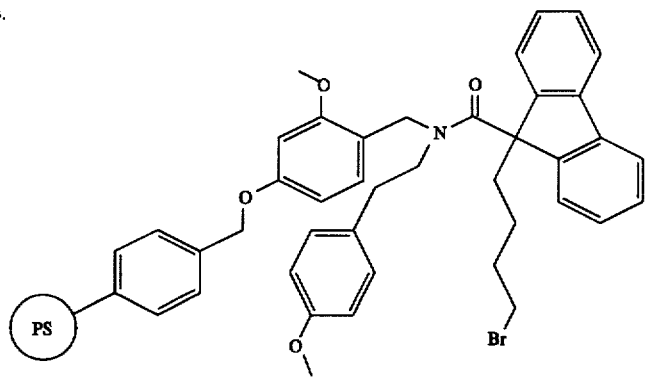

To the Part A resin in the polypropylene tube were added 1 mL of diisopropylethyl amine (5.7 mmol, 10 eq) and 1 mL of CH$_2$Cl$_2$ and the resulting mixture was mixed for 2 min. The tube was cooled to 0° C. in an ice bath and 4 mL (2.2 mmol, 4 eq) of a solution of Example 311 Part C acid chloride in CH$_2$Cl$_2$ was added. The resulting orange reaction mixture was mixed by vortexing at room temperature for 19 h and then rinsed with CH$_2$Cl$_2$ (4×5 mL) to afford title resin which was used in the next step without characterization.

C.

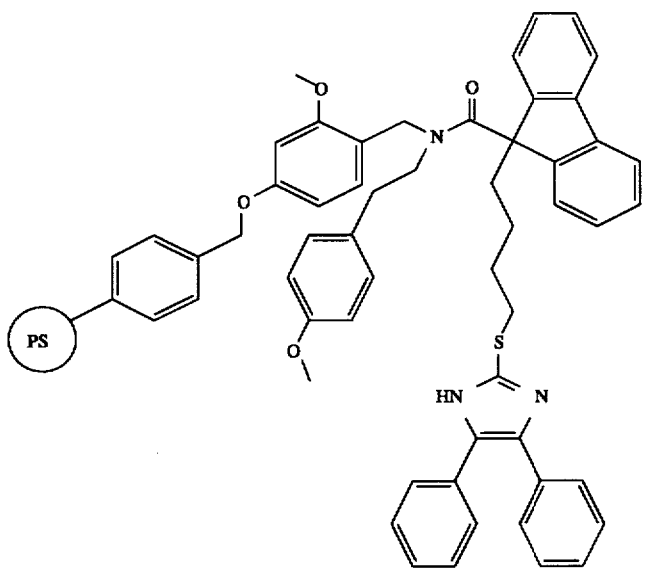

The Part B resin in the sealed polypropylene tube was swollen in 5 mL of dry DMF and vortexed for 2 min. The solvent was removed with N$_2$ and vacuum. To a suspension of 1.4 g (5.5 mmol, 10 eq) of 4,5-diphenyl-2-imidazolethiol in 5 mL of DMF was added 5 mL (5 mmol, 9 eq) of a 1.0M solution of sodium bistrimethylsilylamide in THF. The resulting solution of thiolate anion was added to the resin, vortexing was initiated and the reaction mixture was mixed for 17 h at RT. The reaction solution was filtered away and the title resin was rinsed with DMF (4×5 mL), 1:1 DMF-:water (2×5 mL), water (1×5 mL), DMF (3×5 mL) and dichloromethane (CH$_2$Cl$_2$) (4×5 mL) and used in the next step without characterization.

D. 9-[4-[(4,5-Diphenyl-1H-imidazol-2-yl)-thio]butyl]-N-[2-(4-methoxyphenyl)ethyl]-9H-fluorene-9-carboxamide The Part C resin was treated with 5 mL of 100% trifluoroacetic acid and vortexed for 90 min. The reaction solution was collected, the resin was rinsed with CH$_2$Cl$_2$ (3×1 mL) and the combined reaction solution and rinses were concentrated. The products from 3 parallel reactions were each redissolved in 15 mL of CH$_2$Cl$_2$, pooled and reconcentrated to afford 729 mg (68% crude) of a yellow oil. Flash chromatography on silica gel (50 g) eluted with 2% MeOH in CH$_2$Cl$_2$ (1 L), followed by 5% MeOH in CH$_2$Cl$_2$ (1 L) afforded 208 mg (19%) of title compound as a white foam.

MS(electrospray, pos. ions): m/z 650 (M+H). Anal. Calc'd for C$_{42}$H$_{39}$N$_3$O$_2$S+0.63 CH$_2$Cl$_2$: C, 71.72; H, 5.59; N, 5.97; S, 4.56 Found: C, 71.96; H, 5.64; N, 5.94; S, 4.76.

EXAMPLE 313

9-[4-(2-Thiazolylthio)butyl]-N-(2,2,2-trifluoroethyl)-9H-fluorene-9-carboxamide

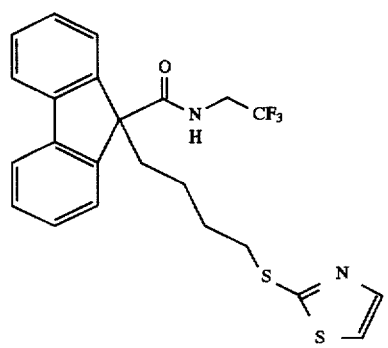

A.

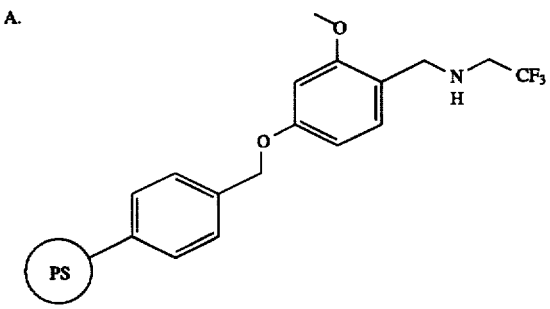

181

To a 25 mL Varian polypropylene tube fitted with a polyethylene frit and a luer stopcock was added 500 mg of Example 311 Part A resin. The tube was sealed with a 19 mm Aldrich Suba septa and the resin was swollen in 5 mL of dry DMF, mixed by vortexing for 1 min and the DMF was removed using vacuum and $N_2$ pressure in order to maintain the vessel under inert atmosphere. Trimethyl orthoformate (1 mL) was added followed by 3.2 mL of DMF and 796 µL (991 mg, 10.0 mmol, 18 eq) of 2,2,2-trifluoroethylamine. The reaction mixture was vortexed for 18 h at room temperature. After removal of the reaction solution by nitrogen pressure and vacuum, 5 mL of a 200 mg/mL solution of sodium triacetoxyboro-hydride in DMF (1 g, 4.7 mmol, 8 eq) and 100 µL of acetic acid were added. The reaction mixture was vortexed for 8 h at room temperature. The reaction solution was removed and the resin was rinsed with DMF (4×5 mL), 1:1 DMF:water (2×5 mL), water (1×5 mL), DMF (3×5 mL) and dichloromethane ($CH_2Cl_2$) (4×5 mL). The last $CH_2Cl_2$ rinse was done with dry $CH_2Cl_2$ in the tube with the septa in place using nitrogen gas and vacuum to filter away the solvent and keep the reaction vessel under inert atmosphere. The title resin was used in the next step without characterization.

182

The tube was cooled to 0° C. in an ice bath and 4 mL (2.2 mmol, 4 eq) of a solution of Example 311 Part C acid chloride in $CH_2Cl_2$ was added. The resulting orange reaction mixture was mixed by vortexing at RT for 19 h. and then rinsed with $CH_2Cl_2$ (4×5 mL) to afford title resin which was used in the next step without characterization.

B.

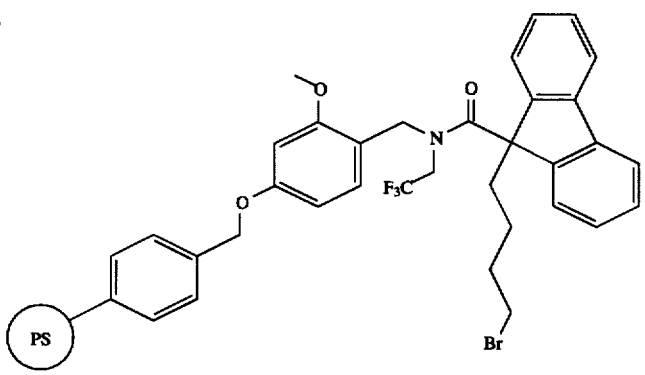

To the Part A resin in the polypropylene tube were added 1 mL of diisopropylethyl amine (5.7 mmol, 10 eq) and 1 mL of $CH_2Cl_2$ and the resulting mixture was mixed for 2 min.

C.

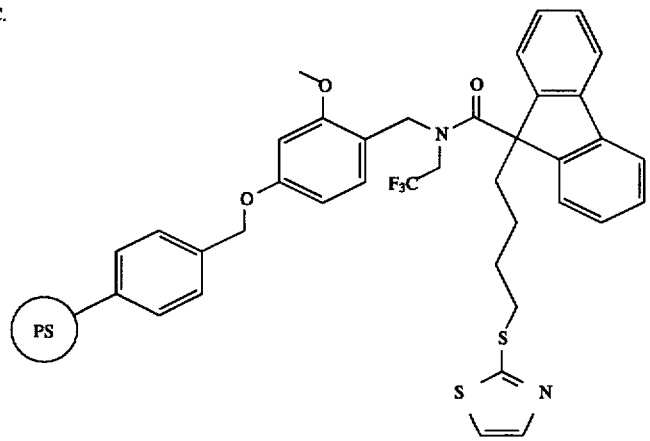

The Part B resin in the sealed polypropylene tube was swollen in 5 mL of dry DMF and vortexed for 2 min. The solvent was removed with $N_2$ and vacuum and a solution of 644 mg (5.5 mmol, 10 eq) of 2-mercaptothiazole in 4 mL of DMF was added to the resin followed by 5 mL (5 mmol, 9 eq) of a 1.0M solution of sodium bistrimethylsilylamide in THF. Vortexing was initiated and the reaction mixture was mixed for 17 h at RT. The reaction solution was filtered away and the title resin was rinsed with DMF (4×5 mL), 1:1 DMF:water (2×5 mL), water (1×5 mL), DMF (3×5 mL) and dichloromethane ($CH_2Cl_2$) (4×5 mL).

D. 9-[4-(2-Thiazolylthio)butyl]-N-(2,2,2-trifluoroethyl)-9H-fluorene-9-carboxamide The Part C resin was treated with 5 mL of 100% trifluoroacetic acid and vortexed for 90 min. The reaction solution was collected, the resin was rinsed with $CH_2Cl_2$ (3×1 mL) and the combined reaction solution and rinses were concentrated. The products from 3 parallel reactions were each redissolved in 15 mL of $CH_2Cl_2$, pooled and reconcentrated to afford 395 mg (52% crude) of an off-white solid. Recrystallization from MeOH afforded 342 mg (45%) of title compound as a white solid.

mp 143°–144° C. MS(electrospray, pos. ions): m/z 463 (M+H). Anal. Calcd for $C_{23}H_{21}N_2O_2S_2F_3$: C, 59.72; H, 4.58; N, 6.06; S, 13.86 Found: C, 59.65; H, 4.58; N, 6.01; S, 13.64.

The following additional compounds were prepared employing solid phase synthesis techniques as described in Examples 311 to 313.

Example 314 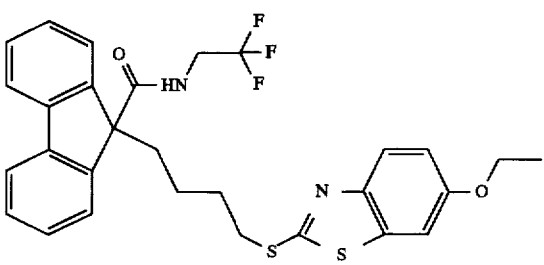 m/z 557 (M + H)

Example 315 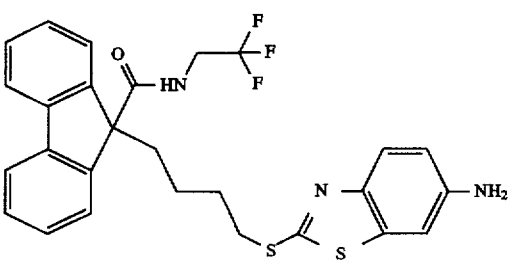 m/z 528 (M + H)

Example 316 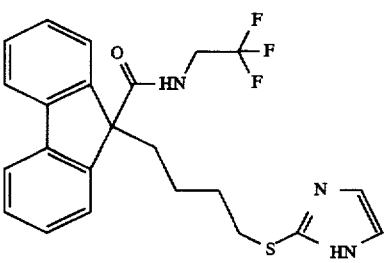 m/z 446 (M + H)

Example 317 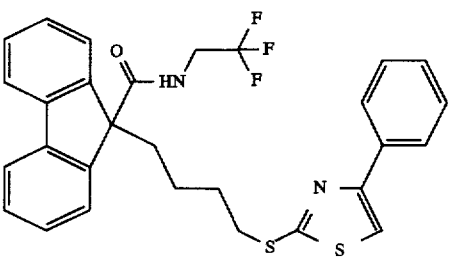 m/z 539 (M + H)

-continued
| | | |
|---|---|---|
| Example 318 | 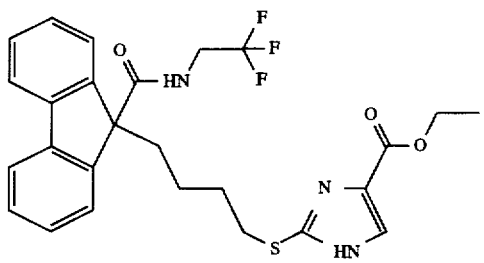 | m/z 518 (M + H) |
| Example 319 | 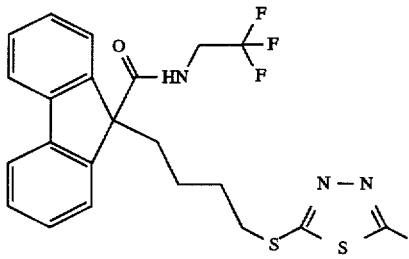 | m/z 478 (M + H) |
| Example 320 | 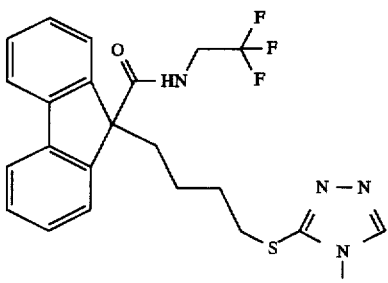 | m/z 461 (M + H) |
| Example 321 | 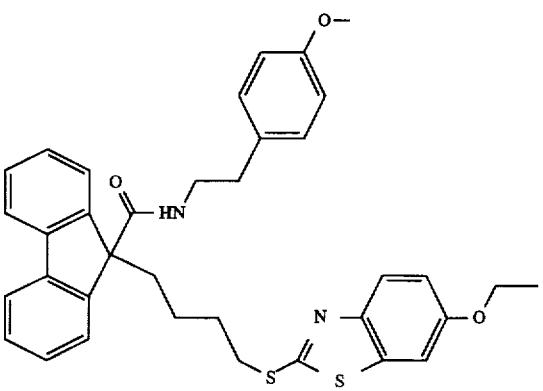 | m/z 609 (M + H) |
| Example 322 | 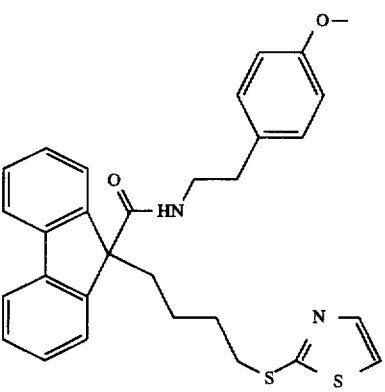 | m/z 515 (M + H) |

-continued
Example 323 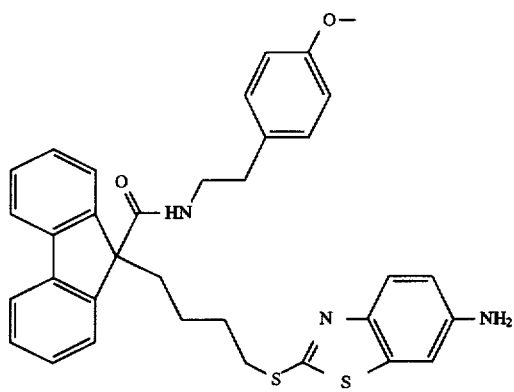 m/z 580 (M + H)
Example 324 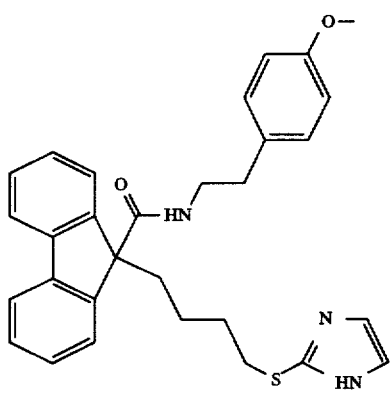 m/z 498 (M + H)
Example 325 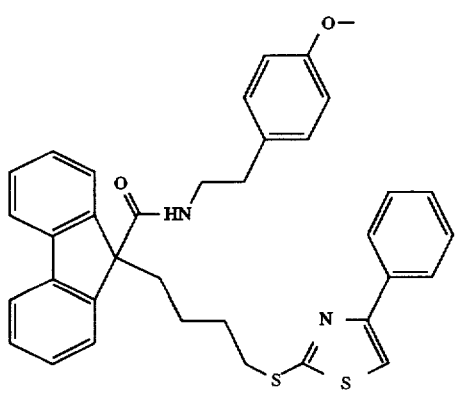 m/z 591 (M + H)
Example 326 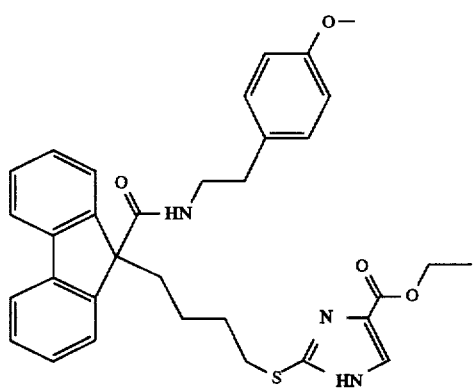 m/z 570 (M + H)

-continued
Example 327 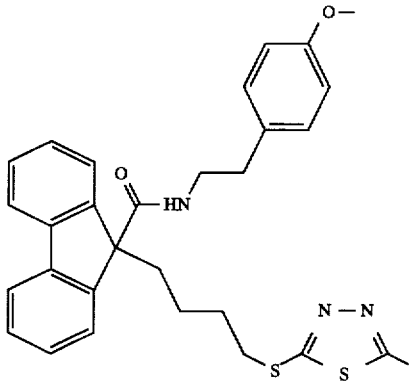 m/z 530 (M + H)
Example 328 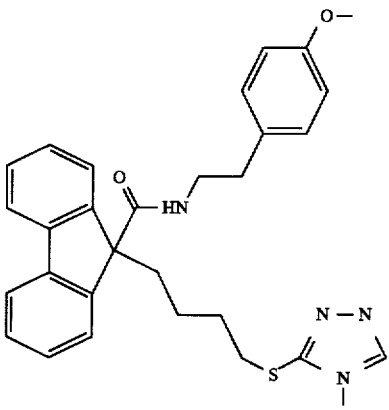 m/z 513 (M + H)
Example 329 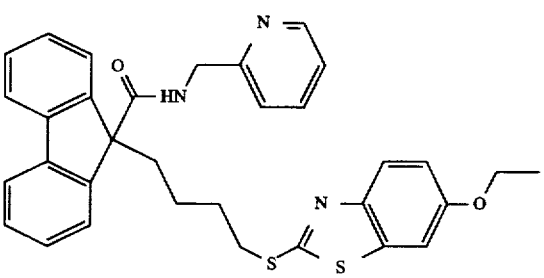 m/z 566 (M + H)
Example 330 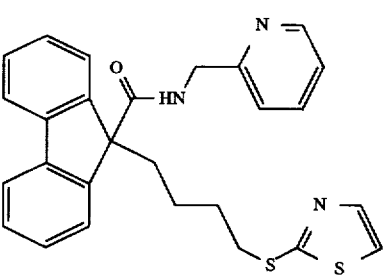 m/z 472 (M + H)
Example 331 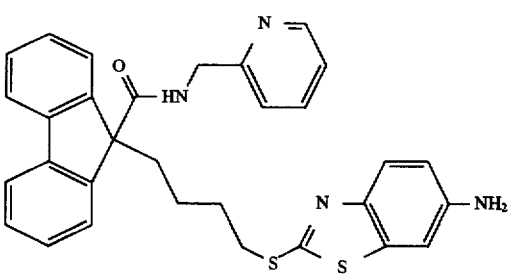 m/z 537 (M + H)

-continued
Example 332 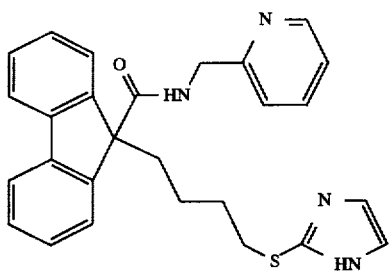 m/z 455 (M + H)
Example 333 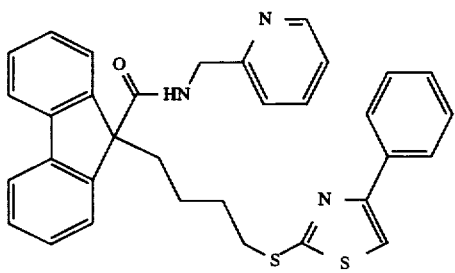 m/z 548 (M + H)
Example 334 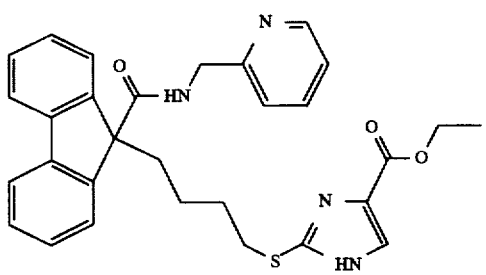 m/z 527 (M + H)
Example 335 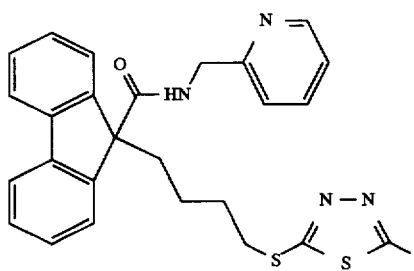 m/z 487 (M + H)
Example 336 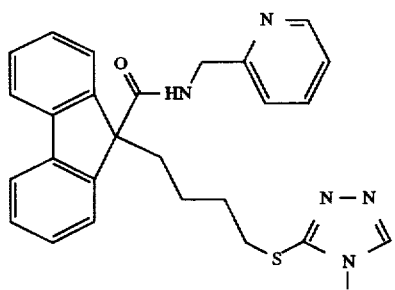 m/z 470 (M + H)

-continued
| | | |
|---|---|---|
| Example 337 | 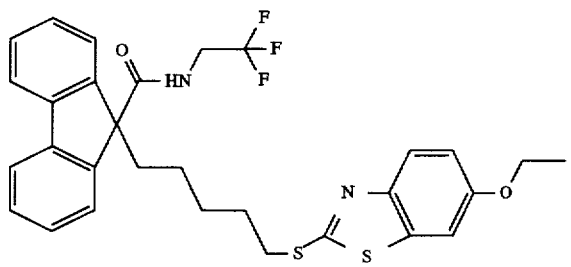 | m/z 571 (M + H) |
| Example 338 | 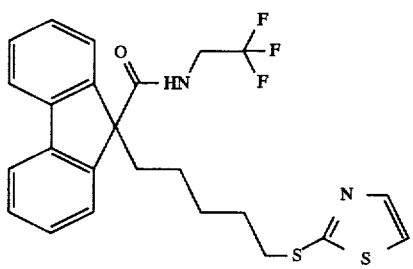 | m/z 477 (M + H) |
| Example 339 | 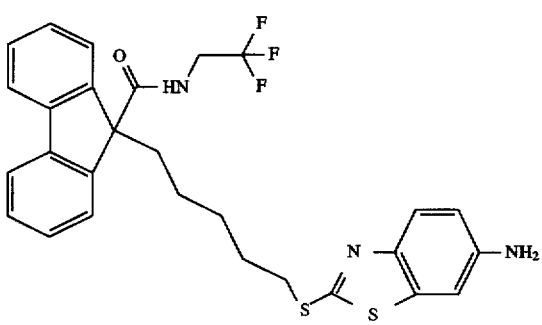 | m/z 542 (M + H) |
| Example 340 | 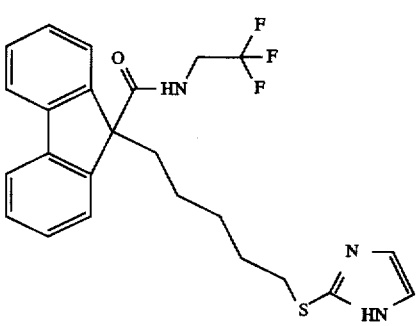 | m/z 460 (M + H) |
| Example 341 | 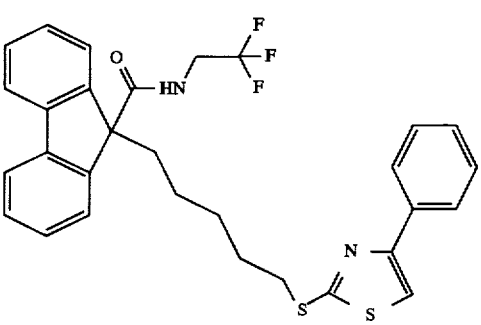 | m/z 553 (M + H) |

| | | |
|---|---|---|
| Example 342 | 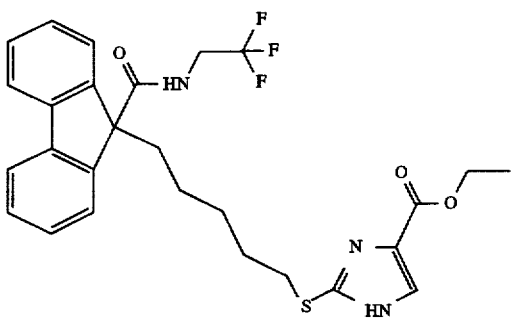 | m/z 532 (M + H) |
| Example 343 | 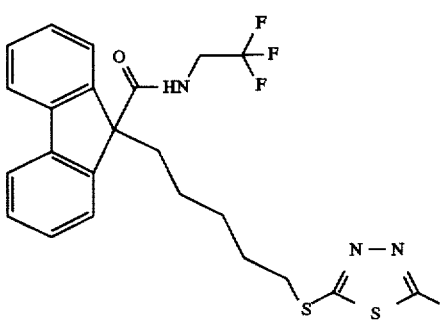 | m/z 492 (M + H) |
| Example 344 | 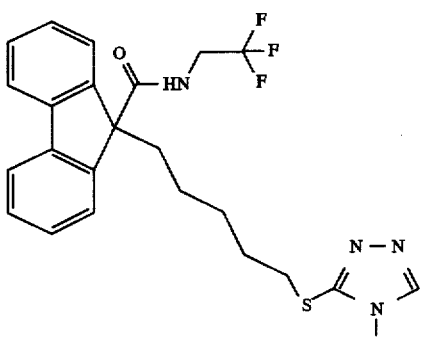 | m/z 475 (M + H) |
| Example 345 | 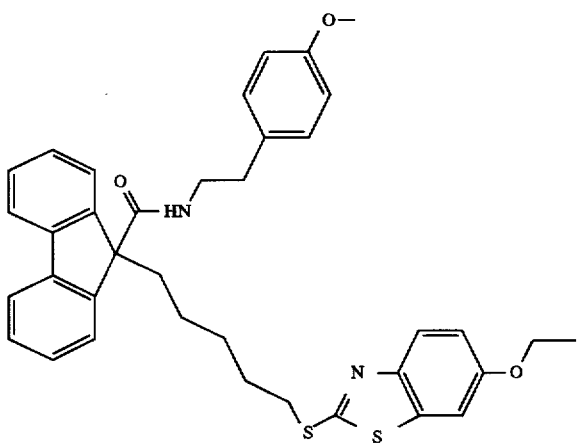 | m/z 623 (M + H) |

| | | |
|---|---|---|
| Example 346 | 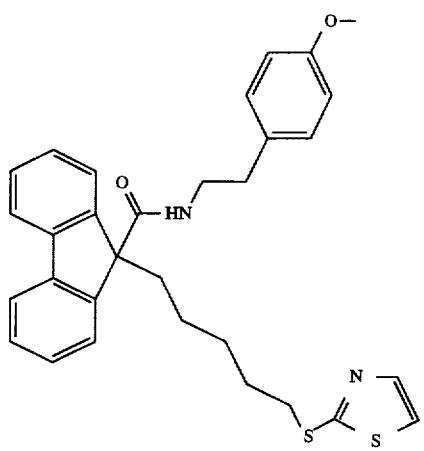 | m/z 529 (M + H) |
| Example 347 | 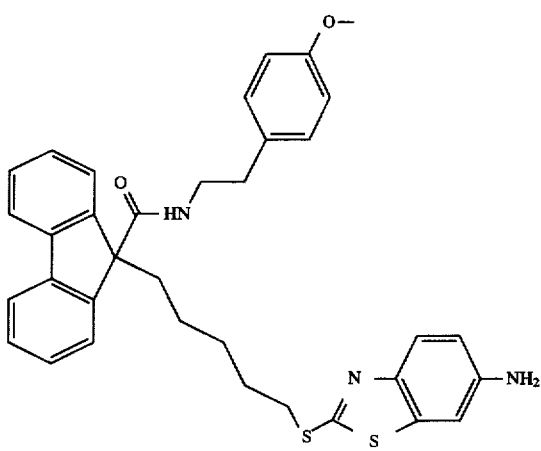 | m/z 594 (M + H) |
| Example 348 | 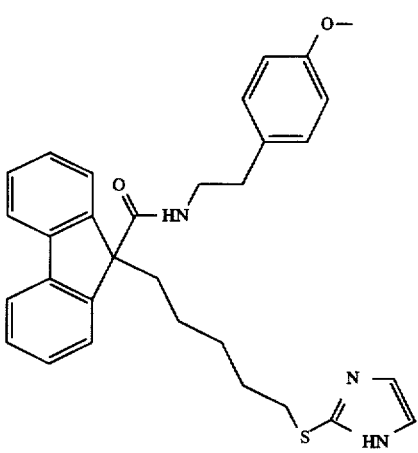 | m/z 512 (M + H) |

| | | |
|---|---|---|
| Example 349 | 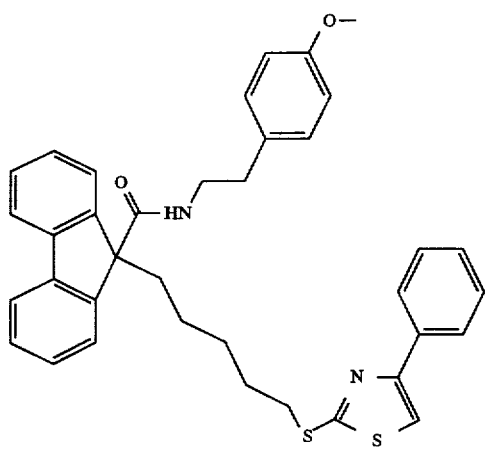 | m/z 605 (M + H) |
| Example 350 | 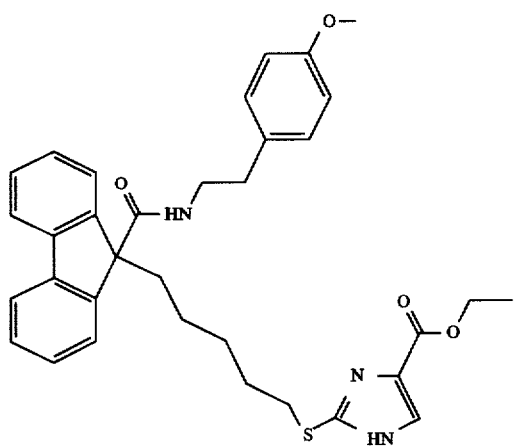 | m/z 584 (M + H) |
| Example 351 | 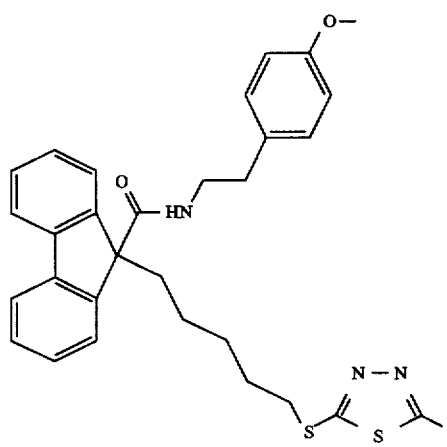 | m/z 544 (M + H) |

-continued
Example 352 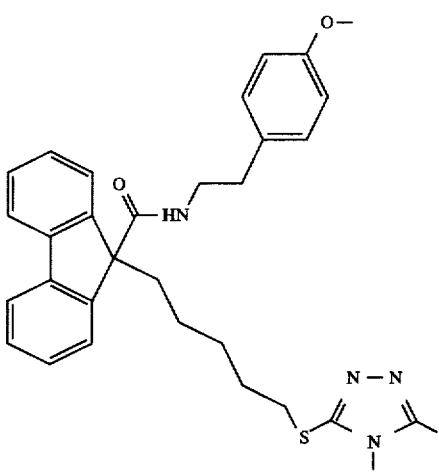 m/z 527 (M + H)
Example 353 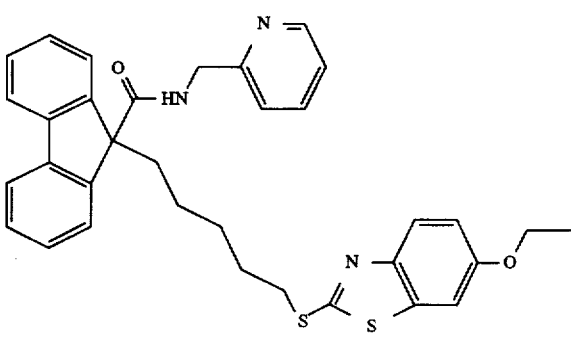 m/z 580 (M + H)
Example 354 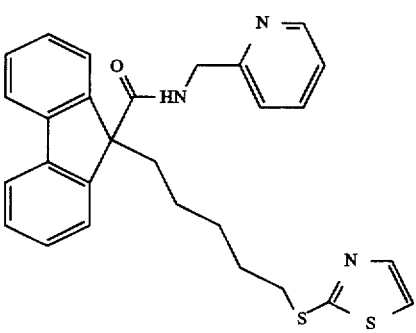 m/z 486 (M + H)
Example 355 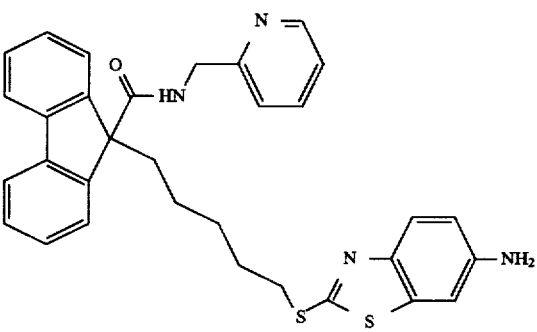 m/z 551 (M + H)

-continued
Example 356 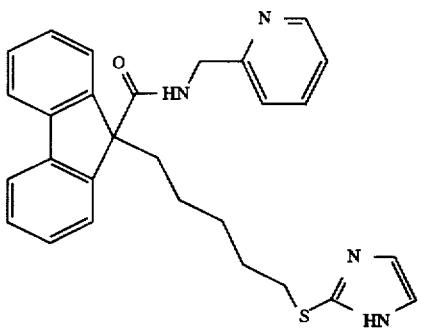 m/z 469 (M + H)
Example 357 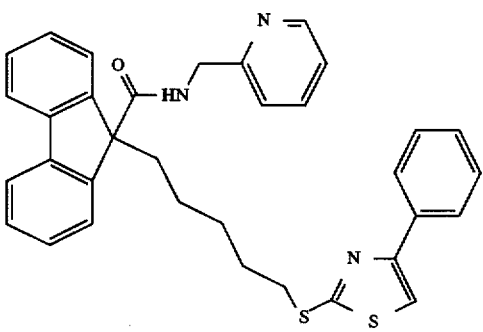 m/z 562 (M + H)
Example 358 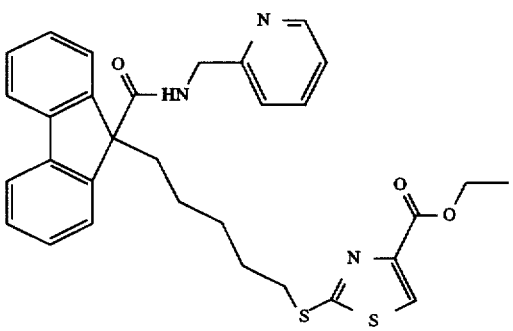 m/z 541 (M + H)
Example 359 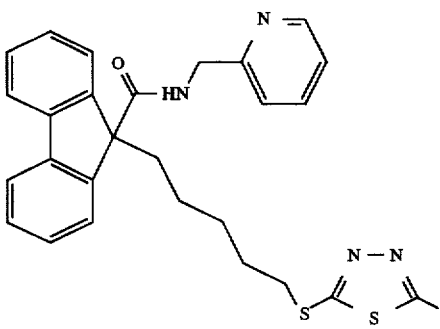 m/z 501 (M + H)

-continued
Example 360
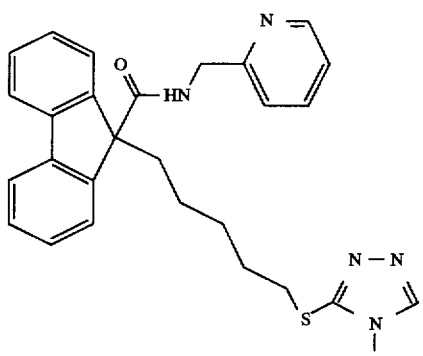
m/z 484 (M + H)
Example 361
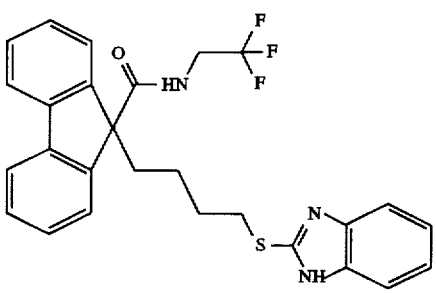
m/z 496 (M + H)
Example 362
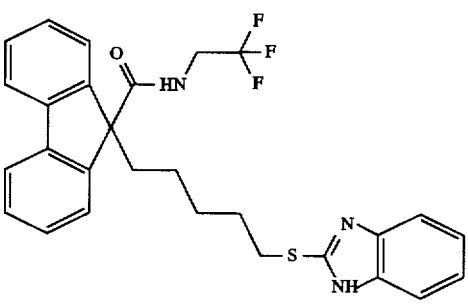
m/z 510 (M + H)
Example 363
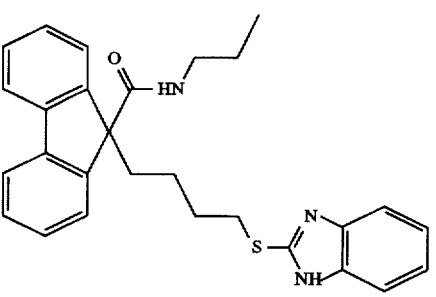
m/z 456 (M + H)
Example 364
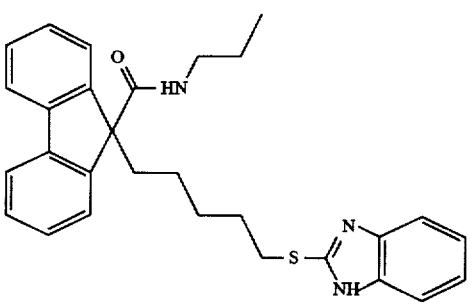
m/z 470 (M + H)

-continued
Example 365 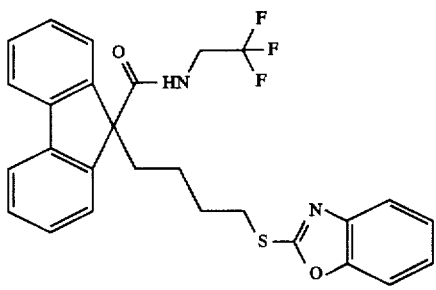 m/z 497 (M + H)
Example 366 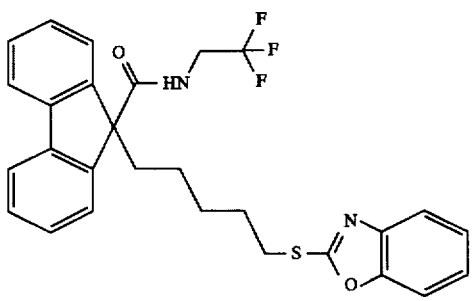 m/z 511 (M + H)
Example 367 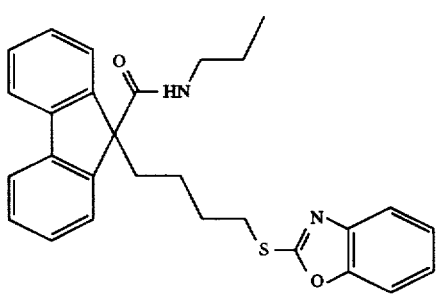 m/z 457 (M + H)
Example 368 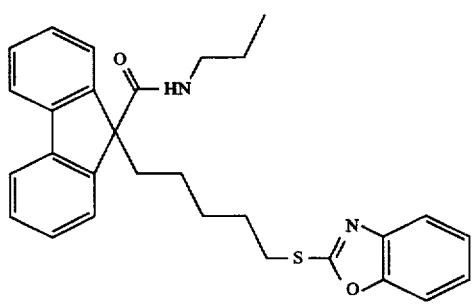 m/z 471 (M + H)
Example 369 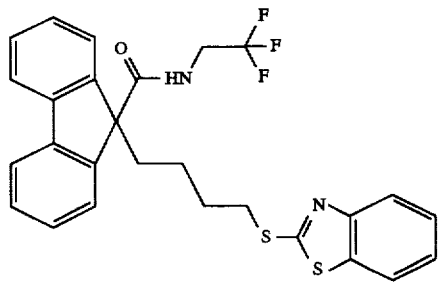 m/z 513 (M + H)

-continued
| | | |
|---|---|---|
| Example 370 | 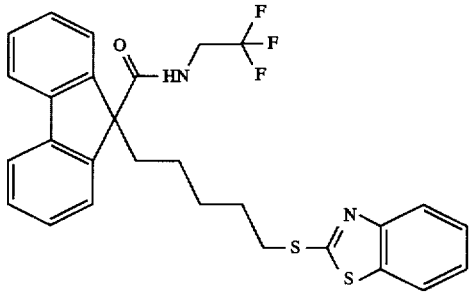 | m/z 527 (M + H) |
| Example 371 | 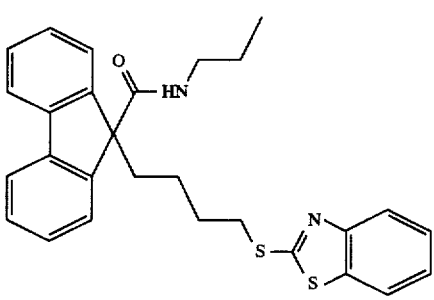 | m/z 473 (M + H) |
| Example 372 | 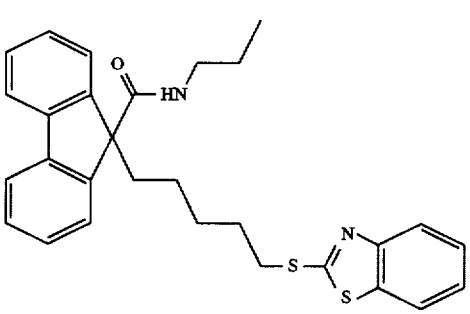 | m/z 487 (M + H) |
| Example 373 | 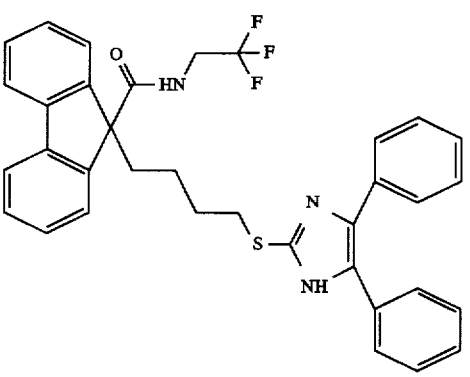 | m/z 598 (M + H) |
| Example 374 | 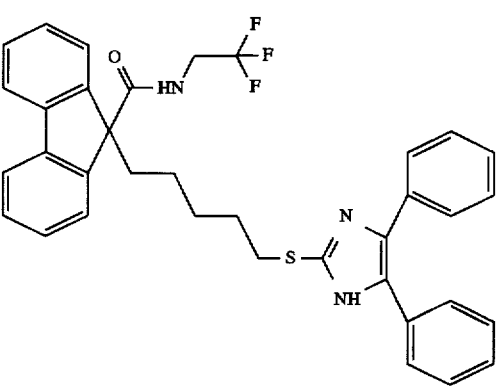 | m/z 612 (M + H) |

Example 375 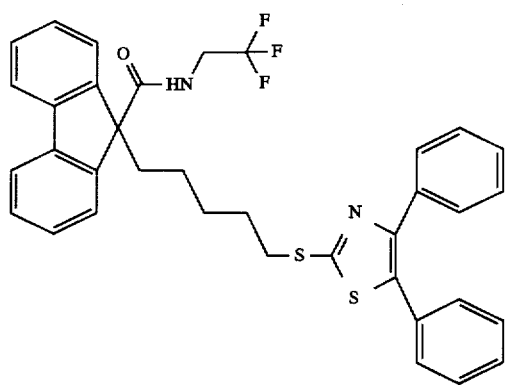 m/z 629 (M + H)
Example 376 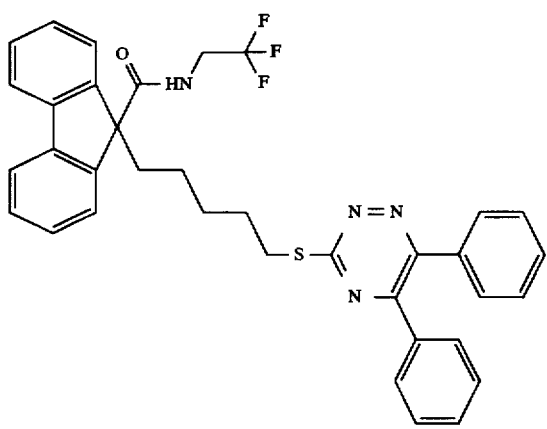 m/z 625 (M + H)
Example 377 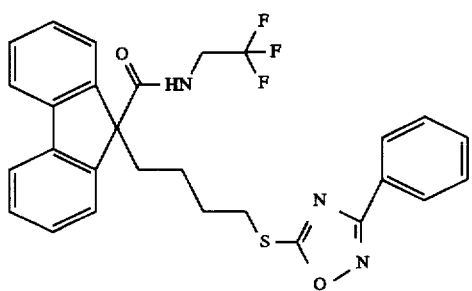 m/z 522 (M + H)
Example 378 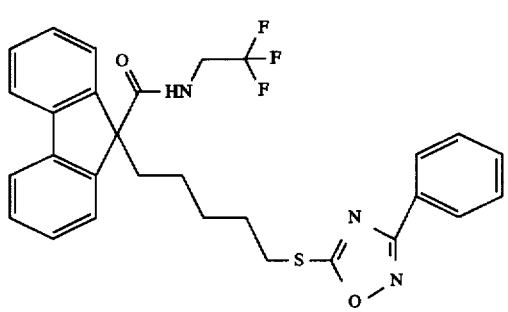 m/z 536 (M + H)

| | | |
|---|---|---|
| Example 379 | 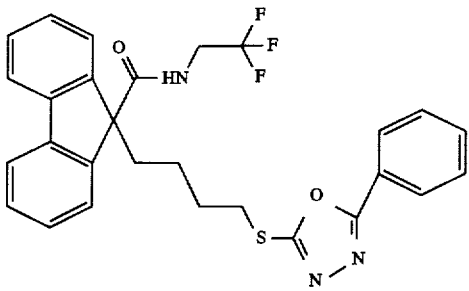 | m/z 524 (M + H) |
| Example 380 | 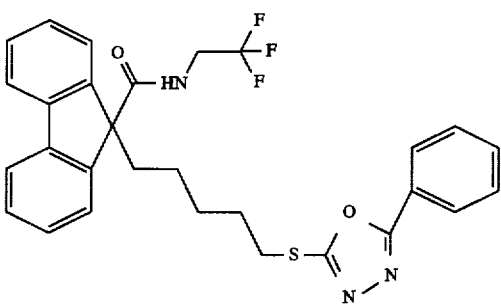 | m/z 538 (M + H) |
| Example 381 | 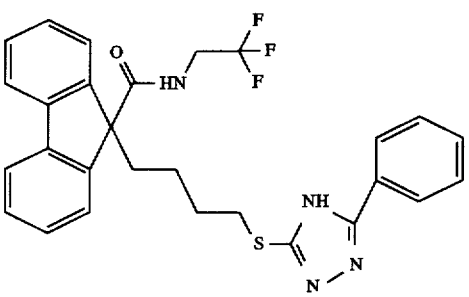 | m/z 523 (M + H) |
| Example 382 | 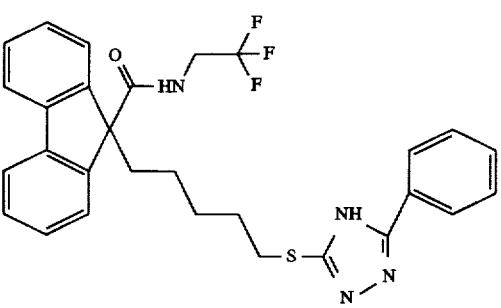 | m/z 537 (M + H) |
| Example 383 | 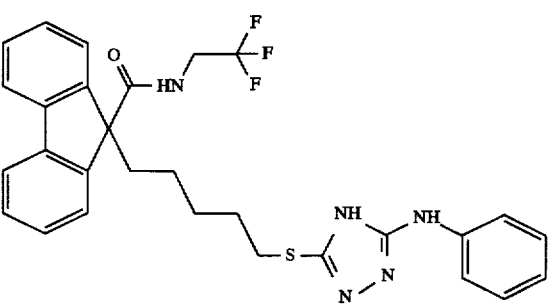 | m/z 552 (M + H) |

-continued
Example 384 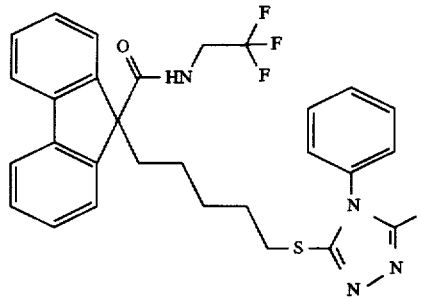 m/z 551 (M + H)
Example 385 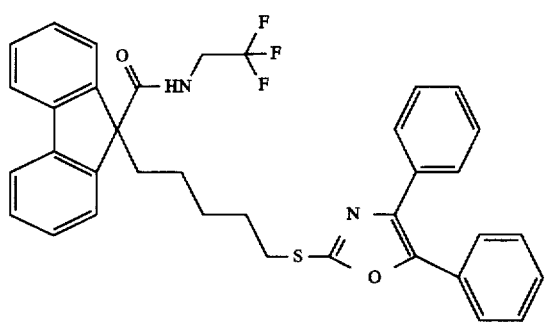 m/z 613 (M + H)
Example 386 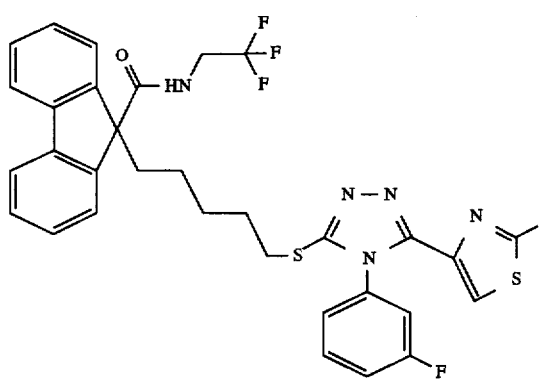 m/z 652 (M + H)
Example 387 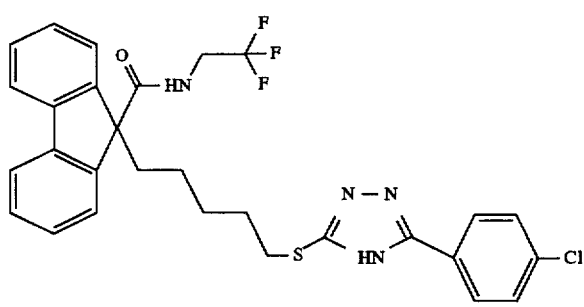 m/z 572 (M + H)
Example 388 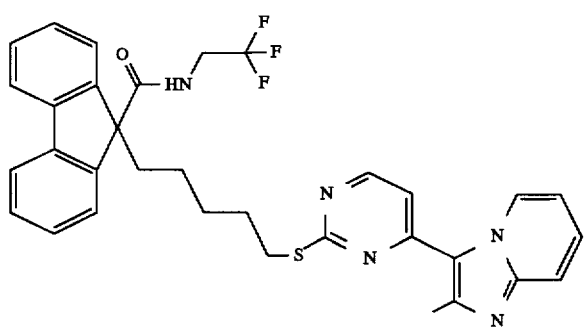 m/z 602 (M + H)

-continued
Example 389 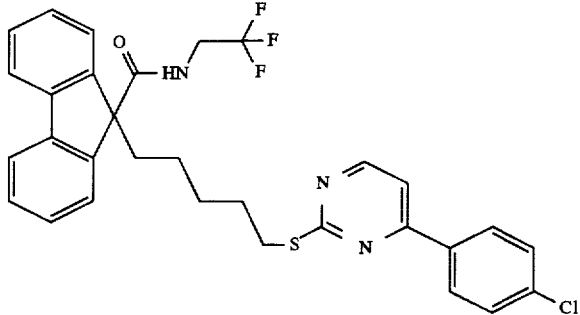 m/z 582 (M + H)
Example 390 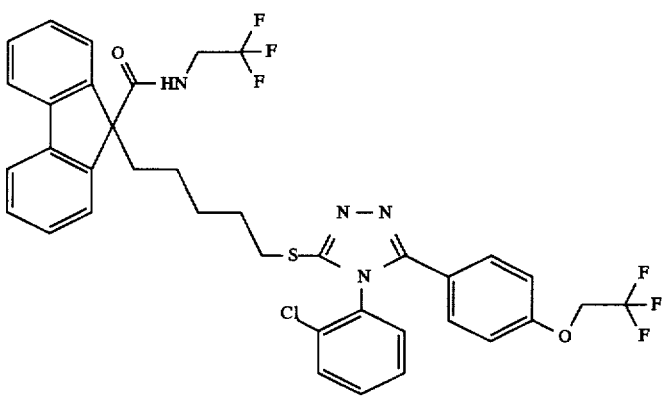 m/z 732 (M + H)
Example 391 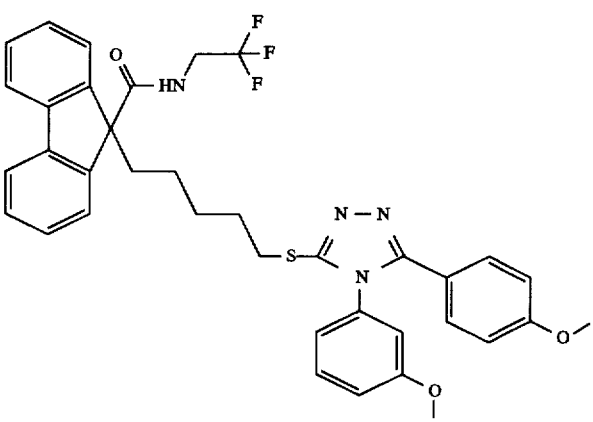 m/z 673 (M + H)
Example 392 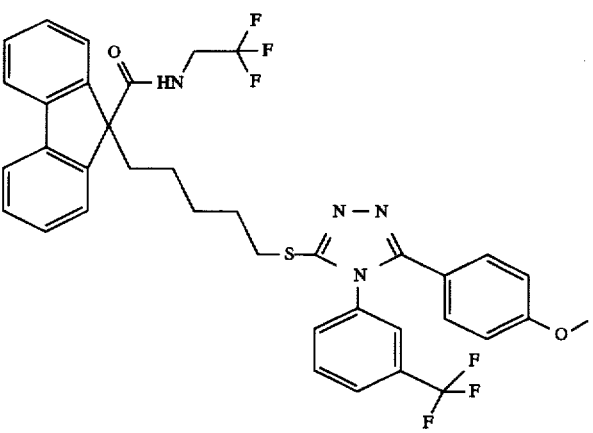 m/z 711 (M + H)

-continued
Example 393 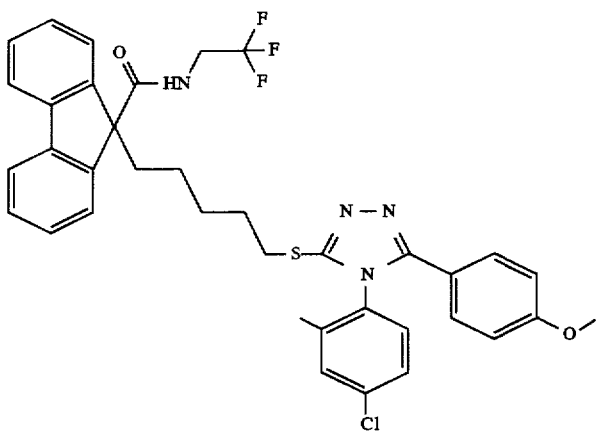 m/z 692 (M + H)
Example 394 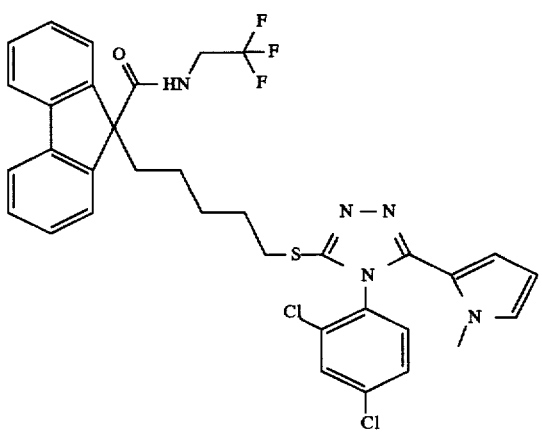 m/z 685 (M + H)
Example 395 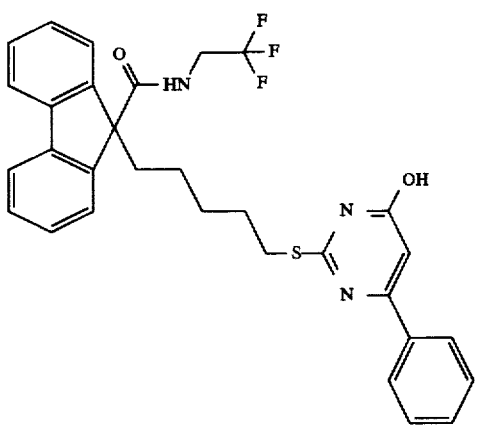 m/z 564 (M + H)

Example 396 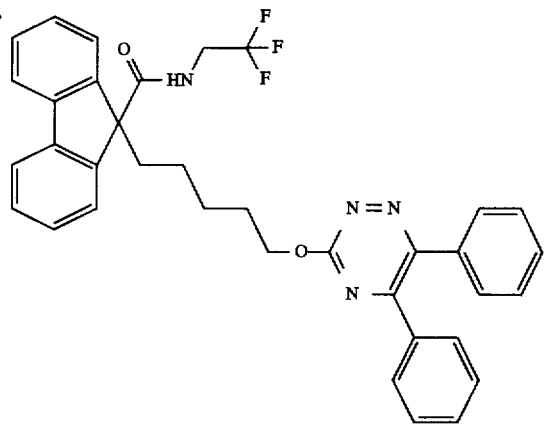 m/z 609 (M + H)
Example 397 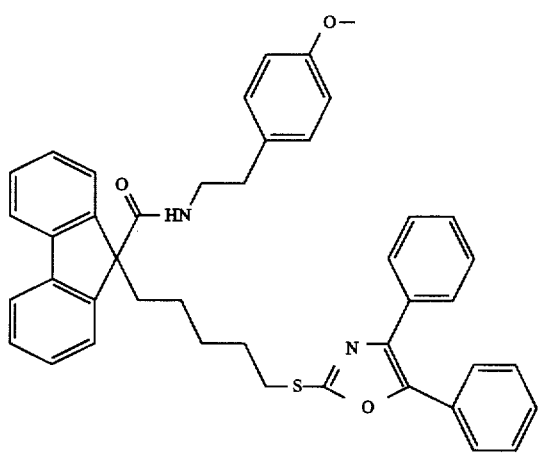 m/z 665 (M + H)
Example 398 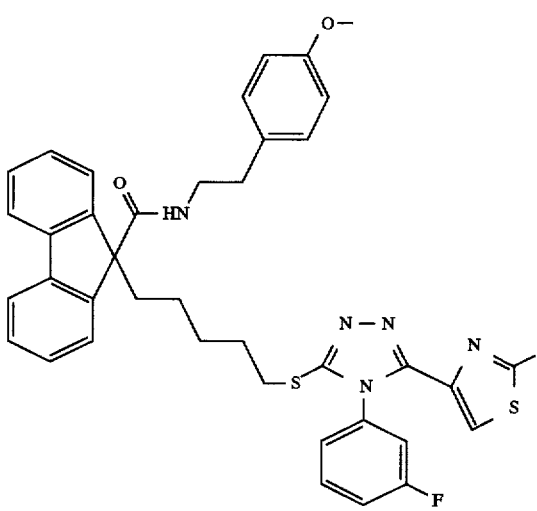 m/z 704 (M + H)

-continued
Example 399 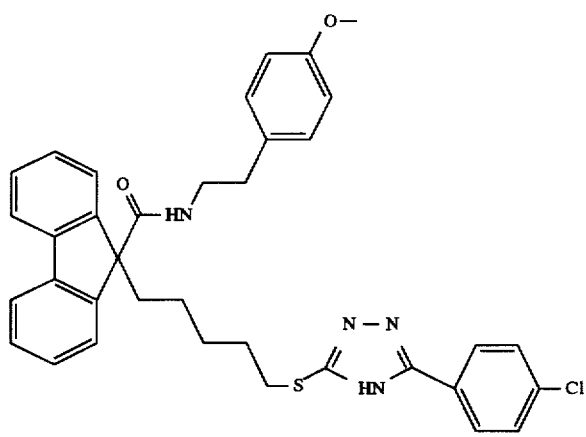 m/z 624 (M + H)
Example 400 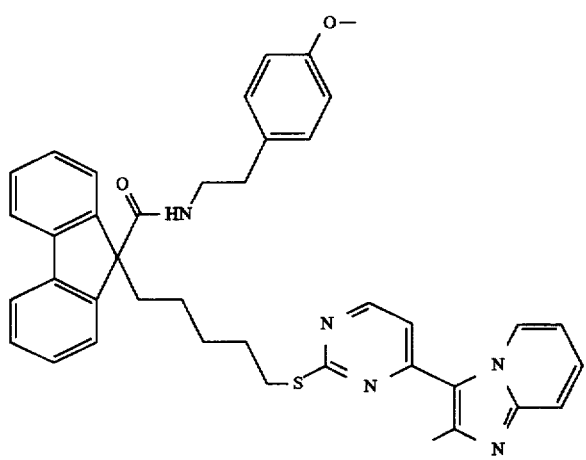 m/z 524 (M + H)
Example 401 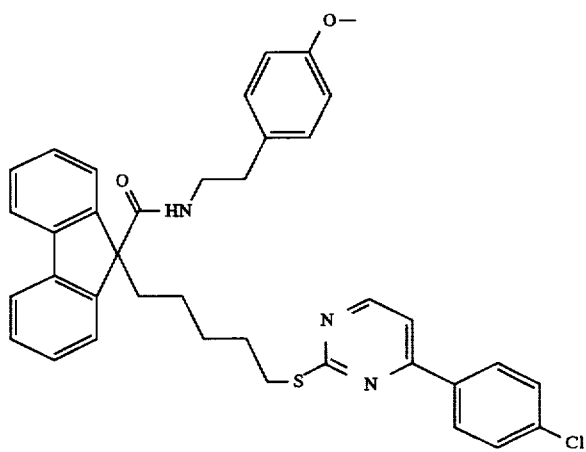 m/z 634 (M + H)

-continued
Example 402    m/z 784 (M + H)
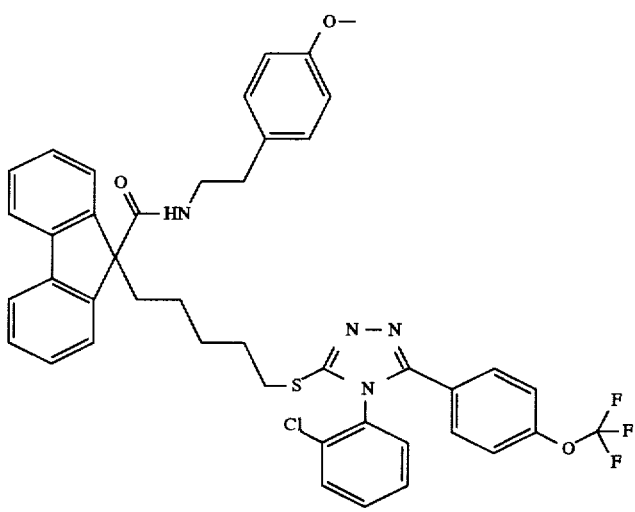
Example 403    m/z 725 (M + H)
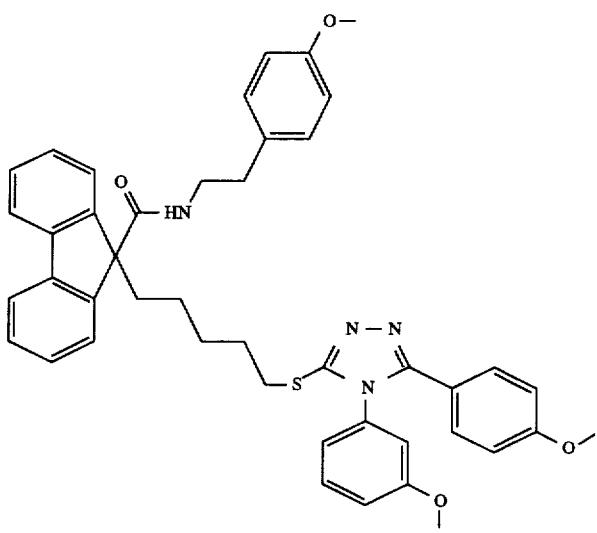
Example 404    m/z 763 (M + H)
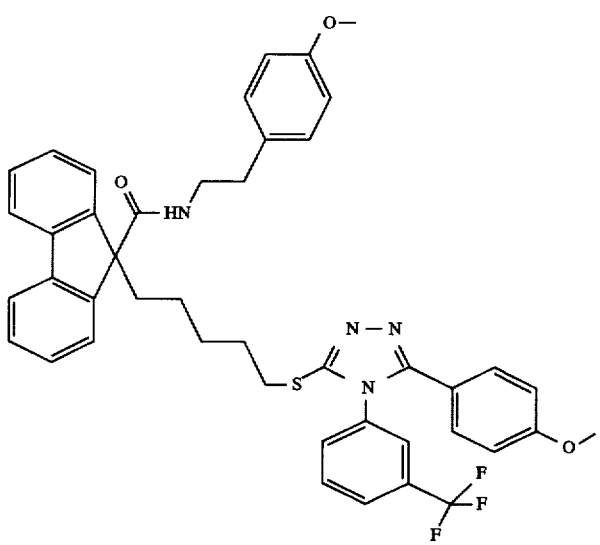

-continued
Example 405 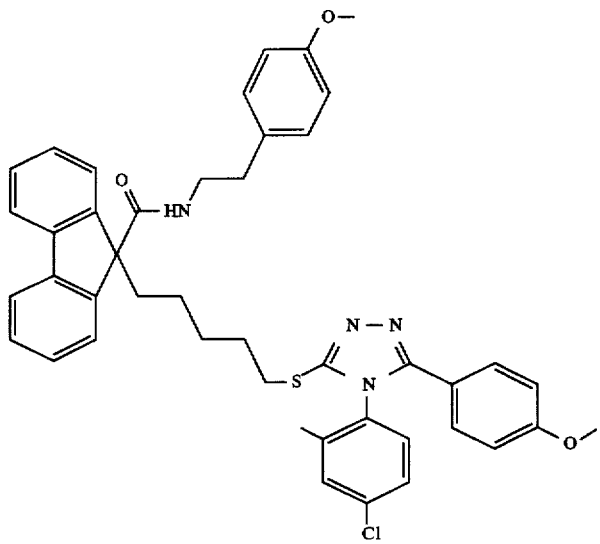 m/z 744 (M + H)
Example 406 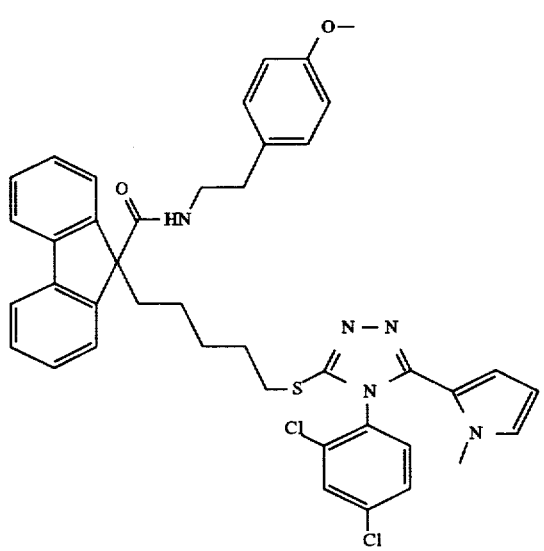 m/z 737 (M + H)
Example 407 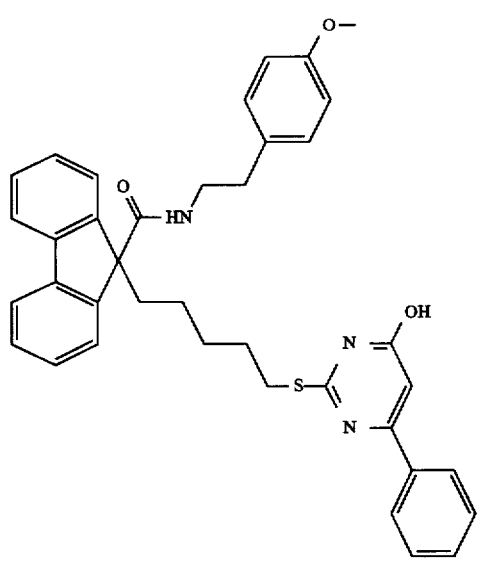 m/z 616 (M + H)

-continued

Example 408 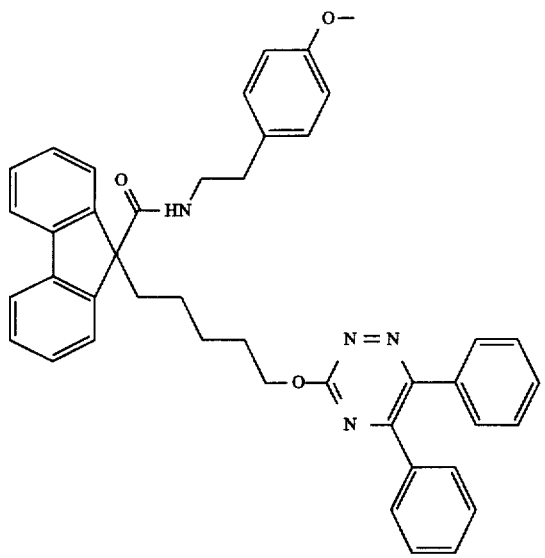 m/z 661 (M + H)

EXAMPLE 409

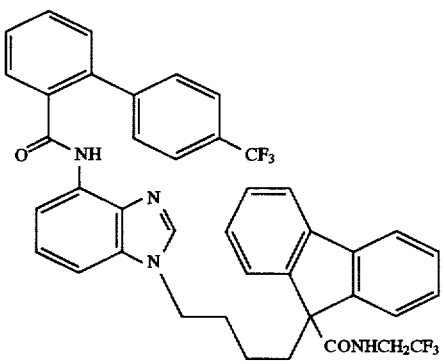

NOTE: The phrase "flash chromatography" refers to chromatography performed on EM Industries Silica Gel 60 (catalog #9385-9), 230–400 mesh under 10–20 psi of nitrogen pressure.

A.

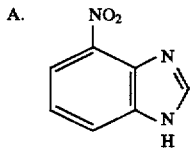

A stirred solution of 7.53 g (50.0 mmol) of

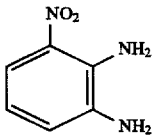

in 100 mL of 98% formic acid was set to reflux under argon for 3 hours. The reaction mixture was cooled and evaporated. The resulting solid residue was stirred with 100 mL of concentrated ammonium hydroxide for 30 min. The solids were collected, washed with 20 mL of water and dried in vacuo at 40° C. to give title compound as a white solid, 7.76 g, 95%, mp 238°–240° C.

B.

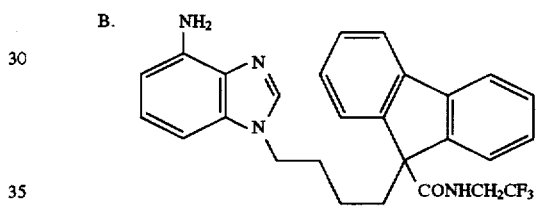

To a stirred solution of 2.50 g (15.0 mmol) of Part A compound in 30 mL of DMF at room temperature under argon was added 3.0 g (22 mmol) of potassium carbonate and, after 30 min, 6.80 g (16.0 mmol) of

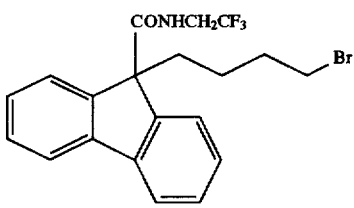

(prepared in Example 273 Part A(2)). After 24 h, the reaction mixture was quenched with 200 mL of water. The gummy solid that formed was collected, washed with water and dissolved in dichloromethane. This solution was washed twice with water, once with brine, dried (MgSO$_4$) and evaporated. The resulting semi-solid was triturated with cold ether and collected. Without characterization, a stirred slurry of this material and 200 mg of 10% palladium-on-charcoal in 50 mL of ethanol was purged with argon and evacuated three times. Hydrogen was introduced to the partially evacuated solution via a bladder. After 20 h, the reaction mixture was purged with argon, passed through a 0.45µ nylon filter, washing with dichloromethane and evaporated. The oily product was purified by flash chromatography on silica gel (5×25 cm column, 3:97 methanol/ethyl acetate) to give title compound as a white amorphous solid, 3.02 g, 42% overall yield from Part A compound.

C.

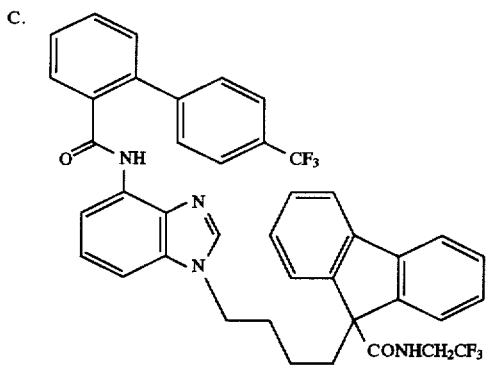

To a solution of 1.50 g (3.13 mmol) of Part B compound, 835 mg (3.13 mmol) of

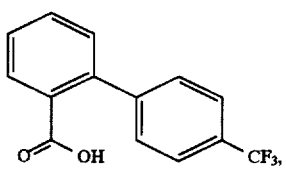

425 mg of HOAt (3.13 mmol) and 220 μL of triethylamine (1.58 mmol) in 10 mL of dichloromethane was added 680 mg (3.6 mmol) of EDAC. After 48 h, the reaction mixture was quenched with saturated sodium bicarbonate solution and extracted twice with ethyl acetate. The extracts were combined, dried (MgSO$_4$) and evaporated. Purification by flash chromatography on silica gel (5×20 cm column, 8:17 hexanes/ethyl acetate) gave title compound as a white amorphous solid, 1.43 g, 63%.

MICROANALYSIS: Calculated for $C_{41}H_{32}F_6N_4O_2$+0.5 EtOAc: C, 67.01; H, 4.71; N, 7.27; F, 14.79 Found: C, 66.95; H, 4.36; N, 7.36; F, 14.76. MS (electrospray, +ions) m/e 727 (M+H).

EXAMPLE 410

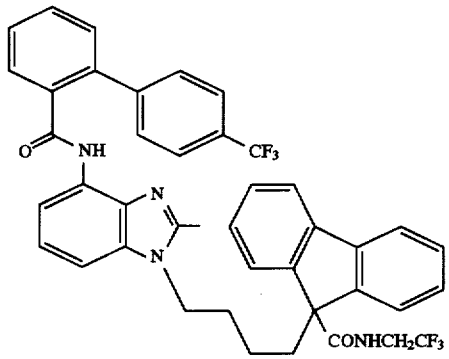

NOTE: The phrase "flash chromatography" refers to chromatography performed on EM Industries Silica Gel 60 (catalog #9385-9), 230–400 mesh under 10–20 psi of nitrogen pressure.

A.

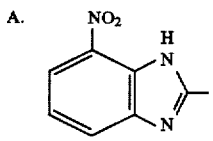

To a refluxing solution of 1.53 g (10.00 mmol) of

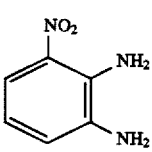

in 45 mL of ethanol and 12 mL of 5M hydrochloric acid under argon was added 2.00 g (20.0 mmol) of 2,4-pentanedione over the course of 5 min. After an additional 25 min at reflux, the reaction was cooled, neutralized with saturated sodium bicarbonate solution and partially evaporated to remove ethanol. The residual mass was extracted twice with ethyl acetate. The extracts were combined, dried (MgSO$_4$) and evaporated to give title compound as a tan solid, 1.35 g, 76%, mp 215°–217° C.

B.

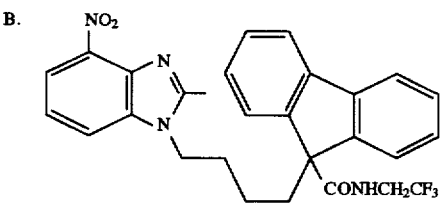

To a stirred slurry of 1.00 g of Part A compound (5.64 mmol) in 10 mL of DMF at room temperature under argon was added 1.00 g (7.2 mmol) of potassium carbonate. After 30 min, 2.55 g (6.0 mmol) of

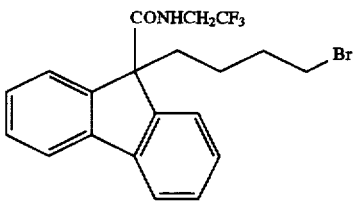

(prepared in Example 273 Part A(2)) was added and the reaction stirred for 86 h. The reaction mixture was quenched with 30 mL of water. The resulting solids were filtered, washed with water and dissolved in dichloromethane. The organic extract was washed with water, dried (MgSO$_4$) and evaporated onto 10 g of silica gel. Purification by flash chromatography (5×25 cm column, 3:7 ethyl acetate/dichloromethane) gave title compound as a white solid, mp 187°–189° C., 2.03 g, 69%.

C.

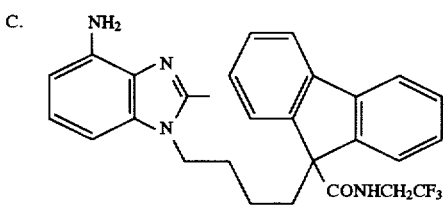

A stirred slurry of 1.00 g (1.91 mmol) of Part B compound and 200 mg of 10% palladium-on-charcoal in 25 mL of ethanol was purged with argon and evacuated three times. Hydrogen was introduced to the partially evacuated solution via a bladder. After 14 h, the reaction mixture was purged with argon and passed through a 0.45μ nylon filter, washing with dichloromethane. The filtrate was evaporated and then re-evaporated twice from dichloromethane to give title compound as a white foam. The material was used in the next reaction without purification or characterization.

D.

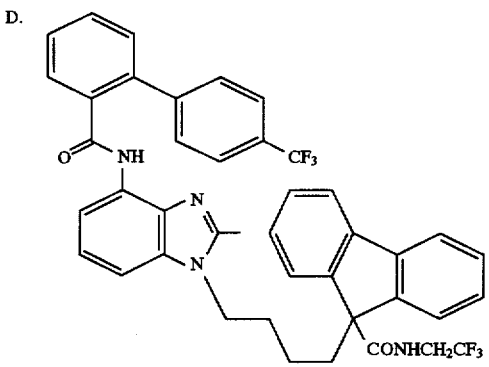

To all of Part C compound, was added 508 mg (1.90 mmol) of

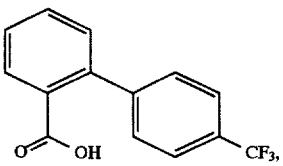

260 mg of HOAt (1.91 mmol) and 132 μL of triethylamine (0.95 mmol) in 10 mL of dichloromethane was added 230 mg (2.2 mmol) of EDAC. After 70 h, the reaction mixture was quenched with saturated sodium bicarbonate solution and extracted twice with dichloromethane. The extracts were combined, dried (MgSO$_4$) and evaporated. Purification by flash chromatography on silica gel (5×20 cm column, 1:4 ether/dichloromethane) gave title compound as a white solid, 1.10 g, 78%, mp 110°–112° C.

MICROANALYSIS: Calculated for $C_{42}H_{34}F_6N_4O_2$: C, 68.10; H, 4.63; N, 7.56; F, 15.39 Found: C, 67.82; H, 4.69; N, 7.31; F, 15.44. MS (electrospray, +ions) m/e 741 (M+H).

EXAMPLE 411

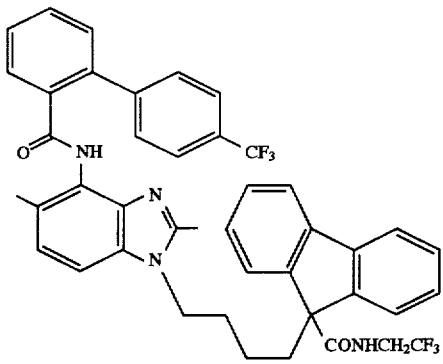

Preparation of compounds Parts A, B and C were by modifications of the procedures found in the following references:

1. S. Grivas, W. Tian, E. Ronne, S. Lindström and K. Olsson; *Acta Chem. Scand.*, 47 521 (1993);
2. W. Tian and S. Grivas; *Synthesis* 29 1305 (1992).

NOTE: The phrase "flash chromatography" refers to chromatography performed on EM Industries Silica Gel 60 (catalog #9385-9), 230–400 mesh under 10–20 psi of nitrogen pressure.

A.

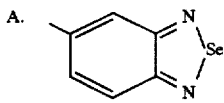

To a stirred solution of 48.95 g (0.400 mol) of

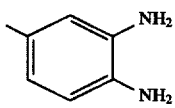

in 500 mL of 2.4M hydrochloric acid at 80° C. under argon, was added a warm solution of 88.77 g (0.800 mol) of selenium dioxide in 300 mL of water dropwise over the course of 30 min. After an additional 90 min, the reaction was cooled to room temperature and the solids were collected, washing with water. The brown solids were dried in vacuo at 50° C. to give title compound, 75.10 g, 95% yield, mp 67°–69° C.

B.

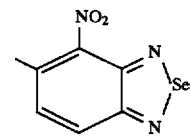

To a stirred solution of 72.00 g (0.365 mol) of Part A compound in 180 mL of 98% sulfuric acid at 10° C. was added a cold solution of 108.0 mL of 2:1 98% sulfuric acid/70% nitric acid over 1 h. The temperature of the reaction mixture was not allowed to rise above 20° C. After an additional 60 min, the reaction was poured as a thin stream into 750 g of ice with rapid stirring. The fine yellow slurry was filtered and the collected solids were washed five times with 200 mL portions of cold water. The moist cake was heated in 500 mL of ethanol to near boiling and then cooled to room temperature and the solid collected. Drying in vacuo at 50° C. gave title compound as a yellow solid, 80.70 g, 91% yield, mp 190°–192° C.

MICROANALYSIS: Calculated for $C_7H_5N_3O_2Se$: C, 34.73; H, 2.08; N, 17.36; Se, 32.61 Found: C, 34.96; H, 1.97; N, 17.35; Se, 32.59.

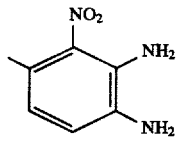

C.

To a stirred solution of hydriodic acid (25.0 mL, 57%, 189 mmol, Aldrich catalog #21,002-1, stabilized with 1.5% hypophosphorous acid) at room temperature in argon was added 5.00 g (20.7 mmol) of Part B compund. The reaction vessel was placed in an oil bath pre-heated to 50° C. and the resulting deep red solution was vigorously stirred for 2 h. After cooling to room temperature the reaction mixture was poured into a stirred slurry of 24 g (0.2 mol) of sodium hydrogen sulfite in 50 mL of water. The resulting light yellow slurry was treated with an ice-cold solution of sodium hydroxide (7.5 g, 188 mmol) in 50 mL of water. Additional 6M sodium hydroxide was added until the aqueous slurry was brought to pH 8. The resulting deep red slurry was filtered and the filtrate extracted three times with 200 mL portions of chloroform. The solids from the filtration were dissolved in 300 mL of chloroform and washed once with 50 mL of water. The organic extracts were combined, dried ($Na_2SO_4$) and evaporated to give title compound as a deep red solid, 3.04 g, 88% yield, mp 132°–133° C.

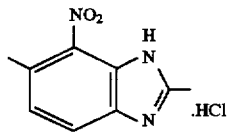

D.

To a refluxing solution of 1.00 g (6.00 mmol) of Part C compound in 27 mL of ethanol and 7.2 mL of 5M hydrochloric acid under argon was added 1.20 g (12.0 mmol) of 2,4-pentanedione over the course of 5 min. After an additional 60 min at reflux, the reaction was cooled and partially evaporated to remove ethanol. The resulting precipitate was filtered, washed with water and dried in vacuo at 40° C. to give title compound as a tan solid, 1.12 g, 98%, mp 232°–234° C.

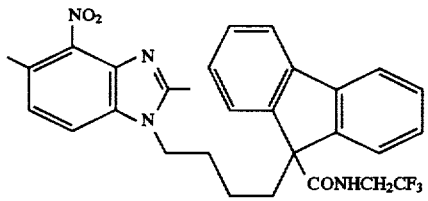

E.

To a stirred slurry of 1.80 g of the free base of Part D compound (9.41 mmol) in 15 mL of DMF at room temperature under argon was added 1.75 g (33 mmol) of potassium carbonate. After 1 h, 4.26 g (10.0 mmol) of

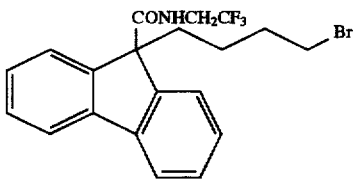

(prepared in Example 273 Part A(2)) was added and the reaction stirred for 86 h. The reaction mixture was quenched with 30 mL of water. The liquids were decanted away from the formed gummy solid, which was then washed with water. The semi-solid residue was triturated with 40 mL of ether. The resulting granular solid was chilled and filtered. The collected solid cake was washed with water, transferred to a round bottom flask and evaporated from toluene. The dried residual solid was triturated with hot ethyl acetate and filtered to give 4.02 g of title compound (80%) as a white solid, mp 181°–183° C. Analytical HPLC indicated that the compound was 98.7% pure.

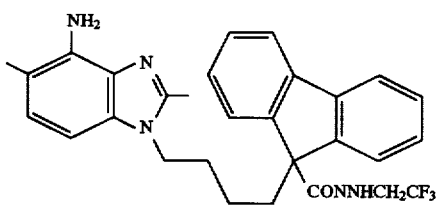

F.

A stirred slurry of 1.05 g (1.96 mmol) of Part E compound and 200 mg of 10% palladium-on-charcoal in 40 mL of ethanol was purged with argon and evacuated three times. Hydrogen was introduced to the partially evacuated solution via a bladder. After 14 h, the reaction mixture was purged with argon and passed through a 0.45µ nylon filter, washing with dichloromethane. The filtrate was evaporated and then re-evaporated twice from dichloromethane to give title compound as a white foam, 0.958 g, 99%.

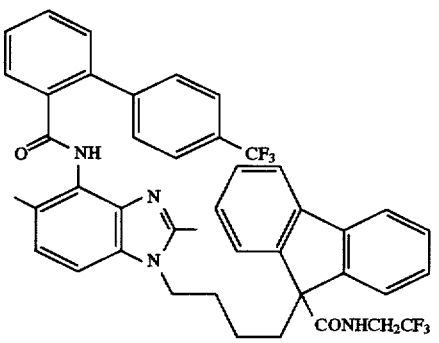

G.

To a solution of 536 mg (1.00 mmol) of Part F compound, 270 mg (1.02 mmol) of

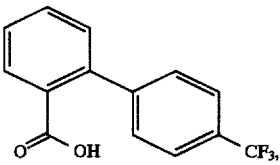

136 mg of HOAt (1.00 mmol) and 70 µL of triethylamine (0.5 mmol) in 2 mL of dichloromethane was added 230 mg (1.2 mmol) of EDAC. After 70 h, the reaction mixture was quenched with saturated sodium bicarbonate solution and extracted twice with dichloromethane. The extracts were combined, dried ($MgSO_4$) and evaporated. Purification by flash chromatography on silica gel (5×20 cm column, 1:9 hexanes/ethyl acetate) gave title compound as a white amorphous solid, 440 mg, 58%.

MICROANALYSIS: Calculated for $C_{43}H_{36}F_6N_4O_2$+1.4 $H_2O$+0.2 EtOAc: C, 65.96; H, 5.11; N, 7.02 Found: C, 65.95; H, 4.72; N, 7.08. MS (electrospray, + ions) m/e 755 (M+H).

237

Preparation of G [ALTERNATIVE]:
To a stirred slurry of 1.72 g (6.47 mmol) of

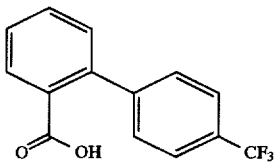

in 15 mL of dichloromethane (protected from atmospheric moisture by a Drierite-filled tube) was added 0.85 mL (9.74 mmol) of oxalyl chloride and then 0.1 mL of DMF. Gas evolves and, within a few minutes, a colorless solution formed. After 1 h, IR indicated that complete reaction had occurred. The reaction was evaporated twice from dichloromethane and then rediluted with 10 mL of dichloromethane. This solution was added dropwise to a solution of 3.21 g of Part F compound and 1.00 mL (7.17 mmol) of triethylamine at 0° C. under argon. Total addition took 20 min and then the reaction was warmed to room temperature. After 90 min, the reaction mixture was quenched with saturated sodium bicarbonate solution and extracted twice with dichloromethane. The extracts were combined, dried (MgSO$_4$) and evaporated. Recrystallization from ethyl acetate/hexanes provided title compound as a white solid, mp 126°–128° C., 3.86 g, 81% yield.

EXAMPLE 412

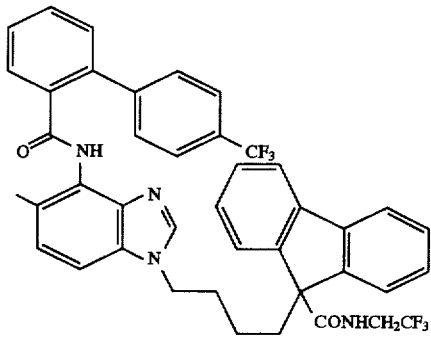

NOTE: The phrase "flash chromatography" refers to chromatography performed on EM Industries Silica Gel 60 (catalog #9385-9), 230–400 mesh under 10–20 psi of nitrogen pressure.

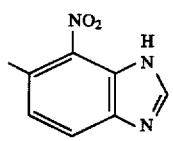   A.

A refluxing solution of 1.586 g (9.49 mmol) of Example 411 Part C in 19 mL of 98% formic acid under argon was stirred for 90 min. The reaction mixture was cooled and evaporated. The syrupy residue was cautiously treated with 20 mL of concentrated ammonium hydroxide solution and stirred for 15 min. The resulting tan solid was collected, washed with 20 mL of cold water and dried in vacuo at 40° C. to give title compound as a tan solid, 1.63 g, 97%, mp 237°–239° C.

MICROANALYSIS: Calculated for C$_8$H$_7$N$_3$O$_2$+0.12 H$_2$O: C, 53.58; H, 4.07; N, 23.43 Found: C, 53.66; H, 3.88; N, 23.62.

238

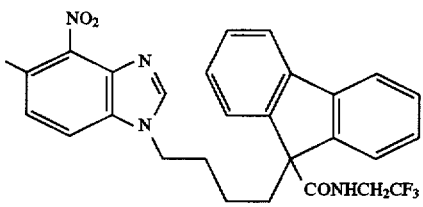   B.

To a stirred slurry of 1.587 g of Part A compound (8.96 mmol) in 15 mL of DMF at room temperature under argon was added 1.50 g (10.9 mmol) of potassium carbonate. After 1 h, 4.26 g (10.0 mmol) of

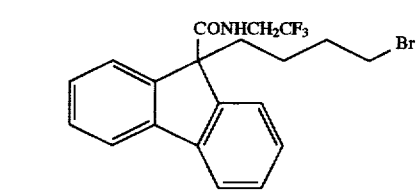

(prepared in Example 273 Part A(2)) was added and the reaction stirred for 20 h. The reaction mixture was quenched with water. The liquids were decanted away from the formed gummy solid, which was then washed with water. The semi-solid residue was dissolved in ethyl acetate, washed twice with water, once with brine and dried (MgSO$_4$). Two purifications by flash chromatography on silica gel (5×20 cm column, 57:43 ethyl acetate/hexanes) gave 3.05 g of title compound (45%) as a white amorphous solid.

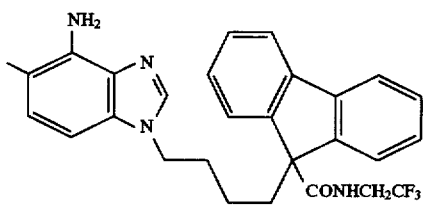   C.

A stirred slurry of 500 mg (0.96 mmol) of Part B compound and 200 mg of 10% palladium-on-charcoal in 20 mL of ethanol was purged with argon and evacuated three times. Hydrogen was introduced to the partially evacuated solution via a bladder. After 14 h, the reaction mixture was purged with argon and passed through a 0.45μ nylon filter, washing with dichloromethane. The filtrate was evaporated and then re-evaporated twice from dichloromethane to give title compound as a white foam, 0.455 g, 97%.

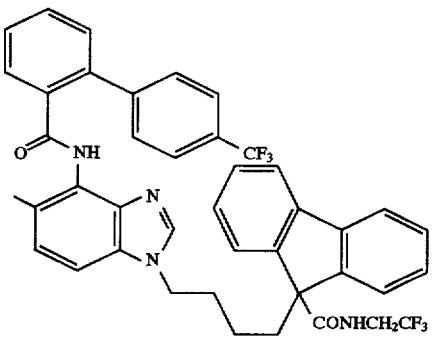   D.

To a solution of 411 mg (0.834 mmol) of Part C compound, 222 mg (0.85 mmol) of

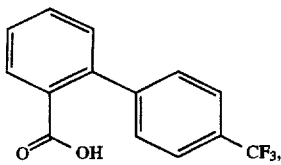

114 mg of HOAt (0.838 mmol) and 58 μL of triethylamine (0.4 mmol) in 4 mL of dichloromethane was added 190 mg (1.0 mmol) of EDAC. After 66 h, the reaction mixture was quenched with saturated sodium bicarbonate solution and extracted twice with dichloromethane. The extracts were combined, dried (MgSO$_4$) and evaporated. Purification by flash chromatography on silica gel (5×20 cm column, 2 L 1:4 hexanes/ethyl acetate, then 1:5 hexanes/ethyl acetate) gave title compound as a white amorphous solid, 258 mg, 42%.

MICROANALYSIS: Calculated for $C_{42}H_{34}F_6N_4O_2+0.5\ H_2O+0.5$ EtOAc: C, 66.58; H, 4.95; N, 7.06 Found: C, 66.63; H, 4.67; N, 7.28. MS (electrospray, + ions) m/e 741 (M+H).

EXAMPLE 413

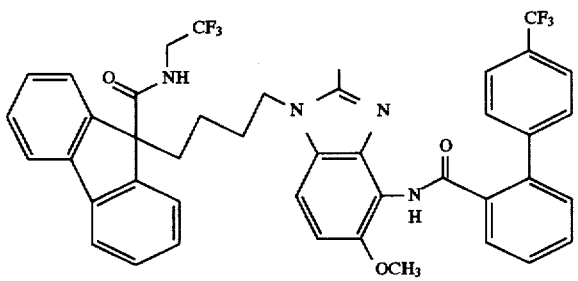

Preparation of compounds of Parts A, B and C were by modifications of the procedures found in the following references:

1. S. Grivas, W. Tian, E. Ronne, S. Lindstrom and K. Olsson; Acta Cehm. Scand., 47 521 (1993).
2. W. Tian and S. Grivas; Synthesis 29 1305 (1992).

NOTE: The phrase "flash chromatography" refers to chromatography performed on EM Industries Silica Gel 60 (catalog #9385-9), 230–400 mesh under 10–20 psi of nitrogen pressure.

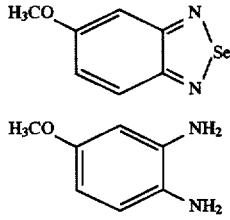

To a stirred solution of (5.30 g, 25.0 mmol) in 75.0 mL of 1M HCl at 80° C. under argon, was added a solution of selenium dioxide (5.55 g, 50.0 mmol) in 37.5 mL of water dropwise over the course of 0.5 h. Some solid was formed. The reaction was stirred an additional 0.5 h at 80° C. and then cooled to 0° C. The resulting solid was collected, washed with water, and dried in vacuum at 50° C. The filtrate was extracted with ethyl acetate (2×80 mL). The combined extracts were washed twice with brine, dried (Na$_2$SO$_4$) and evaporated to give additional solid. The solids were combined to provide title compound as a brown solid, 5.09 g (95.5%), mp 108°–9° C.

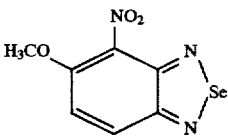

To a stirred solution of Part A compound (4.70 g, 22.1 mmol) in 98% H$_2$SO$_4$ (40 mL) at 5° C. was added a cold solution of 98% H$_2$SO$_4$ (8 mL) and 70% HNO$_3$ (4 mL), dropwise over 0.5 h. After an additional 1 h at 5° C., the reaction mixture was poured into ice (40 g). Some yellow solid was formed. The solution was neutralized to pH 10–11 by 1N NaOH, extracted with ethyl acetate, washed twice with brine, dried (Na$_2$SO$_4$) and evaporated to give title compound, 5.25 g (92.0%) as a yellow solid (mp 234°–5° C.).

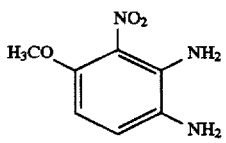

To a stirred solution of Part B compound (5.10 g, 19.8 mmol) in concentrated HCl (60 mL) at room temperature under argon was added a solution of 57% HI (6 mL), dropwise over 15 minutes. After an additional 2 h, a solution of 5% NaHSO$_3$ (60 mL) was added and the reaction mixture was heated to 80° C. for 0.5 h. After cooling to room temperature, the dark mixture was added to ethyl acetate (200 mL) and stirred for 0.5 h. The mixture was neutralized to pH 9–10 by 4N NaOH at 5° C. and filtered through Celite. The ethyl acetate layer was washed twice with brine, dried (Na$_2$SO$_4$) and evaporated to give title compound, 2.07 g (57.1%) as a red solid (mp 114°–6° C.).

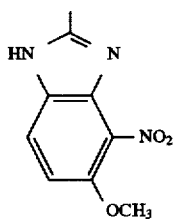

To a stirred refluxing solution of Part C compound (1.00 g, 5.46 mmol) in 5M HCl (6 mL) and EtOH (40 mL) under argon was added 2,4-pentanedione (1.10 g, 11.0 mmol). After refluxing 0.5 h, the reaction mixture was cooled in an ice bath and neutralized with saturated NaHCO$_3$ solution. The resulting yellow precipitate was filtered, washed with water and ethyl ether. The resulting solid was then dissolved in hot ethyl acetate, dried (Na$_2$SO$_4$) and evaporated to give title compound, 0.827 g (73.0%) as a yellow solid (mp 200°–1° C.).

MICROANALYSIS: Calculated for $C_9H_9N_3O_3+0.36Et_2O$: C, 53.62; H, 5.43; N, 17.97 Found: C, 54.04; H, 5.08; N, 18.35.

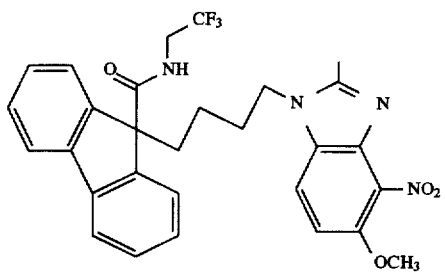

A solution of Part D compound (0.800 g, 3.86 mmol) and K$_2$CO$_3$ (0.680 g, 4.94 mmol) in DMF (5 mL) under argon was stirred for 0.5 h at room temperature. To the mixture was added

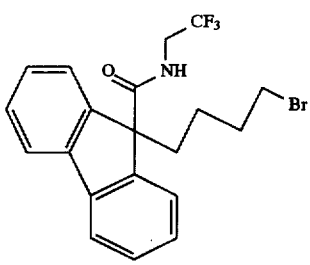

(prepared as in Example 273 Part A(2)) (1.75 g, 4.11 mmol). After 16 h, water (50 mL) was added to the reaction mixture. The resulting yellow precipitate was filtered. The solid was then dissolved in CH$_2$Cl$_2$, washed with water, dried (Na$_2$SO$_4$) and evaporated. The residue was purified by flash chromatography on silica gel (5×18 cm column, ethyl acetate) to give title compound, 1.42 g (66.6%) as a yellow solid (mp 87°–9° C.).

MICROANALYSIS: Calculated for C$_{29}$H$_{27}$F$_3$N$_4$O$_4$+ 0.25AcOEt: C, 62.71; H, 5.09; N, 9.75; F, 9.92 Found: C, 62.33; H, 4.86; N, 9.67; F, 10.17.

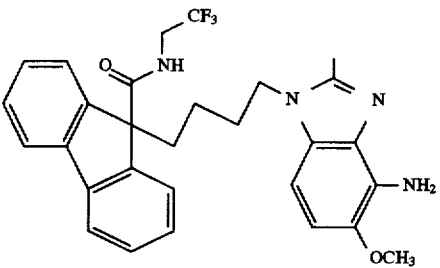

To 10% palladium-on-charcoal (0.230 g, 9.56% mmol) under argon was added EtOH (35 mL) and Part E compound (1.25 g, 2.26 mmol). Hydrogen was introduced to the solution via a bladder at room temperature. After stirring 16 h, the reaction mixture was filtered through Celite and concentrated to give title compound, 1.09 g (92.4%) as a light yellow solid (mp 80°–1° C.).

MICROANALYSIS: Calculated for C$_{29}$H$_{29}$F$_3$N$_4$O$_2$+0.55 H$_2$O: C, 65.41; H, 5.70; N, 10.52; F, 10.70 Found: C, 65.12; H, 5.56; N, 10.72; F, 11.15.

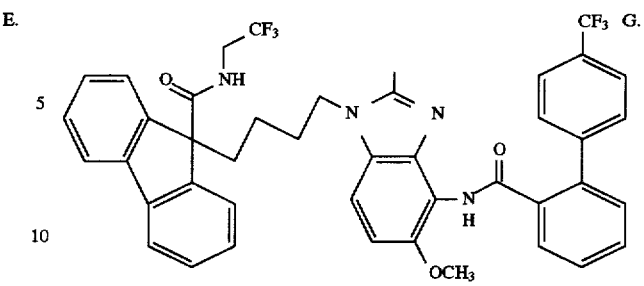

To a solution of Part F compound (0.870 g, 1.58 mmol),

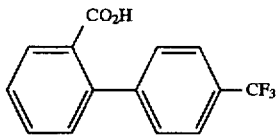

(0.420 g, 1.58 mmol) and HOAt (0.240 g, 1.74 mmol) in CH$_2$Cl$_2$ (2 mL) under argon was added EDAC (0.330 g, 1.74 mmol) and Et$_3$N (0.080 g, 0.790 mmol). After stirring 24 h at room temperature, additional CH$_2$Cl$_2$ (1 mL) was added and stirring was continued for an additional 12 h. Saturated NaHCO$_3$ solution was added to the reaction mixture which was extracted with ethyl acetate, washed with water, dried (Na$_2$SO$_4$) and concentrated. The residue was purified by flash chromatography on silica gel (5×18 cm column, ethyl acetate followed by 1:99 methanol/ethyl acetate) to give title compound, 0.512 g (42.0%) as a white amorphous solid (mp 132°–4° C.).

MICROANALYSIS: Calculated for C$_{43}$H$_{36}$F$_6$N$_4$O$_3$+0.3 AcOEt+0.5 H$_2$O: C, 65.85; H, 4.93; N, 6.95; F, 14.14 Found: C, 65.93; H, 4.69; N, 6.90; F, 14.44.

EXAMPLE 414

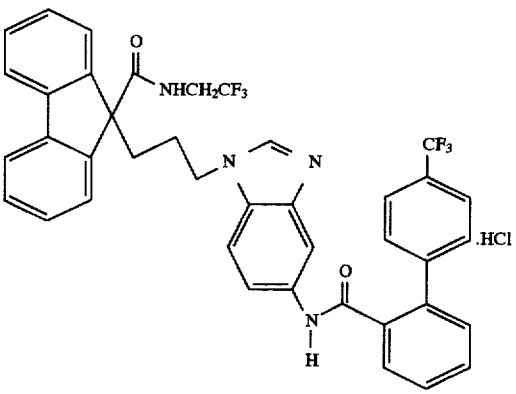

A.

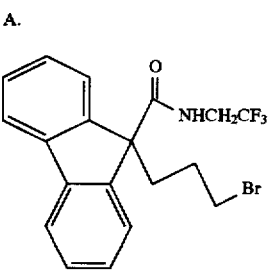

A solution of (9-fluorenecarboxylic acid (20.0 g, 92.3 mmoles) in dry THF (90 ml) was placed under vacuum for 20 minutes to remove dissolved oxygen then cannulated into a cooled (0° C., ice-salt bath) solution of 1.0M lithium t-butoxide in THF (212 ml, 2.23 eq). The ice-bath was removed and the reaction mixture stirred at room temperature for 1.0 hr. after which the green suspension was treated with 1,3-dibromopropane (18.5 ml, 1.96 eq) via syringe. The dark mixture was stirred at room temperature for 19 hours then partitioned between 30% Heptane in EtOAc (300 ml) and $H_2O$ (250 ml), re-extracting the aqueous phase with $H_2O$ (3×70 ml). The combined aqueous extracts were acidified with 2.0N HCl to pH 2.0, extracted with $CH_2Cl_2$ (4×190 ml) and the combined $CH_2Cl_2$ extracts were dried (anhydrous $MgSO_4$), filtered, evaporated to dryness and dried in vacuo to give the crude acid as a syrup (32 g).

The acid was dissolved in dry $CH_2Cl_2$ (190 ml), cooled to 0° C. (ice-salt bath), treated with dry DMF (0.32 ml, 0.4 eq) and $(COCl)_2$ (8.2 ml, 94 mmoles), stirred at 0° C. for 5 minutes then at room temperature for 2.0 hours. Meanwhile, trifluoroethylamine hydrochloride (13.8 g, 102 mmoles) was dissolved in dry $CH_2Cl_2$ (225 ml), cooled to 0° C. (ice-salt bath), treated with $Et_3N$ (51.5 ml) and stirred for 10 minutes. The acid mixture was cannulated into the amine solution, and stirred at 0° C., allowing the reaction mixture to come to room temperature overnight. The reaction mixture was washed sequentially with $H_2O$ (2×190 ml), 1.0N HCl (320 ml), $H_2O$ (190 ml) and saturated $NaHCO_3$ (190 ml), dried (anhydrous $MgSO_4$), filtered, evaporated to dryness and dried in vacuo. The crude product mixture was chromatographed on a silica gel column (Merck, 4"×13"), eluting the column with EtOAc:Hexane (1:4) to give title compound as a solid foam (22 g, 57.8%). $R_f$ 0.38 (Silica gel; EtOAc:Hexane-1:4; UV, PMA); m.p. 106°-108° C.

B.

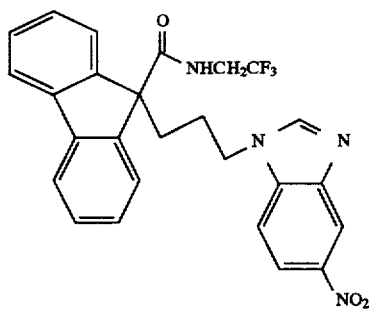

A mixture of Part A compound (2.0 g, 4.85 mmoles), 5-nitrobenzimidazole (870 mg, 5.33 mmoles), and anhydrous $K_2CO_3$ (737 mg, 5.34 mmoles) in dry DMF (7.0 ml) was stirred at room temperature for 3 days then concentrated in vacuo. The residual syrup was partitioned between EtOAc (2×50 ml) and $H_2O$ (13 ml), and the combined organic extracts were washed with $H_2O$ (3×13 ml) and brine (13 ml), dried (anhydrous $Na_2SO_4$), filtered, evaporated to dryness and dried in vacuo. The crude product mixture was triturated with hot $CH_3CN$ (2×25 ml), and filtered while hot to give a white solid (584 mg). The crude filtrate was concentrated to a solid mixture and chromatographed twice on a silica gel column (Merck, 200 g), eluting each column with $CH_2Cl_2$:EtOAc (3:1-4.0 L) to give diastereomerically enriched title compound (1.197 g, 50.3%, m.p. 207°-8° C.). TLC : $R_f$ 0.37 (Silica gel; EtOAc:$CH_2Cl_2$-6:4; UV).

C.

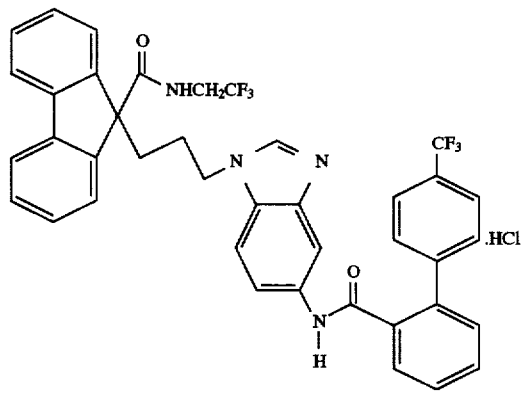

A solution of Part B compound (200 mg, 0.4 mmole) in dry $CH_3OH$ (10 ml) was treated with 10% Pd/C (40 mg) and hydrogenated (balloon) at room temperature for 20 hours. The reaction mixture was diluted with $CH_3OH$ (10 ml) and filtered through a celite pad in a millipore unit, washing the pad well with $CH_3OH$ (3×10 ml). The combined filtrates were evaporated to dryness and dried in vacuo to give the crude amine as a syrup (196 mg).

The amine was dissolved in dry $CH_2Cl_2$ (5.0 ml), treated with the 4'-(trifluoromethyl)-2-biphenylcarboxylic acid (110 mg, 0.42 mmole), HOBt·$H_2O$ (57 mg, 0.42 mmole) and EDAC (88 mg, 0.46 mmole) and stirred at room temperature for 20 hours. The reaction mixture was partitioned between EtOAc (2×15 ml) and saturated $NaHCO_3$ (3.0 ml) and the combined organic extracts were washed with $H_2O$ (3×3.0 ml) and brine (3.0 ml), dried (anhydrous $Na_2SO_4$), filtered, evaporated to dryness and dried in vacuo. The crude product mixture was chromatographed on a silica gel column (Merck, 70 g), eluting the column with EtOAc:Hexane (1:2), EtOAc and $CH_2Cl_2$:MeOH (100:3) to give the clean free base (207 mg).

This adduct (207 mg) was dissolved in dry dioxane (2.6 ml), treated with 4.0M HCl/dioxane (0.21 ml, 2.83 eq), swirled for a few minutes then diluted with dry $Et_2O$ (35 ml), scratching the solids as they formed. The supernatant was decanted and the solids washed with dry $Et_2O$ (2×15 ml) to give title compound as a solid (163.8 mg, 53.6%; m.p. 155°-165° C., shrinking commencing at 150° C.)).

Anal. Calc'd for $C_{40}H_{30}F_6N_4O_2$·HCl·0.8 $H_2O$ (Eff. Mol. Wt.=763.57): C, 62.92; H, 4.30; N, 7.34; Found: C, 62.93; H, 4.37; N, 7.11.

EXAMPLE 415

N-(2,2,2-Trifluoroethyl)-9-[3-[[2-[[[4'-(3,3,3-trifluoromethyl)[1,1'-biphenyl]-2-yl]carbonyl]-amino]-5-pyridinyl]amino]propyl]-9H-fluorene-9-carboxamide, monohydrochloride.

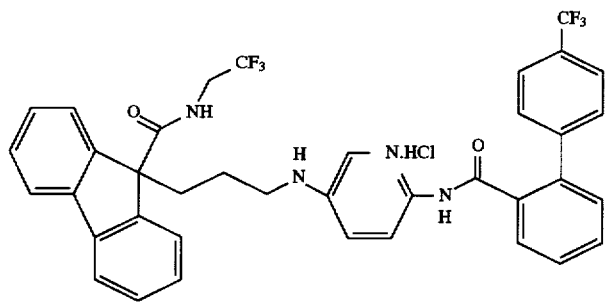

A.

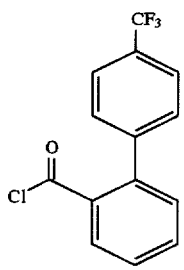

To a stirred solution of

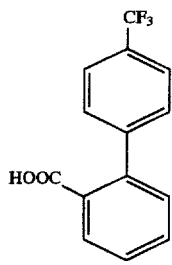

(5.32 g., 20 mmol) in 40 mL of dry CH$_2$Cl$_2$ and 40 mL of DMF at room temperature under nitrogen was slowly added 15.0 mL of 2M oxalyl chloride in CH$_2$Cl$_2$ (30 mmol). The reaction was stirred at room temperature for 2 h and concentrated to an oil, which was dried in vacuo for 2 h and then stored at –40° C. overnight to give crude title compound as an amorphous solid.

B.

-continued

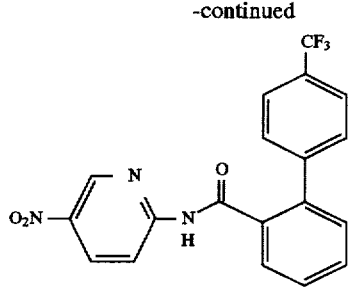

A mixture of 3.41 g (12 mmol) of Part A compound, 1.25 g (9 mmol) of

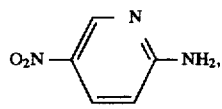

and 2.9 mL (36 mmol) of dry pyridine in 15 mL of dry THF was stirred at room temperature under argon for 20 h and filtered. Evaporation of the filtrate gave a residue which was taken up in $CH_2Cl_2$, water, and 10% $Na_2CO_3$. The $CH_2Cl_2$ was washed with dilute $Na_2CO_3$ (2x) and water (2x), dried ($Na_2SO_4$), and concentrated to a yellow gummy residue (4.72 g). Chromatography of this residue over 450 g of silica gel using $CHCl_3$, concentration, and then concentration from EtOAc afforded 2.63 g (57%) of title compound as a white solid.

C.

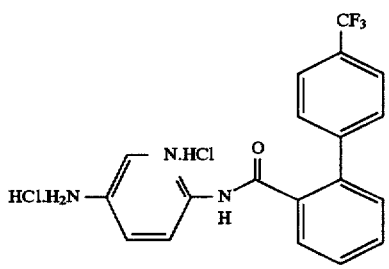

Part B compound (2.45 g, 6.33 mmol) was hydrogenated at 1 atmosphere with 350 mg of 10% Pd/C in 60 mL of glacial AcOH for 1.5 h. Concentrated HCl (1.1 mL, 13 mmol) was added, the mixture was filtered, and the filtrate was concentrated to a residual oil. Concentration of the oil from 95% EtOH and trituration of the oily residue from $Et_2O$ gave 2.41 g (89%) of title compound as a solid.

D.

-continued

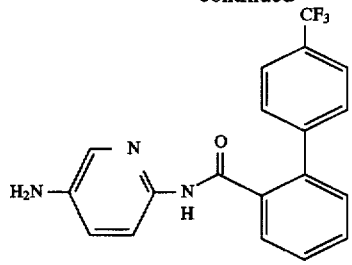

Part C compound (430 mg, 1 mmol) was shaken with $CH_2Cl_2$ and 5% $NaHCO_3$. The $CH_2Cl_2$ extract was washed with 5% $NaHCO_3$ (2x) and then water (2x), dried ($Na_2SO_4$), and concentrated to give 342 mg (96%) of title compound as a yellow foam.

D(1).

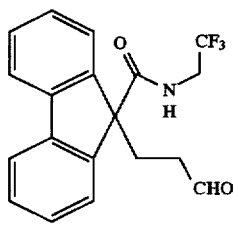

The Part D(1) compound is prepared as described in Example 296 Part A.

E.

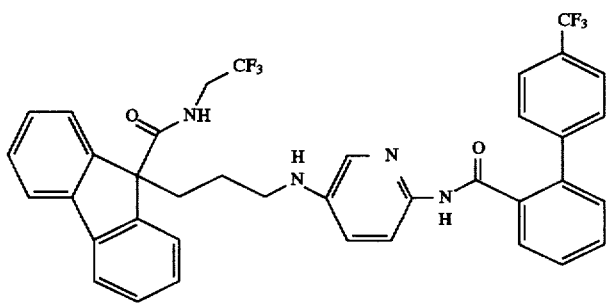

A mixture of Part D compound (342 mg, 0.96 mml), Part D(1) compound (335 mg, 0.96 mmol), glacial AcOH (0.33 mL, 5.8 mmol) and $NaBH(OAc)_3$ (610 mg, 2.88 mmol) in 6 mL of 1,2-dichloroethane was stirred at room temperature under argon for 17 h. The mixture was diluted with $CH_2Cl_2$ and the organics were washed with 5% $NaHCO_3$ (3x) and then water (2x), dried ($Na_2SO_4$) and concentrated to a foamy residue (772 mg). Chromatography of this residue over 70 g of silica gel packed in $CH_2Cl_2$-EtOAc (85:15) by eluting with this solvent and then $CH_2Cl_2$-EtOAc (80:20) afforded 329 mg (50%) of title compound as a residue.

F.

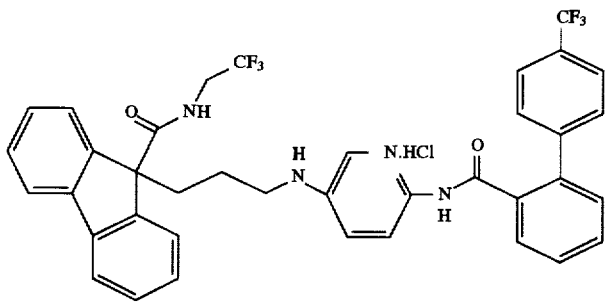

To a solution of Part E compound (320 mg, 0.46 mmol) in 4 mL of dry THF was added 0.5 mL of 4N HCl in dioxane and then Et$_2$O. The precipitate was collected, washed with Et$_2$O, and dried in vacuo at 40° C. for 1 h to give 251 mg (75%) of title compound as a pale yellow solid having mp 128°–132° C.

Anal. Calcd for C$_{38}$H$_{30}$F$_6$N$_4$O$_2$+HCl+0.75 H$_2$O+0.15 Et$_2$O: C, 61.84; H, 4.57; N, 7.47; Cl, 4.73; F, 15.20 Found: C, 61.91; H, 4.41; N, 7.40; Cl, 4.81; F, 15.48.

MS (ESI-NH$_3$, +ions) 689 (M+H); (–ions) 687 (M-H). TLC (silica gel): Rf=0.50, CH$_2$Cl$_2$: CH$_3$OH (19:1).

EXAMPLE 416–417

N-(2,2,2-Trifluoroethyl)-9-[3-[[5-[[[4'-(trifluoromethyl)[1,1'-biphenyl]-2-yl]carbonyl]amino]-2-pyridinyl]oxy]propyl]-9H-fluorene-9-carboxamide, trifluoroacetate

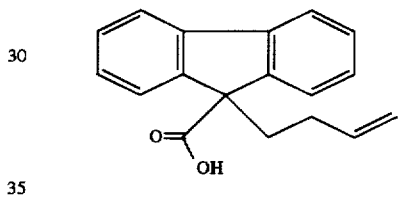

A.

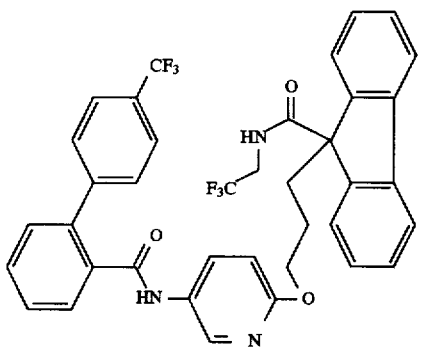

To a solution of the 9H-fluorene carboxylic acid (8.0 g, 38 mmol) in THF at 0° C. (150 ml) was added a 1M solution of lithium tert-butoxide (76 ml, 76 mmol) in THF. Following the addition of base, the reaction mixture was stirred vigorously at RT for 2h. The reaction mixture was treated with 1-bromo-3-butene (8.00 g, 60 mmol) and stirred overnight. TLC indicated a trace of starting acid was still present. The reaction mixture was treated with an additional 5 mL (5 mmol) of lithium tert-butoxide and the mixture stirred overnight. The mixture was quenched with NH$_4$Cl solution and the pH adjusted to 2 with KHSO$_4$ solution. The mixture was diluted with ethyl acetate (400 mL) and washed with water. The organic layer was dried (MgSO$_4$), and the solvent was removed in vacuo to give an off-white foam which was partially purified by trituration with hexane to give a white solid (9.5 g) of the structure

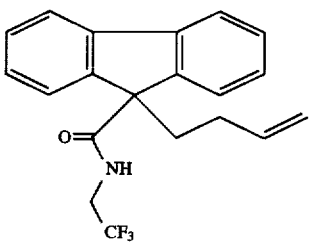

To a solution of the above crude acid (9.5 g, 36 mmol) in dichloromethane (200 mL) was added a 2M solution of oxalyl chloride (23 ml, 46 mmol) in dichloromethane followed by a 2 drops of DMF. The reaction (bubbled vigorously) was stirred under argon at RT for 2 h. The solvent was evaporated in vacuo and the residue was dissolved in THF (150 ml). The mixture was treated with CF$_3$CH$_2$NH$_2$ HCl salt (5.4 g, 40 mmol) and triethylamine (8.00 g, 78 mmol) and stirred at RT for 6 h. The reaction mass was diluted with ethyl acetate (300 mL) and washed 1N HCl and saturated K$_2$CO$_3$ solution. The organic layer was dried (MgSO$_4$), and the solvent was removed in vacuo to give an off-white solid which was purified by recrystalization from methanol to give 4.5 g of title compound as a white solid. The filtrate was concentrated and the residue purified by flash column chromatography to give an additional 3.5 g of title compound as a white solid (overall yield 8.0 g, 64%).

B.

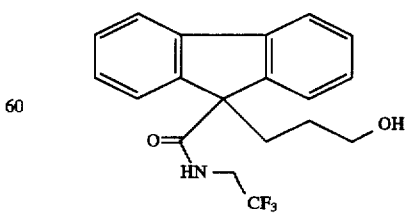

A solution of Part A compound (3.00 g, 8.7 mmol) in a mixture of 50 mL 1:1 dichloromethane/methanol at –78° C.

was treated with a stream of ozone in oxygen for 35 min. The mixture turned light gray and TLC indicated that the starting olefin was consumed. The reaction mixture was treated with NaBH₄ pellets (1.03 g, 27 mmol) and stirred overnight at RT. The mixture was quenched with 50 mL of NH₄Cl solution and 150 mL ethyl acetate. The layers were equilibrated and separated. The organic fraction was dried (MgSO₄) and concentrated. The residue was purified by flash column chromatography on silica gel with 1:1 ethyl acetate/hexanes to give 2.6 g (85%) of title compound as a white solid.

mp: 112°–114° C.

C.

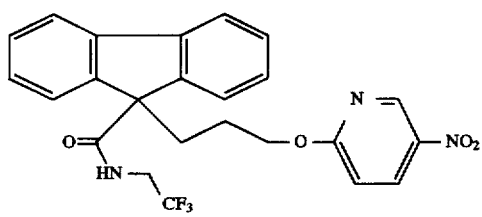

A solution of Part B compound (2.50 g, 7.16 mmol) in THF was treated with NaH (192 mg, 8 mmol) at 0° C. After 1 h the alkoxide was treated with 1.30 g (8 mmol) of 2-bromo-5-nitropyridine. The mixture was stirred at RT overnight and an additional 36 mg (1.5 mmol) of NaH was added. After stirring for an additional 4 hours the reaction mixture was quenched with NaHCO₃ solution and extracted with ethyl acetate. The organic fraction was dried (MgSO₄) and concentrated. The residue was purified by flash column chromatography on silica gel with 6:12:1 ethyl acetate/hexanes/dichloromethane to give 3.12 g (92%) of title compound as a white solid.

D.

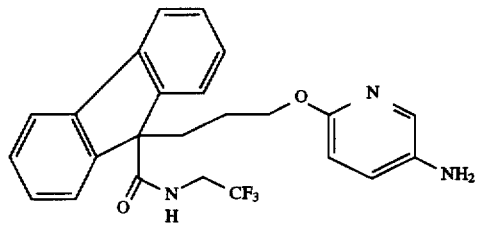

A solution of Part C compound (3.00 g, 6.4 mmol) in ethyl acetate (50 mL) was treated with 200 mg of 10% Pd/carbon and placed under an atmosphere of H₂ (balloon pressure). After stirring overnight the mixture was filtered through a pad of celite and the filtrate concentrated to title compound in the form of a thick oil (3.00 g, =100%).

E.

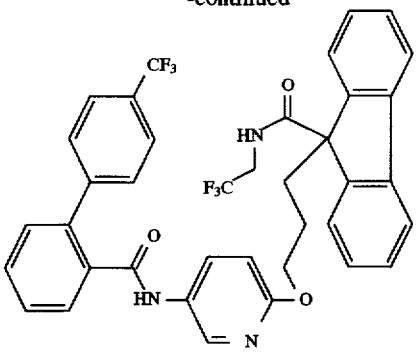

The crude Part D amine (3.0 g, 6.3 mmol) was stripped from toluene (2×20 mL) and pumped to ensure complete drying. The amine was diluted with 100 mL of THF and cooled to 0° C. The solution was treated with the Example 415 Part A acid chloride (1.75 g, 6.1 mmol) in 10 mL of dichloromethane. The mixture was then treated with triethylamine (0.64 g, 6.3 mmol) and a slurry resulted. The thick mixture was stirred for 1 hour at RT and diluted with 50 mL NaHCO₃ solution and 100 mL of ethyl acetate. The layers were equilibrated and separated. The organic fraction was dried (MgSO₄), concentrated and purified by flash column chromatography on silica gel with 3:7 ethyl acetate/hexanes followed by 1:1 ethyl acetate/hexanes to give 4.00 g (92%) of title compound as an off white solid.

mp: 115°–120° C.

TLC Silica gel (3:7 ethyl acetate/hexane) R$_f$=0.50. Mass Spec. (ES-NH₃, +ions) m/z 690 (M+H). Anal. Calc'd for C₃₈H₂₉N₃O₃F₆+0.5 H₂O +HCl C, 61.34; H, 4.33; N, 5.65; Cl, 4.76 Found: C, 60.90; H, 4.30; N, 5.36; Cl, 4.97.

EXAMPLE 418

N-(2,2,2-Trifluoroethyl)-9-[4-[4-[[[4'-(trifluoromethyl)[1,1'-biphenyl]-2-yl]carbonyl]amino]-1H-indol-1 -yl]butyl]-9H-fluorene-9-carboxamide.

A.

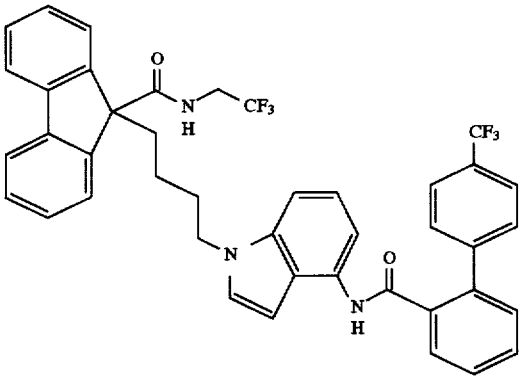

-continued

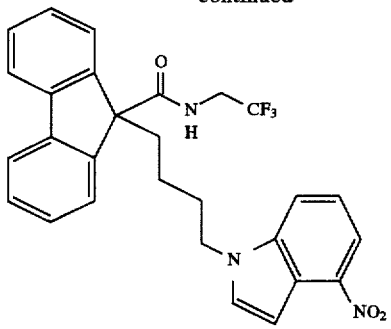

A solution of 4-nitroindole (4.0 g, 24.7 mmol) in DMF (20 mL) was added slowly over 5 min to a suspension of unwashed sodium hydride (1.09 g, 60 wt. % in mineral oil, 27.2 mmol) in DMF (50 mL) at 0° C. An immediate color change to deep red occurred with bubbling of escaping gasses. The reaction mixture was stirred at 0° C. for 5 min and then at RT for 40 min. A solution of Example 273 Part A(2) compound (12.6 g, 29.6 mmol) in DMF (20 mL) was added and the reaction mixture was stirred at RT over a weekend (64 h total). The solvent was removed under high vacuum on a rotary evaporator, and the resulting orange residue was partitioned between EtOAc (200 mL) and H$_2$O (50 mL). The organic layer was washed with H$_2$O (2×50 mL) and brine (50 mL), dried over MgSO$_4$, and concentrated to give a yellow foam. The crude product was purified by flash chromatography on silica gel (600 g) eluting with a step gradient of 20% to 25% to 30% EtOAc/hexane to give title compound (10.9 g, 73%) as a yellow foam.

B.

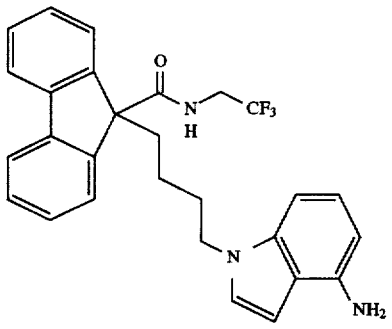

A mixture of Part A compound (7.47 g, 14.7 mmol) and 10% palladium on carbon (780 mg, 0.737 mmol) in EtOAc (50 mL) was hydrogenated under a balloon of H$_2$ at RT for 5 h, filtered through Celite®, and washed with EtOAc (2×50 mL). The filtrate was concentrated and dried under high vacuum to give title compound (7.12 g, 100%) as a white foam.

C.

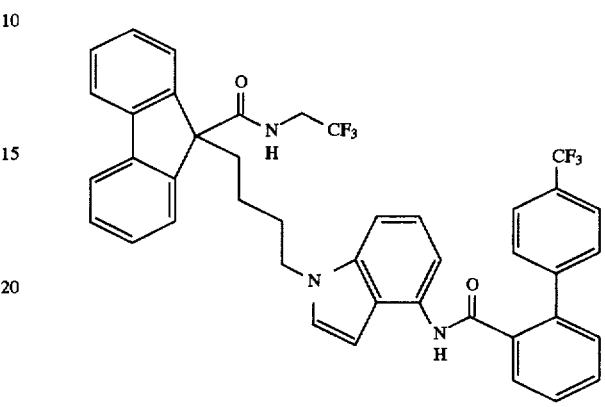

To a solution of Part B compound (5.2 g, 10.9 mmol) and triethylamine (2.0 mL, 14.2 mmol) in CH$_2$Cl$_2$ (30 mL) at 0° C. was added Example 415 Part A compound (12 mL, 1.0M in CH$_2$Cl$_2$, 12.0 mmol) over 5 min. The cloudy reaction mixture was stirred at 0° C. for 10 min, diluted with EtOAc (200 mL), washed with saturated NaHCO$_3$ (2×50 mL) and brine (50 mL), dried over MgSO$_4$, and concentrated to give a golden foam. The crude product was dissolved in a minimal amount of CH$_2$Cl$_2$ and then purified by flash chromatography on silica gel (400 g) eluting with a step gradient of 30% to 40% EtOAc/hexane to give title compound (7.74 g, 89%) as a pale yellow foam. NMR shows product to contain EtOAc.

Anal. Calcd for C$_{42}$H$_{33}$F$_6$N$_3$O$_2$+0.5 C$_4$H$_8$O$_2$: C, 68.65; H, 4.84; N, 5.46; F, 14.81 Found: C, 68.38; H, 4.55; N, 5.44; F, 14.82.

EXAMPLE 419

N-(2,2,2-Trifluoroethyl)-9-[3-[[2-[[[4'-(trifluoromethyl)[1,1'-biphenyl]-2-yl]carbonyl]amino]-5-pyridinyl]oxy]propyl]-9H-fluorene-9-carboxamide

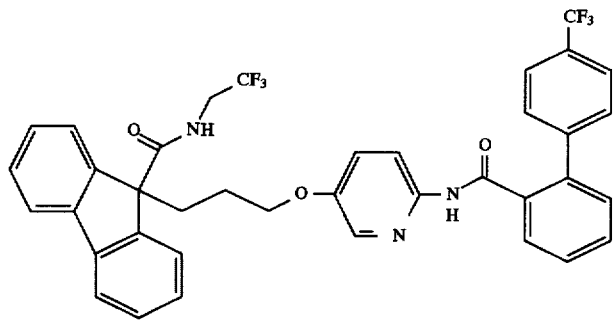

A.

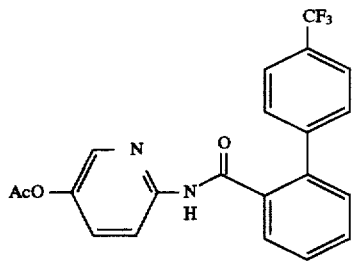

Sodium nitrite (587 mg, 8.5 mmol) was added in portions to a stirred solution of 2.02 g (5.66 mmol) of Example 415 Part D compound in 40 mL of glacial AcOH at room temperature under $N_2$. The reaction was stirred at room temperature for 45 minutes, then 408 mg (6.8 mmol) of urea was added to destroy excess HONO and stirring was continued for 2 hours. The reaction was gradually heated to 90° C. ($N_2$ evolution) and then 115° C., over the course of 3 hours, and then cooled to room temperature. The solvent was removed in vacuo and the residue was taken up in $CH_2Cl_2$ and dilute $NaHCO_3$. The $CH_2Cl_2$ was washed with dilute $NaHCO_3$ (2x) and water (2x), dried ($Na_2SO_4$), and concentrated to an oily residue (2.29 g). Flash chromatography over 200 g of silica gel packed in $CHCl_3$ by eluting with title compound (fraction A, 265 mg and fraction B, 763 mg), which was used without further purification.

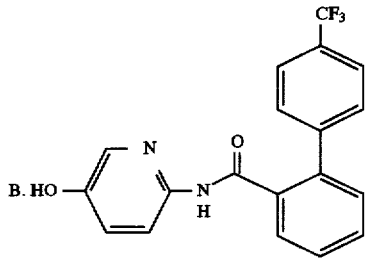

A solution of Part A compound (763 mg) in 10 mL of $CH_3OH$ and 6 mL of 2N KOH was stirred at room temperature for 20 hours and concentrated to a residue, which was taken up in $Et_2O$ and water and extracted twice with $Et_2O$. The aqueous phase was layered with $Et_2O$ and adjusted to pH 5.2 with dilute HCl. After two extractions with $Et_2O$, the acidic $Et_2O$ extract was dried ($Na_2SO_4$) and concentrated to a residue. Crystallization of this residue from $CH_2Cl_2$ gave 439 mg of title compound. Similar treatment of the above 265 mg fraction of Part A compound provided an additional 87 mg of title compound for a total of 526 mg ( 26%, 2 steps) of title compound.

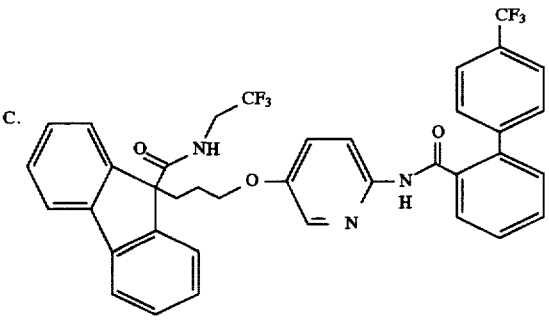

C.

50 mg (0.143 mmol) of Example 417 Part B compound, 64 mg (0.179 mmol) of Part B compound and 41 mg of triphenylphosphine were azeotropically evaporated with toluene (3X), then dried in vacuo for 2 hours before dissolved in 0.5 mL of freshly distilled THF. To above solution cooled at 0° C. was added dropwise diethylazodicarboxylate (24.8 µL, 0.157 mmol), and the resulting mixture was stirred at room temperature under argon for 18 hours, then diluted with EtOAc, washed with water, brine, dried over $MgSO_4$. The filtrate was concentrated, absorbed on Celite, flash chromatographed eluting with 20–30% EtOAc/hexane to give 76.4 mg of the product as an oily residue. Further purication using preparative HPLC, after lyophilization afforded 56.5 mg (57% yield) of the pure title product as a white powder.

MICROANALYSIS: Calculated for $C_{38}H_{29}N_3F_6O_3$+0.60 $H_2O$: C, 65.16; H, 4.35; N, 6.00; F, 16.27 Found: C, 64.86; H, 4.04; N, 5.77; F, 16.59. MS: (electrospray, +ions) m/e @ 690 (M+H).

EXAMPLE 420

9-[3-[[3-Methyl-5-[[[4'-(trifluoromethyl)[1,1'-biphenyl]-2-yl]carbonyl]amino]-2-pyridinyl]oxy]propyl]-N-(2,2,2-trifluoroethyl)-9H-fluorene-9-carboxamide, monohydrochloride

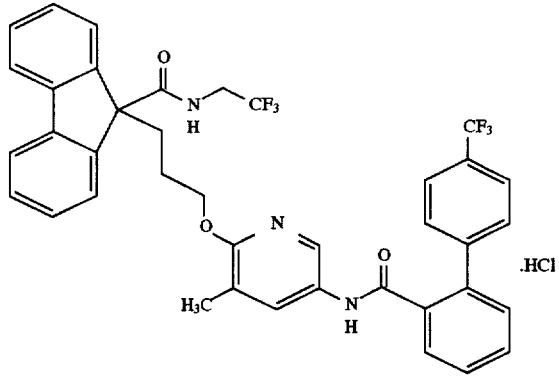

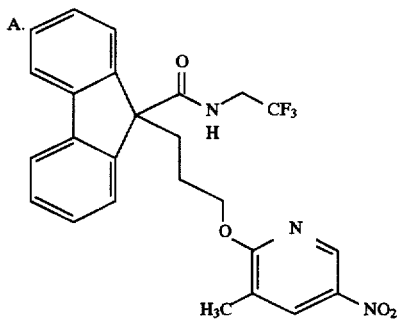

A solution of Example 417 Part B compound (1.25 g, 3.58 mmol) in THF (5 mL) was treated with NaH (173 mg, 60% mineral oil dispersion, 4.3 mmol) and stirred for 15 min at RT. After all the gray solid was consumed, 2-chloro-3-methyl-5-nitropyridine (742 mg, 4.3 mmol) was added to the reaction mixture. The resulting black mixture was stirred at RT for 18 h. Additional 2-chloro-3-methyl-5-nitropyridine (74 mg, 0.43 mmol) was added and stirring was continued for 6 h longer. The mixture was diluted with 5% aq. NaHCO₃ (10 mL) and extracted with EtOAc (3×50 mL). The combined organic extracts were washed with H₂O (10 mL) and brine (10 mL), dried over Na₂SO₄ and concentrated to give a foam. Flash chromatography on Merck silica gel K-60 (50 g) eluting with EtOAc/hexane (0.5:9.5 to 1:4) to give title compound (1.53 g, 90%) as a solid, m.p. 102°–104° C.

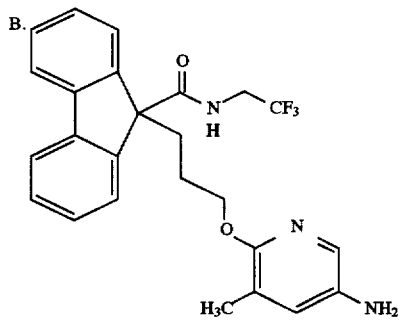

A mixture of Part A compound (250 mg, 0.51 mmol) and 10% palladium on carbon (15 mg) in ethyl acetate (5 mL) was hydrogenated (balloon pressure) at RT for 24 h. The catalyst was removed by filtration through nylon 66 filter, and concentrated in vacuo to give crude title amine (240 mg, quantitative) as an oil.

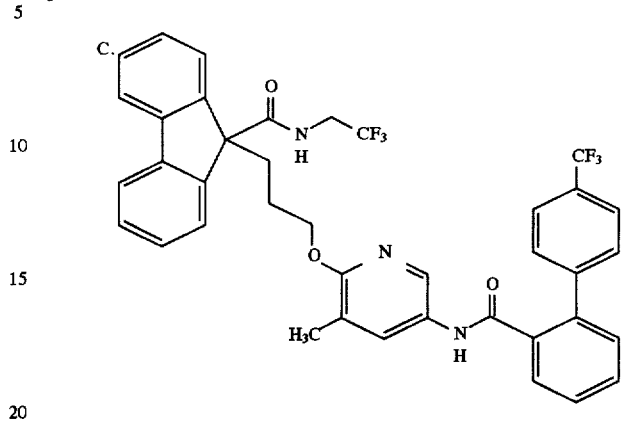

To a solution of crude Part B compound (240 mg, 0.50 mmol) and triethylamine (221 μl, 1.5 mmol) in CH₂Cl₂ (5 mL) at 0° C. was added dropwise 540 μl (0.54 mmol) of 1.0M 4'-(trifluoromethyl)-2-biphenyl carboxylic acid chloride (Example 415 Part A) solution in CH₂Cl₂. The reaction was stirred at 0° C. for 1 h. Dichloromethane (20 mL) was added and the solution was washed with sat. NaHCO₃ solution (2×10 mL), then dried over Na₂SO₄ and concentrated to give an oil. Purification by flash chromatography on Merck silica gel K-60 (20 g) eluting with CH₂Cl₂/MeOH (10:0 to 9.8:0.2) to give 300 mg of title compound as a free base. To the stirred solution of free base title compound (281 mg, 0.4 mmol) in THF was added 4N HCl in dioxane (415 μl, 1.6 mmol). After stirring for 3 min, the clear solution was diluted with Et₂O (50 mL). The separated solid was collected and dried in vacuo (0.5 mm) at RT for 2 h to give title compound (260 mg, 90%) as off white solid.

MS (ESI, +ions) m/z 704 (M+H).

EXAMPLE 421

9-[3-[[3-(Dimethylamino)-5-[[[4'-(trifluoromethyl)[1,1'-biphenyl]-2-yl]carbonyl]amino]-2-pyridinyl]oxy]propyl]-N-(2,2,2-trifluoroethyl)-9H-fluorene-9-carboxamide

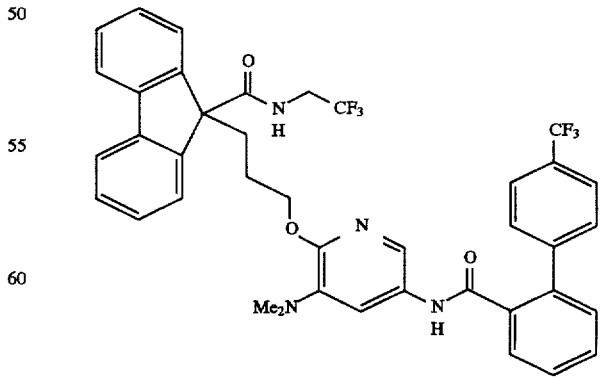

For compounds of Part A(1) and Part A(2), the procedure described in J. Med. Chem. 1992 35, 1895, was followed.

A. 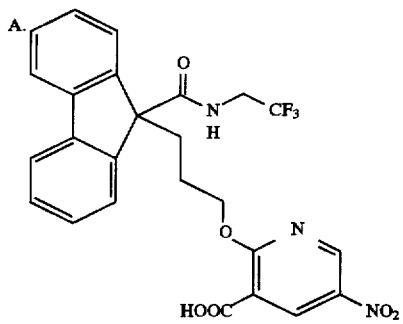

A(1). 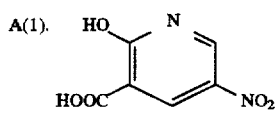

Fuming nitric acid (10 mL, 240 mmol) was added to a suspension of 2-hydroxynicotinic acid (13.9 g, 100 mmol) in concentrated sulfuric acid (40 mL) and the reaction mixture was heated gradually to 50° C., at which point all solids had dissolved. After 5 min at 50° C., the reaction mixture began to exotherm violently, whereupon the heating bath was removed. The reaction mixture turned dark red and emitted red fumes, and within a few minutes, began to cool down. Once at RT (HPLC indicated complete reaction), the yellow solution was poured into ice water (600 mL), and the resulting solid was filtered, washed with ice water (2×100 mL), and air-dried for 1 h to give 12.1 g of a yellow solid. The crude product was recrystallized from H$_2$O (200 mL) and then dried in a vacuum oven at 90° C. to give title compound (10.4 g, 57%) as a yellow solid (mp 238.5°–240.5° C., lit mp 240° C.).

A(2). 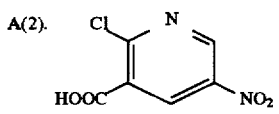

A suspension of Part A(1) compound (7.0 g, 38 mmol) in phosphorus oxychloride (20 mL) was heated at reflux for 2 h, cooled to RT, and added slowly to H$_2$O (100 mL) with stirring, maintaining the temperature below 40° C. with added ice. Following addition, the mixture was stirred at RT for 30 min, whereupon a precipitate formed. The mixture was extracted with Et$_2$O/THF (2:1, 2×200 mL), and the combined organic extracts were washed with brine (100 mL), dried over Na$_2$SO$_4$, and concentrated to give an oily yellow solid. The crude product was taken up in hot Et$_2$O/hexane (1:1, 200 mL), filtered, and the filtrate was concentrated to give title compound (5.78 g, 75%) as a yellow solid (mp 140°–141° C., lit mp 142°–143° C.).

A(3). 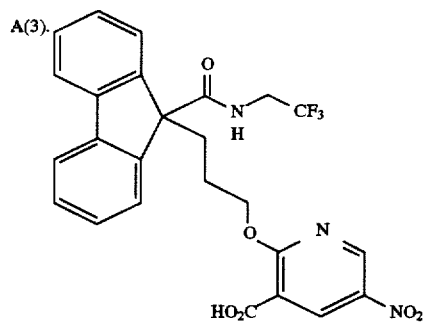

Sodium hydride (124 mg, 60 wt % in mineral oil, 3.09 mmol) was added all at once to a solution of Example 417 Part B compound (430 mg, 1.23 mmol) in DMF (2 mL). After evolution of gasses, the reaction mixture was stirred for 30 min at RT, followed by addition of Part A(2) compound (208 mg, 1.03 mmol) all at once. Bubbling ensued and the reaction mixture was stirred at RT for 30 min, diluted with H$_2$O, and then acidified with 1N HCl (3 mL). The solid mass that formed was extracted with EtOAc (20 mL), washed with a large amount of brine, dried over Na$_2$SO$_4$, and concentrated to give 750 mg crude title carboxylic acid as a yellow oil.

B. 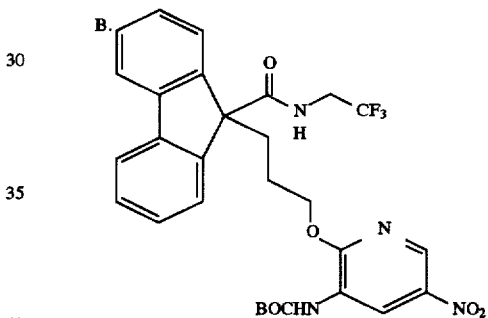

Diphenylphosphoryl azide (477 μL, 2.22 mmol) was added to a solution of Part A compound (955 mg, 1.85 mmol) and triethylamine (385 μL, 2.78 mmol) in freshly distilled tert-butanol. The reaction mixture was heated at 80° C. for 2 h, cooled to RT, and concentrated to give an orange oil. The oil was dissolved in EtOAc (25 mL), washed with saturated NaHCO$_3$ (2×5 mL), H$_2$O (5 mL), and brine (5 mL), dried over MgSO$_4$, and concentrated to give 1.33 g of an orange thick oil. The crude product was purified by flash chromatography on silica gel (100 g) eluting with a step gradient of 15% to 20% EtOAc/hexane to give title compound (355 mg, 33%) as a yellow foam.

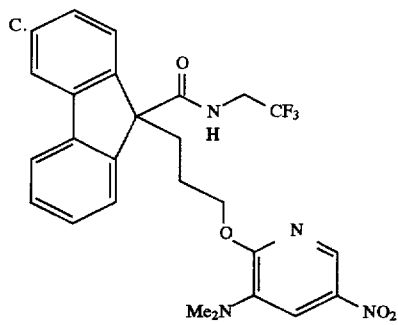

A solution of Part B compound (343 mg, 0.585 mmol) in 4N HCl/dioxane (3 mL) was allowed to stand at RT for 5 h, then concentrated to give the crude amine. To a mixture of the crude free amine, formalin (950 μL, 37%, 11.7 mmol), and AcOH (1 mL, 17.6 mmol) in MeOH (3 mL) was added sodium cyanoborohydride (370 mg, 5.85 mmol) all at once. The reaction mixture was stirred at RT overnight, concentrated, and azeotroped with toluene (15 mL). The residue was dissolved in EtOAc (50 mL), washed with saturated $NaHCO_3$ (2×10 mL) and brine (10 mL), dried over $MgSO_4$, and concentrated to give 400 mg of an orange oil. The crude product was purified by flash chromatography on silica gel (50 g) eluting with 15% EtOAc/hexane to give title compound (230 mg, 76%) as a yellow glass.

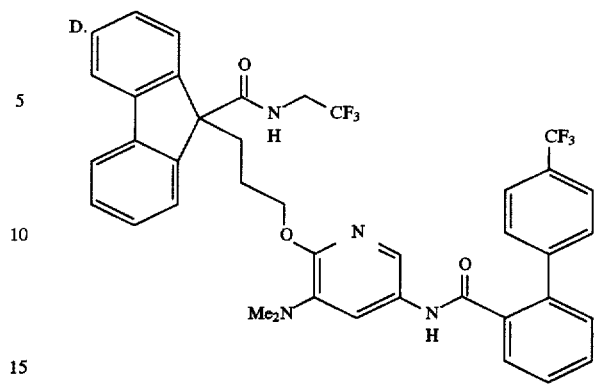

Following the procedure in Example 418 Part C compound(230 mg, 0.447 mmol) was hydrogenated and then acylated with Example 415 Part A compound to give title compound (234 mg, 72%) as a white foam.

MS (ES, +ions) m/z 733 [M+H]. Anal. Calcd for $C_{40}H_{34}F_6N_4O_3$+0.5 $H_2O$: C, 64.77; H, 4.76; N, 7.55; F, 15.37 Found: C, 64.70; H, 4.60; N, 7.28; F, 15.16.

EXAMPLE 422

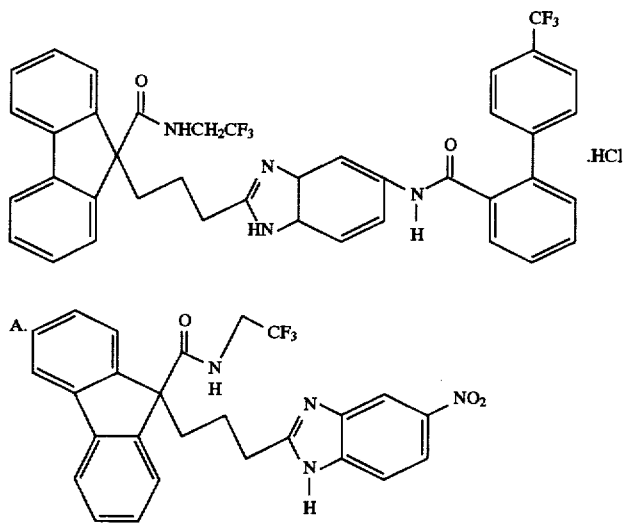

A mixture of Example 416 Part B compound (400 mg, 1.11 mmoles), 5-nitrophenyldiamine (173 mg, 1.11 mmoles) and 2,3-dichloro-5,6-dicyano-1,4-benzoquinone (DDQ) (256.3 mg, 1.11 mmoles) in dry $CH_3CN$ (5.0 ml) was stirred at room temperature for 25 hours and stripped to dryness. The crude mixture chromatographed on a silica gel column (Merck), eluting the column with $CH_2Cl_2$:EtOAc (3:1) to give title compound as a light brick-red solid foam (313 mg, 57.1%).

TLC : $R_f$ 0.47 (Silica gel; EtOAc:$CH_2Cl_2$-6:4; UV)

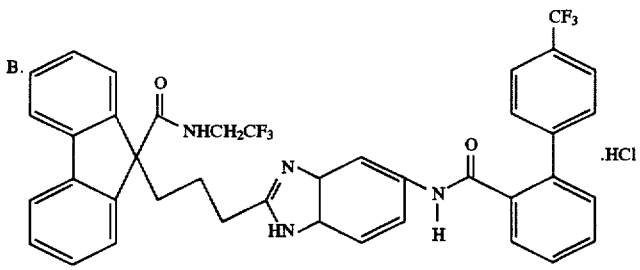

A solution of Part A compound (308 mg, 0.62 mmole) in dry CH₃OH (15 ml) was treated with 10% Pd/C (60 mg) and hydrogenated (balloon) at room temperature for 19 hours. The reaction mixture was diluted with CH₃OH (15 ml) and filtered through a celite pad in a millipore unit, washing the pad well with CH₃OH (3x). The combined filtrates were evaporated to dryness and dried in vacuo to give the crude amine as a syrup (281.7 mg).

The amine was dissolved in dry CH₂Cl₂ (8.0 ml), treated with 4'-(trifluoromethyl)-2-biphenylcarboxylic acid (167 mg, 0.65 mmole), HOBt·H₂O (86 mg, 0.64 mmole) and EDAC (133.4 mg, 0.68 mmole) and stirred at room temperature for 20 hours. The reaction mixture was partitioned between EtOAc (2×25 ml) and saturated NaHCO₃ (4.5 ml) and the combined organic extracts were washed with H₂O (3x) and brine, dried (anhydrous Na₂SO₄), filtered, evaporated to dryness and dried in vacuo. The crude product mixture was chromatographed on a silica gel column (Merck), eluting the column with EtOAc:Hexane mixtures (1:2; 4:1) to give the clean free base (165.7 mg, 37.3%).

This adduct (136 mg, 0.19 mmole) was dissolved in dry dioxane (1.7 ml), treated with 4.0M HCl/dioxane (0.17 ml, 3.5 eq), swirled for a few minutes then diluted with dry Et₂O (25 ml), scratching the solids as they formed. The mixture was filtered and the solids washed with dry Et₂O (2x) to give title compound as a solid (123 mg, m.p. 170°–180° C., shrinking commencing at 150° C.).

MS: (M +H)⁺=713. Anal. Calc'd for C₄₀H₃₀F₆N₄O₂·HCl·0.9 H₂O: C, 62.77; H, 4.32; N, 7.32; Cl, 4.63; F, 14.89 Found: C, 62.73; H, 4.00; N, 7.22; Cl, 4.60; F, 14.51

EXAMPLE 423

9-[3-[[4-Methyl-5-[[[4'-(trifluoromethyl)[1,1'-biphenyl]-2-yl]carbonyl]amino]-2-pyridinyl]oxy]propyl]-N-(2,2,2-trifluoroethyl)-9H-fluorene-9-carboxamide.

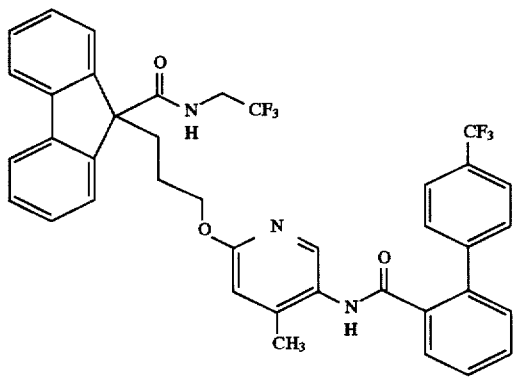

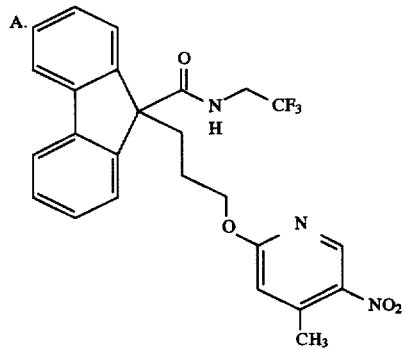

To a stirred solution of Example 417 Part B compound (7.0 g, 20.0 mmol, dried with toluene) in 200 mL of dry THF at 0° C. under argon was added triphenylphosphine (7.9 g, 30.0 mmol) and 2-hydroxy-4-methyl-5-nitropyridine (3.7 g, 24.0 mmol) followed by the dropwise addition of diisopropyl azodicarboxylate (DIAD) (5.9 mL, 30.0 mmol). The reaction mixture was stirred at 0° C. for 1 h and quenched with sat. NaHCO₃ (70 mL) and concentrated to remove THF. Water (300 mL) was added and the mixture was extracted with EtOAc (3×150 mL). The combined organic layers were washed with H₂O (100 mL) and brine (100 mL), dried over Na₂SO₄ and concentrated in vacuo to give a viscous oil. Flash chromatography on Merck silica gel K-60 (800 g) eluting with EtOAc/hexane (0.5:9.5 to 1:4) provided 4.0 g (41%) of title compound as foam.

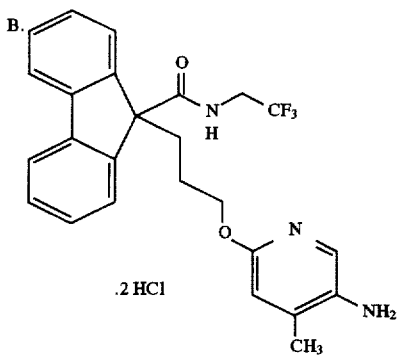

A mixture of Part A compound (1.5 g, 3.09 mmol) and 10% palladium on carbon (200 mg) in ethyl acetate (30 mL) was hydrogenated (balloon pressure) at RT for 24 h. TLC showed the presence of some starting material; therefore an additional quantity of 10% Pd/C (25 mg) was added and hydrogenation was continued for 12 h longer. The catalyst was removed by filtration through nylon 66 filter, and concentrated in vacuo to give crude amine. To the stirred solution of clear amine in Et$_2$O (100 mL) was added 4N HCl in dioxane (2.8 mL, 10.7 mmol). The separated solid was diluted with Et$_2$O (50 mL) and collected, dried in vacuo (0.5 mm) at RT for 3 h to give title compound (1.53 g, 94%) as off white solid.

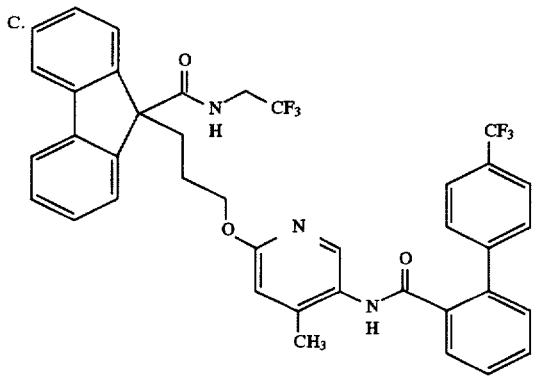

To a solution of crude Part B compound (106 mg, 0.2 mmol) and triethylamine (150 µl, 1.0 mmol) in CH$_2$Cl$_2$ (5 mL) at 0° C. was added dropwise 220 µl of 1.0 M 4'-(trifluoromethyl)-2-biphenyl acid chloride solution in CH$_2$Cl$_2$ (0.22 mmol). The reaction was stirred at 0° C. for 1 h. Dichloromethane (20 mL) was added and the solution was washed with sat. NaHCO$_3$ solution (2×5 mL), then dried over Na$_2$SO$_4$ and concentrated to give 190 mg of foam. Purification by flash chromatography on Merck silica gel K-60 (5 g) eluting with EtOAc/hexane (1:4 to 3:7) provided title compound (110 mg, 78%) as foam.

MS (ESI, +ions) m/z 704 (M +H).

EXAMPLE 424–425

9-[4-[2-Methyl-4-[methyl[[4'-(trifluoromethyl)[1,1'-biphenyl]-2-yl]carbonyl]amino]-1H-benzimidazol-1-yl]butyl]-N-(2,2,2-trifluoroethyl)-9H-fluorene-9-carboxamide.

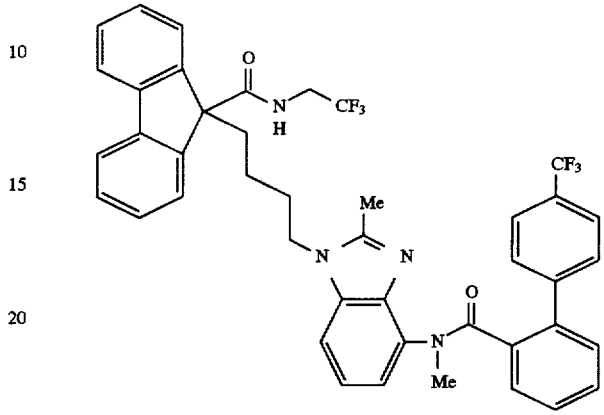

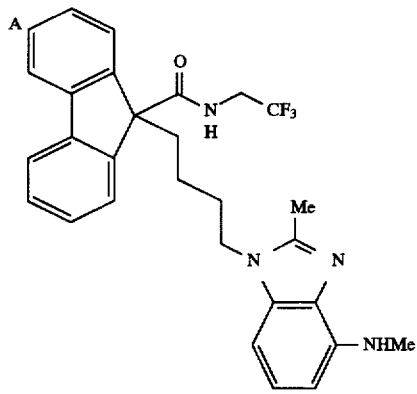

Acetic anhydride (472 µL, 5 mmol) was added to formic acid (5.0 mL) at 0° C. The reaction mixture was stirred at 0° C. for 30 min, and a portion (1.9 mL, 1.9 mmol) was added slowly to a solution of Example 410 Part C compound (300 mg, 0.61 mmol) in THF (0.5 mL) at 0° C. After 30 min, the reaction mixture was partitioned between EtOAc (20 mL) and saturated NaHCO$_3$ (20 mL), and the organic layer was washed with saturated NaHCO$_3$ (5 mL) and brine (5 mL), dried over Na$_2$SO$_4$, and concentrated to give 189 mg of the formamide.

Lithium aluminum hydride (515 µL, 1.0M in THF, 0.515 mmol) was added dropwise to a solution of a portion of the formamide (312 mg) in THF (3 mL) at 0° C. The cooling bath was removed, and the reaction mixture was stirred at RT for 30 min. Following a quench with H$_2$O (0.5 mL), 1M sodium potassium tartrate (5 mL) was added, and the reaction mixture was stirred at RT vigorously for 2 h. The reaction mixture was extracted with EtOAc (2×10 mL), and the organic extracts were washed with brine (5 mL), dried over Na$_2$SO$_4$, and concentrated to give 110 mg of an opaque oil. The crude product was purified by flash chromatography on silica gel (35 g) eluting with a step gradient of 60% to 80% EtOAc/hexane to give title compound (280 mg, 89%) as a yellow foam.

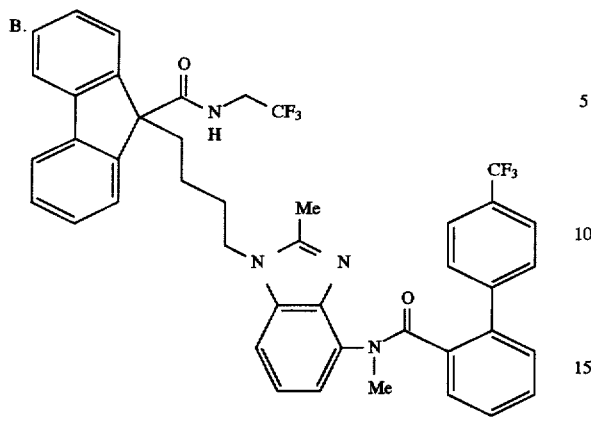

Following the procedure in Example 418 Part C, Part A compound (218 mg, 0.431 mmol) was acylated with Example 415 Part A compound to give title compound (289 mg, 89%) as a white foam.
MS (ES, +ions) m/z 741 [M+H].

The following additional compounds were prepared employing procedures described hereinbefore.

EXAMPLE 426

9-[5-[Bis(3-cyanopropoxy)phosphinyl]pentyl]-N-(2, 2,2-trifluoroethyl)-9H-fluorene-9-carboxamide

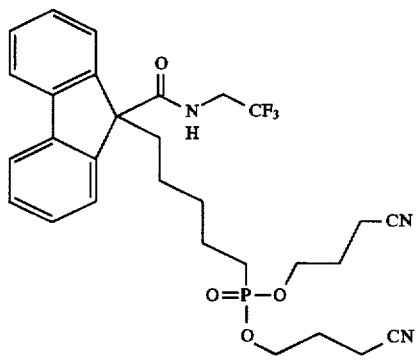

MS (ESI, +ions): 576 (M+H), 593 (M+NH$_4$).

EXAMPLE 427

9-[4-(Dipentylamino)butyl]-N-(2,2,2-trifluoroethyl)-9H-fluorene-9-carboxamide, monohydrochloride

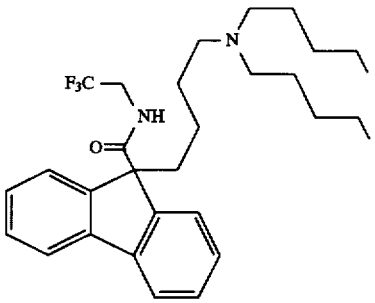

MS (electrospray, −ions) m/z 503 (M+H).

EXAMPLE 428

9-[4-(Dipentylamino)butyl]-N-(2,2,2-trifluoroethyl)-9H-fluorene-9-carboxamide, N-oxide

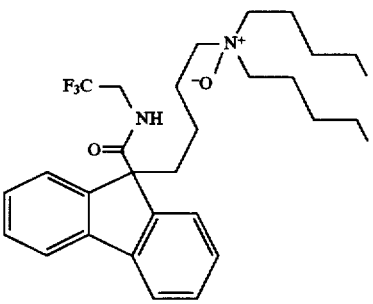

MS (electrospray, −ions) m/z 519 (M+H).

EXAMPLE 429

9-[3-[[2-[[2-(2-Pyridinyl)benzoyl]amino]-5-pyridinyl]amino]propyl]-N-(2,2,2-trifluoroethyl)-9H-fluorene-9-carboxamide, dihydrocholoride

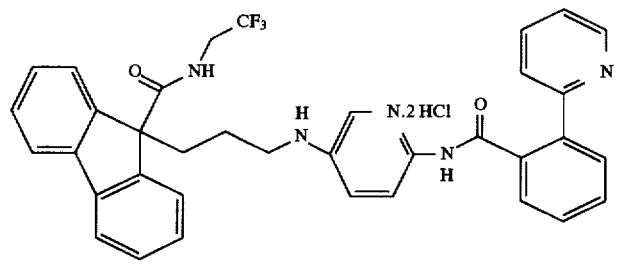

MS (ESI-NH$_3$, +ion) 622 [M+H]; (−ion) 620 [M-H].

EXAMPLE 430

[5-[9-[[(2,2,2-Trifluoroethyl)amino]carbonyl]-9H-fluoren-9-yl]pentyl]phosphonic acid, bis(2-pyridinylmethyl) ester

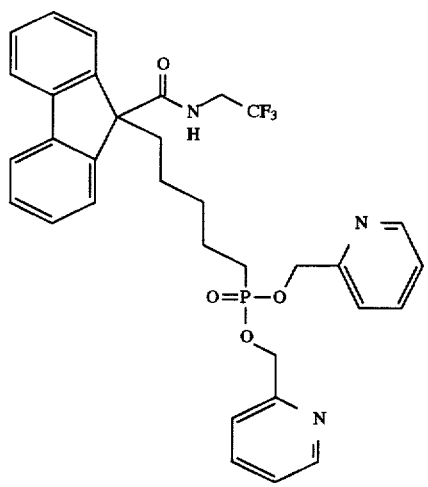

MS (ESI, +ions): 624 (M+H).

EXAMPLE 431

[5-[9-[[(2,2,2-Trifluoroethyl)amino]carbonyl]-9H-fluoren-9-yl]pentyl]phosphonic acid, bis(2-methylpropyl) ester

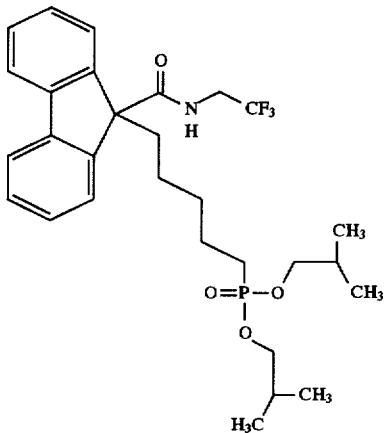

MS (ESI, +ions): 554 (M+H), 571 (M+NH$_4$).

EXAMPLE 432

[5-[9-[[(2,2,2-Trifluoroethyl)amino]carbonyl]-9H-fluoren-9-yl]pentyl]phosphonic acid, bis(2,2-dimethylpropyl) ester

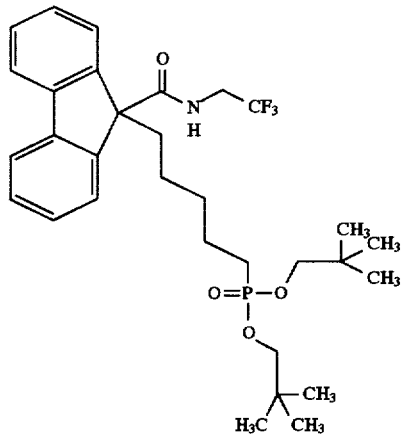

MS (ESI, +ions): 582 (M+H), 599 (M+NH$_4$).

EXAMPLE 433

[5-[9-[[(2,2,2-Trifluoroethyl)amino]carbonyl]-9H-fluoren-9-yl]pentyl]phosphonic acid, bis(tetrahydro-2H-pyran-2-ylmethyl) ester

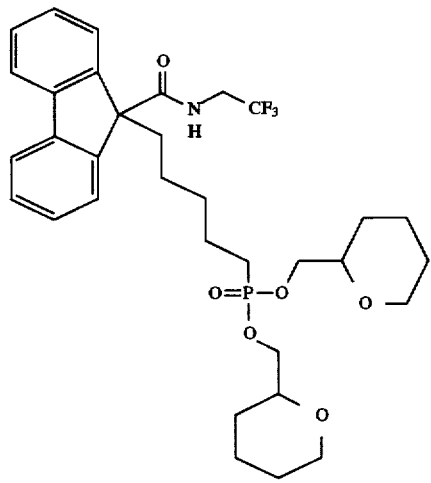

MS (ESI, +ions): 638 (M+H), 655 (M+NH$_4$).

EXAMPLE 434

9-[4-[4-(Benzoylamino)phenyl]butyl]-N-(2,2,2-trifluoroethyl)-9H-fluorene-9-carboxamide

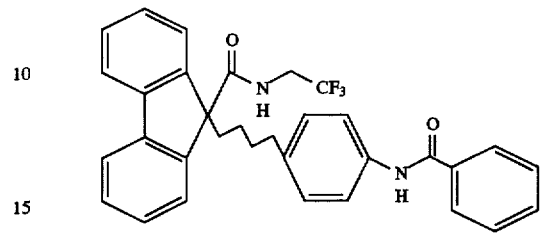

MS (electrospray, +ions) m/z 543 (M+H).

EXAMPLE 435–436

[5-[9-[[(2,2,2-Trifluoroethyl)amino]carbonyl]-9H-fluoren-9-yl]pentyl]phosphonic acid, bis (tetrahydrofuran-2-ylmethyl) ester

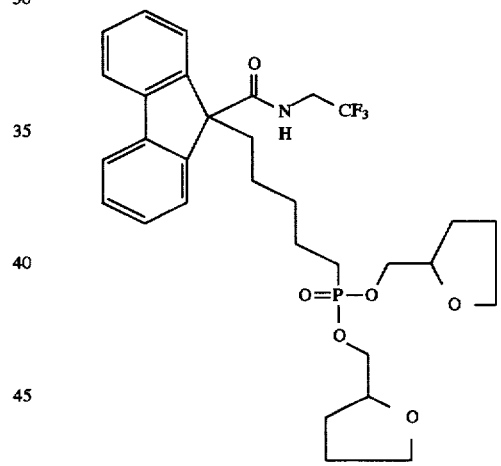

MS (ESI, +ions): 610 (M+H), 627 (M+NH$_4$); (–ion) 608 (M-H).

EXAMPLE 438

9-[6-(Dibutylamino)-6-oxohexyl]-N-(2,2,2-trifluoroethyl)-9H-fluorene-9-carboxamide

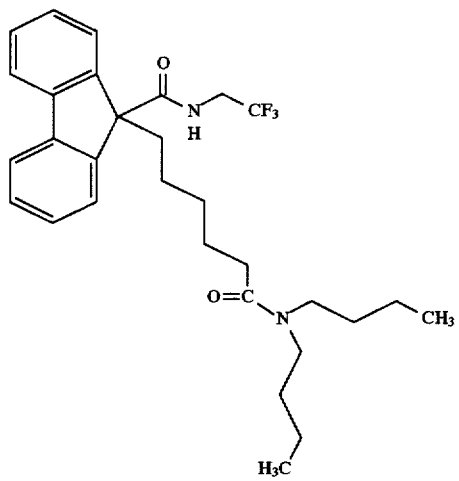

MS (ESI, +ion): 517 (M+H).

EXAMPLE 439

9-[5-(3-Oxo-2,4-dioxa-3-phosphaspiro[5.5]undecan-3-yl)pentyl]-N-(2,2,2-trifluoroethyl)-9H-fluorene-9-carboxamide

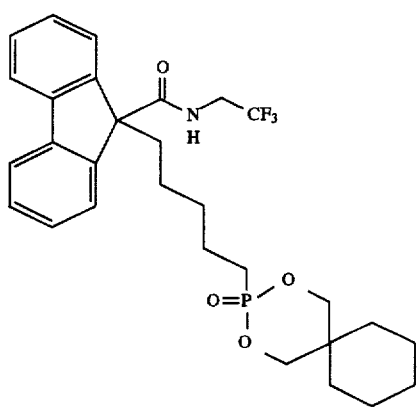

MS (ESI, +ion): 550 (M+H).

EXAMPLE 440

[5-[9-[[(2,2,2-Trifluoroethyl)amino]carbonyl]-9H-fluoren-9-yl]pentyl]phosphonic acid, bis(2-pyridinylmethyl) ester

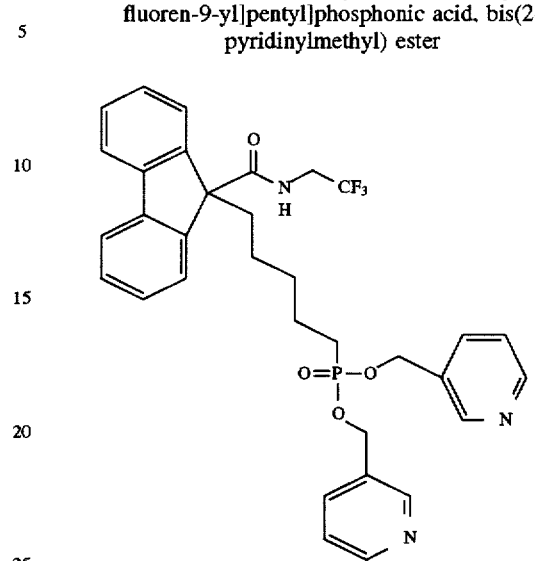

MS (ESI, −ion): 622 (M-H).

EXAMPLE 441

9-[3-[Acetyl[2-[[[4'-(trifluoromethyl)[1,1'-biphenyl]-2-yl]carbonyl]amino]-5-pyridinyl]amino]propyl]-N-(2,2,2-trifluoroethyl)-9H-fluorene-9-carboxamide

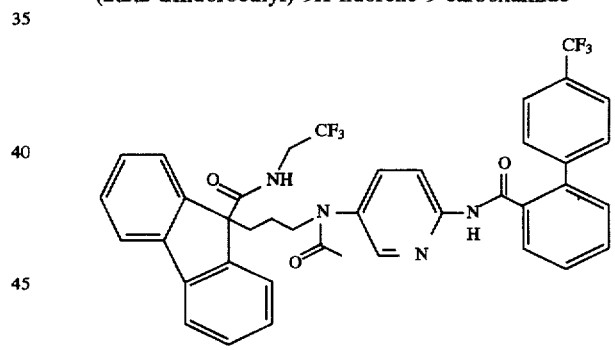

MS (M+H)$^+$@731.

EXAMPLE 442

[5-[9-[[(2,2,2-Trifluoroethyl)amino]carbonyl]-9H-fluoren-9-yl]pentyl]phosphonic acid, bis[2-(2-pyridinyl)ethyl]ester

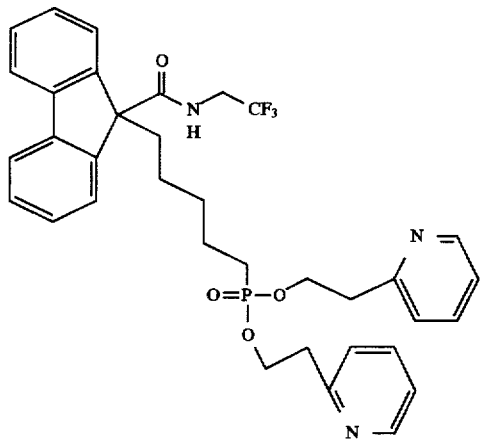

MS (ESI, +ion): 652 (M+H).

EXAMPLE 443

N-(2,2,2-Trifluoroethyl)-9-[3-[6-[[[4'-(1,1,1-trifluoromethyl)[1,1'-biphenyl]-2-yl]carbonyl]amino]-1H-benzimidazol-1-yl]propyl]-9H-fluorene-9-carboxamide, monohydrochloride

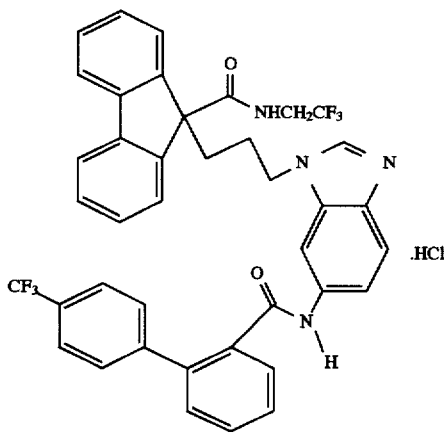

MS: (M+H)⁺=713.

EXAMPLE 444

N-(2,2,2-Trifluoroethyl)-9-[3-[5-[[[4'-(1,1,1-trifluoromethyl)[1,1'-biphenyl]-2-yl]carbonyl]amino]-1H-benzimidazol-1-yl]propyl]-9H-fluorene-9-carboxamide, monohydrochloride

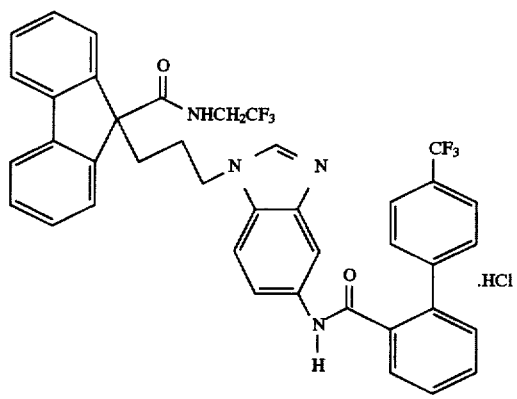

MS: (M+H)⁺=713.

EXAMPLE 445

9-[3-[Methyl[2-[[[4'-(trifluoromethyl)[1,1'-biphenyl]-2-yl]carbonyl]amino]-5-pyridinyl]amino]propyl]-N-(2,2,2-trifluoroethyl)-9H-fluorene-9-carboxamide

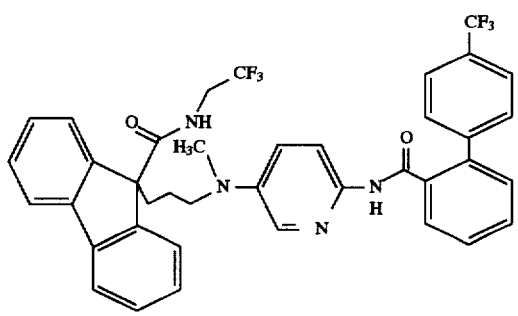

MS: (M+H)⁺@703.

EXAMPLE 446–447

[5-[9-[[(2,2,2-Trifluoroethyl)amino]carbonyl]-9H-fluoren-9-yl]pentyl]phosphonic acid, bis[2-[1-(triphenylmethyl)-1H-imidazol-2-yl]ethyl] ester

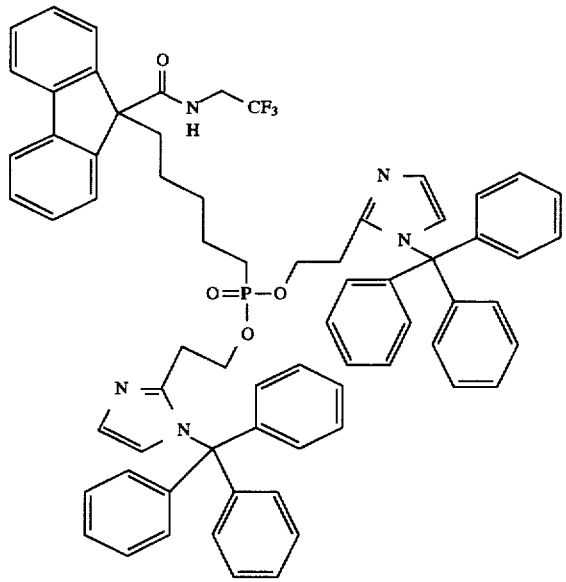

MS (ESI, +ion): 1114 (M+H).

EXAMPLE 448

9-[3-[[2-[(2,5-Dichlorobenzoyl)amino]-5-pyridinyl]amino]propyl]-N-(2,2,2-trifluoroethyl)-9H-fluorene-9-carboxamide

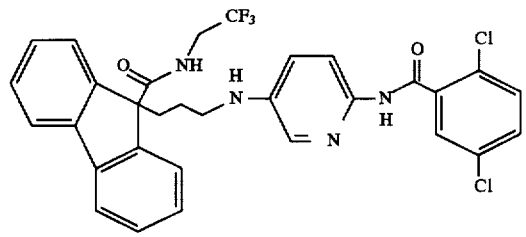

MS: (M+H)$^+$@613.

EXAMPLE 449

[5-[9-[[(2,2,2-Trifluoroethyl)amino]carbonyl]-9H-fluoren-9-yl]pentyl]phosphonic acid, bis(4-pyridinylmethyl) ester

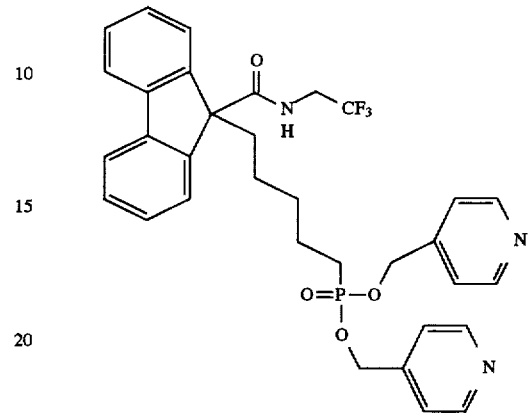

MS (ESI, +ion): 624 (M+H).

EXAMPLE 450

[5-[9-[[(2,2,2-Trifluoroethyl)amino]carbonyl]-9H-fluoren-9-yl]pentyl]phosphonic acid, bis[3-(2-pyridinyl)propyl] ester

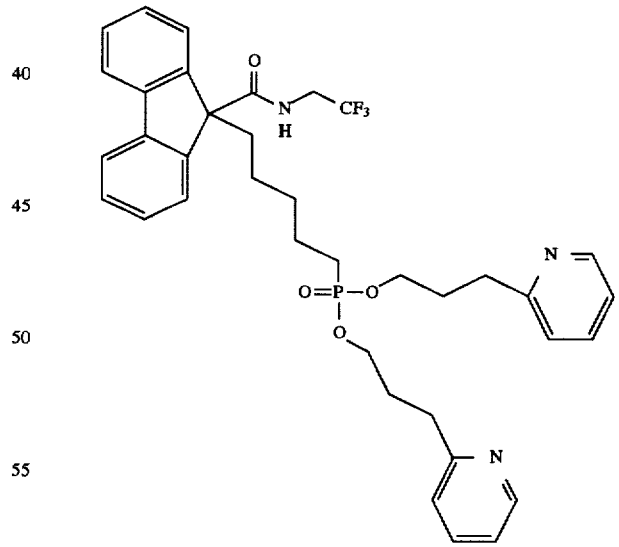

MS (ESI +ion): 680 (M+H).

EXAMPLE 451

9-[3-[[5-[[(2,5-Dichlorophenyl)sulfonyl]amino]-2-pyridinyl]oxy]propyl]-N-(2,2,2-trifluoroethyl)-9H-fluorene-9-carboxamide

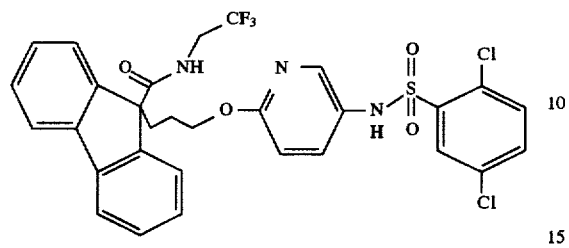

MS: (M+H)+@650; MW 649.

EXAMPLE 452

9-[3-[[5-[[(2-Phenoxyphenyl)sulfonyl]amino]-2-pyridinyl]oxy]propyl]-N-(2,2,2-trifluoroethyl)-9H-fluorene-9-carboxamide

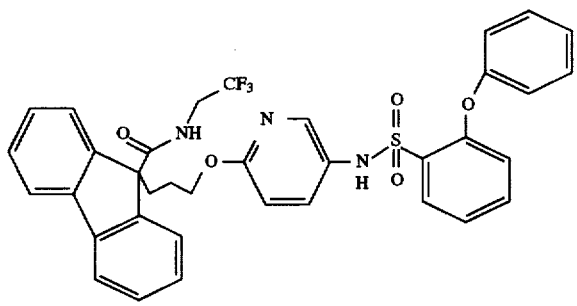

MS: (M+H)=@673

EXAMPLE 453

N-(2,2,2-Trifluoroethyl)-9-[3-[[5-[[[4'-(trifluoromethyl)[1,1'-biphenyl]-2-yl]sulfonyl]amino]-2-pyridinyl]oxy]propyl]-N-(2,2,2-trifluoroethyl)-9H-fluorene-9-carboxamide

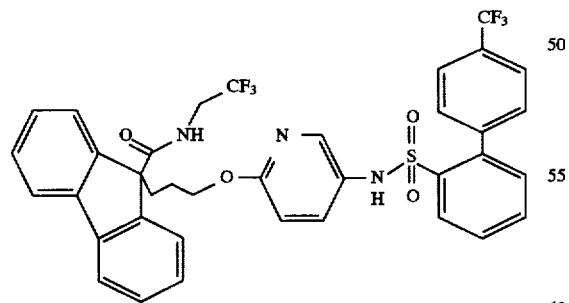

MS: (M+H)+@726.

EXAMPLE 454

[5-[9-[[(2,2,2-Trifluoroethyl)amino]carbonyl]-9H-fluoren-9-yl]pentyl]phosphonic acid, bis[3-(6-methyl-2-pyridinyl)propyl] ester

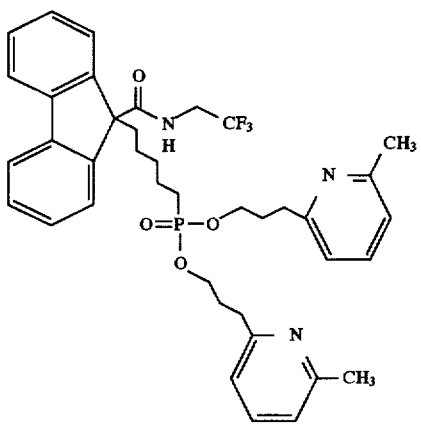

MS (ESI, −ion): 706 (M-H).

EXAMPLE 455

9-[3-[[5-(Benzoylamino)-3-methyl-2-pyridinyl]-oxy]propyl]-N-(2,2,2-trifluoroethyl)-9H-fluorene-9-carboxamide, monohydrochloride

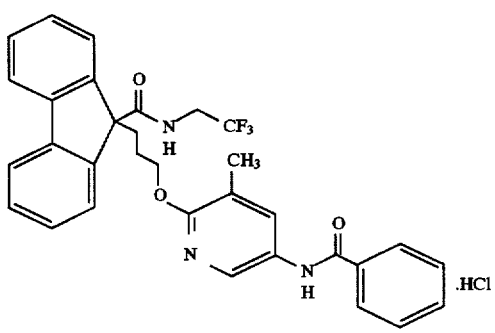

MS (ESI, +ion): 560 (M+H).

EXAMPLE 456

9-[3-[[5-[[([1,1'-Biphenyl]-2-yl)carbonyl]amino]-3-methyl-2-pyridinyl]oxy]propyl]-N-(2,2,2-trifluoroethyl)-9H-fluorene-9-carboxamide, monohydrochloride

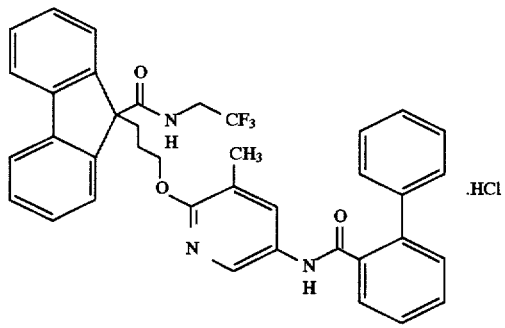

MS (ESI, +ion): 636 (M+H).

EXAMPLE 457

[5-[9-[[(2,2,2-Trifluoroethyl)amino]carbonyl]-9H-fluoren-9-yl]pentyl]phosphonic acid, bis 2-(1H-imidazol-2-yl)ethyl ester

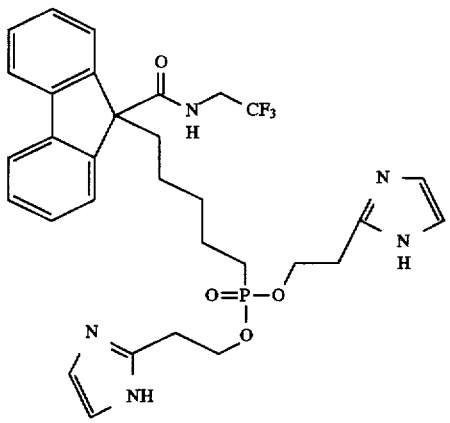

MS (ESI, +ion): 630 (M+H).

EXAMPLE 458

N-(2,2,2-Trifluoroethyl)-9-[3-[5-[[[4'-(trifluoromethyl)[1,1'-biphenyl]-2-yl]sulfonyl]amino]-1H-benzimidazol-1-yl]propyl]-9H-fluorene-9-carboxamide

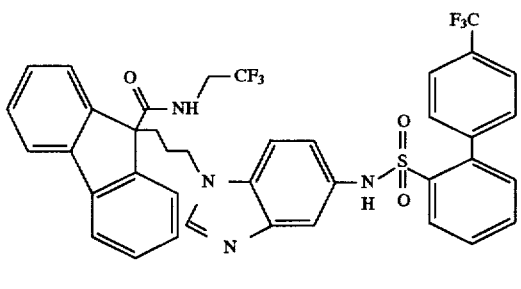

MS: (M+H)$^+$@749; (M-H) @747.

EXAMPLE 459

9-[3-[[3-Methyl-5-[(2-phenoxybenzoyl)amino]-2-pyridinyl]oxy]propyl]-N-(2,2,2-trifluoroethyl)-9H-fluorene-9-carboxamide

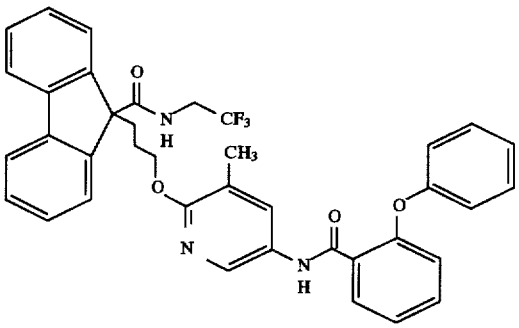

MS (ESI, +ion): 652 (M+H).

EXAMPLE 460

9-[3-[[3-Methyl-5-[[2-(2-pyrinyl)benzoyl]amino]-2-pyridinyl]oxy]propyl]-N-(2,2,2-trifluoroethyl)-9H-fluorene-9-carboxamide

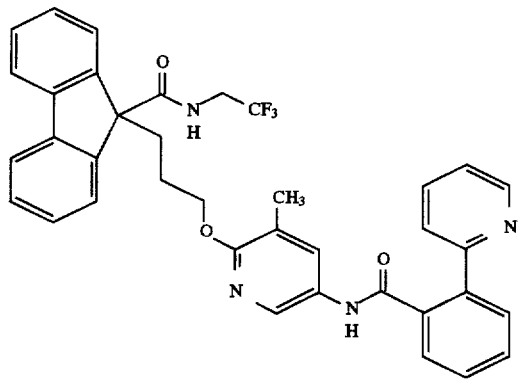

MS (ESI, +ion): 637 (M+H).

EXAMPLE 461

[5-[9-[[(2,2,2-Trifluoroethyl)amino]carbonyl]-9H-fluoren-9-yl]pentyl]phosphonic acid, bis[(6-methyl-2-pyridinyl)methyl] ester

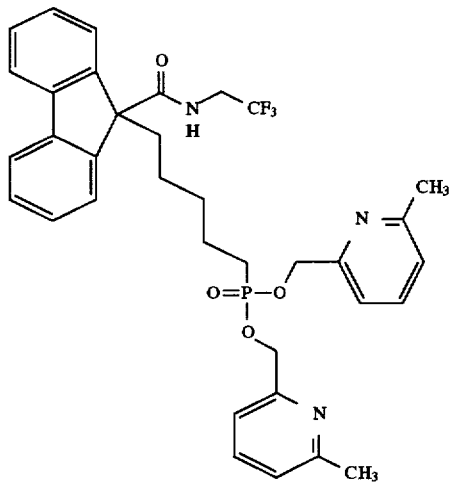

MS (ESI, +ions): 652 (M+H).

EXAMPLE 462-463

9-[3-[[5-[Methyl[[4'-(trifluoromethyl)[1,1'-biphenyl]-2-yl]sulfonyl]amino]-2-pyridinyl]oxy]propyl]-N-(2,2,2-trifluoroethyl)-9H-fluorene-9-carboxamide

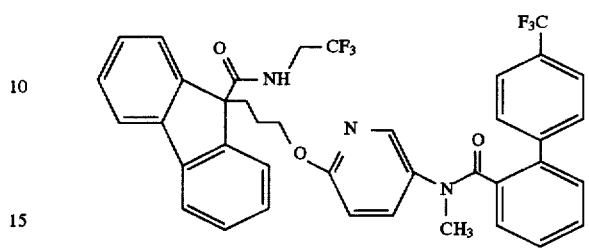

MS: (M+H)+ @704, (M-H) @702.

EXAMPLE 464-465

9-[4-[[5-(Benzoylamino)-2-pyridinyl]oxy]butyl]-N-(2,2,2-trifluoroethyl)-9H-fluorene-9-carboxamide

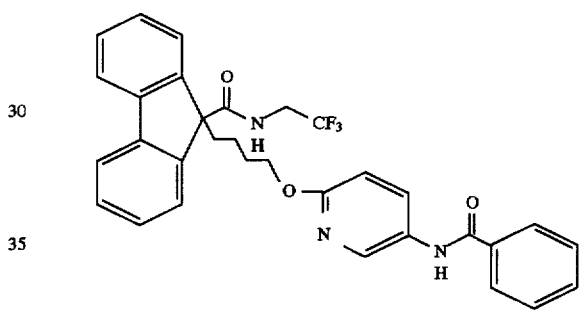

MS (ESI, +ion): 560 (M+H).

EXAMPLE 466

9-[4-[[5-[(2-Phenoxybenzoyl)amino]-2-pyridinyl]oxy]butyl]-N-(2,2,2-trifluoroethyl)-9H-fluorene-9-carboxamide

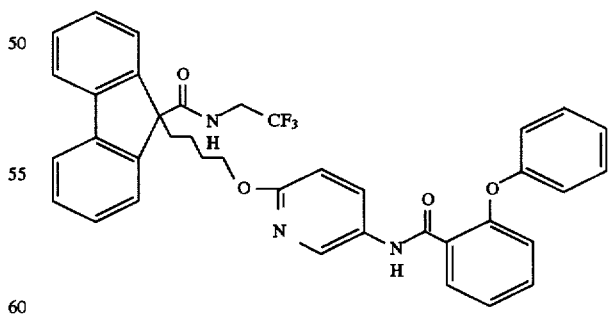

MS (ESI, +ion): 652 (M+H).

EXAMPLE 467

9-[3-[[5-[[(4'-Chloro[1,1'-biphenyl]-2-yl)carbonyl]amino]-4-methyl-2-pyridinyl]oxy]propyl]-N-(2,2,2-trifluoroethyl)-9H-fluorene-9-carboxamide

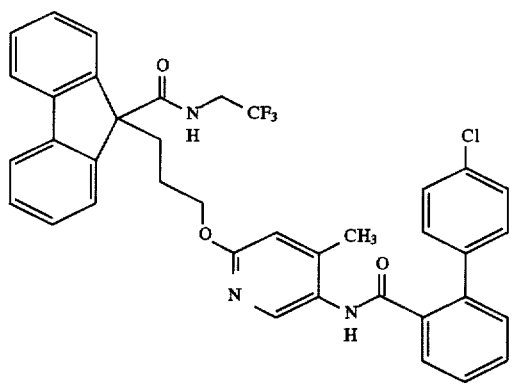

MS (ESI, +ion): 670 (M+H).

EXAMPLE 468

9-[3-[2-(Methylthio)-5-[[[4'-(trifluoromethyl)[1,1'-biphenyl]-2-yl]carbonyl]amino]-1H-benzimidazol-1-yl]propyl]-N-(2,2,2-trifluoroethyl)-9H-fluorene-9-carboxamide

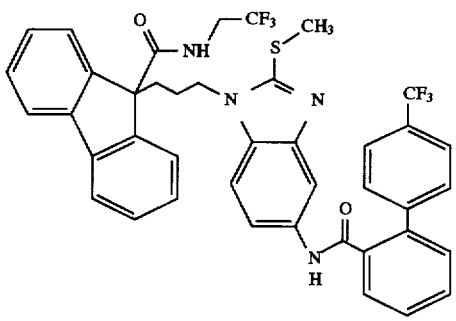

MS: (M+H)⁺@759.

EXAMPLE 469

9-[3-[2-(Methylthio)-6-[[[4'-(trifluoromethyl)[1,1'-biphenyl]-2-yl]carbonyl]amino]-1H-benzimidazol-1-yl]propyl]-N-(2,2,2-trifluoroethyl)-9H-fluorene-9-carboxamide

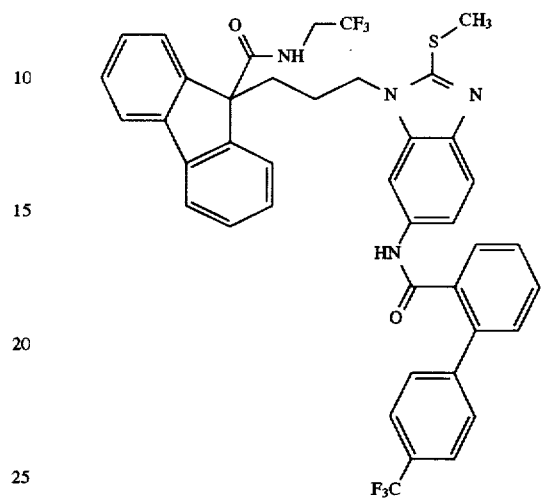

MS: (M+H)+@759.

EXAMPLE 470

9-[3-[[1-Methyl-5-[[[4'-(trifluoromethyl)[1,1'-biphenyl]-2-yl]carbonyl]amino]-1H-benzimidazol-2-yl]thio]propyl]-N-(2,2,2-trifluoroethyl)-9H-fluorene-9-carboxamide

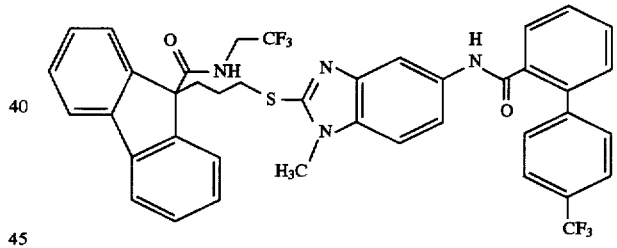

MS: (M+H)⁺@759.

EXAMPLE 471

9-[3-[[1-Methyl-6-[[[4'-(trifluoromethyl)[1,1'-biphenyl]-2-yl]carbonyl]amino]-1H-benzimidazol-2-yl]thio]propyl]-N-(2,2,2-trifluoroethyl)-9H-fluorene-9-carboxamide

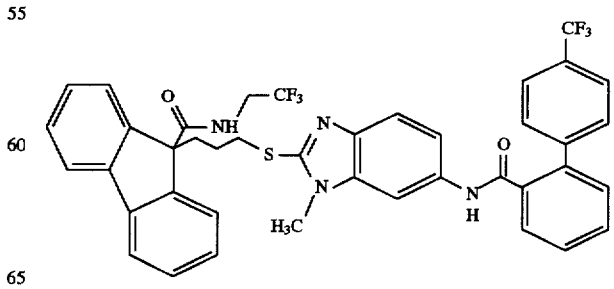

MS: (M+H)⁺@759.

EXAMPLE 472

9-[4-[[5-[[(4'-Chloro[1,1'-biphenyl]-2-yl)carbonyl]amino]-4-methyl-2-pyridinyl]oxy]butyl]-N-(2,2,2-trifluoroethyl)-9H-fluorene-9-carboxamide

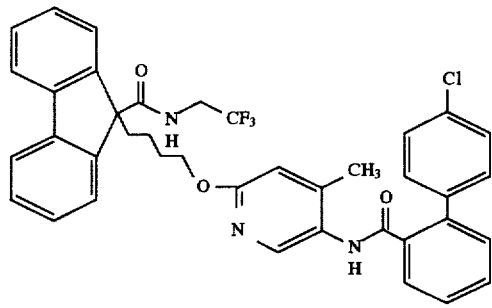

MS (ESI, +ion): 684 (M+H).

EXAMPLE 473

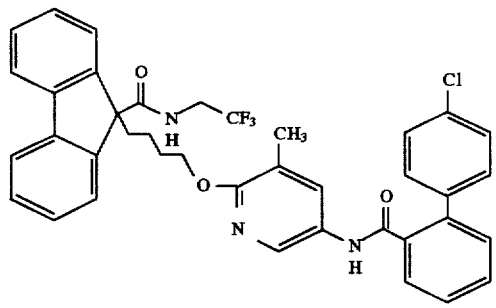

MS (ESI, +ion): 684 (M+H).

EXAMPLE 474

9-[3-[2-[(2-Pyridinylmethyl)thio]-5-[[[4'-(trifluoromethyl)[1,1'-biphenyl]-2-yl]carbonyl]amino]-1 H-benzimidazol-1-yl]propyl]-N-(2,2,2-trifluoroethyl)-9H-fluorene-9-carboxamide

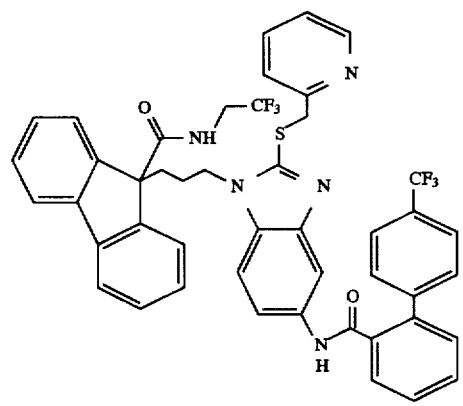

MS: (M+H)+@836; (M-H)- @834.

EXAMPLE 475

9-[3-[2-[(2-Pyridinylmethyl)thio]-6-[[[4'-(trifluoromethyl)[1,1'-biphenyl]-2-yl]carbonyl]amino]-1H-benzimidazol-1-yl]propyl]-N-(2,2,2-trifluoroethyl)-9H-fluorene-9-carboxamide

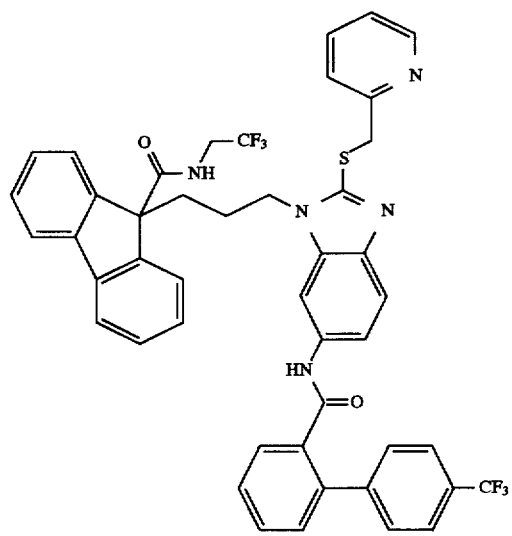

MS: (M+H)+@836; (M-H)- @834.

EXAMPLE 476

9-[3-[2-[(2-Pyridinylmethyl)thio]-6-[[[4'-(trifluoromethyl)[1,1'-biphenyl]-2-yl]carbonyl]amino]-1H-benzimidazol-1 -yl]propyl]-N-(2,2,2-trifluoroethyl)-9H-fluorene-9-carboxamide

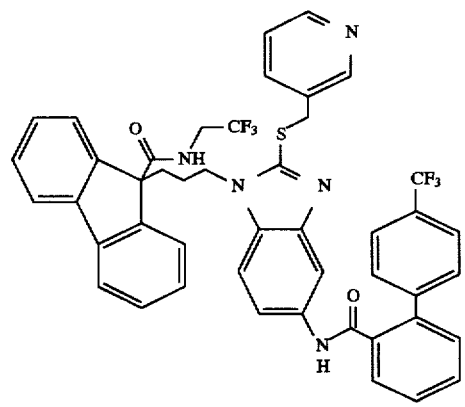

MS: (M+H)+@836; (M-H)- @834.

EXAMPLE 477

9-[3-[2-[(3-Pyridinylmethyl)thio]-5-[[[4'-(trifluoromethyl)[1,1'-biphenyl]-2-yl]carbonyl]amino]-1H-benzimidazol-1-yl]propyl]-N-(2,2,2-trifluoroethyl)-9H-fluorene-9-carboxamide

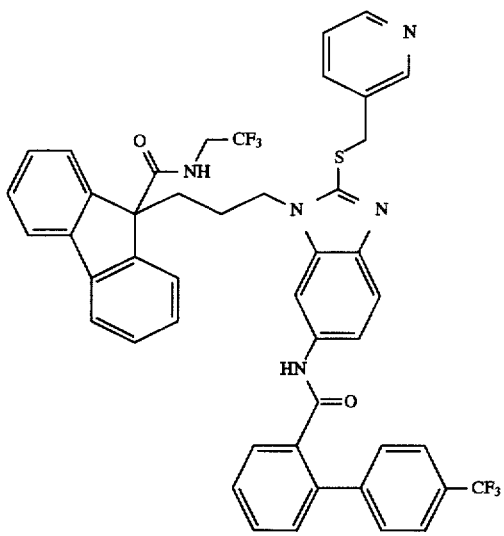

MS: (M+H)+@836; (M-H)- @834.

EXAMPLE 478

9-[4-[4-[[2-(2-Pyridinyl)benzoyl]amino]-1H-imidazol-1-yl]butyl]-N-(2,2,2-trifluoroethyl)-9H-fluorene-9-carboxamide, dihydrochloride.

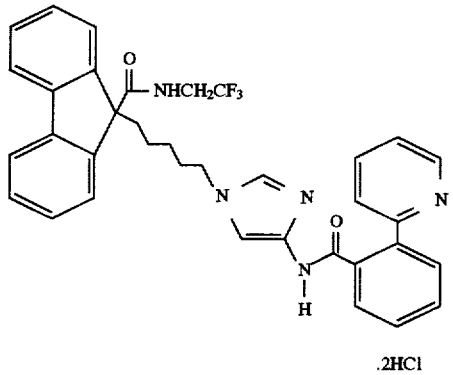

MS: (M+H)$^+$=610.

EXAMPLE 479–483

9-[3-[5-(Benzoylamino)-1H-benzimidazol-1-yl]propyl]-N-(2,2,2-trifluoroethyl)-9H-fluorene-9-carboxamide, monohydrochloride

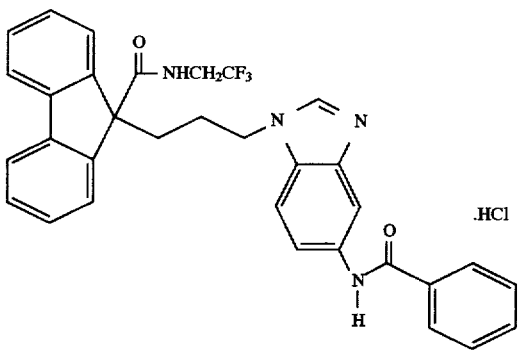

MS (M+H)$^+$=569.

EXAMPLE 484

N-(2,2,2-Trifluoroethyl)-9-[4-[4-[[[[4'-(trifluoromethyl)[1,1'-biphenyl]-2-yl]carbonyl]amino]methyl]-1H-imidazol-1-yl]butyl]-9H-fluorene-9-carboxamide, monohydrochloride

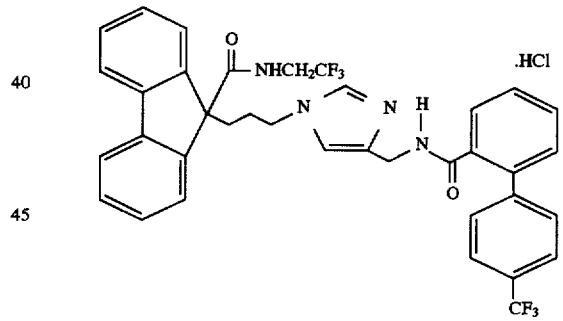

MS (M+H)$^+$=691.

EXAMPLE 485

N-(2,2,2-Trifluoroethyl)-9-[4-[5-[[[4'-(1,1,1-trifluoromethyl)[1,1'-biphenyl]-2-yl]carbonyl]amino]-1H-benzimidazol-1-yl]butyl]-9H-fluorene-9-carboxamide, monohydrochloride.

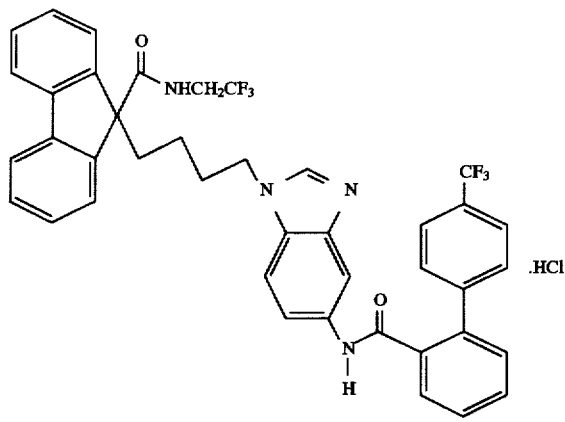

MS (M+H)$^+$=727.

EXAMPLE 486

9-[4-[5-(Benzoylamino)-1H-benzimidazol-1-yl]butyl]-N-(2,2,2-trifluoroethyl)-9H-fluorene-9-carboxamide, monohydrochloride

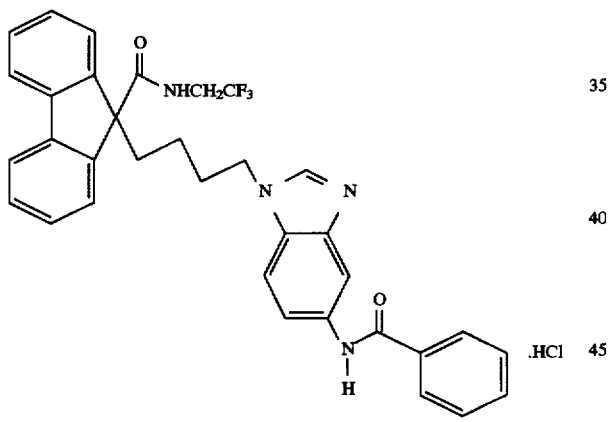

MS (M+H)$^+$=583.

EXAMPLE 487

N-(2,2,2-Trifluoroethyl)-9-[4-[6-[[[4'-(1,1,1-trifluoromethyl)[1,1'-biphenyl]-2-yl]carbonyl]amino]-1H-benzimidazol-1-yl]butyl]-9H-fluorene-9-carboxamide, monohydrochloride

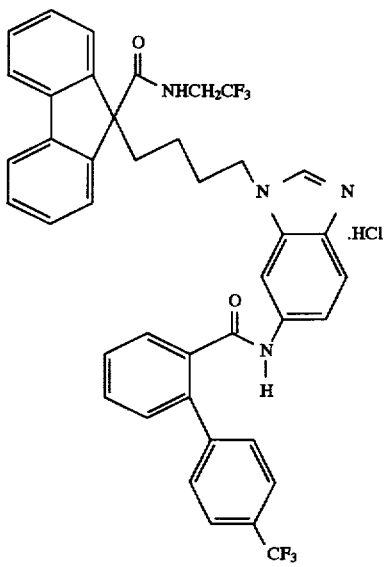

MS (M+H)$^+$=727.

EXAMPLE 488

N-(2,2,2-Trifluoroethyl)-9-[4-[6-[[[4'-(trifluoromethyl)[1,1'-biphenyl]-2-yl]carbonyl]amino]-9H-purin-9-yl]butyl]-9H-fluorene-9-carboxamide

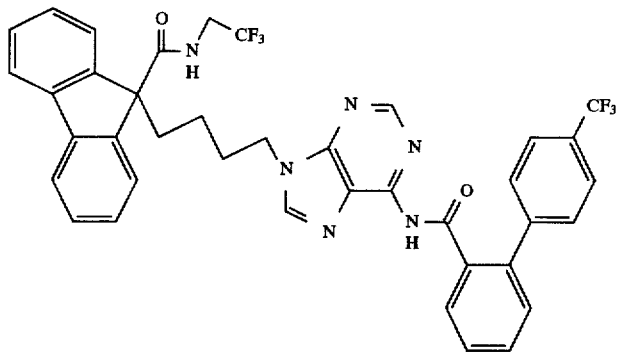

MS: (electrospray, +ions) m/z 729 (M+H).

EXAMPLE 489

N-(2,2,2-Trifluoroethyl)-9-[3-[6-[[[4'-(trifluoromethyl)[1,1'-biphenyl]-2-yl]carbonyl]amino]-9H-purin-9-yl]propyl]-9H-fluorene-9-carboxamide

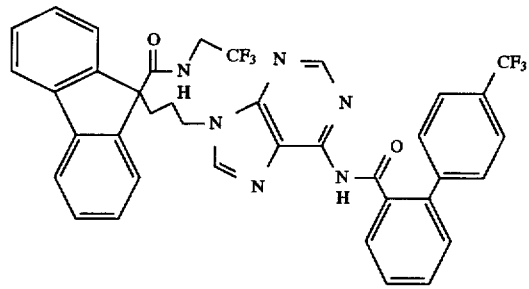

MS: (electrospray, +ions) m/z 715 (M+H).

EXAMPLE 490

N-(2,2,2-Trifluoroethyl)-9-[[3-[5-[[[4'-(trifluoromethyl)[1,1'-biphenyl]-2-yl]carbonyl]amino]-1H-benzimidazol-2-yl]propyl]thio]-9H-fluorene-9-carboxamide, monohydrochloride

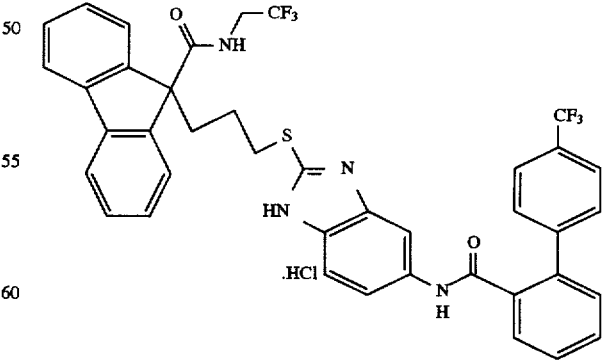

MS: (M+H)$^+$@745.

EXAMPLE 491

9-[4-[5-Methoxy-2-methyl-4-[[[4'-(trifluoromethyl)[1,1'-biphenyl]-2-yl]carbonyl]amino]-1H-benzimidazol-1-yl]butyl]-N-(2,2,2-trifluoroethyl)-9H-fluorene-9-carboxamide

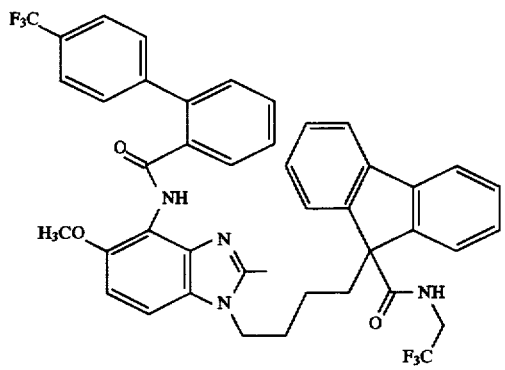

MS: (electrospray, +ions).

EXAMPLE 492

N-(2,2,2-Trifluoroethyl)-9-[4-[7-[[[4'-(trifluoromethyl)[1,1'-biphenyl]-2-yl]carbonyl]amino]-1H-benzimidazol-1-yl]butyl]-9H-fluorene-9-carboxamide

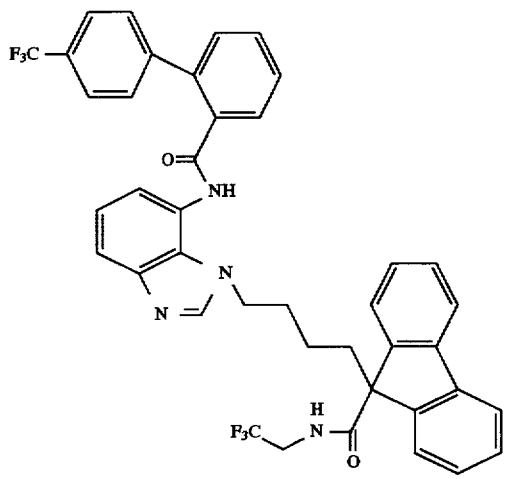

MS: (electrospray, +ions) m/z 727 (M+H).

EXAMPLE 493

9-[3-[5-[[2-(2-Benzothiazolyl)benzoyl]amino]-1H-benzimidazol-1-yl]propyl]-N-(2,2,2-trifluoroethyl)-9H-fluorene-9-carboxamide, monohydrochloride

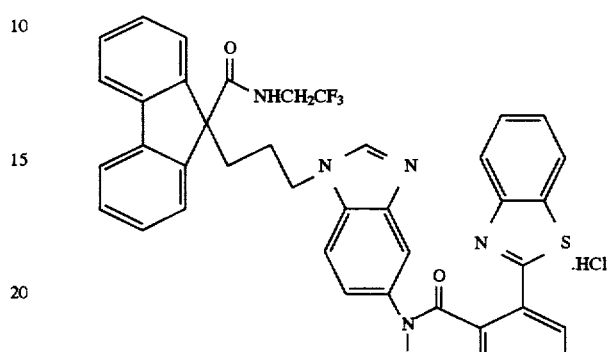

MS: (M+H)$^+$=702.

EXAMPLE 494

N-(2,2,2-Trifluoroethyl)-9-[3-[4-[[[4'-(trifluoromethyl)[1,1'-biphenyl]-2-yl]carbonyl]amino]-1H-benzimidazol-1-yl]propyl]-9H-fluorene-9-carboxamide

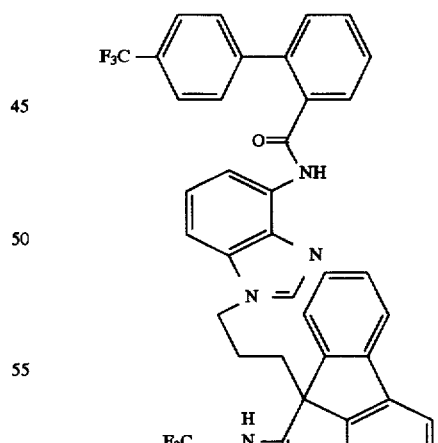

MS: (electrospray, +ions) m/z 713 (M+H).

EXAMPLE 495

N-(2,2,2-Trifluoroethyl)-9-[3-[7-[[[4'-(trifluoromethyl)[1,1'-biphenyl]-2-yl]carbonyl]amino]-1H-benzimid-azol-1-yl]propyl]-9H-fluorene-9-carboxamide

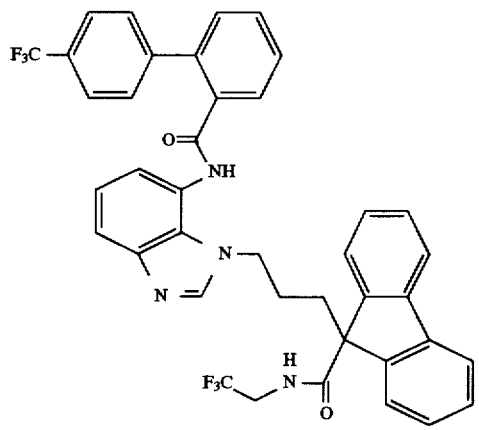

MS: (electrospray, +ions) m/z 713 (M+H).

EXAMPLE 496

N-(2,2,2-Trifluoroethyl)-9-[3-[5-[[[4'-(trifluoromethyl)(1,1'-biphenyl]-2-yl]carbonyl]amino]-1H-indazol-1-yl]propyl]-9H-fluorene-9-carboxamide

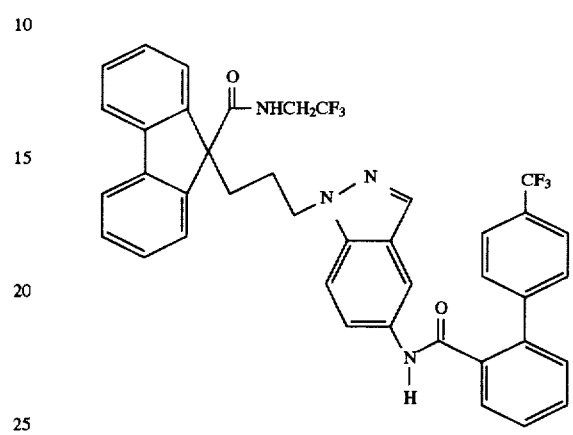

MS: $(M+H)^+=713$.

EXAMPLE 497–498

N-(2,2,2-Trifluoroethyl)-9-[4-[5-[[[4'-(trifluoromethyl)[1,1'-biphenyl]-2-yl]carbonyl]amino]-1 H-benzimdazol-2-yl]butyl]-9H-fluorene-9-carboxamide, monohydrochloride

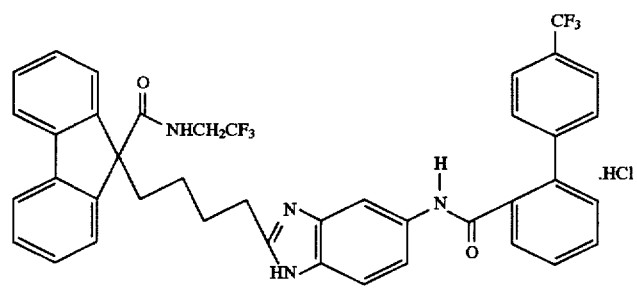

MS $(M+H)^+=727$.

EXAMPLE 499

9-[3-[2-Methyl-5-[[[4'-(trifluoromethyl)[1,1'-biphenyl]-2-yl]carbonyl]amino]-1H-benzimidazol-1-yl]propyl]-N-(2,2,2-trifluoroethyl)-9H-fluorene-9-carboxamide, monohydrochloride

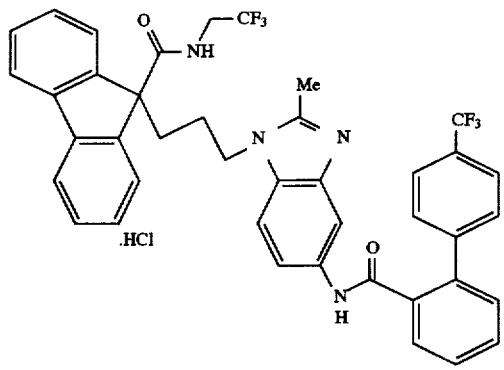

MS: (M)+@726.

EXAMPLE 500

9-[4-[2-Methyl-5-([[[4'-(trifluoromethyl)[1,1'-biphenyl]-2-yl]carbonyl]amino]-1H-benzimidazol-1-yl]butyl]-N-(2,2,2-trifluoroethyl)-9H-fluorene-9-carboxamide

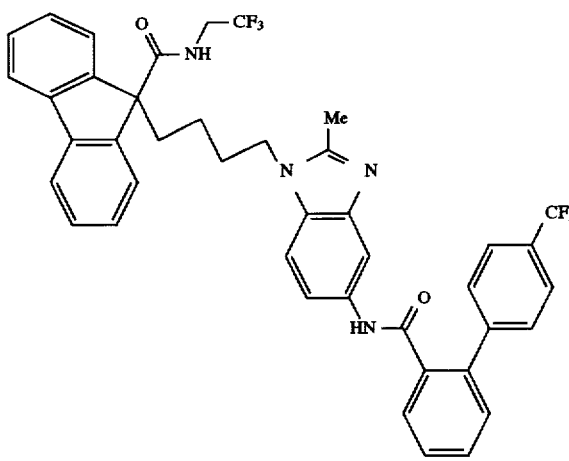

MS: (M)+.

EXAMPLE 501

9-[3-[1-Methyl-5-[[[4'-(trifluoromethyl)[1,1'-biphenyl]-2-yl]carbonyl]amino]-1H-benzimdazol-2-yl]propyl]-N-(2,2,2-trifluoroethyl)-9H-fluorene-9-carboxamide

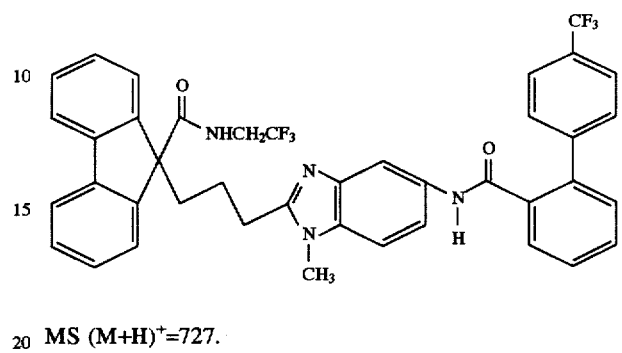

MS (M+H)+=727.

EXAMPLE 502

9-[3-[1-Methyl-6-[[[4'-(trifluoromethyl)[1,1'-biphenyl]-2-yl]carbonyl]amino]-1H-benzimdazol-2-yl]propyl]-N-(2,2,2-trifluoroethyl)-9H-fluorene-9-carboxamide

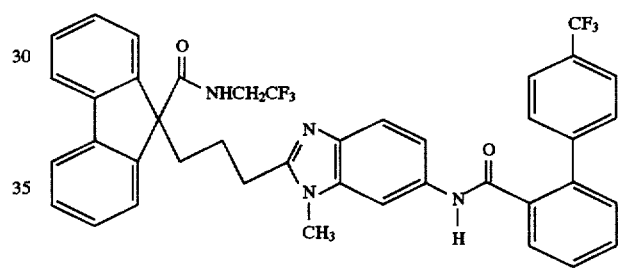

MS (M+H)+727.

EXAMPLE 503

9-[3-[5-[[[3',5'-Bis(trifluoromethyl)[1,1'-biphenyl]-2-yl]carbonyl]amino]-1H-benzimidazol-1-yl]propyl]-N-(2,2,2-trifluoroethyl)-9H-fluorene-9-carboxamide

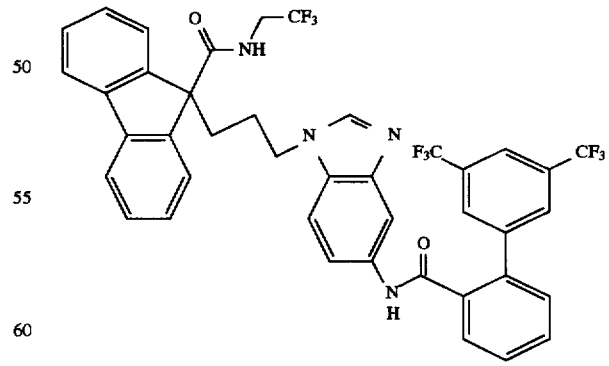

MS: (M)+@780.

EXAMPLE 504

N-(2,2,2-Trifluoroethyl)-9-[3-[5-[[[3'-(trifluoromethyl)[1,1'-biphenyl]-2-yl]carbonyl]amino]-1H-benzimidazol-1-yl]propyl]-9H-fluorene-9-carboxamide

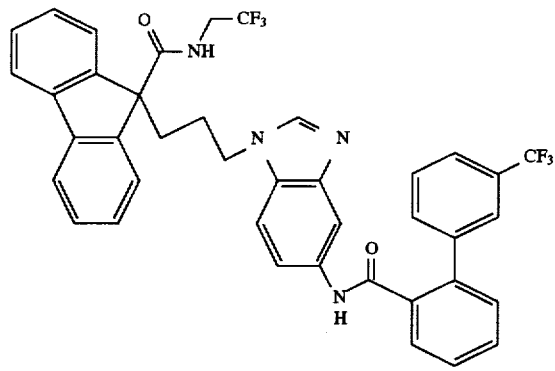

MS: (M)⁺@712.

EXAMPLE 505

N-(2,2,2-Trifluoroethyl)-9-[3-[5-[[[4'-(trifluoromethoxy)[1,1'-biphenyl]-2-yl]carbonyl]amino]-1H-benzimidazol-1-yl]propyl]-9H-fluorene-9-carboxamide

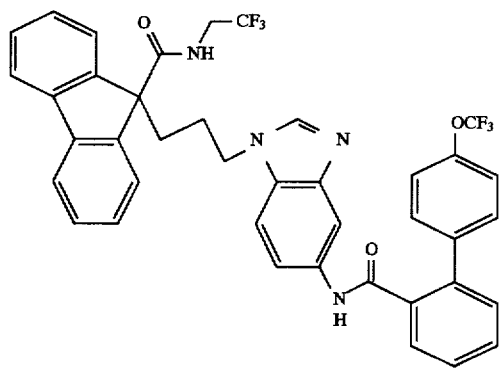

MS: (M)⁺@728.

EXAMPLE 506

9-[[5-(Diethoxyphosphinyl)pentyl]amino]-N-(2,2,2-trifluoroethyl)-9H-fluorene-9-carboxamide

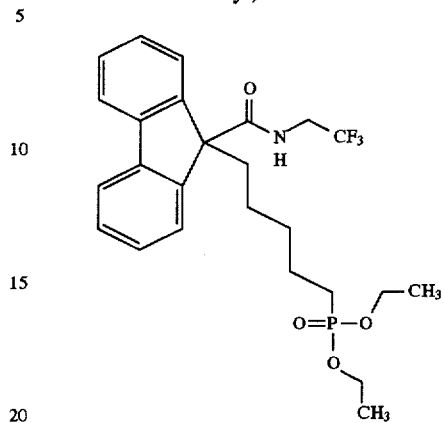

MS (ESI, +ions): 498 (M+H), 515 (M+NH₄).

EXAMPLE 507 trans-[3-[9-[[(2,2,2-Trifluoroethyl)amino]carbonyl]-9H-fluoren-9-yl]propyl][4-[[[4'-(trifluoromethyl)[1,1'-biphenyl]-2-yl]carbonyl]amino]cyclohexyl]carbamic acid, phenylmethyl ester

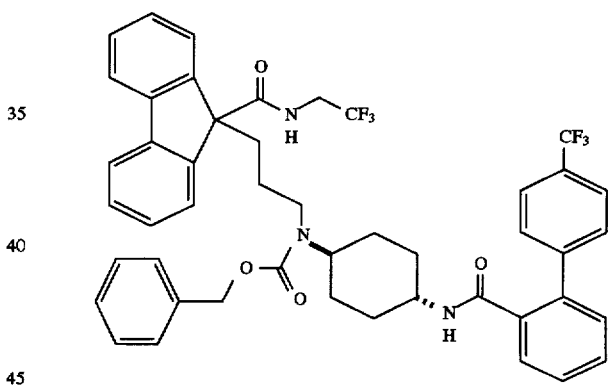

MS (ES, +ions) m/z 845 [M+NH₄].

EXAMPLE 508 trans-N-(2,2,2-Trifluoroethyl)-9-[3-[[4-[[[4'-(trifluoromethyl)[1,1'-biphenyl]-2-yl]carbonyl]amino]cyclohexyl]amino]propyl]-9H-fluorene-9-carboxamide, monohydrochloride

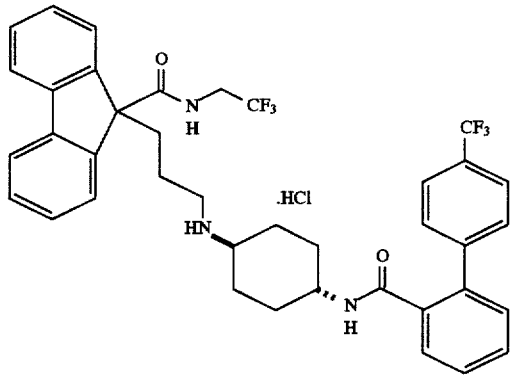

trans isomer

MS (ES, +ions) m/z 694 (M+H)

EXAMPLE 509 trans-9-[3-[[4-(Benzoylamino)cyclohexyl]amino]propyl]-N-(2,2,2-trifluoroethyl)-9H-fluorene-9-carboxamide, monohydrochloride

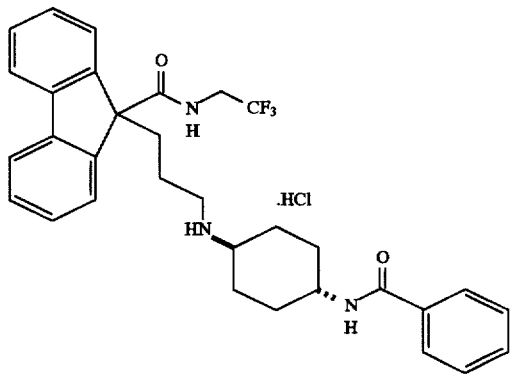

MS (ES, +ions) m/z 550 [M+H].

EXAMPLE 510 trans-9-[3-[[4-(Benzoylamino)cyclohexyl]methylamino]propyl]-N-(2,2,2-trifluoroethyl)-H-fluorene-9-carboxamide, monohydrochloride

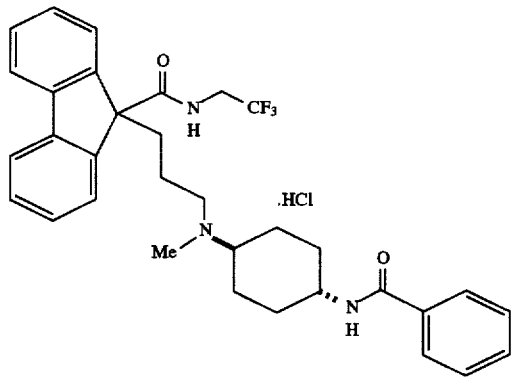

MS (ES, +ions) m/z 647 [M+H].

EXAMPLE 511

N-(2,2,2-Trifluoroethyl)-9-[4-[5-[[[4'-(trifluoromethyl)[1,1'-biphenyl]-2-yl]carbonyl]amino]-2-pyridinyl]butyl]-9H-fluorene-9-carboxamide, N-oxide

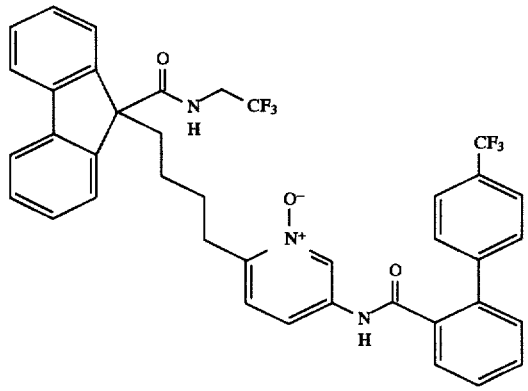

MS (ES, +ions) m/z 704 [M+H].

EXAMPLE 512

N-(2,2,2-Trifluoroethyl)-9-[4-[2-[[[4'-(trifluoromethyl)[1,1'-biphenyl]-2-yl]carbonyl]amino]-5-pyridinyl]butyl]-9H-fluorene-9-carboxamide, N-oxide

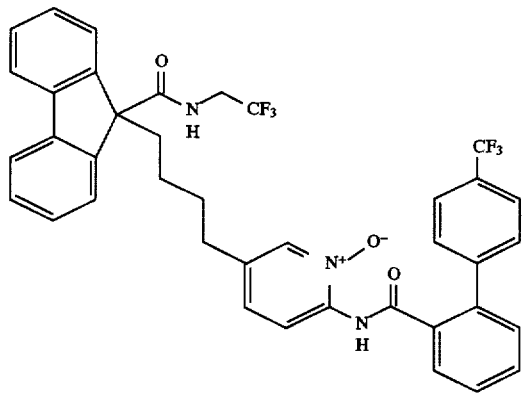

MS (ES, +ions) m/z 704 [M+H].

EXAMPLE 513

9-[4-(3-Oxo-2,4-dioxa-3-phosphaspiro[5.5]undecan-3-yl)butyl]-N-(2,2,2-trifluoroethyl)-9H-fluorene-9-carboxamide

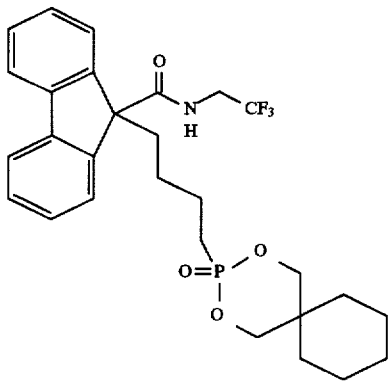

MS (ESI, +ion): 536 (M+H).

EXAMPLE 514

N-(2,2,2-Trifluoroethyl)-9-[4-[[5-[[[4'-(trifluoromethyl)[1,1'-biphenyl]-2-yl]carbonyl]amino]-2-pyridinyl]oxy]butyl]-9H-fluorene-9-carboxamide

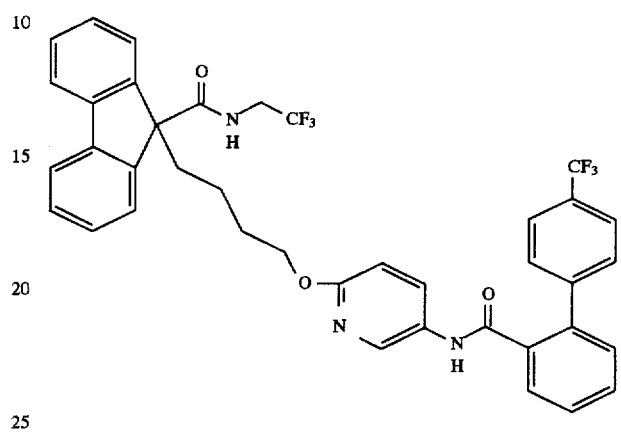

MS (ESI, +ion): 704 (M+H).

EXAMPLE 515

9-[4-[[4-Methyl-5-[[[4'-(trifluoromethyl)[1,1'-biphenyl]-2-yl]carbonyl]amino]-2-pyridinyl]oxy]butyl]-N-(2,2,2-trifluoroethyl)-9H-fluorene-9-carboxamide

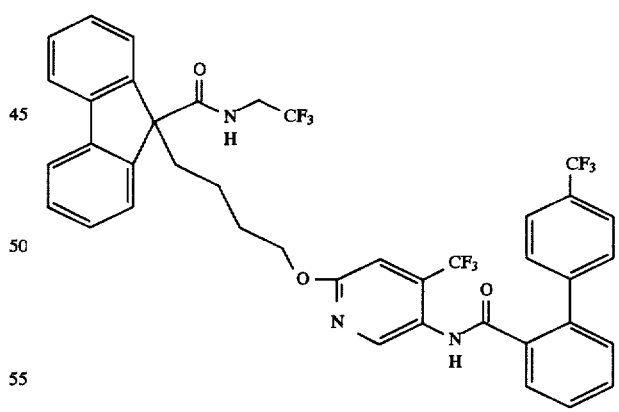

MS (ESI, +ion): 718 (M+H).

EXAMPLE 516

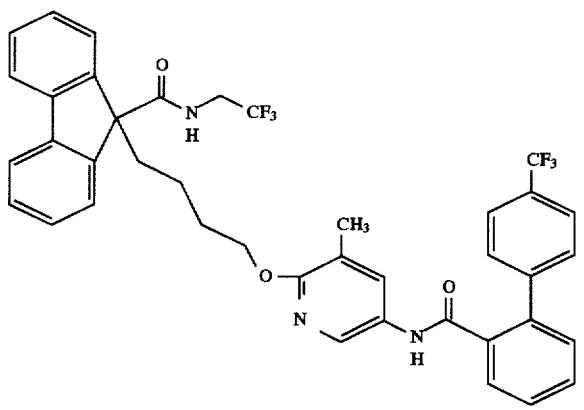

MS (ESI, +ion): 718 (M+H).

EXAMPLE 517

9-[4-[4-[[(3'-Chloro[1,1'-biphenyl]-2-yl)carbonyl]amino]-1H-benzimidazol-1-yl]butyl]-N-(2,2,2-trifluoroethyl)-9H-fluorene-9-carboxamide

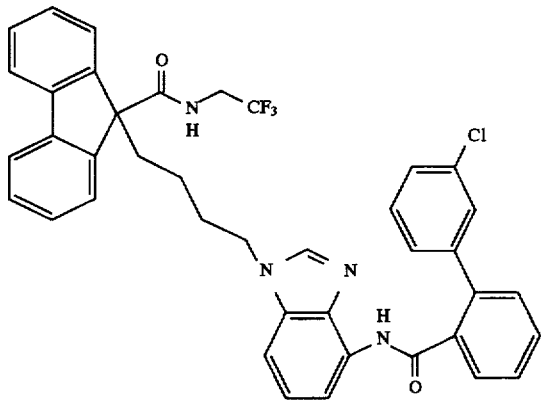

MS (ESI, +ion): 693 (M+H).

EXAMPLE 518

9-[4-[4-[[2-(1,1-Dimethylethyl)benzoyl]amino]-1H-benzimidazol-1-yl]butyl]-N-(2,2,2-trifluoroethyl)-9H-fluorene-9-carboxamide

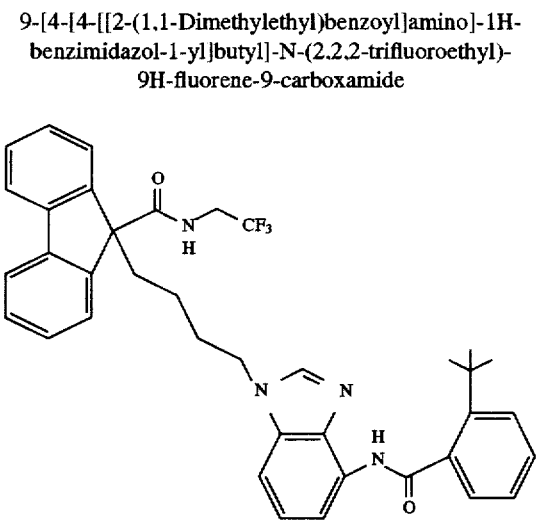

MS (ESI, +ion): 639 (M+H).

EXAMPLE 519

9-[4-[4-[[2-(1,1-Dimethylethyl)benzoyl]amino]-2-methyl-1H-benzimidazol-1-yl]butyl]-N-(2,2,2-trifluoroethyl)-9H-fluorene-9-carboxamide

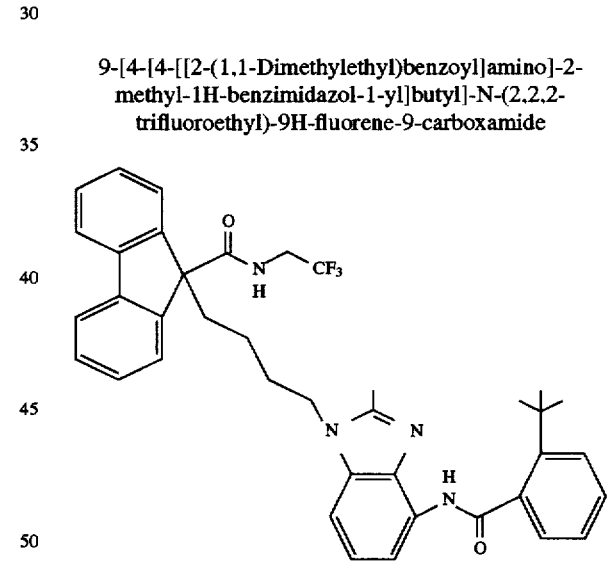

MS (ESI, +ion): (M+H).

EXAMPLE 520

N-(2,2,2-Trifluoroethyl)-9-[4-[5-[[[4'-(trifluoromethyl)[1,1'-biphenyl]-2-yl]carbonyl]amino]-2-pyridinyl]butyl]-9H-fluorene-9-carboxamide, monohydrochloride

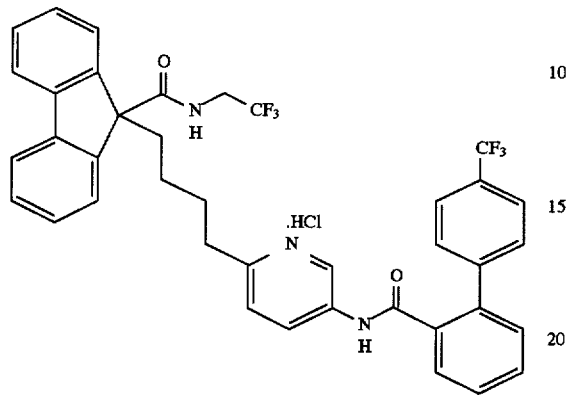

MS (ES, +ions) m/z 688 [M+H].

EXAMPLE 521

N-(2,2,2-Trifluoroethyl)-9-[4-[2-[[[4'-(trifluoromethyl)[1,1'-biphenyl]-2-yl]carbonyl]amino]-5-pyridinyl]-butyl]-9H-fluorene-9-carboxamide, monohydrochloride

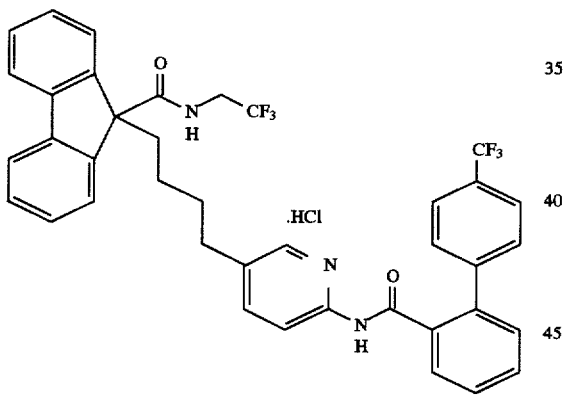

MS (ES, +ions) m/z 688 [M+H].

EXAMPLE 522

9-[4-[2-(Benzoylamino)-5-pyridinyl]butyl]-N-(2,2,2-trifluoroethyl)-9H-fluorene-9-carboxamide, monohydrochloride

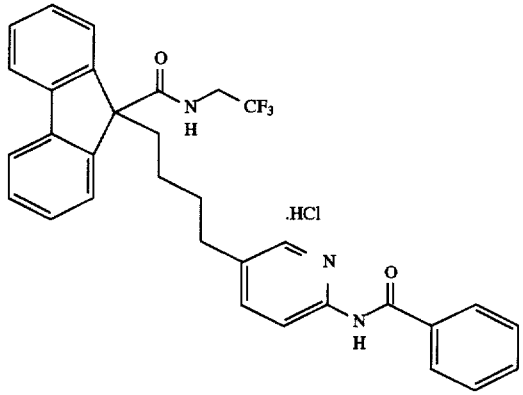

MS (ES, +ions) m/z 544 [M+H].

EXAMPLE 523

9-[4-[4-(Benzoylamino)-1H-indol-1-yl]butyl]-N-(2,2,2-trifluoroethyl)-9H-fluorene-9-carboxamide

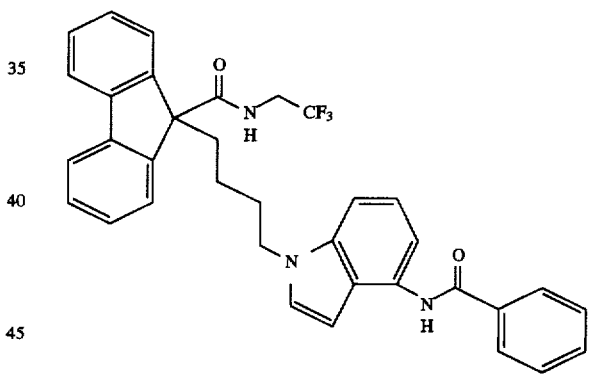

MS (ES, +ions) m/z 582 [M+H].

EXAMPLE 524

N-(2,2,2-Trifluoroethyl)-9-[4-[2-[[[4'-(trifluoromethyl)[1,1'-biphenyl]-2-yl]carbonyl]amino]-5-pyrimidinyl]butyl]-9H-fluorene-9-carboxamide, monohydrochloride

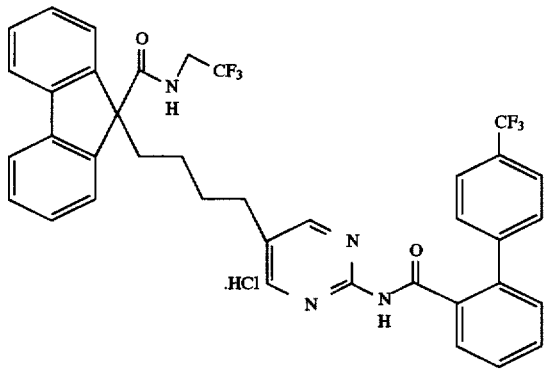

MS (ES, +ions) m/z 689 (M+H).

EXAMPLE 525

9-[4-[2-(Benzoylamino)-5-pyrimidinyl]butyl]-N-(2,2,2-trifluoroethyl)-9H-fluorene-9-carboxamide, monohydrochloride

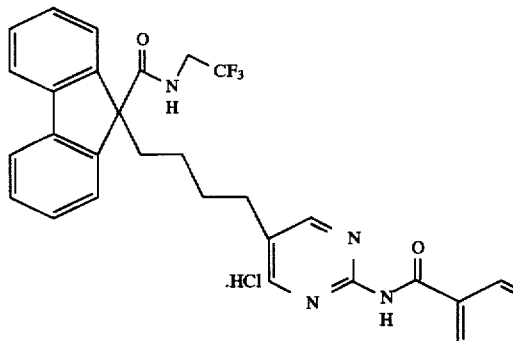

MS (ES, +ions) m/z 545 (M+H).

EXAMPLE 526–529

9-[4-[5-[[2-(2-Pyridinyl)benzoyl]amino]-2-pyridinyl]butyl]-N-(2,2,2-trifluoroethyl)-9H-fluorene-9-carboxamide, dihydrochloride

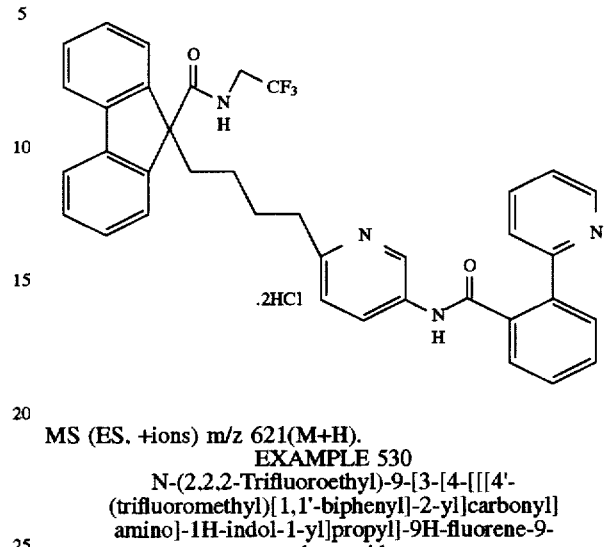

MS (ES, +ions) m/z 621(M+H).

EXAMPLE 530

N-(2,2,2-Trifluoroethyl)-9-[3-[4-[[[4'-(trifluoromethyl)[1,1'-biphenyl]-2-yl]carbonyl]amino]-1H-indol-1-yl]propyl]-9H-fluorene-9-carboxamide

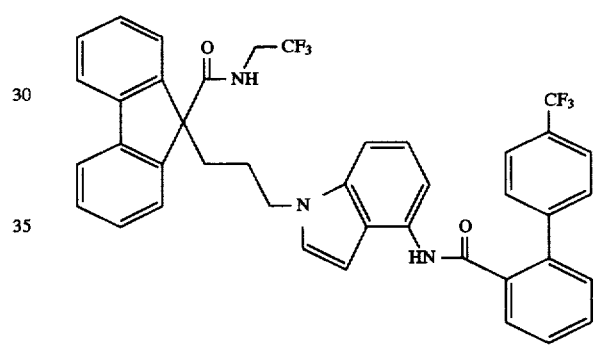

MS (ES, +ions) m/z 729 (M+NH$_4$).

EXAMPLE 531–532

N-(2,2,2-Trifluoroethyl)-9-[3-[5-[[[4'-(trifluoromethyl)[1,1'-biphenyl]-2-yl]carbonyl]amino]-1H-indol-5-yl]propyl]-9H-fluorene-9-carboxamide

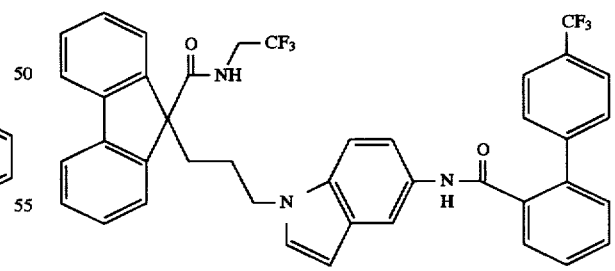

MS (ES, +ions) m/z 729 (M+NH$_4$).

EXAMPLE 533

N-(2,2,2-Trifluoroethyl)-9-[3-[[5-[[[4'-(trifluoromethyl)[1,1'-biphenyl]-2-yl]carbonyl]amino]-2-pyridinyl]thio]propyl]-9H-fluorene-9-carboxamide

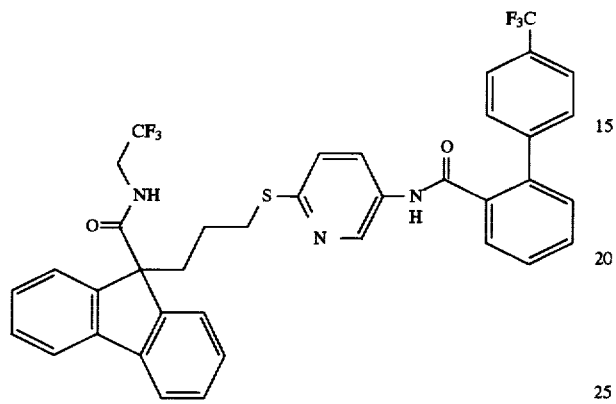

MS (ES, +ions) m/z @ 706 [M+H]+.

EXAMPLE 534

9-[4-[4-[[2-(2-Pyridinyl)benzoyl]amino]-1H-indol-1-yl]butyl]-N-(2,2,2-trifluoroethyl)-9H-fluorene-9-carboxamide

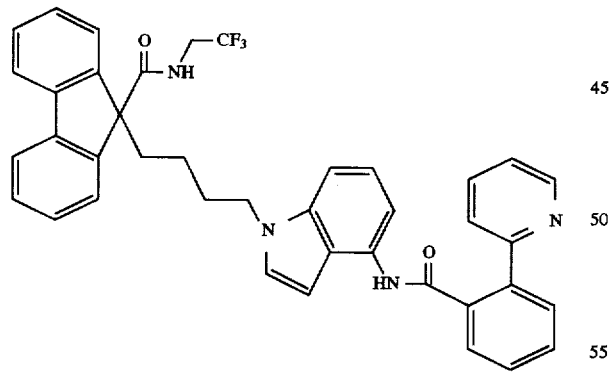

MS (ES, +ions) m/z 659 (M+H).

EXAMPLE 535

N-(2,2,2-Trifluoroethyl)-9-[4-[4-[[[4'-(trifluoromethyl)[1,1'-biphenyl]-2-yl]carbonyl]amino]-2H-indazol-2-yl]butyl]-9H-fluorene-9-carboxamide

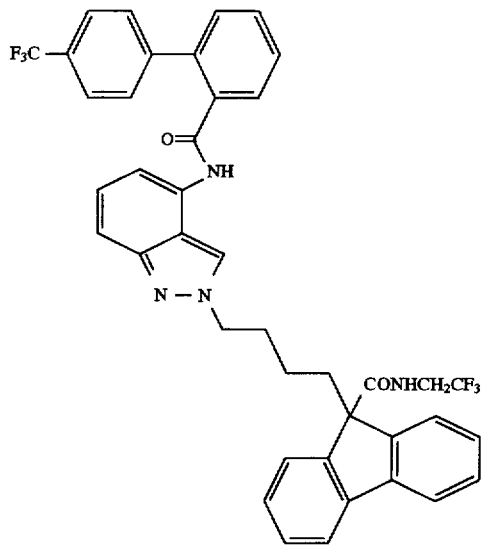

MS: (electrospray, +ions) m/z 727 (M+H).

EXAMPLE 536

N-(2,2,2-Trifluoroethyl)-9-[4-[4-[[[4'-(trifluoromethyl)[1,1'-biphenyl]-2-yl]carbonyl]amino]-1H-indazol-1-yl]butyl]-9H-fluorene-9-carboxamide

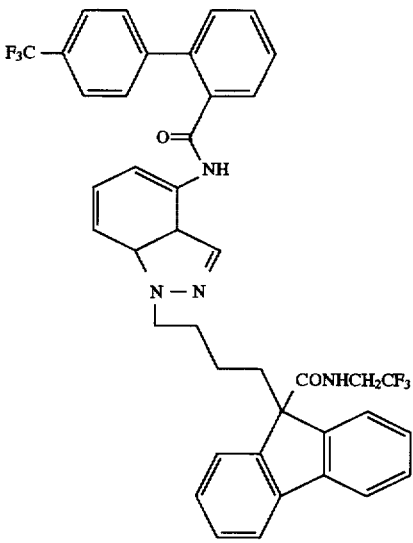

MS: (electrospray, +ions) m/z 727 (M+H).

EXAMPLE 537

N-(2,2,2-Trifluoroethyl)-9-[4-[4-[[[4'-(trifluoromethyl)[1,1'-biphenyl]-2-yl]carbonyl]amino]-1H-pyrrolo[2,3-b]pyridin-1-yl]butyl]-9H-fluorene-9-carboxamide

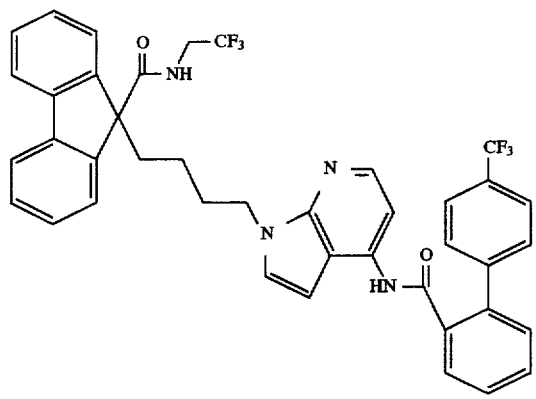

MS (ES, +ions) m/z 727 (M+H).

EXAMPLE 538–544

9-[4-[2-Propyl-4-[[[4'-(trifluoromethyl)[1,1'-biphenyl]-2-yl]carbonyl]amino]-1H-benzimidazol-1-yl]butyl]-N-(2,2,2-trifluoroethyl)-9H-fluorene-9-carboxamide

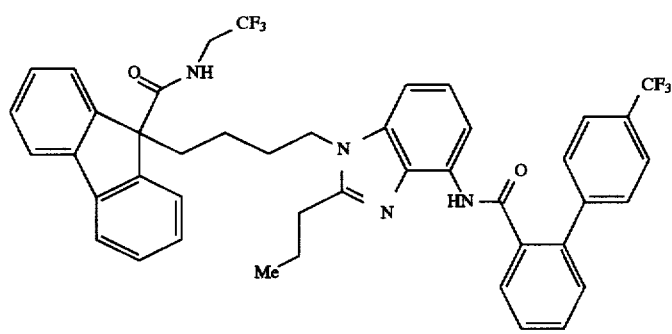

MS: m/z [M+H]$^+$769; [M-H]$^-$767.

EXAMPLE 545

9-[4-[2-(Diethylamino)-4-[[[4'-(1,1,1-trifluoromethyl)[1,1'-biphenyl]-2-yl]carbonyl]amino]-1H-benzimidazol-1-yl]butyl]-N-(2,2,2-trifluoroethyl)-9H-fluorene-9-carboxamide

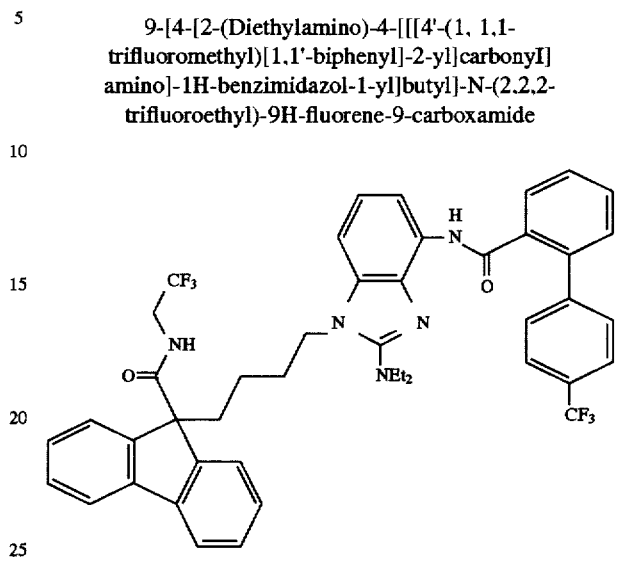

EXAMPLE 546

9-[4-[2-Methoxy-4-[[[4'-(trifluoromethyl)[1,1'-biphenyl]-2-yl]carbonyl]amino]-1H-benzimidazol-1-yl]butyl]-N-(2,2,2-trifluoroethyl)-9H-fluorene-9-carboxamide

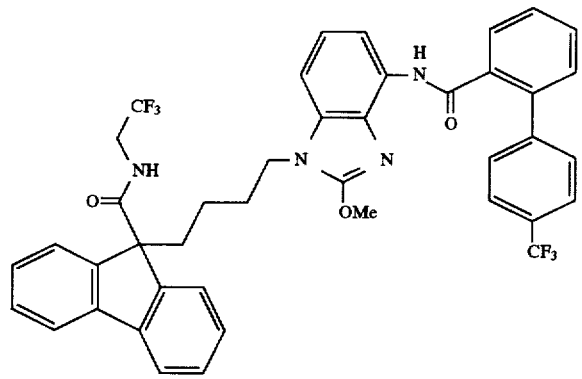

EXAMPLE 547

9-[4-[2-(Methylthio)-4-[[[4'-(trifluoromethyl)[1,1'-biphenyl]-2-yl]carbonyl]amino]-1H-benzimidazol-1-yl]butyl]-N-(2,2,2-trifluoroethyl)-9H-fluorene-9-carboxamide

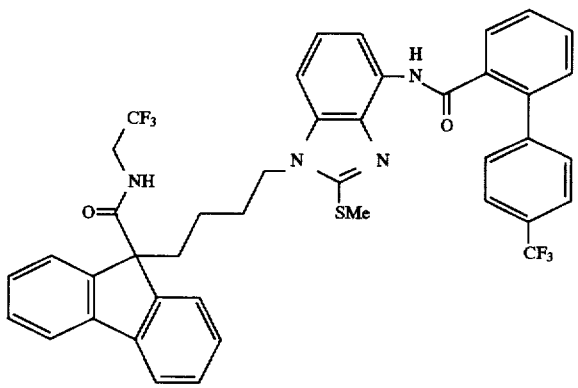

EXAMPLE 548

9-[4-[2-Chloro-4-[[[4'-(trifluoromethyl)[1,1'-biphenyl]-2-yl]carbonyl]amino]-1H-benzimidazol-1-yl]butyl]-N-(2,2,2-trifluoroethyl)-9H-fluorene-9-carboxamide

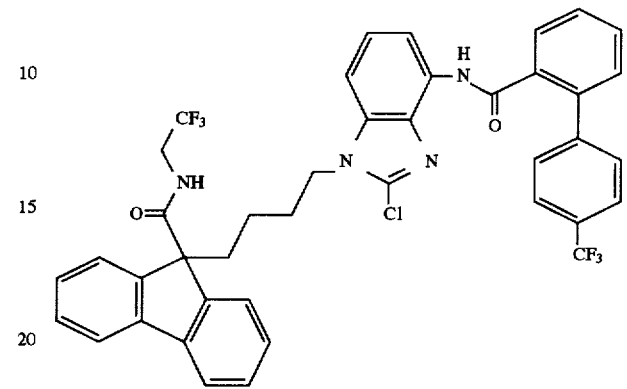

EXAMPLE 549

[[[2-[9-[[(2,2,2-Trifluoroethyl)amino]carbonyl]-9H-fluoren-9-yl]ethyl]amino]methyl]phosphonic acid, bis(1-methylethyl) ester

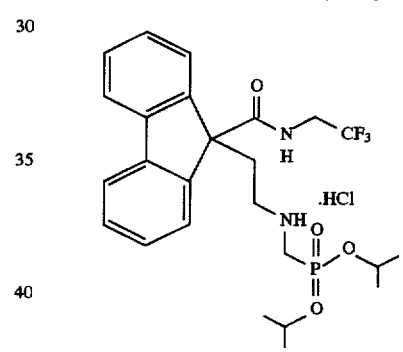

MS (ES, +ions) m/z 513 [M+H].

EXAMPLE 550

N-(2,2,2-Trifluoroethyl)-9-[4-[5-[[[4'-(trifluoromethyl)[1,1'-biphenyl]-2-yl]carbonyl]amino]-1H-indol-1-yl]butyl]-9H-fluorene-9-carboxamide

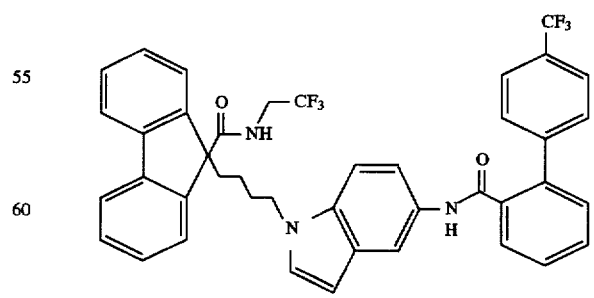

MS (ES, +ions) m/z 726 [M+H].

EXAMPLE 551

9-[4-[5-(Benzoylamino)-1H-indol-1-yl]butyl]-N-(2,2,2-trifluoroethyl)-9H-fluorene-9-carboxamide

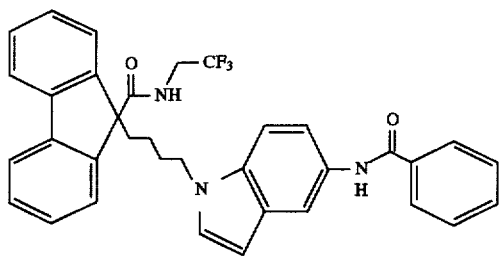

MS (ES, +ions) m/z 582 [M+H].

EXAMPLE 552

N-(2,2,2-Trifluoroethyl)-9-[4-[5-[[[4'-(trifluoromethyl)[1,1'-biphenyl]-2-yl]carbonyl]amino]-2-pyridinyl]-3-butenyl]-9H-fluorene-9-carboxamide

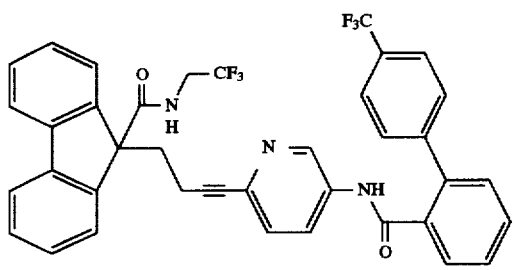

MS (ES, +ions) m/z 684 (M+H).

EXAMPLE 552A

N-(2,2,2-Trifluoroethyl)-9-[4-[5-[[[4'-(trifluoromethyl)[1,1'-biphenyl]-2-yl]carbonyl]amino]-2-pyridinyl]-3-butenyl]-9H-fluorene-9-carboxamide, trifluoroacetate

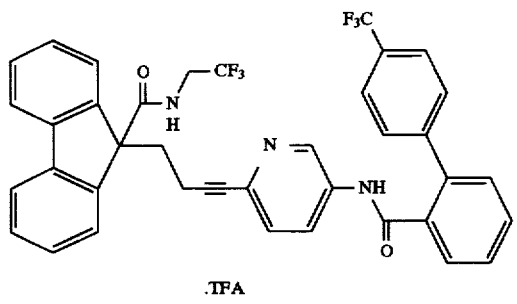

MS (ES, +ions) m/z 684 (M+H).

EXAMPLE 553

2-[3-[9-[[(2,2,2-Trifluoroethyl)amino]carbonyl]-9H-fluoren-9-yl]propoxyl-5-[([4'-(trifluoromethyl)[1,1'-biphenyl]-2-yl]carbonyl]amino]-3-pyridinecarboxylic acid, methyl ester

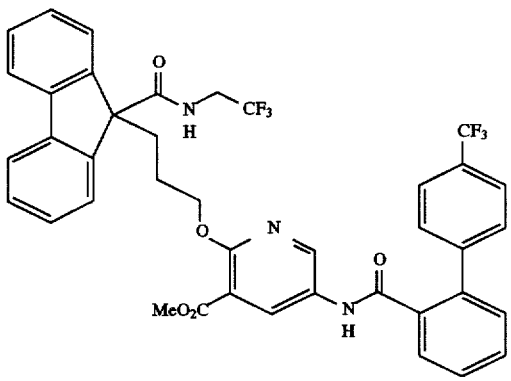

MS (ES, +ions) m/z 748 [M+H].

EXAMPLE 554

2-[3-[9-[[(2,2,2-Trifluoroethyl)amino]carbonyl]-9H-fluoren-9-yl]propoxy]-5-[[[4'-(trifluoromethyl)[1,1'-biphenyl]-2-yl]carbonyl]amino]-3-pyridinecarboxylic acid

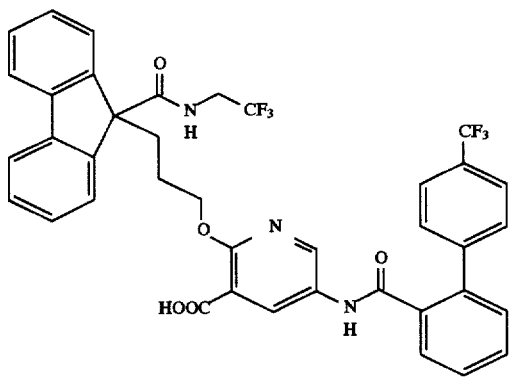

MS (ES, +ions) m/z 734 [M+H].

EXAMPLE 555

N-(2,2,2-Trifluoroethyl)-9-[4-[4-[[[4'-(trifluoromethyl)[1,1'-biphenyl]-2-yl]sulfonyl]amino]-1H-indol-1-yl]butyl]-9H-fluorene-9-carboxamide

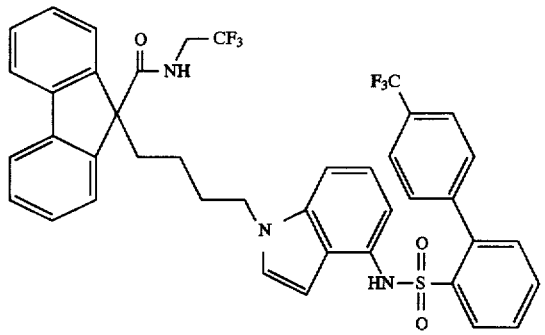

MS (ES, +ions) m/z 762 (M+H).

EXAMPLE 556

N-(2,2,2-Trifluoroethyl)-9-[4-[4-[[[4'-(trifluoromethyl)[1,1'-biphenyl]-2-yl]carbonyl]amino]-1H-benzotriazol-1-yl]butyl]-9H-fluorene-9-carboxamide

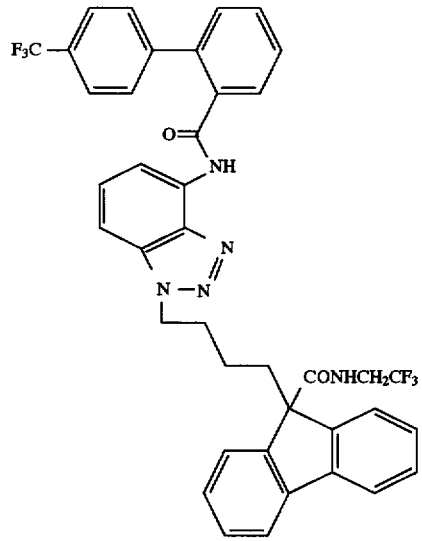

MS: (electrospray, +ions) m/z 728 (M+H).

EXAMPLE 557

N-(2,2,2-Trifluoroethyl)-9-[5-[4-[[[4'-(trifluoromethyl)[1,1'-biphenyl]-2-yl]-carbonyl]amino]-1H-benzimidazol-1-yl]pentyl]-9H-fluorene-9-carboxamide

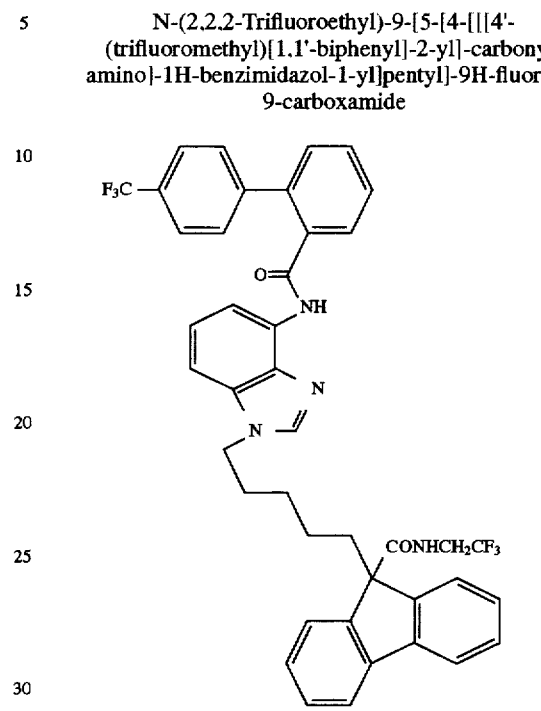

MS: (electrospray, +ions) m/z 741(M+H).

EXAMPLE 558

9-[4-[4-[Methyl[[4'-(trifluoromethyl)[1,1'-biphenyl]-2-yl]carbonyl]amino]-1H-benzimidazol-1-yl]butyl]-N-(2,2,2-trifluoroethyl)-9H-fluorene-9-carboxamide

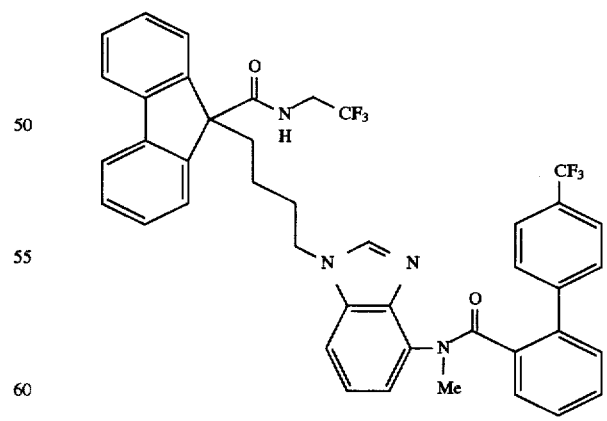

MS (ES, +ions) m/z 741[M+H].

EXAMPLE 559

9-[3-[5-[Methyl[[4'-(trifluoromethyl)[1,1'-biphenyl]-2-yl]carbonyl]amino]-1H-benzimidazol-1-yl]propyl]-N-(2,2,2-trifluoroethyl)-9H-fluorene-9-carboxamide

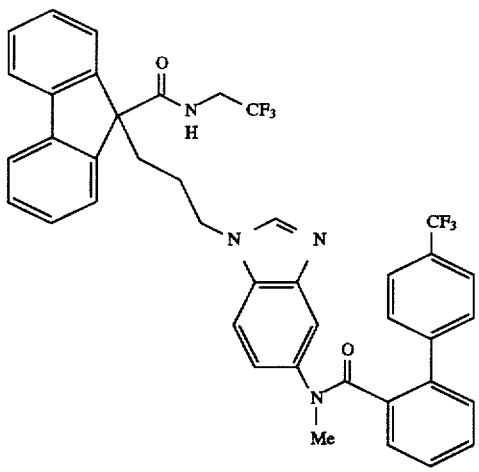

MS (ES, +ions) m/z 727 [M+H].

EXAMPLE 560

N-(2,2,2-Trifluoroethyl)-9-[4-[4-[[[4'-(trifluoromethyl)[1,1'-biphenyl]-2-yl]carbonyl]amino]-6H-pyrrolo[2,3-c]pyridin-6-yl]butyl]-9H-fluorene-9-carboxamide

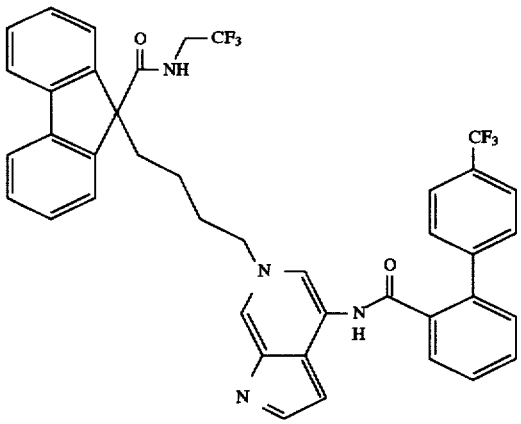

MS (ES, +ions) m/z 727 (M+H).

EXAMPLE 561

9-[4-[2-(1-Methylethyl)-4-[[[4'-(trifluoromethyl)[1,1'-biphenyl]-2-yl]carbonyl]amino]-1H-benzimidazol-1-yl]butyl]-N-(2,2,2-trifluoroethyl)-9H-fluorene-9-carboxamide

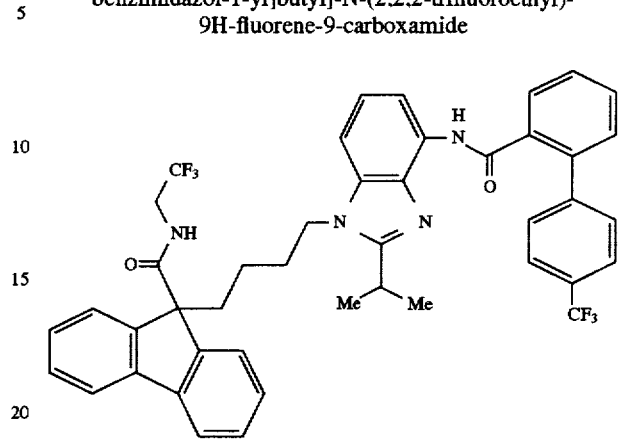

MS: m/z 769 (M+H)$^+$.

EXAMPLE 562

9-[3-[2-(Diethylamino)-5-[[[4'-(trifluoromethyl)[1,1'-biphenyl]-2-yl]carbonyl]amino]-1H-benzimidazol-1-yl]propyl]-N-(2,2,2-trifluoroethyl)-9H-fluorene-9-carboxamide

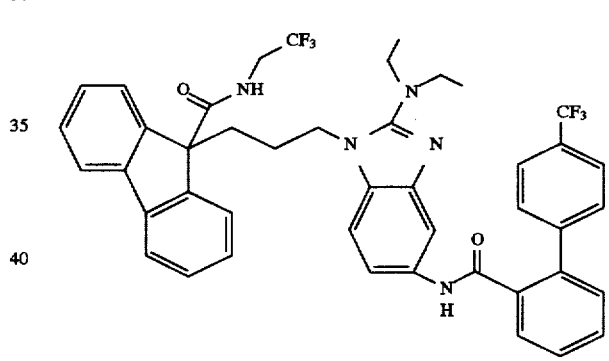

MS: (M+H)$^+$.=784.

EXAMPLE 563

N-(2,2,2-Trifluoroethyl)-9-[4-[4-[[[4'-(1,1,1-trifluoromethyl)[1,1'-biphenyl]-2-yl]carbonyl]amino]-1H-imidazol-1-yl]butyl]-9H-fluorene-9-carboxamide, monohydrochloride

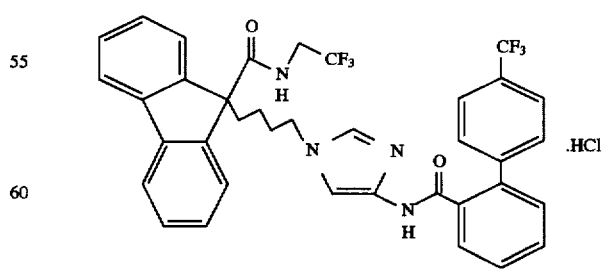

MS: (M+H)$^+$.=677.

EXAMPLE 564
N-(2,2,2-Trifluoroethyl)-9-[3-[[5-[[[4'-(trifluoromethyl)[1,1'-biphenyl]-2-yl]carbonyl]amino]-2-pyridinyl]amino]propyl]-9H-fluorene-9-carboxamide, trifluoroacetate
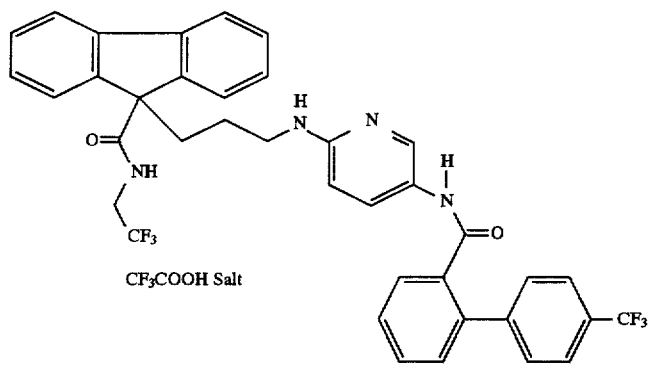
CF$_3$COOH Salt
MS (ES, NH$_3$, +ions) m/z 689 (M+H).
EXAMPLE 565
[4-[9-[[(2,2,2-Trifluoroethyl)amino]carbonyl]-9H-fluoren-9-yl]butyl]phosphonic acid, butyl 3-[[[4'-(trifluoromethyl)[1,1'-biphenyl]-2-yl]carbonyl]amino]propyl ester
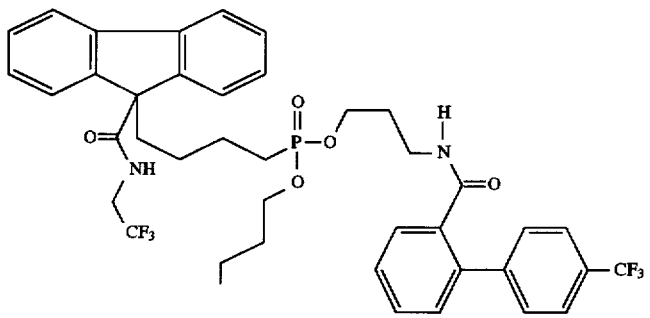
MS (ES, NH$_3$, +ions) m/z 806 (M+NH$_4$), 789 (M+H).

EXAMPLE 566

[4-[9-[[(2,2,2-Trifluoroethyl)amino]carbonyl]-9H-fluoren-9-yl]butylphosphonic acid, butyl 2-[[[4'-(trifluoromethyl)[1,1'-biphenyl]-2-yl]carbonyl]amino]ethyl ester

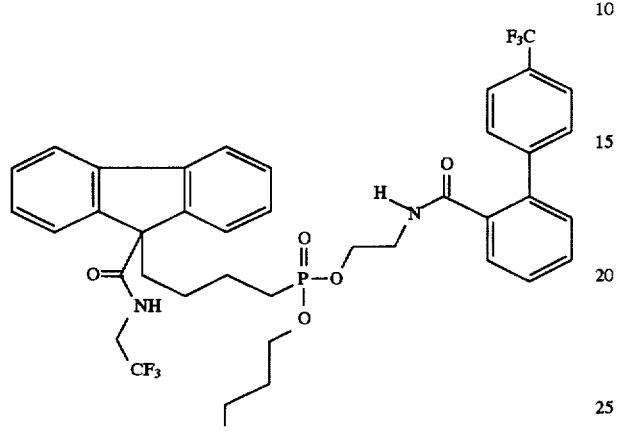

MS (ES, NH$_3$, +ions) m/z 792 (M+NH$_4$), 775 (M+H).

EXAMPLE 567

9-[3-[[5-(Benzoylamino)-2-pyridinyl]amino]propyl]-N-(2,2,2-trifluoroethyl)-9H-fluorene-9-carboxamide, monohydrochloride

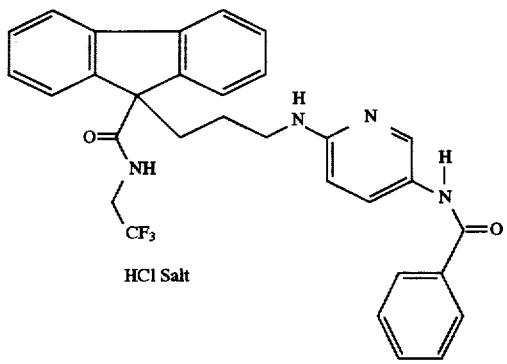

HCl Salt

MS (ES, NH$_3$, +ions) m/z 545 (M+H).

EXAMPLE 568

9-[3-[[5-[[2-(2-Benzothiazolyl)benzoyl]amino]-2-pyridinyl]oxy]propyl]-N-(2,2,2-trifluoroethyl)-9H-fluorene-9-carboxamide, monohydrochloride

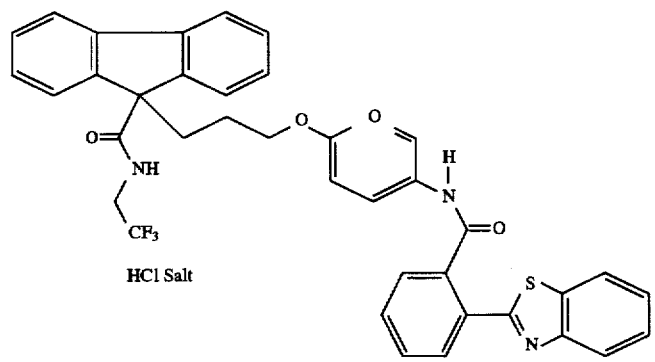

HCl Salt

MS (ES, NH$_3$, +ions) m/z 679 (M+H).

EXAMPLE 569

9-[3-[[5-[[2-(2-Pyridinyl)benzoyl]amino]-2-pyridinyl]oxy]propyl]-N-(2,2,2-trifluoroethyl)-9H-fluorene-9-carboxamide, dihydrochloride

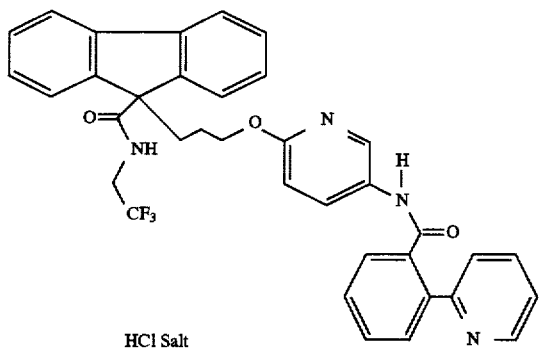

HCl Salt

MS (ES, NH$_3$, +ions) m/z 623 (M+H).

EXAMPLE 570–572

N-(2,2,2-Trifluoroethyl)-9-[5-[[5-[[[4'-(trifluoromethyl)[1,1'-biphenyl]-2-yl]carbonyl]amino]-2-pyridinyl]oxy]pentyl]-9H-fluorene-9-carboxamide

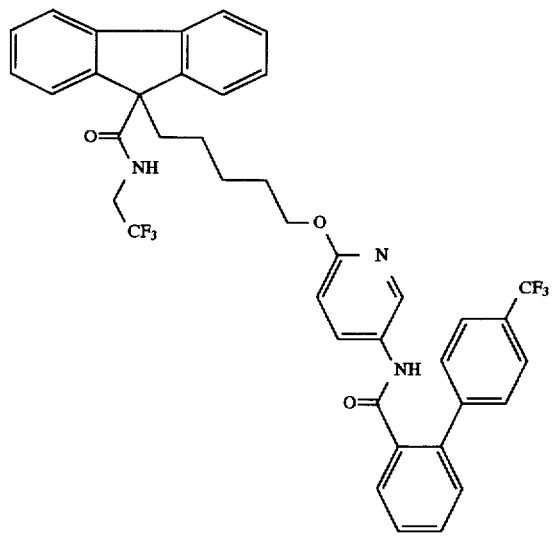

MS (ES, NH$_3$, +ions) m/z 718 (M+H)

EXAMPLE 573

9-[5-[[5-(Benzoylamino)-2-pyridinyl]oxy]pentyl]-N-(2,2,2-trifluoroethyl)-9H-fluorene-9-carboxamide

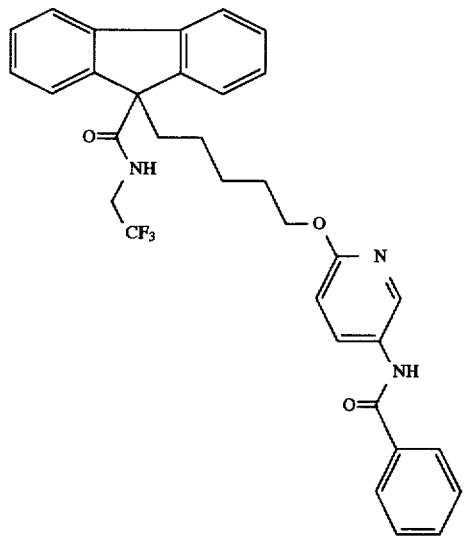

MS (ES, NH$_3$, +ions) m/z 574 (M+H).

EXAMPLE 574

9-[3-[5-[[(4'-Chloro[1,1'-biphenyl]-2-yl)carbonyl]amino]-1H-benzimidazol-1-yl]propyl]-N-(2,2,2-trifluoroethyl)-9H-fluorene-9-carboxamide

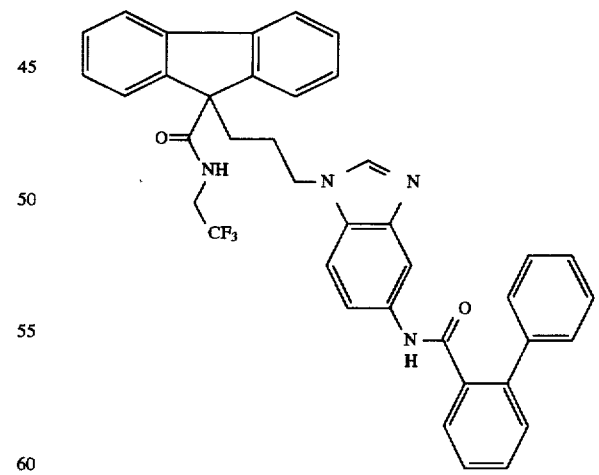

MS (ES, NH$_3$, +ions) m/z 680 (M+H).

EXAMPLE 575

9-[3-[[5-[[(4'-Chloro[1,1'-biphenyl]-2-yl)carbonyl]amino]-2-pyridinyl]oxy]propyl]-N-(2,2,2-trifluoroethyl)-9H-fluorene-9-carboxamide, hydrochloride

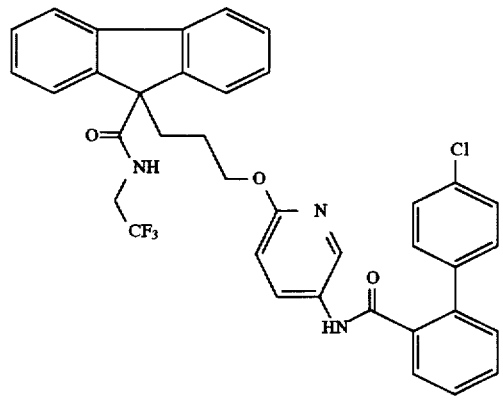

MS (ES, NH$_3$, +ions) m/z 656 (M).

EXAMPLE 576

9-[4-[4-[[(4'-Chloro[1,1'-biphenyl]-2-yl)carbonyl]amino]-1H-benzimidazol-1-yl]butyl]-N-(2,2,2-trifluoroethyl)-9H-fluorene-9-carboxamide

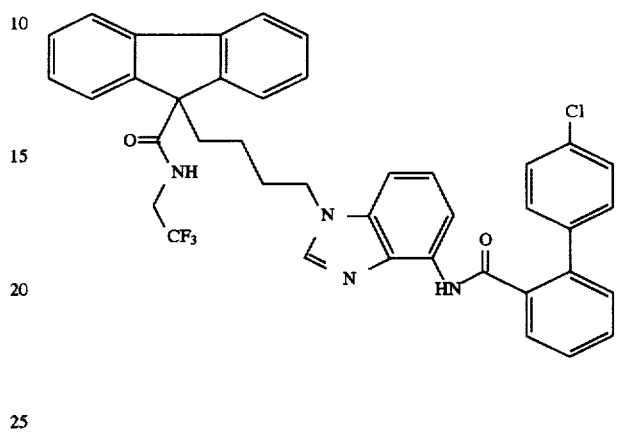

MS (ES, NH$_3$, +ions) m/z 693 (M).

EXAMPLE 577

9-[4-[4-[[(4'-Chloro[1,1'-biphenyl]-2-yl)carbonyl]amino]-1H-indol-1-yl]butyl]-N-(2,2,2-trifluoroethyl)-9H-fluorene-9-carboxamide

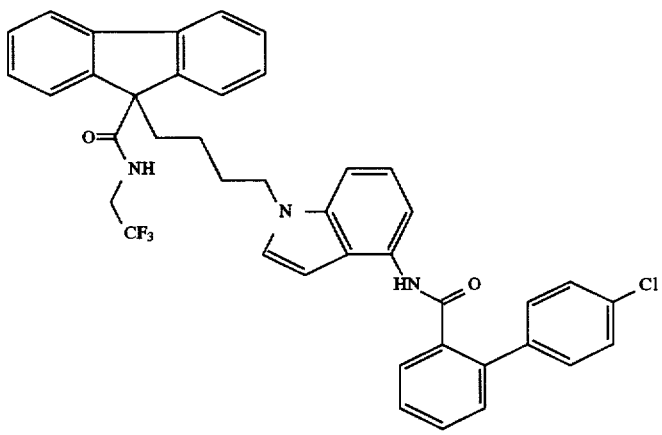

MS (ES, NH$_3$, +ions) m/z 692 (M).

EXAMPLE 578

N-(2,2,2-Trifluoroethyl)-9-[3-[5-[([4'-(1,1,1-trifluoromethyl)[1,1'-biphenyl]-2-yl]carbonyl]amino]-2H-indazol-2-yl]propyl]-9H-fluorene-9-carboxamide

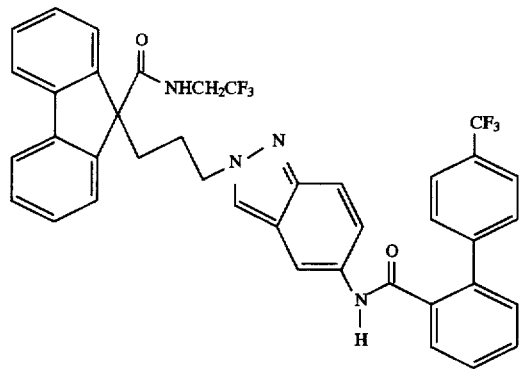

MS (M+H)⁺=713.

EXAMPLE 579

9-[4-[[5-Amino-1-[[4'-(trifluoromethyl)[1,1'-biphenyl]-2-yl]carbonyl]-1H-1,2,4-triazol-3-yl]thio]butyl]-N-(2,2,2-trifluoroethyl)-9H-fluorene-9-carboxamide

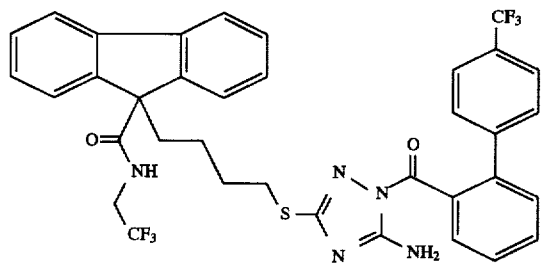

MS (ES, NH₃, +ions) m/z 710 (M+H).

EXAMPLE 580

9-[4-[[5-Amino-1-[(4'-chloro[1,1'-biphenyl]-2-yl)carbonyl]-1H-1,2,4-triazol-3-yl]thio]butyl]-N-(2,2,2-trifluoroethyl)-9H-fluorene-9-carboxamide

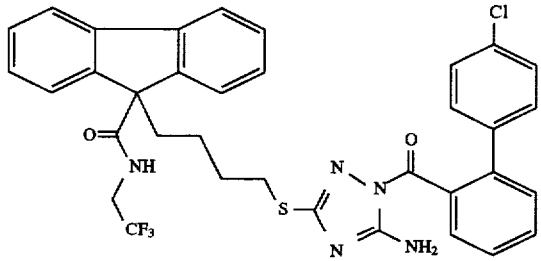

MS (ES, NH₃, +ions) m/z 676 (M+H).

EXAMPLE 581

9-[3-[[5-Amino-1-[[4'-(trifluoromethyl)[1,1'-biphenyl]-2-yl]carbonyl]-1H-1,2,4-triazol-3-yl]thio]propyl]-N-(2,2,2-trifluoroethyl)-9H-fluorene-9-carboxamide

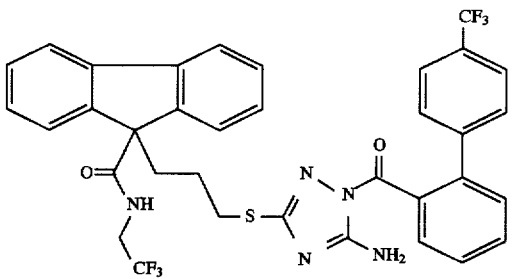

MS (ES, NH₃, +ions) m/z 696 (M+H).

EXAMPLE 582

9-[3-[[5-Amino-1-[(4'-chloro[1,1'-biphenyl]-2-yl)carbonyl]-1H-1,2,4-triazol-3-yl]thio]propyl]-N-(2,2,2-trifluoroethyl)-9H-fluorene-9-carboxamide

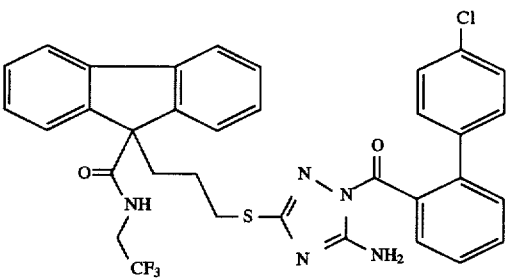

MS (ES, NH₃, +ions) m/z 662 (M+H).

EXAMPLE 583

N-(2,2,2-Trifluoroethyl)-9-[4-[4-[[[4'-(trifluoromethyl)[1,1'-biphenyl]-2-yl]carbonyl]amino]-6H-pyrrolo[2,3-c]pyridin-6-yl]butyl]-9H-fluorene-9-carboxamide

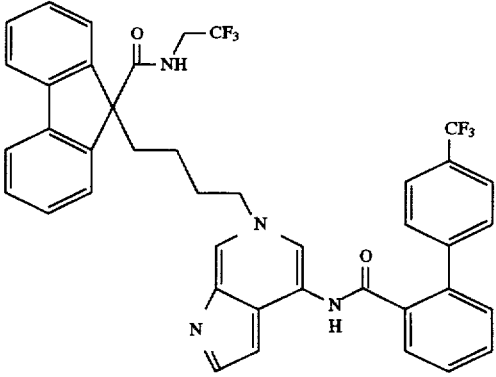

MS (ES, +ions) m/z 727 (M+H).

EXAMPLE 584

N-(2,2,2-Trifluoroethyl)-9-[4-[4-[[[4'-(trifluoromethoxy)[1,1'-biphenyl]-2-yl]carbonyl]amino]-1H-benzimidazol-1-yl]butyl]-9H-fluorene-9-carboxamide

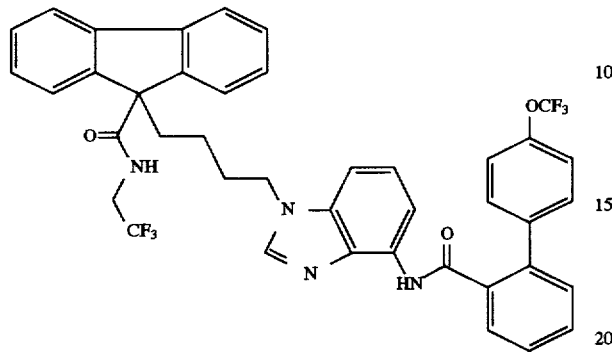

MS (ES, NH$_3$, +ions) m/z 743 (M+H).

EXAMPLE 585

9-[4-[4-[[[3',5'-Bis(trifluoromethyl)[1,1'-biphenyl]-2-yl]carbonyl]amino]-1H-benzimidazol-1-yl]butyl]-N-(2,2,2-trifluoroethyl)-9H-fluorene-9-carboxamide

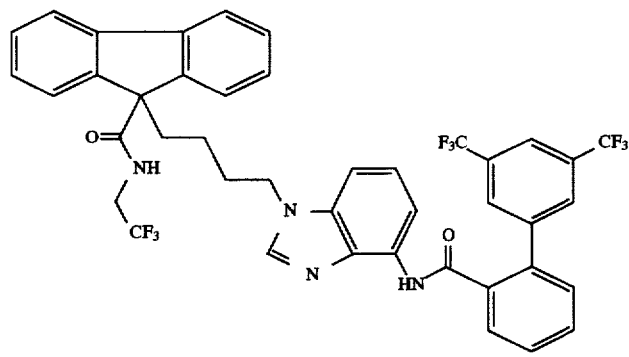

MS (ES, NH$_3$, +ions) m/z 795 (M+H).

EXAMPLE 586

N-(2,2,2-Trifluoroethyl)-9-[4-[4-[[[3'-(trifluoromethyl)[1,1'-biphenyl]-2-yl]carbonyl]amino]-1H-benzimidazol-1-yl]butyl]-9H-fluorene-9-carboxamide

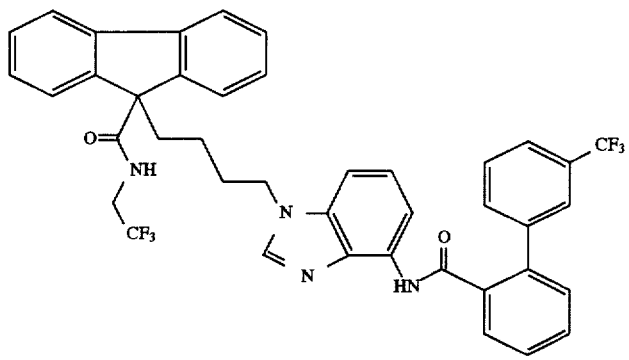

MS (ES, NH$_3$, +ions) m/z 727 (M+H).

EXAMPLE 587–588

9-[4-[2-Methyl-4-[[[3'-(trifluoromethyl)[1,1'-biphenyl]-2-yl]carbonyl]amino]-1H-benzimidazol-1-yl]butyl]-N-(2,2,2-trifluoroethyl)-9H-fluorene-9-carboxamide

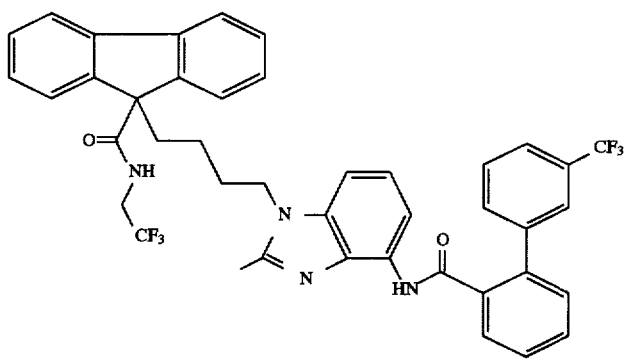

MS (ES, NH$_3$, +ions) m/z 741(M+H).

EXAMPLE 589

9-[4-[1-Methyl-5-[[[4'-(trifluoromethyl)[1,1'-biphenyl]-2-yl]carbonyl]amino]-1H-benzimdazol-2-yl]butyl]-N-(2,2,2-trifluoroethyl)-9H-fluorene-9-carboxamide, and 9-[4-[1-methyl-6-[[[4'-(trifluoromethyl)[1,1'-biphenyl]-2-yl]carbonyl]amino]-1H-benzimidazol-2-yl]butyl]-N-(2,2,2-trifluoroethyl)-9H-fluorene-9-carboxamide (1:1)

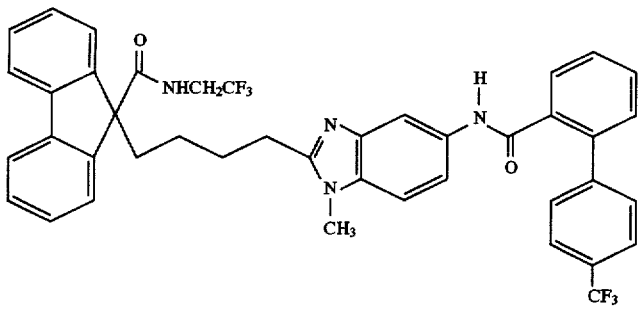
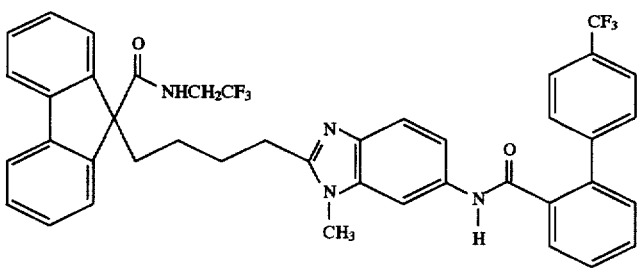
MS: (M+H)⁺=741.
EXAMPLE 590
9-[4-[(6-Ethoxy-2-benzothiazolyl)thio]butyl]-N-propyl-9H-fluorene-9-carboxamide
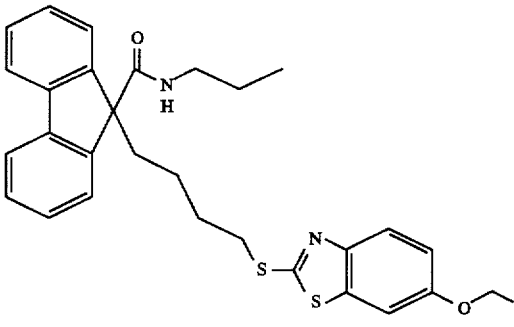
MS (ES) 517 (M+H)
EXAMPLE 591
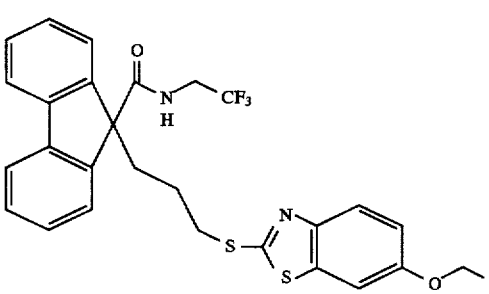
MS (ESI, +ions): m/z 543 (M+H).
EXAMPLE 592
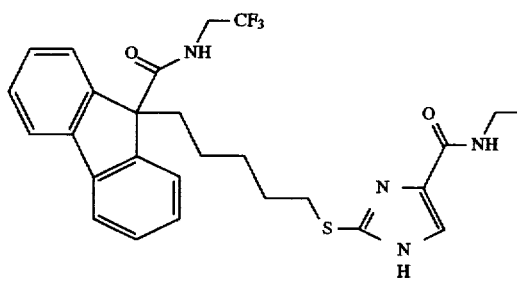
MS (eletrospray, pos. ions): m/z 531(M+H).
EXAMPLE 593
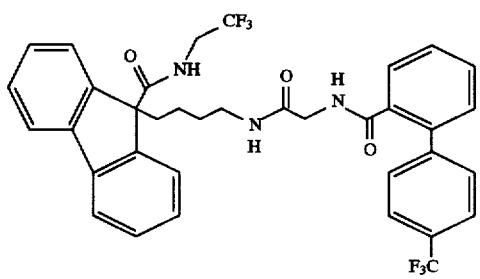
MS (eletrospray, pos. ions): m/z 668 (M+H).

EXAMPLE 594

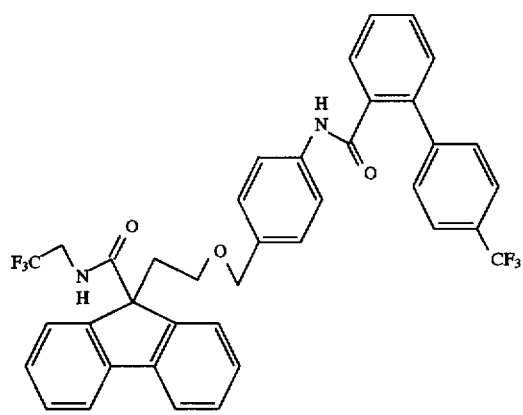

MS: (ESI, +ions) m/z 689 (M+H), 706 (M+NH₄).

EXAMPLE 595

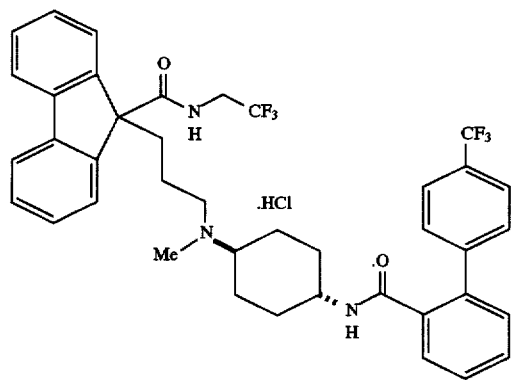

MS (ES, +ions) m/z 708 [M+H].

EXAMPLE 596

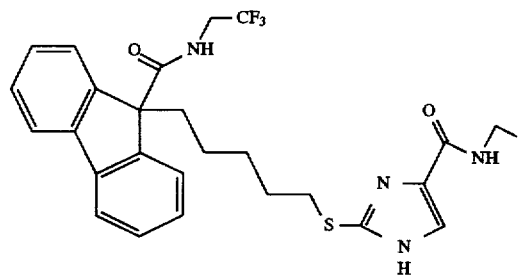

The reaction sequence for preparation of title compound was carried out in batch mode until the final amide coupling which was carried out using a Varian Vac Elute SPS 24 as one of a 24 compound run. During the amide formation and cleavage all mixing was done by having the Vac Elute SPS 24 mounted to an orbital shaker. Mixing was done at 265 rpm unless otherwise noted.

A.

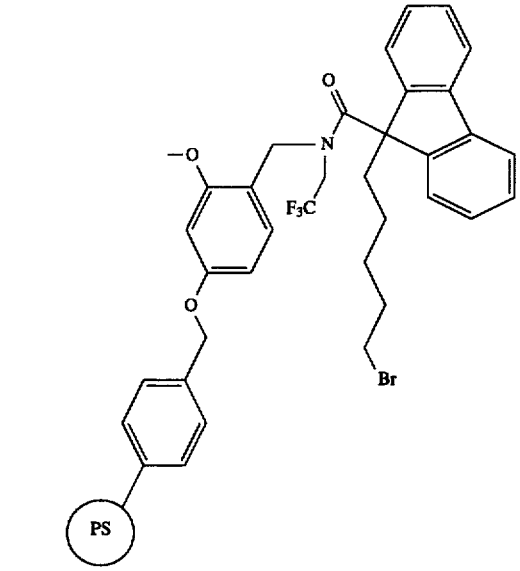

PS = 1% Divinylbenzene cross-linked polystyrene resin, 100–200 mesh

Title resin was prepared as described for Example 688 Part E except that 9-(5-bromopentyl)-9H-fluorene carboxylic acid chloride was used for the acylation with Example 689 Part A resin.

B.

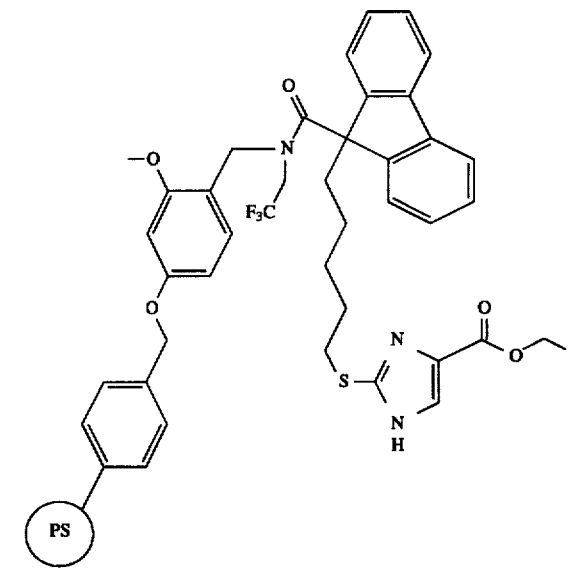

Title resin was prepared as descibed for Example 689 Part D compound employing 4-ethoxycarbonylimidazole-2-thiol (Maybridge Chemical Co.).

C.

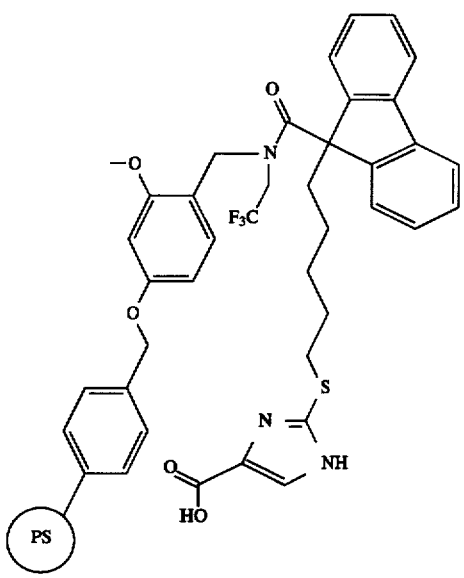

Part B resin (6.6 mmol) was swollen in 40 mL of THF, followed by draining of the solvent using nitrogen pressure. The resin was treated with a solution of 5.6 g (99 mmol, 15 eq) of KOH in 15 mL of water, 30 mL of MeOH and 30 mL of THF. The reaction mixture was heated at 50° C. and vortexed for 4 days. The reaction mixture was cooled to RT and the reaction solution was removed. The resin was rinsed with 1:1THF:water (3×50 mL), THF (3×50 mL), 5% acetic acid in THF (3×30 mL), THF (3×50 mL), $CH_2Cl_2$ (3×50 mL) and MeOH (3×50 mL). The title resin was used in the next step without characterization.

D.

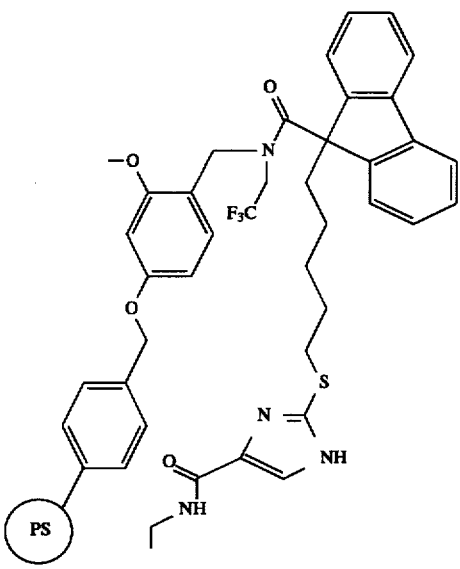

Method A.

Part C resin (300 mg, 0.28 mmol) in a 25 mL polypropylene tube was swollen in 3 mL of $CH_2Cl_2$ and drained. The resin was suspended in 3 mL of a 1:1 $CH_2Cl_2$:DMF solution and treated with 376 mg (1.9 mmol, 7 eq) of 1-(3-dimethylaminopropyl)-3-ethylcarbodiimide hydrochloride (EDC) and 267 mg (1.9 mmol, 7 eq) of 1-hydroxy-7-azabenzotriazole (HOAt). Diethylamine gas (was then bubbled into the reaction mixture for 5 min (≧10 eq). The reaction mixture was shaken for 18 h, the reaction solution was drained and the resin was retreated under the same conditions. After 72 h, the reaction solution was again drained and the resin was rinsed with DMF (4×5 mL) and $CH_2Cl_2$ (4×5 mL). The title resin was used in the next step without characterization.

Method B

The Part C resin was swollen in 3 mL of $CH_2Cl_2$ and drained. The resin was suspended in 3 mL of a 1:1$CH_2Cl_2$:DMF solution and treated with 307 μL (247 mg, 1.9 mmol, 7 eq) diisopropylcarbodiimide and 342 mg (2.8 mmol, 10 eq) of 4-dimethylaminopyridine (DMAP). The required amine (10 eq) was and the reaction mixture was shaken for 18 h. The reaction solution was drained and the resin was retreated under the same conditions. After 72 h, the reaction solution was again drained and the resin was rinsed with DMF (4×5 mL) and $CH_2Cl_2$ (4×5 mL). The resin was used in the next step without characterization.

E.

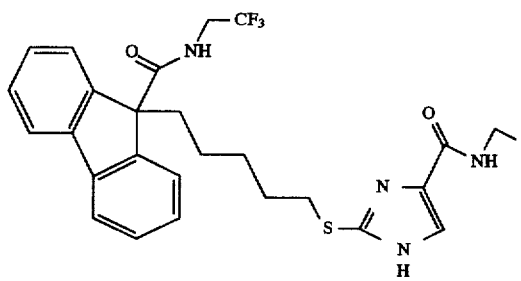

The Part D resin was treated with 2 mL of 100% trifluoroacetic acid and shaken for 90 min. The cleavage solution was collected, the resin was rinsed with $CH_2Cl_2$ (2×1mL) and the combined cleavage solution and rinses were concentrated on a Speed Vac at RT. After 18 h, the sample was reconstituted in 4 mL of $CH_2Cl_2$ and reconcentrated on the Speed Vac. After 18 h, the sample was again reconstituted in 4 mL of $CH_2Cl_2$ and aliquots were removed for HPLC and MS analysis. The tube was concentrated again on the Speed Vac at −40° C, followed by exposure to high vacuum (1mm Hg) on a lyophilizer for 14 h to afford 161 mg of crude product mixture of which 6 was 26%. The desired product was purified by preparative HPLC using a YMC-Pack ODS-A 250×30 mm, S-5 μm, 120 A column with a 70–100%B gradient over 30 min, holding at 100% B for 15 min at a flow of 25 mL/min (Solvent A: 90% $H_2O$/10% MeOH with 0.1% TFA; Solvent B: 90% MeOH/10% $H_2O$ with 0.1% TFA) to provide 25 mg (17% based on starting aldehyde resin) of title compound as a cloudy oil.

HPLC: retention time: 4.7 min; 90% purity. HPLC conditions: YMC S3 ODS 4.6×50 mm Rapid Resolution column; linear gradient from 50% B to 100% B over 8 min and held at 100% B for 2 min (method name: SMET4); flow rate 2.5 mL/min; detection at 215 nm; Solvent A: 90% $H_2O$/10% MeOH with 0.2% $H_3PO_4$; Solvent B: 90% MeOH/10% $H_2O$ with 0.2% $H_3PO_4$.

MS(electrospray, pos. ions): m/z 531(M+H)

EXAMPLE 597
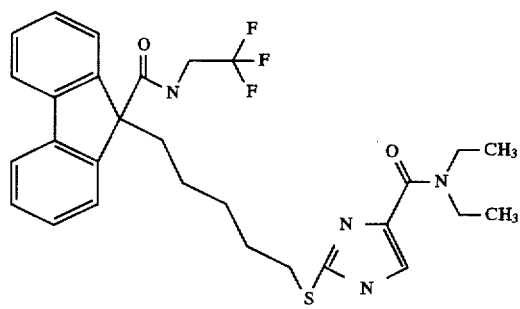
MS: m/z 559 (M+H)
EXAMPLE 598–600
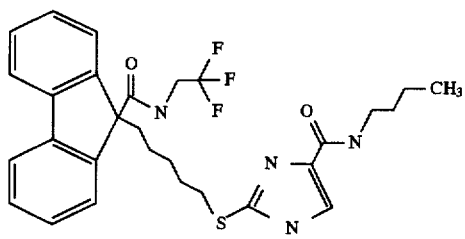
MS: m/z 559 (M+H)
EXAMPLE 601
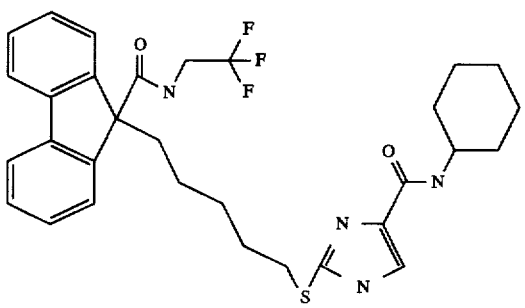
MS: m/z 585 (M+H)
EXAMPLE 602–603
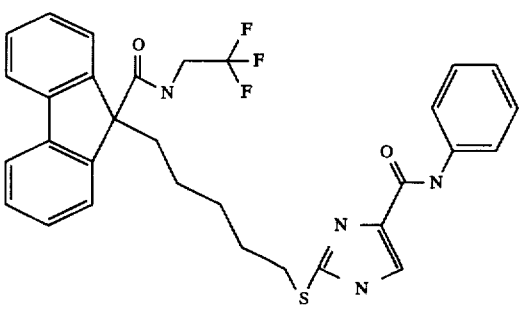
MS: m/z 593 (M+H)
EXAMPLE 604
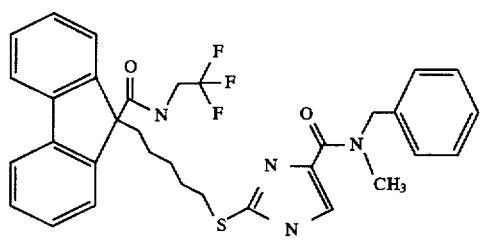
MS: m/z 607 (M+H)
EXAMPLE 605
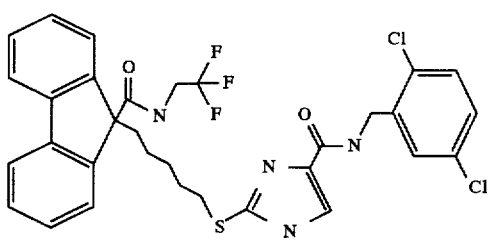
MS: m/z 661 (M+H)
EXAMPLE 606
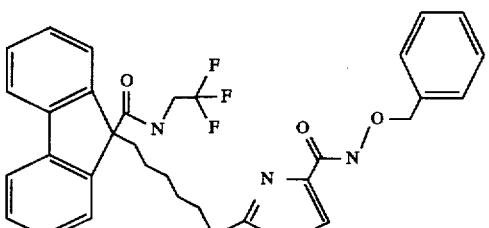
MS: m/z 609 (M+H)
EXAMPLE 607
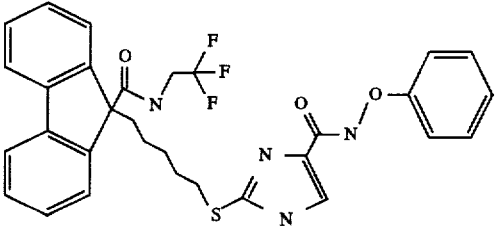
MS: m/z 595 (M+H)

347
EXAMPLE 608
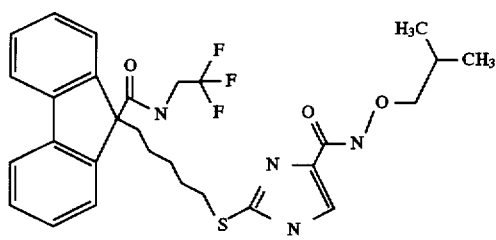
MS: m/z 575 (M+H)
EXAMPLE 609
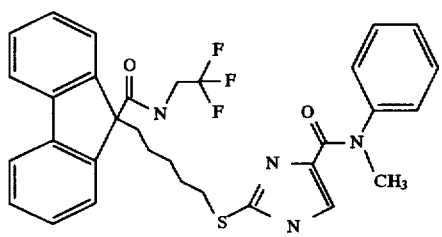
MS: m/z 593 (M+H)
EXAMPLE 610
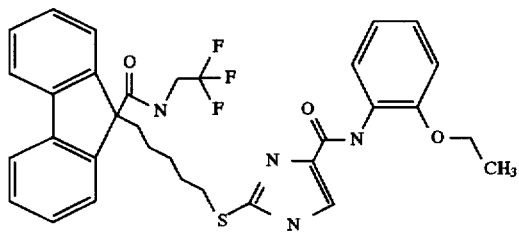
MS: m/z 623 (M+H)
EXAMPLE 611
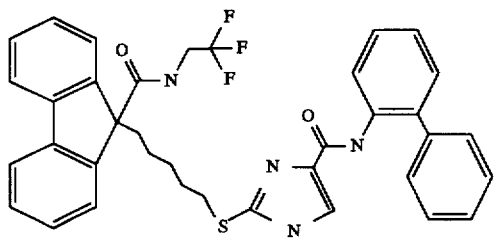
MS: m/z 655 (M+H)
348
EXAMPLE 612
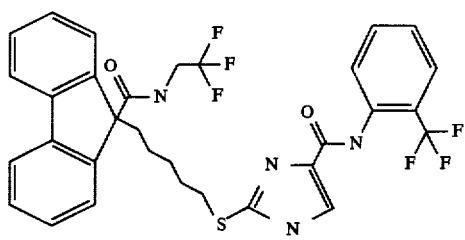
MS: m/z 647 (M+H)
EXAMPLE 613
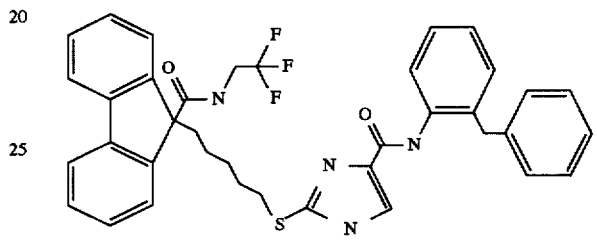
MS: m/z 669 (M+H)
EXAMPLE 614
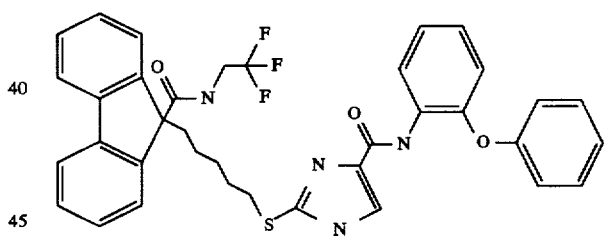
MS: m/z 671 (M+H)
EXAMPLE 615–617
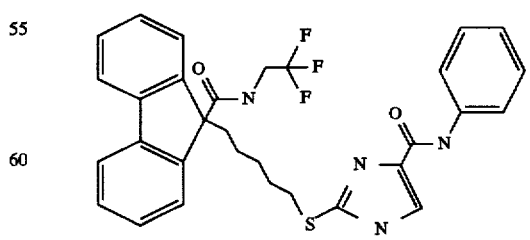
MS: m/z 579 (M+H)

EXAMPLE 618
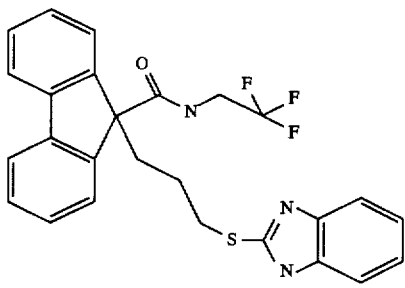
MS: m/z 482 (M+H)
EXAMPLE 619
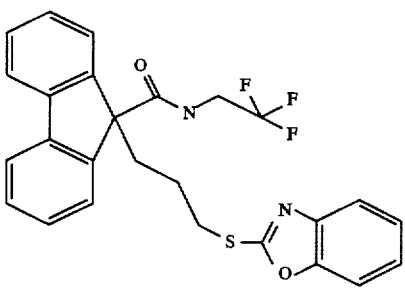
MS: m/z 483 (M+H)
EXAMPLE 620
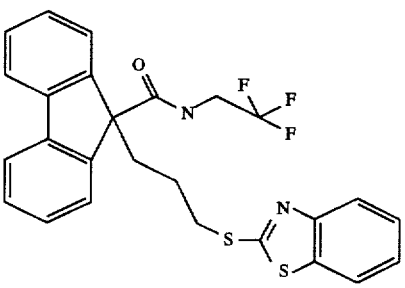
MS: m/z 499 (M+H)
EXAMPLE 621
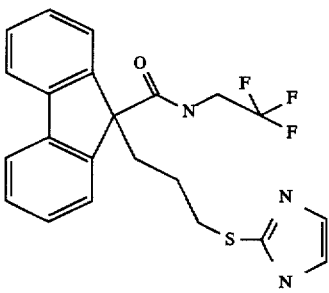
MS: m/z 432 (M+H)
EXAMPLE 622
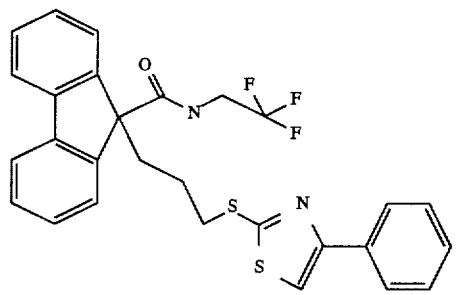
MS: m/z 525 (M+H)
EXAMPLE 623
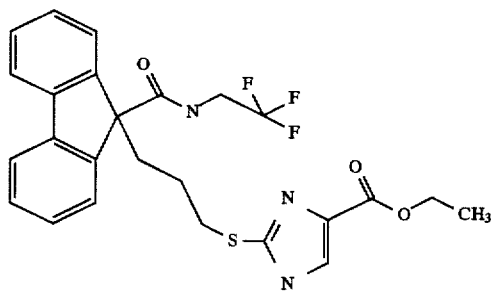
MS: m/z 504 (M+H)
EXAMPLE 624
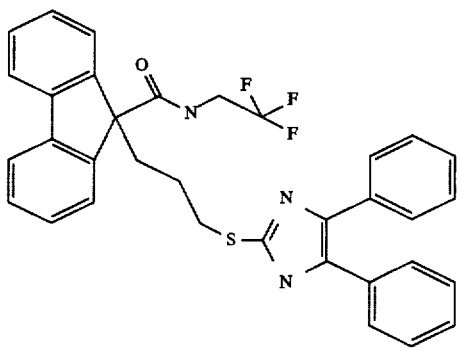
MS: m/z 584 (M+H)
EXAMPLE 625
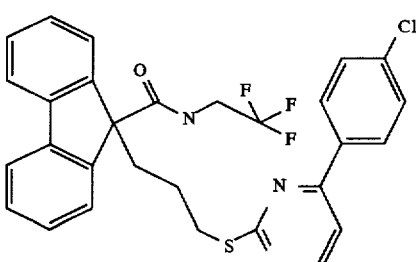
MS: m/z 554 (M+H)

EXAMPLE 626

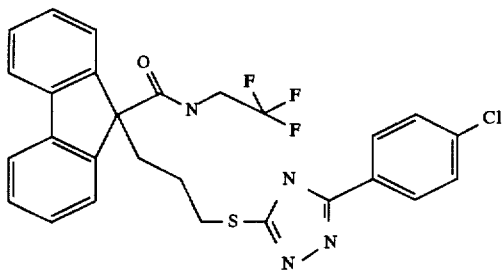

MS: m/z 543 (M+H)

EXAMPLE 627

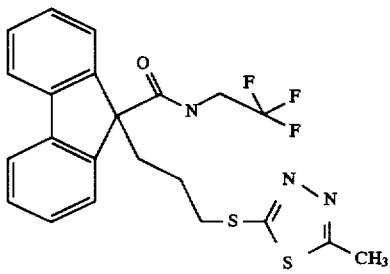

MS: m/z 464 (M+H)

EXAMPLE 628

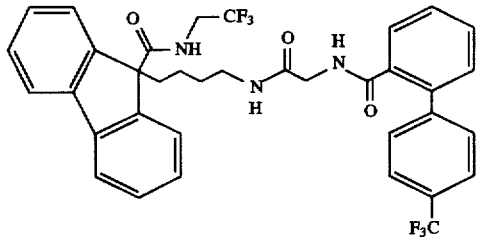

The reaction sequence for preparation of title compound was carried out using the 48-Weller solid phase reactor mounted to an orbital shaker as part of a 48 compound run. Shaking was done at 300 rpm.

A.

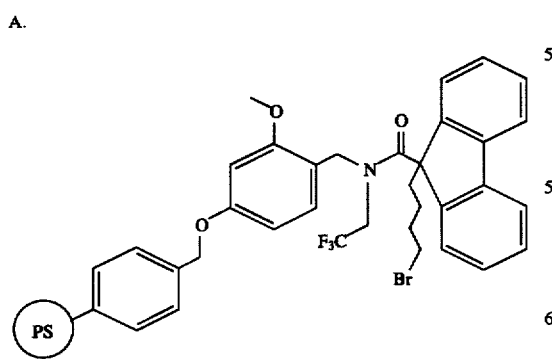

PS = 1% Divinylbenzene cross-linked polystyrene resin, 100–200 mesh

The title resin was prepared as described for Example 688 Part E except that 9-(4-bromobutyl)-9H-fluorene carboxylic acid chloride was used for the acylation with Example 689 Part A resin.

B.

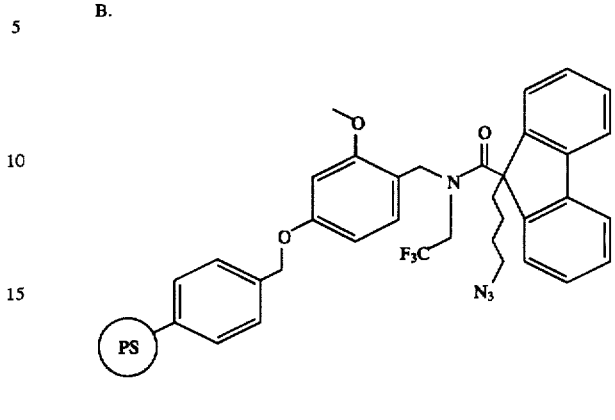

Part A resin (0.2 mmol) was swollen in 2 mL of dry DMF and drained using argon pressure. The resin was suspended in 1mL of dry DMF and a solution of 284 mg (1mmol, 5 eq) of tetrabutylammonium azide in 1mL of DMF was added. After shaking for 16 h at RT, the reaction solution was drained and the title resin was rinsed with DMF (2×2 mL) and THF (2×2 mL). The title resin was used in the next step without characterization.

C.

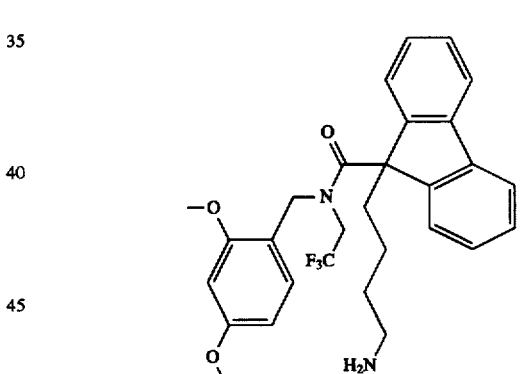

To the THF swollen Part B resin was added a solution of 262 mg (1 mmol, 5 eq) of triphenylphosphine and 1.26 mL (1.4 mmol, 7 eq) of water in 2 mL of THF. After shaking for 7 h at RT, the reaction solution was drained and the resin was rinsed with THF (3×2 mL) and DMF (2×2 mL). The title resin was used in the next step without characterization.

D.

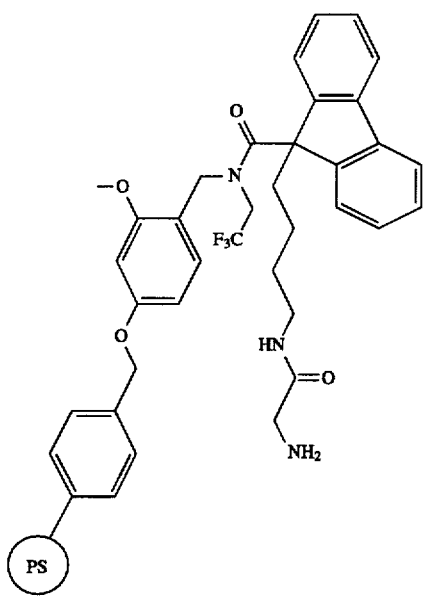

To the DMF swollen Part C resin were added a solution of 135 mg (1mmol, 5 eq) of N-hydroxybenzotriazole and 293 mg (1mmol, 5 eq) of FMOC-glycine in 1.5 mL of DMF and a solution of 126 mg (1mmol, 5 eq) of diisopropylcarbodiimide in $CH_2Cl_2$. After shaking for 12 h at RT, the reaction solution was drained and the resin was retreated under the same conditions for 3 h. The reaction solution was drained and the resin was rinsed with DMF (1×2 mL), $CH_2Cl_2$ (2×2 mL) and DMF (2×2 mL). The resin was then treated with 3 mL of 30% piperidine in DMF. After shaking at RT for 30 min, the reaction solution was drained and the resin was treated again with 3 mL of 30% piperidine in DMF. After draining the reaction solution, the title resin was rinsed with DMF (3×2 mL). The title resin was used in the next step without characterization.

E.

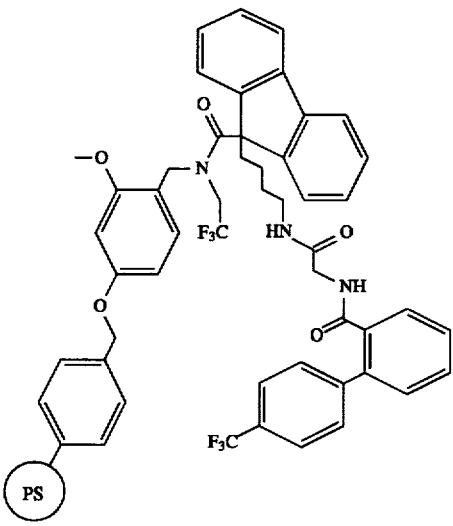

To the DMF swollen Part D resin were added solutions of 135 mg (1 mmol, 5 eq) of N-hydroxy-benzotriazole in 1 mL of DMF, 266 mg (1 mmol, 5 eq) of 4'-(trifluoromethyl)-2-biphenylcarboxylic acid in 1 mL of DMF and 126 mg (1 mmol, 5 eq) of diisopropylcarbodiimide in 0.5 mL of $CH_2Cl_2$. After shaking for 72 h at RT, the reaction solution was drained and the title resin was rinsed with DMF (1×2 mL) and $CH_2Cl_2$ (4×2 mL). The title resin was used in the next step without characterization.

F.

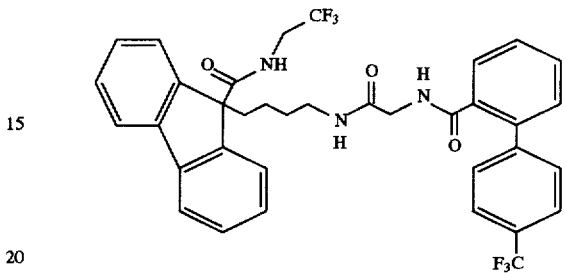

The Part E resin was treated with 2 mL of 100% trifluoroacetic acid and shaken for 1 h. The cleavage solution was collected, the resin was rinsed with $CH_2Cl_2$ (2×1 mL) and the combined cleavage solution and rinses were concentrated on a Speed Vac at RT. After 18 h, the sample was reconstituted in 4 mL of $CH_2Cl_2$ and reconcentrated on the Speed Vac. After 18 h, the sample was again reconstituted in 4 mL of $CH_2Cl_2$ and aliquots were removed for HPLC and MS analysis. The tube was concentrated again on the Speed Vac followed by exposure to high vacuum (1 mm Hg) on a lyophilizer for 14 h to afford 110 mg (82% yield based on starting aldehyde resin) of title compound as clear yellow oil.

HPLC: retention time: 7.7 min; 86% purity. HPLC conditions: YMC S3 ODS 4.6×50 mm Rapid Resolution column; linear gradient from 20% B to 100% B over 8 min and held at 100% B for 2 min (method name: SMET2); flow rate 2.5 mL/min; detection at 215 nm; Solvent A: 90% $H_2O$/10% MeOH with 0.2% $H_3PO_4$; Solvent B: 90% MeOH/10% $H_2O$ with 0.2% $H_3PO_4$.

MS (electrospray, pos. ions): m/z 668 (M+H)

EXAMPLE 629

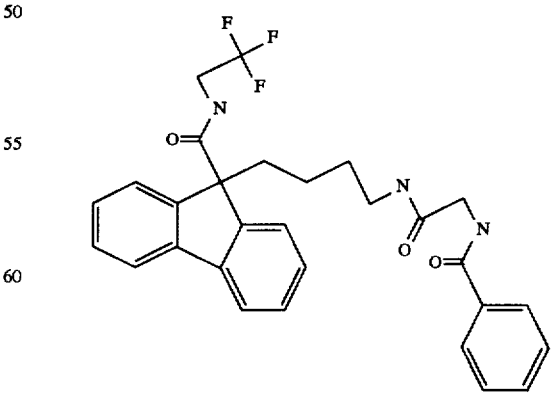

MS: m/z 524 (M+H)

EXAMPLE 630–631
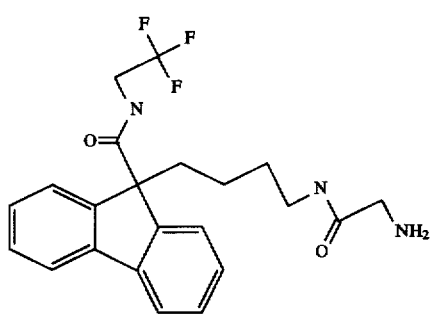
MS: m/z 621 (M+H)
EXAMPLE 632
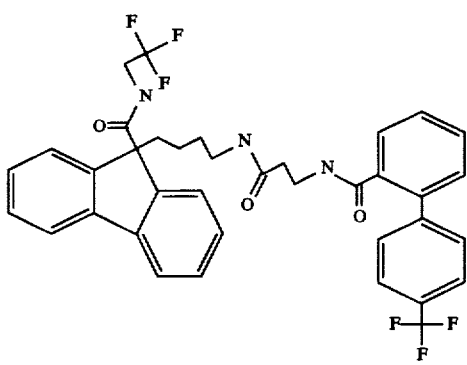
MS: m/z 682 (M+H)
EXAMPLE 634–635
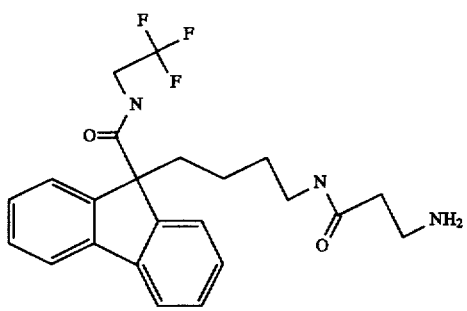
MS: m/z 434 (M+H)
EXAMPLE 636
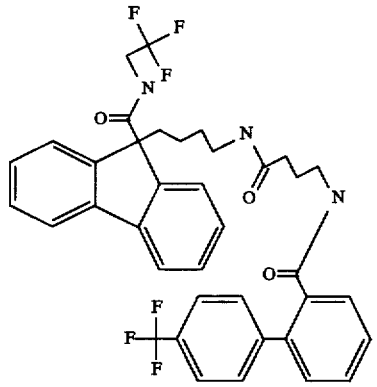
MS: m/z 696 (M+H)
EXAMPLE 637
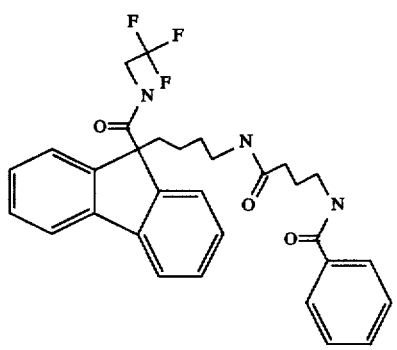
MS: m/z 552 (M+H)
EXAMPLE 638–639
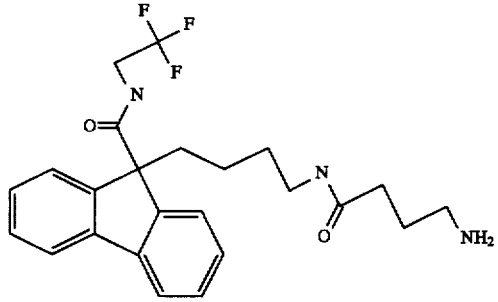
MS: m/z 448 (M+H)

357
EXAMPLE 640
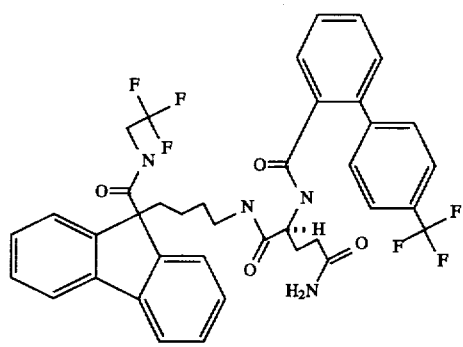
MS: m/z 739 (M+H)
EXAMPLE 641
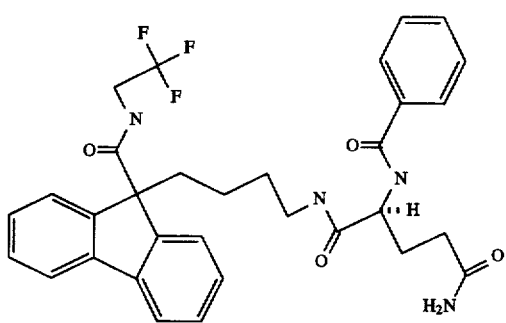
MS: m/z 595 (M+H)
EXAMPLE 642–643
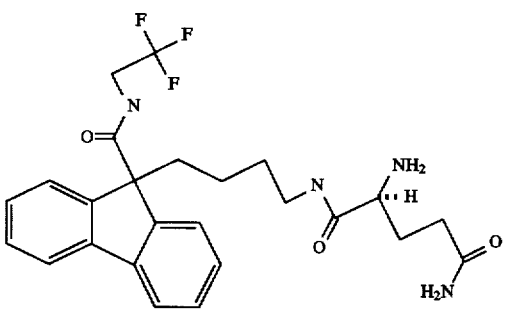
MS: m/z 491 (M+H)
358
EXAMPLE 644
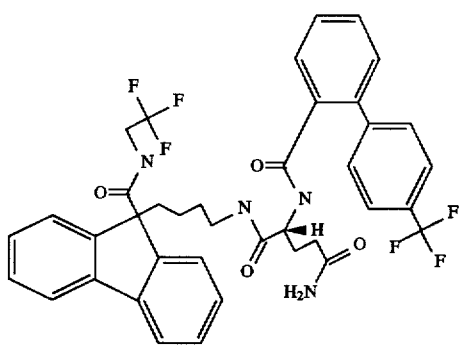
MS: m/z 739 (M+H)
EXAMPLE 645
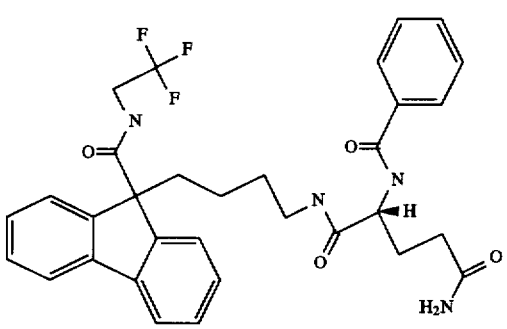
MS: m/z 595 (M+H)
EXAMPLE 646–651
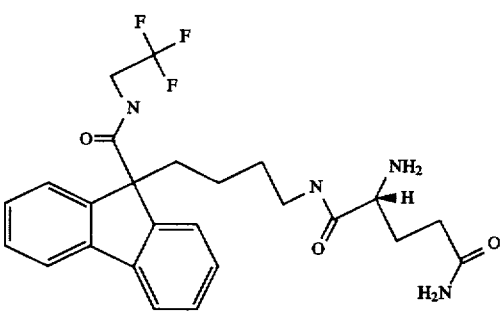
MS: m/z 491 (M+H)

EXAMPLE 652
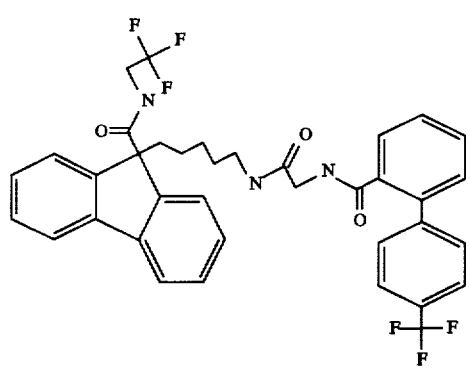
MS: m/z 682 (M+H)
EXAMPLE 653
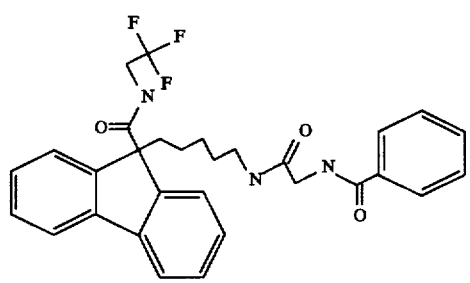
MS: m/z 538 (M+H)
EXAMPLE 654
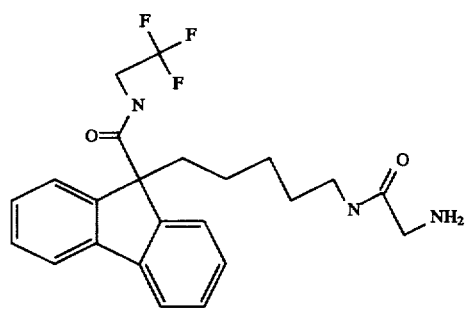
MS: m/z 434 (M+H)
EXAMPLE 655
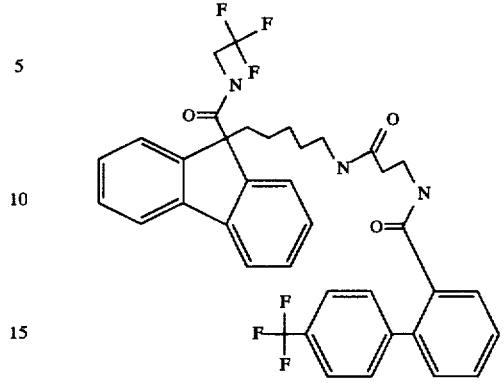
MS: m/z 696 (M+H)
EXAMPLE 656
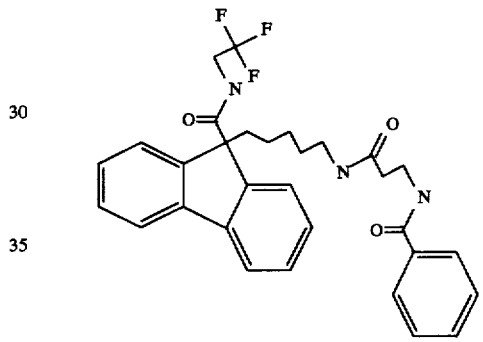
MS: m/z 552 (M+H)
EXAMPLE 657–658
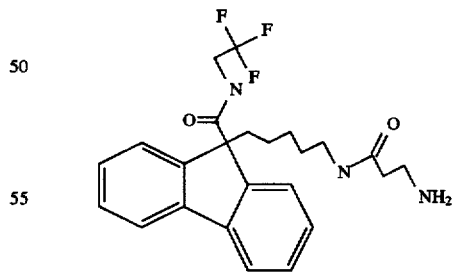
MS: m/z 448 (M+H)

EXAMPLE 659
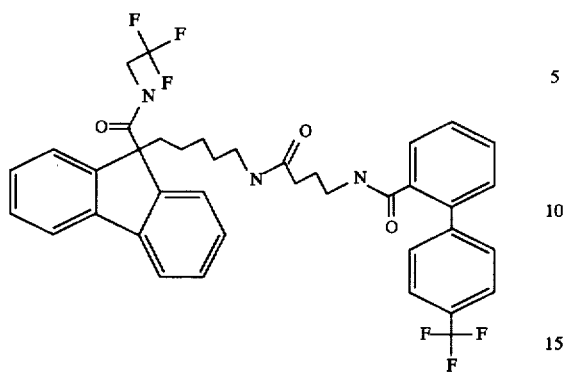
MS: m/z 710 (M+H)
EXAMPLE 660
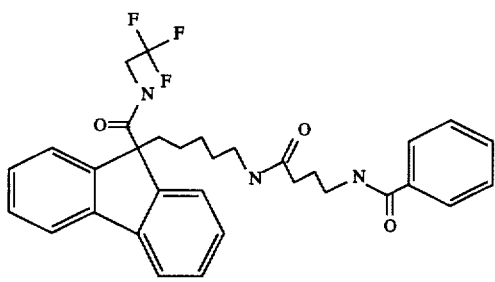
MS: m/z 566 (M+H)
EXAMPLE 661–662
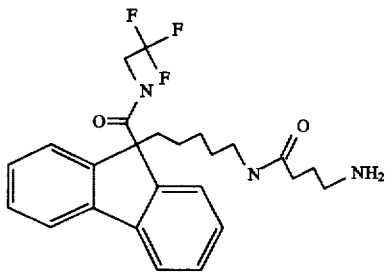
MS: m/z 462 (M+H)
EXAMPLE 663
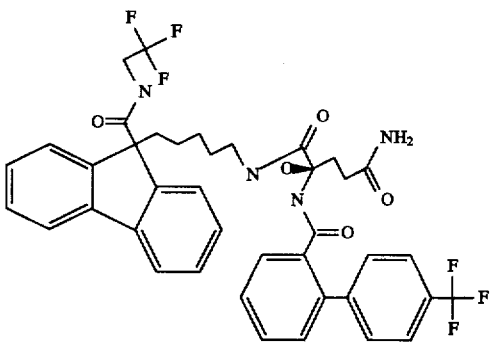
MS: m/z 753 (M+H)
EXAMPLE 664
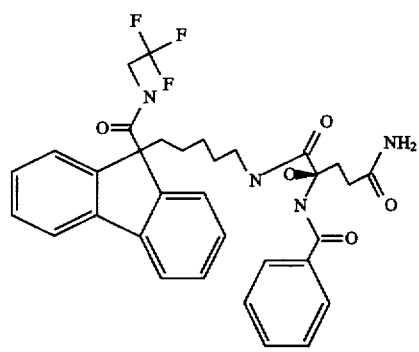
MS: m/z 609 (M+H)
EXAMPLE 665–666
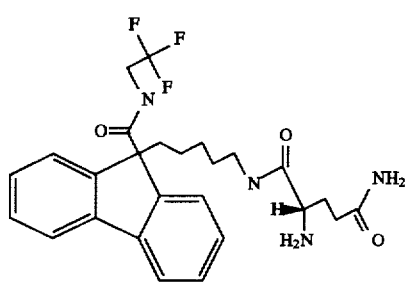
MS: m/z 505 (M+H)
EXAMPLE 667
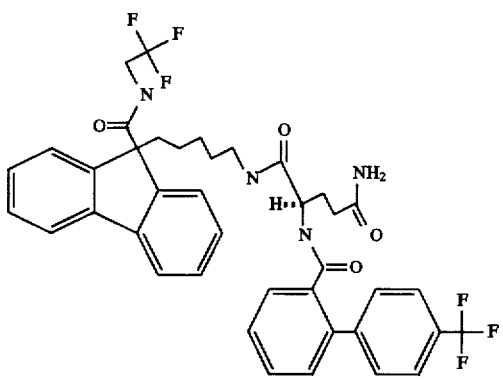
MS: m/z 753 (M+H)

EXAMPLE 668
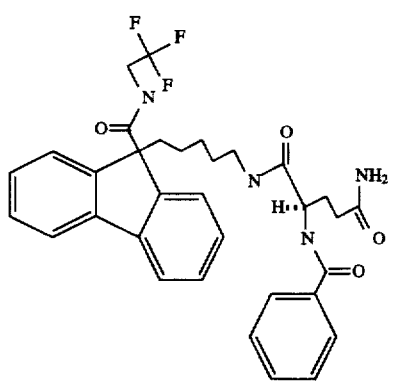
MS: m/z 609 (M+H)
EXAMPLE 669–670
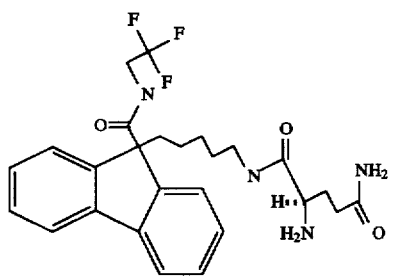
MS: m/z 505 (M+H)
EXAMPLE 671–674
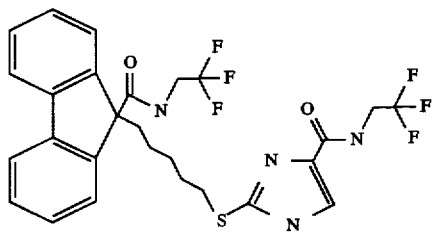
MS: m/z 585 (M+H)
EXAMPLE 675
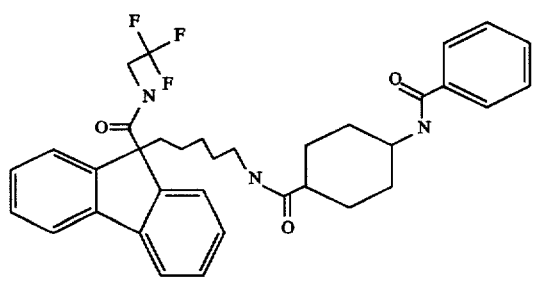
MS: m/z 592 (M+H)
EXAMPLE 676
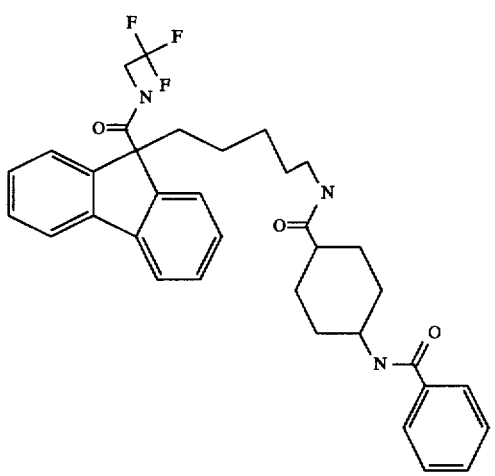
MS: m/z 606 (M+H)
EXAMPLE 677
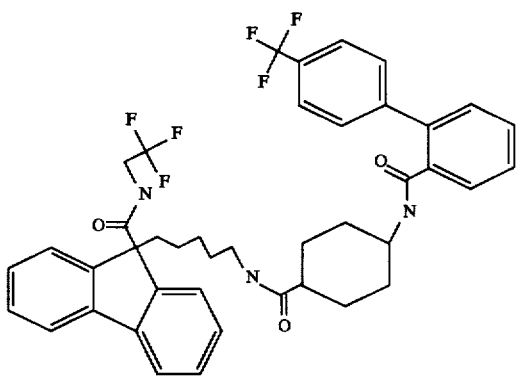
MS: m/z 736 (M+H)
EXAMPLE 678
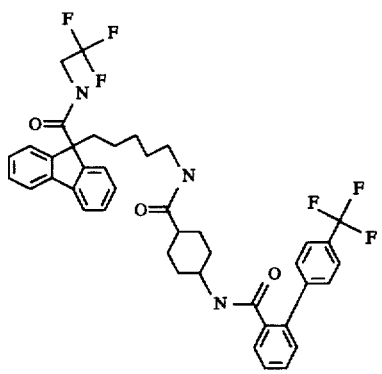
MS: m/z 750 (M+H)

EXAMPLE 679
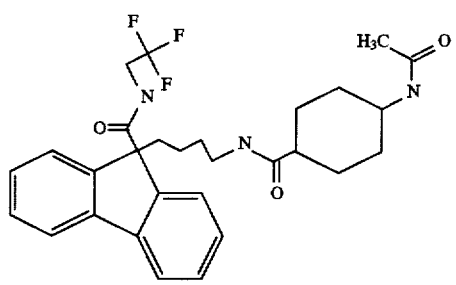
MS: m/z 530 (M+H)
EXAMPLE 680
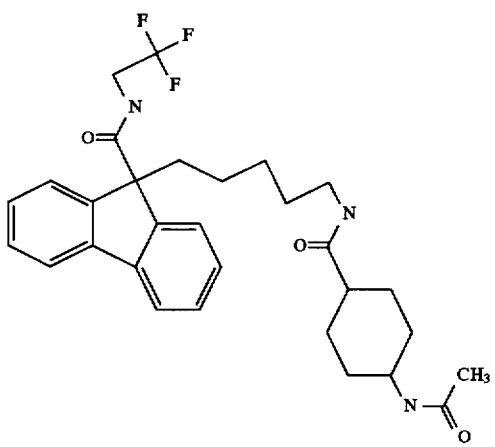
MS: m/z 544 (M+H)
EXAMPLE 681
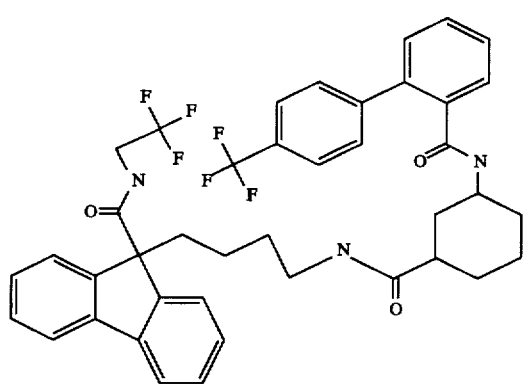
MS: m/z 736 (M+H)
EXAMPLE 682
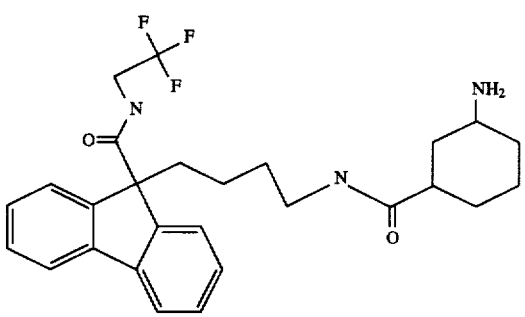
MS: m/z 488 (M+H)
EXAMPLE 683
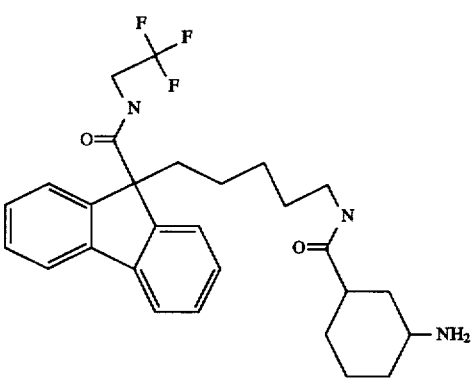
MS: m/z 502 (M+H)
EXAMPLE 684
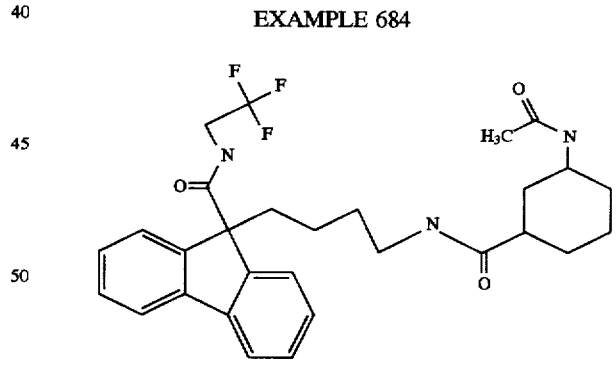
MS: m/z 530 (M+H)

EXAMPLE 685

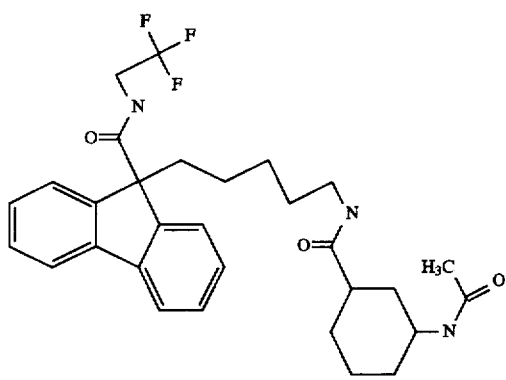

MS: m/z 544 (M+H)

EXAMPLE 686

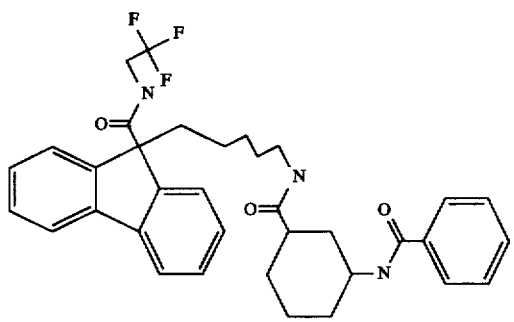

MS: m/z 606 (M+H)

EXAMPLE 687

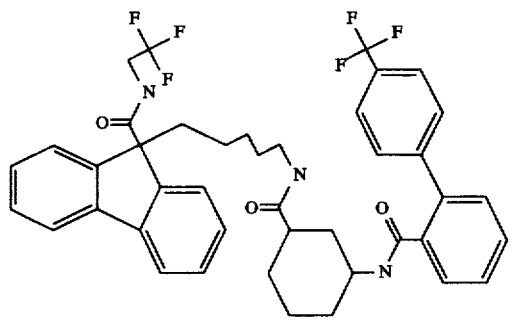

MS: m/z 750 (M+H)

EXAMPLE 688

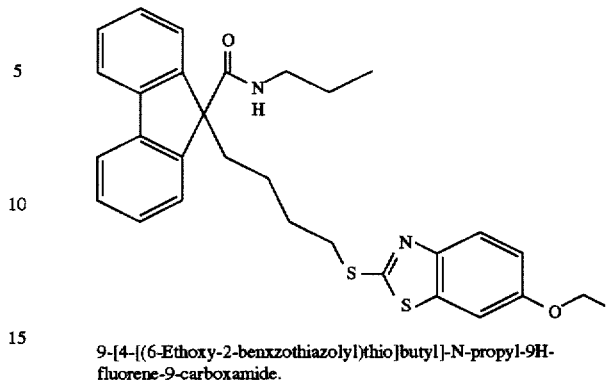

9-[4-[(6-Ethoxy-2-benxzothiazolyl)thio]butyl]-N-propyl-9H-fluorene-9-carboxamide.

A.

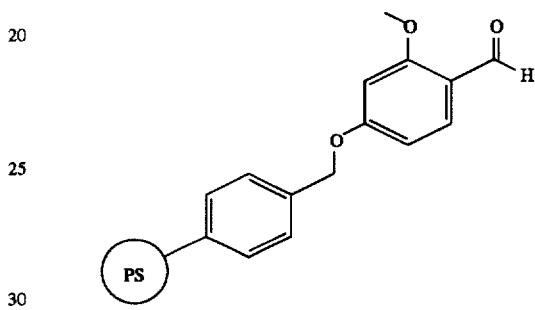

PS = 1% Divinylbenzene cross-linked polystyrene resin, 100–200 mesh

To a magnetically stirred suspension of 4.8 g (120 mmol, 10 eq) of sodium hydride (60% mineral oil dispersion) in 30 mL of dimethylformamide (DMF) at 0° C. was added a solution of 18.2 g (120 mmol, 10 eq) of 4-hydroxy-2-methoxybenzaldehyde in 50 mL of DMF dropwise over 75 min. The reaction was allowed to warm to room temperature (RT) and stirred for an additional 75 min. The stirbar was removed and 10 g (12 mmol, 1 eq) of Merrifield resin (with a loading of 1.2 mmol/g (Advanced Chemtech)) was added. The flask was placed in a heating mantel mounted on a vortex mixer and heated at 70° C. (internal temperature) while vortexing for 26 h. The contents of the reaction vessel were transferred to a large filter funnel with a scintered-glass frit (porosity C) and rinsed sequentially with DMF (3×100 mL), 1:1 DMF:water (3×100 mL), water (2×100 mL) and MeOH (5×100 mL). The resin was dried under high vacuum (0.1 mm Hg) for 72 h to afford 11.16 g (98% of expected weight) of title compound as a tacky non-freeflowing tan resin. The resin was characterized by gel-phase $^{13}$C-NMR and elemental analysis (chlorine and oxygen).

Elemental Analysis:

Chlorine: Expected 0% Cl for 100% loading; found 0.21%. Starting Cl content of resin was 4.26%. Residual Cl consistent with 95% resin loading. Oxygen: Expected 5.76% for 100% loading; found 6.21%.

B.

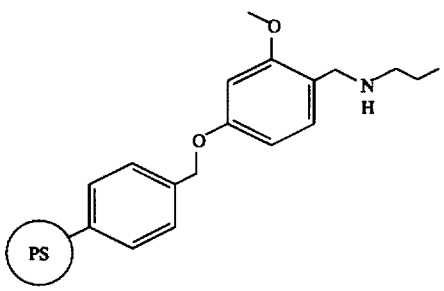

To a 25 mL Varian polypropylene tube fitted with a polyethylene frit and a luer stopcock was added 500 mg of Part A resin. The tube was sealed with a 19 mm Aldrich Suba septa and the resin was swollen in 5 mL of dry DMF, mixed by vortexing for 1 min and the DMF was removed using vacuum and N₂ pressure in order to maintain the vessel under inert atmosphere. Trimethyl orthoformate (1 mL) was added followed by 3.2 mL of DMF and 0.8 mL (10.0 mmol, 18 eq) of n-propylamine. The reaction mixture was vortexed for 18 h at RT. After removal of the reaction solution by nitrogen pressure and vacuum, 5 mL of a 200 mg/mL solution of sodium triacetoxyborohydride in DMF (1 g, 4.7 mmol, 8 eq) and 100 µL of acetic acid were added. The reaction mixture was vortexed for 8 h at RT. The reaction solution was removed and the so-formed title resin was rinsed with DMF (4×5 mL), 1:1 DMF:water (2×5 mL), water (1×5 mL), DMF (3×5 mL) and dichloromethane (CH₂Cl₂) (4×5 mL). The last CH₂Cl₂ rinse was done with dry CH₂Cl₂ in the tube with the septa in place using nitrogen gas and vacuum to filter away the solvent and keep the reaction vessel under inert atmosphere. The title resin was used in the next step without characterization.

C.

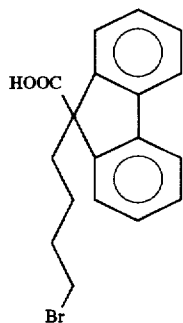

The title compound was prepared as described in Example 273 Part A(l).

D.

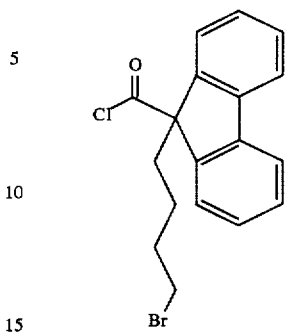

To 3.45 g (10 mmol, 1 eq) of 9-(4-bromobutyl)-9H-fluorene carboxylic acid (Part C) in 15 mL of CH₂Cl₂ was added 100 µL of DMF. The resulting solution was cooled to 0° C. and 7.5 mL (15 mmol, 1.5 eq) of a 2.0M oxalyl chloride solution in CH₂Cl₂ was added. The bubbling reaction mixture was stirred at 0° C. for 15 min and then allowed to warm to RT. After 2 h, the reaction mixture was concentrated to afford the title crude acid chloride as a yellowish orange solid/oil mixture which was dissolved in CH₂Cl₂ and used without purification.

E.

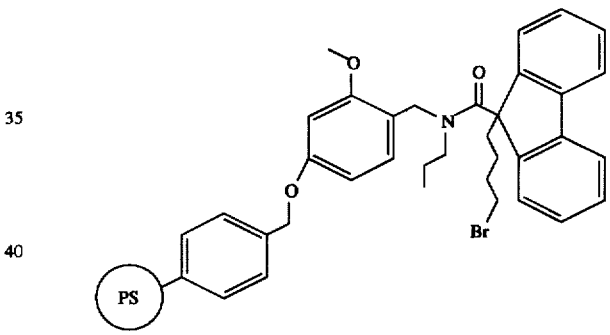

To the Part B resin in the polypropylene tube were added 1 mL of diisopropylethyl amine (5.7 mmol, 10 eq) and 1 mL of CH₂Cl₂ and the resulting mixture was mixed for 2 min. The tube was cooled to 0° C. in an ice bath and 4 mL (2.2 mmol, 4 eq) of a solution of Part D acid chloride in CH₂Cl₂ was added. The resulting orange reaction mixture was mixed by vortexing at RT for 19 h, and then rinsed with CH₂Cl₂ (4×5 mL) to afford title resin which was in the next step without characterization.

F.

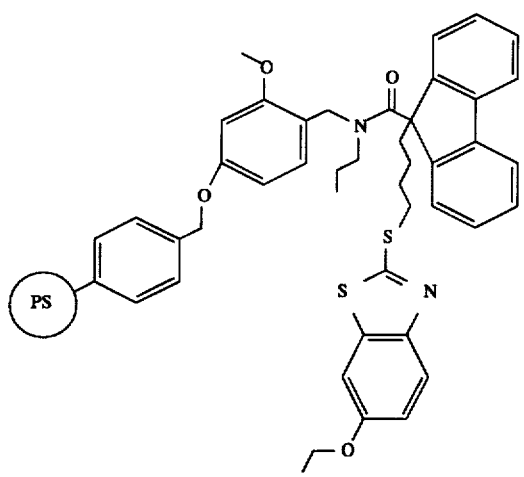

The Part E resin in the sealed polypropylene tube was swollen in 5 mL of dry DMF and vortexed for 2 min. The solvent was removed with N₂ and vacuum and a solution of 1.16 g (5.5 mmol, 10 eq) of 6-ethoxy-2-mercaptobenzothiazole (Aldrich) in 4 mL of DMF was added to the resin followed by 5 mL (5 mmol, 9 eq) of a 1.0M solution of sodium bistrimethylsilylamide in THF. Vortexing was initiated and the reaction mixture was mixed for 17 h at RT. The reaction solution was filtered away and the title resin was rinsed with DMF (4×5 mL), 1:1 DMF-:water (2×5 mL), water (1×5 mL), DMF (3×5 mL) and dichloromethane (CH₂Cl₂) (4×5 mL).

G.

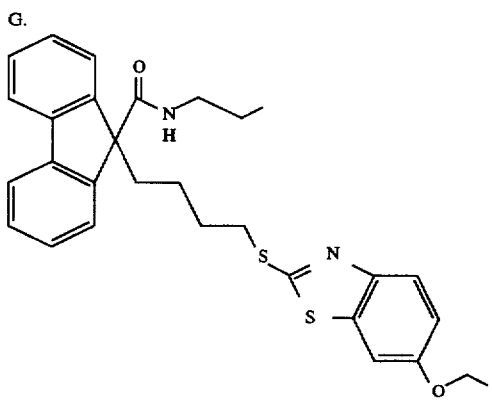

The Part F resin was treated with 5 mL of 100% trifluoroacetic acid and vortexed for 90 min. The reaction solution was collected, the resin was rinsed with CH₂Cl₂ (3×1 mL) and the combined reaction solution and rinses were concentrated. The products from 3 parallel reactions were each redissolved in 15 mL of CH₂Cl₂, pooled and reconcentrated to afford 393 mg (46% crude) of an off-white solid. Recrystallization from MeOH afforded 339 mg (40%) of title compound as a white solid.

m.p. 112°–113.5° C.

TLC (silica gel, 5% MeOH in CH₂Cl₂, UV and I₂) R$_f$=0.75;

IR(KBr): 3343, 2924, 1653, 1522, 1449, 1225, 739 cm$^{-1}$;

MS(electrospray, pos. ions): m/z 517 (M+H);

Anal. Calcd for C$_{30}$H$_{32}$N$_2$O$_2$S$_2$: C, 69.73; H, 6.24; N, 5.42; S, 12.41 Found: C, 69.48; H, 6.22; N, 5.39; S, 12.25.

EXAMPLE 689

Example 689

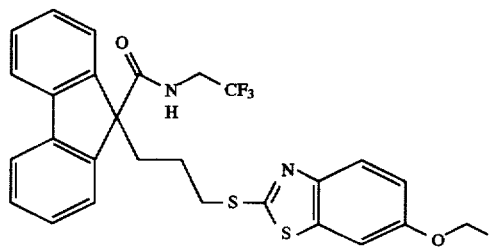

A.

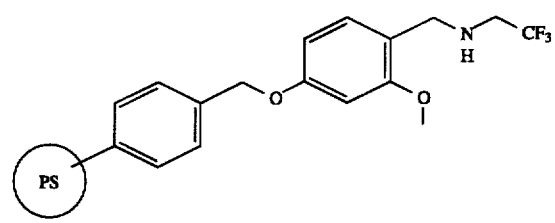

B.

Example 688 Part A resin (250 mg, 0.3 mmol) was swollen in 3.0 mL of dimethylformamide (DMF). The solvent was drained, and 406 mg (3.0 mmol, 10 eq) of trifluoroethylamine, 261 μL (1.5 nmol, 5 eq) of diisopropylethylamine, 0.5 mL of trimethylorthoformate and 1.8 mL of DMF were added. The reaction mixture was shaken on a vortex mixer for 3.5 hours. The reaction solution was drained and 2.5 mL of a 200 mg/mL solution of sodium triacetoxyborohydride (500 mg) and 100 μL of acetic acid were added. The mixture was shaken for 16 hours. The resin was rinsed with 3×3 mL of the following: DMF, 1:1 DMF:H₂O, H₂O, DMF, followed by 5×3 mL each of CH₂Cl₂ and CH₃OH. The resin was dried under vacuum to provide 262 mg of title compound as a white resin.

-continued

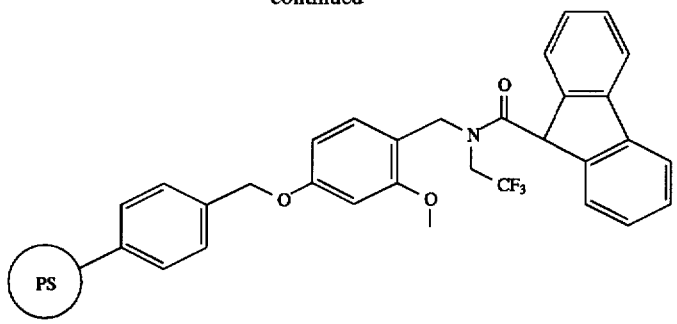

The Part A resin (262 mg, 0.3 mmol) was swollen in 3.0 mL of methylene chloride. A solution of 204 mg of 1-hydroxy-7-azabenzotriazole (1.5 mmol, 5 eq) and 315 mg of 9-fluorenecarboxylic acid (1.5 mmol, 5 eq) in 1.0 mL of DMF and 2.0 mL of methylene chloride was treated with 235 µL of diisopropylcarbodiimide (1.5 mmol, 5 eq). The resin was drained, the reagent solution was added and the mixture was shaken for 17 hours. The reaction solution was drained and rinsed with 3×3 mL of the following: DMF, 1:1 DMF:H$_2$O, H$_2$O, DMF, followed by 5×3 mL each of CH$_2$Cl$_2$ and CH$_3$OH. The resin was dried under vacuum to provide 356 mg of title compound as a yellow resin.

C.

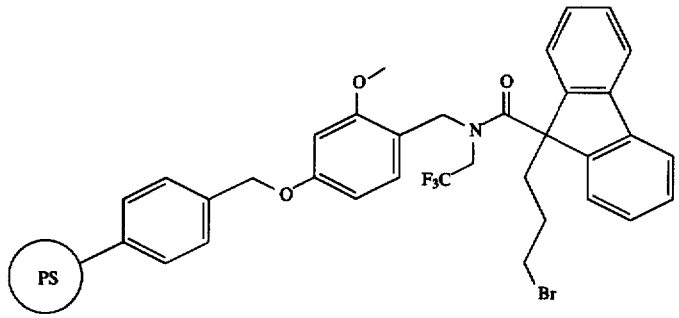

The Part B resin (323 mg, 0.27 mmol) was swollen in 3.0 mL of DMF (new Sure-Seal) and then drained under an atmosphere of argon. DMF (2.5 mL) was added, followed by the dropwise addition of 324 µL (3.2 mmol, 1.2 eq) of a 1.0M solution of sodium bis(trimethylsilyl)amide in tetrahydrofuran (THF). The reaction mixture was shaken under argon for two hours. The reaction solution was drained and the resin was rinsed with 6×3 mL of DMF maintaining an argon atmosphere. The resin was suspended in 2.5 mL of DMF and 137 µL of 1,3 dibromopropane (1.35 mmol, 5 eq) was added. The mixture was shaken for 4 hours. The reaction solution was drained and the resin was rinsed with 3×3 mL of the following: DMF, 1:1 DMF:H$_2$O, H$_2$O, followed by 4×3 mL of DMF to provide title resin, used as is in the next step.

D.

-continued

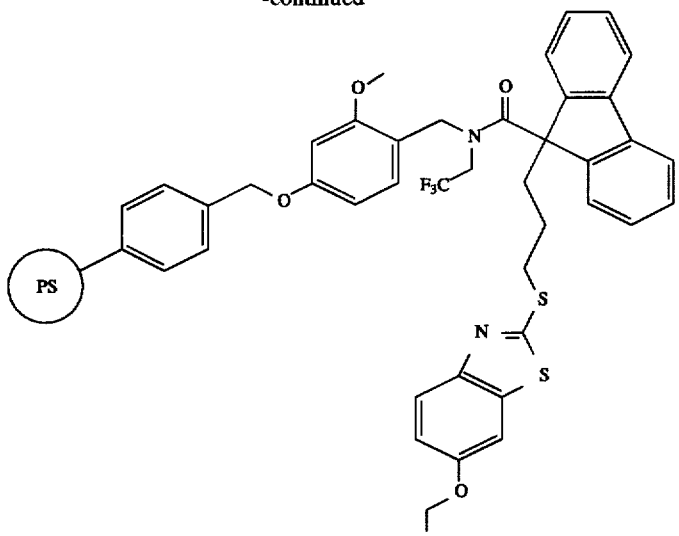

The Part C resin (0.27 mmol) was swollen in 3.0 mL of DMF. The solvent was drained and a solution of 570 mg of 6-ethoxy-2-mercaptobenzothiazole (2.7 mmol, 10 eq) in 3.0 mL of DMF was added, followed by the dropwise addition of 2.7 mL (2.7 mmol, 10 eq) of a 1.0M solution of sodium bis(trimethylsilyl)amide in THF. After the addition was completed, the mixture was shaken for 14 hours. The resin was rinsed with 3×3 mL of the following: DMF, 1:1 DMF:H$_2$O, H$_2$O, DMF, followed by 8×3 mL of CH$_2$Cl$_2$ to provide title resin, used as is in the next step.

E.

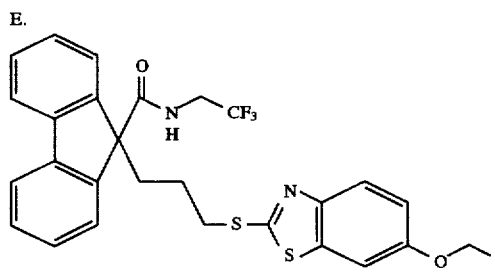

The Part D resin (0.27 mmol) was treated with 3.0 mL of trifluoroacetic acid for 90 minutes and then rinsed with methylene chloride, and the solutions were concentrated to provide 86 mg (58%) of a brown solid. This solid was combined with another batch of product prepared by the same route and purified by flash chromatography on silica gel (50 g) packed, loaded, and eluted with 25% hexane in methylene chloride followed by 100% methylene chloride. The 100% methylene chloride fractions were concentrated to provide 198 mg of title compound as an off-white foam.

TLC Silica gel (9:1 methylene chloride/hexane, visualization by UV) R$_f$=0.25. HPLC Purity=97%. Retention time=9.0 min. Column: Zorbax SB- C18 Rapid Resolution 4.6×75 mm. Solvent A: 10% methanol:90% water:0.2% H$_3$PO$_4$. Solvent B: 90% methanol:10% water:0.2% H$_3$PO4. Elution: Linear gradient from 20 to 100% B over 8 minutes followed by isocratic 100% B for 2 minutes (Short Method 2-SMET2).

MS (ESI, +ions): m/z 543 (M+H).

IR (KBr) 2930, 1684, 1601, 1512, 1449, 1273, 1223, 1163, 1038, 997, 745 cm$^{-1}$.

Anal. Calcd for C$_{28}$H$_{25}$N$_2$O$_2$S$_2$F$_3$: C, 61.98; H, 4.64; N, 5.16; S, 11.82; F, 10.50

Found: C, 61.90; H, 4.72; N, 5.06; S, 12.09; F, 10.23.

What is claimed is:

1. A compound which has the structure

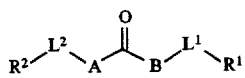

including pharmaceutically acceptable salts thereof, N-oxides thereof, wherein

A is

where

R$^5$ is H or lower alkyl;

B is a fluorenyl-type group of the structure

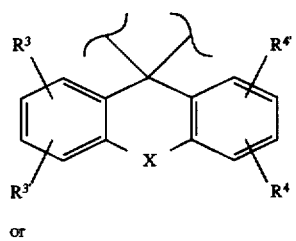

or

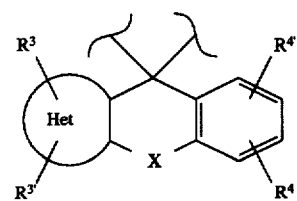

or

-continued

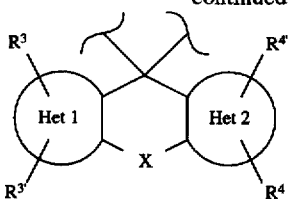

or

R¹ is heteroaryl, heteroarylamino, heteroaryloxy, heteroetrylsulfonylamino, heteroarylthio, heteroarylsulfinyl, heteroarylsulfonyl, the R¹ group may optionally be substituted with 1, 2, 3 or 4 substituents, which can be any of the R³ or R¹ groups or alkyl, alkenyl, alkynyl, alkoxyl, cycloalkyl cycloalkenyl, substituted alkylamino, substituted arylalkylamino, aryl, arylalkyl, arylamino, aryloxy, arylthio, arylsulfinyl, arylsulfonyl, alkylthio, alkylsulfinyl alkylsulfonyl —PO(R¹³)(R¹⁴), (where R¹³ and R¹⁴ are independently alkyl, aryl, alkoxy, aryloxy, heteroaryl, heteroarylalkyl, heteroaryloxy, heteroarylalkoxy, cycloheteroalkyl, cycloheteroalkylalkyl, cycloheteroalkoxy, or cycloheteroalkylalkoxy); aminocarbonyl (where the amino may optionally be substituted with one or two aryl, alkyl or heteroaryl groups); cyano, or alkylcarbonylamino, cycloalkylcarbonylamino, arylcarbonylamino, heteroarylcarbonylamino, alkoxycarbonylamino, aryloxycarbonylamino, heteroaryloxylcarbonylamino, uriedo (where the uriedo nitrogens may optionally be substituted with alkyl, aryl or heteroaryl), alkylsulfonylamino, arylsulfonylamino, or heteroarylsulfonylamino;

R² is independently any of the groups set out for R¹, alkyl, alkenyl, alkynyl, alkoxyl, (alkyl or aryl)₃ Si (where each alkyl or aryl group is independent), cycloalkyl, cycloalkennyl, substituted alkylamino, substituted arylalkylamino, aryl, arylalkyl, arylamino, aryloxy, arylsulfonylamino, arylthio, arylsulfinyl, arylsulfonyl, alkylthio, alkylsulfinyl, alkylsulfonyl, —PO(R¹³)(R¹⁴), (where R¹³ and R¹⁴ are independently alkyl, aryl, alkoxy, aryloxy, heteroaryl, heteroarylalkyl, heteroaryloxy, heteroarylalkoxy, cycloheteroalkyl, cycloheteroalkylalkyl, cycloheteroalkoxy, or cycloheteroalkylalkoxy); aminocarbonyl (where the amino may optionally be substituted with one or two aryl, alkyl or heteroaryl groups); cyano, H, or polyhaloalkyl, and may be optionally substituted with one to four of any of the groups defined for R³ or substituents defined for R¹;

L¹ is a linking group containing from 1 to 10 carbons; in a linear chain including alkylene, alkenylene or alkynylene, which may contain, within the linking chain any of the following: one or two alkenes, one or two alkynes, an oxygen, an amino group, an oxo group, and may be substituted with one to five alkyl or halo groups;

L² may be the same or different from L¹ and may independently be any of the L¹ groups set out above or a single bond;

R³, R³', R⁴ and R⁴' may be the same or different and are independently selected from H, halogen, CF₃, haloalkyl, hydroxy, alkoxy, alkyl, aryl, alkenyl, alkenyloxy, alkynyl, alkynyloxy, alkanoyl, nitro, amino, thiol, alkylthio, alkylsulfinyl, alkylsulfonyl, carboxy, alkoxycarbonyl, aminocarbonyl, alkylcarbonyloxy, alkylcarbonylamino, cyano, Ar-, Ar-alkyl, ArO, Ar-amino, Ar-thio, Ar-sulfinyl, Ar-sulfonyl, Ar-carbonyl, Ar-carbonyloxy or Ar-carbonylamino, wherein Ar is aryl or hetertoaryl and Ar may optionally include 1, 2 or 3 additional rings fused to Ar;

R³ᵃ and R³ᵇ are the same or different and are independently any of the R³ groups except hydroxy, nitro, amino or thio;

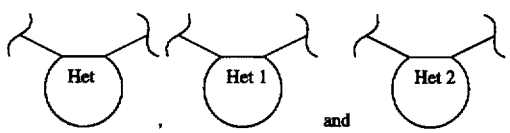

are the same or different and independently represent a 5 or 6 membered heteroaryl ring which contains 1, 2, 3 or 4 heteroatoms in the ring which are independently N, S or O; and including N-oxides;

X is a bond, or is one of the following groups:

(1) 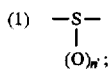

(2) —O—;

(3) 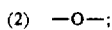

(4) 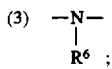

(5) 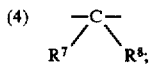

(6) 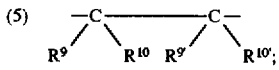

or (7) 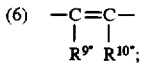

wherein

Y is O, N—R⁶ or S;

n' is 0, 1 or 2;

R⁶ is H, lower alkyl, aryl, —C(O)—R¹¹ or —C(O)—O—R¹¹;

R⁷ and R⁸ are the same or different and are independently H, alkyl, aryl, halogen, —O—R¹², or R⁷ and R⁸ together can be oxygen to form a ketone;

R⁹, R¹⁰, R⁹' and R¹⁰' are the same or different and are independently H, lower alkyl, aryl or -O-R¹¹;

R⁹'' and R¹⁰'' are the same or different and are independently H, lower alkyl, aryl, halogen or —O—R¹¹;

R¹¹ is alky or aryl;

R¹² is H, alkyl or aryl.

2. The compound as defined in claim 1 wherein B is a fluorenyl-type group.

3. The compound as defined in claim 1 wherein B is

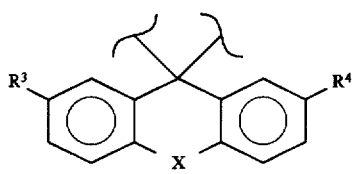

A is NH;

X is a bond, oxygen or sulfur;

$R^3$ and $R^4$ are the same or different and are H or F;

$R^1$ is heteroaryl, imidazolyl, pyridyl, heteroarylthio, benzimidazolyl, indolyl, benzthiazole-2-thio, imidazole-2-thio, or 1,3-dioxan-2-yl, wherein each of the above is optionally substituted;

$R^2$ is alkyl, polyfluoroalkyl, alkenyl, aryl, phenyl, heteroaryl, imidazolyl or pyridyl, wherein each of the above is optionally substituted;

$L^1$ is a chain containing 1 to 5 atoms in a linear chain;

$L^2$ is a bond or lower alkylene.

4. The compound as defined in claim 3 wherein A is NH and $R^2L^2$ is $CF_3CH_2$.

5. The compound as defined in claim 1 having the formula

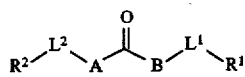

wherein B is

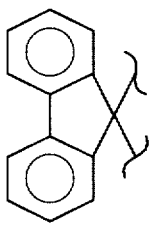

A is NH $L^2R^2$ is $CH_2CF_3$ $L^1$ is —$CH_2CH_2CH_2$— or —$CH_2CH_2CH_2CH_2$—, and $R^1$ is heteroaryl which is a 5-membered aromatic ring which includes 2 nitrogen atoms, which ring is fused to an aryl ring and is substituted on the aryl moiety.

6. The compound as defined in claim 1 wherein $R^1$ is

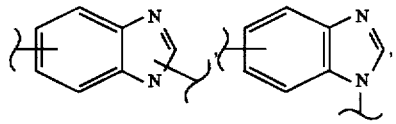

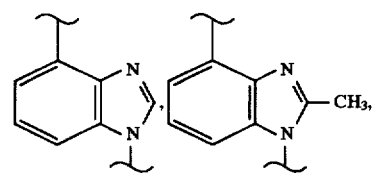

-continued

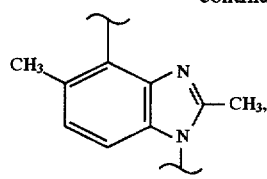

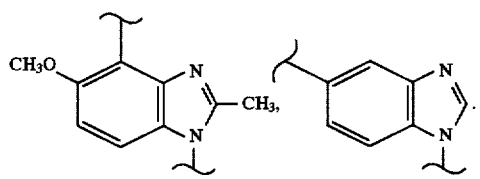

7. The compound as defined in claim 1 wherein $R^1$ is

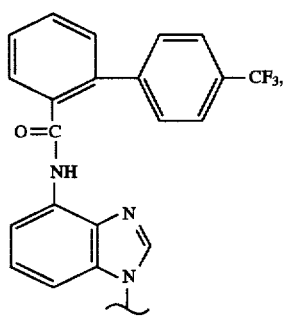

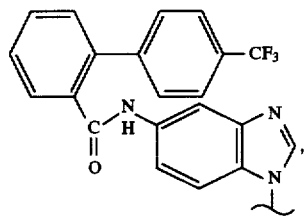

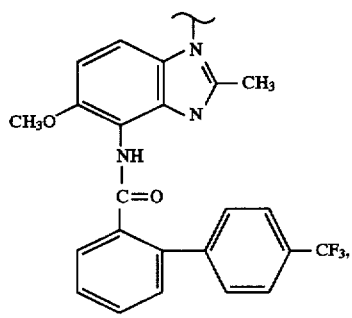

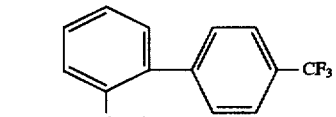

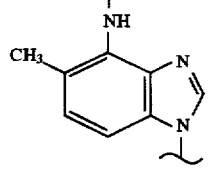

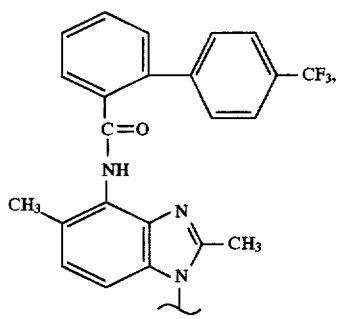
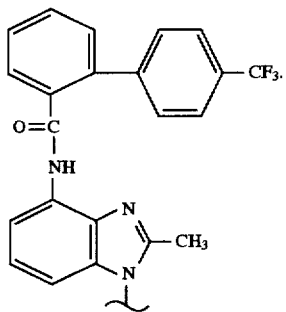
8. The compound as defined in claim 5 having the structures
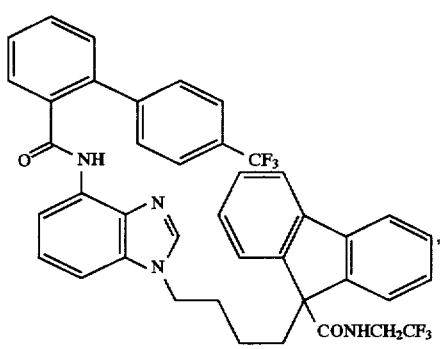
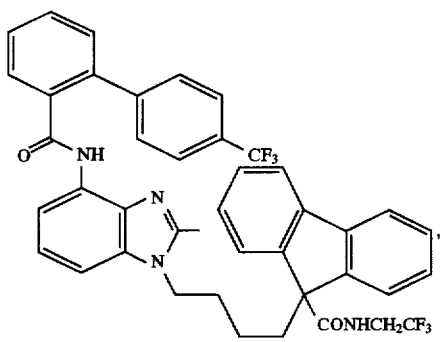
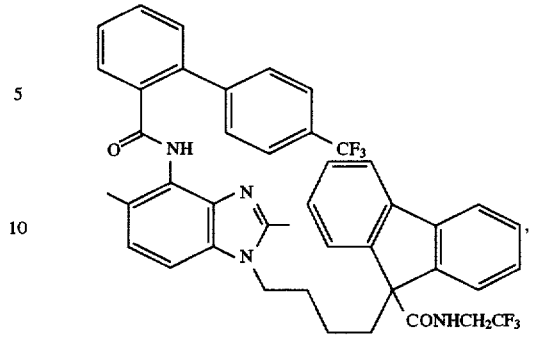
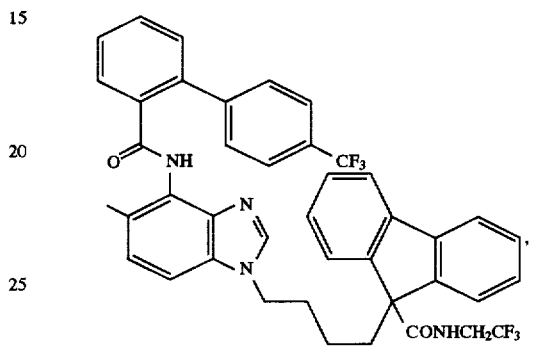
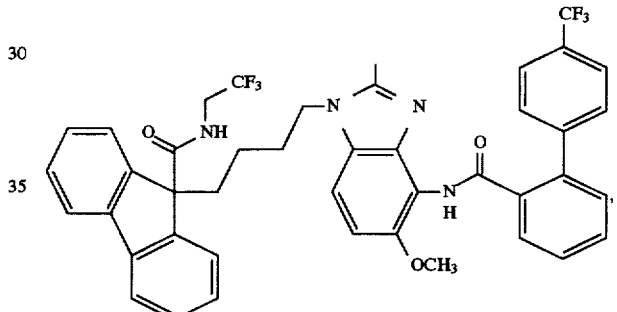
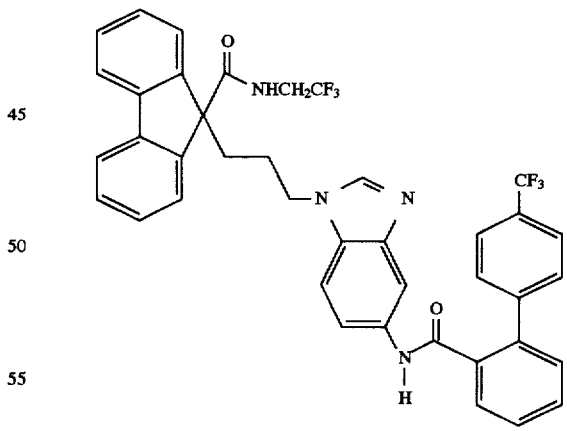
or a pharmaceutically acceptable salt thereof.

9. A compound of the structure

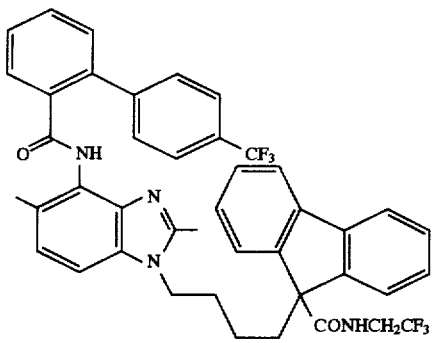

or a pharmaceutically acceptable salt thereof.

10. The compound as defined in claim 1 which is
9-[[2,2-bis(trifluoromethyl)-1,3-dioxolan-4-yl]methyl-N-ethyl-9H-fluorene-9-carboxamide;
9-[5-[(6-ethoxy-2-benzothiazolyl)thio]pentyl]-N-propyl-9H-fluorene-9-carboxamide;
9-(3-phenylpropyl)-N-(2-pyridinylmethyl)-9H-fluorene-9-carboxamide;
2,7-difluoro-9-(3-phenylpropyl)-N-(4-pyridinylmethyl)-9H-fluorene-9-carboxamide;
9-[3-(1,3-dioxan-2-yl)propyl]-N-propyl-9H-fluorene-9-carboxamide;
9-[3-(1,3-dioxolan-2-yl)propyl]-N-propyl-9H-fluorene-9-carboxamide;
(Z)-9-[4-[(6-ethoxy-2-benzothiazolyl)thio]-2-butenyl]-N-propyl-9H-fluorene-9-carboxamide;
9-[4-[4-(benzoylamino)-1H-imidazol-1-yl]-butyl-N-(2,2,2-trifluoroethyl)-9H-fluorene-9-carboxamide;
9-[4-5-(benzoylamino)-2-pyridinyl]butyl]-N-(2,2,2-trifluoroethyl)-9H-fluorene-9-carboxamide;
9-[4-[4-[(2-phenoxybenzoyl)amino]-1H-imidazol-1-yl)butyl]-N-(2,2,2-trifluoroethyl)-9H-fluorene-9-carboxamide;
9-[4-[(2-bromo-5-pyridinyl)amino]butyl]-N-propy-9H-fluorene-9-carboxamide;
9-[4-[(6-ethoxy-2-benzothiazolyl)thio]butyl]-N-propyl-9H-fluorene-9-carboxamide;
9-[3-[(6-ethoxy-2-benzothiazolyl)thio]propyl]-N-propyl-9H-fluorene-9-carboxamide;
9-[3-[[5-[(2-phenoxybenzoyl)amino]-2-pyridinyl]oxy]propyl]-N-(2,2,2-trifluoroethyl)-9H-fluorene-9-carboxamide;
9-[4-[5-[(2-phenoxybenzoyl)amino]-2-pyridinyl]-butyl]-N-(2,2,2-trifluoroethyl)-9H-fluorene-9-carboxamide;
9-[4-[4-(benzoylamino)-2-methyl-1H-imidazol-1-yl]butyl]-N-(2,2,2-trifluoroethyl)-9H-fluorene-9-carboxamide;
9-[4-[4-[(2-phenoxybenzoyl)amino]-2-methyl-1H-imidazol-1-yl]butyl-N-(2,2,2-trifluoroethyl)-9H-fluorene-9-carboxamide;
9-[3-[[2-(benzoylamino)-5-pyridinyl]amino]-propyl]-N-(2,2,2-trifluoroethyl)-9H-fluorene-9-carboxamide;
9-[3-[[5-[(2-phenoxybenzoyl)amino]-2-pyridinyl]oxy]propyl]-N-propyl-9H-fluorene-9-carboxamide;
9-[6-[(6-ethoxy-2-benzothiazolyl)thio]hexyl]-N-(2,2,2-trifluoroethyl)-9H-fluorene-9-carboxamide;
[1-[4-[9-[[(2,2,2-trifluoroethyl)amino]-carbonyl]-9H-fluoren-9-yl]butyl]-1H-imidazol-4-yl]-carbamic acid;
9-[4-[(4,5-diphenyl-1H-imidazol-2-yl)thio]-butyl]-N-[2-(4-methoxyphenyl)ethyl]-9H-fluorene-9-carboxamide;
9-[4-[(6-ethoxy-2-benzothiazolyl)thio]butyl]-N-propyl-9H-fluorene-9-carboxamide;
9-[4-(2-thiazolylthio)butyl]-N-(2,2,2-trifluoroethyl)-9H-fluorene-9-carboxamide;

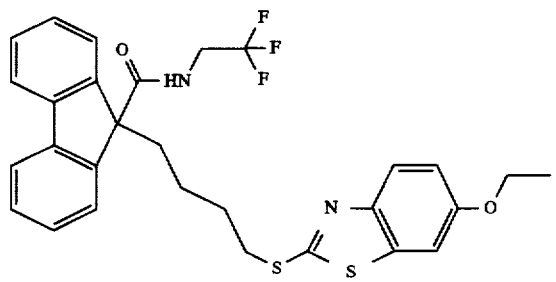

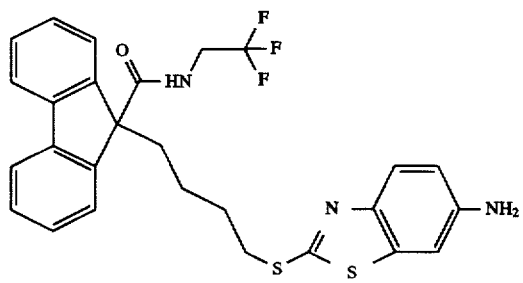

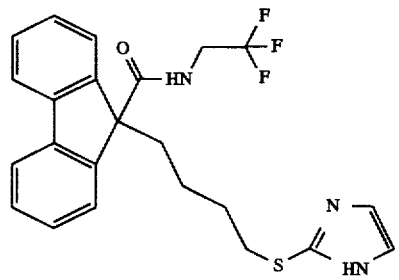

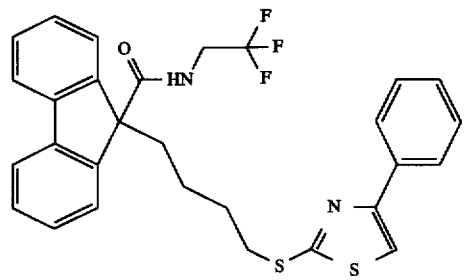

385
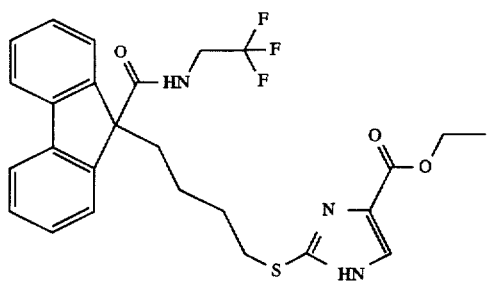
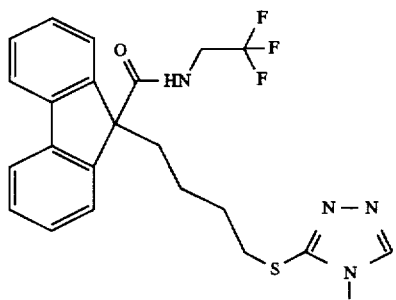
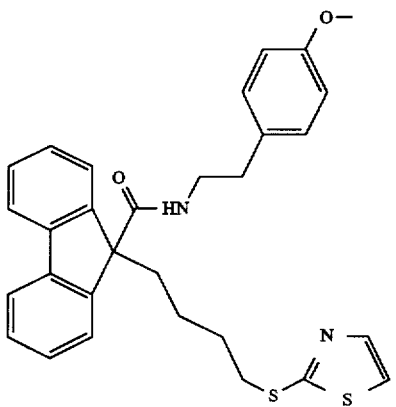
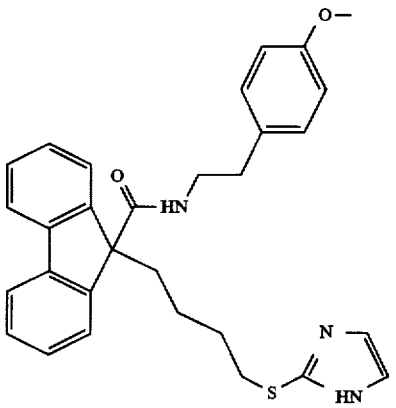
386
-continued
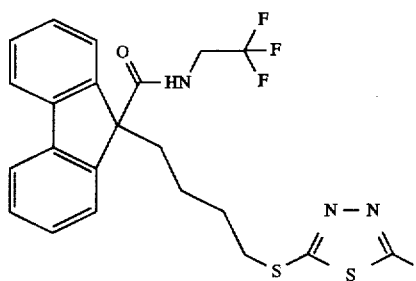
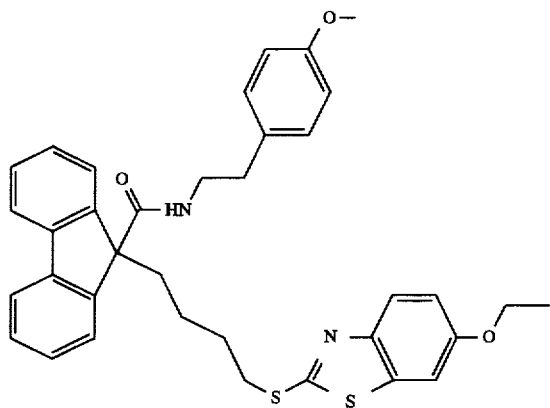
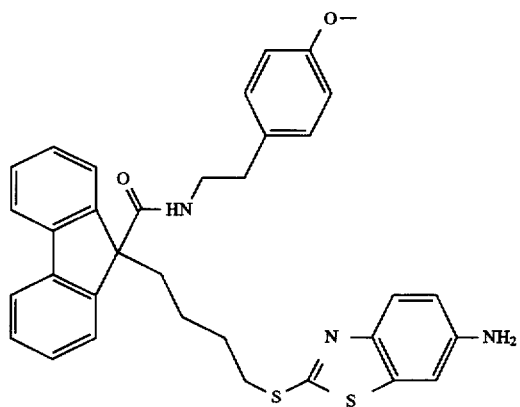
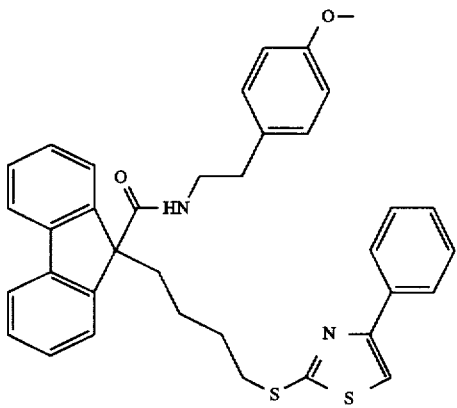

387
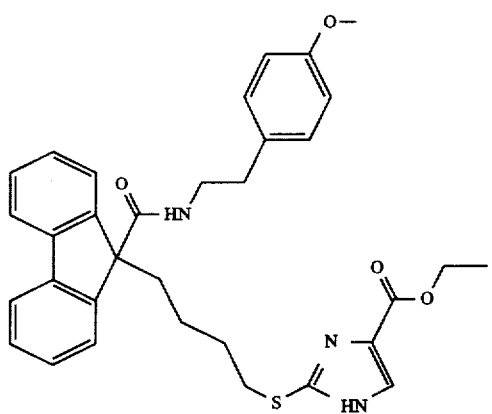
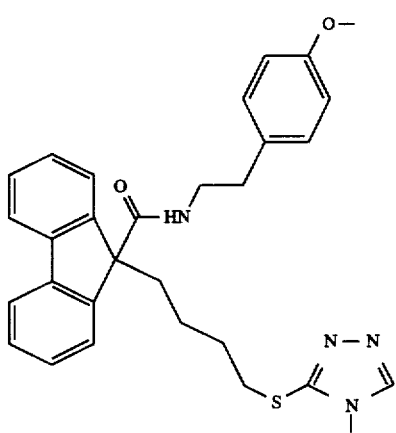
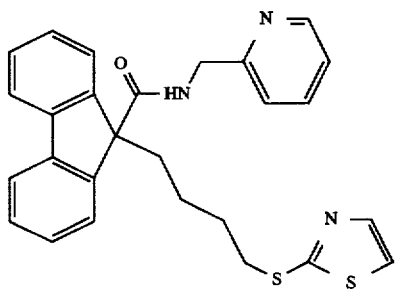
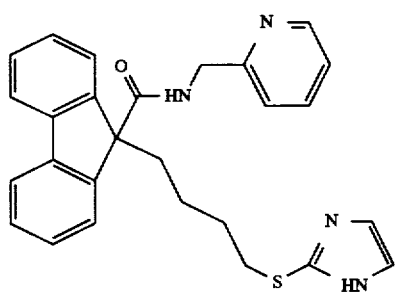
388
-continued
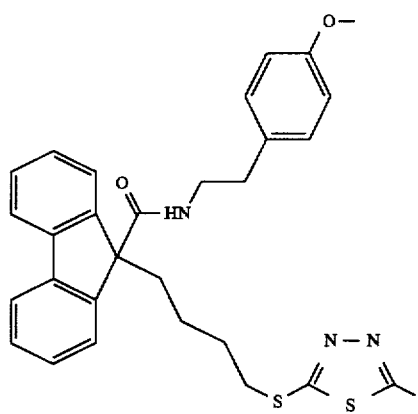
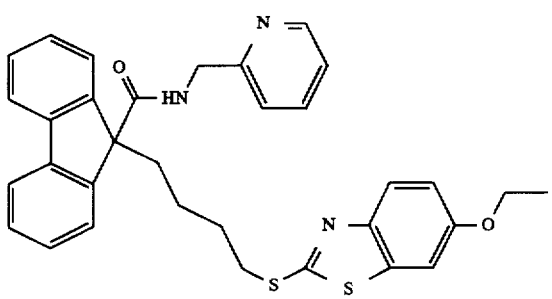
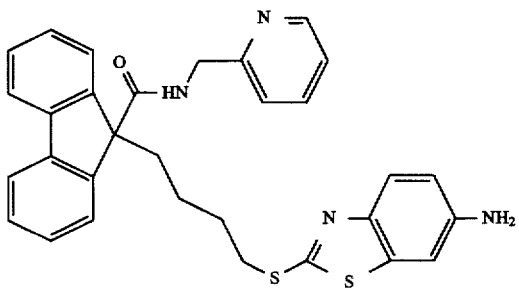
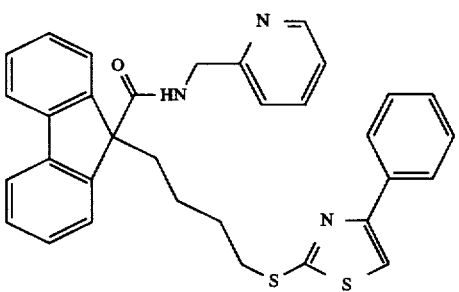

389
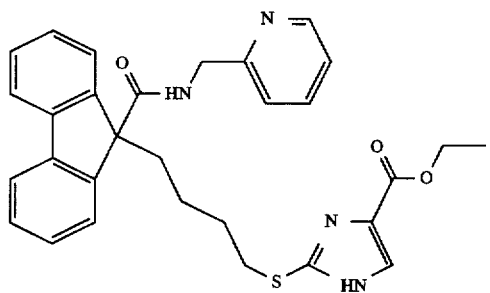
390
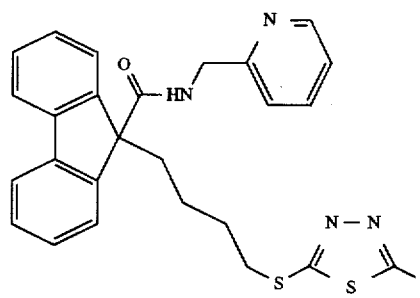
-continued
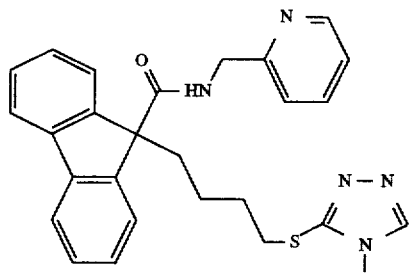
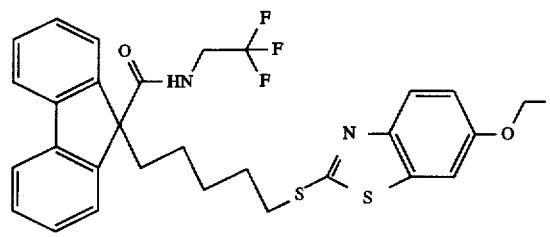
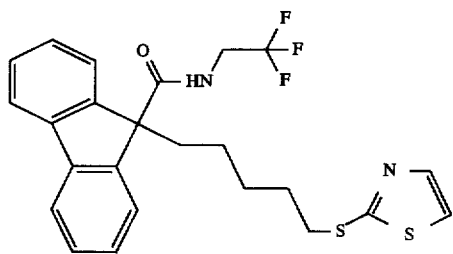
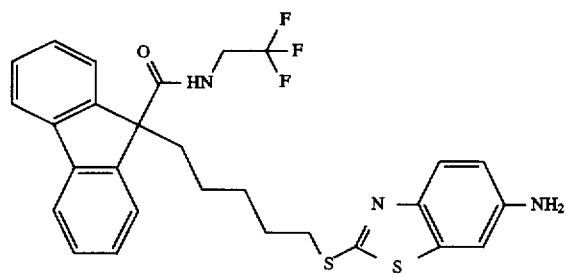
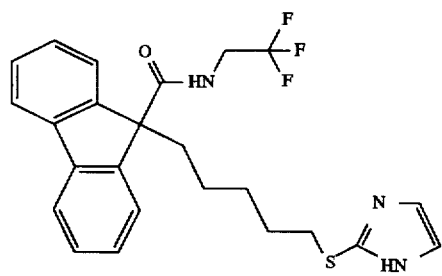
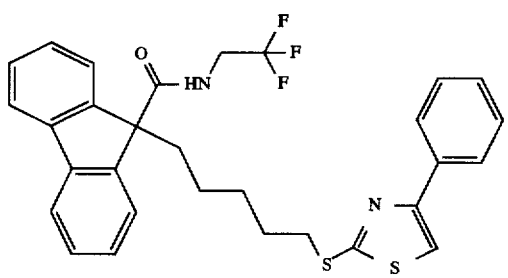
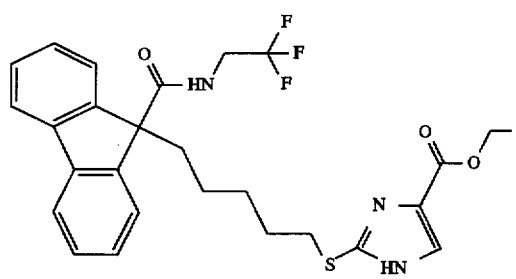
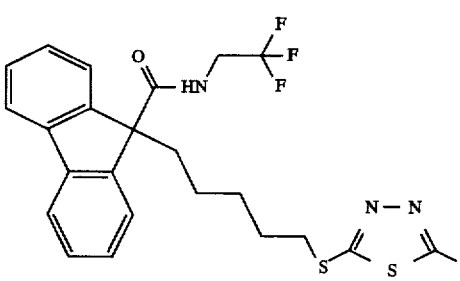

391
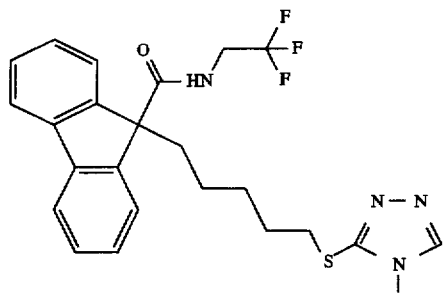
392
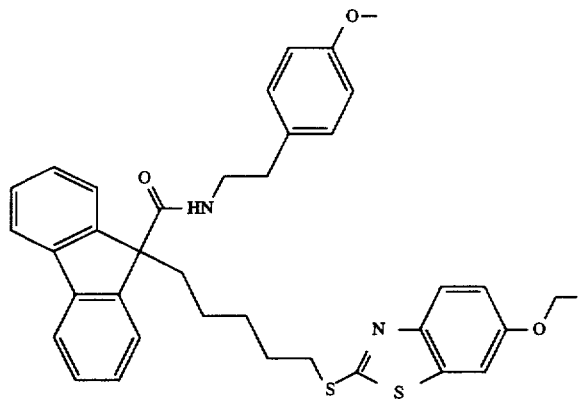
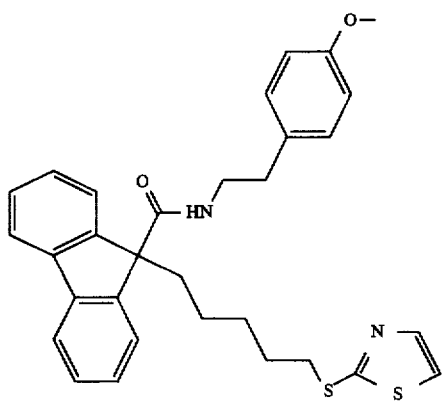
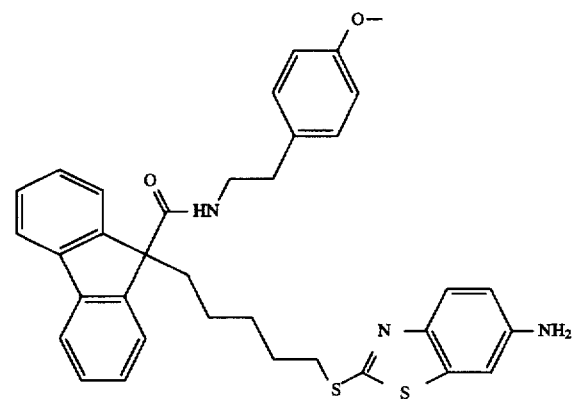
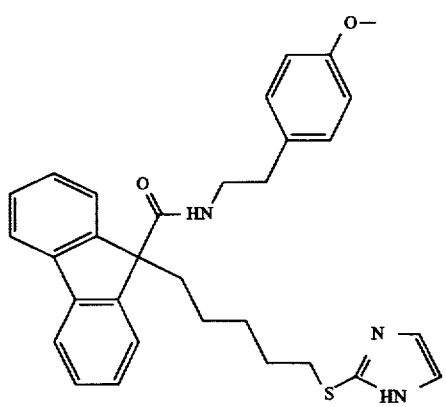
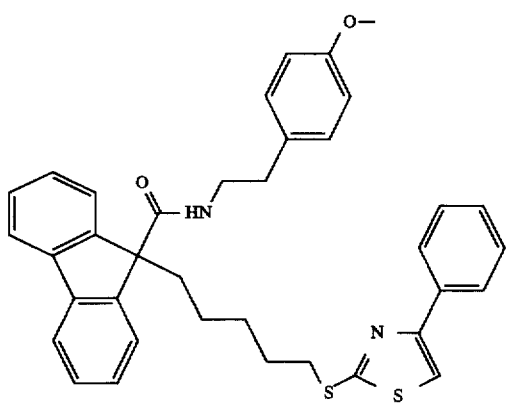
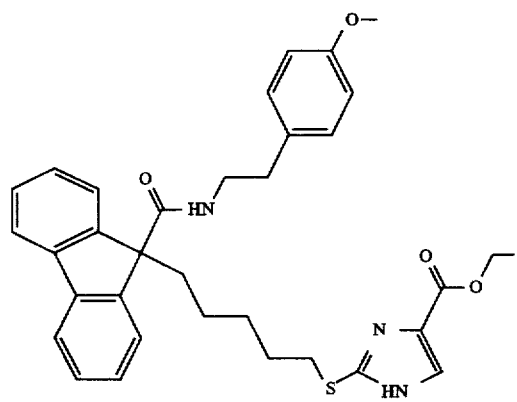

393
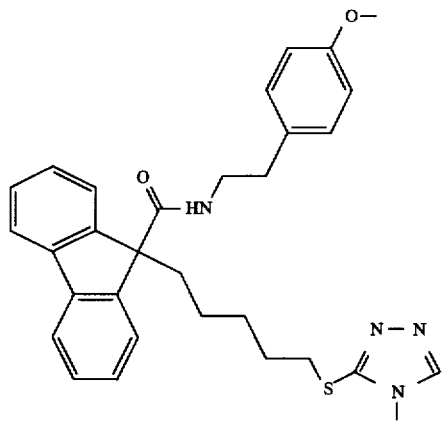
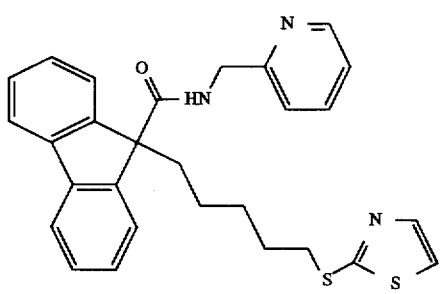
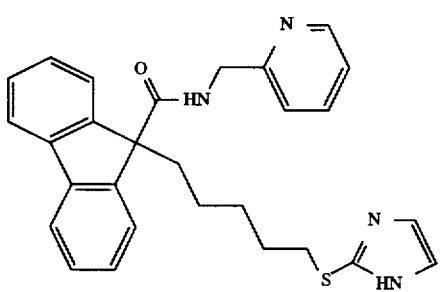
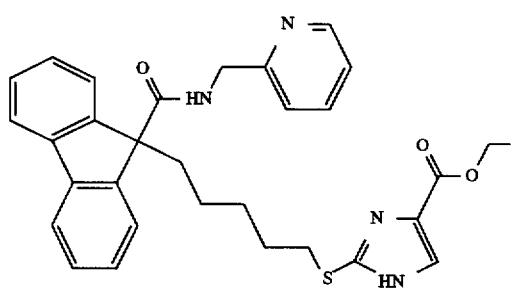
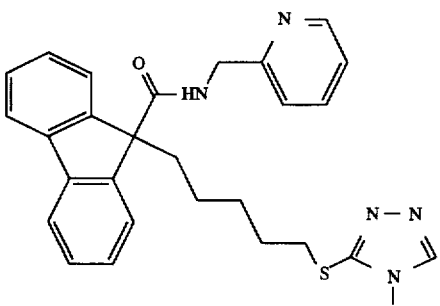
394
-continued
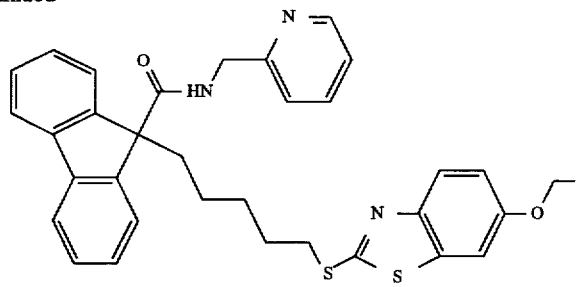
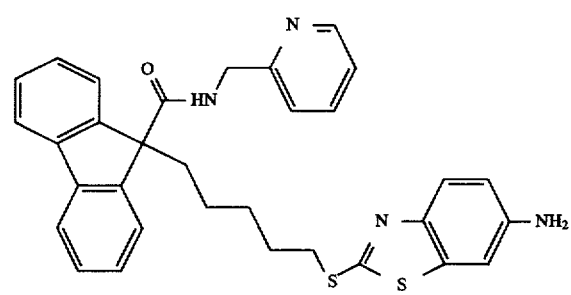
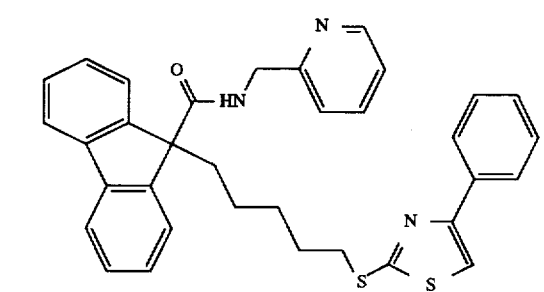
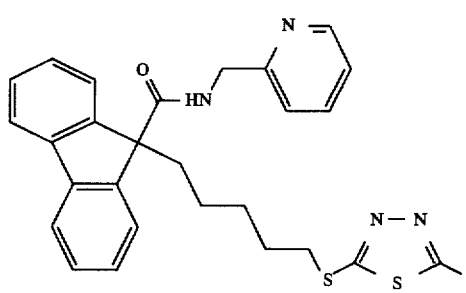
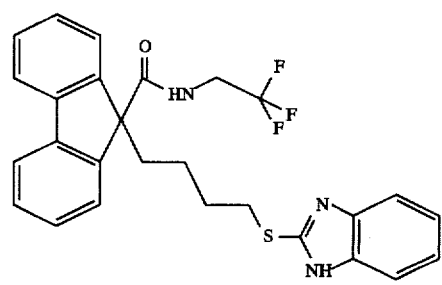

395 396
-continued
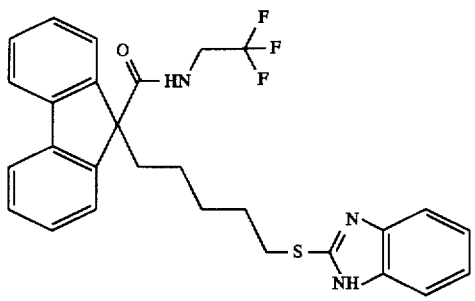 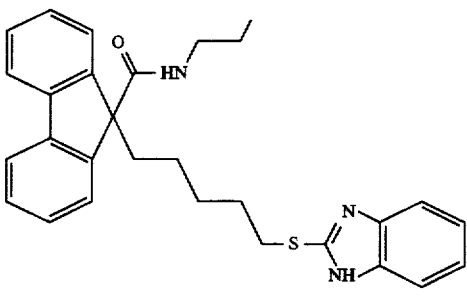
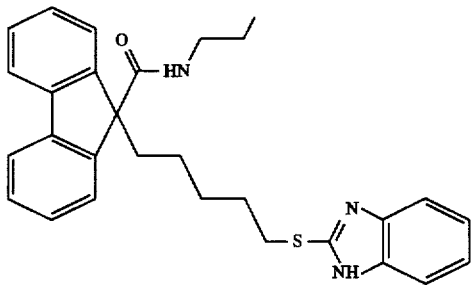 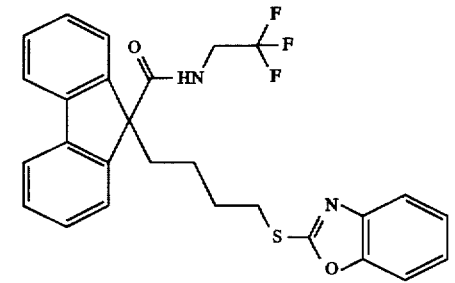
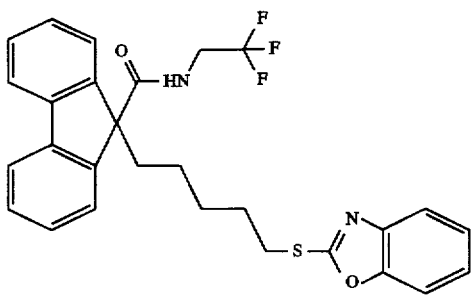 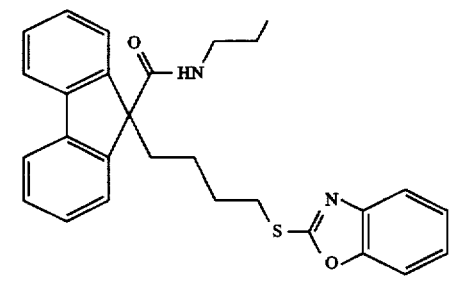
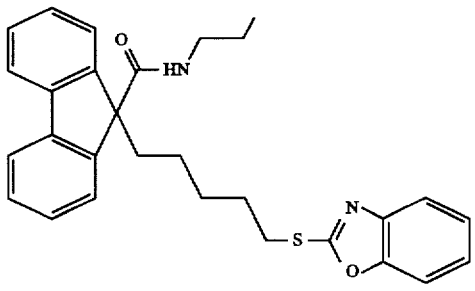 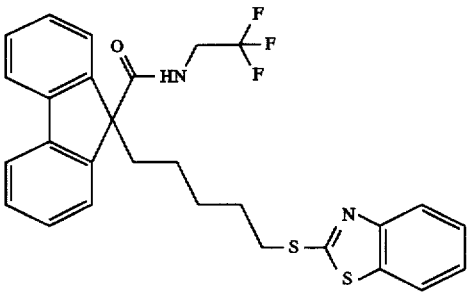
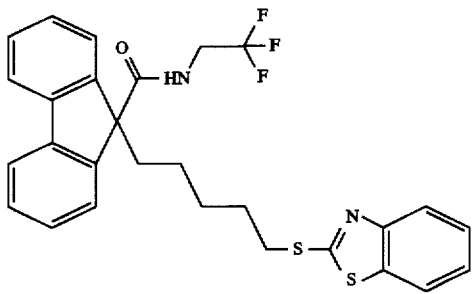

-continued
397
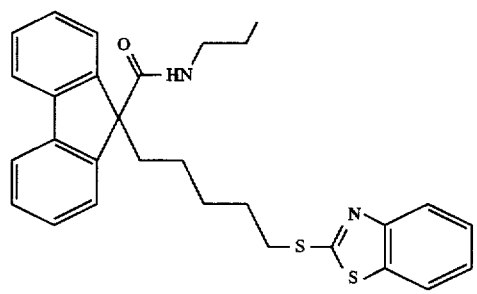
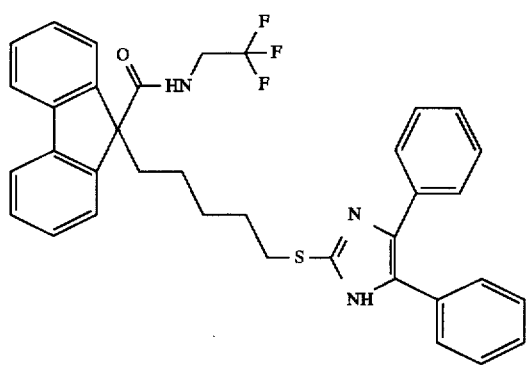
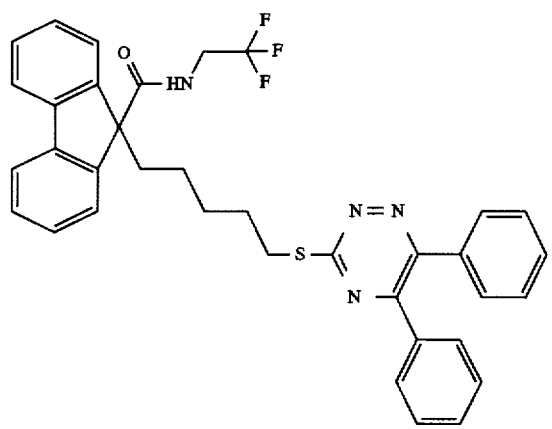
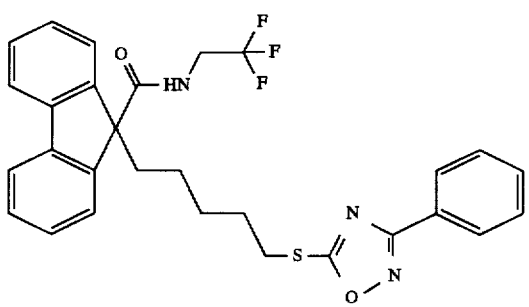
398
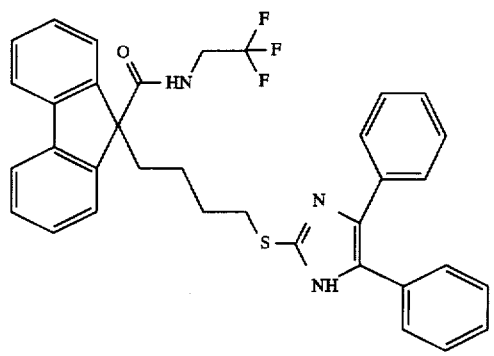
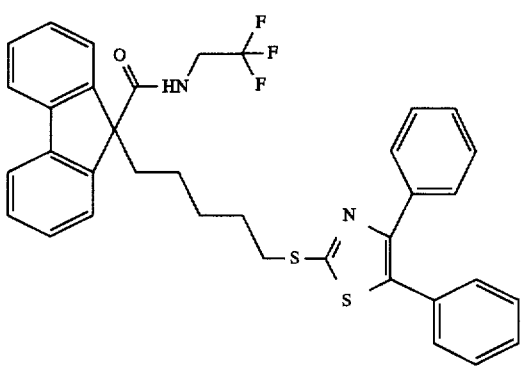
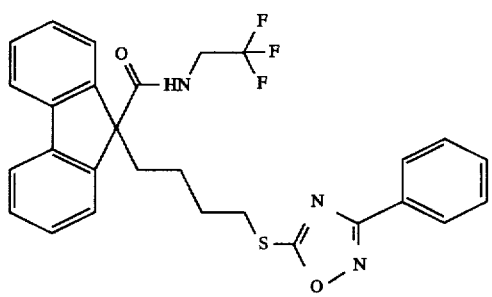
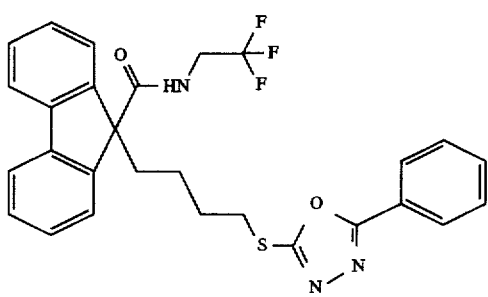

399
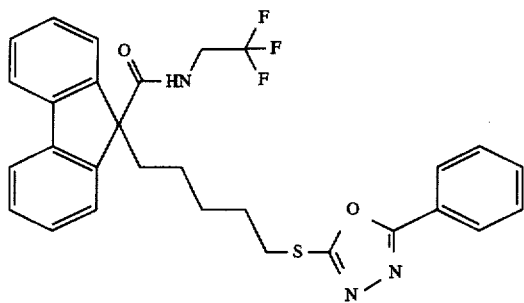
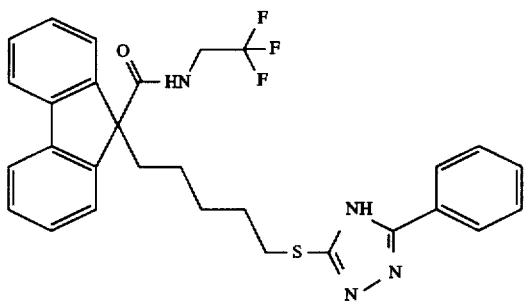
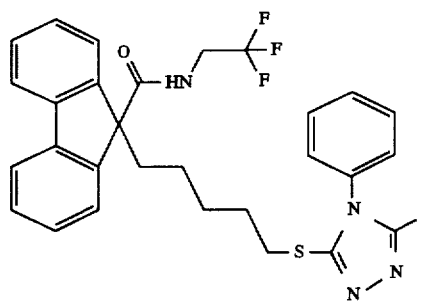
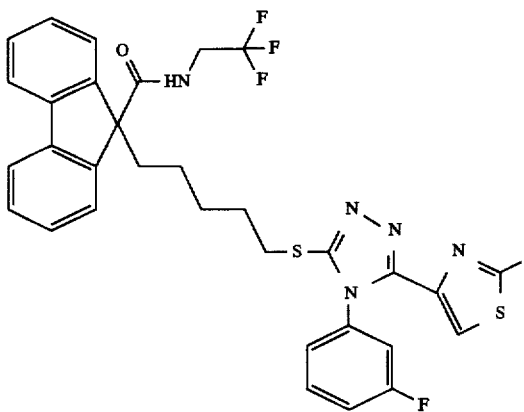
400
-continued
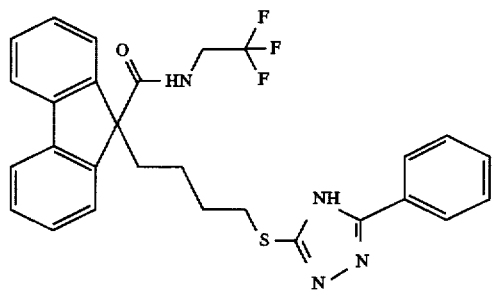
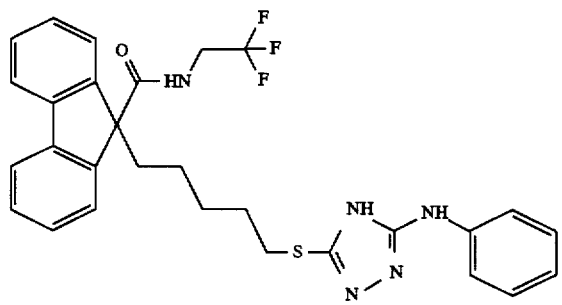
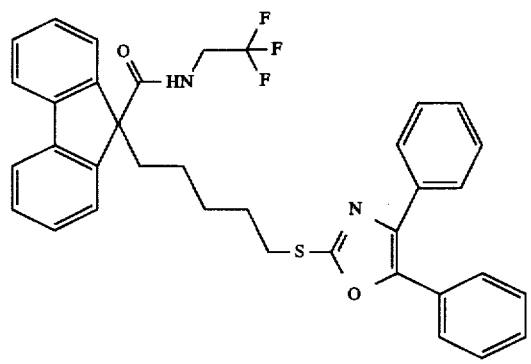
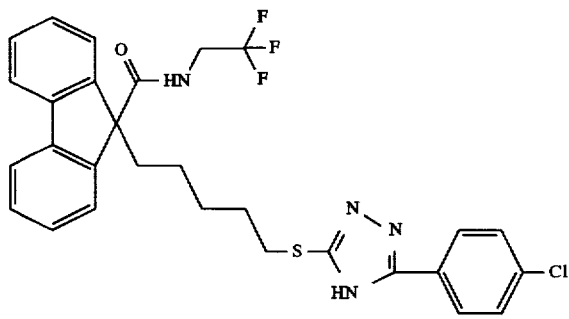

401 402
-continued
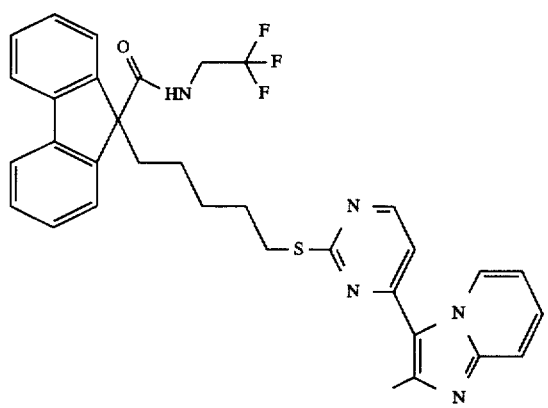
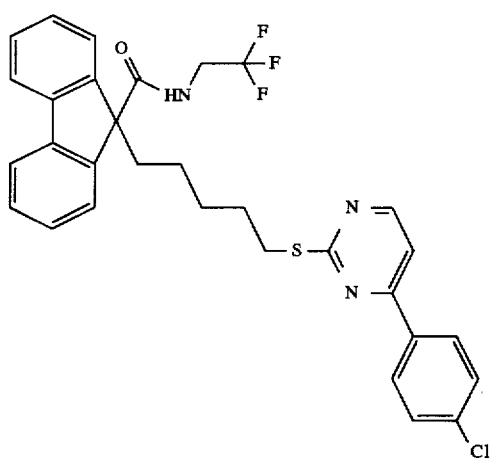
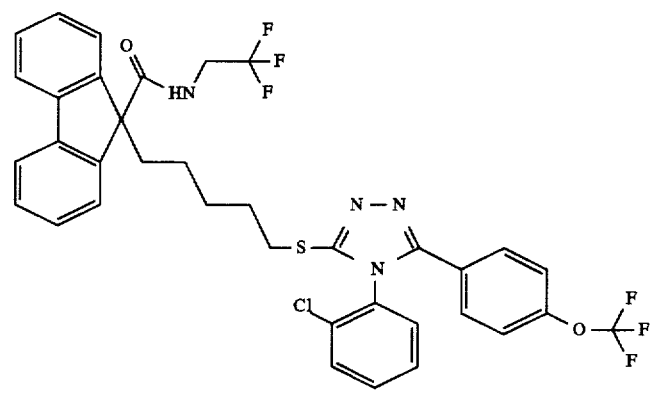
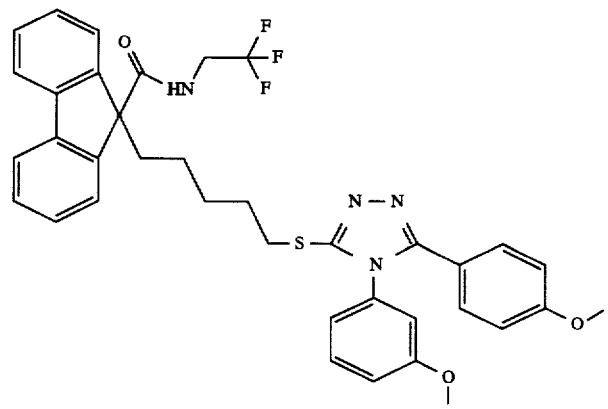

-continued
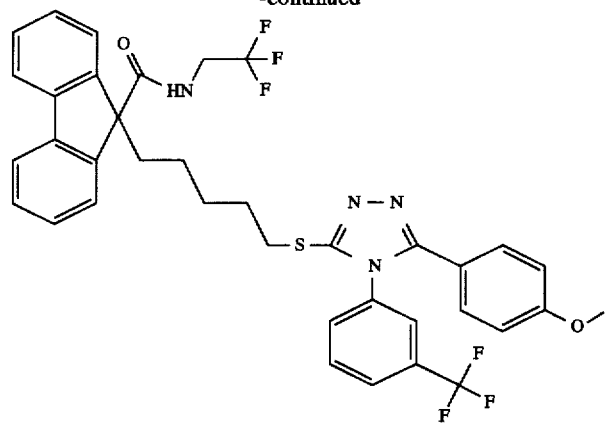
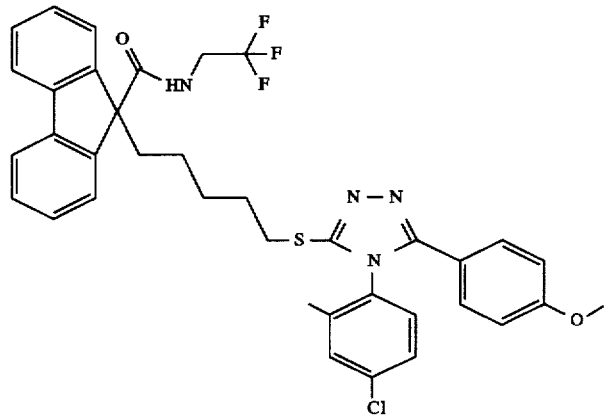
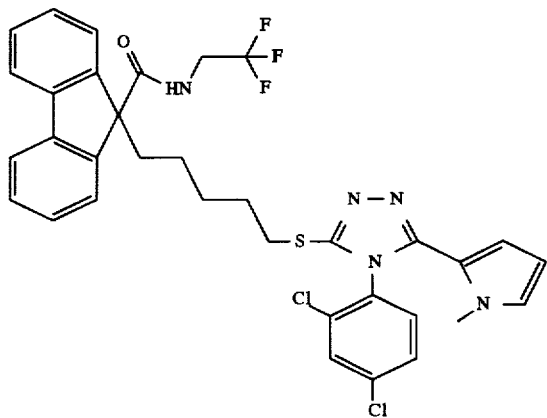
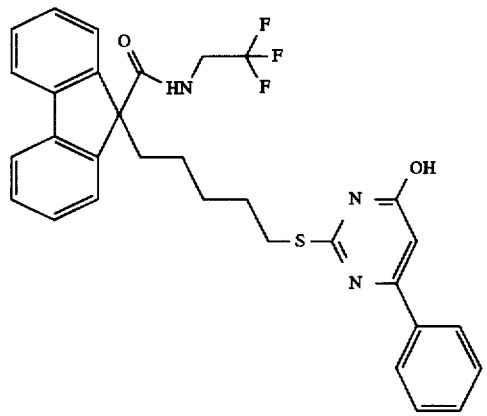
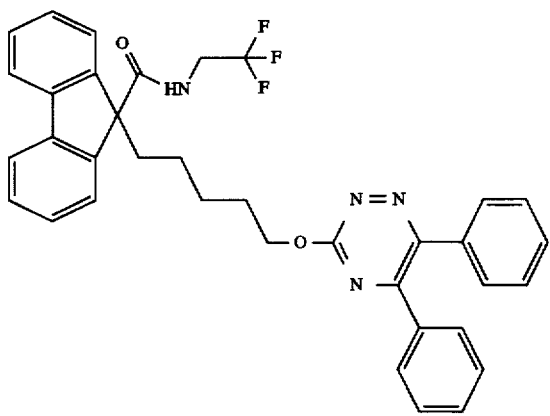
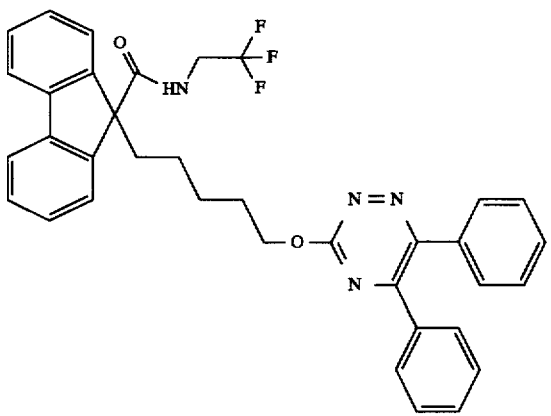

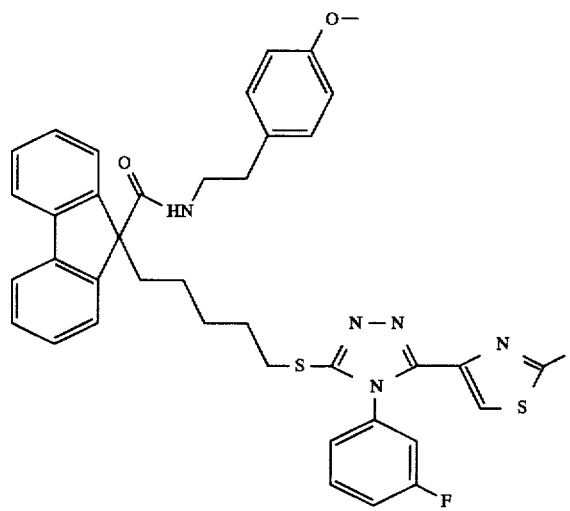
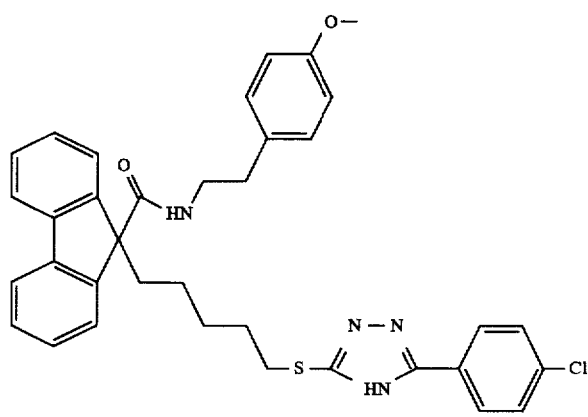
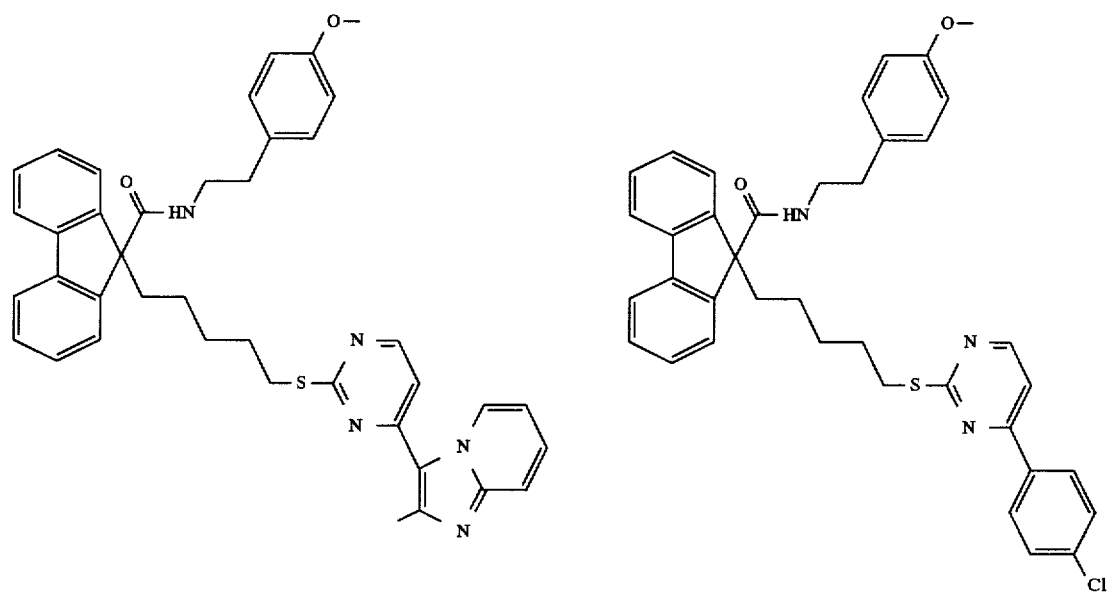

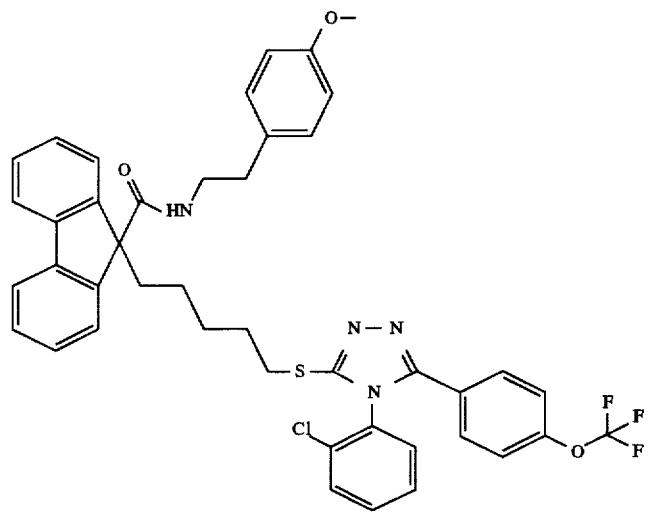
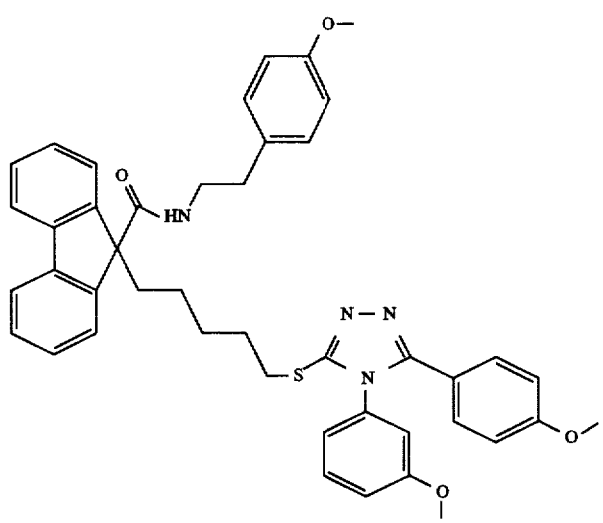
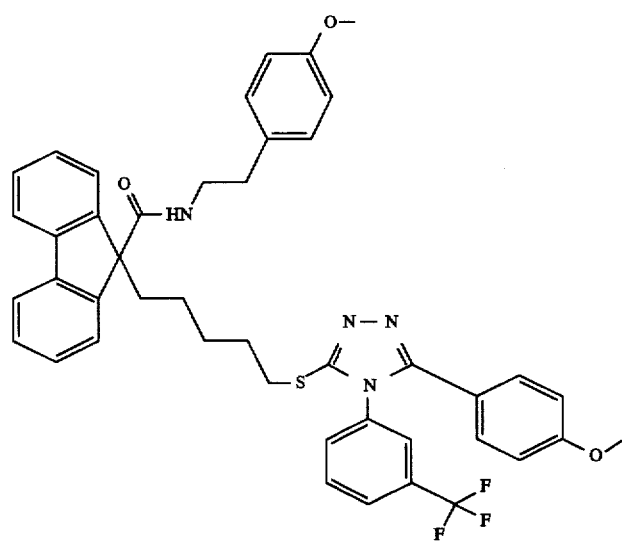

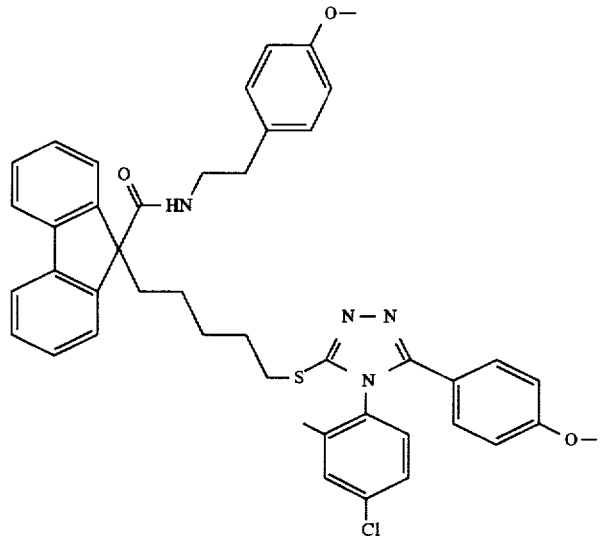
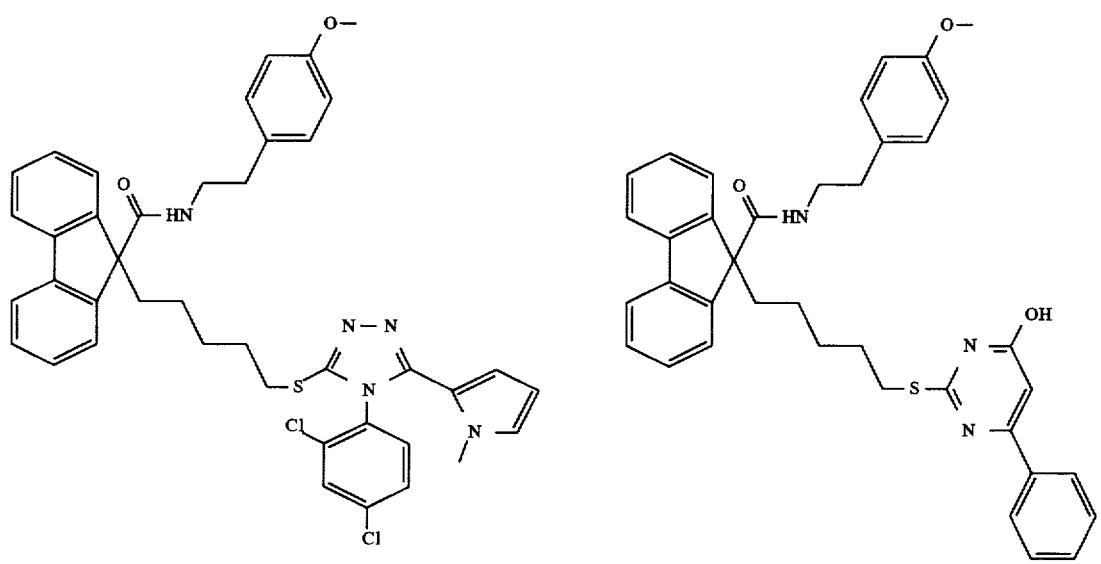
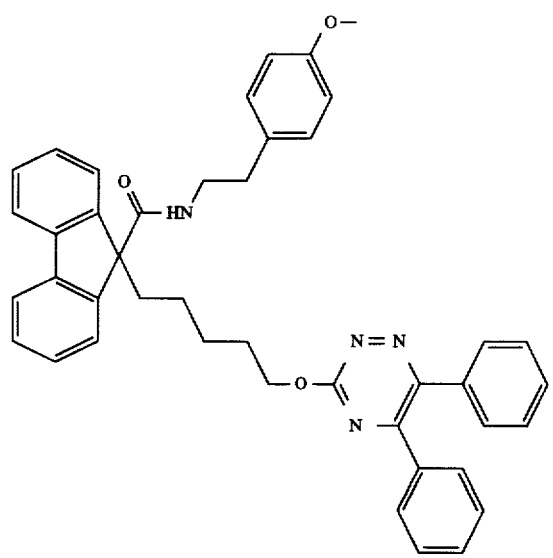

-continued
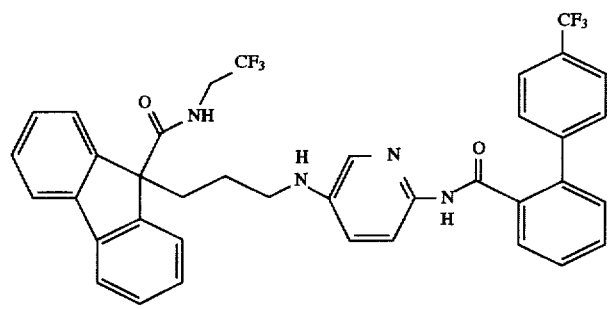
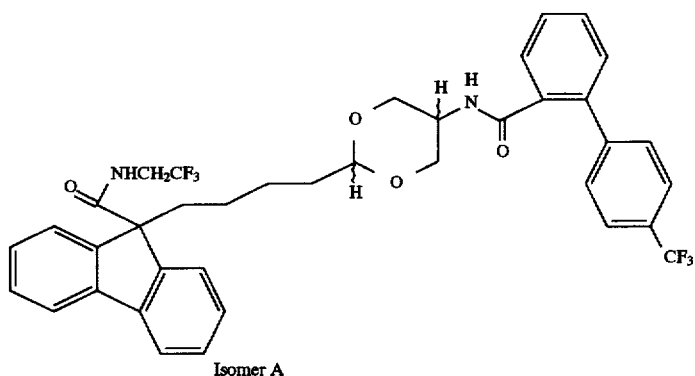
Isomer A
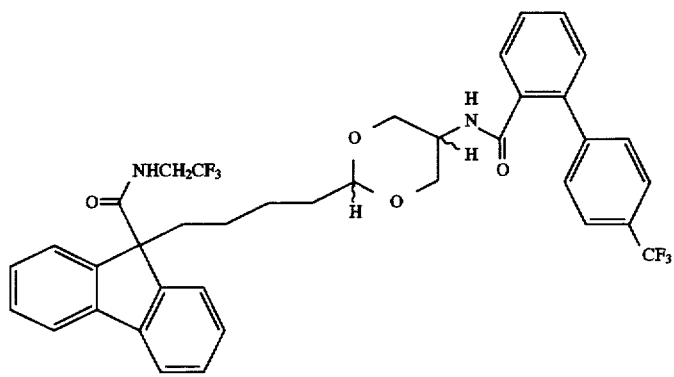
Isomer B
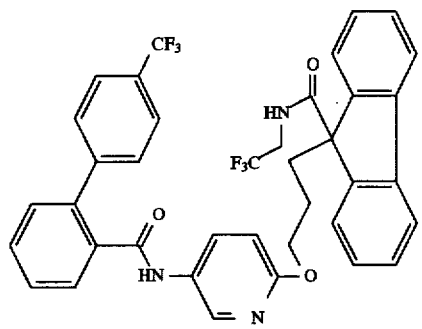
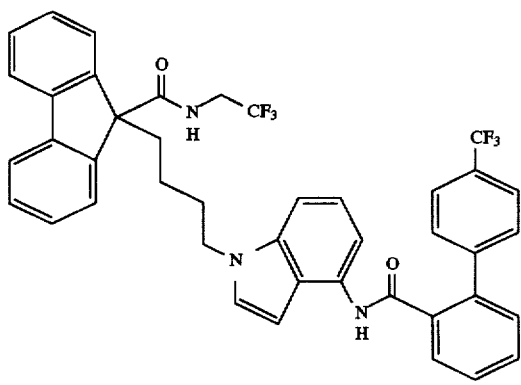

-continued
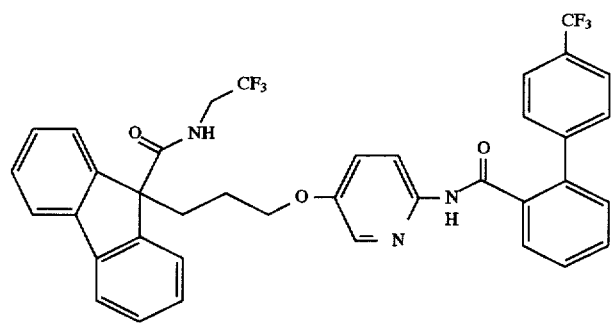
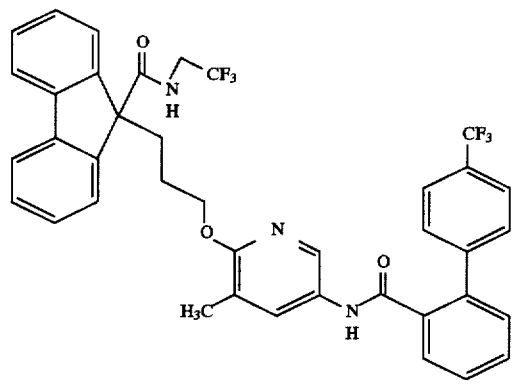
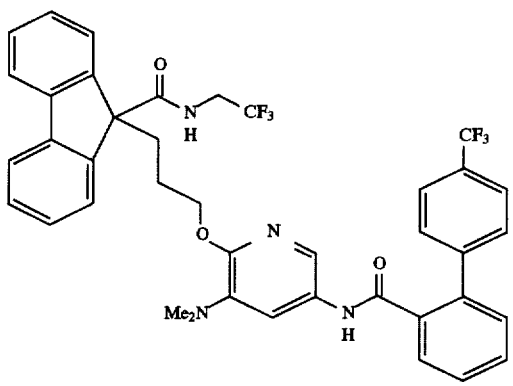
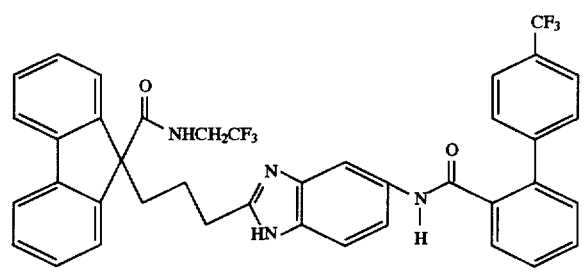
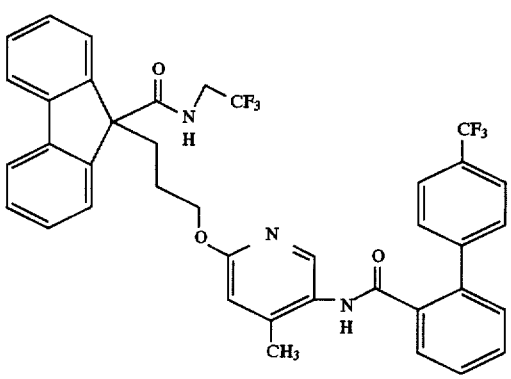
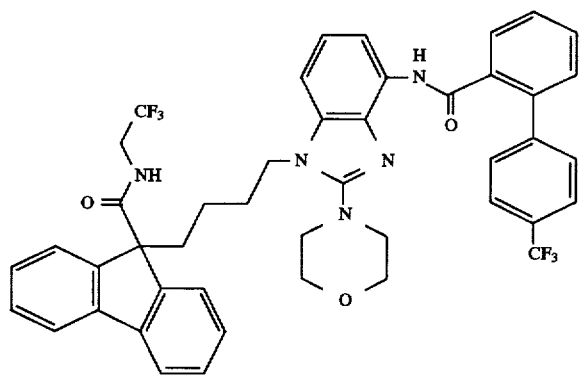
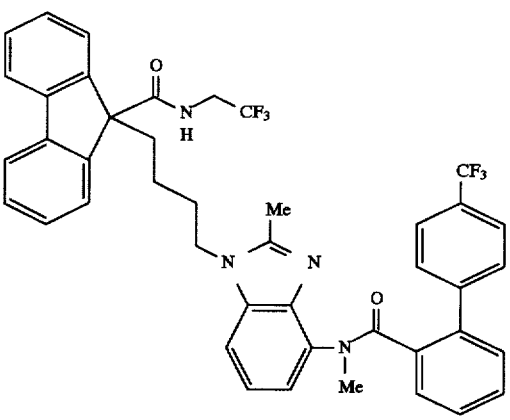

-continued
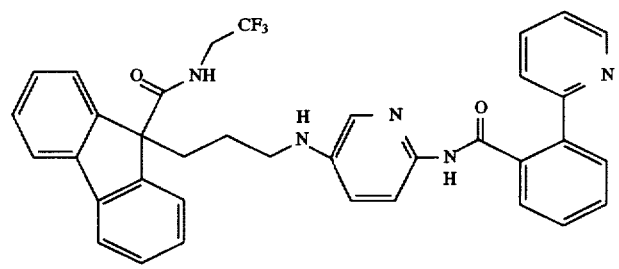
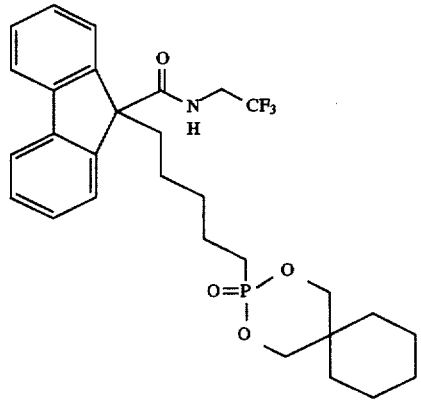
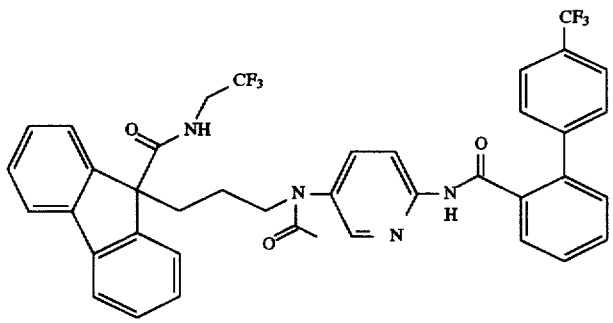
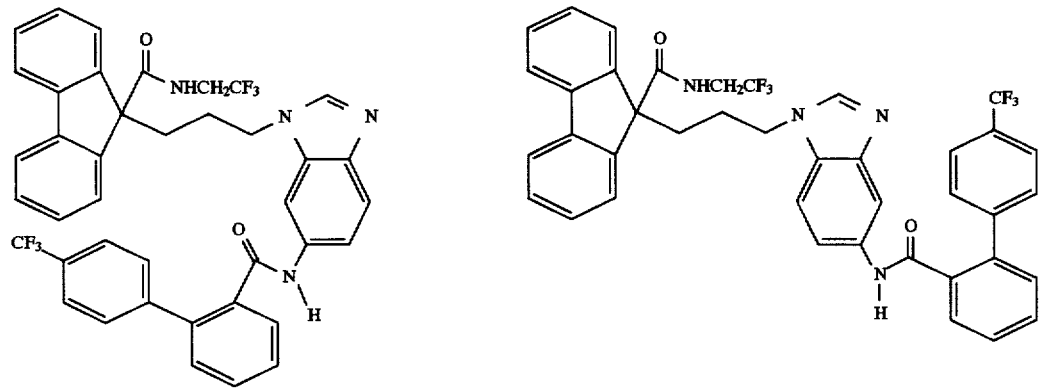

-continued
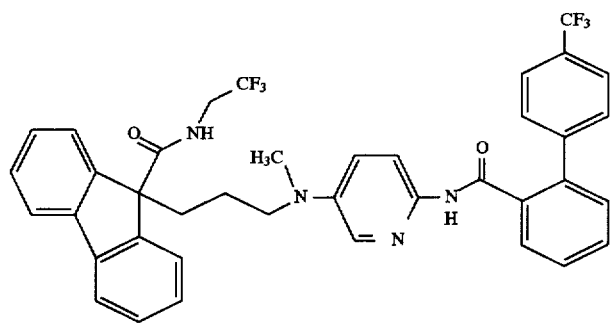
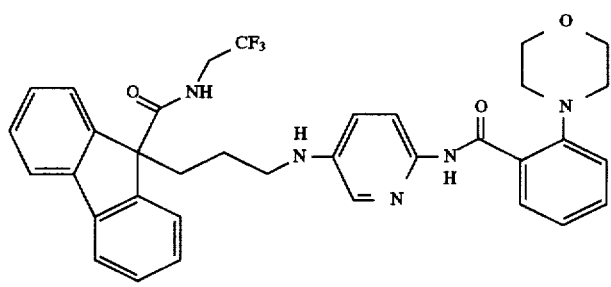
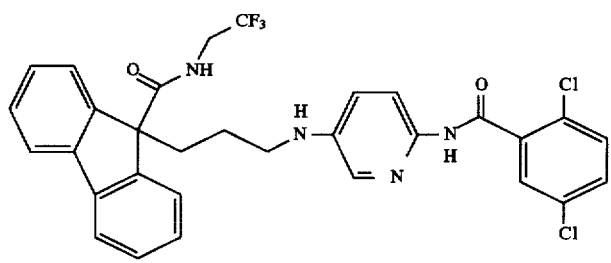
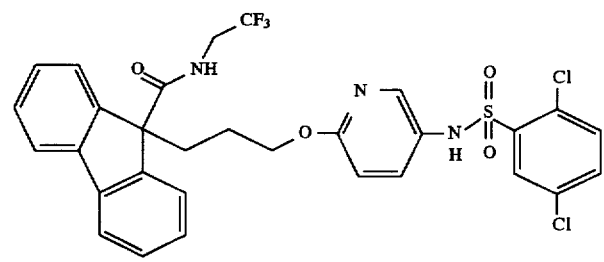
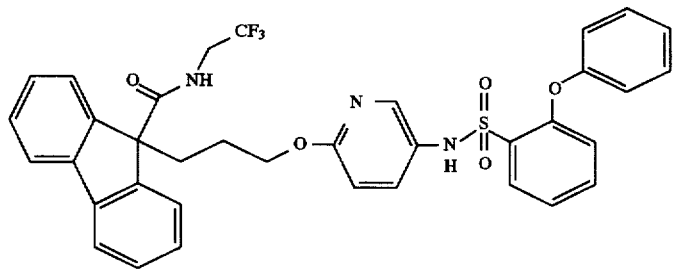

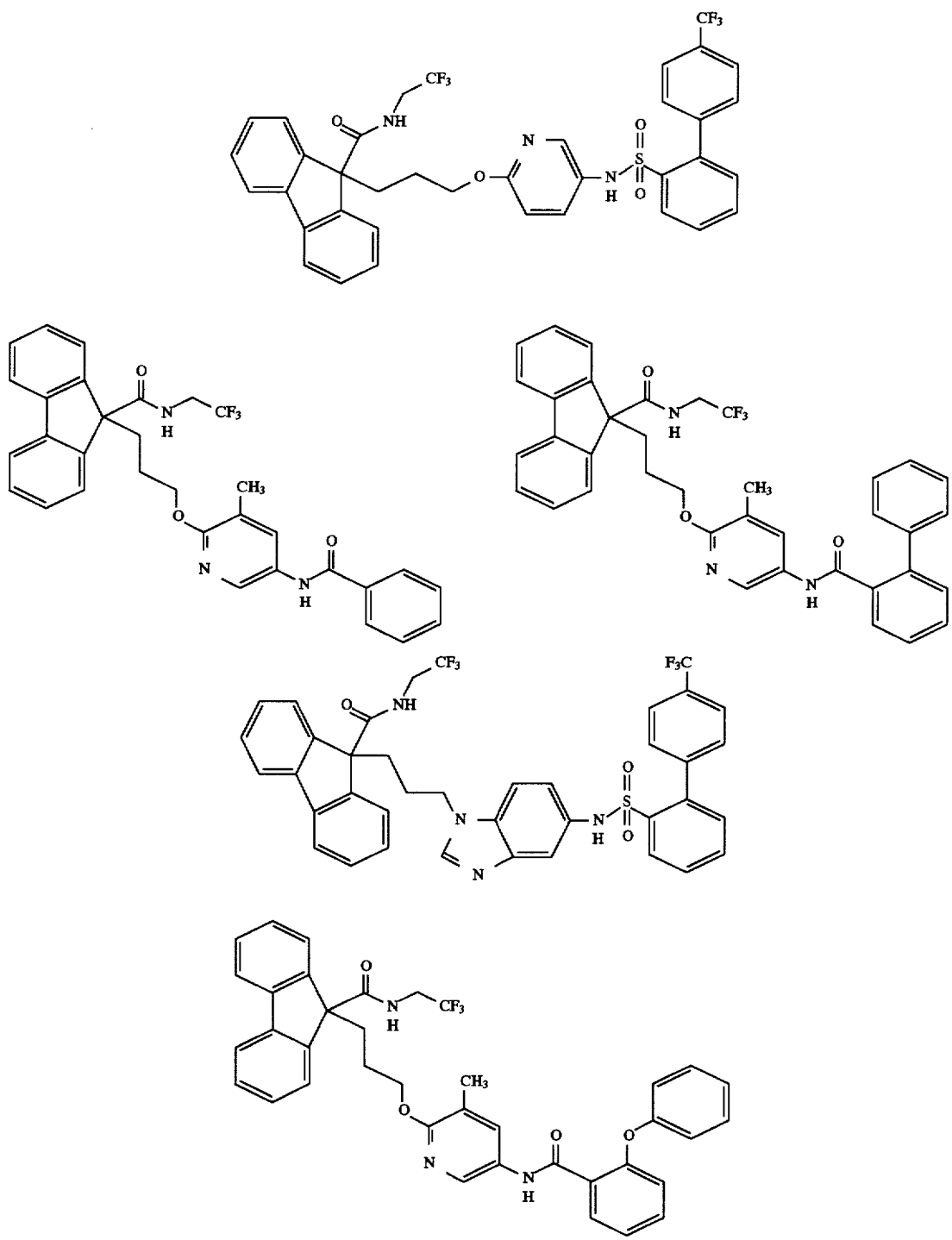

421
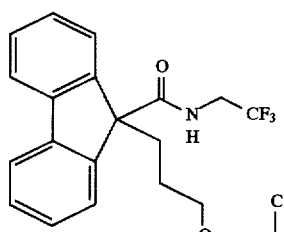
422
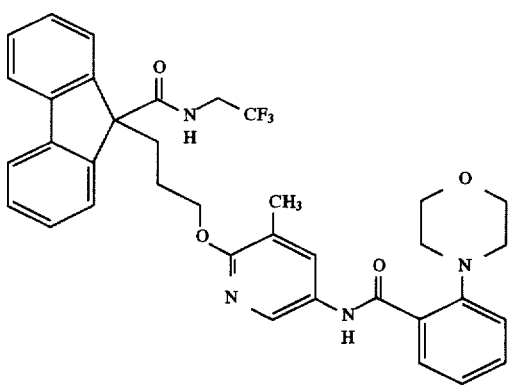
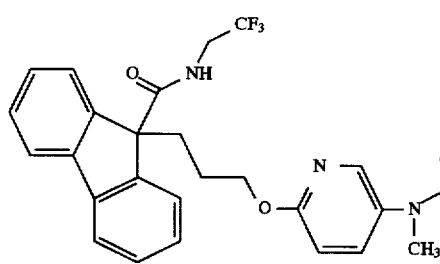
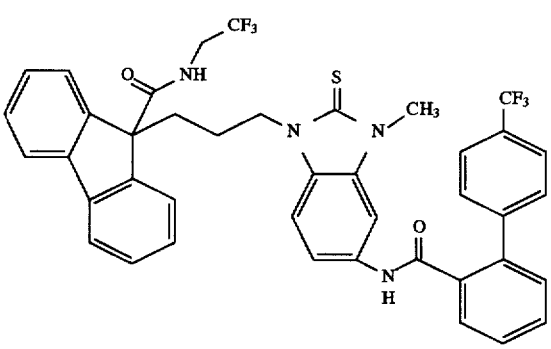
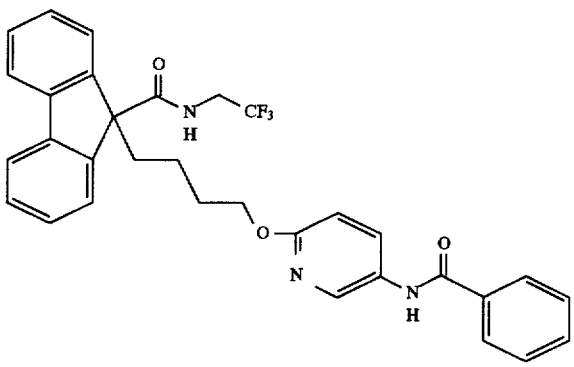
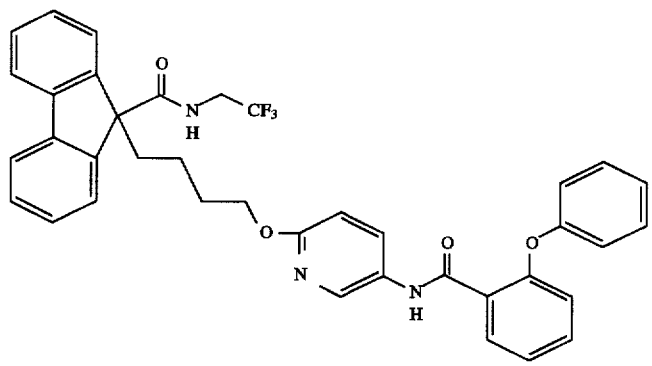

423
424
-continued
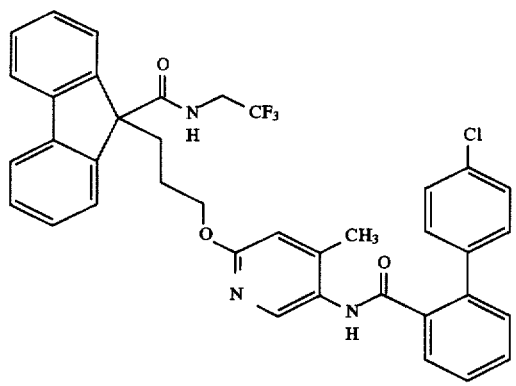
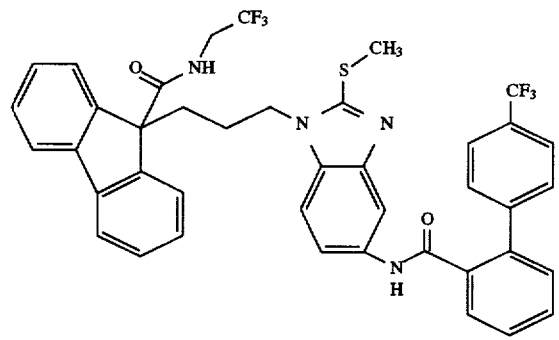
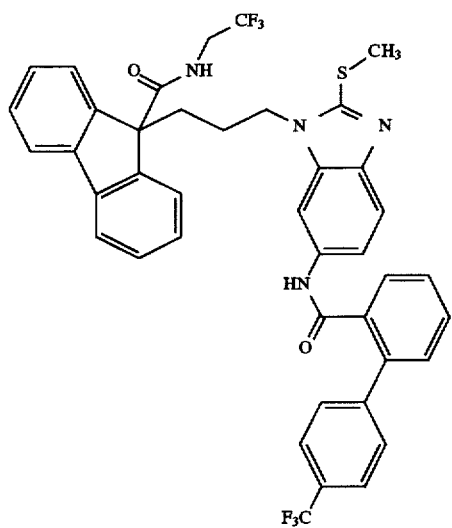
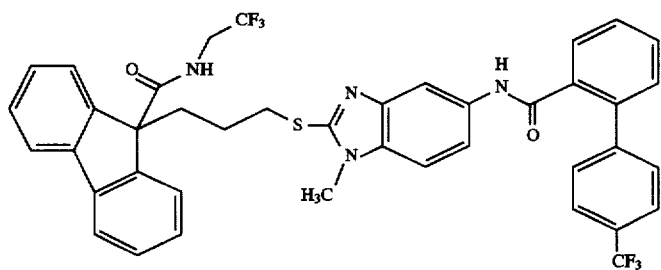
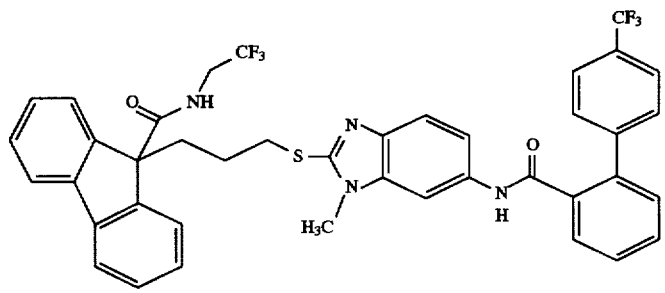

425 426
-continued
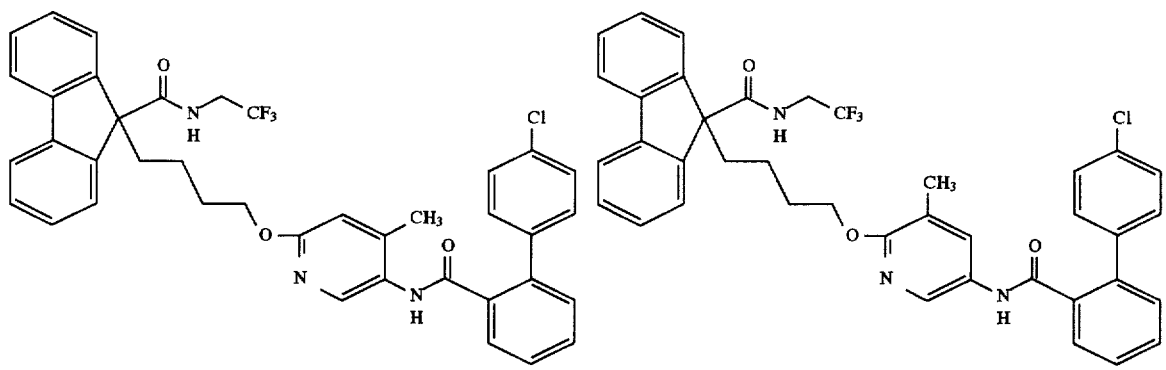
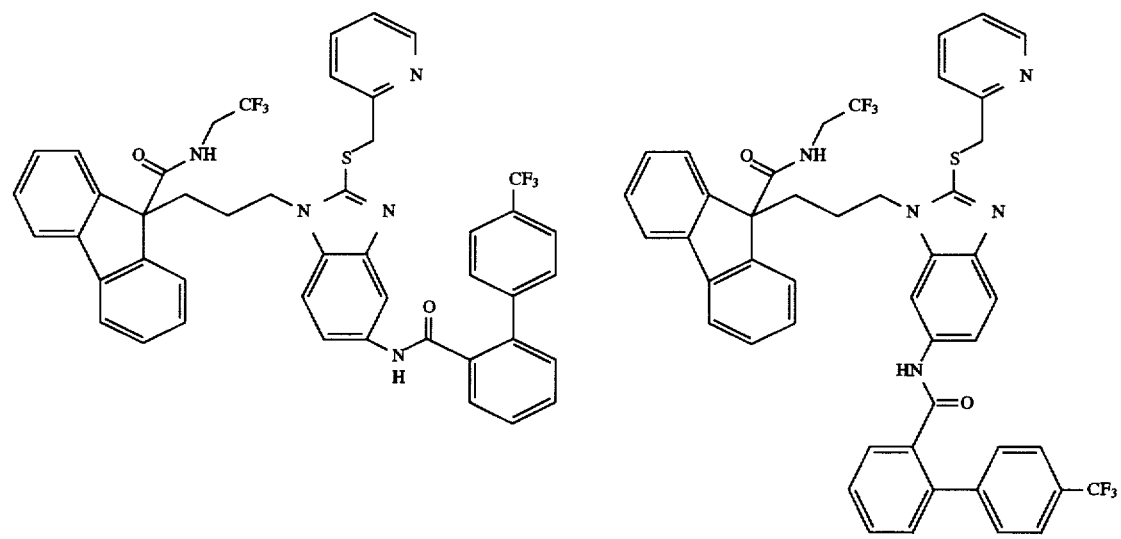
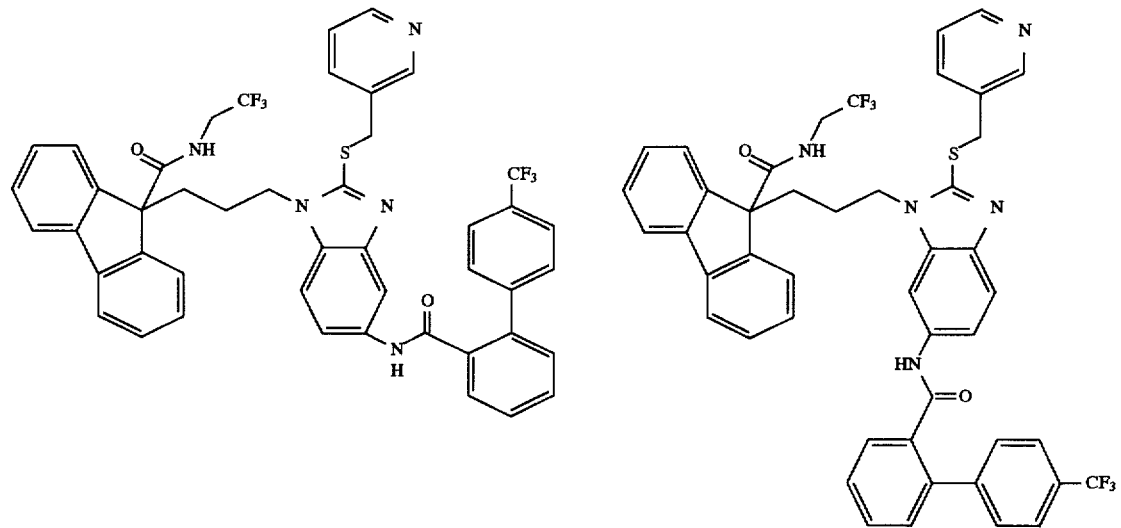

-continued
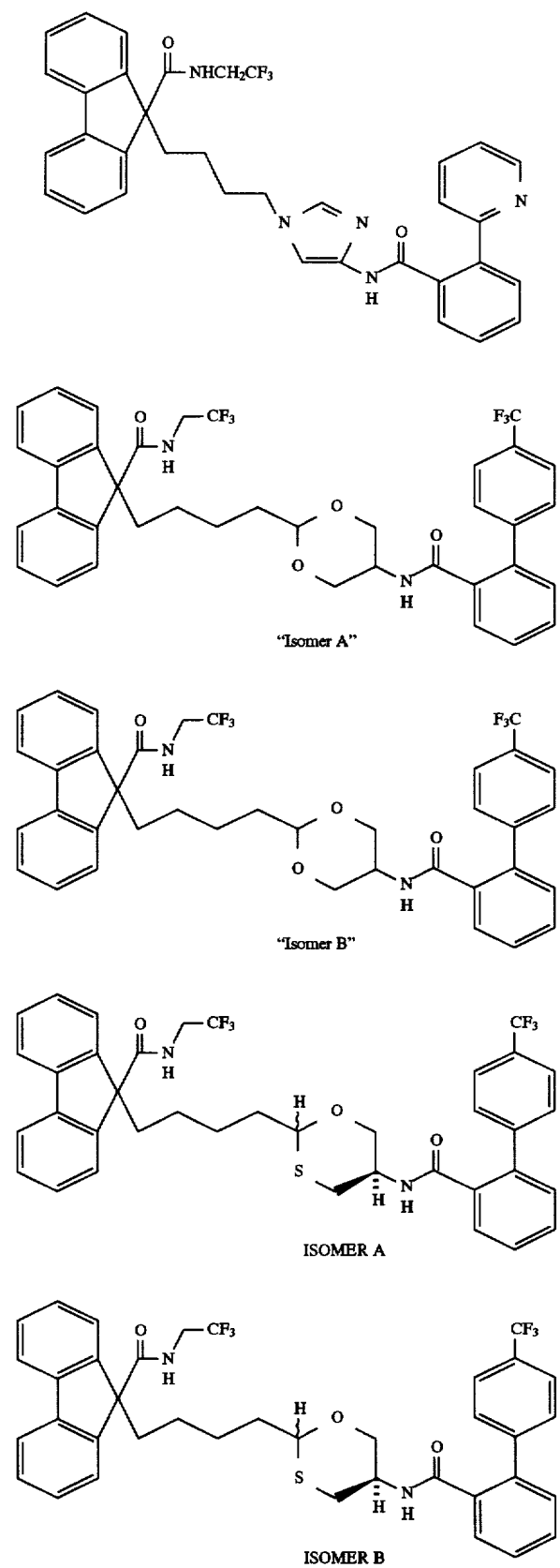
"Isomer A"
"Isomer B"
ISOMER A
ISOMER B

-continued
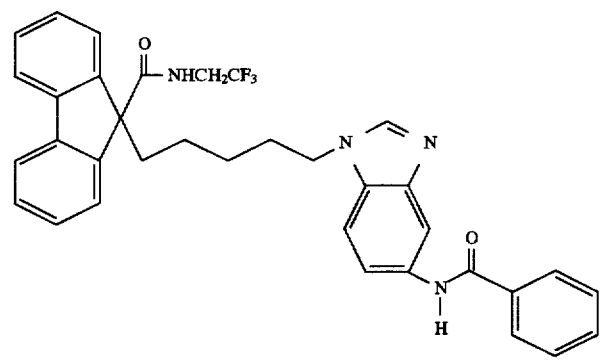
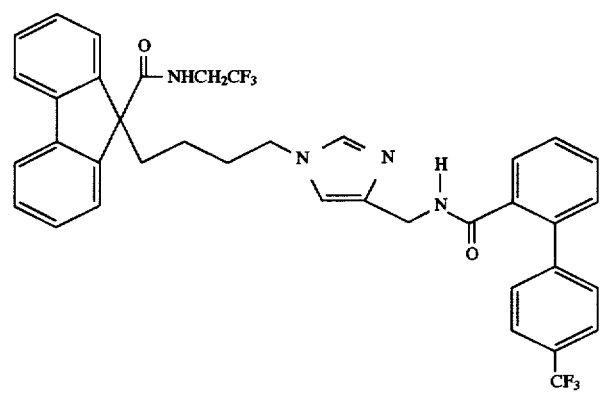
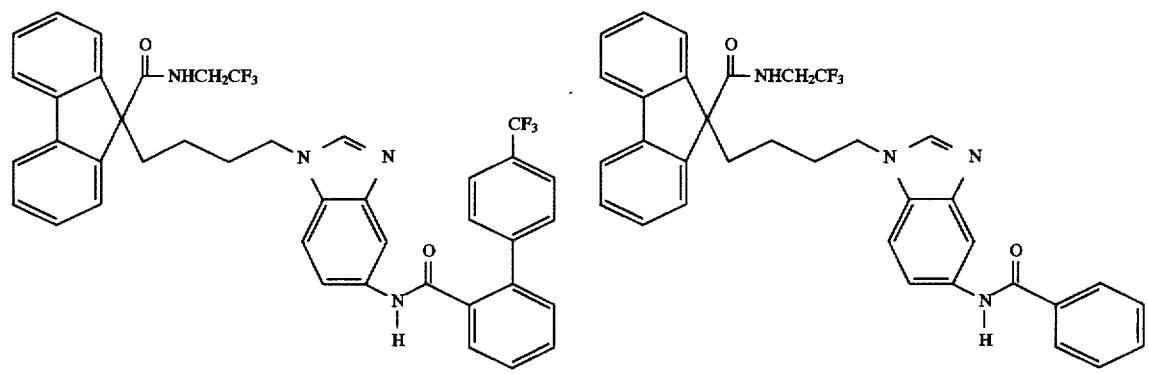
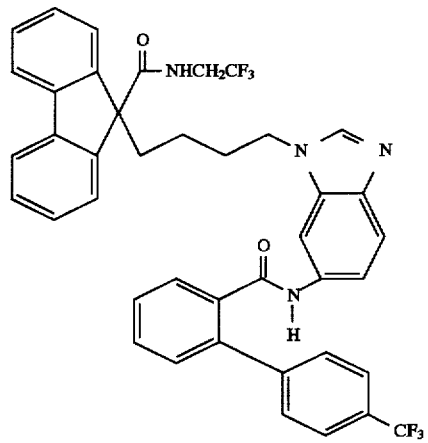

-continued
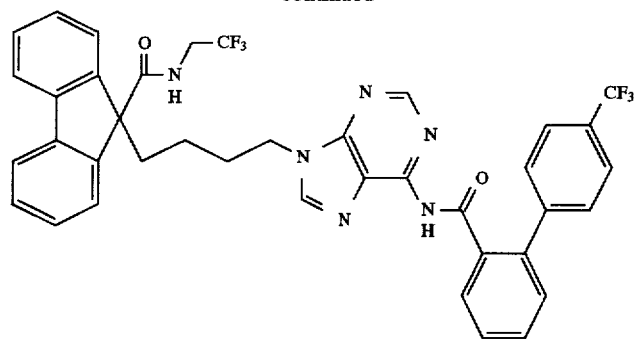
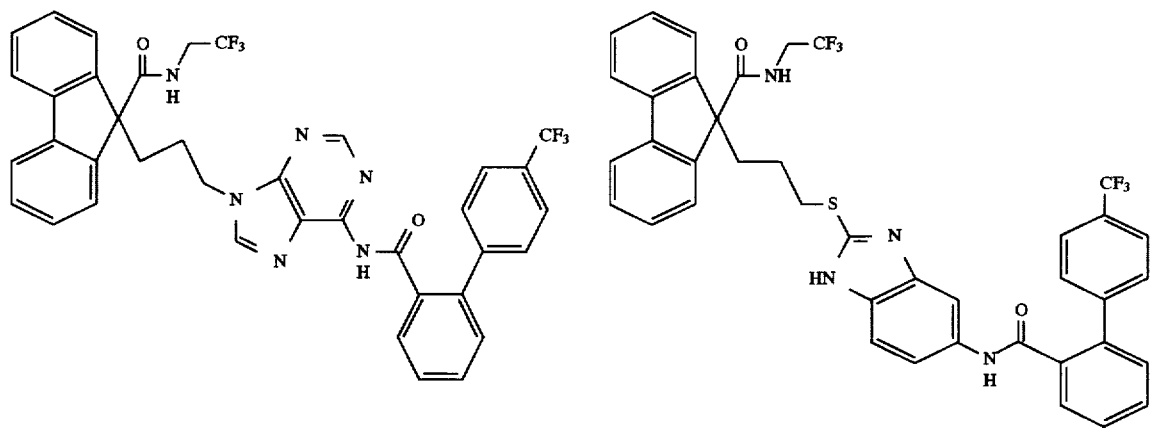
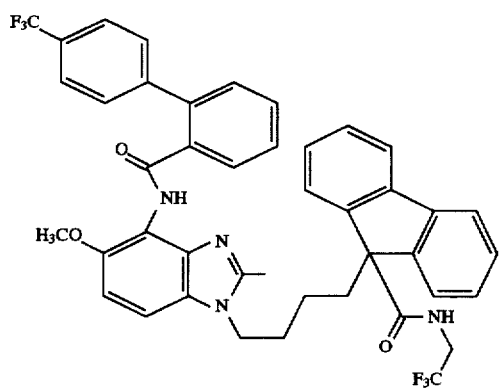
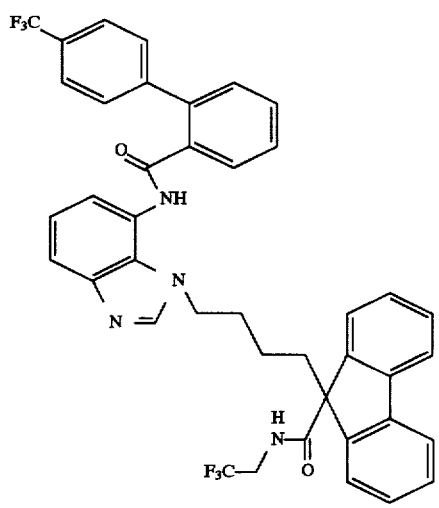
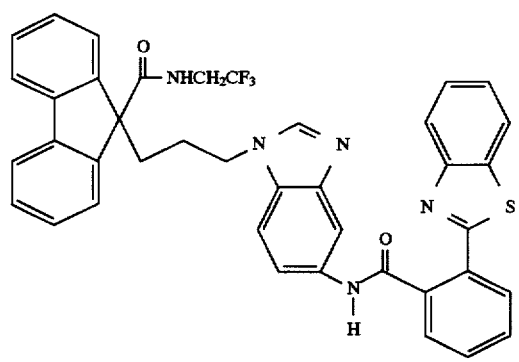

-continued
433
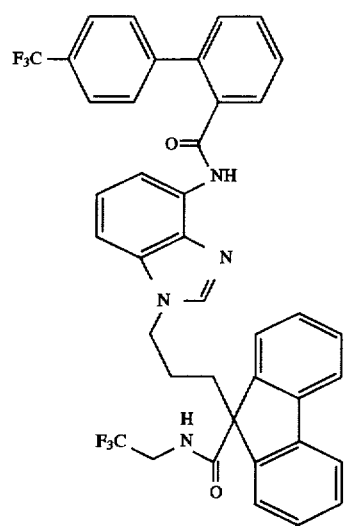
434
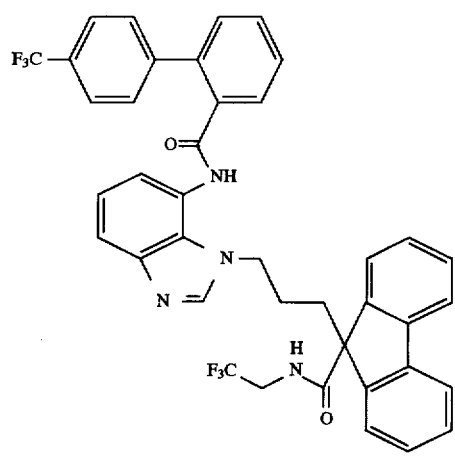
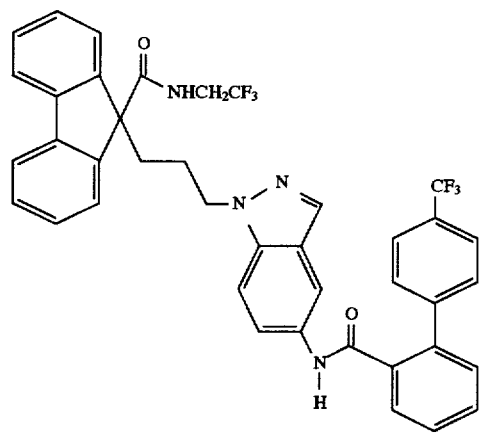
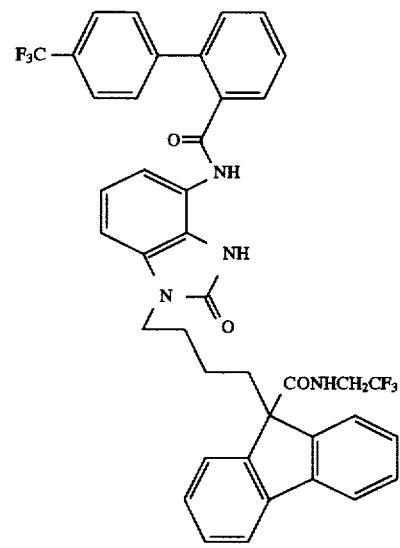
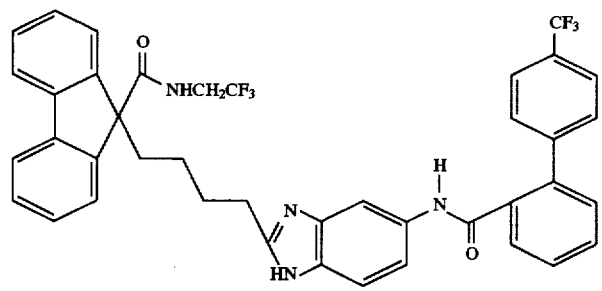

435 436
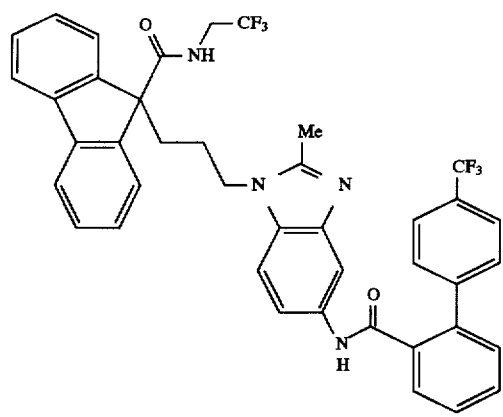 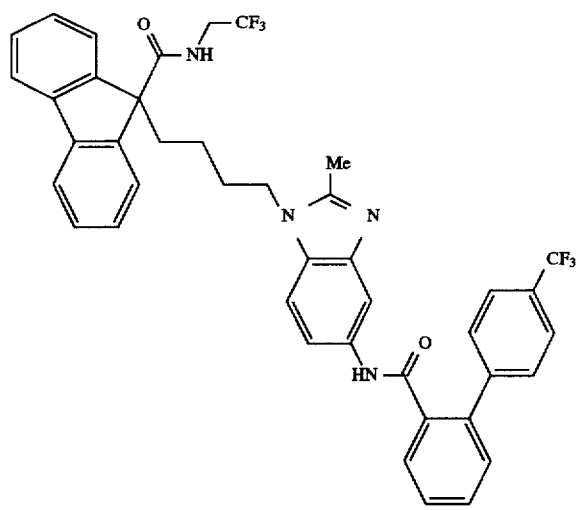
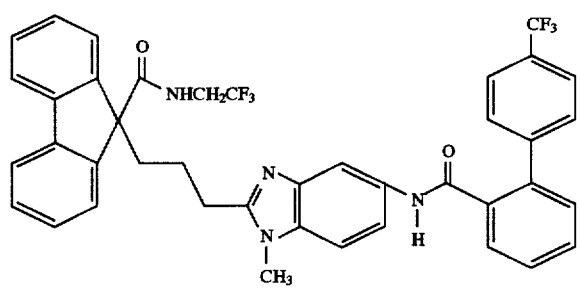
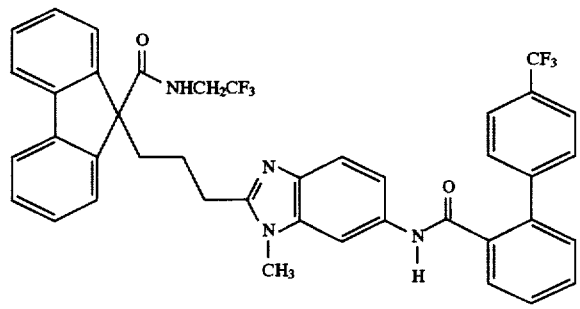
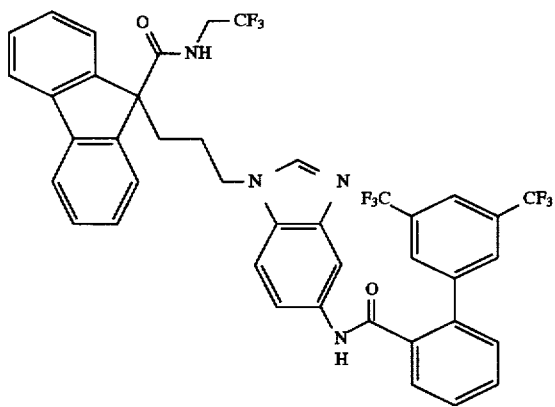

437 438
-continued
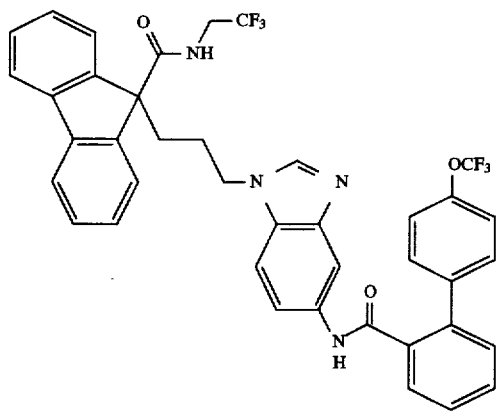
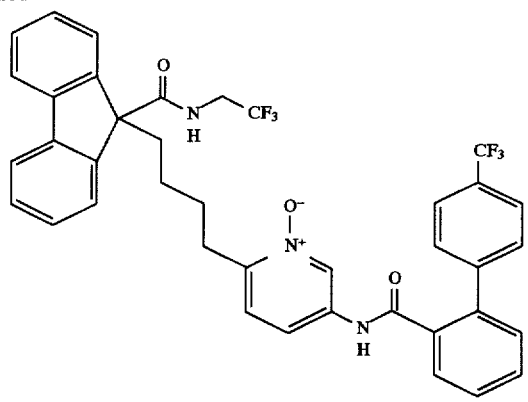
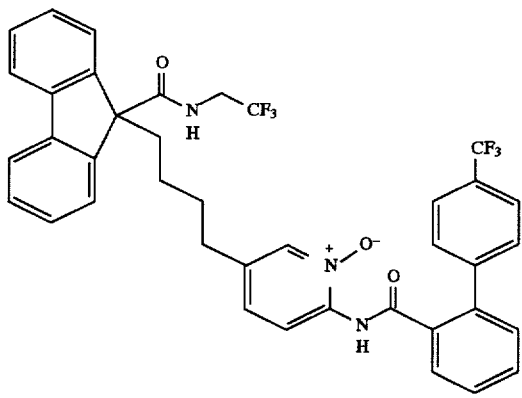
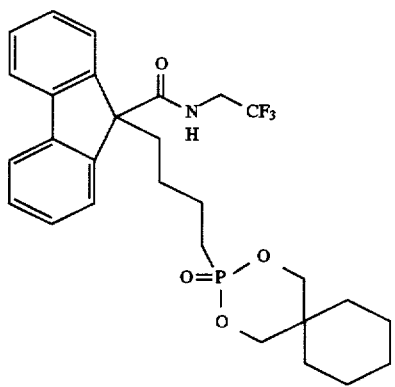
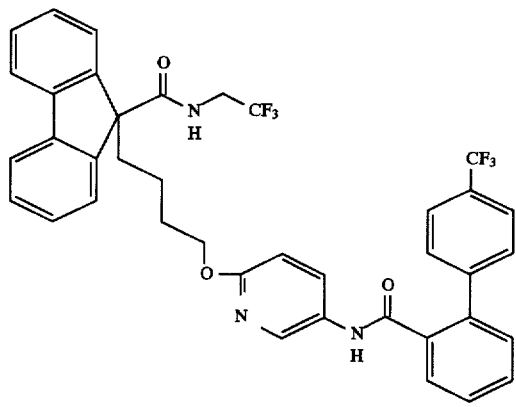
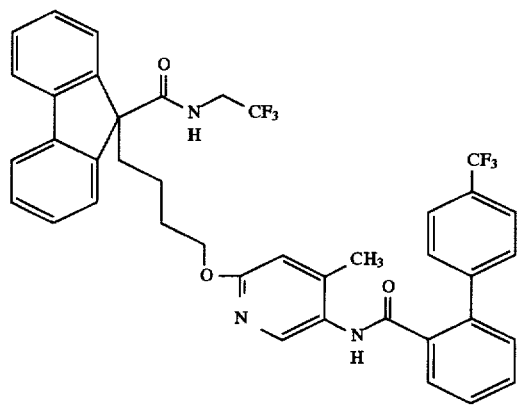
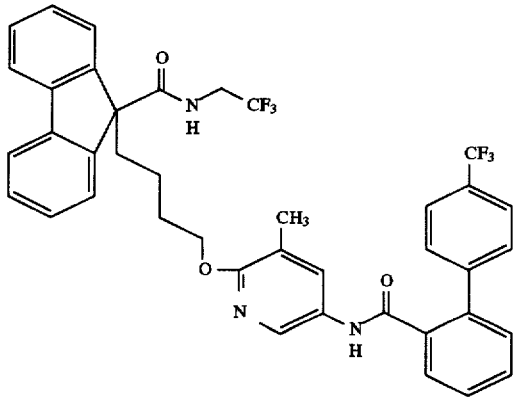
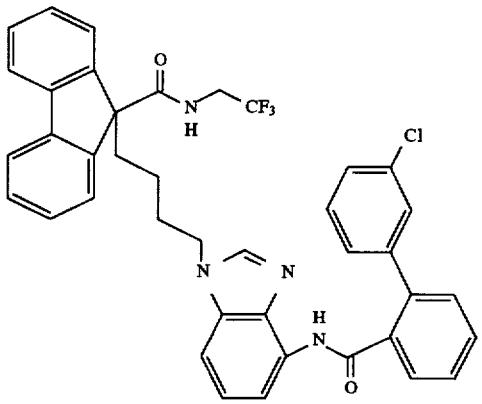

439 440
-continued
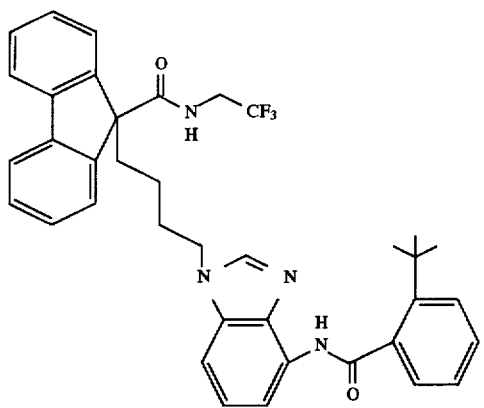 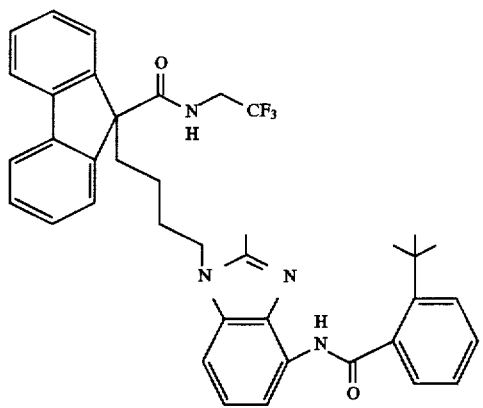
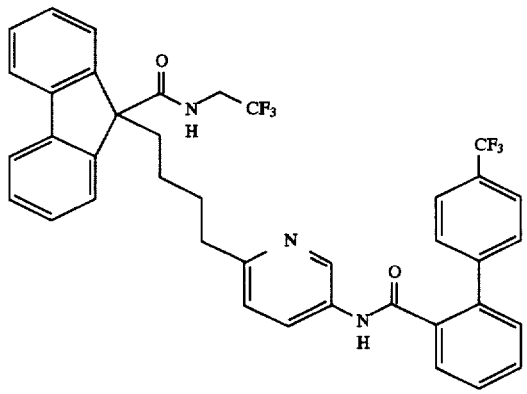 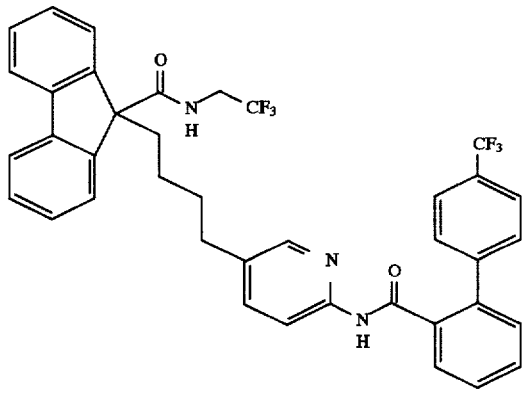
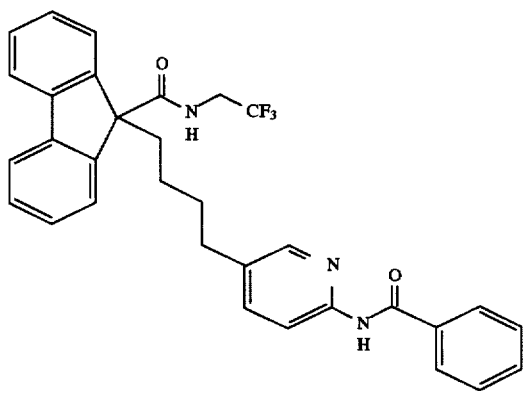 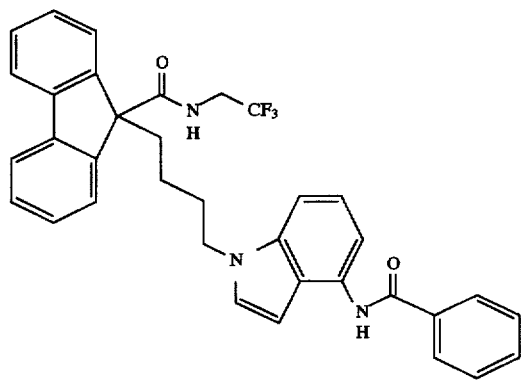
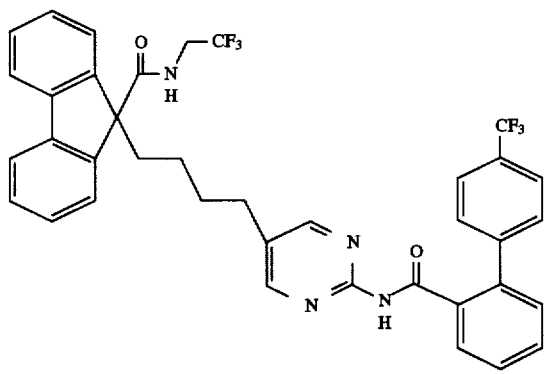 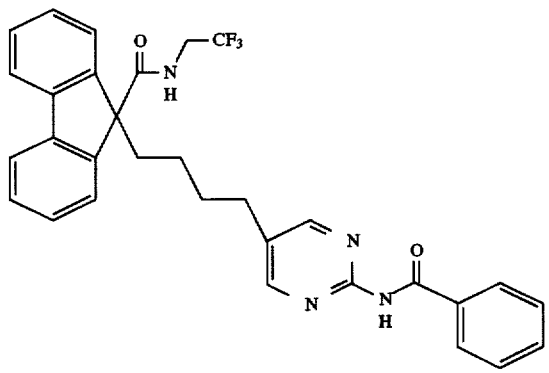

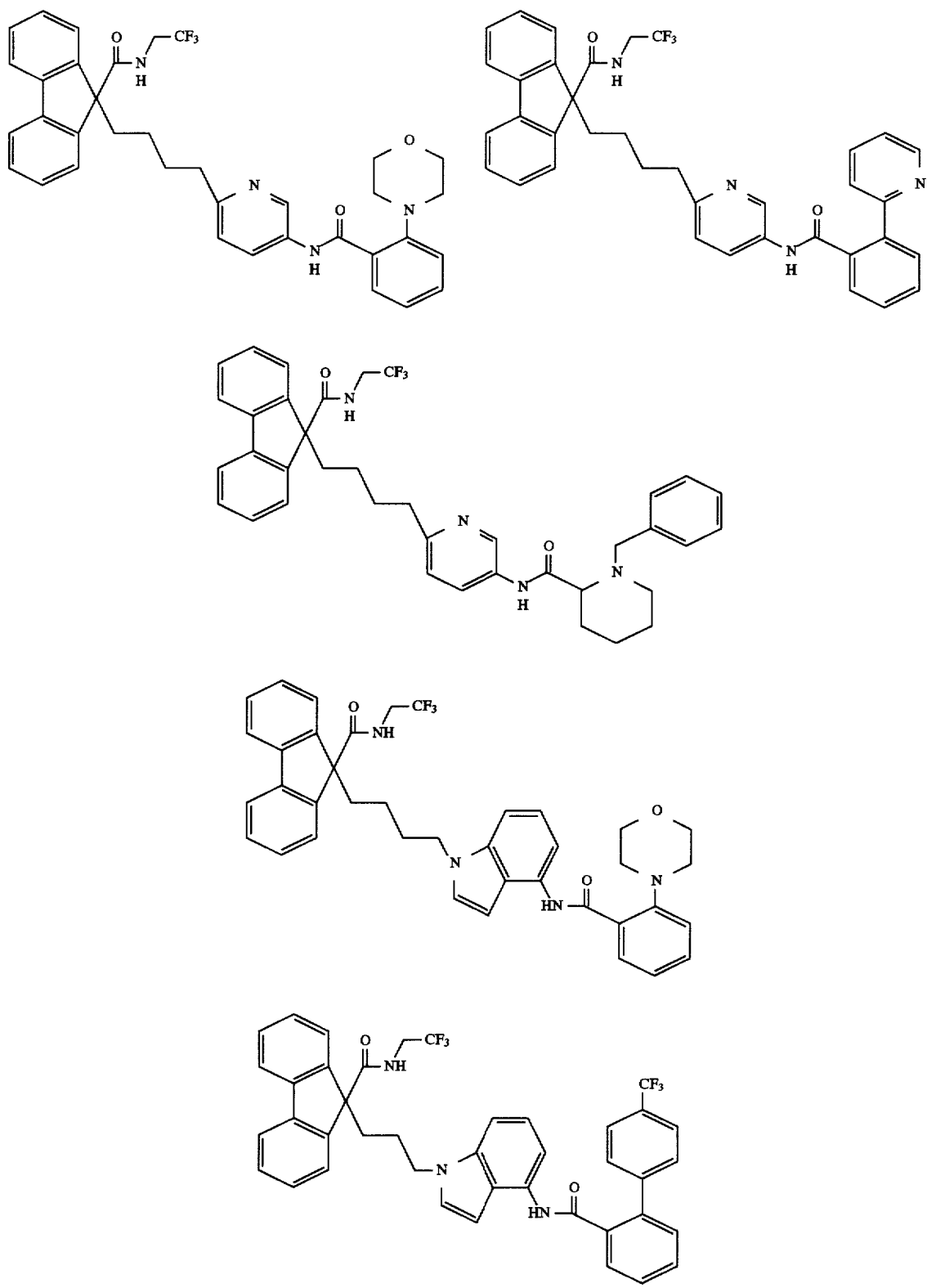

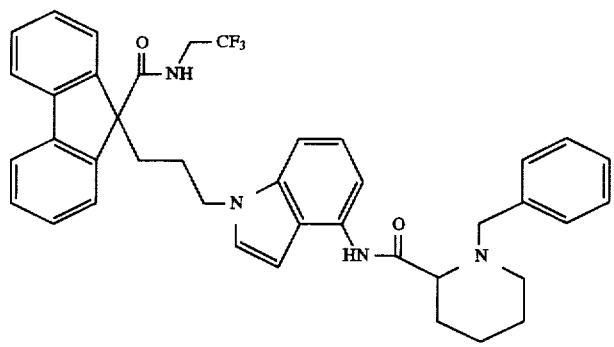
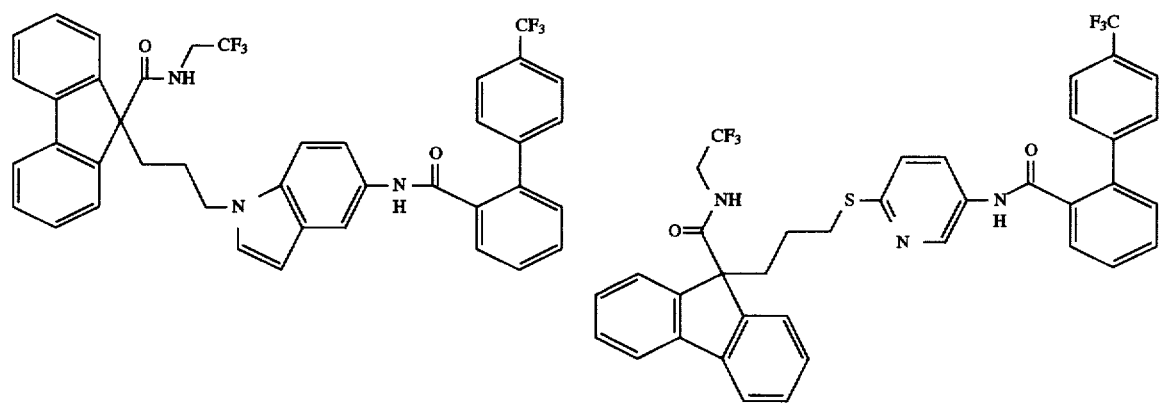
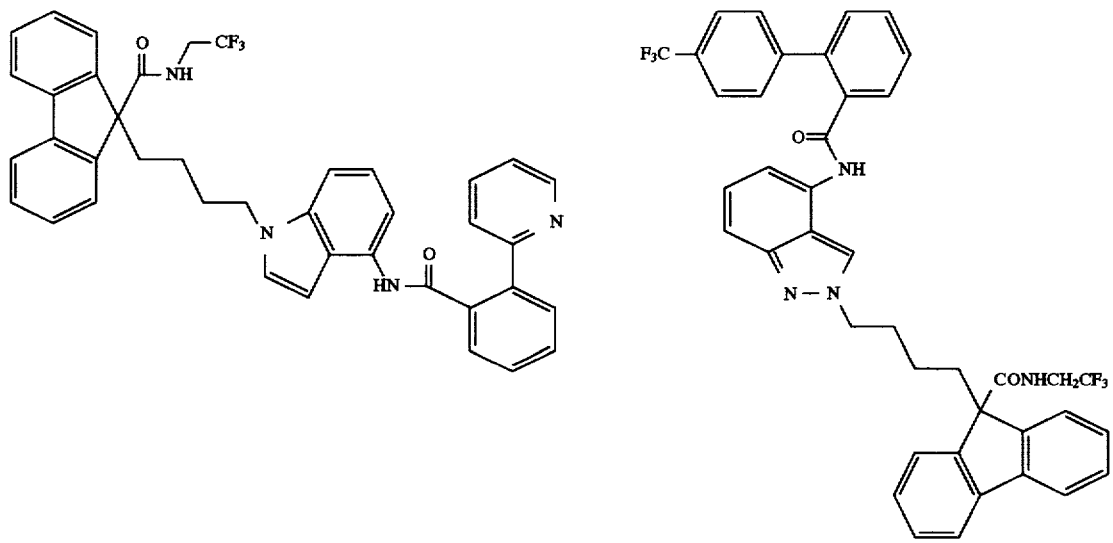

445 446
-continued
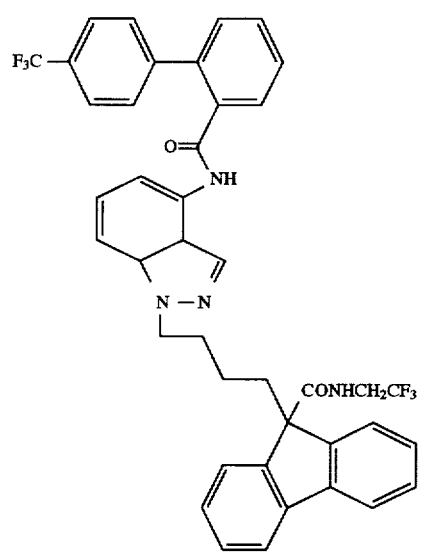
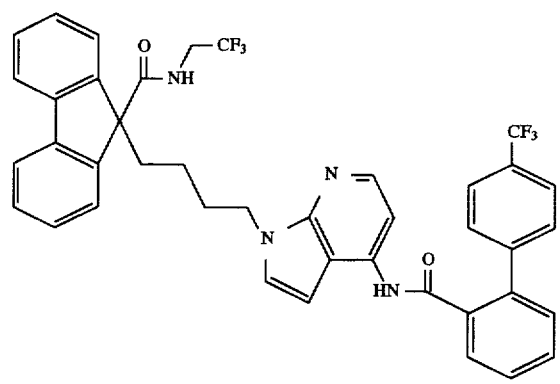
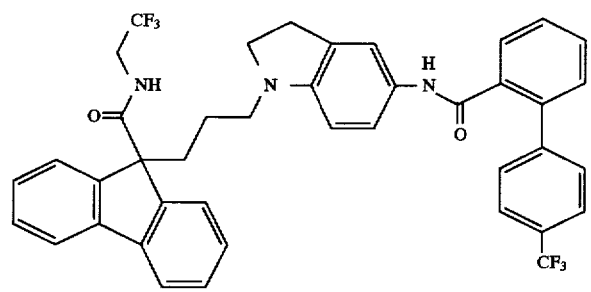
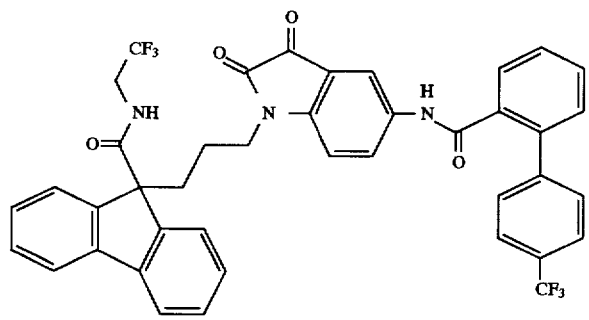
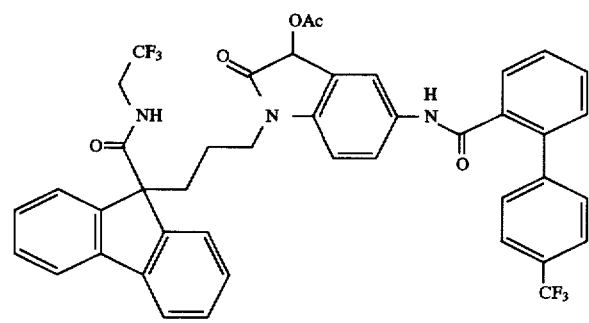

-continued
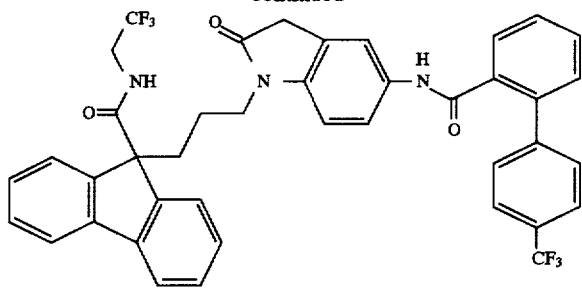
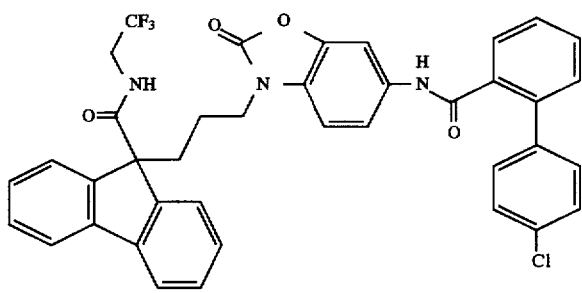
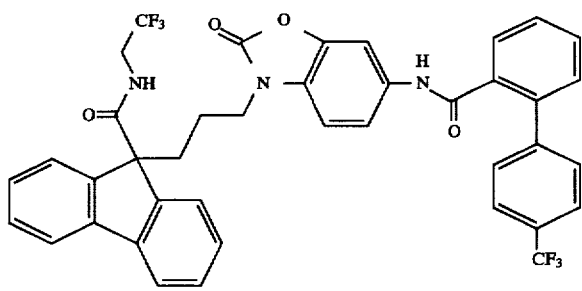
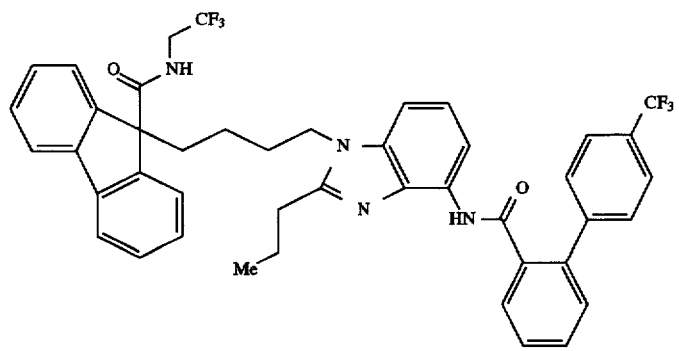
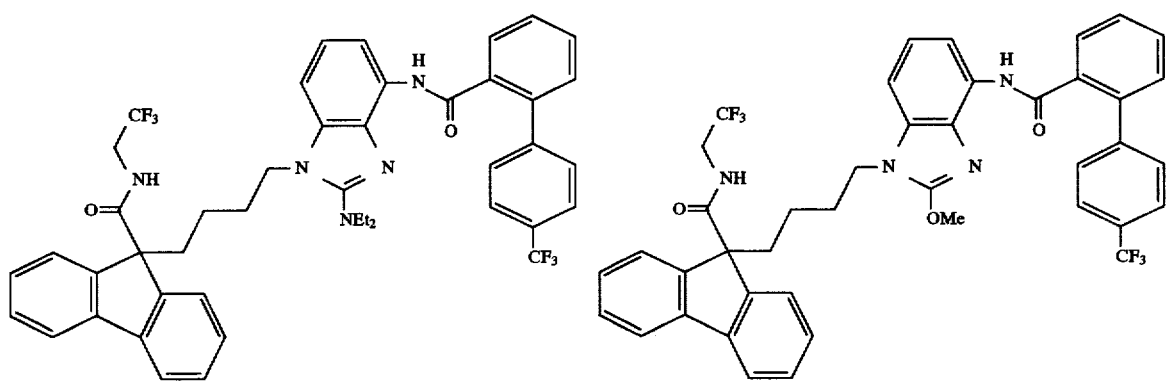

449    450
-continued
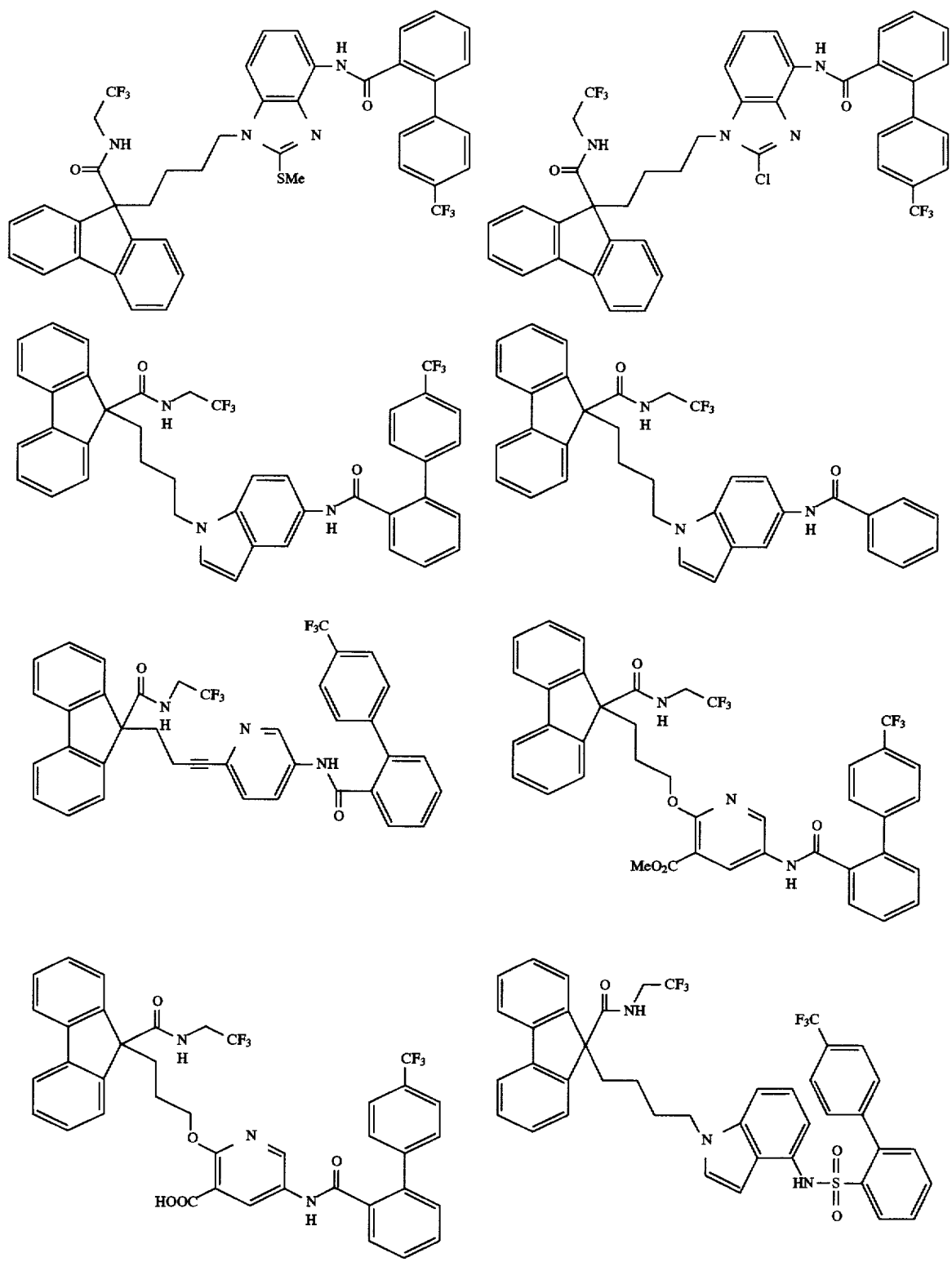

451 452
-continued
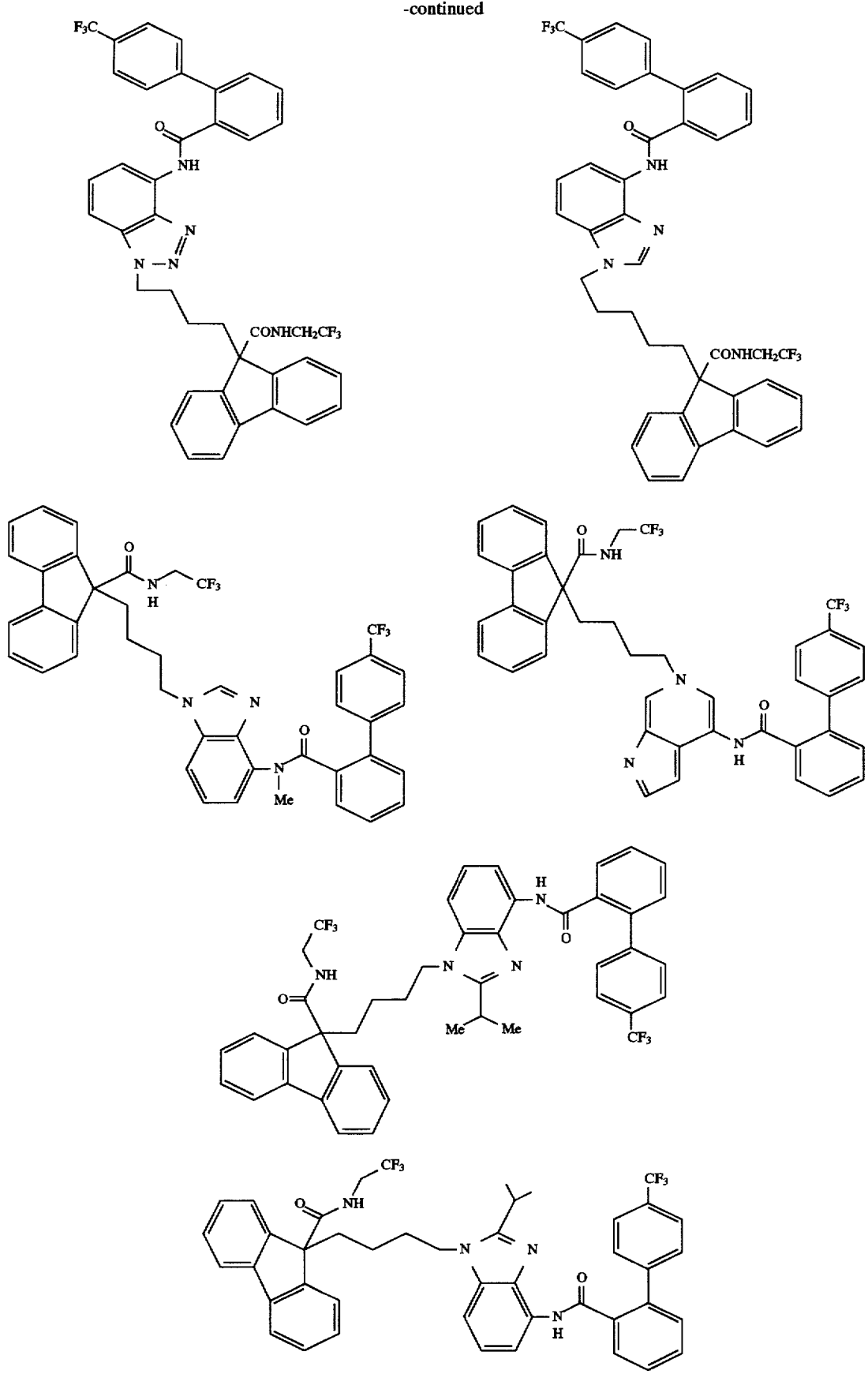

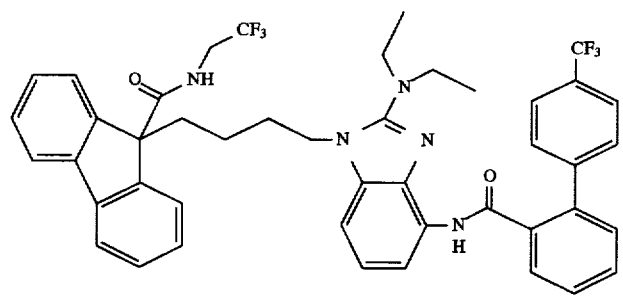
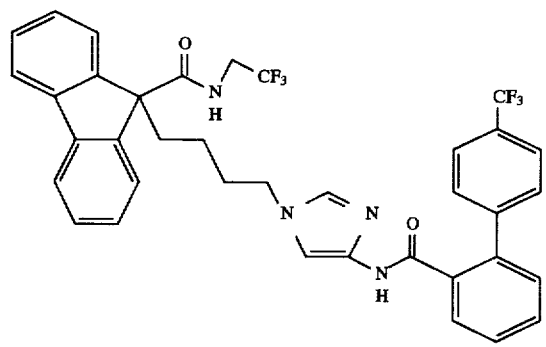
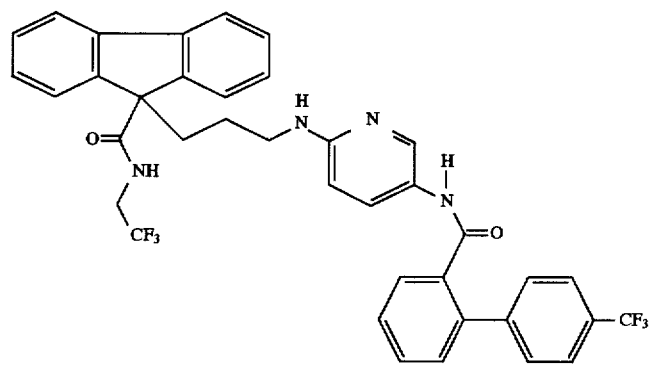
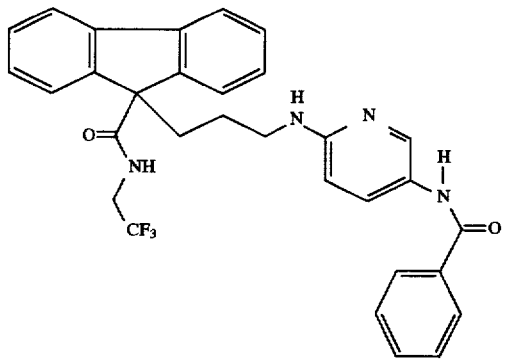

-continued
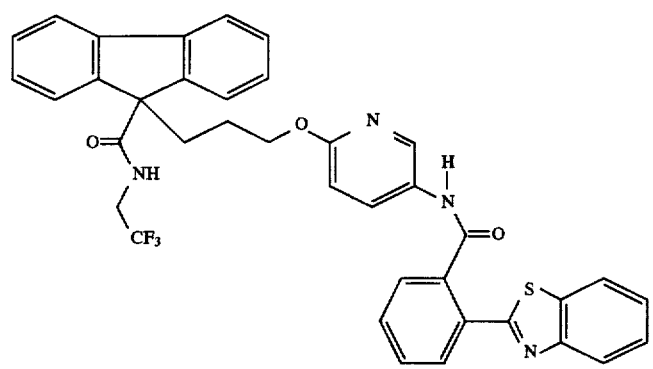
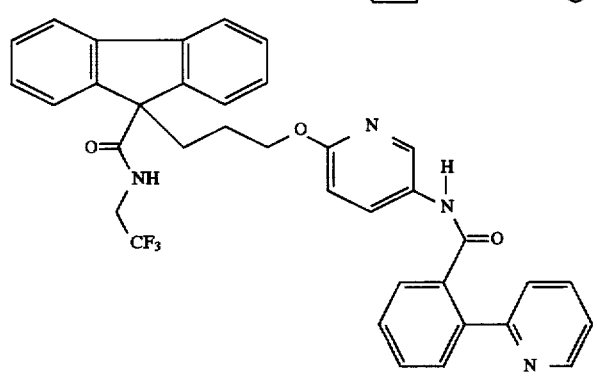
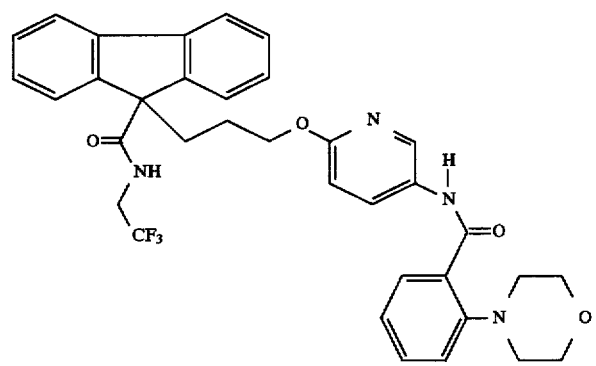
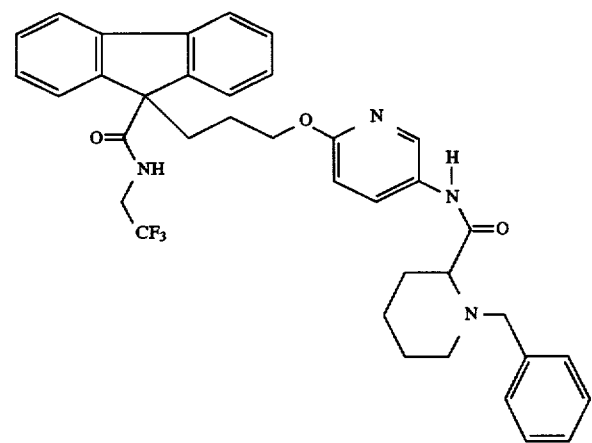

457
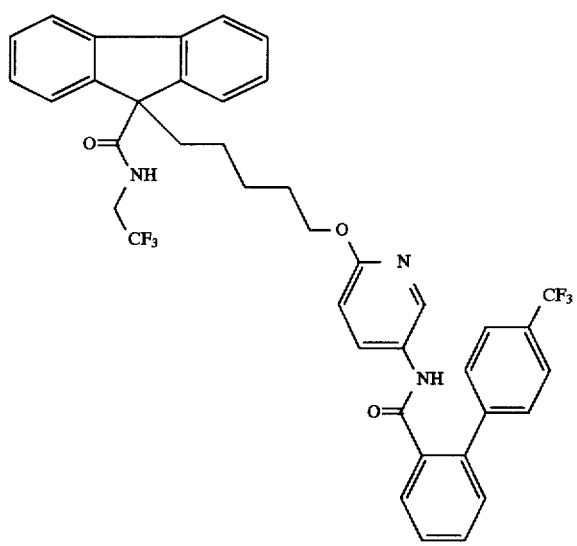
458
-continued
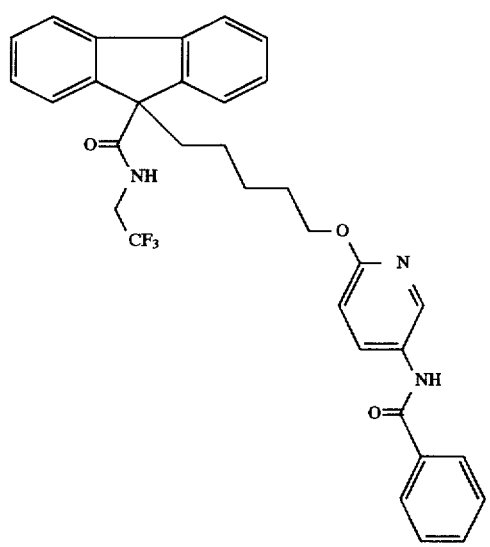
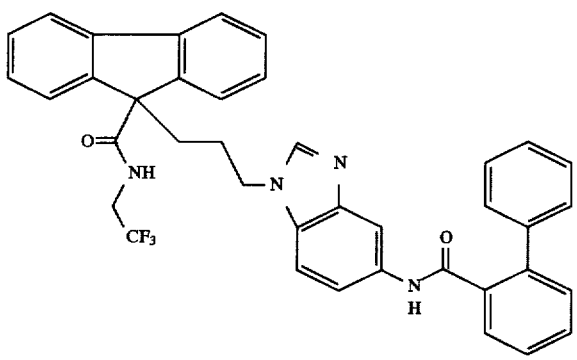
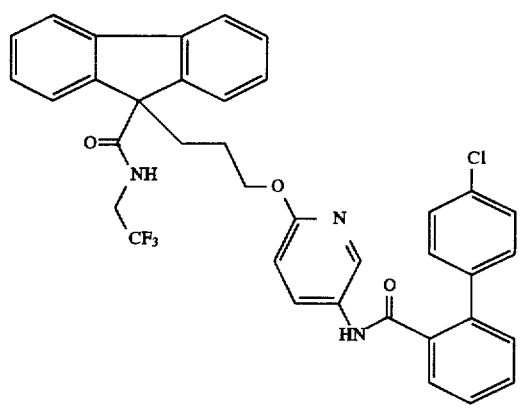
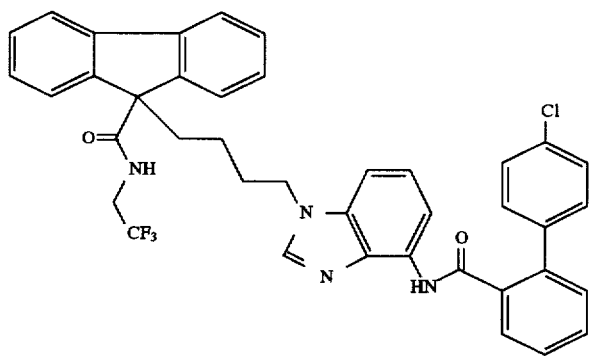

459                                    460
-continued
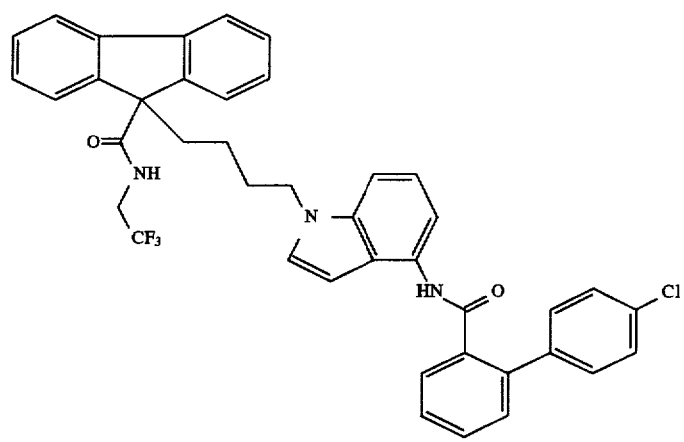
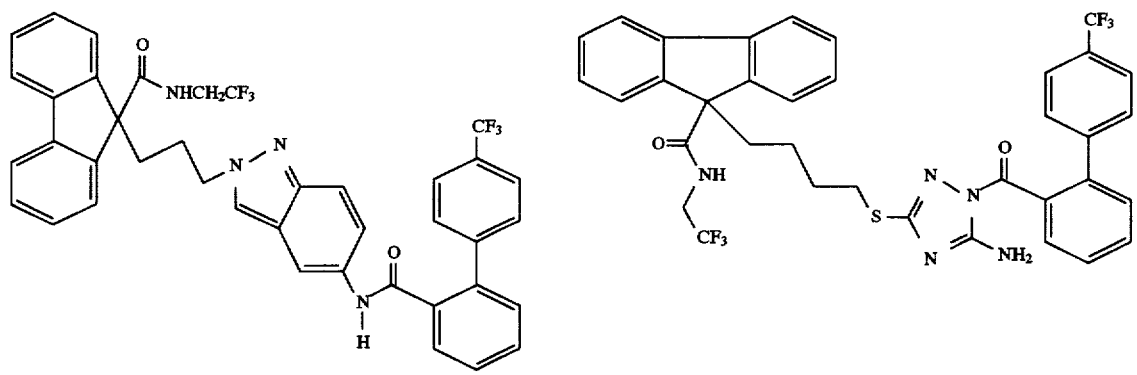
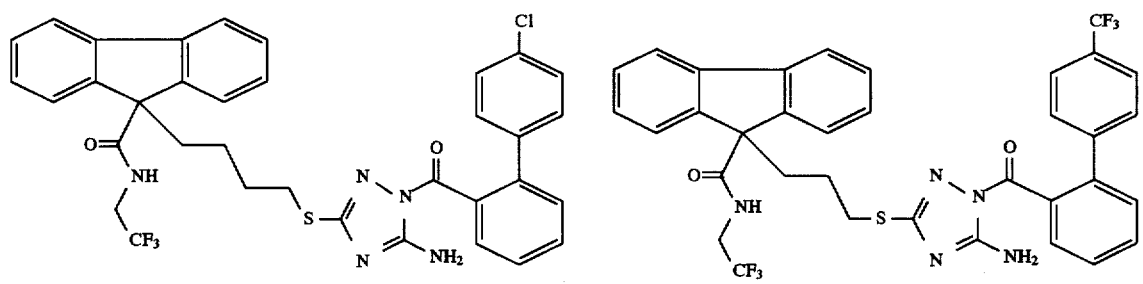
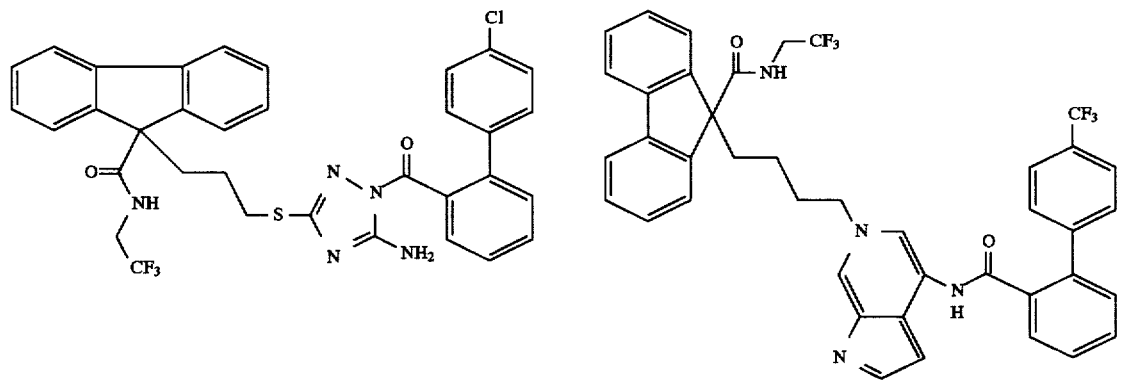

-continued
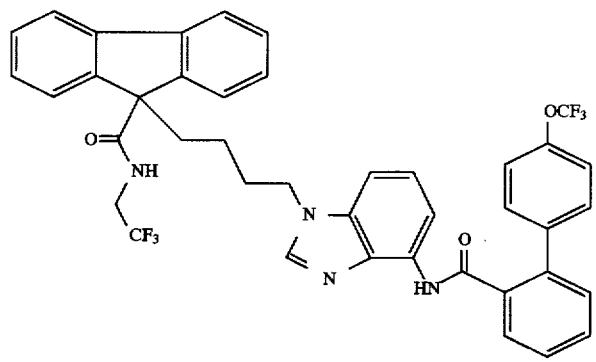
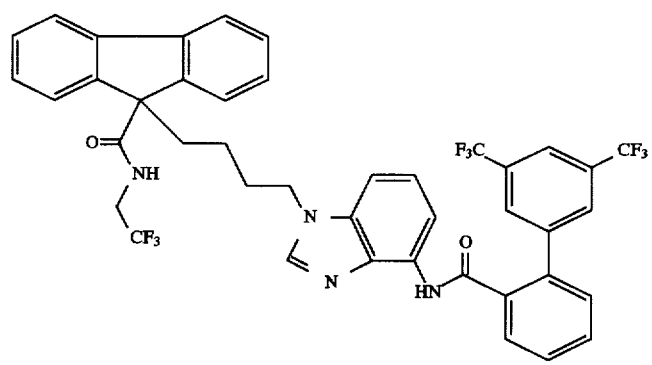
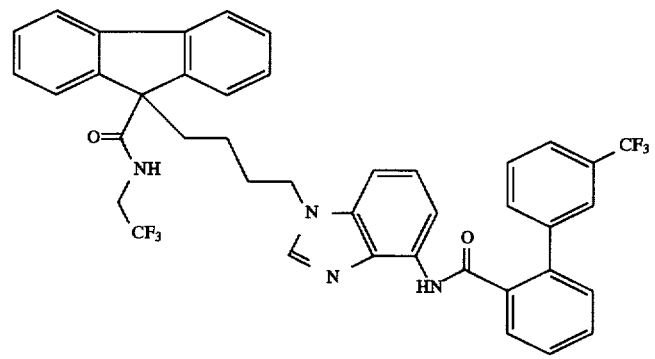
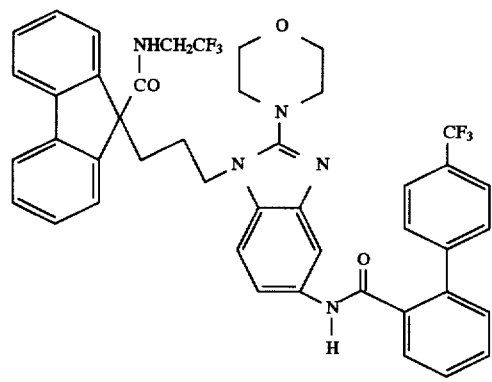

-continued
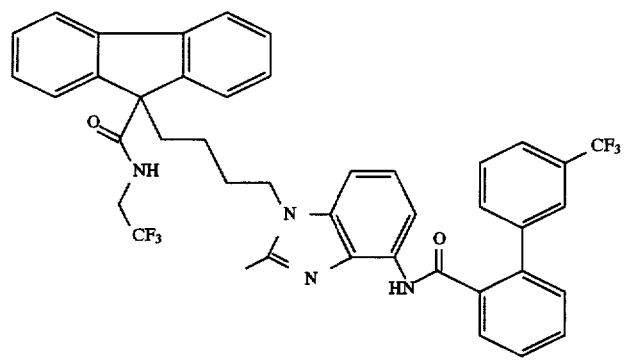
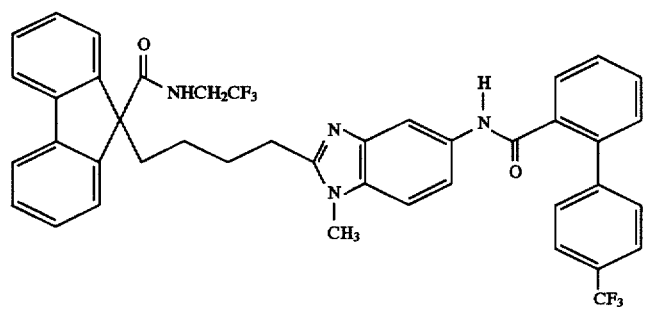
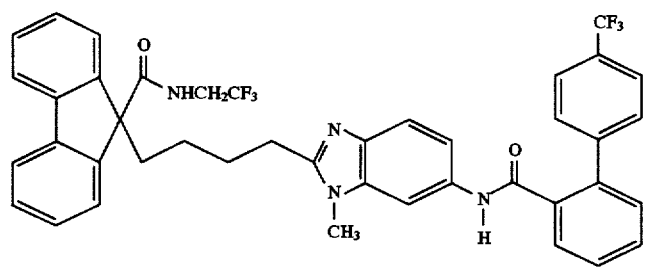
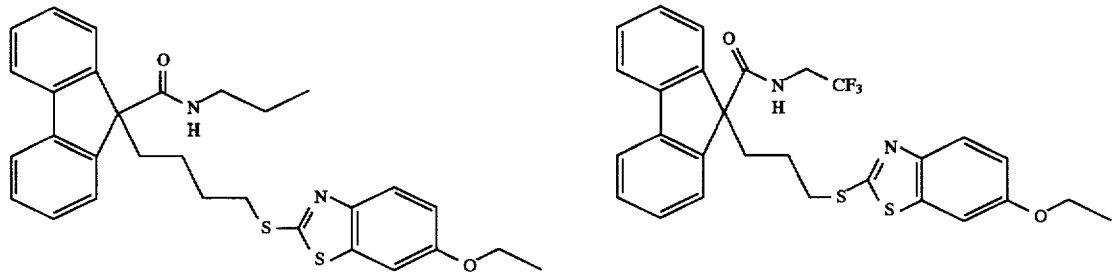
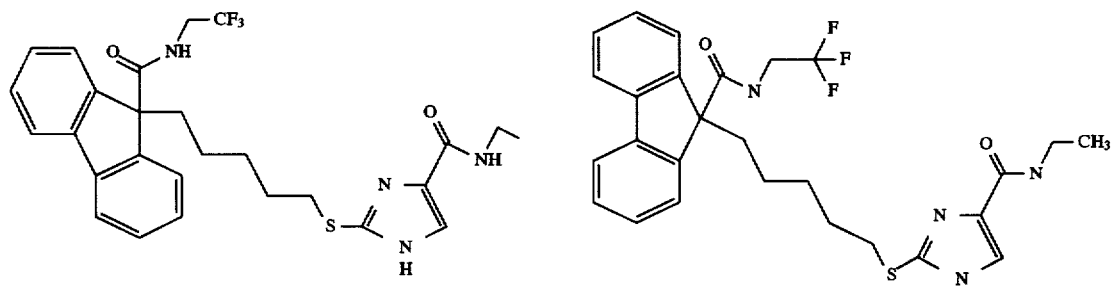

465
466
-continued
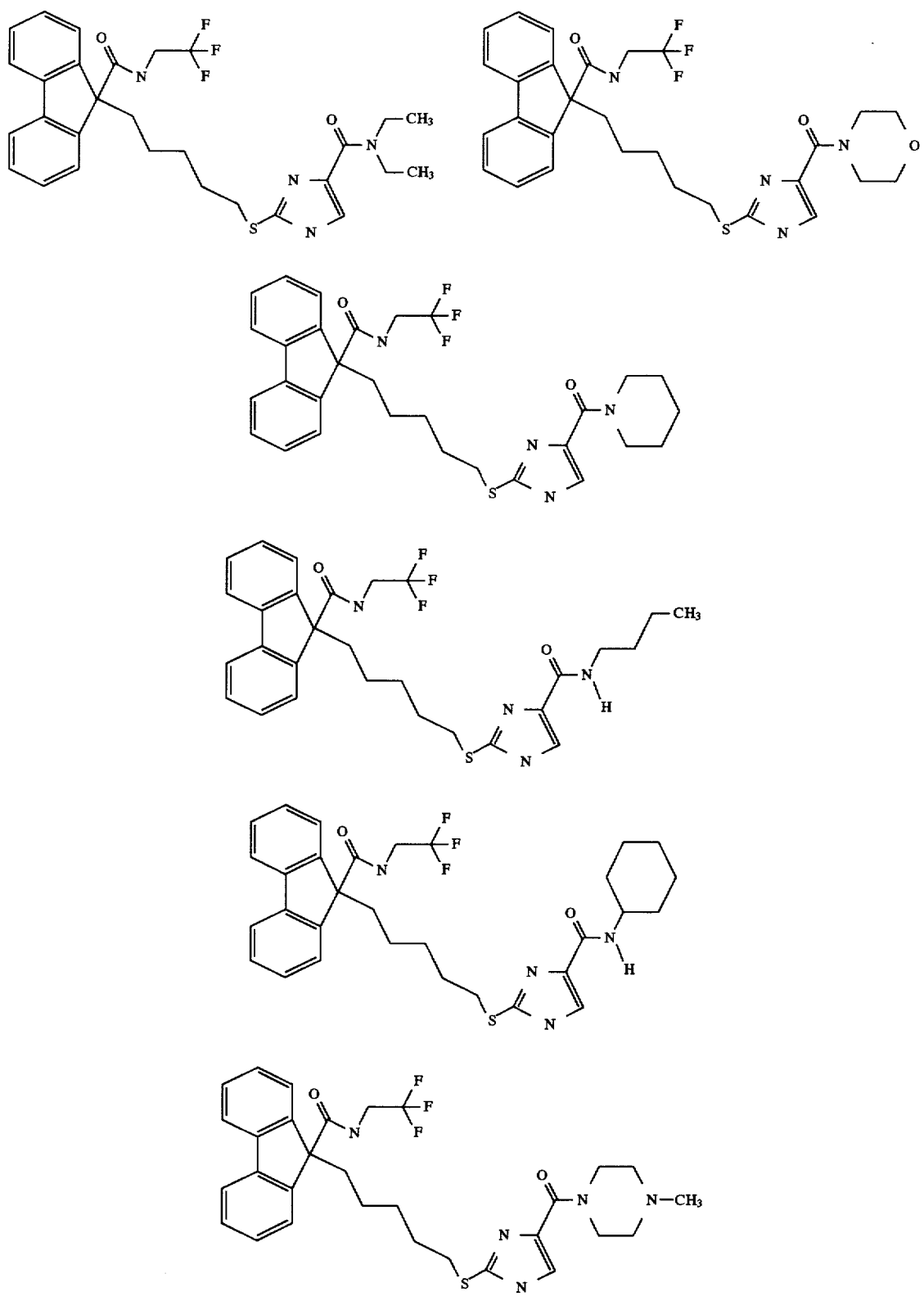

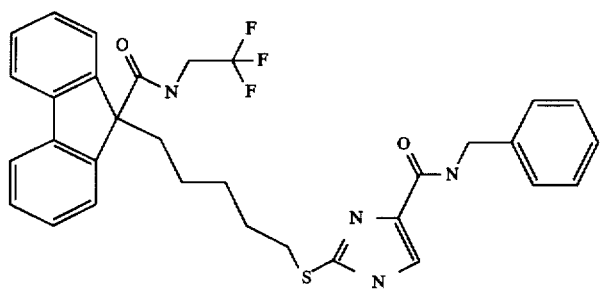
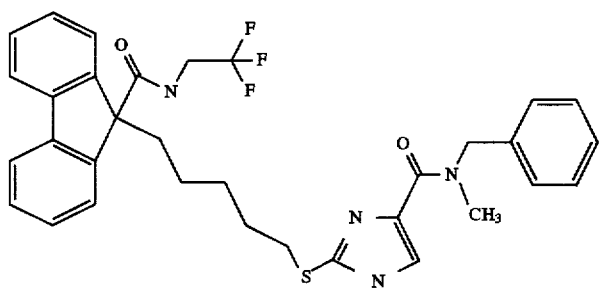
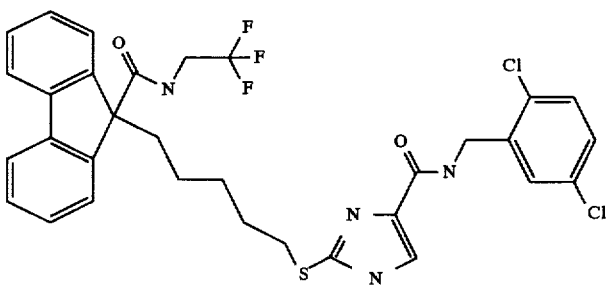
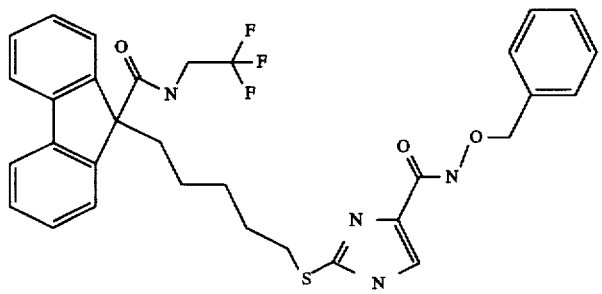
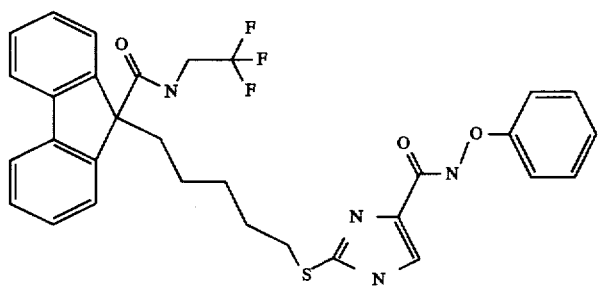

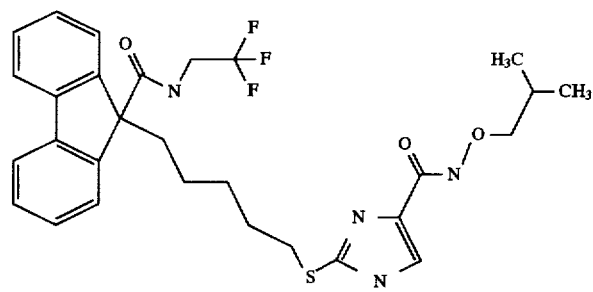
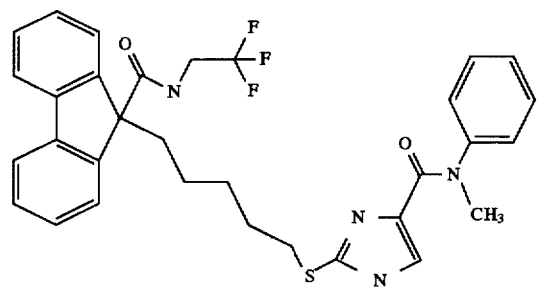
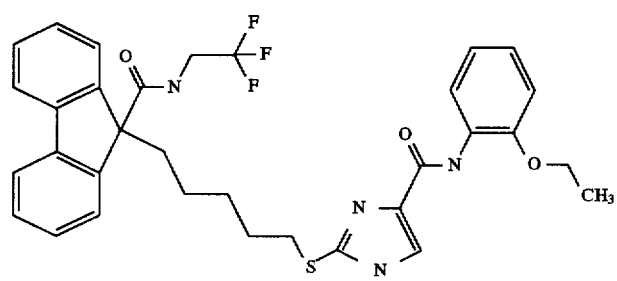
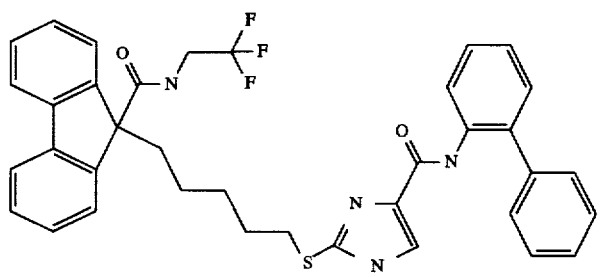
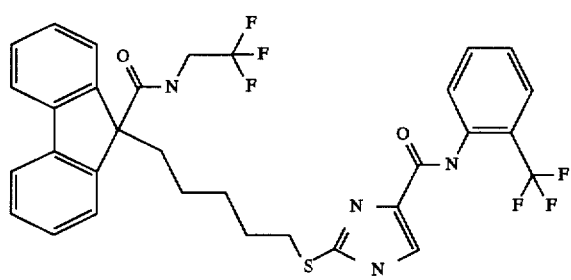

-continued
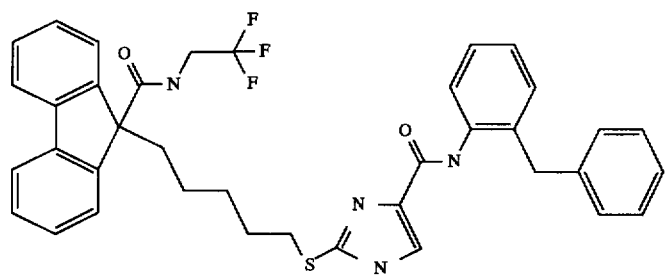
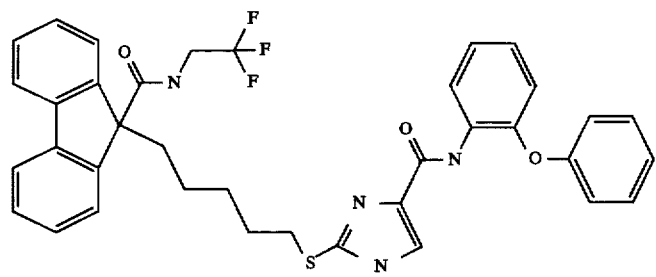
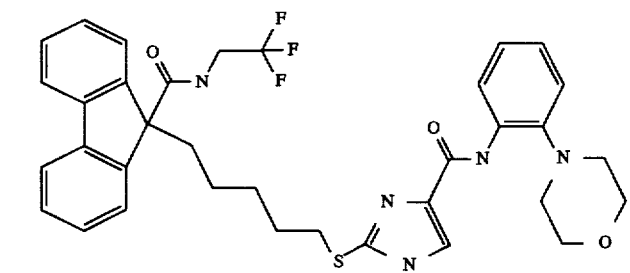
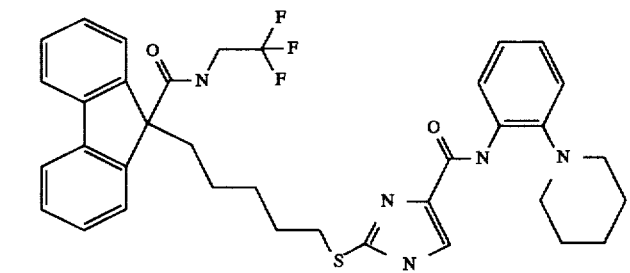
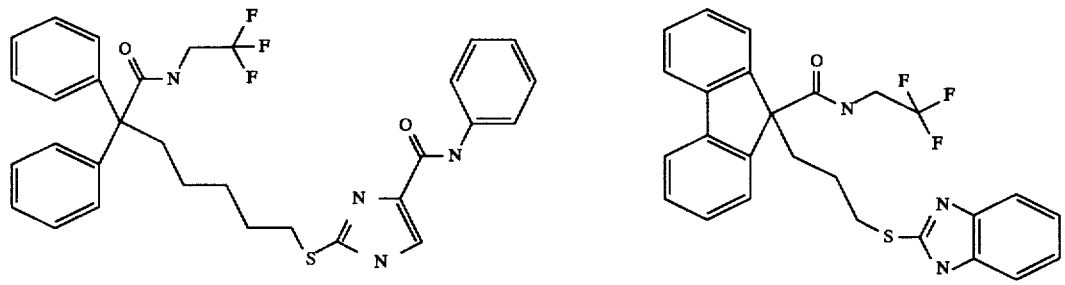

473
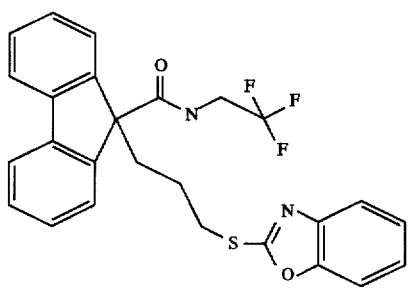
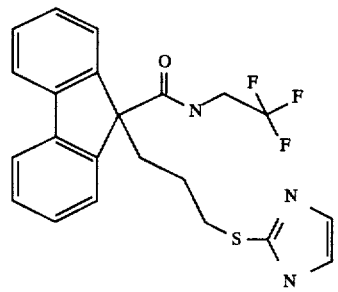
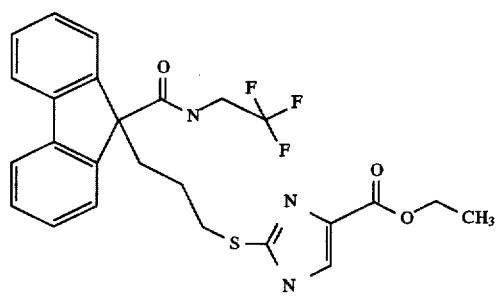
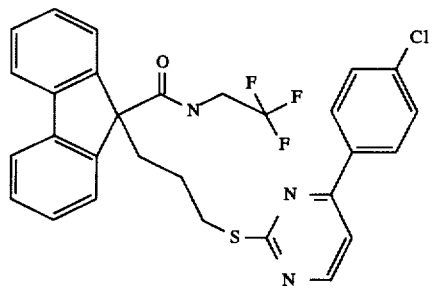
474
-continued
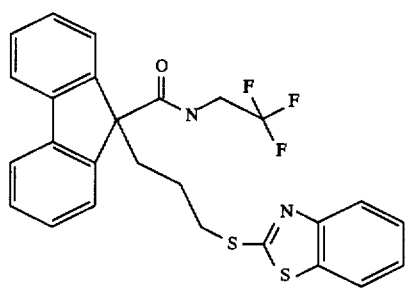
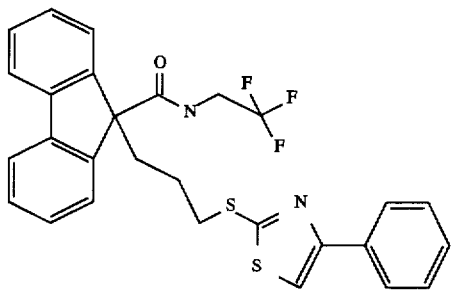
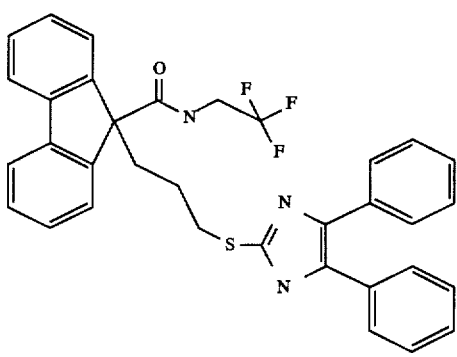
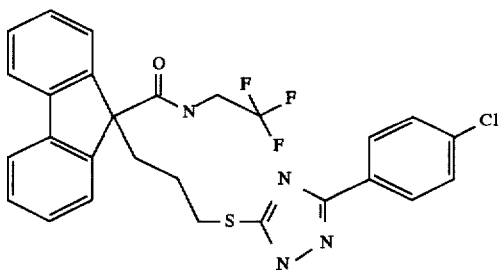
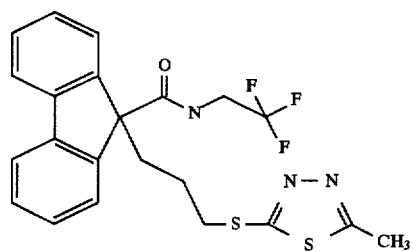

475
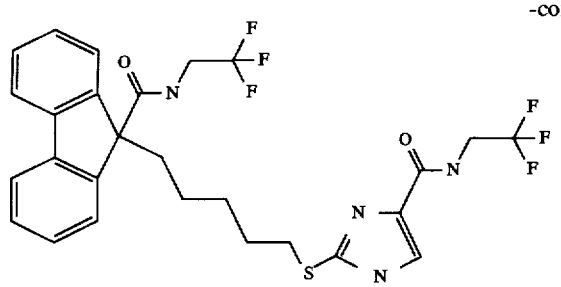
476
-continued
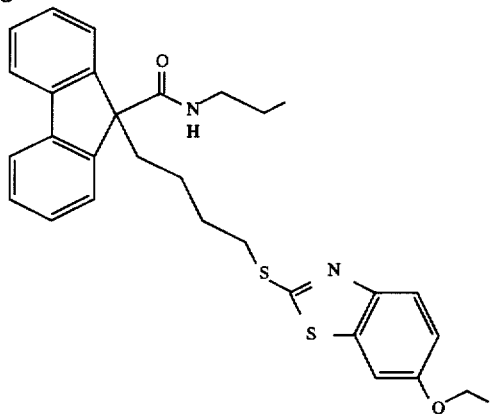
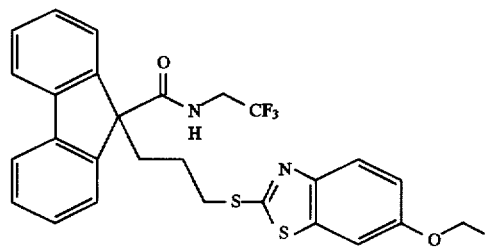
* * * * *